US009045475B2

(12) United States Patent
Elmore et al.

(10) Patent No.: US 9,045,475 B2
(45) Date of Patent: *Jun. 2, 2015

(54) APOPTOSIS-INDUCING AGENTS FOR THE TREATMENT OF CANCER AND IMMUNE AND AUTOIMMUNE DISEASES

(71) Applicants: AbbVie Inc., North Chicago, IL (US); Genentech, Inc., South San Francisco, CA (US); The Walter and Eliza Institute of Medical Research, Parkville (AU)

(72) Inventors: Steven W. Elmore, Northbrook, IL (US); Andrew J. Souers, Evanston, IL (US); Zhi-Fu Tao, Gurnee, IL (US)

(73) Assignees: ABBVIE INC., North Chicago, IL (US); GENENTECH, INC., South San Francisco, CA (US); THE WALTER AND ELIZA INSTITUTE OF MEDICAL RESEARCH, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,926

(22) Filed: Mar. 14, 2013

(65) Prior Publication Data

US 2013/0267534 A1    Oct. 10, 2013

Related U.S. Application Data

(63) Continuation of application No. 12/787,682, filed on May 26, 2010, now Pat. No. 8,546,399.

(60) Provisional application No. 61/181,203, filed on May 26, 2009.

(51) Int. Cl.
| | |
|---|---|
| A61K 31/407 | (2006.01) |
| C07D 401/12 | (2006.01) |
| C07D 471/04 | (2006.01) |
| C07D 401/14 | (2006.01) |
| C07D 519/00 | (2006.01) |
| C07D 209/82 | (2006.01) |
| C07D 403/12 | (2006.01) |
| A61K 31/496 | (2006.01) |

(52) U.S. Cl.
CPC ............ *C07D 471/04* (2013.01); *C07D 401/14* (2013.01); *C07D 519/00* (2013.01); *C07D 209/82* (2013.01); *C07D 403/12* (2013.01); *A61K 31/496* (2013.01)

(58) Field of Classification Search
CPC ..................................................... C07D 401/12
USPC .................................... 544/362; 514/252.18
See application file for complete search history.

(56) References Cited

U.S. PATENT DOCUMENTS

| | | |
|---|---|---|
| 4,707,487 A | 11/1987 | Arrang et al. |
| 6,720,338 B2 | 4/2004 | Augeri et al. |
| 6,787,534 B2 | 9/2004 | Haneda et al. |
| 6,803,374 B2 | 10/2004 | Priestley et al. |
| 6,858,638 B2 | 2/2005 | Damour et al. |
| 7,390,799 B2 | 6/2008 | Bruncko et al. |
| 7,504,512 B2 | 3/2009 | Augeri et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,642,260 B2 | 1/2010 | Bruncko et al. |
| 7,709,467 B2 | 5/2010 | Bruncko et al. |
| 7,754,886 B2 | 7/2010 | Augeri et al. |
| 7,767,684 B2 | 8/2010 | Bruncko et al. |
| 7,842,681 B2 | 11/2010 | Elmore et al. |
| 7,902,238 B2 | 3/2011 | Galley et al. |
| 7,973,161 B2 | 7/2011 | Bruncko et al. |
| 8,071,773 B2 | 12/2011 | Herold et al. |
| 8,084,607 B2 | 12/2011 | Bruncko et al. |
| 8,173,811 B2 | 5/2012 | Bruncko et al. |
| 8,188,077 B2 | 5/2012 | Ding et al. |
| 8,338,466 B2 | 12/2012 | Kunzer et al. |
| 8,354,404 B2 | 1/2013 | Bruncko et al. |
| 8,410,124 B2 | 4/2013 | Masse et al. |
| 8,426,422 B2 | 4/2013 | Hexamer et al. |
| 8,563,735 B2 | 10/2013 | Bruncko et al. |
| 8,580,794 B2 | 11/2013 | Doherty et al. |
| 2002/0055631 A1 | 5/2002 | Augeri et al. |
| 2003/0144507 A1 | 7/2003 | Haneda et al. |

(Continued)

FOREIGN PATENT DOCUMENTS

| | | |
|---|---|---|
| EP | 0324377 A2 | 7/1989 |
| EP | 0400835 A1 | 5/1990 |

(Continued)

OTHER PUBLICATIONS

Sophie et al., "Synthesis of "Trioxaquantel" Derivatives as Potential New Antischistosomal Drugs," European Journal of Organic Chemistry, 2008, vol. 5, pp. 895-913.
International Searching Authority, International Search Report for Application No. PCT/US2010/057587, (Apr. 23, 2011), 4 pages.
Becker et al., "Azaadamantane Benzamide 5-HT4 Agonists: Gastrointestinal Prokinetic SC-54750," Bioorganic and Med Chem Letters, (2004), pp. 5509-5512, vol. 14, issue 22.
Beylot et al., "In Vivo Studies of Intrahepatic Metabolic Pathways," Diabetes Metabolism, (1997), pp. 251-257, vol. 23, Issue 3.
Blagojevic et al., "Role of heavy water in Boron Neutron Capture Therapy," Topics in Dosimetry & Treatment Planning for Neutron Capture Therapy, (1994), pp. 125-134.

(Continued)

*Primary Examiner* — Shawquia Jackson
(74) *Attorney, Agent, or Firm* — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

2 Claims, No Drawings

(56) References Cited

U.S. PATENT DOCUMENTS

| | | |
|---|---|---|
| 2004/0067976 A1 | 4/2004 | Priestley et al. |
| 2005/0159427 A1 | 7/2005 | Bruncko et al. |
| 2006/0128706 A1 | 6/2006 | Bruncko et al. |
| 2007/0015787 A1 | 1/2007 | Bruncko et al. |
| 2007/0027135 A1 | 2/2007 | Bruncko et al. |
| 2007/0072860 A1 | 3/2007 | Bruncko et al. |
| 2008/0076779 A1 | 3/2008 | Elmore et al. |
| 2008/0182845 A1 | 7/2008 | Bardwell et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0022773 A1 | 1/2010 | Bruncko et al. |
| 2010/0152183 A1 | 6/2010 | Bruncko et al. |
| 2010/0160322 A1 | 6/2010 | Bruncko et al. |
| 2010/0184750 A1 | 7/2010 | Hexamer et al. |
| 2010/0184766 A1 | 7/2010 | Kunzer et al. |
| 2010/0227838 A1 | 9/2010 | Shah et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2011/0124628 A1 | 5/2011 | Bruncko et al. |
| 2011/0237553 A1 | 9/2011 | Ding et al. |
| 2012/0108590 A1 | 5/2012 | Birtalan et al. |
| 2012/0129853 A1 | 5/2012 | Elmore et al. |
| 2012/0157470 A1 | 6/2012 | Catron et al. |
| 2012/0190688 A1 | 7/2012 | Bruncko et al. |
| 2012/0277210 A1 | 11/2012 | Catron et al. |
| 2013/0267514 A1 | 10/2013 | Bruncko et al. |
| 2013/0267534 A1 | 10/2013 | Bruncko et al. |
| 2014/0057889 A1 | 2/2014 | Bruncko et al. |
| 2014/0088106 A1 | 3/2014 | Bruncko et al. |
| 2014/0094471 A1 | 4/2014 | Bruncko et al. |
| 2014/0107119 A1 | 4/2014 | Bruncko et al. |
| 2014/0113910 A1 | 4/2014 | Bruncko et al. |

FOREIGN PATENT DOCUMENTS

| | | |
|---|---|---|
| EP | 0514193 A1 | 11/1992 |
| RU | 2001103044 A | 8/2003 |
| RU | 2239631 C2 | 11/2004 |
| RU | 2004130280 A | 6/2005 |
| RU | 2387653 C2 | 4/2010 |
| WO | 9412461 A1 | 9/1994 |
| WO | 9507271 A1 | 3/1995 |
| WO | 9710223 A1 | 3/1997 |
| WO | 9918099 A1 | 4/1999 |
| WO | 0001389 A1 | 1/2000 |
| WO | 0073264 A1 | 12/2000 |
| WO | 0177087 A1 | 10/2001 |
| WO | 0224636 A2 | 3/2002 |
| WO | 02065470 A1 | 8/2002 |
| WO | 02098848 A1 | 12/2002 |
| WO | 2005049593 A2 | 6/2005 |
| WO | 2005049594 A1 | 6/2005 |
| WO | 2005099353 A2 | 10/2005 |
| WO | 2006008754 A1 | 1/2006 |
| WO | 2006124863 A2 | 11/2006 |
| WO | 2007002325 A1 | 1/2007 |
| WO | 2008030836 A2 | 3/2008 |
| WO | 2008124878 A1 | 10/2008 |
| WO | 2009049841 A1 | 4/2009 |
| WO | 2010065865 A2 | 6/2010 |
| WO | 2010072734 A2 | 7/2010 |
| WO | 2010077740 A2 | 7/2010 |
| WO | 2010083441 A2 | 7/2010 |
| WO | 2010072734 A3 | 8/2010 |
| WO | 2010077740 A3 | 9/2010 |
| WO | 2010065824 A2 | 10/2010 |
| WO | 2010138588 A2 | 12/2010 |
| WO | 2011149492 A1 | 12/2011 |
| WO | 2012058392 A1 | 5/2012 |
| WO | 2012071336 A1 | 5/2012 |
| WO | 2012071374 A1 | 5/2012 |
| WO | 2012121758 A1 | 9/2012 |

OTHER PUBLICATIONS

Bruncko et al., "Studies Leading to Potent, Dual Inhibitors of Bcl-2 and Bcl-XL," Journal of Medicinal Chemistry, (2007), pp. 641-662, vol. 50, Issue 4.

Certo et al., "Mitochondria Primed by Death Signals Determine Cellular Addiction to Antiapoptotic Bcl-2 Family Members," Cancer Cell, (2006), pp. 351-365, vol. 9, issue 5.

Eliel et al., "Stereochemistry of Organic Compounds," TOC. (1994), pp. 119-120, vol. 1206, John Wiley & Sons, Inc. New York.

International Searching Authority, "International Search Report for Application No. for PCT/US2010/036919," (Aug. 19, 2010), 5 pages.

International Searching Authority, "International Search Report for Application No. PCT/US2009/066722," (Aug. 4, 2010), 4 pages.

International Searching Authority, "International Search Report for Application No. PCT/US2009/066790," (Jul. 28, 2010), 5 pages.

International Searching Authority, "International Search Report for Application No. PCT/US201 01036844," (Aug. 16, 2010), 5 pages.

Korolkovas A., "Development of Drugs in: Essentials of Medicinal Chemistry," Second Edition, (1988), pp. 97-118, John Wiley and Sons.

Mason et al, "Programmed anuclear cell death delimits platelet life span," Cell, (2007), pp. 1173-1186, vol. 128, Issue 6.

Park et al. "Discovery of an Orally Bioavailable Small Molecule Inhibitor of Prosurvival B-Cell Lymphoma 2 Proteins," J of Med. Chem., (2008), pp. 6902-6915, vol. 51, issue 21.

Wendt M., "Discovery of ABT-263, a Bcl-Famiy Protein Inhibtor," Expert Opinion on Drug Discovery, (2008), pp. 1123-1143. vol. 3, Issue 9.

International Searching Authority, "Written Opinion for Application No. PCT/US2007/077579," (Jul. 29, 2008), 9 pages.

International Searching Authority, Written Opinion for Application No. PCT/US2010/036844, (Jun. 9, 2011), 10 pages.

International Searching Authority, Written Opinion for Application No. PCT/U52010/036919, (Jun. 9, 2011), 9 pages.

Zang et al., "Bcl-2 Family Proteins are Essential for Platelets Survival," Cell Death and Differentiation,(2007), pp. 943-951, vol. 14, Issue 5.

Blake et al., "Studies with deuterated drugs," J. Pharm. Sci., (1975), pp. 367-391, vol. 64, Issue 3.

Brickner S. J., et al., "Synthesis and antibacterial activity of U-100592 and U-100766, two oxazolidinone antibacterial agents for the potential treatment of multidrug-resistant gram-positive bacterial infections," J Med Chem., (1996), pp. 673-679, vol. 39, Issue 3.

Czajka D. M., "Effect of deuterium oxide on the reproductive potential of mice," Ann NY Acad Sci, (1960), pp. 770-779, vol. 84.

Czajka D.M., et al., "Physiological effects of deuterium on dogs," Am. J. Physiol., (1961), pp. 357-362, vol. 201, Issue 2.

Del Gaizo Moore et al., "BCL-2 dependence and ABT-737 sensitivity in acute lymphoblastic leukemia," Blood, (2008); pp. 2300-2309, vol. 111, issue 4.

Foster et al., "Deuterium Isotope Effects in the Metabolism of Drugs and Xenobiotics," Advances in Drug Research, (1985), pp. 2-36, vol. 14, Academic Press, London.

Holzelova et al., "Autoimmune Lymphoproliferative Syndrome with Somatic Fas Mutations," New England Journal of Medicine, (2004), pp. 1409-1418, vol. 351.

Science (1999), pp. 531-537, vol. 286.

Jones et al., "Effects of Substituent Modification on Face Select in ion Reduction," Journal Org. Chem., (1998), pp. 2758-2760, vol. 63.

Kato et al., "Synthesis of Deuterated Mosapride Citrate," J. Labelled Comp. Radiopharmaceut. (1995), pp. 927-932, vol. 36, Issue 10.

Kushner et al., "Pharmacological uses and perspectives of heavy water and deuterated compounds," Can J Physiol Pharmacol, (1999), pp. 79-88, vol. 77.

(56) References Cited

OTHER PUBLICATIONS

Lizondo et al., "Linezolid: Oxazolidinone antibacterial," Drugs of the Future. (1996), pp. 1116-1123, vol. 21, Issue 11.
Mallesham et al., "Highly efficient Cut-catalyzed coupling of aryl bromides with oxazolidinones using Buchwald's protocol," Org. Lett., (2003), pp. 963-965, vol. 5, Issue 7.
Puck et al., "Immune Disorders Cause by Defects in the Caspase Cascade," Current Allergy and Asthma Reports, (2003), pp. 378-384, vol. 3.
Rengan et al., "Actin cytoskeletal function is spared, but apoptosis is increased, in WAS patient hematopoietic cells," Blood, (2000), pp. 1283-1292, vol. 95, Issue 4.
Shimazaki et al., "Evaluation of apoptosis as a prognostic factor in myelodysplastic syndromes", British J Haematology, (2000), pp. 584-590, vol. 110, Issue 3.
Sutton et al. "Bcl-2 prevents apoptosis induced by perforin and granzyme B, but not that mediated by whole cytotoxic lymphocytes", J Immunology, (1997), pp. 5783-5790, vol. 158, Issue 12.
Thomason J. F., "Physiological Effects of D20 in Mammals." Ann. New York Acad. Sci., (1960), pp. 736-744, vol. 84.
Tse et al., "ABT-263: A Potent and Orally Bioavailable Bcl-2 Family Inhibitor," Cancer Research, (2008), pp. 3421-3428, vol. 68, Issue 9.
Wang Z.X., "An exact mathematical expression for describing competitive binding of two different ligands to a protein molecule", FEBS Lett. (1995), pp. 111-114, vol. 360, Issue 2.
Skoug J.W. and Gao, Y., "Enabling Discovery through Formulation," American Association of Pharmaceutical Scientists (AAPS) Webinar, (Mar. 18, 2010).
International Searching Authority, "Written Opinion for Application No. PCT/US2009/066722," (Jun. 7, 2011), 8 pages.
International Searching Authority, "Supplementary International Search Repot for Application No. PCT/US2009/066722," (Feb. 24, 2011), 2 pp.
International Searching Authority, "Supplementary International Search Report for Application No. PCT/US2009/066790," (Mar. 24, 2011), 2 pp.
International Searching Authority, "Supplementary International Search Report for Application No. PCT/US2010/057587," (May 24, 2012), 2 pp.
Cancer and Metastasis Reviews (1998), vol. 17. pp. 91-106, Issue 1.
Cancer [online], [retrieved on Jul. 6, 2007]. Retrieved fom the internet URL http://www.nlm.nih.gov/medlineplus/cancer.html>.
Cancer [online], (retrieved on Jul. 6, 2007). Retrieved from the internet, URL: http://en.wikipedia.orgiwikiiCancer.
Roberti et al., "Synthesis and Biological Evaluation of Resveratrol and Analogues as Apoptosis-inducing Agents," J Med. Chem. (2003), pp. 3546-3554, vol. 46.
Harada H., et al., "Survival Factor-Induced Extracellular Signa-Regulated Kinase Phosphorylated Bim, Inhibiting its Association with Bax and Proapoptotic Activity," D Proceedings of the National Academy of Sciences, (2004), pp. 15313-15317, vol. 101, Issue 43.
International Searching Authority, "Written Opinion for PCT/US2010/036198," (Feb. 9, 2011).
International Searching Authority, "Written Opinion for PCT/US2010/057587," (Nov. 27, 2012).
Banker et al, "Modern Pharmaceutics." 3rd Ed., (1996), p. 596.
Testa et al., "Pure Appl. Chem.," (2004), pp. 907-914. vol. 76.
Oltersdorf, T, et al., 2005, "An inhibitor of Bcl-2 family proteins induces regression of solid tumours," Nature pp. 677-681, vol. 435.
Vandenberg, CJ, et al., "ABT-199, a new Bcl-2-specific 8H3 mimetic, has in vivo efficacy against aggressive Myc-driven mouse lymphomas without provoking thrombocytopenia," Blood, Prepublished online (Jan. 22, 2013) doi: 10.1182/blood-2013-01-475855.
Bardwell, PD, et al., "The Bcl-2 family antagonist ABT-737 significantly inhibits animal models of autoimmunity," J. Immunol., (2009), pp. 7482-7489, vol. 182, Issue 12.
Souers, AJ, et al., "ABT-199, a potent and selective BCL-2 inhibitor, achieves antitumor activity while sparing platelets," (2013). Nature Medicine, pp. 202-208. vol. 19.
Asian Scientist Magazine, (accessed online http://www.asianscientist.com/tech-pharma/abt-199-bh-3-mimetic-wehi-phase-ia-trial-chronic-lymphocytic-leukemia/), (Aug. 12, 2011).
Humerickhouse, R., "Clinical Activity of the Potent and Slective Bcl-2 Inhibitor ABT-199 . . . " Symposium presentation, (Apr. 9, 2013), pp. 1-31. AACR Annual Meeting, Washington, D.C.
Cross, L.C. et al., "IUPAC Commission on Nomenclature of Organic Chemistry: Rules of the Nomenclature of Organic Chemistry, Section E: Stereochemistry," Pure and Applied Chemistry, (1976), pp. 11-30, vol. 45.
International Searching Authority, Supplementary International Search Report for Application No. PCT/US2010/036844, (Feb. 16, 2012), 4 pages.
European Patent Office, Extended European Search Report, Application No. EP12 16 3746, (Sep. 7, 2012).
Burger's Medicinal Chemistry, edited by Manfred E. Wolff, 5th Ed., (1995), pp. 975-977, Part 1.
International Searching Authority, "Supplementary International Search Report for PCT/US2010/036198," (Sep. 8, 2011).
United States Patent and Trademark Office, "Office Action for U.S. Appl. No. 13/430,610." (May 22, 2012).
United States Patent and Trademark Office, Office Action for U.S. Appl. No. 12/787,682 (Sep. 17, 2012).
United States Patent and Trademark Office, "Applicants' Amendment and Response to Restriction Requirement, U.S. Appl. No. 12/787,682," (Jun. 8, 2012).
United States Patent and Trademark Office, "Restriction Requirement for U.S. Appl. No. 12/951,344," (May 9, 2012).
United States Patent and Trademark Office, "Applicant's Amendment and Response for U.S. Appl. No. 12/951,344," (Jul. 9, 2013).
United States Patent and Trademark Office, "Office Action for U.S. Appl. No. 12/951,344," (Oct. 11, 2012).
United States Patent and Trademark Office, "Applicant's Amendment and Response for U.S. Appl. No. 12/951,344," (Dec. 21, 2012).
United States Patent and Trademark Office, "Notice of Allowance for U.S. Appl. No. 12/951,344," (Feb. 22, 2013).
United States Patent and Trademark Office, "Applicant's Amendment and Request for Continued Examination, for U.S. Appl. No. 12/951,344," (May 21, 2013).
United States Patent and Trademark Office, "Notice of Allowance for U.S. Appl. No. 12/951,344," Jun. 10, 2013).
United States Patent and Trademark Office, "Restriction Requirement for U.S. Appl. No. 12/787,682," (May 9, 2012).
United States Patent and Trademark Office, "Applicant's Amemdment and Response to Restriction Requirement for U.S. Appl. No. 12/787,682," (Jun. 8, 2012).
United States Patent and Trademark Office, "Office Action for U.S. Appl. No. 12/787,682," (Dec. 17, 2012).
United States Patent and Trademark Office, "Applicant's Amendment and Response to Office Action for U.S. Appl. No. 12/787,682," (Dec. 17, 2012).
United States Patent and Trademark Office, "Notcie of Allowance for U.S. Appl. No. 12/787,682," (Feb. 5, 2013).
United States Patent and Trademark Office, "Applicant's Amendment and Request for Continued Examination for U.S. Appl. No. 12/787,682," (May 6, 2013).
United States Patent and Trademark Office, "Notice of Allowance for U.S. Appl. No. 12/787,682," (May 21, 2013).
United States Patent and Trademark Office, "U.S. Appl. No. 13/831,184," filed Mar. 14, 2013.
Unted States Patent and Trademark Office, "Applicant's Preliminary Amendment for U.S. Appl. No. 13/831,184," filed Mar. 14, 2013.
Hales, et al., "Novel inhibitors of prolyl 4-hydroxylase. 5.1 The intriguing structure-activity relationships seen with 2,2'-bipyridine and its 5,5'-dicarboxylic acid derivatives," J.Med.Chem, (1993), vol. 36, pp. 3853-3858.
United States Patent and Trademark Office, "Non-Final Office Action for U.S. Appl. No. 14/038,409," (Mailed Apr. 23, 2014), 6 pages.
United States Patent and Trademark Office, "Non-Final Office Action for U.S. Appl. No. 13/331,184," (May 2, 2014), 10 pages.
Office of the Intellectual Property Office of Taiwan, "Office Acton for International Application No. TW 099116922, including English translation" (Issued Apr. 18, 2014), 20 pages.

```
                            SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
1               5                   10                  15
```

APOPTOSIS-INDUCING AGENTS FOR THE TREATMENT OF CANCER AND IMMUNE AND AUTOIMMUNE DISEASES

This application is a continuation of U.S. application Ser. No. 12/787,682, filed May 26, 2010, which claims the benefit of U.S. Provisional Application No. 61/181,203 filed May 26, 2009, which are incorporated herein by reference in their entireties.

FIELD OF THE INVENTION

This invention pertains to compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

SUMMARY OF THE INVENTION

One embodiment of this invention, therefore, pertains to compounds or therapeutically acceptable salts, which are useful as inhibitors of anti-apoptotic Bcl-2 proteins, the compounds having Formula (I)

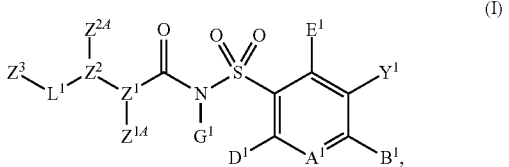

wherein
$A^1$ is N or $C(A^2)$;
$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)NH$_2$, NHC(O)NH$R^1$, NHC(O)N($R^1$)$_2$, $NR^1C(O)NHR^1$, $NR^1C(O)N(R^1)_2$, $SO_2NH_2$, $SO_2NHR^1$, $SO_2N(R^1)_2$, NHSO$_2R^1$, $NR^1SO_2R^1$, NHSO$_2$NH$R^1$, NHSO$_2$N($R^1$)$_2$, $NR^1SO_2NHR^1$, $NR^1SO_2N(R^1)_2$, C(O)NHNOH, C(O)NHNO$R^1$, C(O)NHSO$_2R^1$, C(NH)NH$_2$, C(NH)NH$R^1$, C(NH)N($R^1$)$_2$ NHSO$_2$NH$R^1$, NHSO$_2$N(CH$_3$)$R^1$, N(CH$_3$)SO$_2$N(CH$_3$)$R^1$, F, Cl, Br, I, CN, NO$_2$, N$_3$, OH, C(O)H, CHNOH, CH(NOCH$_3$), CF$_3$, C(O)OH, C(O)NH$_2$ or C(O)O$R^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)NH$_2$, NHC(O)NH$R^1$, NHC(O)N($R^1$)$_2$, $NR^1C(O)NHR^1$, $NR^1C(O)N(R^1)_2$, $SO_2NH_2$, $SO_2NHR^1$, $SO_2N(R^1)_2$, NHSO$_2R^1$, $NR^1SO_2R^1$, NHSO$_2$NH$R^1$, NHSO$_2$N($R^1$)$_2$, $NR^1SO_2NHR^1$, $NR^1SO_2N(R^1)_2$, C(O)NHNOH, C(O)NHNO$R^1$, C(O)NHSO$_2R^1$, C(NH)NH$_2$, C(NH)NH$R^1$, C(NH)N($R^1$)$_2$ NHSO$_2$NH$R^1$, NHSO$_2$N(CH$_3$)$R^1$, N(CH$_3$)SO$_2$N(CH$_3$)$R^1$, F, Cl, Br, I, CN, NO$_2$, N$_3$, OH, C(O)H, CHNOH, CH(NOCH$_3$), CF$_3$, C(O)OH, C(O)NH$_2$ or C(O)O$R^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)NH$_2$, NHC(O)NH$R^1$, NHC(O)N($R^1$)$_2$, $NR^1C(O)NHR^1$, $NR^1C(O)N(R^1)_2$, $SO_2NH_2$, $SO_2NHR^1$, $SO_2N(R^1)_2$, NHSO$_2R^1$, $NR^1SO_2R^1$, NHSO$_2$NH$R^1$, NHSO$_2$N($R^1$)$_2$, $NR^1SO_2NHR^1$, $NR^1SO_2N(R^1)_2$, C(O)NHNOH, C(O)NHNO$R^1$, C(O)NHSO$_2R^1$, C(NH)NH$_2$, C(NH)NH$R^1$, C(NH)N($R^1$)$_2$ NHSO$_2$NH$R^1$, NHSO$_2$N(CH$_3$)$R^1$, N(CH$_3$)SO$_2$N(CH$_3$)$R^1$, F, Cl, Br, I, CN, NO$_2$, N$_3$, OH, C(O)H, CHNOH, CH(NOCH$_3$), CF$_3$, C(O)OH, C(O)NH$_2$ or C(O)O$R^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)NH$_2$, NHC(O)NH$R^1$, NHC(O)N($R^1$)$_2$, $NR^1C(O)NHR^1$, $NR^1C(O)N(R^1)_2$, $SO_2NH_2$, $SO_2NHR^1$, $SO_2N(R^1)_2$, NHSO$_2R^1$, $NR^1SO_2R^1$, NHSO$_2$NH$R^1$, NHSO$_2$N($R^1$)$_2$, $NR^1SO_2NHR^1$, $NR^1SO_2N(R^1)_2$, C(O)NHNOH, C(O)NHNO$R^1$, C(O)NHSO$_2R^1$, C(NH)NH$_2$, C(NH)NH$R^1$, C(NH)N($R^1$)$_2$ NHSO$_2$NH$R^1$, NHSO$_2$N(CH$_3$)$R^1$, N(CH$_3$)SO$_2$N(CH$_3$)$R^1$, F, Cl, Br, I, CN, NO$_2$, N$_3$, OH, C(O)H, CHNOH, CH(NOCH$_3$), CF$_3$, C(O)OH, C(O)NH$_2$ or C(O)O$R^{1A}$; and $Y^1$ is H, CN, NO$_2$, C(O)OH, F, Cl, Br, I, CF$_3$, OCF$_3$, CF$_2$CF$_3$, OCF$_2$CF$_3$, $R^{17}$, $OR^{17}$, $C(O)R^{17}$, $C(O)OR^{17}$, $SR^{17}$, $SO_2R^{17}$, NH$_2$, NH$R^{17}$, N($R^{17}$)$_2$, NHC(O)$R^{17}$, C(O)NH$_2$, C(O)NH$R^{17}$, C(O)N($R^{17}$)$_2$, NHS(O)$R^{17}$ or NHSO$_2R^{17}$; or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)O$R^1$, $NR^1C(O)OR^1$, NHC(O)NH$_2$, NHC(O)NH$R^1$, NHC(O)N($R^1$)$_2$, $NR^1C(O)NHR^1$, $NR^1C(O)N(R^1)_2$, $SO_2NH_2$, $SO_2NHR^1$, $SO_2N(R^1)_2$, NHSO$_2R^1$, $NR^1SO_2R^1$, NHSO$_2$NH$R^1$, NHSO$_2$N($R^1$)$_2$, $NR^1SO_2NHR^1$, $NR^1SO_2N(R^1)_2$, C(O)NHNOH, C(O)NHNO$R^1$, C(O)NHSO$_2R^1$, C(NH)NH$_2$, C(NH)NH$R^1$, C(NH)N($R^1$)$_2$ NHSO$_2$NH$R^1$, NHSO$_2$N(CH$_3$)$R^1$, N(CH$_3$)SO$_2$N(CH$_3$)$R^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or Y$^1$ and B$^1$, together with the atoms to which they are attached, are benzene, naphthylene, heteroarene, cycloalkane, cycloalkene, heterocycloalkane or heterocycloalkene; and A$^2$, D$^1$, and E$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or A$^2$ and B$^1$, together with the atoms to which they are attached, are benzene, naphthylene, heteroarene cycloalkane, cycloalkene, heterocycloalkane or heterocycloalkene; and D$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$;

G$^1$ is H, or C(O)OR;

R is alkyl;

R$^1$ is R$^2$, R$^3$, R$^4$ or R$^5$;

R$^{1A}$ is cycloalkyl, cycloalkenyl or cycloalkynyl;

R$^2$ is phenyl, which is unfused or fused with R$^{2A}$; R$^{2A}$ is benzene, heteroarene, cycloalkane, cycloalkene, heterocycloalkane or heterocycloalkene;

R$^3$ is heteroaryl, which is unfused or fused with R$^{3A}$; R$^{3A}$ is benzene, heteroarene, cycloalkane, cycloalkene, heterocycloalkane or heterocycloalkene;

R$^4$ is cycloalkyl, cycloalkenyl, heterocycloalkyl or heterocycloalkenyl, each of which is unfused or fused with R$^{4A}$; R$^{4A}$ is benzene, heteroarene, cycloalkane, cycloalkene, heterocycloalkane or heterocycloalkene;

R$^5$ is alkyl, alkenyl or alkynyl, each of which is unsubstituted or substituted with one or two or three of independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^7$, OH, (O), C(O)OH, N$_3$, CN, NH$_2$, CF$_3$, CF$_2$CF$_3$, F, Cl, Br or I;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl, which is unfused or fused with R$^{8A}$; R$^{8A}$ is benzene, heteroarene, cycloalkane, cycloalkene, heterocycloalkane or heterocycloalkene;

R$^9$ is heteroaryl, which is unfused or fused with R$^{9A}$; R$^{9A}$ is benzene, heteroarene, cycloalkane, cycloalkene, heterocycloalkane or heterocycloalkene;

R$^{10}$ is cycloalkyl, cycloalkenyl, heterocycloalkyl or heterocycloalkenyl, each of which is unfused or fused with R$^{10A}$; R$^{10A}$ is benzene, heteroarene, cycloalkane, cycloalkene, heterocycloalkane or heterocycloalkene;

R$^{11}$ is alkyl, alkenyl or alkynyl, each of which is unsubstituted or substituted with one or two or three of independently selected R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{12}$ is R$^{13}$, R$^{14}$, R$^{15}$ or R$^{16}$;

R$^{13}$ is phenyl, which is unfused or fused with R$^{13A}$; R$^{13A}$ is benzene, heteroarene, cycloalkane, cycloalkene, heterocycloalkane or heterocycloalkene;

R$^{14}$ is heteroaryl, which is unfused or fused with R$^{14A}$; R$^{14A}$ is benzene, heteroarene, cycloalkane, cycloalkene, heterocycloalkane or heterocycloalkene;

R$^{15}$ is cycloalkane, cycloalkene, heterocycloalkane or heterocycloalkene, each of which is unfused or fused with R$^{15A}$; R$^{15A}$ is benzene, heteroarene, cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl, which is unfused or fused with R$^{18A}$; R$^{18A}$ is benzene, heteroarene, cycloalkane, cycloalkene, heterocycloalkane or heterocycloalkene;

R$^{19}$ is heteroaryl, which is unfused or fused with R$^{19A}$; R$^{19A}$ is benzene, heteroarene, cycloalkane, cycloalkene, heterocycloalkane or heterocycloalkene;

R$^{20}$ is cycloalkyl, cycloalkenyl, heterocycloalkyl or heterocycloalkenyl each of which is unfused or fused with R$^{20A}$; R$^{20A}$ is benzene, heteroarene, cycloalkane, cycloalkene, heterocycloalkane or heterocycloalkene;

R$^{21}$ is alkyl, alkenyl or alkynyl, each of which is unsubstituted or substituted with one or two or three of independently selected R$^{22}$, OR$^{22}$, SR$^{22}$, S(O)R$^{22}$, SO$_2$R$^{22}$, C(O)R$^{22}$, CO(O)R$^{22}$, OC(O)R$^{22}$, OC(O)OR$^{22}$, NH$_2$, NHR$^{22}$, N(R$^{22}$)$_2$, NHC(O)R$^{22}$, NR$^{22}$C(O)R$^{22}$, NHS(O)$_2$R$^{22}$, NR$^{22}$S(O)$_2$R$^{22}$, NHC(O)OR$^{22}$, NR$^{22}$C(O)OR$^{22}$, NHC(O)NH$_2$, NHC(O)

NHR$^{22}$, NHC(O)N(R$^{22}$)$_2$, NR$^{22}$C(O)NHR$^{22}$, NR$^{22}$C(O)N(R$^{22}$)$_2$, C(O)NH$_2$, C(O)NHR$^{22}$, C(O)N(R$^{22}$)$_2$, C(O)NHOH, C(O)NHOR$^{22}$, C(O)NHSO$_2$R$^{22}$, C(O)NR$^{22}$SO$_2$R$^{22}$, SO$_2$NH$_2$, SO$_2$NHR$^{22}$, SO$_2$N(R$^{22}$)$_2$, C(O)H, C(O)OH, C(N)NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is R$^{23}$, R$^{24}$ or R$^{25}$;
R$^{23}$ is phenyl, which is unfused or fused with R$^{23A}$; R$^{23A}$ is benzene, heteroarene, cycloalkane, cycloalkene, heterocycloalkane or heterocycloalkene;
R$^{24}$ is heteroarene, which is unfused or fused with R$^{24A}$; R$^{24A}$ is benzene, heteroarene, cycloalkane, cycloalkene, heterocycloalkane or heterocycloalkene;
R$^{25}$ is cycloalkyl, cycloalkenyl, heterocycloalkyl or heterocycloalkenyl, each of which is unfused or fused with R$^{25A}$; R$^{25A}$ is benzene, heteroarene, cycloalkane, cycloalkene, heterocycloalkane or heterocycloalkene;
Z$^1$ is R$^{26}$ or R$^{27}$;
Z$^2$ is R$^{28}$, R$^{29}$ or R$^{30}$;
Z$^{1A}$ and Z$^{2A}$ are both absent or are taken together to form CH$_2$, CH$_2$CH$_2$ or Z$^{12A}$;
Z$^{12A}$ is C$_2$-C$_6$-alkylene having one or two CH$_2$ moieties replaced by NH, N(CH$_3$), S, S(O) or SO$_2$;
L$^1$ is a R$^{37}$, OR$^{37}$, SR$^{37}$, S(O)R$^{37}$, SO$_2$R$^{37}$, C(O)R$^{37}$, CO(O)R$^{37}$, OC(O)R$^{37}$, OC(O)OR$^{37}$, NHR$^{37}$, C(O)NH, C(O)NR$^{37}$, C(O)NHOR$^{37}$, C(O)NHSO$_2$R$^{37}$, SO$_2$NH, SO$_2$NHR$^{37}$, C(N)NH, C(N)NHR$^{37}$;
R$^{26}$ is phenylene, which is unfused or fused with R$^{26A}$; R$^{26A}$ is benzene, heteroarene, cycloalkane, cycloalkene, heterocycloalkane or heterocycloalkene;
R$^{27}$ is heteroarylene, which is unfused or fused with R$^{27A}$; R$^{27A}$ is benzene, heteroarene, cycloalkane, cycloalkene, heterocycloalkane or heterocycloalkene;
R$^{28}$ is phenylene, which is unfused or fused with R$^{28A}$; R$^{28A}$ is benzene, heteroarene, cycloalkane, cycloalkene, heterocycloalkane or heterocycloalkene;
R$^{29}$ is heteroarylene, which is unfused or fused with R$^{29A}$; R$^{29A}$ is benzene, heteroarene, cycloalkane, cycloalkene, heterocycloalkane or heterocycloalkene;
R$^{30}$ is cycloalkylene, cycloalkenylene, heterocycloalkylene or heterocycloalkenylene, each of which is unfused or fused with R$^{30A}$; R$^{30A}$ is benzene, heteroarene, cycloalkane, cycloalkene, heterocycloalkane or heterocycloalkene;
R$^{37}$ is a bond or R$^{37A}$;
R$^{37A}$ is alkylene, alkenylene, or alkynylene, each of which is unsubstituted or substituted with one or two or three independently selected R$^{37B}$, OR$^{37B}$, SR$^{37B}$, S(O)R$^{37B}$, SO$_2$R$^{37B}$, C(O)R$^{37B}$, CO(O)R$^{37B}$, OC(O)R$^{37B}$, OC(O)OR$^{37B}$, NH$_2$, NHR$^{37B}$, N(R$^{37B}$)$_2$, NHC(O)R$^{37B}$, NR$^{37B}$C(O)R$^{37B}$, NHS(O)$_2$R$^{37B}$, NR$^{37B}$S(O)$_2$R$^{37B}$, NHC(O)OR$^{37B}$, NR$^{37B}$C(O)OR$^{37B}$, NHC(O)NH$_2$, NHC(O)NHR$^{37B}$, NHC(O)N(R$^{37B}$)$_2$, NR$^{37B}$C(O)NHR$^{37B}$, NR$^{37B}$C(O)N(R$^{37B}$)$_2$, C(O)NH$_2$, C(O)NHR$^{37B}$, C(O)N(R$^{37B}$)$_2$, C(O)NHOH, C(O)NHOR$^{37B}$, C(O)NHSO$_2$R$^{37B}$, C(O)NR$^{37B}$SO$_2$R$^{37B}$, SO$_2$NH$_2$, SO$_2$NHR$^{37B}$, SO$_2$N(R$^{37B}$)$_2$, C(O)H, C(O)OH, C(N)NH$_2$, C(N)NHR$^{37B}$, C(N)N(R$^{37B}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br and I substituents;
R$^{37B}$ is alkyl, alkenyl, alkynyl, or R$^{37C}$;
R$^{37C}$ is phenyl, heteroaryl, cycloalkyl, cycloalkenyl, heterocycloalkyl, or heterocycloalkenyl;
Z$^3$ is R$^{38}$, R$^{39}$ or R$^{40}$;
R$^{38}$ is phenyl, which is unfused or fused with R$^{38A}$; R$^{38A}$ is benzene, heteroarene, cycloalkane, cycloalkene, heterocycloalkane or heterocycloalkene;
R$^{39}$ is heteroaryl, which is unfused or fused with R$^{39A}$; R$^{39A}$ is benzene, heteroarene, cycloalkane, cycloalkene, heterocycloalkane or heterocycloalkene;
R$^{40}$ is cycloalkyl, cycloalkenyl, heterocycloalkyl or heterocycloalkenyl, each of which is unfused or fused with R$^{40A}$; R$^{40A}$ is benzene, heteroarene, cycloalkane, cycloalkene, heterocycloalkane or heterocycloalkene;
wherein the moieties represented by R$^{26}$ and R$^{27}$ are substituted (i.e., if Z$^{1A}$ and Z$^{2A}$ are absent) or further substituted (i.e., if Z$^{1A}$ and Z$^{2A}$ are present) with R$^{41}$, OR$^{41}$, SR$^{41}$, S(O)R$^{41}$, SO$_2$R$^{41}$, C(O)R$^{41}$, CO(O)R$^{41}$, OC(O)R$^{41}$, OC(O)OR$^{41}$, NHR$^{41}$, N(R$^{41}$)$_2$, NHC(O)R$^{41}$, NR$^{41}$C(O)R$^{41}$, NHS(O)$_2$R$^{41}$, NR$^{41}$S(O)$_2$R$^{41}$, NHC(O)OR$^{41}$, NR$^{41}$C(O)OR$^{41}$, NHC(O)NHR$^{41}$, NHC(O)N(R$^{41}$)$_2$, NR$^{41}$C(O)NHR$^{41}$, NR$^{41}$C(O)N(R$^{41}$)$_2$, C(O)NHR$^{41}$, C(O)N(R$^{41}$)$_2$, C(O)NHOR$^{41}$, C(O)NHSO$_2$R$^{41}$, C(O)NR$^{41}$SO$_2$R$^{41}$, SO$_2$NHR$^{41}$, SO$_2$N(R$^{41}$)$_2$, C(N)NHR$^{41}$, or C(N)N(R$^{41}$)$_2$;
R$^{41}$ is heteroaryl, which is fused with R$^{43A}$; R$^{43A}$ is benzene, heteroarene, cycloalkane, cycloalkene, heterocycloalkane or heterocycloalkene; which is unfused or fused with benzene, heteroarene or R$^{43B}$; R$^{43B}$ is cycloalkane, cycloalkene, heterocycloalkane or heterocycloalkene;
wherein the cyclic moieties represented by E$^1$ and Y$^1$ together, Y$^1$ and B$^1$ together, A$^2$ and B$^1$ together, A$^2$ and D$^1$ together, R$^{1A}$, R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{18}$, R$^{18A}$, R$^{19}$, R$^{19A}$, R$^{20}$, R$^{20A}$, R$^{23}$, R$^{23A}$, R$^{24}$, R$^{24A}$, R$^{25}$, R$^{25A}$, R$^{26}$, R$^{26A}$, R$^{27}$, R$^{27A}$, R$^{28}$, R$^{28A}$, R$^{29}$, R$^{29A}$, R$^{30}$, R$^{30A}$, R$^{37B}$, R$^{38}$, R$^{38A}$, R$^{39}$, R$^{39A}$, R$^{40}$, and R$^{40A}$ are independently unsubstituted, further unsubstituted, substituted or further substituted with one or two or three or four or five of independently selected R$^{57A}$, R$^{57}$, OR$^{57}$, SR$^{57}$, S(O)R$^{57}$, SO$_2$R$^{57}$, C(O)R$^{57}$, CO(O)R$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;
R$^{57A}$ is spiroalkyl, or spiroheteroalkyl;
R$^{57}$ is R$^{58}$, R$^{59}$, R$^{60}$ or R$^{61}$;
R$^{58}$ is phenyl, which is unfused or fused with R$^{58A}$; R$^{58A}$ is benzene, heteroarene, cycloalkane, cycloalkene, heterocycloalkane or heterocycloalkene;
R$^{59}$ is heteroaryl, which is unfused or fused with R$^{59A}$; R$^{59A}$ is benzene, heteroarene, cycloalkane, cycloalkene, heterocycloalkane or heterocycloalkene;
R$^{60}$ is cycloalkyl, cycloalkenyl, heterocycloalkyl or heterocycloalkenyl, each of which is unfused or fused with R$^{60A}$; R$^{60A}$ is benzene, heteroarene, cycloalkane, cycloalkene, heterocycloalkane or heterocycloalkene;
R$^{61}$ is alkyl, alkenyl or alkynyl, each of which is unsubstituted or substituted with one or two or three of independently selected R$^{62}$, OR$^{62}$, SR$^{62}$, S(O)R$^{62}$, SO$_2$R$^{62}$, C(O)R$^{62}$, CO(O)R$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

$R^{62}$ is $R^{63}$, $R^{64}$, $R^{65}$ or $R^{66}$;

$R^{63}$ is phenyl, which is unfused or fused with $R^{63A}$; $R^{63A}$ is benzene, heteroarene, cycloalkane, cycloalkene, heterocycloalkane or heterocycloalkene;

$R^{64}$ is heteroaryl, which is unfused or fused with $R^{64A}$; $R^{64A}$ is benzene, heteroarene, cycloalkane, cycloalkene, heterocycloalkane or heterocycloalkene;

$R^{65}$ is cycloalkyl, cycloalkenyl, heterocycloalkyl, or heterocycloalkenyl, each of which is unfused or fused with $R^{65A}$; $R^{65A}$ is benzene, heteroarene, cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{68}$ is $R^{69}$, $R^{70}$, $R^{71}$ or $R^{72}$;

$R^{69}$ is phenyl, which is unfused or fused with $R^{69A}$; $R^{69A}$ is benzene, heteroarene, cycloalkane, cycloalkene, heterocycloalkane or heterocycloalkene;

$R^{70}$ is heteroaryl, which is unfused or fused with $R^{70A}$; $R^{70A}$ is benzene, heteroarene, cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with $R^{71A}$; $R^{71A}$ is benzene, heteroarene, cycloalkane, cycloalkene, heterocycloalkane or heterocycloalkene;

$R^{72}$ is alkyl, alkenyl or alkynyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{73}$ is alkyl, alkenyl, alkynyl, phenyl, heteroaryl, cycloalkyl, cycloalkenyl, heterocycloalkyl or heterocycloalkenyl; and wherein the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, (O), $CN$, $N_3$, $NO_2$, $CF_3$, $CF_2CF_3$, $OCF_3$, $OCF_2CF_3$, F, Cl, Br or I.

Another embodiment of this invention pertains to compounds or therapeutically acceptable salts, which are useful as inhibitors of anti-apoptotic Bcl-2 proteins, the compounds having Formula (II)

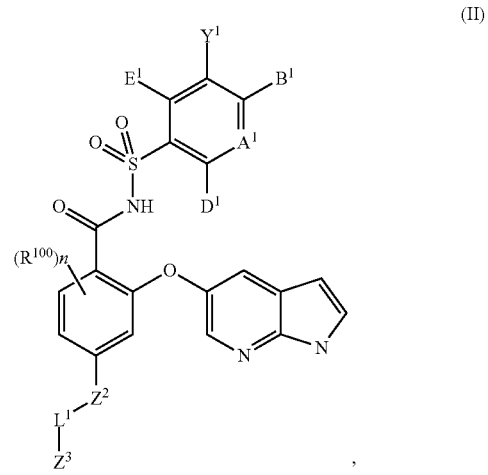

(II)

or a therapeutically acceptable salt thereof, wherein $R^{100}$ is as described for substituents on $R^{26}$;

n is 0, 1, 2, or 3;

$A^1$ is N or $C(A^2)$;

$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)$

NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$;

E$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; and Y$^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, SO$_2$R$^{17}$, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$; or E$^1$ and Y$^1$, together with the atoms to which they are attached, are benzene, naphthylene, heteroarene, cycloalkane, cycloalkene, heterocycloalkane or heterocycloalkene; and A$^2$, B$^1$, and D$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or Y$^1$ and B$^1$, together with the atoms to which they are attached, are benzene, naphthylene, heteroarene, cycloalkane, cycloalkene, heterocycloalkane or heterocycloalkene; and A$^2$, D$^1$, and E$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or A$^2$ and B$^1$, together with the atoms to which they are attached, are benzene, naphthylene, heteroarene cycloalkane, cycloalkene, heterocycloalkane or heterocycloalkene; and D$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$;

R$^1$ is R$^2$, R$^3$, R$^4$ or R$^5$;

R$^{1A}$ is cycloalkyl, cycloalkenyl or cycloalkynyl;

R$^2$ is phenyl, which is unfused or fused with R$^{2A}$; R$^{2A}$ is benzene, heteroarene, cycloalkane, cycloalkene, heterocycloalkane or heterocycloalkene;

R$^3$ is heteroaryl, which is unfused or fused with R$^{3A}$; R$^{3A}$ is benzene, heteroarene, cycloalkane, cycloalkene, heterocycloalkane or heterocycloalkene;

R$^4$ is cycloalkyl, cycloalkenyl, heterocycloalkyl or heterocycloalkenyl, each of which is unfused or fused with R$^{4A}$; R$^{4A}$ is benzene, heteroarene, cycloalkane, cycloalkene, heterocycloalkane or heterocycloalkene;

R$^5$ is alkyl, alkenyl or alkynyl, each of which is unsubstituted or substituted with one or two or three of independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^7$, OH, (O), C(O)OH, N$_3$, CN, NH$_2$, CF$_3$, CF$_2$CF$_3$, F, Cl, Br or I;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl, which is unfused or fused with R$^{8A}$; R$^{8A}$ is benzene, heteroarene, cycloalkane, cycloalkene, heterocycloalkane or heterocycloalkene;

R$^9$ is heteroaryl, which is unfused or fused with R$^{9A}$; R$^{9A}$ is benzene, heteroarene, cycloalkane, cycloalkene, heterocycloalkane or heterocycloalkene;

R$^{10}$ is cycloalkyl, cycloalkenyl, heterocycloalkyl or heterocycloalkenyl, each of which is unfused or fused with R$^{10A}$; R$^{10A}$ is benzene, heteroarene, cycloalkane, cycloalkene, heterocycloalkane or heterocycloalkene;

R$^{11}$ is alkyl, alkenyl or alkynyl, each of which is unsubstituted or substituted with one or two or three of independently selected R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{12}$ is R$^{13}$, R$^{14}$, R$^{15}$ or R$^{16}$;

R$^{13}$ is phenyl, which is unfused or fused with R$^{13A}$; R$^{13A}$ is benzene, heteroarene, cycloalkane, cycloalkene, heterocycloalkane or heterocycloalkene;

R$^{14}$ is heteroaryl, which is unfused or fused with R$^{14A}$; R$^{14A}$ is benzene, heteroarene, cycloalkane, cycloalkene, heterocycloalkane or heterocycloalkene;

R$^{15}$ is cycloalkane, cycloalkene, heterocycloalkane or heterocycloalkene, each of which is unfused or fused with R$^{15A}$; R$^{15A}$ is benzene, heteroarene, cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl, which is unfused or fused with R$^{18A}$; R$^{18A}$ is benzene, heteroarene, cycloalkane, cycloalkene, heterocycloalkane or heterocycloalkene;

R$^{19}$ is heteroaryl, which is unfused or fused with R$^{19A}$; R$^{19A}$ is benzene, heteroarene, cycloalkane, cycloalkene, heterocycloalkane or heterocycloalkene;

R$^{20}$ is cycloalkyl, cycloalkenyl, heterocycloalkyl or heterocycloalkenyl each of which is unfused or fused with R$^{20A}$; R$^{20A}$ is benzene, heteroarene, cycloalkane, cycloalkene, heterocycloalkane or heterocycloalkene;

R$^{21}$ is alkyl, alkenyl or alkynyl, each of which is unsubstituted or substituted with one or two or three of independently selected R$^{22}$, OR$^{22}$, SR$^{22}$, S(O)R$^{22}$, SO$_2$R$^{22}$, C(O)R$^{22}$, CO(O)R$^{22}$, OC(O)R$^{22}$, OC(O)OR$^{22}$, NH$_2$, NHR$^{22}$, N(R$^{22}$)$_2$, NHC(O)R$^{22}$, NR$^{22}$C(O)R$^{22}$, NHS(O)$_2$R$^{22}$, NR$^{22}$S(O)$_2$R$^{22}$, NHC(O)OR$^{22}$, NR$^{22}$C(O)OR$^{22}$, NHC(O)NH$_2$, NHC(O)NHR$^{22}$, NHC(O)N(R$^{22}$)$_2$, NR$^{22}$C(O)NHR$^{22}$, NR$^{22}$C(O)N(R$^{22}$)$_2$, C(O)NH$_2$, C(O)NHR$^{22}$, C(O)N(R$^{22}$)$_2$, C(O)NHOH, C(O)NHOR$^{22}$, C(O)NHSO$_2$R$^{22}$, C(O)NR$^{22}$SO$_2$R$^{22}$, SO$_2$NH$_2$, SO$_2$NHR$^{22}$, SO$_2$N(R$^{22}$)$_2$, C(O)H, C(O)OH, C(N)NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is R$^{23}$, R$^{24}$ or R$^{25}$;

R$^{23}$ is phenyl, which is unfused or fused with R$^{23A}$; R$^{23A}$ is benzene, heteroarene, cycloalkane, cycloalkene, heterocycloalkane or heterocycloalkene;

R$^{24}$ is heteroarene, which is unfused or fused with R$^{24A}$; R$^{24A}$ is benzene, heteroarene, cycloalkane, cycloalkene, heterocycloalkane or heterocycloalkene;

R$^{25}$ is cycloalkyl, cycloalkenyl, heterocycloalkyl or heterocycloalkenyl, each of which is unfused or fused with R$^{25A}$; R$^{25A}$ is benzene, heteroarene, cycloalkane, cycloalkene, heterocycloalkane or heterocycloalkene;

Z$^2$ is R$^{28}$, R$^{29}$ or R$^{30}$;

L$^1$ is a R$^{37}$, OR$^{37}$, SR$^{37}$, S(O)R$^{37}$, SO$_2$R$^{37}$, C(O)R$^{37}$, CO(O)R$^{37}$, OC(O)R$^{37}$, OC(O)OR$^{37}$, NHR$^{37}$, C(O)NH, C(O)NR$^{37}$, C(O)NHOR$^{37}$, C(O)NHSO$_2$R$^{37}$, SO$_2$NH, SO$_2$NHR$^{37}$, C(N)NH, C(N)NHR$^{37}$;

R$^{28}$ is phenylene, which is unfused or fused with R$^{28A}$; R$^{28A}$ is benzene, heteroarene, cycloalkane, cycloalkene, heterocycloalkane or heterocycloalkene;

R$^{29}$ is heteroarylene, which is unfused or fused with R$^{29A}$; R$^{29A}$ is benzene, heteroarene, cycloalkane, cycloalkene, heterocycloalkane or heterocycloalkene;

R$^{30}$ is cycloalkylene, cycloalkenylene, heterocycloalkylene or heterocycloalkenylene, each of which is unfused or fused with R$^{30A}$; R$^{30A}$ is benzene, heteroarene, cycloalkane, cycloalkene, heterocycloalkane or heterocycloalkene;

R$^{37}$ is a bond or R$^{37A}$;

R$^{37A}$ is alkylene, alkenylene, or alkynylene, each of which is unsubstituted or substituted with one or two or three independently selected R$^{37B}$, OR$^{37B}$, SR$^{37B}$, S(O)R$^{37B}$, SO$_2$R$^{37B}$, C(O)R$^{37B}$, CO(O)R$^{37B}$, OC(O)R$^{37B}$, OC(O)OR$^{37B}$, NH$_2$, NHR$^{37B}$, N(R$^{37B}$)$_2$, NHC(O)R$^{37B}$, NR$^{37B}$C(O)R$^{37B}$, NHS(O)$_2$R$^{37B}$, NR$^{37B}$S(O)$_2$R$^{37B}$, NHC(O)OR$^{37B}$, NR$^{37B}$C(O)OR$^{37B}$, NHC(O)NH$_2$, NHC(O)NHR$^{37B}$, NHC(O)N(R$^{37B}$)$_2$, NR$^{37B}$C(O)NHR$^{37B}$, NR$^{37B}$C(O)N(R$^{37B}$)$_2$, C(O)NH$_2$, C(O)NHR$^{37B}$, C(O)N(R$^{37B}$)$_2$, C(O)NHOH, C(O)NHOR$^{37B}$, C(O)NHSO$_2$R$^{37B}$, C(O)NR$^{37B}$SO$_2$R$^{37B}$, SO$_2$NH$_2$, SO$_2$NHR$^{37B}$, SO$_2$N(R$^{37B}$)$_2$, C(O)H, C(O)OH, C(N)NH$_2$, C(N)NHR$^{37B}$, C(N)N(R$^{37B}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br and I substituents;

R$^{37B}$ is alkyl, alkenyl, alkynyl, or R$^{37C}$;

R$^{37C}$ is phenyl, heteroaryl, cycloalkyl, cycloalkenyl, heterocycloalkyl, or heterocycloalkenyl;

Z$^3$ is R$^{38}$, R$^{39}$ or R$^{40}$;

R$^{38}$ is phenyl, which is unfused or fused with R$^{38A}$; R$^{38A}$ is benzene, heteroarene, cycloalkane, cycloalkene, heterocycloalkane or heterocycloalkene;

R$^{39}$ is heteroaryl, which is unfused or fused with R$^{39A}$; R$^{39A}$ is benzene, heteroarene, cycloalkane, cycloalkene, heterocycloalkane or heterocycloalkene;

R$^{40}$ is cycloalkyl, cycloalkenyl, heterocycloalkyl or heterocycloalkenyl, each of which is unfused or fused with R$^{40A}$; R$^{40A}$ is benzene, heteroarene, cycloalkane, cycloalkene, heterocycloalkane or heterocycloalkene;

wherein the cyclic moieties represented by E$^1$ and Y$^1$ together, Y$^1$ and B$^1$ together, A$^2$ and B$^1$ together, A$^2$ and D$^1$ together, R$^{1A}$, R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{18}$, R$^{18A}$, R$^{19}$, R$^{19A}$, R$^{20}$, R$^{20A}$, R$^{23}$, R$^{23A}$, R$^{24}$, R$^{24A}$, R$^{25}$, R$^{25A}$, R$^{26}$, R$^{26A}$, R$^{27}$, R$^{27A}$, R$^{28}$, R$^{28A}$, R$^{29}$, R$^{29A}$, R$^{30}$, R$^{30A}$, R$^{37B}$, R$^{38}$, R$^{38A}$, R$^{39}$, R$^{39A}$, R$^{40}$, and R$^{40A}$ are independently unsubstituted, further unsubstituted, substituted or further substituted with one or two or three or four or five of independently selected R$^{57A}$, R$^{57}$, OR$^{57}$, SR$^{57}$, S(O)R$^{57}$, SO$_2$R$^{57}$, C(O)R$^{57}$, CO(O)R$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{57A}$ is spiroalkyl or heterospiroalkyl;

R$^{57}$ is R$^{58}$, R$^{59}$, R$^{60}$ or R$^{61}$;

R$^{58}$ is phenyl, which is unfused or fused with R$^{58A}$; R$^{58A}$ is benzene, heteroarene, cycloalkane, cycloalkene, heterocycloalkane or heterocycloalkene;

R$^{59}$ is heteroaryl, which is unfused or fused with R$^{59A}$; R$^{59A}$ is benzene, heteroarene, cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with R$^{60A}$; R$^{60A}$ is benzene, heteroarene, cycloalkane, cycloalkene, heterocycloalkane or heterocycloalkene;

R$^{61}$ is alkyl, alkenyl or alkynyl, each of which is unsubstituted or substituted with one or two or three of independently selected R$^{62}$, OR$^{62}$, SR$^{62}$, S(O)R$^{62}$, SO$_2$R$^{62}$, C(O)R$^{62}$, CO(O)R$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N (R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{62}$ is R$^{63}$, R$^{64}$, R$^{65}$ or R$^{66}$;

R$^{63}$ is phenyl, which is unfused or fused with R$^{63A}$; R$^{63A}$ is benzene, heteroarene, cycloalkane, cycloalkene, heterocycloalkane or heterocycloalkene;

R$^{64}$ is heteroaryl, which is unfused or fused with R$^{64A}$; R$^{64A}$ is benzene, heteroarene, cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with R$^{65A}$; R$^{65A}$ is benzene, heteroarene, cycloalkane, cycloalkene, heterocycloalkane or heterocycloalkene;

R$^{66}$ is alkyl, alkenyl or alkynyl, each of which is unsubstituted or substituted with one or two or three of independently selected R$^{67}$, OR$^{67}$, SR$^{67}$, S(O)R$^{67}$, SO$_2$R$^{67}$, C(O)R$^{67}$, CO(O)R$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the cyclic moieties represented by R$^{57A}$, R$^{58}$, R$^{59}$, R$^{60}$, R$^{63}$, R$^{64}$, R$^{65}$, and R$^{67}$ are unsubstituted or substituted with one or two or three or four of independently selected R$^{68}$, OR$^{68}$, SR$^{68}$, S(O)R$^{68}$, SO$_2$R$^{68}$, C(O)R$^{68}$, CO(O)R$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{68}$ is R$^{69}$, R$^{70}$, R$^{71}$ or R$^{72}$;

R$^{69}$ is phenyl, which is unfused or fused with R$^{69A}$; R$^{69A}$ is benzene, heteroarene, cycloalkane, cycloalkene, heterocycloalkane or heterocycloalkene;

R$^{70}$ is heteroaryl, which is unfused or fused with R$^{70A}$; R$^{70A}$ is benzene, heteroarene, cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with R$^{71A}$; R$^{71A}$ is benzene, heteroarene, cycloalkane, cycloalkene, heterocycloalkane or heterocycloalkene;

R$^{72}$ is alkyl, alkenyl or alkynyl, each of which is unsubstituted or substituted with one or two or three of independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{73}$ is alkyl, alkenyl, alkynyl, phenyl, heteroaryl, cycloalkyl, cycloalkenyl, heterocycloalkyl or heterocycloalkenyl; and wherein the moieties represented by R$^{69}$, R$^{70}$, and R$^{71}$ are unsubstituted or substituted with one or two or three or four of independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I.

Another embodiment pertains to compounds of Formula (I) wherein A$^1$ is N or C(A$^2$); A$^2$ is H, and G$^1$ is H.

Another embodiment pertains to compounds of Formula (I) wherein A$^1$ is N or C(A$^2$); A$^2$ is H; G$^1$ is H, and B$^1$ is NHR$^1$.

Another embodiment pertains to compounds of Formula (I) wherein A$^1$ is N or C(A$^2$); A$^2$ is H; G$^1$ is H, B$^1$ is NHR$^1$; and D$^1$ is H.

Another embodiment pertains to compounds of Formula (I) wherein A$^1$ is N or C(A$^2$); A$^2$ is H; G$^1$ is H, B$^1$ is NHR$^1$; D$^1$ is H; and E$^1$ is H.

Another embodiment pertains to compounds of Formula (I) wherein A$^1$ is N or C(A$^2$); A$^2$ is H; G$^1$ is H, B$^1$ is NHR$^1$; D$^1$ is H; E$^1$ is H; and Y$^1$ is NO$_2$.

Still another embodiment pertains to compounds having Formula (I) or Formula (II), which are 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-(2-naphthylsulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl] methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide;

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide;

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(1-methylpiperidin-4-yl) methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(2,2-dimethyltetrahydro- 2H-pyran-4-yl)methoxy]-3-nitrophenyl}sulfonyl)-2-(1H-pyrrolo[2,3-b]pyridin-5-yloxy)benzamide;

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide;

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[8-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-({4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate;

4-(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide;

4-(4-{[8-(4-chlorophenyl)spiro[4.5]dec-7-en-7-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(1-tetrahydro- 2H-pyran-4-ylpiperidin-4-yl)oxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide;

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

and therapeutically acceptable salts, and metabolites thereof.

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yl oxy)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-morpholin-4-ylcyclohexyl)methyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide;

4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{3-nitro-4-({[(3R)-1-tetrahydro-2H-pyran-4-ylpyrrolidin-3-yl]methyl}amino)phenyl}sulfonyl}-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide;

Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide;

tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate;

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide;

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide;

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide;

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]ethyl]piperidin-4-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide;

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({4-[3-(dimethylamino)propoxy]benzyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({[(E)-4-hydroxy-1-adamantyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({[(Z)-4-hydroxy-1-adamantyl]methyl}amino)-3-nitrophenyl]sulfonyl}-2-(1H-pyrrolo[2,3-b]pyridin-5-yloxy)benzamide;

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide;

4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide;

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid;

4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H- pyran-4-yl)methoxy]-3-[(trifluoromethyl)sulfonyl]
phenyl}sulfonyl)-2-(1H-pyrrolo[2,3-b]pyridin-5-yloxy)
benzamide;

4-(4-{[2-(4-chlorophenyl)-4,4-dimethylcyclohex-1-en-1-yl]
methyl}piperazin-1-yl)-N-({4-[(4-methyltetrahydro-2H-
pyran-4-yl)methoxy]-3-nitrophenyl}sulfonyl)-2-(1H-pyr-
rolo[2,3-b]pyridin-5-yloxy)benzamide;

ethyl 4-(4-{[4-(4-{[2-(4-chlorophenyl)-4,4-dimethylcyclo-
hex-1-en-1-yl]methyl}piperazin-1-yl)-2-(1H-pyrrolo[2,3-
b]pyridin-5-yloxy)benzoyl]sulfamoyl}-2-nitrophenyl)
piperazine-1-carboxylate;

4-(4-{[2-(4-chlorophenyl)-4,4-dimethylcyclohex-1-en-1-yl]
methyl}piperazin-1-yl)-N-({-4-[4-(morpholin-4-yl)pip-
eridin-1-yl]-3-nitrophenyl}sulfonyl)-2-(1H-pyrrolo[2,3-
b]pyridin-5-yloxy)benzamide;

4-(4-{[2-(4-chlorophenyl)-4,4-dimethylcyclohex-1-en-1-yl]
methyl}piperazin-1-yl)-N-[(3-nitro-4-{[(3R)-1-(oxetan-
3-yl)pyrrolidin-3-yl]amino}phenyl)sulfonyl]-2-(1H-pyr-
rolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(3R)-1-(1,3-difluoropro-
pan-2-yl)pyrrolidin-3-yl]amino}-3-[(trifluoromethyl)sul-
fonyl]phenyl)sulfonyl]-2-(1H-pyrrolo[2,3-b]pyridin-5-
yloxy)benzamide;

4-(4-{[2-(4-chlorophenyl)-4,4-dimethylcyclohex-1-en-1-yl]
methyl}piperazin-1-yl)-N-({4-[(1-isopropylpiperidin-4-
yl)amino]-3-nitrophenyl}sulfonyl)-2-(1H-pyrrolo[2,3-b]
pyridin-5-yloxy)benzamide;

N-({4-[(1-tert-butylpiperidin-4-yl)amino]-3-
nitrophenyl}sulfonyl)-4-(4-{[2-(4-chlorophenyl)-4,4-
dimethylcyclohex-1-en-1-yl]methyl}piperazin-1-yl)-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({[1-(2-methoxyethyl)pip-
eridin-3-yl]methyl}amino)-3-nitrophenyl]sulfonyl}-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({[1-(cyanomethyl)piperi-
din-3-yl]methyl}amino)-3-nitrophenyl]sulfonyl}-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(4-fluoro-1-methylpiperi-
din-4-yl)methoxy]-3-[(trifluoromethyl)sulfonyl]
phenyl}sulfonyl)-2-(1H-pyrrolo[2,3-b]pyridin-5-yloxy)
benzamide;

N-[(5-chloro-6-{[(3R)-1-(1,3-difluoropropan-2-yl)pyrroli-
din-3-yl]amino}pyridin-3-yl)sulfonyl]-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;

tert-butyl 4-[(4-{[4-(4-{[2-(4-chlorophenyl)-4,4-dimethyl-
cyclohex-1-en-1-yl]methyl}piperazin-1-yl)-2-(1H-pyr-
rolo[2,3-b]pyridin-5-yloxy)benzoyl]sulfamoyl}-2-nitro-
phenyl)amino]piperazine-1-carboxylate;

4-(4-{[2-(4-chlorophenyl)-4,4-dimethylcyclohex-1-en-1-yl]
methyl}piperazin-1-yl)-N-({3-(pentafluoro-λ⁶-sulfanyl)-
4-[(tetrahydro-2H-pyran-4-ylmethyl)amino]
phenyl}sulfonyl)-2-(1H-pyrrolo[2,3-b]pyridin-5-yloxy)
benzamide;

4-(4-{[2-(4-chlorophenyl)-4,4-dimethylcyclohex-1-en-1-yl]
methyl}piperazin-1-yl)-N-({4-[(4-methoxytetrahydro-
2H-pyran-4-yl)methoxy]-3-nitrophenyl}sulfonyl)-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(3R)-1-(1,3-difluoropro-
pan-2-yl)pyrrolidin-3-yl]oxy}-3-nitrophenyl)sulfonyl]-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(3-nitro-4-{[4-(oxetan-3-yl)
piperazin-1-yl]amino}phenyl)sulfonyl]-2-(1H-pyrrolo[2,
3-b]pyridin-5-yloxy)benzamide;

4-(4-{[2-(4-chlorophenyl)-4,4-dimethylcyclohex-1-en-1-yl]
methyl}piperazin-1-yl)-N-[(3-nitro-4-{[4-(tetrahydro-
2H-pyran-4-yl)piperazin-1-yl]amino}phenyl)sulfonyl]-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({3-nitro-4-[(3R)-tetrahydro-
furan-3-ylamino]phenyl}sulfonyl)-2-(1H-pyrrolo[2,3-b]
pyridin-5-yloxy)benzamide;

4-(4-{[2-(4-chlorophenyl)-4,4-dimethylcyclohex-1-en-1-yl]
methyl}piperazin-1-yl)-N-[(4-{[(4,4-difluorocyclohexyl)
methyl]amino}-3-nitrophenyl)sulfonyl]-2-(1H-pyrrolo[2,
3-b]pyridin-5-yloxy)benzamide;

N-({4-[(1-tert-butylpiperidin-4-yl)amino]-3-[(trifluorom-
ethyl)sulfonyl]phenyl}sulfonyl)-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-({[4-(oxetan-3-yl)morpho-
lin-2-yl]methyl}amino)-3-[(trifluoromethyl)sulfonyl]
phenyl}sulfonyl)-2-(1H-pyrrolo[2,3-b]pyridin-5-yloxy)
benzamide;

N-[(5-chloro-6-{[(4-fluorotetrahydro-2H-pyran-4-yl)me-
thyl]amino}pyridin-3-yl)sulfonyl]-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;

N-({5-chloro-6-[(1-cyclopropylpiperidin-4-yl)amino]pyri-
din-3-yl}sulfonyl)-4-(4-{[2-(4-chlorophenyl)-4,4-dim-
ethylcyclohex-1-en-1-yl]methyl}piperazin-1-yl)-2-(1H-
pyrrolo[2,3-b]pyridin-5-yloxy)benzamide;

N-[(5-chloro-6-{[(2S)-4-(cyanomethyl)morpholin-2-yl]
methoxy}pyridin-3-yl)sulfonyl]-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide;

N-[(5-chloro-6-{[(2S)-4-(N,N-dimethylglycyl)morpholin-
2-yl]methoxy}pyridin-3-yl)sulfonyl]-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;

N-[(5-chloro-6-{[(2R)-4-(cyanomethyl)morpholin-2-yl]
methoxy}pyridin-3-yl)sulfonyl]-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide;

N-[(5-chloro-6-{[(2R)-4-(N,N-dimethylglycyl)morpholin-
2-yl]methoxy}pyridin-3-yl)sulfonyl]-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;

4-(4-{[2-(4-chlorophenyl)-4,4-dimethylcyclohex-1-en-1-yl]
methyl}piperazin-1-yl)-N-({5-fluoro-6-[(4-fluorotetrahy-
dro-2H-pyran-4-yl)methoxy]pyridin-3-yl}sulfonyl)-2-
(1H-pyrrolo[2,3-b]pyridin-5-yloxy)benzamide;

N-({5-chloro-6-[3-hydroxy-2-(hydroxymethyl)-2-methyl-
propoxy]pyridin-3-yl}sulfonyl)-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({6-[(4-fluorotetrahydro-2H-
pyran-4-yl)methoxy]pyridin-3-yl}sulfonyl)-2-(1H-pyr-
rolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({[4-(1,3-difluoropropan- 2-yl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide;

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-{4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl)phenyl}sulfonyl)benzamide;

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-cyano cyclohexyl)methyl]amino}-3-nitrophenyl)sulfonyl]-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide;

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoro ethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluoro-1-methylpiperidin-4-yl)methoxy]phenyl}sulfonyl)-4-(4-{[2-(4-chlorophenyl)-4,4- dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide;
N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide;
N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide;
N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
Trans-4-(4-{[2-(4-chlorophenyl)-4,4-dimethylcyclohexyl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide;
N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide;
N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide;
N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide;
N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide;
N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;
N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide;
N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperidin-1-yl)-N-({3-nitro-4-[(tetrahydro-2H- pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide;

methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate;

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide;

4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[5-(4-chlorophenyl)spiro[2.5]oct-5-en-6-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide;

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide;

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide;

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide;

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide;

N-({5-chloro-6-[(trans-4-hydroxy-4-methylcyclohexyl)
methoxy]pyridin-3-yl}sulfonyl)-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide;
N-({5-chloro-6-[(cis-4-hydroxy-4-methylcyclohexyl)meth-
oxy]pyridin-3-yl}sulfonyl)-4-(4-{[2-(4-chlorophenyl)-4,
4-dimethylcyclohex-1-en-1-yl]methyl}piperazin-1-yl)-2-
(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-{[4-({4-[(2,2-difluorocyclo-
propyl)amino]cyclohexyl}amino)-3-nitrophenyl]sulfo-
nyl}-2-(1H-pyrrolo[2,3-b]pyridin-5-yloxy)benzamide;
N-({5-chloro-6-[(cis-1-fluoro-4-hydroxycyclohexyl)meth-
oxy]pyridin-3-yl}sulfonyl)-4-(4-{[2-(4-chlorophenyl)-4,
4-dimethylcyclohex-1-en-1-yl]methyl}piperazin-1-yl)-2-
(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-{[3-nitro-4-(2-oxaspiro[3.5]
non-7-ylmethoxy)phenyl]sulfonyl}-2-(1H-pyrrolo[2,3-b]
pyridin-5-yloxy)benzamide;
4-(4-{[2-(4-chlorophenyl)-4,4-dimethylcyclohex-1-en-1-yl]
methyl}piperazin-1-yl)-N-({4-[(trans-4-hydroxy-4-meth-
ylcyclohexyl)methoxy]-3-nitrophenyl}sulfonyl)-2-(1H-
pyrrolo[2,3-b]pyridin-5-yloxy)benzamide;
4-(4-{[2-(4-chlorophenyl)-5,5-bis(fluoromethyl)cyclohex-
1-en-1-yl]methyl}piperazin-1-yl)-N-({3-nitro-4-[(tet-
rahydro-2H-pyran-4-ylmethyl)amino]phenyl}sulfonyl)-
2-(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-({4-[(4-cyclopropylmorpho-
lin-2-yl)methoxy]-3-nitrophenyl}sulfonyl)-2-(1H-pyrrolo
[2,3-b]pyridin-5-yloxy)benzamide;
N-({5-chloro-6-[(trans-1-fluoro-4-hydroxy-4-methylcyclo-
hexyl)methoxy]pyridin-3-yl}sulfonyl)-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;
N-({5-chloro-6-[(cis-1-fluoro-4-hydroxy-4-methylcyclo-
hexyl)methoxy]pyridin-3-yl}sulfonyl)-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;
4-(4-{[2-(4-chlorophenyl)-4,4-dimethylcyclohex-1-en-1-yl]
methyl}piperazin-1-yl)-N-[(3-cyano-4-{[4-fluoro-1-(ox-
etan-3-yl)piperidin-4-yl]methoxy}phenyl)sulfonyl]-2-
(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-[(4-{[(trans-4-ethyl-4-hy-
droxycyclohexyl)methyl]amino}-3-nitrophenyl)sulfo-
nyl]-2-(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-[(4-{[(cis-4-ethyl-4-hydroxy-
cyclohexyl)methyl]amino}-3-nitrophenyl)sulfonyl]-2-
(1H-pyrrolo[2,3-b]pyridin-5-yloxy)benzamide;
4-(4-{[2-(4-chlorophenyl)-5-(methoxymethyl)-5-methylcy-
clohex-1-en-1-yl]methyl}piperazin-1-yl)-N-({3-nitro-4-
[(tetrahydro-2H-pyran-4-ylmethyl)amino]
phenyl}sulfonyl)-2-(1H-pyrrolo[2,3-b]pyridin-5-yloxy)
benzamide;
4-(4-{[2-(4-chlorophenyl)-4,4-dimethylcyclohex-1-en-1-yl]
methyl}piperazin-1-yl)-N-{[3-nitro-4-({[(2S)-4-(oxetan-
3-yl)morpholin-2-yl]methyl}amino)phenyl]sulfonyl}-2-
(1H-pyrrolo[2,3-b]pyridin-5-yloxy)benzamide;
N-({3-chloro-4-[(trans-4-hydroxy-4-methylcyclohexyl)
methoxy]phenyl}sulfonyl)-4-(4-{[2-(4-chlorophenyl)-4,
4-dimethylcyclohex-1-en-1-yl]methyl}piperazin-1-yl)-2-
(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-{[4-({4-[(2-cyanoethyl)(cyclo-
propyl)amino]-1-fluorocyclohexyl}methoxy)-3-nitrophe-
nyl]sulfonyl}-2-(1H-pyrrolo[2,3-b]pyridin-5-yloxy)
benzamide;
4-(4-{[2-(4-chlorophenyl)-4,4-dimethylcyclohex-1-en-1-yl]
methyl}piperazin-1-yl)-N-({5-nitro-6-[(tetrahydro-2H-
pyran-4-ylmethyl)amino]pyridin-3-yl}sulfonyl)-2-(1H-
pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-({3-nitro-4-[(2-oxaspiro[3.5]
non-7-ylmethyl)amino]phenyl}sulfonyl)-2-(1H-pyrrolo
[2,3-b]pyridin-5-yloxy)benzamide;
4-(4-{[2-(4-chlorophenyl)-4,4-dimethylcyclohex-1-en-1-yl]
methyl}piperazin-1-yl)-N-[(4-{[(4-cyano-4-methylcyclo-
hexyl)methyl]amino}-3-nitrophenyl)sulfonyl]-2-(1H-
pyrrolo[2,3-b]pyridin-5-yloxy)benzamide;
{[4-(4-{[2-(4-chlorophenyl)-4,4-dimethylcyclohex-1-en-1-
yl]methyl}piperazin-1-yl)-2-(1H-pyrrolo[2,3-b]pyridin-
5-yloxy)benzoyl]({4-[(4-fluorotetrahydro-2H-pyran-4-
yl)methoxy]-3-nitrophenyl}sulfonyl)amino}methyl
pivalate;
{[4-(4-{[2-(4-chlorophenyl)-4,4-dimethylcyclohex-1-en-1-
yl]methyl}piperazin-1-yl)-2-(1H-pyrrolo[2,3-b]pyridin-
5-yloxy)benzoyl]({4-[(4-fluorotetrahydro-2H-pyran-4-
yl)methoxy]-3-nitrophenyl}sulfonyl)amino}methyl
butyrate;
4-(4-{[2-(4-chlorophenyl)-4,4-dimethylcyclohex-1-en-1-yl]
methyl}piperazin-1-yl)-2-(1H-pyrrolo[2,3-b]pyridin-5-
yloxy)-N-{[3-(tetrahydro-2H-pyran-4-ylmethyl)-3H-[1,
2,3]triazolo[4,5-b]pyridin-6-yl]sulfonyl}benzamide;
4-(4-{[2-(4-chlorophenyl)-4,4-dimethylcyclohex-1-en-1-yl]
methyl}piperazin-1-yl)-N-[(6-{[(trans-4-hydroxy-4-me-
thylcyclohexyl)methyl]amino}-5-nitropyridin-3-yl)sulfo-
nyl]-2-(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-[(5-cyano-6-{[4-fluoro-1-(ox-
etan-3-yl)piperidin-4-yl]methoxy}pyridin-3-yl)sulfonyl]-
2-(1H-pyrrolo[2,3-b]pyridin-5-yloxy)benzamide;
N-(4-{[4-(4-{[2-(4-chlorophenyl)-4,4-dimethylcyclohex-1-
en-1-yl]methyl}piperazin-1-yl)-2-(1H-pyrrolo[2,3-b]py-
ridin-5-yloxy)benzoyl]sulfamoyl}-2-nitrophenyl)mor-
pholine-4-carboxamide;
4-(4-{[2-(4-chlorophenyl)-4,4-dimethylcyclohex-1-en-1-yl]
methyl}piperazin-1-yl)-N-{[4-({[4-(methoxymethyl)cy-
clohexyl]methyl}amino)-3-nitrophenyl]sulfonyl}-2-(1H-
pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-[(5-chloro-6-{[1-(1,3-thiazol-
2-yl)piperidin-4-yl]methoxy}pyridin-3-yl)sulfonyl]-2-
(1H-pyrrolo[2,3-b]pyridin-5-yloxy)benzamide;
4-(4-{[2-(4-chlorophenyl)-4,4-dimethylcyclohex-1-en-1-yl]
methyl}piperazin-1-yl)-N-[(6-{[(cis-4-hydroxy-4-meth-
ylcyclohexyl)methyl]amino}-5-nitropyridin-3-yl)sulfo-
nyl]-2-(1H-pyrrolo[2,3-b]pyridin-5-yloxy)benzamide;
4-(4-{[2-(4-chlorophenyl)-5-methoxy-5-methylcyclohex-1-
en-1-yl]methyl}piperazin-1-yl)-N-[(4-{[(trans-4-hy-
droxy-4-methylcyclohexyl)methyl]amino}-3-nitrophe-
nyl)sulfonyl]-2-(1H-pyrrolo[2,3-b]pyridin-5-yloxy)
benzamide;
4-(4-{[2-(4-chlorophenyl)-5-methoxy-5-methylcyclohex-1-
en-1-yl]methyl}piperazin-1-yl)-N-({3-nitro-4-[(tetrahy-
dro-2H-pyran-4-ylmethyl)amino]phenyl}sulfonyl)-2-
(1H-pyrrolo[2,3-b]pyridin-5-yloxy)benzamide;  and
therapeutically acceptable salts, and metabolites thereof.
Another embodiment pertains to the compound 4-(4-{[2-
(4-chlorophenyl)-4,4-dimethylcyclohex-1-en-1-yl]

methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a pharmaceutically acceptable salt thereof.

Another embodiment pertains to the compound Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide or a pharmaceutically acceptable salt thereof.

Another embodiment pertains to the compound Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide or a pharmaceutically acceptable salt thereof.

Another embodiment pertains to the compound N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; or a pharmaceutically acceptable salt thereof.

Another embodiment pertains to the compound N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; or a pharmaceutically acceptable salt thereof.

Still another embodiment pertains to compounds having Formula (I) or Formula (II), which are N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide or a pharmaceutically acceptable salt thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of Formula (I) or Formula (II).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of Formula (I) or Formula (II).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) or Formula (II) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkenyl" means a straight or branched hydrocarbon chain containing at least one carbon-carbon double bond containing x to y carbon atoms. The term "$C_3$-$C_6$ alkenyl" means an alkenyl group containing 3-6 carbon atoms. Representative examples of alkenyl include, but are not limited to, buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkenylene" means a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 2 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. For example "$C_3$-$C_6$ alkynyl" means a straight or branched chain hydrocarbon group containing from 3 to 6 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or "cycloalkyl" or "cycloalkane" as used herein, means a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four to ten carbon atoms and zero heteroatoms. The four-membered ring systems have one double bond, the five- or six-membered ring systems have one or two double bonds, the seven- or eight-membered ring systems have one, two, or three double bonds, and the nine- or ten-membered rings have one, two, three, or four double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bridged cycloalkenyl groups include, but are not limited to, 4,5,6,7-tetrahydro-3aH-indene, octahydronaphthalenyl, and 1,6-dihydro-pentalene. The monocyclic and bridged cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. Representative examples of heterocycloalkane groups include, but are not limited to, morpholinyl, tetrahydropyranyl, pyrrolidinyl, piperidinyl, dioxolanyl, tetrahydrofuranyl, thiomorpholinyl, 1,4-dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. Representative examples of heterocycloalkene groups include, but are not limited to, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenyl," as used herein, means a monovalent radical formed by removal of a hydrogen atom from benzene.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, $CNOCH_3$, S, S(O), $SO_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, $CNOCH_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, $CNOCH_3$, S, S(O), $SO_2$ or NH and one or two CH moieties replaced with N.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999)).

In addition, non-radioactive isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czajka D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Suitable groups for $A^1$, $B^1$, $D^1$, $E^1$, $G^1$, $Y^1$, $L^1$, $Z^{1A}$, $Z^{2A}$, $Z^1$, $Z^2$, and $Z^3$ in compounds of Formula (I) are independently selected. The described embodiments of the present invention may be combined. Such combination is contemplated and within the scope of the present invention. For example, it is contemplated that embodiments for any of $A^1$, $B^1$, $D^1$, $E^1$, $G^1$, $Y^1$, $L^1$, $Z^{1A}$, $Z^{2A}$, $Z^1$, $Z^2$, and $Z^3$ can be combined with embodiments defined for any other of $A^1$, $B^1$, $D^1$, $E^1$, $G^1$, $Y^1$, $L^1$, $Z^{1A}$, $Z^{2A}$, $Z^1$, $Z^2$, and $Z^3$.

One embodiment of this invention, therefore, pertains to compounds or therapeutically acceptable salts, which are useful as inhibitors of anti-apoptotic Bcl-2 proteins, the compounds having Formula (I)

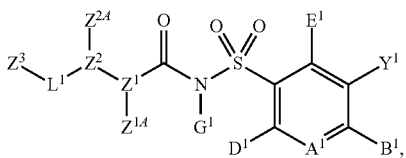

wherein

A$^1$ is N or C(A$^2$);

A$^2$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$;

B$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$;

D$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$;

E$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$; and Y$^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, SO$_2$R$^{17}$, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$; or E$^1$ and Y$^1$, together with the atoms to which they are attached, are benzene, naphthylene, heteroarene, cycloalkane, cycloalkene, heterocycloalkane or heterocycloalkene; and A$^2$, B$^1$, and D$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$; or Y$^1$ and B$^1$, together with the atoms to which they are attached, are benzene, naphthylene, heteroarene, cycloalkane, cycloalkene, heterocycloalkane or heterocycloalkene; and A$^2$, D$^1$, and E$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$; or A$^2$ and B$^1$, together with the atoms to which they are attached, are benzene, naphthylene, heteroarene cycloalkane, cycloalkene, heterocycloalkane or heterocycloalkene; and D$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$; or A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1.4}$;

G$^1$ is H, or C(O)OR;

R is alkyl;

R$^1$ is R$^2$, R$^3$, R$^4$ or R$^5$;

R$^{1.4}$ is cycloalkyl, cycloalkenyl or cycloalkynyl;

R$^2$ is phenyl, which is unfused or fused with R$^{2.4}$; R$^{2.4}$ is benzene, heteroarene, cycloalkane, cycloalkene, heterocycloalkane or heterocycloalkene;

$R^3$ is heteroaryl, which is unfused or fused with $R^{3A}$; $R^{3A}$ is benzene, heteroarene, cycloalkane, cycloalkene, heterocycloalkane or heterocycloalkene;

$R^4$ is cycloalkyl, cycloalkenyl, heterocycloalkyl or heterocycloalkenyl, each of which is unfused or fused with $R^{4A}$; $R^{4A}$ is benzene, heteroarene, cycloalkane, cycloalkene, heterocycloalkane or heterocycloalkene;

$R^5$ is alkyl, alkenyl or alkynyl, each of which is unsubstituted or substituted with one or two or three of independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^7$, $OH$, $(O)$, $C(O)OH$, $N_3$, $CN$, $NH_2$, $CF_3$, $CF_2CF_3$, $F$, $Cl$, $Br$ or $I$;

$R^6$ is $C_2$-$C_5$-spiroalkyl, each of which is unsubstituted or substituted with $OH$, $(O)$, $N_3$, $CN$, $CF_3$, $CF_2CF_3$, $F$, $Cl$, $Br$, $I$, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with $O$, $C(O)$, $CNOH$, $CNOCH_3$, $S$, $S(O)$, $SO_2$ or $NH$;

$R^7$ is $R^8$, $R^9$, $R^{10}$ or $R^{11}$;

$R^8$ is phenyl, which is unfused or fused with $R^{8A}$; $R^{8A}$ is benzene, heteroarene, cycloalkane, cycloalkene, heterocycloalkane or heterocycloalkene;

$R^9$ is heteroaryl, which is unfused or fused with $R^{9A}$; $R^{9A}$ is benzene, heteroarene, cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with $R^{10A}$; $R^{10A}$ is benzene, heteroarene, cycloalkane, cycloalkene, heterocycloalkane or heterocycloalkene;

$R^{11}$ is alkyl, alkenyl or alkynyl, each of which is unsubstituted or substituted with one or two or three of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$;

$R^{12}$ is $R^{13}$, $R^{14}$, $R^{15}$ or $R^{16}$;

$R^{13}$ is phenyl, which is unfused or fused with $R^{13A}$; $R^{13A}$ is benzene, heteroarene, cycloalkane, cycloalkene, heterocycloalkane or heterocycloalkene;

$R^{14}$ is heteroaryl, which is unfused or fused with $R^{14A}$; $R^{14A}$ is benzene, heteroarene, cycloalkane, cycloalkene, heterocycloalkane or heterocycloalkene;

$R^{15}$ is cycloalkane, cycloalkene, heterocycloalkane or heterocycloalkene, each of which is unfused or fused with $R^{15A}$; $R^{15A}$ is benzene, heteroarene, cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl, which is unfused or fused with $R^{18A}$; $R^{18A}$ is benzene, heteroarene, cycloalkane, cycloalkene, heterocycloalkane or heterocycloalkene;

$R^{19}$ is heteroaryl, which is unfused or fused with $R^{19A}$; $R^{19A}$ is benzene, heteroarene, cycloalkane, cycloalkene, heterocycloalkane or heterocycloalkene;

$R^{20}$ is cycloalkyl, cycloalkenyl, heterocycloalkyl or heterocycloalkenyl each of which is unfused or fused with $R^{20A}$; $R^{20A}$ is benzene, heteroarene, cycloalkane, cycloalkene, heterocycloalkane or heterocycloalkene;

$R^{21}$ is alkyl, alkenyl or alkynyl, each of which is unsubstituted or substituted with one or two or three of independently selected $R^{22}$, $OR^{22}$, $SR^{22}$, $S(O)R^{22}$, $SO_2R^{22}$, $C(O)R^{22}$, $CO(O)R^{22}$, $OC(O)R^{22}$, $OC(O)OR^{22}$, $NH_2$, $NHR^{22}$, $N(R^{22})_2$, $NHC(O)R^{22}$, $NR^{22}C(O)R^{22}$, $NHS(O)_2R^{22}$, $NR^{22}S(O)_2R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $C(O)NH_2$, $C(O)NHR^{22}$, $C(O)N(R^{22})_2$, $C(O)NHOH$, $C(O)NHOR^{22}$, $C(O)NHSO_2R^{22}$, $C(O)NR^{22}SO_2R^{22}$, $SO_2NH_2$, $SO_2NHR^{22}$, $SO_2N(R^{22})_2$, $C(O)H$, $C(O)OH$, $C(N)NH_2$, $C(N)NHR^{22}$, $C(N)N(R^{22})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$;

$R^{22}$ is $R^{23}$, $R^{24}$ or $R^{25}$;

$R^{23}$ is phenyl, which is unfused or fused with $R^{23A}$; $R^{23A}$ is benzene, heteroarene, cycloalkane, cycloalkene, heterocycloalkane or heterocycloalkene;

$R^{24}$ is heteroarene, which is unfused or fused with $R^{24A}$; $R^{24A}$ is benzene, heteroarene, cycloalkane, cycloalkene, heterocycloalkane or heterocycloalkene;

$R^{25}$ is cycloalkyl, cycloalkenyl, heterocycloalkyl or heterocycloalkenyl, each of which is unfused or fused with $R^{25A}$; $R^{25A}$ is benzene, heteroarene, cycloalkane, cycloalkene, heterocycloalkane or heterocycloalkene;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by $NH$, $N(CH_3)$, $S$, $S(O)$ or $SO_2$;

$L^1$ is a $R^{37}$, $OR^{37}$, $SR^{37}$, $S(O)R^{37}$, $SO_2R^{37}$, $C(O)R^{37}$, $CO(O)R^{37}$, $OC(O)R^{37}$, $OC(O)OR^{37}$, $NHR^{37}$, $C(O)NH$, $C(O)NR^{37}$, $C(O)NHOR^{37}$, $C(O)NHSO_2R^{37}$, $SO_2NH$, $SO_2NHR^{37}$, $C(N)NH$, $C(N)NHR^{37}$;

$R^{26}$ is phenylene, which is unfused or fused with $R^{26A}$; $R^{26A}$ is benzene, heteroarene, cycloalkane, cycloalkene, heterocycloalkane or heterocycloalkene;

$R^{27}$ is heteroarylene, which is unfused or fused with $R^{27A}$; $R^{27A}$ is benzene, heteroarene, cycloalkane, cycloalkene, heterocycloalkane or heterocycloalkene;

$R^{28}$ is phenylene, which is unfused or fused with $R^{28A}$; $R^{28A}$ is benzene, heteroarene, cycloalkane, cycloalkene, heterocycloalkane or heterocycloalkene;

$R^{29}$ is heteroarylene, which is unfused or fused with $R^{29A}$; $R^{29A}$ is benzene, heteroarene, cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with $R^{30A}$; $R^{30A}$ is benzene, heteroarene, cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)

NHSO$_2$R$^{37B}$, C(O)NR$^{37B}$SO$_2$R$^{37B}$, SO$_2$NH$_2$, SO$_2$NHR$^{37B}$, SO$_2$N(R$^{37B}$)$_2$, C(O)H, C(O)OH, C(N)NH$_2$, C(N)NHR$^{37B}$, C(N)N(R$^{37B}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br and I substituents;

R$^{37B}$ is alkyl, alkenyl, alkynyl, or R$^{37C}$;

R$^{37C}$ is phenyl, heteroaryl, cycloalkyl, cycloalkenyl, heterocycloalkyl, or heterocycloalkenyl;

Z$^3$ is R$^{38}$, R$^{39}$ or R$^{40}$;

R$^{38}$ is phenyl, which is unfused or fused with R$^{38A}$; R$^{38A}$ is benzene, heteroarene, cycloalkane, cycloalkene, heterocycloalkane or heterocycloalkene;

R$^{39}$ is heteroaryl, which is unfused or fused with R$^{39A}$; R$^{39A}$ is benzene, heteroarene, cycloalkane, cycloalkene, heterocycloalkane or heterocycloalkene;

R$^{40}$ is cycloalkyl, cycloalkenyl, heterocycloalkyl or heterocycloalkenyl, each of which is unfused or fused with R$^{40A}$;

R$^{40A}$ is benzene, heteroarene, cycloalkane, cycloalkene, heterocycloalkane or heterocycloalkene;

wherein the moieties represented by R$^{26}$ and R$^{27}$ are substituted (i.e., if Z$^{1A}$ and Z$^{2A}$ are absent) or further substituted (i.e., if Z$^{1A}$ and Z$^{2A}$ are present) with R$^{41}$, OR$^{41}$, SR$^{41}$, S(O) R$^{41}$, SO$_2$R$^{41}$, C(O)R$^{41}$, CO(O)R$^{41}$, OC(O)R$^{41}$, OC(O)OR$^{41}$, NHR$^{41}$, N(R$^{41}$)$_2$, NHC(O)R$^{41}$, NR$^{41}$C(O)R$^{41}$, NHS(O)$_2$R$^{41}$, NR$^{41}$S(O)$_2$R$^{41}$, NHC(O)OR$^{41}$, NR$^{41}$C(O)OR$^{41}$, NHC(O)NHR$^{41}$, NHC(O)N(R$^{41}$)$_2$, NR$^{41}$C(O)NHR$^{41}$, NR$^{41}$C(O)N(R$^{41}$)$_2$, C(O)NHR$^{41}$, C(O)N(R$^{41}$)$_2$, C(O)NHOR$^{41}$, C(O)NHSO$_2$R$^{41}$, C(O)NR$^{41}$SO$_2$R$^{41}$, SO$_2$NHR$^{41}$, SO$_2$N(R$^{41}$)$_2$, C(N)NHR$^{41}$, or C(N)N(R$^{41}$)$_2$;

R$^{41}$ is heteroaryl, which is fused with R$^{43A}$; R$^{43A}$ is benzene, heteroarene, cycloalkane, cycloalkene, heterocycloalkane or heterocycloalkene; which is unfused or fused with benzene, heteroarene or R$^{43B}$; R$^{43B}$ is cycloalkane, cycloalkene, heterocycloalkane or heterocycloalkene;

wherein the cyclic moieties represented by E$^1$ and Y$^1$ together, Y$^1$ and B$^1$ together, A$^2$ and B$^1$ together, A$^2$ and D$^1$ together, R$^{1A}$, R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{18}$, R$^{18A}$, R$^{19}$, R$^{19A}$, R$^{20}$, R$^{20A}$, R$^{23}$, R$^{23A}$, R$^{24}$, R$^{24A}$, R$^{25}$, R$^{25A}$, R$^{26}$, R$^{26A}$, R$^{27}$, R$^{27A}$, R$^{28}$, R$^{28A}$, R$^{29}$, R$^{29A}$, R$^{30}$, R$^{30A}$, R$^{37B}$, R$^{38}$, R$^{38A}$, R$^{39}$, R$^{39A}$, R$^{40}$, and R$^{40A}$ are independently unsubstituted, further unsubstituted, substituted or further substituted with one or two or three or four or five of independently selected R$^{57A}$, R$^{57}$, OR$^{57}$, SR$^{57}$, S(O)R$^{57}$, SO$_2$R$^{57}$, C(O)R$^{57}$, CO(O)R$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{57A}$ is spiroalkyl, or spiroheteroalkyl;

R$^{57}$ is R$^{58}$, R$^{59}$, R$^{60}$ or R$^{61}$;

R$^{58}$ is phenyl, which is unfused or fused with R$^{58A}$; R$^{58A}$ is benzene, heteroarene, cycloalkane, cycloalkene, heterocycloalkane or heterocycloalkene;

R$^{59}$ is heteroaryl, which is unfused or fused with R$^{59A}$; R$^{59A}$ is benzene, heteroarene, cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with R$^{60A}$;

R$^{60A}$ is benzene, heteroarene, cycloalkane, cycloalkene, heterocycloalkane or heterocycloalkene;

R$^{61}$ is alkyl, alkenyl or alkynyl, each of which is unsubstituted or substituted with one or two or three of independently selected R$^{62}$, OR$^{62}$, SR$^{62}$, S(O)R$^{62}$, SO$_2$R$^{62}$, C(O)R$^{62}$, CO(O)R$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{62}$ is R$^{63}$, R$^{64}$, R$^{65}$ or R$^{66}$;

R$^{63}$ is phenyl, which is unfused or fused with R$^{63A}$; R$^{63A}$ is benzene, heteroarene, cycloalkane, cycloalkene, heterocycloalkane or heterocycloalkene;

R$^{64}$ is heteroaryl, which is unfused or fused with R$^{64A}$; R$^{64A}$ is benzene, heteroarene, cycloalkane, cycloalkene, heterocycloalkane or heterocycloalkene;

R$^{65}$ is cycloalkyl, cycloalkenyl, heterocycloalkyl, or heterocycloalkenyl, each of which is unfused or fused with R$^{65A}$; R$^{65A}$ is benzene, heteroarene, cycloalkane, cycloalkene, heterocycloalkane or heterocycloalkene;

R$^{66}$ is alkyl, alkenyl or alkynyl, each of which is unsubstituted or substituted with one or two or three of independently selected R$^{67}$, OR$^{67}$, SR$^{67}$, S(O)R$^{67}$, SO$_2$R$^{67}$, C(O)R$^{67}$, CO(O)R$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the cyclic moieties represented by R$^{57A}$, R$^{58}$, R$^{59}$, R$^{60}$, R$^{63}$, R$^{64}$, R$^{65}$, and R$^{67}$ are unsubstituted or substituted with one or two or three or four of independently selected R$^{68}$, OR$^{68}$, SR$^{68}$, S(O)R$^{68}$, SO$_2$R$^{68}$, C(O)R$^{68}$, CO(O)R$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{68}$ is R$^{69}$, R$^{70}$, R$^{71}$ or R$^{72}$;

R$^{69}$ is phenyl, which is unfused or fused with R$^{69A}$; R$^{69A}$ is benzene, heteroarene, cycloalkane, cycloalkene, heterocycloalkane or heterocycloalkene;

R$^{70}$ is heteroaryl, which is unfused or fused with R$^{70A}$; R$^{70A}$ is benzene, heteroarene, cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with R$^{71A}$; R$^{71A}$ is benzene, heteroarene, cycloalkane, cycloalkene, heterocycloalkane or heterocycloalkene;

R$^{72}$ is alkyl, alkenyl or alkynyl, each of which is unsubstituted or substituted with one or two or three of independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{73}$ is alkyl, alkenyl, alkynyl, phenyl, heteroaryl, cycloalkyl, cycloalkenyl, heterocycloalkyl or heterocycloalkenyl; and wherein the moieties represented by R$^{69}$, R$^{70}$, and R$^{71}$ are unsubstituted or substituted with one or two or three or four of independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I.

Another embodiment of this invention pertains to compounds of Formula (I), wherein A$^1$ is N or C(A$^2$);

A$^2$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$;

B$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$;

D$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$;

E$^1$ is H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$; and Y$^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, SO$_2$R$^{17}$, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$; or E$^1$ and Y$^1$, together with the atoms to which they are attached, are benzene, naphthylene, heteroarene, cycloalkane, cycloalkene, heterocycloalkane or heterocycloalkene; and A$^2$, B$^1$, and D$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$; or Y$^1$ and B$^1$, together with the atoms to which they are attached, are benzene, naphthylene, heteroarene, cycloalkane, cycloalkene, heterocycloalkane or heterocycloalkene; and A$^2$, D$^1$, and E$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$; or A$^2$ and B$^1$, together with the atoms to which they are attached, are benzene, naphthylene, heteroarene cycloalkane, cycloalkene, heterocycloalkane or heterocycloalkene; and D$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1,4}$; or A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHOH, C(O)NHNOR$^1$, C(O)NHSO$_2$R$^1$, C(NH)NH$_2$, C(NH)NHR$^1$, C(NH)N(R$^1$)$_2$ NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$;

G$^1$ is H, or C(O)OR;

R is alkyl;

R$^1$ is R$^2$, R$^3$, R$^4$ or R$^5$;

R$^{1A}$ is cycloalkyl, cycloalkenyl or cycloalkynyl;

R$^2$ is phenyl, which is unfused or fused with R$^{2A}$; R$^{2A}$ is benzene, heteroarene, cycloalkane, cycloalkene, heterocycloalkane or heterocycloalkene;

R$^3$ is heteroaryl, which is unfused or fused with R$^{3A}$; R$^{3A}$ is benzene, heteroarene, cycloalkane, cycloalkene, heterocycloalkane or heterocycloalkene;

R$^4$ is cycloalkyl, cycloalkenyl, heterocycloalkyl or heterocycloalkenyl, each of which is unfused or fused with R$^{4A}$; R$^{4A}$ is benzene, heteroarene, cycloalkane, cycloalkene, heterocycloalkane or heterocycloalkene;

R$^5$ is alkyl, alkenyl or alkynyl, each of which is unsubstituted or substituted with one or two or three of independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^7$, OH, (O), C(O)OH, N$_3$, CN, NH$_2$, CF$_3$, CF$_2$CF$_3$, F, Cl, Br or I;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl, which is unfused or fused with R$^{8A}$; R$^{8A}$ is benzene, heteroarene, cycloalkane, cycloalkene, heterocycloalkane or heterocycloalkene;

R$^9$ is heteroaryl, which is unfused or fused with R$^{9A}$; R$^{9A}$ is benzene, heteroarene, cycloalkane, cycloalkene, heterocycloalkane or heterocycloalkene;

R$^{10}$ is cycloalkyl, cycloalkenyl, heterocycloalkyl or heterocycloalkenyl, each of which is unfused or fused with R$^{10A}$; R$^{10A}$ is benzene, heteroarene, cycloalkane, cycloalkene, heterocycloalkane or heterocycloalkene;

R$^{11}$ is alkyl, alkenyl or alkynyl, each of which is unsubstituted or substituted with one or two or three of independently selected R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{12}$ is R$^{13}$, R$^{14}$, R$^{15}$ or R$^{16}$;

R$^{13}$ is phenyl, which is unfused or fused with R$^{13A}$; R$^{13A}$ is benzene, heteroarene, cycloalkane, cycloalkene, heterocycloalkane or heterocycloalkene;

R$^{14}$ is heteroaryl, which is unfused or fused with R$^{14A}$; R$^{14A}$ is benzene, heteroarene, cycloalkane, cycloalkene, heterocycloalkane or heterocycloalkene;

R$^{15}$ is cycloalkane, cycloalkene, heterocycloalkane or heterocycloalkene, each of which is unfused or fused with R$^{15A}$; R$^{15A}$ is benzene, heteroarene, cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl, which is unfused or fused with R$^{18A}$; R$^{18A}$ is benzene, heteroarene, cycloalkane, cycloalkene, heterocycloalkane or heterocycloalkene;

R$^{19}$ is heteroaryl, which is unfused or fused with R$^{19A}$; R$^{19A}$ is benzene, heteroarene, cycloalkane, cycloalkene, heterocycloalkane or heterocycloalkene;

R$^{20}$ is cycloalkyl, cycloalkenyl, heterocycloalkyl or heterocycloalkenyl each of which is unfused or fused with R$^{20A}$; R$^{20A}$ is benzene, heteroarene, cycloalkane, cycloalkene, heterocycloalkane or heterocycloalkene;

R$^{21}$ is alkyl, alkenyl or alkynyl, each of which is unsubstituted or substituted with one or two or three of independently selected R$^{22}$, OR$^{22}$, SR$^{22}$, S(O)R$^{22}$, SO$_2$R$^{22}$, C(O)R$^{22}$, CO(O)R$^{22}$, OC(O)R$^{22}$, OC(O)OR$^{22}$, NH$_2$, NHR$^{22}$, N(R$^{22}$)$_2$, NHC(O)R$^{22}$, NR$^{22}$C(O)R$^{22}$, NHS(O)$_2$R$^{22}$, NR$^{22}$S(O)$_2$R$^{22}$, NHC(O)OR$^{22}$, NR$^{22}$C(O)OR$^{22}$, NHC(O)NH$_2$, NHC(O)NHR$^{22}$, NHC(O)N(R$^{22}$)$_2$, NR$^{22}$C(O)NHR$^{22}$, NR$^{22}$C(O)N(R$^{22}$)$_2$, C(O)NH$_2$, C(O)NHR$^{22}$, C(O)N(R$^{22}$)$_2$, C(O)NHOH, C(O)NHOR$^{22}$, C(O)NHSO$_2$R$^{22}$, C(O)NR$^{22}$SO$_2$R$^{22}$, SO$_2$NH$_2$, SO$_2$NHR$^{22}$, SO$_2$N(R$^{22}$)$_2$, C(O)H, C(O)OH, C(N)NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is R$^{23}$, R$^{24}$ or R$^{25}$;

R$^{23}$ is phenyl, which is unfused or fused with R$^{23A}$; R$^{23A}$ is benzene, heteroarene, cycloalkane, cycloalkene, heterocycloalkane or heterocycloalkene;

R$^{24}$ is heteroarene, which is unfused or fused with R$^{24A}$; R$^{24A}$ is benzene, heteroarene, cycloalkane, cycloalkene, heterocycloalkane or heterocycloalkene;

R$^{25}$ is cycloalkyl, cycloalkenyl, heterocycloalkyl or heterocycloalkenyl, each of which is unfused or fused with R$^{25A}$; R$^{25A}$ is benzene, heteroarene, cycloalkane, cycloalkene, heterocycloalkane or heterocycloalkene;

Z$^1$ is R$^{26}$ or R$^{27}$;

Z$^2$ is R$^{28}$, R$^{29}$ or R$^{30}$;

Z$^{1A}$ and Z$^{2A}$ are both absent or are taken together to form CH$_2$, CH$_2$CH$_2$ or Z$^{12A}$;

Z$^{12A}$ is C$_2$-C$_6$-alkylene having one or two CH$_2$ moieties replaced by NH, N(CH$_3$), S, S(O) or SO$_2$;

L$^1$ is a R$^{37}$, OR$^{37}$, SR$^{37}$, S(O)R$^{37}$, SO$_2$R$^{37}$, C(O)R$^{37}$, CO(O)R$^{37}$, OC(O)R$^{37}$, OC(O)OR$^{37}$, NHR$^{37}$, C(O)NH, C(O)NR$^{37}$, C(O)NHOR$^{37}$, C(O)NHSO$_2$R$^{37}$, SO$_2$NH, SO$_2$NHR$^{37}$, C(N)NH, C(N)NHR$^{37}$;

R$^{26}$ is phenylene, which is unfused or fused with R$^{26A}$; R$^{26A}$ is benzene, heteroarene, cycloalkane, cycloalkene, heterocycloalkane or heterocycloalkene;

R$^{27}$ is heteroarylene, which is unfused or fused with R$^{27A}$; R$^{27A}$ is benzene, heteroarene, cycloalkane, cycloalkene, heterocycloalkane or heterocycloalkene;

R$^{28}$ is phenylene, which is unfused or fused with R$^{28A}$; R$^{28A}$ is benzene, heteroarene, cycloalkane, cycloalkene, heterocycloalkane or heterocycloalkene;

R$^{29}$ is heteroarylene, which is unfused or fused with R$^{29A}$; R$^{29A}$ is benzene, heteroarene, cycloalkane, cycloalkene, heterocycloalkane or heterocycloalkene;

R$^{30}$ is cycloalkylene, cycloalkenylene, heterocycloalkylene or heterocycloalkenylene, each of which is unfused or fused with R$^{30A}$; R$^{30A}$ is benzene, heteroarene, cycloalkane, cycloalkene, heterocycloalkane or heterocycloalkene;

R$^{37}$ is a bond or R$^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br and I substituents;

$R^{37B}$ is alkyl, alkenyl, alkynyl, or $R^{37C}$;

$R^{37C}$ is phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with $R^{38A}$; $R^{38A}$ is benzene, heteroarene, cycloalkane, cycloalkene, heterocycloalkane or heterocycloalkene;

$R^{39}$ is heteroaryl, which is unfused or fused with $R^{39A}$; $R^{39A}$ is benzene, heteroarene, cycloalkane, cycloalkene, heterocycloalkane or heterocycloalkene;

$R^{40}$ is cycloalkyl, cycloalkenyl, heterocycloalkyl or heterocycloalkenyl, each of which is unfused or fused with $R^{40A}$; $R^{40A}$ is benzene, heteroarene, cycloalkane, cycloalkene, heterocycloalkane or heterocycloalkene;

wherein the moieties represented by $R^{26}$ and $R^{27}$ are substituted (i.e., if $Z^{1A}$ and $Z^{2A}$ are absent) or further substituted (i.e., if $Z^{1A}$ and $Z^{2A}$ are present) with $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NHR^{41}$, $NHC(O)N(R^{41})_2$, $NR^{41}C(O)NHR^{41}$, $NR^{41}C(O)N(R^{41})_2$, $C(O)NHR^{41}$, $C(O)N(R^{41})_2$, $C(O)NHOR^{41}$, $C(O)NHSO_2R^{41}$, $C(O)NR^{41}SO_2R^{41}$, $SO_2NHR^{41}$, $SO_2N(R^{41})_2$, $C(N)NHR^{41}$, or $C(N)N(R^{41})_2$;

$R^{41}$ is heteroaryl, which is fused with $R^{43A}$; $R^{43A}$ is benzene, heteroarene, cycloalkane, cycloalkene, heterocycloalkane or heterocycloalkene; which is unfused;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{26}$, $R^{26A}$, $R^{27}$, $R^{27A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{57A}$ is spiroalkyl, or spiroheteroalkyl;

$R^{57}$ is $R^{58}$, $R^{59}$, $R^{60}$ or $R^{61}$;

$R^{58}$ is phenyl, which is unfused or fused with $R^{58A}$; $R^{58A}$ is benzene, heteroarene, cycloalkane, cycloalkene, heterocycloalkane or heterocycloalkene;

$R^{59}$ is heteroaryl, which is unfused or fused with $R^{59A}$; $R^{59A}$ is benzene, heteroarene, cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with $R^{60A}$; $R^{60A}$ is benzene, heteroarene, cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with $R^{63A}$; $R^{63A}$ is benzene, heteroarene, cycloalkane, cycloalkene, heterocycloalkane or heterocycloalkene;

$R^{64}$ is heteroaryl, which is unfused or fused with $R^{64A}$; $R^{64A}$ is benzene, heteroarene, cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with $R^{65A}$; $R^{65A}$ is benzene, heteroarene, cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{68}$ is $R^{69}$, $R^{70}$, $R^{71}$ or $R^{72}$;

$R^{69}$ is phenyl, which is unfused or fused with $R^{69A}$; $R^{69A}$ is benzene, heteroarene, cycloalkane, cycloalkene, heterocycloalkane or heterocycloalkene;

$R^{70}$ is heteroaryl, which is unfused or fused with $R^{70A}$; $R^{70A}$ is benzene, heteroarene, cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with $R^{71A}$;

$R^{71A}$ is benzene, heteroarene, cycloalkane, cycloalkene, heterocycloalkane or heterocycloalkene;

$R^{72}$ is alkyl, alkenyl or alkynyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{73}$ is alkyl, alkenyl, alkynyl, phenyl, heteroaryl, cycloalkyl, cycloalkenyl, heterocycloalkyl or heterocycloalkenyl; and wherein the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, F, Cl, Br or I.

Another embodiment of this invention pertains to compounds of Formula (I), wherein $A^1$ is N or $C(A^2)$;

$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$; or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$; or $A^2$ and $B^1$, together with the atoms to which they are attached, are benzene, naphthylene, heteroarene cycloalkane, cycloalkene, heterocycloalkane or heterocycloalkene; and $D^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$ $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, $C(O)OH$, $C(O)NH_2$ or $C(O)OR^{14}$; or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂ NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR$^{1A}$;

G¹ is H, or C(O)OR;

R is alkyl;

R¹ is R², R³, R⁴ or R⁵;

R$^{1A}$ is cycloalkyl, cycloalkenyl or cycloalkynyl;

R² is phenyl, which is unfused or fused with R$^{2A}$; R$^{2A}$ is benzene, heteroarene, cycloalkane, cycloalkene, heterocycloalkane or heterocycloalkene;

R³ is heteroaryl, which is unfused or fused with R$^{3A}$; R$^{3A}$ is benzene, heteroarene, cycloalkane, cycloalkene, heterocycloalkane or heterocycloalkene;

R⁴ is cycloalkyl, cycloalkenyl, heterocycloalkyl or heterocycloalkenyl, each of which is unfused or fused with R$^{4A}$; R$^{4A}$ is benzene, heteroarene, cycloalkane, cycloalkene, heterocycloalkane or heterocycloalkene;

R⁵ is alkyl, alkenyl or alkynyl, each of which is unsubstituted or substituted with one or two or three of independently selected R⁶, NC(R$^{6A}$)(R$^{6B}$), R⁷, OR⁷, SR⁷, S(O)R⁷, SO₂R⁷, NHR⁷, N(R⁷)₂, C(O)R⁷, C(O)NH₂, C(O)NHR⁷, C(O)N(R⁷)₂, NHC(O)R⁷, NR⁷C(O)R⁷, NHSO₂R⁷, NHC(O)OR⁷, SO₂NH₂, SO₂NHR⁷, SO₂N(R⁷)₂, NHC(O)NH₂, NHC(O)NHR⁷, NHC(O)CH(CH₃)NHC(O)CH(CH₃)NH₂, NHC(O)CH(CH₃)NHC(O)CH(CH₃)NHR⁷, OH, (O), C(O)OH, N₃, CN, NH₂, CF₃, CF₂CF₃, F, Cl, Br or I;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl, which is unfused or fused with R$^{8A}$; R$^{8A}$ is benzene, heteroarene, cycloalkane, cycloalkene, heterocycloalkane or heterocycloalkene;

R⁹ is heteroaryl, which is unfused or fused with R$^{9A}$; R$^{9A}$ is benzene, heteroarene, cycloalkane, cycloalkene, heterocycloalkane or heterocycloalkene;

R¹⁰ is cycloalkyl, cycloalkenyl, heterocycloalkyl or heterocycloalkenyl, each of which is unfused or fused with R$^{10A}$; R$^{10A}$ is benzene, heteroarene, cycloalkane, cycloalkene, heterocycloalkane or heterocycloalkene;

R¹¹ is alkyl, alkenyl or alkynyl, each of which is unsubstituted or substituted with one or two or three of independently selected R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, (O), CN, N₃, NO₂, CF₃, CF₂CF₃, OCF₃, OCF₂CF₃, F, Cl, Br or I;

R¹² is R¹³, R¹⁴, R¹⁵ or R¹⁶;

R¹³ is phenyl, which is unfused or fused with R$^{13A}$; R$^{13A}$ is benzene, heteroarene, cycloalkane, cycloalkene, heterocycloalkane or heterocycloalkene;

R¹⁴ is heteroaryl, which is unfused or fused with R$^{14A}$; R$^{14A}$ is benzene, heteroarene, cycloalkane, cycloalkene, heterocycloalkane or heterocycloalkene;

R¹⁵ is cycloalkane, cycloalkene, heterocycloalkane or heterocycloalkene, each of which is unfused or fused with R$^{15A}$; R$^{15A}$ is benzene, heteroarene, cycloalkane, cycloalkene, heterocycloalkane or heterocycloalkene;

R¹⁶ is alkyl, alkenyl or alkynyl;

R¹⁷ is R¹⁸, R¹⁹, R²⁰ or R²¹;

R¹⁸ is phenyl, which is unfused or fused with R$^{18A}$; R$^{18A}$ is benzene, heteroarene, cycloalkane, cycloalkene, heterocycloalkane or heterocycloalkene;

R¹⁹ is heteroaryl, which is unfused or fused with R$^{19A}$; R$^{19A}$ is benzene, heteroarene, cycloalkane, cycloalkene, heterocycloalkane or heterocycloalkene;

R²⁰ is cycloalkyl, cycloalkenyl, heterocycloalkyl or heterocycloalkenyl each of which is unfused or fused with R$^{20A}$; R$^{20A}$ is benzene, heteroarene, cycloalkane, cycloalkene, heterocycloalkane or heterocycloalkene;

R²¹ is alkyl, alkenyl or alkynyl, each of which is unsubstituted or substituted with one or two or three of independently selected R²², OR²², SR²², S(O)R²², SO₂R²², C(O)R²², CO(O)R²², OC(O)R²², OC(O)OR²², NH₂, NHR²², N(R²²)₂, NHC(O)R²², NR²²C(O)R²², NHS(O)₂R²², NR²²S(O)₂R²², NHC(O)OR²², NR²²C(O)OR²², NHC(O)NH₂, NHC(O)NHR²², NHC(O)N(R²²)₂, NR²²C(O)NHR²², NR²²C(O)N(R²²)₂, C(O)NH₂, C(O)NHR²², C(O)N(R²²)₂, C(O)NHOH, C(O)NHOR²², C(O)NHSO₂R²², C(O)NR²²SO₂R²², SO₂NH₂, SO₂NHR²², SO₂N(R²²)₂, C(O)H, C(O)OH, C(N)NH₂, C(N)NHR²², C(N)N(R²²)₂, CNOH, CNOCH₃, OH, (O), CN, N₃, NO₂, CF₃, CF₂CF₃, OCF₃, OCF₂CF₃, F, Cl, Br or I;

R²² is R²³, R²⁴ or R²⁵;

R²³ is phenyl, which is unfused or fused with R$^{23A}$; R$^{23A}$ is benzene, heteroarene, cycloalkane, cycloalkene, heterocycloalkane or heterocycloalkene;

R²⁴ is heteroarene, which is unfused or fused with R$^{24A}$; R$^{24A}$ is benzene, heteroarene, cycloalkane, cycloalkene, heterocycloalkane or heterocycloalkene;

R²⁵ is cycloalkyl, cycloalkenyl, heterocycloalkyl or heterocycloalkenyl, each of which is unfused or fused with R$^{25A}$; R$^{25A}$ is benzene, heteroarene, cycloalkane, cycloalkene, heterocycloalkane or heterocycloalkene;

Z¹ is R²⁶ or R²⁷;

Z² is R²⁸, R²⁹ or R³⁰;

Z$^{1A}$ and Z$^{2A}$ are both absent or are taken together to form CH₂, CH₂CH₂ or Z$^{12A}$;

Z$^{12A}$ is C₂-C₆-alkylene having one or two CH₂ moieties replaced by NH, N(CH₃), S, S(O) or SO₂;

L¹ is a R³⁷, OR³⁷, SR³⁷, S(O)R³⁷, SO₂R³⁷, C(O)R³⁷, CO(O)R³⁷, OC(O)R³⁷, OC(O)OR³⁷, NHR³⁷, C(O)NH, C(O)NR³⁷, C(O)NHOR³⁷, C(O)NHSO₂R³⁷, SO₂NH, SO₂NHR³⁷, C(N)NH, C(N)NHR³⁷;

R²⁶ is phenylene, which is unfused or fused with R$^{26A}$; R$^{26A}$ is benzene, heteroarene, cycloalkane, cycloalkene, heterocycloalkane or heterocycloalkene;

R²⁷ is heteroarylene, which is unfused or fused with R$^{27A}$; R$^{27A}$ is benzene, heteroarene, cycloalkane, cycloalkene, heterocycloalkane or heterocycloalkene;

R²⁸ is phenylene, which is unfused or fused with R$^{28A}$; R$^{28A}$ is benzene, heteroarene, cycloalkane, cycloalkene, heterocycloalkane or heterocycloalkene;

$R^{29}$ is heteroarylene, which is unfused or fused with $R^{29A}$; $R^{29A}$ is benzene, heteroarene, cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with $R^{30A}$; $R^{30A}$ is benzene, heteroarene, cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $OCF_2CF_3$, F, Cl, Br and I substituents;

$R^{37B}$ is alkyl, alkenyl, alkynyl, or $R^{37C}$;

$R^{37C}$ is phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with $R^{38A}$; $R^{38A}$ is benzene, heteroarene, cycloalkane, cycloalkene, heterocycloalkane or heterocycloalkene;

$R^{39}$ is heteroaryl, which is unfused or fused with $R^{39A}$; $R^{39A}$ is benzene, heteroarene, cycloalkane, cycloalkene, heterocycloalkane or heterocycloalkene;

$R^{40}$ is cycloalkyl, cycloalkenyl, heterocycloalkyl or heterocycloalkenyl, each of which is unfused or fused with $R^{40A}$; $R^{40A}$ is benzene, heteroarene, cycloalkane, cycloalkene, heterocycloalkane or heterocycloalkene;

wherein the moieties represented by $R^{26}$ and $R^{27}$ are substituted (i.e., if $Z^{1A}$ and $Z^{2A}$ are absent) or further substituted (i.e., if $Z^{1A}$ and $Z^{2A}$ are present) with $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NHR^{41}$, $NHC(O)N(R^{41})_2$, $NR^{41}C(O)NHR^{41}$, $NR^{41}C(O)N(R^{41})_2$, $C(O)NHR^{41}$, $C(O)N(R^{41})_2$, $C(O)NHOR^{41}$, $C(O)NHSO_2R^{41}$, $C(O)NR^{41}SO_2R^{41}$, $SO_2NHR^{41}$, $SO_2N(R^{41})_2$, $C(N)NHR^{41}$, or $C(N)N(R^{41})_2$;

$R^{41}$ is heteroaryl, which is fused with $R^{43A}$; $R^{43A}$ is benzene, heteroarene, cycloalkane, cycloalkene, heterocycloalkane or heterocycloalkene; which is fused with benzene, heteroarene or $R^{43B}$; $R^{43B}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{26}$, $R^{26A}$, $R^{27}$, $R^{27A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{57A}$ is spiroalkyl, or spiroheteroalkyl;

$R^{57}$ is $R^{58}$, $R^{59}$, $R^{60}$ or $R^{61}$;

$R^{58}$ is phenyl, which is unfused or fused with $R^{58A}$; $R^{58A}$ is benzene, heteroarene, cycloalkane, cycloalkene, heterocycloalkane or heterocycloalkene;

$R^{59}$ is heteroaryl, which is unfused or fused with $R^{59A}$; $R^{59A}$ is benzene, heteroarene, cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with $R^{60A}$; $R^{60A}$ is benzene, heteroarene, cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with $R^{63A}$; $R^{63A}$ is benzene, heteroarene, cycloalkane, cycloalkene, heterocycloalkane or heterocycloalkene;

$R^{64}$ is heteroaryl, which is unfused or fused with $R^{64A}$; $R^{64A}$ is benzene, heteroarene, cycloalkane, cycloalkene, heterocycloalkane or heterocycloalkene;

$R^{65}$ is cycloalkyl, cycloalkenyl, heterocycloalkyl, or heterocycloalkenyl, each of which is unfused or fused with $R^{65A}$; $R^{65A}$ is benzene, heteroarene, cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{68}$ is R$^{69}$, R$^{70}$, R$^{71}$ or R$^{72}$;

R$^{69}$ is phenyl, which is unfused or fused with R$^{69A}$; R$^{69A}$ is benzene, heteroarene, cycloalkane, cycloalkene, heterocycloalkane or heterocycloalkene;

R$^{70}$ is heteroaryl, which is unfused or fused with R$^{70A}$; R$^{70A}$ is benzene, heteroarene, cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with R$^{71A}$; R$^{71A}$ is benzene, heteroarene, cycloalkane, cycloalkene, heterocycloalkane or heterocycloalkene;

R$^{72}$ is alkyl, alkenyl or alkynyl, each of which is unsubstituted or substituted with one or two or three of independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{73}$ is alkyl, alkenyl, alkynyl, phenyl, heteroaryl, cycloalkyl, cycloalkenyl, heterocycloalkyl or heterocycloalkenyl; and wherein the moieties represented by R$^{69}$, R$^{70}$, and R$^{71}$ are unsubstituted or substituted with one or two or three or four of independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I.

In one embodiment of Formula (I), A$^1$ is N, and G$^1$ is H. In another embodiment of Formula (I), A$^1$ is C(A$^2$) and G$^1$ is H. In another embodiment of Formula (I), A$^1$ is C(A$^2$); A$^2$ is H, F, Cl, Br, or I; and G$^1$ is H. In another embodiment of Formula (I), A$^1$ is C(A$^2$); A$^2$ is H; and G$^1$ is H.

In one embodiment of Formula (I), B$^1$ is R$^1$, OR$^1$, NHR$^1$, NHC(O)R$^1$, F, Cl, Br, or I. In another embodiment of Formula (I), A$^1$ is C(A$^2$); A$^2$ is H; B$^1$ is NHR$^1$, and G$^1$ is H. In another embodiment of Formula (I), A$^1$ is C(A$^2$); A$^2$ is H; B$^1$ is OR$^1$, and G$^1$ is H. In another embodiment of Formula (I), A$^1$ is C(A$^2$); A$^2$ is H; B$^1$ is Cl; and G$^1$ is H. In another embodiment of Formula (I), A$^1$ is C(A$^2$); A$^2$ is H; B$^1$ is R$^1$; and G$^1$ is H. In another embodiment of Formula (I), A$^1$ is N; B$^1$ is NHR$^1$; and G$^1$ is H. In another embodiment of Formula (I), A$^1$ is N; B$^1$ is OR$^1$; and G$^1$ is H. In another embodiment of Formula (I), A$^1$ is N; B$^1$ is Cl; and G$^1$ is H. In another embodiment of Formula (I), A$^1$ is N; B$^1$ is R$^1$; and G$^1$ is H.

In one embodiment of Formula (I), D$^1$ is H or Cl. In another embodiment of Formula (I), A$^1$ is C(A$^2$); A$^2$ is H; B$^1$ is NHR$^1$; D$^1$ is H; and G$^1$ is H. In another embodiment of Formula (I), A$^1$ is C(A$^2$); A$^2$ is H; B$^1$ is NHR$^1$; D$^1$ is Cl; and G$^1$ is H. In another embodiment of Formula (I), A$^1$ is C(A$^2$); A$^2$ is H; B$^1$ is OR$^1$; D$^1$ is H; and G$^1$ is H. In another embodiment of Formula (I), A$^1$ is C(A$^2$); A$^2$ is H; B$^1$ is Cl; D$^1$ is H; and G$^1$ is H. In another embodiment of Formula (I), A$^1$ is C(A$^2$); A$^2$ is H; B$^1$ is R$^1$; D$^1$ is H; and G$^1$ is H. In another embodiment of Formula (I), A$^1$ is N; B$^1$ is NHR$^1$; D$^1$ is H; and G$^1$ is H. In another embodiment of Formula (I), A$^1$ is N; B$^1$ is NHR$^1$; D$^1$ is Cl; and G$^1$ is H. In another embodiment of Formula (I), A$^1$ is N; B$^1$ is OR$^1$; D$^1$ is H; and G$^1$ is H. In another embodiment of Formula (I), A$^1$ is N; B$^1$ is Cl; D$^1$ is H; and G$^1$ is H. In another embodiment of Formula (I), A$^1$ is N; B$^1$ is R$^1$; D$^1$ is H; and G$^1$ is H.

In one embodiment of Formula (I), E$^1$ is H. In another embodiment of Formula (I), A$^1$ is C(A$^2$); A$^2$ is H; B$^1$ is NHR$^1$; D$^1$ is H; E$^1$ is H; and G$^1$ is H. In another embodiment of Formula (I), A$^1$ is C(A$^2$); A$^2$ is H; B$^1$ is NHR$^1$; E$^1$ is H; D$^1$ is Cl; and G$^1$ is H. In another embodiment of Formula (I), A$^1$ is C(A$^2$); A$^2$ is H; B$^1$ is OR$^1$; D$^1$ is H; E$^1$ is H; and G$^1$ is H. In another embodiment of Formula (I), A$^1$ is C(A$^2$); A$^2$ is H; B$^1$ is Cl; D$^1$ is H; E$^1$ is H; and G$^1$ is H. In another embodiment of Formula (I), A$^1$ is C(A$^2$); A$^2$ is H; B$^1$ is R$^1$; D$^1$ is H; E$^1$ is H; and G$^1$ is H. In another embodiment of Formula (I), A$^1$ is N; B$^1$ is NHR$^1$; D$^1$ is H; E$^1$ is H; and G$^1$ is H. In another embodiment of Formula (I), A$^1$ is N; B$^1$ is NHR$^1$; E$^1$ is H; D$^1$ is Cl, and G$^1$ is H. In another embodiment of Formula (I), A$^1$ is N; B$^1$ is OR$^1$; D$^1$ is H; E$^1$ is H; and G$^1$ is H. In another embodiment of Formula (I), A$^1$ is N; B$^1$ is Cl; D$^1$ is H; E$^1$ is H; and G$^1$ is H. In another embodiment of Formula (I), A$^1$ is N; B$^1$ is R$^1$; D$^1$ is H; E$^1$ is H; and G$^1$ is H.

In one embodiment of Formula (I), Y$^1$ is H, CN, NO$_2$, F, Cl, Br, I, CF$_3$, R$^{17}$, OR$^{17}$, SR$^{17}$, SO$_2$R$^{17}$, or C(O)NH$_2$. In another embodiment of Formula (I), Y$^1$ is H. In another embodiment of Formula (I), Y$^1$ is CN. In another embodiment of Formula (I), Y$^1$ is F, Cl, Br, or I. In another embodiment of Formula (I), Y$^1$ is CF$_3$. In another embodiment of Formula (I), Y$^1$ is SR$^{17}$. In another embodiment of Formula (I), Y$^1$ is OR$^{17}$. In another embodiment of Formula (I), Y$^1$ is NO$_2$. In another embodiment of Formula (I), Y$^1$ is SO$_2$R$^{17}$; wherein R$^{17}$ is as defined herein. In another embodiment of Formula (I), Y$^1$ is SO$_2$R$^{17}$; wherein R$^{17}$ is alkyl. In another embodiment of Formula (I), Y$^1$ is R$^{17}$; wherein R$^{17}$ is alkynyl. In another embodiment of Formula (I), A$^1$ is C(A$^2$); A$^2$ is H; B$^1$ is NHR$^1$; D$^1$ is H; E$^1$ is H; G$^1$ is H; and Y$^1$ is NO$_2$ or SO$_2$R$^{17}$; wherein R$^{17}$ is alkyl or alkynyl. In another embodiment of Formula (I), A$^1$ is C(A$^2$); A$^2$ is H; B$^1$ is NHR$^1$; D$^1$ is H; E$^1$ is H; G$^1$ is H; and Y$^1$ is NO$_2$. In another embodiment of Formula (I), A$^1$ is C(A$^2$); A$^2$ is H; B$^1$ is NHR$^1$; D$^1$ is H; E$^1$ is H; G$^1$ is H; and Y$^1$ is SO$_2$R$^{17}$; wherein R$^{17}$ is alkyl substituted with three F. In another embodiment of Formula (I), A$^1$ is N; B$^1$ is NHR$^1$; D$^1$ is H; E$^1$ is H; G$^1$ is H; and Y$^1$ is NO$_2$ or SO$_2$R$^{17}$; wherein R$^{17}$ is alkyl or alkynyl. In another embodiment of Formula (I), A$^1$ is N; B$^1$ is NHR$^1$; D$^1$ is H; E$^1$ is H; G$^1$ is H; and Y$^1$ is NO$_2$. In another embodiment of Formula (I), A$^1$ is N; B$^1$ is NHR$^1$; D$^1$ is H; E$^1$ is H; G$^1$ is H; and Y$^1$ is SO$_2$R$^{17}$; wherein R$^{17}$ is alkyl substituted with three F.

In one embodiment of Formula (I), G$^1$ is H; A$^1$ is N or C(A$^2$); and A$^2$ is H. In another embodiment of Formula (I), G$^1$ is H; A$^1$ is N or C(A$^2$); A$^2$ is H; and B$^1$ is NHR$^1$. In another embodiment of Formula (I), G$^1$ is H; A$^1$ is N or C(A$^2$); A$^2$ is H; B$^1$ is NHR$^1$; and D$^1$ is H. In another embodiment of Formula (I), G$^1$ is H; A$^1$ is N or C(A$^2$); A$^2$ is H; B$^1$ is NHR$^1$; D$^1$ is H; and E$^1$ is H. In another embodiment of Formula (I), G$^1$ is H; A$^1$ is N or C(A$^2$); A$^2$ is H; B$^1$ is NHR$^1$; D$^1$ is H; E$^1$ is H; and Y$^1$ is NO$_2$.

In one embodiment of Formula (I), Y$^1$ and B$^1$, together with the atoms to which they are attached, are benzene. In another embodiment of Formula (I), Y$^1$ and B$^1$, together with the atoms to which they are attached, are heteroarene. In another embodiment of Formula (I), A$^1$ is C(A$^2$); A$^2$, G$^1$, E$^1$, and D$^1$ are independently selected H; and Y$^1$ and B$^1$, together with the atoms to which they are attached, are benzene. In another embodiment of Formula (I), A$^1$ is C(A$^2$); A$^2$, G$^1$, E$^1$, and B$^1$ are independently selected H; and Y$^1$ and B$^1$, together with the atoms to which they are attached, are heteroarene.

In one embodiment of Formula (I), R$^1$ is R$^4$ or R$^5$. In one embodiment of Formula (I), R$^1$ is R$^4$. In one embodiment of Formula (I), $R^1$ is $R^5$. In one embodiment of Formula (I), $R^1$ is $R^4$; and $R^4$ is cycloalkyl, cycloalkenyl, heterocycloalkyl or heterocycloalkenyl. In one embodiment of Formula (I), $R^1$ is $R^4$; and $R^4$ is cycloalkyl or heterocycloalkyl. In one embodiment of Formula (I), $R^1$ is $R^4$; and $R^4$ is cycloalkyl. In one embodiment of Formula (I), $R^1$ is $R^4$; and $R^4$ is heterocycloalkyl.

In one embodiment of Formula (I), $R^1$ is $R^4$; and $R^4$ is cycloalkyl; wherein $R^4$ is unsubstituted or substituted as defined herein. In another embodiment of Formula (I), $R^1$ is $R^4$; and $R^4$ is cycloalkyl; wherein the cycloalkyl ring is substituted as defined herein. In another embodiment of Formula (I), $R^1$ is $R^4$; and $R^4$ is cycloalkyl; wherein the cycloalkyl ring is substituted with $R^{57}$ or $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (I), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (I), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl. In another embodiment of Formula (I), $R^1$ is $R^4$; and $R^4$ is cycloalkyl; wherein the cycloalkyl ring is substituted with $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $N(R^{57})_2$; $R^{57}$ is $R^{61}$; and $R^{61}$ is alkyl which is unsubstituted or substituted with $R^{62}$. In another embodiment of Formula (I), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is unsubstituted or substituted with $R^{62}$; $R^{62}$ is $R^{65}$; and $R^{65}$ is cycloalkyl. In another embodiment of Formula (I), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is substituted with $R^{62}$; $R^{62}$ is $R^{65}$; and $R^{65}$ is cyclopropyl.

In one embodiment of Formula (I), $R^1$ is $R^4$; and $R^4$ is heterocycloalkyl; wherein $R^4$ is unsubstituted or substituted as defined herein. In another embodiment of Formula (I), $R^1$ is $R^4$; and $R^4$ is heterocycloalkyl; wherein the heterocycloalkyl ring is substituted as defined herein. In another embodiment of Formula (I), $R^1$ is $R^4$; and $R^4$ is heterocycloalkyl; wherein the heterocycloalkyl ring is substituted with $R^{57}$. In another embodiment of Formula (I), $R^1$ is $R^4$; and $R^4$ is heterocycloalkyl; wherein the heterocycloalkyl ring is piperidinyl or piperizinyl; and wherein the heterocycloalkyl ring is substituted with $R^{57}$; and $R^{57}$ is $R^{60}$ or $R^{61}$. In another embodiment of Formula (I), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$ or $R^{61}$; $R^{60}$ is heterocycloalkyl; and $R^{61}$ is alkyl. In another embodiment of Formula (I), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$; $R^{60}$ is heterocycloalkyl; wherein the heterocycloalkyl is tetrahydropyranyl. In another embodiment of Formula (I), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{61}$; $R^{61}$ is alkyl; and the alkyl is methyl. In another embodiment of Formula (I), $R^1$ is $R^4$; $R^4$ is heterocycloalkyl; wherein the heterocycloalkyl ring is piperidinyl or piperizinyl; and wherein the piperidinyl or piperizinyl ring is substituted with $C(O)OR^{57}$; $R^{57}$ is $R^{61}$; $R^{61}$ is alkyl; and the alkyl is methyl.

In one embodiment of Formula (I), $R^1$ is $R^5$; and $R^5$ is alkyl which is unsubstituted or substituted. In one embodiment of Formula (I), $R^1$ is $R^5$; and $R^5$ is alkyl which is unsubstituted or substituted with $R^7$, $OR^7$, OH, CN, or F. In another embodiment of Formula (I), $R^1$ is $R^5$; and $R^5$ is alkyl which is substituted with $R^7$, $OR^7$, $NHR^7$, or $N(R^7)_2$.

In one embodiment of Formula (I), $R^7$ is $R^8$, $R^9$, $R^{10}$ or $R^{11}$ which are unsubstituted or substituted as defined herein. In another embodiment of Formula (I), $R^7$ is $R^8$ which is unsubstituted or substituted as defined herein. In another embodiment of Formula (I), $R^7$ is $R^9$ which is unsubstituted or substituted as defined herein. In another embodiment of Formula (I), $R^7$ is $R^{10}$ which is unsubstituted or substituted as defined herein. In another embodiment of Formula (I), $R^7$ is $R^{11}$ which is unsubstituted or substituted as defined herein.

In one embodiment of Formula (I), $R^8$ is phenyl which is unsubstituted or substituted as defined herein.

In one embodiment of Formula (I), $R^9$ is heteroaryl which is unsubstituted or substituted as defined herein. In another embodiment of Formula (I), $R^9$ is furanyl; which is unsubstituted or substituted as defined herein. In another embodiment of Formula (I), $R^9$ is furanyl; which is unsubstituted.

In one embodiment of Formula (I), $R^{10}$ is cycloalkyl, cycloalkenyl, heterocycloalkyl or heterocycloalkenyl, heterocycloalkyl which are unsubstituted or substituted as defined herein. In another embodiment of Formula (I), $R^{10}$ is heterocycloalkyl which is unsubstituted or substituted as defined herein. In another embodiment of Formula (I), $R^{10}$ is tetrahydrofuranyl, tetrahydropyranyl, morpholinyl, dioxanyl, oxetanyl, piperidinyl, or pyrrolidinyl, which are unsubstituted or substituted as defined herein. In another embodiment of Formula (I), $R^{10}$ is tetrahydropyranyl; which is unsubstituted or substituted as defined herein. In another embodiment of Formula (I), $R^{10}$ is morpholinyl; which is unsubstituted or substituted as defined herein. In another embodiment of Formula (I), $R^{10}$ is cycloalkyl which is unsubstituted or substituted as defined herein. In another embodiment of Formula (I), $R^{10}$ is cycloalkyl which is unsubstituted or substituted as defined herein. In another embodiment of Formula (I), $R^{10}$ is cyclohexyl, cyclopropyl, cyclobutyl, or bicyclo[2.2.1]heptanyl, which is unsubstituted or substituted as defined herein. In another embodiment of Formula (I), $R^{10}$ is heterocycloalkyl which is fused with $R^{10A}$; and $R^{10A}$ is heteroarene. In another embodiment of Formula (I), $R^{10}$ is 5,6,7,8-tetrahydroimidazo[1,2-a]pyridinyl.

In one embodiment of Formula (I), $R^{11}$ is alkyl, alkenyl or alkynyl which are unsubstituted or substituted as defined herein. In another embodiment of Formula (I), $R^{11}$ is alkyl. In another embodiment of Formula (I), $R^{11}$ is methyl; which is unsubstituted or substituted as defined herein. In another embodiment of Formula (I), $R^{11}$ is alkyl; which is substituted as defined herein. In another embodiment of Formula (I), $R^{11}$ is alkyl; which is substituted with $R^{12}$, $OR^{12}$, or $CF_3$. In another embodiment of Formula (I), $R^{11}$ is alkyl; which is substituted with $OR^{12}$, $R^{12}$ is $R^{16}$; and $R^{16}$ is alkyl. In another embodiment of Formula (I), $R^{11}$ is alkyl; which is substituted with $CF_3$. In another embodiment of Formula (I), $R^{11}$ is alkyl; which is substituted with $R^{12}$; $R^{12}$ is $R^{14}$; and $R^{14}$ is heteroaryl.

In one embodiment of Formula (I), $A^1$ is N or $C(A^2)$;
$A^2$ is H, F, Br, I, or Cl;

B$^1$ is R$^1$, OR$^1$, NHR$^1$, NHC(O)R$^1$, F, Br, I or Cl;

D$^1$ is H, F, Br, I, or Cl;

E$^1$ is H; and

Y$^1$ is H, CN, NO$_2$, F, Cl, Br, I, CF$_3$, R$^{17}$, OR$^{17}$, SR$^{17}$, SO$_2$R$^{17}$, or C(O)NH$_2$; or

Y$^1$ and B$^1$, together with the atoms to which they are attached, are benzene, heteroarene, or heterocycloalkene; and A$^2$, D$^1$, and E$^1$ are independently selected H;

G$^1$ is H, or C(O)OR;

R is alkyl;

R$^1$ is R$^4$ or R$^5$;

R$^4$ is cycloalkyl, or heterocycloalkyl;

R$^5$ is alkyl, or alkynyl, each of which is unsubstituted or substituted with one or two or three of independently selected R$^7$, OR$^7$, NHR$^7$, N(R$^7$)$_2$, CN, OH, F, Cl, Br or I;

R$^7$ is R$^8$, R$^9$, R$^{10}$, or R$^{11}$;

R$^8$ is phenyl;

R$^9$ is heteroaryl;

R$^{10}$ is cycloalkyl, cycloalkenyl, or heterocycloalkyl; each of which is unfused or fused with R$^{10A}$, R$^{10A}$ is heteroarene;

R$^{11}$ is alkyl each of which is unsubstituted or substituted with one or two or three of independently selected R$^{12}$, OR$^{12}$ or CF$_3$;

R$^{12}$ is R$^{14}$ or R$^{16}$;

R$^{14}$ is heteroaryl;

R$^{16}$ is alkyl;

R$^{17}$ is R$^{21}$;

R$^{21}$ is alkyl, or alkynyl, each of which is unsubstituted or substituted with one or two or three of independently selected R$^{22}$, F, Cl, Br or I;

R$^{22}$ is R$^{25}$;

R$^{25}$ is heterocycloalkyl;

Z$^1$ is R$^{26}$;

Z$^2$ is R$^{30}$;

Z$^{1A}$ and Z$^{2A}$ are both absent;

L$^1$ is a R$^{37}$;

R$^{26}$ is phenylene;

R$^{30}$ is heterocycloalkylene;

R$^{37}$ is R$^{37A}$;

R$^{37A}$ is alkylene;

Z$^3$ is R$^{38}$, or R$^{40}$;

R$^{38}$ is phenyl;

R$^{40}$ is cycloalkyl, cycloalkenyl, or heterocycloalkenyl;

wherein the moiety represented by R$^{26}$ is substituted with OR$^{41}$;

R$^{41}$ is heteroaryl, which is fused with R$^{43A}$; R$^{43A}$ is heteroarene; which is unfused or fused with benzene;

wherein the cyclic moieties represented by Y$^1$ and B$^1$ together, R$^4$, R$^8$, R$^{10}$, R$^{25}$, R$^{30}$, R$^{38}$, and R$^{40}$ are independently unsubstituted, further unsubstituted, substituted or further substituted with one or two or three or four or five of independently selected R$^{57A}$, R$^{57}$, OR$^{57}$, SO$_2$R$^{57}$, C(O)R$^{57}$, CO(O)R$^{57}$, C(O)N(R$^{57}$)$_2$, NH$_2$, NHR$^{57}$, N(R$^{57}$)$_2$, NHC(O)R$^{57}$, NHS(O)$_2$R$^{57}$, OH, CN, (O), F, Cl, Br or I;

R$^{57A}$ is spiroalkyl, or spiroheteroalkyl;

R$^{57}$ is R$^{58}$, R$^{59}$, R$^{60}$ or R$^{61}$;

R$^{58}$ is phenyl;

R$^{59}$ is heteroaryl;

R$^{60}$ is cycloalkyl, or heterocycloalkyl;

R$^{61}$ is alkyl which is unsubstituted or substituted with one or two or three of independently selected R$^{62}$, OR$^{62}$, N(R$^{62}$)$_2$, C(O)OH, CN, F, Cl, Br or I;

R$^{62}$ is R$^{65}$, or R$^{66}$;

R$^{65}$ is cycloalkyl, or heterocycloalkyl;

R$^{66}$ is alkyl which is unsubstituted or substituted with OR$^{67}$;

R$^{67}$ is alkyl;

wherein the cyclic moieties represented by R$^{57A}$, R$^{58}$, and R$^{60}$ are unsubstituted or substituted with one or two or three or four of independently selected R$^{68}$, F, Cl, Br or I;

R$^{68}$ is R$^{71}$ or R$^{72}$;

R$^{71}$ is heterocycloalkyl; and

R$^{72}$ is alkyl, which is unsubstituted or substituted with one or two F.

Still another embodiment pertains to compounds having Formula (I), which are

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

2-(9H-carbazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(9H-carbazol-4-yloxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-(2-naphthylsulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide;

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide;

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide;

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({4-[(1-acetylpiperidin-4-yl)amino]-3-nitrophenyl}sulfonyl)-4-(4-{[2-(4-chlorophenyl)-4,4- dimethylcyclohex-1-en-1-yl]methyl}piperazin-1-yl)-2-(1H-pyrrolo[2,3-b]pyridin-5-yloxy)benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide;

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[8-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate;

4-(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide;

4-(4-{[8-(4-chlorophenyl)spiro[4.5]dec-7-en-7-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide;

N-({3-chloro-5-fluoro-4-[(tetrahydro-2H-pyran-4-ylmethyl)amino]phenyl}sulfonyl)-4-(4-{[2-(4-chlorophenyl)-4,4- dimethylcyclohex-1-en-1-yl]methyl}piperazin-1-yl)-2-(1H-pyrrolo[2,3-b]pyridin-5-yloxy)benzamide;
and therapeutically acceptable salts, and metabolites thereof
4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yl oxy)benzamide;
N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(4-{[(1-morpholin-4-ylcyclohexyl)methyl]amino}-3-nitrophenyl)sulfonyl]-2-(1H-pyrrolo[2,3-b]pyridin-5-yloxy)benzamide;
Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide;
4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;
N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide;
N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
Trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-(4-{[(1S,3R)-3-morpholin-4-ylcyclopentyl]amino}-3-nitrophenyl)sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;
4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;
2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide;
2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide;
Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide;
Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide;
Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide;
tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate;

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide;

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide;

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide;

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide;

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide;

4-(2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide;

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid;

4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide;

ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate;

4-(4-{[2-(4-chlorophenyl)-4,4-dimethylcyclohex-1-en-1-yl] methyl}piperazin-1-yl)-N-({-4-[4-(morpholin-4-yl)piperidin-1-yl]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide;

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-[(4-fluoro-1-methylpiperidin-4-yl)methoxy]-3-[(trifluoromethyl)sulfonyl] phenyl}sulfonyl)-2-(1H-pyrrolo[2,3-b]pyridin-5-yloxy) benzamide;

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide;

tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate;

4-(4-{[2-(4-chlorophenyl)-4,4-dimethylcyclohex-1-en-1-yl] methyl}piperazin-1-yl)-N-({3-(pentafluoro-$\lambda^6$-sulfanyl)-4-[(tetrahydro-2H-pyran-4-ylmethyl)amino] phenyl}sulfonyl)-2-(1H-pyrrolo[2,3-b]pyridin-5-yloxy) benzamide;

4-(4-{[2-(4-chlorophenyl)-4,4-dimethylcyclohex-1-en-1-yl] methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(3-nitro-4-{[4-(oxetan-3-yl) piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({3-nitro-4-[(3R)-tetrahydrofuran-3-ylamino]phenyl}sulfonyl)-2-(1H-pyrrolo[2,3-b] pyridin-5-yloxy)benzamide;

4-(4-{[2-(4-chlorophenyl)-4,4-dimethylcyclohex-1-en-1-yl] methyl}piperazin-1-yl)-N-[(4-{[(4,4-difluorocyclohexyl) methyl]amino}-3-nitrophenyl)sulfonyl]-2-(1H-pyrrolo[2,3-b]pyridin-5-yloxy)benzamide;

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({4-({[4-(oxetan-3-yl)morpholin-2-yl]methyl}amino)-3-[(trifluoromethyl)sulfonyl] phenyl}sulfonyl)-2-(1H-pyrrolo[2,3-b]pyridin-5-yloxy) benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(cyanomethyl)morpholin-2-yl] methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide;

N-[(5-chloro-6-{[(2R)-4-(cyanomethyl)morpholin-2-yl] methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(cyanomethyl)piperidin-4-yl] methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{1-(oxetan-3-yl)azetidin-3-yl]amino}phenyl)sulfonyl]-2-(1H-pyrrolo[2,3-b]pyridin-5-yloxy)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide;

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-{4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl)phenyl}sulfonyl)benzamide;

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-cyano cyclohexyl)methyl]amino}-3-nitrophenyl)sulfonyl]-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide;

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoro ethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide;

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide;

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide;

N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohexyl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide;

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide;

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide;

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide;

N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;

N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide;

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide;

methyl 2-{[(4-{[4-(4-{[2-(4-chlorophenyl)-4,4-dimethylcyclohex-1-en-1-yl]methyl}piperazin-1-yl)-2-(1H-pyrrolo

[2,3-b]pyridin-5-yloxy)benzoyl]sulfamoyl}-2-nitrophenyl)amino]methyl}morpholine-4-carboxylate;

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide;

4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[5-(4-chlorophenyl)spiro[2.5]oct-5-en-6-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide;

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide;

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide;

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide;

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide;

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-(2-oxaspiro[3.5]non-7-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide;

4-(4-{[2-(4-chlorophenyl)-5,5-bis(fluoromethyl)cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide;

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5-(methoxymethyl)-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide;

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide;

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl pivalate;

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl butyrate;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide;

4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide;

N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide;

4-(4-{[2-(4-chlorophenyl)-4,4-dimethylcyclohex-1-en-1-yl]methyl}piperazin-1-yl)-N-{[4-({[4-(methoxymethyl)cyclohexyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; and therapeutically acceptable salts, and metabolites thereof.

Still another embodiment pertains to 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; and therapeutically acceptable salts, and metabolites thereof.

Still another embodiment pertains to Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide; and therapeutically acceptable salts, and metabolites thereof.

Still another embodiment pertains to Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide; and therapeutically acceptable salts, and metabolites thereof.

Still another embodiment pertains to Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide; and therapeutically acceptable salts, and metabolites thereof.

Still another embodiment pertains to 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide; and therapeutically acceptable salts, and metabolites thereof.

Another embodiment pertains to the compound N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide; or a pharmaceutically acceptable salt thereof.

Another embodiment pertains to the compound 4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; or a pharmaceutically acceptable salt thereof.

Another embodiment pertains to the compound N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide; or a pharmaceutically acceptable salt thereof.

Still another embodiment pertains to compounds having Formula (I) or Formula (II), which are 4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;
4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; or a pharmaceutically acceptable salt thereof.

Another embodiment pertains to the compound N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; or a pharmaceutically acceptable salt thereof.

Still another embodiment pertains to compounds having Formula (I) or Formula (II), which are N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide; or a pharmaceutically acceptable salt thereof.

Another embodiment pertains to the compound 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide or a pharmaceutically acceptable salt thereof.

In another aspect, the present invention provides compounds of Formula (II)

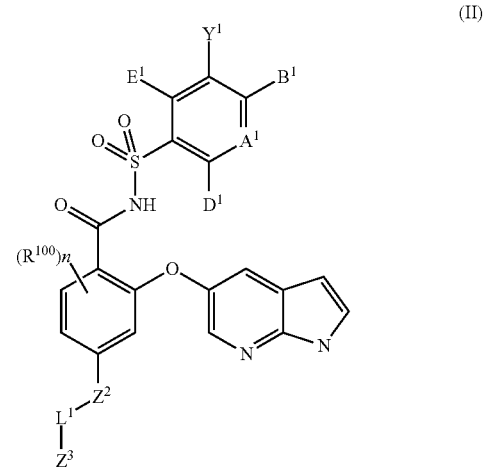

(II)

and therapeutically acceptable salts, and metabolites thereof, wherein $A^1$, $B^1$, $D^1$, $E^1$, $Y^1$, $Z^2$, $L^1$, and $Z^3$ are as described herein for Formula (II); n is 0, 1, 2, or 3; describing the number of substituents on $Z^1$; and $R^{100}$ is as described for substituents on $R^{26}$.

In one embodiment of Formula (II), n is 0 or 1. In another embodiment of Formula (II), n is 0.

In one embodiment of Formula (II), $A^1$ is N. In another embodiment of Formula (II), $A^1$ is $C(A^2)$. In another embodiment of Formula (II), $A^1$ is $C(A^2)$; and $A^2$ is H, F, Cl, Br, or I. In another embodiment of Formula (II), $A^1$ is $C(A^2)$; and $A^2$ is H.

In one embodiment of Formula (II), $B^1$ is $R^1$, $OR^1$, $NHR^1$, $NHC(O)R^1$, F, Cl, Br, or I. In another embodiment of Formula (II), $A^1$ is $C(A^2)$; $A^2$ is H; and $B^1$ is $NHR^1$. In another embodiment of Formula (II), $A^1$ is $C(A^2)$; $A^2$ is H; and $B^1$ is $OR^1$. In another embodiment of Formula (II), $A^1$ is $C(A^2)$; $A^2$ is H; and $B^1$ is Cl. In another embodiment of Formula (II), $A^1$ is $C(A^2)$; $A^2$ is H; and $B^1$ is $R^1$. In another embodiment of Formula (II), $A^1$ is N; and $B^1$ is $NHR^1$. In another embodiment of Formula (II), $A^1$ is N; and $B^1$ is $OR^1$. In another embodiment of Formula (II), $A^1$ is N; and $B^1$ is Cl. In another embodiment of Formula (II), $A^1$ is N; and $B^1$ is $R^1$.

In one embodiment of Formula (II), $D^1$ is H or Cl. In another embodiment of Formula (II), $A^1$ is $C(A^2)$; $A^2$ is H; $B^1$ is $NHR^1$; and $D^1$ is H. In another embodiment of Formula (II), $A^1$ is $C(A^2)$; $A^2$ is H; $B^1$ is $NHR^1$; and $D^1$ is Cl. In another embodiment of Formula (II), $A^1$ is $C(A^2)$; $A^2$ is H; $B^1$ is $OR^1$; and $D^1$ is H. In another embodiment of Formula (II), $A^1$ is $C(A^2)$; $A^2$ is H; $B^1$ is Cl; and $D^1$ is H. In another embodiment of Formula (II), $A^1$ is $C(A^2)$; $A^2$ is H; $B^1$ is $R^1$; and $D^1$ is H. In another embodiment of Formula (II), $A^1$ is N; $B^1$ is $NHR^1$; and $D^1$ is H. In another embodiment of Formula (II), $A^1$ is N; $B^1$ is $NHR^1$; and $D^1$ is Cl. In another embodiment of Formula (II), $A^1$ is N; $B^1$ is $OR^1$; and $D^1$ is H. In another embodiment of Formula (II), $A^1$ is N; $B^1$ is Cl; and $D^1$ is H. In another embodiment of Formula (II), $A^1$ is N; $B^1$ is $R^1$; and $D^1$ is H.

In one embodiment of Formula (II), $E^1$ is H. In another embodiment of Formula (II), $A^1$ is $C(A^2)$; $A^2$ is H; $B^1$ is $NHR^1$; $D^1$ is H; and $E^1$ is H. In another embodiment of Formula (II), $A^1$ is $C(A^2)$; $A^2$ is H; $B^1$ is $NHR^1$; $E^1$ is H; and $D^1$ is Cl. In another embodiment of Formula (II), $A^1$ is $C(A^2)$; $A^2$ is H; $B^1$ is $OR^1$; $D^1$ is H; and $E^1$ is H. In another embodiment of Formula (II), $A^1$ is $C(A^2)$; $A^2$ is H; $B^1$ is Cl; $D^1$ is H; and $E^1$ is H. In another embodiment of Formula (II), $A^1$ is $C(A^2)$; $A^2$ is H; $B^1$ is $R^1$; $D^1$ is H; and $E^1$ is H. In another embodiment of Formula (II), $A^1$ is N; $B^1$ is $NHR^1$; $D^1$ is H; and $E^1$ is H. In another embodiment of Formula (II), $A^1$ is N; $B^1$ is $NHR^1$; $E^1$ is H; and $D^1$ is Cl. In another embodiment of Formula (II), $A^1$ is N; $B^1$ is $OR^1$; $D^1$ is H; and $E^1$ is H. In another embodiment of Formula (II), $A^1$ is N; $B^1$ is Cl; $D^1$ is H; and $E^1$ is H. In another embodiment of Formula (II), $A^1$ is N; $B^1$ is $R^1$; $D^1$ is H; and $E^1$ is H.

In one embodiment of Formula (II), $Y^1$ is H, CN, $NO_2$, F, Cl, Br, I, $CF_3$, $R^{17}$, $OR^{17}$, $SR^{17}$, $SO_2R^{17}$, or $C(O)NH_2$. In another embodiment of Formula (II), $Y^1$ is H. In another embodiment of Formula (II), $Y^1$ is CN. In another embodiment of Formula (II), $Y^1$ is F, Cl, Br, or I. In another embodiment of Formula (II), $Y^1$ is $CF_3$. In another embodiment of Formula (II), $Y^1$ is $SR^{17}$. In another embodiment of Formula (II), $Y^1$ is $OR^{17}$. In another embodiment of Formula (II), $Y^1$ is $NO_2$. In another embodiment of Formula (II), $Y^1$ is $SO_2R^{17}$; wherein $R^{17}$ is as defined herein. In another embodiment of Formula (II), $Y^1$ is $SO_2R^{17}$; wherein $R^{17}$ is alkyl. In another embodiment of Formula (II), $Y^1$ is $R^{17}$; wherein $R^{17}$ is alkynyl. In another embodiment of Formula (II), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (II), $A^1$ is $C(A^2)$; $A^2$ is H; $B^1$ is $NHR^1$; $D^1$ is H; $E^1$ is H; and $Y^1$ is $NO_2$. In another embodiment of Formula (II), $A^1$ is $C(A^2)$; $A^2$ is H; $B^1$ is $NHR^1$; $D^1$ is H; $E^1$ is H; and $Y^1$ is $SO_2R^{17}$; wherein $R^{17}$ is alkyl substituted with three F. In another embodiment of Formula (II), $A^1$ is N; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (II), $A^1$ is N; $B^1$ is $NHR^1$; $D^1$ is H; $E^1$ is H; and $Y^1$ is $NO_2$. In another embodiment of Formula (II), $A^1$ is N; $B^1$ is $NHR^1$; $D^1$ is H; $E^1$ is H; and $Y^1$ is $SO_2R^{17}$; wherein $R^{17}$ is alkyl substituted with three F.

In one embodiment of Formula (II), $G^1$ is H; $A^1$ is N or $C(A^2)$; and $A^2$ is H. In another embodiment of Formula (II), $G^1$ is H; $A^1$ is N or $C(A^2)$; $A^2$ is H; and $D^1$ is $NHR^1$. In another embodiment of Formula (II), $G^1$ is H; $A^1$ is N or $C(A^2)$; $A^2$ is H; $D^1$ is NHR^1$; and $D^1$ is H. In another embodiment of Formula (II), $G^1$ is H; $A^1$ is N or $C(A^2)$; $A^2$ is H; $D^1$ is $NHR^1$; $D^1$ is H; and $E^1$ is H. In another embodiment of Formula (II), $G^1$ is H; $A^1$ is N or $C(A^2)$; $A^2$ is H; $B^1$ is $NHR^1$; $D^1$ is H; $E^1$ is H; and $Y^1$ is $NO_2$.

In one embodiment of Formula (II), $Y^1$ and $B^1$, together with the atoms to which they are attached, are benzene. In another embodiment of Formula (II), $Y^1$ and $B^1$, together with the atoms to which they are attached, are heteroarene. In another embodiment of Formula (II), $A^1$ is $C(A^2)$; $A^2$, $G^1$, $E^1$, and $D^1$ are independently selected H; and $Y^1$ and $B^1$, together with the atoms to which they are attached, are benzene. In another embodiment of Formula (II), $A^1$ is $C(A^2)$; $A^2$, $G^1$, $E^1$, and $D^1$ are independently selected H; and $Y^1$ and $B^1$, together with the atoms to which they are attached, are heteroarene.

In one embodiment of Formula (II), $R^1$ is $R^4$ or $R^5$. In one embodiment of Formula (II), $R^1$ is $R^4$. In one embodiment of Formula (II), $R^1$ is $R^5$. In one embodiment of Formula (II), $R^1$ is $R^4$; and $R^4$ is cycloalkyl, cycloalkenyl, heterocycloalkyl or heterocycloalkenyl. In one embodiment of Formula (II), $R^1$ is $R^4$; and $R^4$ is cycloalkyl or heterocycloalkyl. In one embodiment of Formula (II), $R^1$ is $R^4$; and $R^4$ is cycloalkyl. In one embodiment of Formula (II), $R^1$ is $R^4$; and $R^4$ is heterocycloalkyl.

In one embodiment of Formula (II), $R^1$ is $R^4$; and $R^4$ is cycloalkyl; wherein $R^4$ is unsubstituted or substituted as defined herein. In another embodiment of Formula (II), $R^1$ is $R^4$; and $R^4$ is cycloalkyl; wherein the cycloalkyl ring is substituted as defined herein. In another embodiment of Formula (II), $R^1$ is $R^4$; and $R^4$ is cycloalkyl; wherein the cycloalkyl ring is substituted with $R^{57}$ or $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (II), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (II), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl. In another embodiment of Formula (II), $R^1$ is $R^4$; and $R^4$ is cycloalkyl; wherein the cycloalkyl ring is substituted with $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $N(R^{57})_2$; $R^{57}$ is $R^{61}$; and $R^{61}$ is alkyl which is unsubstituted or substituted with $R^{62}$. In another embodiment of Formula (II), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is unsubstituted or substituted with $R^{62}$; $R^{62}$ is $R^{65}$; and $R^{65}$ is cycloalkyl. In another embodiment of Formula (II), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is substituted with $R^{62}$; $R^{62}$ is $R^{65}$; and $R^{65}$ is cyclopropyl In one embodiment of Formula (II), $R^1$ is $R^4$; and $R^4$ is heterocycloalkyl; wherein $R^4$ is unsubstituted or substituted as defined herein. In another embodiment of Formula (II), $R^1$ is $R^4$; and $R^4$ is heterocycloalkyl; wherein the heterocycloalkyl ring is substituted as defined herein. In another embodiment of Formula (II), $R^1$ is $R^4$; and $R^4$ is heterocycloalkyl; wherein the heterocycloalkyl ring is substituted with $R^{57}$. In another embodiment of Formula (II), $R^1$ is $R^4$; and $R^4$ is heterocycloalkyl; wherein the heterocycloalkyl ring is piperidinyl or piperizinyl; and wherein the heterocycloalkyl ring is substituted with $R^{57}$; and $R^{57}$ is $R^{60}$ or $R^{61}$. In another embodiment of Formula (II), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$ or $R^{61}$; $R^{60}$ is heterocycloalkyl; and $R^{61}$ is alkyl. In another embodiment of Formula (II), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$; $R^{60}$ is heterocycloalkyl; wherein the heterocycloalkyl is tetrahydropyranyl. In another embodiment of Formula (II), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{61}$; $R^{61}$ is alkyl; and the alkyl is methyl. In another embodiment of Formula (II), $R^1$ is $R^4$; $R^4$ is heterocycloalkyl; wherein the heterocycloalkyl ring is piperidinyl or piperizinyl; and wherein the piperidinyl or piperizinyl ring is substituted with $C(O)OR^{57}$; $R^{57}$ is $R^{61}$; $R^{61}$ is alkyl; and the alkyl is methyl.

In one embodiment of Formula (II), $R^1$ is $R^5$; and $R^5$ is alkyl which is unsubstituted or substituted. In one embodiment of Formula (II), $R^1$ is $R^5$; and $R^5$ is alkyl which is unsubstituted or substituted with $R^7$, $OR^7$, OH, CN, or F. In another embodiment of Formula (II), $R^1$ is $R^5$; and $R^5$ is alkyl which is substituted with $R^7$, $OR^7$, $NHR^7$, or $N(R^7)_2$.

In one embodiment of Formula (II), $R^7$ is $R^8$, $R^9$, $R^{10}$ or $R^{11}$ which are unsubstituted or substituted as defined herein. In another embodiment of Formula (II), $R^7$ is $R^8$ which is unsubstituted or substituted as defined herein. In another embodiment of Formula (II), $R^7$ is $R^9$ which is unsubstituted or substituted as defined herein. In another embodiment of Formula (II), $R^7$ is $R^{10}$ which is unsubstituted or substituted as defined herein. In another embodiment of Formula (II), $R^7$ is $R^{11}$ which is unsubstituted or substituted as defined herein.

In one embodiment of Formula (II), $R^8$ is phenyl which is unsubstituted or substituted as defined herein.

In one embodiment of Formula (II), $R^9$ is heteroaryl which is unsubstituted or substituted as defined herein. In another embodiment of Formula (II), $R^9$ is furanyl; which is unsubstituted or substituted as defined herein. In another embodiment of Formula (II), $R^9$ is furanyl; which is unsubstituted.

In one embodiment of Formula (II), $R^{10}$ is cycloalkyl, cycloalkenyl, heterocycloalkyl or heterocycloalkenyl, heterocycloalkyl which are unsubstituted or substituted as defined herein. In another embodiment of Formula (II), $R^{10}$ is heterocycloalkyl which is unsubstituted or substituted as defined herein. In another embodiment of Formula (II), $R^{10}$ is tetrahydrofuranyl, tetrahydropyranyl, morpholinyl, dioxanyl, oxetanyl, piperidinyl, or pyrrolidinyl, which are unsubstituted or substituted as defined herein. In another embodiment of Formula (II), $R^{10}$ is tetrahydropyranyl, which is unsubstituted or substituted as defined herein. In another embodiment of Formula (II), $R^{10}$ is morpholinyl; which is unsubstituted or substituted as defined herein. In another embodiment of Formula (II), $R^{10}$ is cycloalkyl which is unsubstituted or substituted as defined herein. In another embodiment of Formula (II), $R^{10}$ is cycloalkyl which is unsubstituted or substituted as defined herein. In another embodiment of Formula (II), $R^{10}$ is cyclohexyl, cyclopropyl, cyclobutyl, or bicyclo[2.2.1]heptanyl, which is unsubstituted or substituted as defined herein. In another embodiment of Formula (II), $R^{10}$ is heterocycloalkyl which is fused with $R^{10A}$; and $R^{10A}$ is heteroarene. In another embodiment of Formula (II), $R^{10}$ is 5,6,7,8-tetrahydroimidazo[1,2-a]pyridinyl.

In one embodiment of Formula (II), $R^{11}$ is alkyl, alkenyl or alkynyl which are unsubstituted or substituted as defined herein. In another embodiment of Formula (II), $R^{11}$ is alkyl. In another embodiment of Formula (II), $R^{11}$ is methyl; which is unsubstituted or substituted as defined herein. In another embodiment of Formula (II), $R^{11}$ is alkyl; which is substituted as defined herein. In another embodiment of Formula (II), $R^{11}$ is alkyl; which is substituted with $R^{12}$, $OR^{12}$, or $CF_3$. In another embodiment of Formula (II), $R^{11}$ is alkyl; which is substituted with $OR^{12}$; $R^{12}$ is $R^{16}$; and $R^{16}$ is alkyl. In another embodiment of Formula (II), $R^{11}$ is alkyl; which is substituted with $CF_3$. In another embodiment of Formula (II), $R^{11}$ is alkyl; which is substituted with $R^{12}$, $R^{12}$ is $R^{14}$, and $R^{14}$ is heteroaryl.

In one embodiment of Formula (II),
n is 0;
$A^1$ is N or $C(A^2)$;
$A^2$ is H, F, Br, I, or Cl;
$B^1$ is $R^1$, $OR^1$, $NHR^1$, $NHC(O)R^1$, F, Br, I or Cl;
$D^1$ is H, F, Br, I, or Cl;
$E^1$ is H; and $Y^1$ is H, CN, $NO_2$, F, Cl, Br, I, $CF_3$, $R^{17}$, $OR^{17}$, $SR^{17}$, $SO_2R^{17}$, or $C(O)NH_2$; or
$Y^1$ and $B^1$, together with the atoms to which they are attached, are benzene, heteroarene, or heterocycloalkene; and
$A^2$, $D^1$, and $E^1$ are independently selected H;
$R^1$ is $R^4$ or $R^5$;
$R^4$ is cycloalkyl, or heterocycloalkyl;
$R^5$ is alkyl, or alkynyl, each of which is unsubstituted or substituted with one or two or three of independently selected $R^7$, $OR^7$, $NHR^7$, $N(R^7)_2$, CN, OH, F, Cl, Br or I;
$R^7$ is $R^8$, $R^9$, $R^{10}$, or $R^{11}$;
$R^8$ is phenyl;
$R^9$ is heteroaryl;
$R^{10}$ is cycloalkyl, cycloalkenyl, or heterocycloalkyl; each of which is unfused or fused with $R^{10A}$, $R^{10A}$ is heteroarene;
$R^{11}$ is alkyl each of which is unsubstituted or substituted with one or two or three of independently selected $R^{12}$, $OR^{12}$ or $CF_3$;
$R^{12}$ is $R^{14}$ or $R^{16}$;
$R^{14}$ is heteroaryl;
$R^{16}$ is alkyl;
$R^{17}$ is $R^{21}$;
$R^{21}$ is alkyl, or alkynyl, each of which is unsubstituted or substituted with one or two or three of independently selected $R^{22}$, F, Cl, Br or I;
$R^{22}$ is $R^{25}$;
$R^{25}$ is heterocycloalkyl;
$Z^2$ is $R^{30}$;
$Z^{1A}$ and $Z^{2A}$ are both absent;
$L^1$ is a $R^{37}$;
$R^{30}$ is heterocycloalkylene;
$R^{37}$ is $R^{37A}$;
$R^{37A}$ is alkylene;
$Z^3$ is $R^{38}$, or $R^{40}$;
$R^{38}$ is phenyl;
$R^{40}$ is cycloalkyl, cycloalkenyl, or heterocycloalkenyl;
wherein the cyclic moieties represented by $Y^1$ and $B^1$ together, $R^4$, $R^8$, $R^{10}$, $R^{25}$, $R^{30}$, $R^{38}$, and $R^{40}$ are independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br or I;
$R^{57A}$ is spiroalkyl, or spiroheteroalkyl;
$R^{57}$ is $R^{58}$, $R^{60}$ or $R^{61}$;
$R^{58}$ is phenyl;
$R^{60}$ is cycloalkyl, or heterocycloalkyl;
$R^{61}$ is alkyl which is unsubstituted or substituted with one or two or three of independently selected $R^{62}$, $OR^{62}$, $N(R^{62})_2$, C(O)OH, CN, F, Cl, Br or I;
$R^{62}$ is $R^{65}$, or $R^{66}$;
$R^{65}$ is cycloalkyl, or heterocycloalkyl;
$R^{66}$ is alkyl which is unsubstituted or substituted with $OR^{67}$;
$R^{67}$ is alkyl;
wherein the cyclic moieties represented by $R^{57A}$, $R^{58}$, and $R^{60}$ are unsubstituted or substituted with one or two or three or four of independently selected $R^{68}$, F, Cl, Br or I;
$R^{68}$ is $R^{71}$ or $R^{72}$;
$R^{71}$ is heterocycloalkyl; and
$R^{72}$ is alkyl, which is unsubstituted or substituted with one or two F.

Still another embodiment pertains to compounds having Formula (II), which are 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-(2-naphthylsulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]

pyridin-5-yloxy)-N-({4-[(tetrahydro-2H-pyran-4-ylmethyl)amino]-3-[(trifluoromethyl)sulfonyl]phenyl}sulfonyl)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide;

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide;

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide;

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-{4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide;

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[8-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

Trans-4-(4-{[8-(4-chlorophenyl)spiro[4.5]dec-7-en-7-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-5,5-dimethylcyclohex-1-en-1-yl]
methyl}piperazin-1-yl)-N-{[5-cyano-6-(tetrahydro-2H-
pyran-4-ylmethoxy)pyridin-3-yl]sulfonyl}-2-(1H-pyrrolo
[2,3-b]pyridin-5-yloxy)benzamide;

tert-butyl 3-{[4-({[4-(4-{[2-(4-chlorophenyl)-4,4-dimethyl-
cyclohex-1-en-1-yl]methyl}piperazin-1-yl)-2-(1H-pyr-
rolo[2,3-b]pyridin-5-yloxy)benzoyl]amino}sulfonyl)-2-
nitrophenoxy]methyl}morpholine-4-carboxylate;

4-(4-{[2-(4-chlorophenyl)-4,4-dimethylcyclohex-1-en-1-yl]
methyl}piperazin-1-yl)-N-{[4-(morpholin-3-ylmethoxy)-
3-nitrophenyl]sulfonyl}-2-(1H-pyrrolo[2,3-b]pyridin-5-
yloxy)benzamide;

4-(4-{[8-(4-chlorophenyl)spiro[4.5]dec-7-en-7-yl]
methyl}piperazin-1-yl)-N-({3-nitro-4-[(tetrahydro-2H-
pyran-4-ylmethyl)amino]phenyl}sulfonyl)-2-(1H-pyrrolo
[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[1-(methylsulfonyl)pip-
eridin-4-yl]amino}-3-nitrophenyl)sulfonyl]-2-(1H-pyr-
rolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(1,1-dioxidotetrahydro-
2H-thiopyran-4-yl)amino]-3-nitrophenyl}sulfonyl)-2-
(1H-pyrrolo[2,3-b]pyridin-5-yloxy)benzamide;

N-[(4-chloro-3-nitrophenyl)sulfonyl]-4-(4-{[2-(4-chlo-
rophenyl)-4,4-dimethylcyclohex-1-en-1-yl]
methyl}piperazin-1-yl)-2-(1H-pyrrolo[2,3-b]pyridin-5-
yloxy)benzamide;

4-(4-{[2-(4-chlorophenyl)-4,4-dimethylcyclohex-1-en-1-yl]
methyl}piperazin-1-yl)-N-[(3-nitro-4-{[1-(2,2,2-trifluo-
roethyl)piperidin-4-yl]amino}phenyl)sulfonyl]-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({5-cyano-6-[(1-tetrahydro-
2H-pyran-4-ylpiperidin-4-yl)oxy]pyridin-3-yl}sulfonyl)-
2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[5-isopropyl-6-(tetrahydro-
2H-pyran-4-ylmethoxy)pyridin-3-yl]sulfonyl}-2-(1H-
pyrrolo[2,3-b]pyridin-5-yloxy)benzamide;

N-({3-chloro-5-fluoro-4-[(tetrahydro-2H-pyran-4-ylmethyl)
amino]phenyl}sulfonyl)-4-(4-{[2-(4-chlorophenyl)-4,4-
dimethylcyclohex-1-en-1-yl]methyl}piperazin-1-yl)-2-
(1H-pyrrolo[2,3-b]pyridin-5-yloxy)benzamide;

and therapeutically acceptable salts, and metabolites thereof 4-(4-{[2-(4-chlorophenyl)-4,4-dimethylcyclohex-1-en-1-yl]
methyl}piperazin-1-yl)-N-{[4-({1-[2-fluoro-1-(fluorom-
ethyl)ethyl]piperidin-4-yl}amino)-3-nitrophenyl]sulfo-
nyl}-2-(1H-pyrrolo[2,3-b]pyridin-5-yl oxy)benzamide;

N-({5-chloro-6-[(4-fluorotetrahydro-2H-pyran-4-yl)meth-
oxy]pyridin-3-yl}sulfonyl)-4-(4-{[2-(4-chlorophenyl)-4,
4-dimethylcyclohex-1-en-1-yl]methyl}piperazin-1-yl)-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[1-(2,2-difluoroethyl)pip-
eridin-4-yl]amino}-3-nitrophenyl)sulfonyl]-2-(1H-pyr-
rolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(1-cyclopropylpiperidin-
4-yl)amino]-3-nitrophenyl}sulfonyl)-2-(1H-pyrrolo[2,3-
b]pyridin-5-yloxy)benzamide;

4-(4-{[2-(4-chlorophenyl)-4,4-dimethylcyclohex-1-en-1-yl]
methyl}piperazin-1-yl)-N-[(4-{[(1-morpholin-4-ylcyclo-
hexyl)methyl]amino}-3-nitrophenyl)sulfonyl]-2-(1H-
pyrrolo[2,3-b]pyridin-5-yloxy)benzamide;

Trans-4-(4-{[2-(4-chlorophenyl)-4,4-dimethylcyclohex-1-
en-1-yl]methyl}piperazin-1-yl)-N-[(4-{[4-(dicyclopropy-
lamino)cyclohexyl]amino}-3-nitrophenyl)sulfonyl]-2-
(1H-pyrrolo[2,3-b]pyridin-5-yloxy)benzamide;

4-(4-{[2-(4-chlorophenyl)-6,6-dimethylcyclohex-1-en-1-yl]
methyl}piperazin-1-yl)-N-({3-nitro-4-[(tetrahydro-2H-
pyran-4-ylmethyl)amino]phenyl}sulfonyl)-2-(1H-pyrrolo
[2,3-b]pyridin-5-yloxy)benzamide;

N-({5-bromo-6-[(4-ethylmorpholin-3-yl)methoxy]pyridin-
3-yl}sulfonyl)-4-(4-{[2-(4-chlorophenyl)-4,4-dimethyl-
cyclohex-1-en-1-yl]methyl}piperazin-1-yl)-2-(1H-pyr-
rolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(4-ethylmorpholin-3-yl)
methoxy]-3-nitrophenyl}sulfonyl)-2-(1H-pyrrolo[2,3-b]
pyridin-5-yloxy)benzamide;

4-(4-{[2-(4-chlorophenyl)-4,4-dimethylcyclohex-1-en-1-yl]
methyl}piperazin-1-yl)-N-({3-nitro-4-[(4-tetrahydro-2H-
pyran-4-ylmorpholin-3-yl)methoxy]phenyl}sulfonyl)-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(3-nitro-4-{[(3S)-1-tetrahy-
dro-2H-pyran-4-ylpiperidin-3-yl]amino}phenyl)sulfo-
nyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({5-cyano-6-[(tetrahydro-2H-
pyran-4-ylmethyl)amino]pyridin-3-yl}sulfonyl)-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(1,1-dioxidothiomorpho-
lin-4-yl)amino]-3-nitrophenyl}sulfonyl)-2-(1H-pyrrolo
[2,3-b]pyridin-5-yloxy)benzamide;

N-[(4-{[(4-aminotetrahydro-2H-pyran-4-yl)methyl]amino}-
3-nitrophenyl)sulfonyl]-4-(4-{[2-(4-chlorophenyl)-4,4-
dimethylcyclohex-1-en-1-yl]methyl}piperazin-1-yl)-2-
(1H-pyrrolo[2,3-b]pyridin-5-yloxy)benzamide;

Trans-4-(4-{[2-(4-chlorophenyl)-4,4-dimethylcyclohex-1-
en-1-yl]methyl}piperazin-1-yl)-N-({5-cyano-6-[(4-mor-
pholin-4-ylcyclohexyl)amino]pyridin-3-yl}sulfonyl)-2-
(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({3-cyano-4-[(tetrahydro-2H-
pyran-4-ylmethyl)amino]phenyl}sulfonyl)-2-(1H-pyrrolo
[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(1S,3R)-3-morpholin-4-
ylcyclopentyl]amino}-3-nitrophenyl)sulfonyl]-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(1R,3S)-3-morpholin-4-
ylcyclopentyl]amino}-3-nitrophenyl)sulfonyl]-2-(1H-
pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(morpholin-2-ylmethyl)
amino]-3-nitrophenyl}sulfonyl)-2-(1H-pyrrolo[2,3-b]py-
ridin-5-yloxy)benzamide;

4-(4-{[2-(4-chlorophenyl)-4,4-dimethylcyclohex-1-en-1-yl]
methyl}piperazin-1-yl)-N-({3-nitro-4-[(tetrahydrofuran-
3-ylmethyl)amino]phenyl}sulfonyl)-2-(1H-pyrrolo[2,3-
b]pyridin-5-yloxy)benzamide;

4-(4-{[2-(4-chlorophenyl)-4,4-dimethylcyclohex-1-en-1-yl]
methyl}piperazin-1-yl)-N-{[4-({1-[cis-3-fluorotetrahy-
dro-2H-pyran-4-yl]piperidin-4-yl}amino)-3-nitrophenyl]
sulfonyl}-2-(1H-pyrrolo[2,3-b]pyridin-5-yloxy)
benzamide;

4-(4-{[2-(4-chlorophenyl)-4,4-dimethylcyclohex-1-en-1-yl]
methyl}piperazin-1-yl)-N-({3-nitro-4-[(1-tetrahydro-2H-
pyran-4-ylazetidin-3-yl)amino]phenyl}sulfonyl)-2-(1H-
pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide;

Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide;

tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate;

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide;

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide;

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide;

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide;

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide;

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide;

4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide;

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid;

4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide;

ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate;

4-(4-{[2-(4-chlorophenyl)-4,4-dimethylcyclohex-1-en-1-yl]methyl}piperazin-1-yl)-N-({4-[4-(morpholin-4-yl)piperidin-1-yl]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide;

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide;

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate;

4-(4-{[2-(4-chlorophenyl)-4,4-dimethylcyclohex-1-en-1-yl]methyl}piperazin-1-yl)-N-({3-(pentafluoro-$\lambda^6$-sulfanyl)-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3R)-tetrahydrofuran-3-ylamino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide;

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide;

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-{4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[9-(4-chlorophenyl)-3-(1,3-difluoropropan-2-yl)-3-azaspiro[5.5]undec-8-en-8-yl]methyl}piperazin-1-yl)-N-{5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[9-(4-chlorophenyl)-3-isopropyl-3-azaspiro[5.5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl)phenyl}sulfonyl)benzamide;

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-cyano cyclohexyl)methyl]amino}-3-nitrophenyl)sulfonyl]-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide;

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoro ethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide;

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide;

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide;

N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohexyl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide;

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide;

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide;

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide;

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H- pyran-4-yl)methoxy]-3-(trifluoromethyl)
phenyl}sulfonyl)-2-(1H-pyrrolo[2,3-b]pyridin-5-yloxy)
benzamide;

4-(4-{[2-(4-chlorophenyl)-4,4-dimethylcyclohex-1-en-1-yl]
methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide;

N-[(3-chloro-4-{[1-(oxetan-3-yl)piperidin-4-yl]
methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;

N-[(3-chloro-4-{[1-(1-methyl-L-prolyl)piperidin-4-yl]
methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide;

N-[(5-chloro-6-{[(2S)-4-cyclopropylmorpholin-2-yl]
methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide;

methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate;

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide;

4-(4-{[2-(4-chlorophenyl)-4,4-dimethylcyclohex-1-en-1-yl]
methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]
methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-[(3-chloro-4-{[4-fluoro-1-(oxetan-3-yl)piperidin-4-yl]
methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide;

4-(4-{[2-(4-chlorophenyl)-5,5-difluorocyclohex-1-en-1-yl]
methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]
methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[5-(4-chlorophenyl)spiro[2.5]oct-5-en-6-yl]
methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-{[5-chloro-6-({4-[cyclopropyl(oxetan-3-yl)amino]
cyclohexyl}methoxy)pyridin-3-yl]sulfonyl}-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide;

4-(4-{[5-(4-chlorophenyl)spiro[2.5]oct-5-en-6-yl]
methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

N-({3-chloro-4-[(4-cyclopropylmorpholin-2-yl)methoxy]
phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[(4-cyclopropylmorpholin-2-yl)methyl]
amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide;

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]
sulfamoyl}pyridin-2-yl)oxy]methyl}-N-ethyl-N-methylmorpholine-4-carboxamide;

N-[(5-chloro-6-{[(4-cyclopropylmorpholin-2-yl)methyl]
amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide;

4-(4-{[2-(4-chlorophenyl)-4,4-dimethylcyclohex-1-en-1-yl]
methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide;

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide;

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-(2-oxaspiro[3.5]non-7-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide;

4-(4-{[2-(4-chlorophenyl)-5,5-bis(fluoromethyl)cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide;

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5-(methoxymethyl)-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide;

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide;

4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide;

N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide;

4-(4-{[2-(4-chlorophenyl)-4,4-dimethylcyclohex-1-en-1-yl]methyl}piperazin-1-yl)-N-{[4-({[4-(methoxymethyl)cyclohexyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; and therapeutically acceptable salts, and metabolites thereof.

In another aspect, the present invention provides compounds of Formula (III)

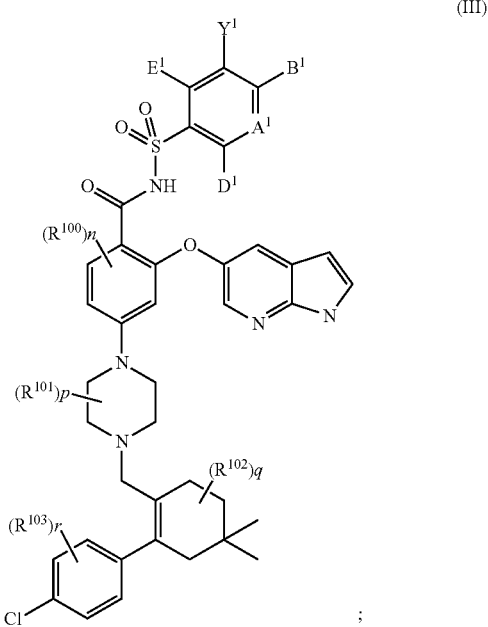

(III)

and therapeutically acceptable salts, and metabolites thereof, wherein $A^1$, $B^1$, $D^1$, $E^1$, and $Y^1$ are as described herein for Formula (I); $R^{100}$ is as described for substituents on $R^{26}$; n is 0, 1, 2, or 3; $R^{101}$ is as described for substituents on $R^{30}$; p is 0, 1, 2, 3, 4, 5, or 6; $R^{102}$ is as described for substituents on $R^{40}$; q is 0, 1, 2, 3, 4, 5, or 6; $R^{103}$ is as described for substituents on $R^{58}$; and r is 0, 1, 2, 3, or 4.

In one embodiment of Formula (III), n, p, r, and q are each 0.

In one embodiment of Formula (III), $A^1$ is N. In another embodiment of Formula (III), $A^1$ is $C(A^2)$. In another embodiment of Formula (III), $A^1$ is $C(A^2)$; and $A^2$ is H, F, Cl, Br, or I. In another embodiment of Formula (III), $A^1$ is $C(A^2)$; and $A^2$ is H.

In one embodiment of Formula (III), $B^1$ is $R^1$, $OR^1$, $NHR^1$, $NHC(O)R^1$, F, Cl, Br, or I. In another embodiment of Formula (III), $A^1$ is $C(A^2)$; $A^2$ is H; and $B^1$ is $NHR^1$. In another embodiment of Formula (III), $A^1$ is $C(A^2)$; $A^2$ is H; and $B^1$ is $OR^1$. In another embodiment of Formula (III), $A^1$ is $C(A^2)$; $A^2$ is H; and $B^1$ is Cl. In another embodiment of Formula (III), $A^1$ is $C(A^2)$; $A^2$ is H; and $B^1$ is $R^1$. In another embodiment of Formula (III), $A^1$ is N; and $B^1$ is $NHR^1$. In another embodiment of Formula (III), $A^1$ is N; and $B^1$ is $OR^1$. In another embodiment of Formula (III), $A^1$ is N; and $B^1$ is Cl. In another embodiment of Formula (III), $A^1$ is N; and $B^1$ is $R^1$.

In one embodiment of Formula (III), $D^1$ is H or Cl. In another embodiment of Formula (III), $A^1$ is $C(A^2)$; $A^2$ is H; $B^1$ is $NHR^1$; and $D^1$ is H. In another embodiment of Formula (III), $A^1$ is $C(A^2)$; $A^2$ is H; $B^1$ is $NHR^1$; and $D^1$ is Cl. In another embodiment of Formula (III), $A^1$ is $C(A^2)$; $A^2$ is H; $B^1$ is $OR^1$; and $D^1$ is H. In another embodiment of Formula (III), $A^1$ is $C(A^2)$; $A^2$ is H; $B^1$ is Cl; and $D^1$ is H. In another embodiment of Formula (III), $A^1$ is $C(A^2)$; $A^2$ is H; $B^1$ is $R^1$; and $D^1$ is H. In another embodiment of Formula (III), $A^1$ is N; $B^1$ is $NHR^1$; and $D^1$ is H. In another embodiment of Formula (III), $A^1$ is N; $B^1$ is $NHR^1$; and $D^1$ is Cl. In another embodiment of Formula (III), $A^1$ is N; $B^1$ is $OR^1$; and $D^1$ is H. In another embodiment of Formula (III), $A^1$ is N; $B^1$ is Cl; and $D^1$ is H. In another embodiment of Formula (III), $A^1$ is N; $B^1$ is $R^1$; and $D^1$ is H.

In one embodiment of Formula (III), $E^1$ is H. In another embodiment of Formula (III), $A^1$ is $C(A^2)$; $A^2$ is H; $B^1$ is $NHR^1$; $D^1$ is H; and $E^1$ is H. In another embodiment of Formula (III), $A^1$ is $C(A^2)$; $A^2$ is H; $B^1$ is $NHR^1$; $E^1$ is H; and $D^1$ is Cl. In another embodiment of Formula (III), $A^1$ is $C(A^2)$; $A^2$ is H; $B^1$ is OR %; $D^1$ is H; and $E^1$ is H. In another embodiment of Formula (III), $A^1$ is $C(A^2)$; $A^2$ is H; $B^1$ is Cl; $D^1$ is H; and $E^1$ is H. In another embodiment of Formula (III), $A^1$ is $C(A^2)$; $A^2$ is H; $B^1$ is $R^1$; $D^1$ is H; and $E^1$ is H. In another embodiment of Formula (III), $A^1$ is N; $B^1$ is $NHR^1$; $D^1$ is H; and $E^1$ is H. In another embodiment of Formula (III), $A^1$ is N; $B^1$ is $NHR^1$; $E^1$ is H; and $D^1$ is Cl. In another embodiment of Formula (III), $A^1$ is N; $B^1$ is $OR^1$; $D^1$ is H; and $E^1$ is H. In another embodiment of Formula (III), $A^1$ is N; $B^1$ is Cl; $D^1$ is H; and $E^1$ is H. In another embodiment of Formula (III), $A^1$ is N; $B^1$ is $R^1$; $D^1$ is H; and $E^1$ is H.

In one embodiment of Formula (III), $Y^1$ is H, CN, $NO_2$, F, Cl, Br, I, $CF_3$, $R^{17}$, $OR^{17}$, $SR^{17}$, $SO_2R^{17}$, or $C(O)NH_2$. In another embodiment of Formula (III), $Y^1$ is H. In another embodiment of Formula (III), $Y^1$ is CN. In another embodiment of Formula (III), $Y^1$ is F, Cl, Br, or I. In another embodiment of Formula (III), $Y^1$ is $CF_3$. In another embodiment of Formula (III), $Y^1$ is $SR^{17}$. In another embodiment of Formula (III), $Y^1$ is $OR^{17}$. In another embodiment of Formula (III), $Y^1$ is $NO_2$. In another embodiment of Formula (III), $Y^1$ is $SO_2R^{17}$; wherein $R^{17}$ is as defined herein. In another embodiment of Formula (III), $Y^1$ is $SO_2R^{17}$; wherein $R^{17}$ is alkyl. In another embodiment of Formula (III), $Y^1$ is $R^{17}$; wherein $R^{17}$ is alkynyl. In another embodiment of Formula (III), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (III), $A^1$ is $C(A^2)$; $A^2$ is H; $B^1$ is $NHR^1$; $D^1$ is H; $E^1$ is H; and $Y^1$ is $NO_2$. In another embodiment of Formula (III), $A^1$ is $C(A^2)$; $A^2$ is H; $B^1$ is $NHR^1$; $D^1$ is H; $E^1$ is H; and $Y^1$ is $SO_2R^{17}$; wherein $R^{17}$ is alkyl substituted with three F. In another embodiment of Formula (III), $A^1$ is N; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (III), $A^1$ is N; $B^1$ is $NHR^1$; $D^1$ is H; $E^1$ is H; and $Y^1$ is NO$_2$. In another embodiment of Formula (III), A$^1$ is N; B$^1$ is NHR$^1$; D$^1$ is H; E$^1$ is H; and Y$^1$ is SO$_2$R$^{17}$; wherein R$^{17}$ is alkyl substituted with three F.

In one embodiment of Formula (III), Y$^1$ and B$^1$, together with the atoms to which they are attached, are benzene. In another embodiment of Formula (III), Y$^1$ and B$^1$, together with the atoms to which they are attached, are heteroarene. In another embodiment of Formula (III), A$^1$ is C(A$^2$); A$^2$, G$^1$, E$^1$, and D$^1$ are independently selected H; and Y$^1$ and B$^1$, together with the atoms to which they are attached, are benzene. In another embodiment of Formula (III), A$^1$ is C(A$^2$); A$^2$, G$^1$, E$^1$, and D$^1$ are independently selected H; and Y$^1$ and B$^1$, together with the atoms to which they are attached, are heteroarene.

In one embodiment of Formula (III), R$^1$ is R$^4$ or R$^5$. In one embodiment of Formula (III), R$^1$ is R$^4$. In one embodiment of Formula (III), R$^1$ is R$^5$. In one embodiment of Formula (III), R$^1$ is R$^4$; and R$^4$ is cycloalkyl, cycloalkenyl, heterocycloalkyl or heterocycloalkenyl. In one embodiment of Formula (III), R$^1$ is R$^4$; and R$^4$ is cycloalkyl or heterocycloalkyl. In one embodiment of Formula (III), R$^1$ is R$^4$; and R$^4$ is cycloalkyl. In one embodiment of Formula (III), R$^1$ is R$^4$; and R$^4$ is heterocycloalkyl.

In one embodiment of Formula (III), R$^1$ is R$^4$; and R$^4$ is cycloalkyl; wherein R$^4$ is unsubstituted or substituted as defined herein. In another embodiment of Formula (III), R$^1$ is R$^4$; and R$^4$ is cycloalkyl; wherein the cycloalkyl ring is substituted as defined herein. In another embodiment of Formula (III), R$^1$ is R$^4$; and R$^4$ is cycloalkyl; wherein the cycloalkyl ring is substituted with R$^{57}$ or N(R$^{57}$)$_2$. In another embodiment of Formula (III), R$^1$ is R$^4$; and R$^4$ is cycloalkyl; wherein the cycloalkyl ring is cyclohexyl; and wherein the cyclohexyl ring is substituted with R$^{57}$; and R$^{57}$ is R$^{60}$. In another embodiment of Formula (III), R$^1$ is R$^4$; R$^4$ is cycloalkyl; wherein the cycloalkyl ring is cyclohexyl; and wherein the cyclohexyl ring is substituted with R$^{57}$; R$^{57}$ is R$^{60}$; and R$^{60}$ is heterocycloalkyl. In another embodiment of Formula (III), R$^1$ is R$^4$; R$^4$ is cycloalkyl; wherein the cycloalkyl ring is cyclohexyl; and wherein the cyclohexyl ring is substituted with R$^{57}$; R$^{57}$ is R$^{60}$; R$^{60}$ is heterocycloalkyl; wherein the heterocycloalkyl ring is morpholinyl. In another embodiment of Formula (III), R$^1$ is R$^4$; and R$^4$ is cycloalkyl; wherein the cycloalkyl ring is substituted with N(R$^{57}$)$_2$. In another embodiment of Formula (III), R$^1$ is R$^4$; and R$^4$ is cycloalkyl; wherein the cycloalkyl ring is cyclohexyl; and wherein the cyclohexyl ring is substituted with N(R$^{57}$)$_2$. In another embodiment of Formula (III), R$^1$ is R$^4$; and R$^4$ is cycloalkyl; wherein the cycloalkyl ring is cyclohexyl; and wherein the cyclohexyl ring is substituted with N(R$^{57}$)$_2$; R$^{57}$ is R$^{61}$; and R$^{61}$ is alkyl which is unsubstituted or substituted with R$^{62}$. In another embodiment of Formula (III), R$^1$ is R$^4$; and R$^4$ is cycloalkyl; wherein the cycloalkyl ring is cyclohexyl; and wherein the cyclohexyl ring is substituted with R$^{57}$; R$^{57}$ is R$^{61}$; and R$^{61}$ is alkyl which is unsubstituted or substituted with R$^{62}$; R$^{62}$ is R$^{65}$; and R$^{65}$ is cycloalkyl. In another embodiment of Formula (III), R$^1$ is R$^4$; and R$^4$ is cycloalkyl; wherein the cycloalkyl ring is cyclohexyl; and wherein the cyclohexyl ring is substituted with R$^{57}$; R$^{57}$ is R$^{61}$; and R$^{61}$ is alkyl which is substituted with R$^{62}$; R$^{62}$ is R$^{65}$; and R$^{65}$ is cyclopropyl.

In one embodiment of Formula (III), R$^1$ is R$^4$; and R$^4$ is heterocycloalkyl; wherein R$^4$ is unsubstituted or substituted as defined herein. In another embodiment of Formula (III), R$^1$ is R$^4$; and R$^4$ is heterocycloalkyl; wherein the heterocycloalkyl ring is substituted as defined herein. In another embodiment of Formula (III), R$^1$ is R$^4$; and R$^4$ is heterocycloalkyl; wherein the heterocycloalkyl ring is substituted with R$^{57}$. In another embodiment of Formula (III), R$^1$ is R$^4$; and R$^4$ is heterocycloalkyl; wherein the heterocycloalkyl ring is piperidinyl or piperizinyl; and wherein the heterocycloalkyl ring is substituted with R$^{57}$; and R$^{57}$ is R$^{60}$ or R$^{61}$. In another embodiment of Formula (III), R$^1$ is R$^4$; R$^4$ is heterocycloalkyl; wherein the heterocycloalkyl ring is piperidinyl or piperizinyl; and wherein the piperidinyl or piperizinyl ring is substituted with R$^{57}$; R$^{57}$ is R$^{60}$ or R$^{61}$; R$^{60}$ is heterocycloalkyl; and R$^{61}$ is alkyl. In another embodiment of Formula (III), R$^1$ is R$^4$; R$^4$ is heterocycloalkyl; wherein the heterocycloalkyl ring is piperidinyl or piperizinyl; and wherein the piperidinyl or piperizinyl ring is substituted with R$^{57}$; R$^{57}$ is R$^{60}$; R$^{60}$ is heterocycloalkyl; wherein the heterocycloalkyl is tetrahydropyranyl. In another embodiment of Formula (III), R$^1$ is R$^4$; R$^4$ is heterocycloalkyl; wherein the heterocycloalkyl ring is piperidinyl or piperizinyl; and wherein the piperidinyl or piperizinyl ring is substituted with R$^{57}$; R$^{57}$ is R$^{61}$; R$^{61}$ is alkyl; and the alkyl is methyl. In another embodiment of Formula (III), R$^1$ is R$^4$; R$^4$ is heterocycloalkyl; wherein the heterocycloalkyl ring is piperidinyl or piperizinyl; and wherein the piperidinyl or piperizinyl ring is substituted with C(O)OR$^{57}$; R$^{57}$ is R$^{61}$; R$^{61}$ is alkyl; and the alkyl is methyl.

In one embodiment of Formula (III), R$^1$ is R$^5$; and R$^5$ is alkyl which is unsubstituted or substituted. In one embodiment of Formula (III), R$^1$ is R$^5$; and R$^5$ is alkyl which is unsubstituted or substituted with R$^7$, OR$^7$, OH, CN, or F. In another embodiment of Formula (III), R$^1$ is R$^5$; and R$^5$ is alkyl which is substituted with R$^7$, OR$^7$, NHR$^7$, or N(R$^7$)$_2$.

In one embodiment of Formula (III), R$^7$ is R$^8$, R$^9$, R$^{10}$ or R$^{11}$ which are unsubstituted or substituted as defined herein. In another embodiment of Formula (III), R$^7$ is R$^8$ which is unsubstituted or substituted as defined herein. In another embodiment of Formula (III), R$^7$ is R$^9$ which is unsubstituted or substituted as defined herein. In another embodiment of Formula (III), R$^7$ is R$^{10}$ which is unsubstituted or substituted as defined herein. In another embodiment of Formula (III), R$^7$ is R$^{11}$ which is unsubstituted or substituted as defined herein.

In one embodiment of Formula (III), R$^8$ is phenyl which is unsubstituted or substituted as defined herein.

In one embodiment of Formula (III), R$^9$ is heteroaryl which is unsubstituted or substituted as defined herein. In another embodiment of Formula (III), R$^9$ is furanyl; which is unsubstituted or substituted as defined herein. In another embodiment of Formula (III), R$^9$ is furanyl; which is unsubstituted.

In one embodiment of Formula (III), R$^{10}$ is cycloalkyl, cycloalkenyl, heterocycloalkyl or heterocycloalkenyl, heterocycloalkyl which are unsubstituted or substituted as defined herein. In another embodiment of Formula (III), R$^{10}$ is heterocycloalkyl which is unsubstituted or substituted as defined herein. In another embodiment of Formula (III), R$^{10}$ is tetrahydrofuranyl, tetrahydropyranyl, morpholinyl, dioxanyl, oxetanyl, piperidinyl, or pyrrolidinyl, which are unsubstituted or substituted as defined herein. In another embodiment of Formula (III), R$^{10}$ is tetrahydropyranyl; which is unsubstituted or substituted as defined herein. In another embodiment of Formula (III), R$^{10}$ is morpholinyl; which is unsubstituted or substituted as defined herein. In another embodiment of Formula (III), R$^{10}$ is cycloalkyl which is unsubstituted or substituted as defined herein. In another embodiment of Formula (III), R$^{10}$ is cycloalkyl which is unsubstituted or substituted as defined herein. In another embodiment of Formula (III), R$^{10}$ is cyclohexyl, cyclopropyl, cyclobutyl, or bicyclo[2.2.1]heptanyl; which is unsubstituted or substituted as defined herein. In another embodiment of Formula (III), R$^{10}$ is heterocycloalkyl which is fused with R$^{10A}$; and R$^{10A}$ is heteroarene. In another embodiment of Formula (III), R$^{10}$ is 5,6,7,8-tetrahydroimidazo[1,2-a]pyridinyl.

In one embodiment of Formula (III), $R^{11}$ is alkyl, alkenyl or alkynyl which are unsubstituted or substituted as defined herein. In another embodiment of Formula (III), $R^{11}$ is alkyl. In another embodiment of Formula (III), $R^{11}$ is methyl; which is unsubstituted or substituted as defined herein. In another embodiment of Formula (III), $R^{11}$ is alkyl; which is substituted as defined herein. In another embodiment of Formula (III), $R^{11}$ is alkyl; which is substituted with $R^{12}$, $OR^{12}$, or $CF_3$. In another embodiment of Formula (III), $R^{11}$ is alkyl; which is substituted with $OR^{12}$; $R^{12}$ is $R^{16}$; and $R^{16}$ is alkyl. In another embodiment of Formula (III), $R^{11}$ is alkyl; which is substituted with $CF_3$. In another embodiment of Formula (III), $R^{11}$ is alkyl; which is substituted with $R^{12}$; $R^{12}$ is $R^{14}$; and $R^{14}$ is heteroaryl.

In one embodiment of Formula (III),
n, p, r, and q are each 0;
$A^1$ is N or $C(A^2)$;
$A^2$ is H, F, Br, I, or Cl;
$B^1$ is $R^1$, $OR^1$, $NHR^1$, $NHC(O)R^1$, F, Br, I or Cl;
$D^1$ is H, F, Br, I, or Cl;
$E^1$ is H; and
$Y^1$ is H, CN, $NO_2$, F, Cl, Br, I, $CF_3$, $R^{17}$, $OR^{17}$, $SR^{17}$, $SO_2R^{17}$, or $C(O)NH_2$; or
$Y^1$ and $B^1$, together with the atoms to which they are attached, are benzene, heteroarene, or heterocycloalkene; and
$A^2$, $D^1$, and $E^1$ are independently selected H;
$R^1$ is $R^4$ or $R^5$;
$R^4$ is cycloalkyl, or heterocycloalkyl;
$R^5$ is alkyl, or alkynyl, each of which is unsubstituted or substituted with one or two or three of independently selected $R^7$, $OR^7$, $NHR^7$, $N(R^7)_2$, CN, OH, F, Cl, Br or I;
$R^7$ is $R^8$, $R^9$, $R^{10}$, or $R^{11}$;
$R^8$ is phenyl;
$R^9$ is heteroaryl;
$R^{10}$ is cycloalkyl, cycloalkenyl, or heterocycloalkyl; each of which is unfused or fused with $R^{10A}$, $R^{10A}$ is heteroarene;
$R^{11}$ is alkyl each of which is unsubstituted or substituted with one or two or three of independently selected $R^{12}$, $OR^{12}$ or $CF_3$;
$R^{12}$ is $R^{14}$ or $R^{16}$;
$R^{14}$ is heteroaryl;
$R^{16}$ is alkyl;
$R^{17}$ is $R^{21}$;
$R^{21}$ is alkyl, or alkynyl, each of which is unsubstituted or substituted with one or two or three of independently selected $R^{22}$, F, Cl, Br or I;
$R^{22}$ is $R^{25}$;
$R^{25}$ is heterocycloalkyl;
wherein the cyclic moieties represented by $Y^1$ and $B^1$ together, $R^4$, $R^8$, $R^{10}$, and $R^{25}$, are independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br or I;
$R^{57A}$ is spiroalkyl, or spiroheteroalkyl;
$R^{57}$ is $R^{58}$, $R^{60}$ or $R^{61}$;
$R^{58}$ is phenyl;
$R^{60}$ is cycloalkyl, or heterocycloalkyl;
$R^{61}$ is alkyl which is unsubstituted or substituted with one or two or three of independently selected $R^{62}$, $OR^{62}$, $N(R^{62})_2$, C(O)OH, CN, F, Cl, Br or I;
$R^{62}$ is $R^{65}$, or $R^{66}$;
$R^{65}$ is cycloalkyl, or heterocycloalkyl;
$R^{66}$ is alkyl which is unsubstituted or substituted with $OR^{67}$;
$R^{67}$ is alkyl;

wherein the cyclic moieties represented by $R^{57A}$, $R^{58}$, and $R^{60}$ are unsubstituted or substituted with one or two or three or four of independently selected $R^{68}$, F, Cl, Br or I;
$R^{68}$ is $R^{71}$ or $R^{72}$;
$R^{71}$ is heterocycloalkyl; and
$R^{72}$ is alkyl, which is unsubstituted or substituted with one or two F.

Still another embodiment pertains to compounds having Formula (III), which are 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-(2-naphthylsulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide;

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide;

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide;

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide;

N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide;

tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate;

4-(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide;

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-morpholin-4-ylcyclohexyl)methyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide;

N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[1-tetrahydro-2H-pyran-4-ylazetidin-3-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide;

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide;

Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide;

tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate;

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide;

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[trans-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide;

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide;

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide;

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[cis-3-morpholin-4-yl-cyclopentyl]methyl}amino)-3-nitrophenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide;

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide;

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid;

4-(4-{[2-(4-chlorophenyl)-4,4-dimethylcyclohex-1-en-1-yl]methyl}piperazin-1-yl)-N-{[3-nitro-4-({[4-(oxetan-3-yl)

morpholin-2-yl]methyl}amino)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide;

ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate;

4-(4-{[2-(4-chlorophenyl)-4,4-dimethylcyclohex-1-en-1-yl]methyl}piperazin-1-yl)-N-({-4-[4-(morpholin-4-yl)piperidin-1-yl]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide;

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide;

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate;

4-(4-{[2-(4-chlorophenyl)-4,4-dimethylcyclohex-1-en-1-yl]methyl}piperazin-1-yl)-N-({3-(pentafluoro-$\lambda^6$-sulfanyl)-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(3R)-tetrahydrofuran-3-ylamino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide;

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide;

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide;

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoro ethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide;

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-cyano cyclohexyl)methyl]amino}-3-nitrophenyl)sulfonyl]-2-(1H-pyrrolo[2,3-b]pyridin-5-yloxy)benzamide;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide;

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide;

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide;

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{5-fluoro-6-(tetrahydro-2H-pyran-4-ylmethoxy)pyridin-3-yl]sulfonyl}-2-(1H-pyrrolo[2,3-b]pyridin-5-yloxy)benzamide;

N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide;

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide;

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide;

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide;

N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide;

N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide;

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate;

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide;

4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide;

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[5-(4-chlorophenyl)spiro[2.5]oct-5-en-6-yl]
methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide;

N-({3-chloro-4-[(4-cyclopropylmorpholin-2-yl)methoxy]
phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-[(3-chloro-4-{[(4-cyclopropylmorpholin-2-yl)methyl]
amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)
amino]methyl}-N-ethyl-N-methylmorpholine-4-carboxamide;

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]
sulfamoyl}pyridin-2-yl)oxy]methyl}-N-ethyl-N-methylmorpholine-4-carboxamide;

N-[(5-chloro-6-{[(4-cyclopropylmorpholin-2-yl)methyl]
amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide;

4-(4-{[2-(4-chlorophenyl)-4,4-dimethylcyclohex-1-en-1-yl]
methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide;

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(trans-4-hydroxy-4-methylcyclohexyl)
methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide;

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide;

N-[(5-chloro-6-{[4-fluoro-1-(oxetan-3-yl)piperidin-4-yl]
methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide;

N-({5-chloro-6-[(trans-4-hydroxy-4-methylcyclohexyl)
methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide;

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{3-nitro-4-(2-oxaspiro[3.5]
non-7-ylmethoxy)phenyl]sulfonyl}-2-(1H-pyrrolo[2,3-b]
pyridin-5-yloxy)benzamide;

4-(4-{[2-(4-chlorophenyl)-4,4-dimethylcyclohex-1-en-1-yl]
methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-({4-[(4-cyclopropylmorpholin-2-yl)methoxy]-3-nitrophenyl}sulfonyl)-2-(1H-pyrrolo
[2,3-b]pyridin-5-yloxy)benzamide;

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide;

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide;

N-({3-chloro-4-[(trans-4-hydroxy-4-methylcyclohexyl)
methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]
methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)
benzamide;

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide;

4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide;

N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide;

4-(4-{[2-(4-chlorophenyl)-4,4-dimethylcyclohex-1-en-1-yl]methyl}piperazin-1-yl)-N-{4-({[4-(methoxymethyl)cyclohexyl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

and therapeutically acceptable salts, and metabolites thereof.

In another aspect, the present invention provides compounds of Formula (IV)

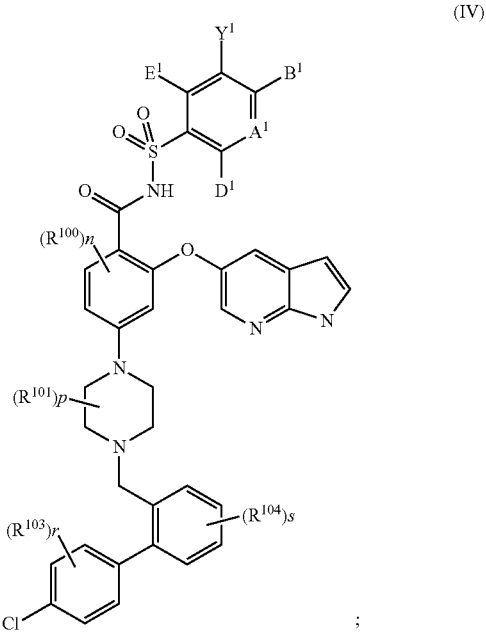

(IV)

and therapeutically acceptable salts, and metabolites thereof, wherein $A^1$, $B^1$, $D^1$, $E^1$, and $Y^1$ are as described herein for Formula (I); $R^{100}$ is as described for substituents on $R^{26}$; n is 0, 1, 2, or 3; $R^{101}$ is as described for substituents on $R^{30}$; p is 0, 1, 2, 3, 4, 5, or 6; $R^{104}$ is as described for substituents on $R^{38}$; s is 0, 1, 2, 3, 4, 5, or 6; $R^{103}$ is as described for substituents on $R^{58}$; and r is 0, 1, 2, 3, or 4.

In one embodiment of Formula (IV), n, p, r, and s are each 0.

In one embodiment of Formula (IV), $A^1$ is N. In another embodiment of Formula (IV), $A^1$ is $C(A^2)$. In another embodiment of Formula (IV), $A^1$ is $C(A^2)$; and $A^2$ is H, F, Cl, Br, or I. In another embodiment of Formula (IV), $A^1$ is $C(A^2)$; and $A^2$ is H.

In one embodiment of Formula (IV), $B^1$ is $R^1$, $OR^1$, $NHR^1$, $NHC(O)R^1$, F, Cl, Br, or I. In another embodiment of Formula (IV), $A^1$ is $C(A^2)$; $A^2$ is H; and $B^1$ is $NHR^1$. In another embodiment of Formula (IV), $A^1$ is $C(A^2)$; $A^2$ is H; and $B^1$ is $OR^1$. In another embodiment of Formula (IV), $A^1$ is $C(A^2)$; $A^2$ is H; and $B^1$ is Cl. In another embodiment of Formula (IV), $A^1$ is $C(A^2)$; $A^2$ is H; and $B^1$ is $R^1$. In another embodiment of Formula (IV), $A^1$ is N; and $B^1$ is $NHR^1$. In another embodiment of Formula (IV), $A^1$ is N; and $B^1$ is $OR^1$. In another embodiment of Formula (IV), $A^1$ is N; and $B^1$ is Cl. In another embodiment of Formula (IV), $A^1$ is N; and $B^1$ is $R^1$.

In one embodiment of Formula (IV), $D^1$ is H or Cl. In another embodiment of Formula (IV), $A^1$ is $C(A^2)$; $A^2$ is H; $B^1$ is $NHR^1$; and $D^1$ is H. In another embodiment of Formula (IV), $A^1$ is $C(A^2)$; $A^2$ is H; $B^1$ is $NHR^1$; and $D^1$ is Cl. In another embodiment of Formula (IV), $A^1$ is $C(A^2)$; $A^2$ is H; $B^1$ is $OR^1$; and $D^1$ is H. In another embodiment of Formula (IV), $A^1$ is $C(A^2)$; $A^2$ is H; $B^1$ is Cl; and $D^1$ is H. In another embodiment of Formula (IV), $A^1$ is $C(A^2)$; $A^2$ is H; $B^1$ is $R^1$; and $D^1$ is H. In another embodiment of Formula (IV), $A^1$ is N; $B^1$ is $NHR^1$; and $D^1$ is H. In another embodiment of Formula (IV), $A^1$ is N; $B^1$ is $NHR^1$; and $D^1$ is Cl. In another embodiment of Formula (IV), $A^1$ is N; $B^1$ is $OR^1$; and $D^1$ is H. In another embodiment of Formula (IV), $A^1$ is N; $B^1$ is Cl; and $D^1$ is H. In another embodiment of Formula (IV), $A^1$ is N; $B^1$ is $R^1$; and $D^1$ is H.

In one embodiment of Formula (IV), $E^1$ is H. In another embodiment of Formula (IV), $A^1$ is $C(A^2)$; $A^2$ is H; $B^1$ is $NHR^1$; $D^1$ is H; and $E^1$ is H. In another embodiment of Formula (IV), $A^1$ is $C(A^2)$; $A^2$ is H; $B^1$ is $NHR^1$; $E^1$ is H; and $D^1$ is Cl. In another embodiment of Formula (IV), $A^1$ is $C(A^2)$; $A^2$ is H; $B^1$ is OR %; $D^1$ is H; and $E^1$ is H. In another embodiment of Formula (IV), $A^1$ is $C(A^2)$; $A^2$ is H; $B^1$ is Cl; $D^1$ is H; and $E^1$ is H. In another embodiment of Formula (IV), $A^1$ is $C(A^2)$; $A^2$ is H; $B^1$ is $R^1$; $D^1$ is H; and $E^1$ is H. In another embodiment of Formula (IV), $A^1$ is N; $B^1$ is $NHR^1$; $D^1$ is H; and $E^1$ is H. In another embodiment of Formula (IV), $A^1$ is N; $B^1$ is $NHR^1$; $E^1$ is H; and $D^1$ is Cl. In another embodiment of Formula (IV), $A^1$ is N; $B^1$ is $OR^1$; $D^1$ is H; and $E^1$ is H. In another embodiment of Formula (IV), $A^1$ is N; $B^1$ is Cl; $D^1$ is H; and $E^1$ is H. In another embodiment of Formula (IV), $A^1$ is N; $B^1$ is $R^1$; $D^1$ is H; and $E^1$ is H.

In one embodiment of Formula (IV), $Y^1$ is H, CN, $NO_2$, F, Cl, Br, I, $CF_3$, $R^{17}$, $OR^{17}$, $SR^{17}$, $SO_2R^{17}$, or $C(O)NH_2$. In another embodiment of Formula (IV), $Y^1$ is H. In another embodiment of Formula (IV), $Y^1$ is CN. In another embodiment of Formula (IV), $Y^1$ is F, Cl, Br, or I. In another embodiment of Formula (IV), $Y^1$ is $CF_3$. In another embodiment of Formula (IV), $Y^1$ is $SR^{17}$. In another embodiment of Formula (IV), $Y^1$ is $OR^{17}$. In another embodiment of Formula (IV), $Y^1$ is $NO_2$. In another embodiment of Formula (IV), $Y^1$ is $SO_2R^{17}$; wherein $R^{17}$ is as defined herein. In another embodiment of Formula (IV), $Y^1$ is $SO_2R^{17}$; wherein $R^{17}$ is alkyl. In another embodiment of Formula (IV), $Y^1$ is $R^{17}$; wherein $R^{17}$ is alkynyl. In another embodiment of Formula (IV), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (IV), $A^1$ is $C(A^2)$; $A^2$ is H; $B^1$ is $NHR^1$; $D^1$ is H; $E^1$ is H; and $Y^1$ is $NO_2$. In another embodiment of Formula (IV), $A^1$ is $C(A^2)$; $A^2$ is H; $B^1$ is $NHR^1$; $D^1$ is H; $E^1$ is H; and $Y^1$ is $SO_2R^{17}$; wherein $R^{17}$ is alkyl substituted with three F. In another embodiment of Formula (IV), $A^1$ is N; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (IV), $A^1$ is N; $B^1$ is $NHR^1$; $D^1$ is H; $E^1$ is H; and $Y^1$ is $NO_2$. In another embodiment of Formula (IV), $A^1$ is N; $B^1$ is $NHR^1$; $D^1$ is H; $E^1$ is H; and $Y^1$ is $SO_2R^{17}$; wherein $R^{17}$ is alkyl substituted with three F.

In one embodiment of Formula (IV), $Y^1$ and $B^1$, together with the atoms to which they are attached, are benzene. In another embodiment of Formula (IV), $Y^1$ and $B^1$, together with the atoms to which they are attached, are heteroarene. In another embodiment of Formula (IV), $A^1$ is $C(A^2)$; $A^2$, $G^1$, $E^1$, and $D^1$ are independently selected H; and $Y^1$ and $B^1$, together with the atoms to which they are attached, are benzene. In another embodiment of Formula (IV), $A^1$ is $C(A^2)$; $A^2$, $G^1$, $E^1$, and $D^1$ are independently selected H; and $Y^1$ and $B^1$, together with the atoms to which they are attached, are heteroarene.

In one embodiment of Formula (IV), $R^1$ is $R^4$ or $R^5$. In one embodiment of Formula (IV), $R^1$ is $R^4$. In one embodiment of Formula (IV), $R^1$ is $R^5$. In one embodiment of Formula (IV), $R^1$ is $R^4$; and $R^4$ is cycloalkyl, cycloalkenyl, heterocycloalkyl or heterocycloalkenyl. In one embodiment of Formula (IV), $R^1$ is $R^4$; and $R^4$ is cycloalkyl or heterocycloalkyl. In one embodiment of Formula (IV), $R^1$ is $R^4$; and $R^4$ is cycloalkyl. In one embodiment of Formula (IV), $R^1$ is $R^4$; and $R^4$ is heterocycloalkyl.

In one embodiment of Formula (IV), $R^1$ is $R^4$; and $R^4$ is cycloalkyl; wherein $R^4$ is unsubstituted or substituted as defined herein. In another embodiment of Formula (IV), $R^1$ is $R^4$; and $R^4$ is cycloalkyl; wherein the cycloalkyl ring is substituted as defined herein. In another embodiment of Formula (IV), $R^1$ is $R^4$; and $R^4$ is cycloalkyl; wherein the cycloalkyl ring is substituted with $R^{57}$ or $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{60}$. In another embodiment of Formula (IV), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (IV), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl. In another embodiment of Formula (IV), $R^1$ is $R^4$; and $R^4$ is cycloalkyl; wherein the cycloalkyl ring is substituted with $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $N(R^{57})_2$; $R^{57}$ is $R^{61}$; and $R^{61}$ is alkyl which is unsubstituted or substituted with $R^{62}$. In another embodiment of Formula (IV), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is unsubstituted or substituted with $R^{62}$, $R^{62}$ is $R^{65}$; and $R^{65}$ is cycloalkyl. In another embodiment of Formula (IV), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is substituted with $R^{62}$; $R^{62}$ is $R^{65}$; and $R^{65}$ is cyclopropyl In one embodiment of Formula (IV), $R^1$ is $R^4$; and $R^4$ is heterocycloalkyl; wherein $R^4$ is unsubstituted or substituted as defined herein. In another embodiment of Formula (IV), $R^1$ is $R^4$; and $R^4$ is heterocycloalkyl; wherein the heterocycloalkyl ring is substituted as defined herein. In another embodiment of Formula (IV), $R^1$ is $R^4$; and $R^4$ is heterocycloalkyl; wherein the heterocycloalkyl ring is substituted with $R^{57}$. In another embodiment of Formula (IV), $R^1$ is $R^4$; and $R^4$ is heterocycloalkyl; wherein the heterocycloalkyl ring is piperidinyl or piperizinyl; and wherein the heterocycloalkyl ring is substituted with $R^{57}$; and $R^{57}$ is $R^{60}$ or $R^{61}$. In another embodiment of Formula (IV), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$ or $R^{61}$; $R^{60}$ is heterocycloalkyl; and $R^{61}$ is alkyl. In another embodiment of Formula (IV), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$; $R^{60}$ is heterocycloalkyl; wherein the heterocycloalkyl is tetrahydropyranyl. In another embodiment of Formula (IV), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{61}$; $R^{61}$ is alkyl; and the alkyl is methyl. In another embodiment of Formula (IV), $R^1$ is $R^4$; $R^4$ is heterocycloalkyl; wherein the heterocycloalkyl ring is piperidinyl or piperizinyl; and wherein the piperidinyl or piperizinyl ring is substituted with $C(O)OR^{57}$; $R^{57}$ is $R^{61}$; $R^{61}$ is alkyl; and the alkyl is methyl.

In one embodiment of Formula (IV), $R^1$ is $R^5$; and $R^5$ is alkyl which is unsubstituted or substituted. In one embodiment of Formula (IV), $R^1$ is $R^5$; and $R^5$ is alkyl which is unsubstituted or substituted with $R^7$, $OR^7$, OH, CN, or F. In another embodiment of Formula (IV), $R^1$ is $R^5$; and $R^5$ is alkyl which is substituted with $R^7$, $OR^7$, $NHR^7$, or $N(R^7)_2$.

In one embodiment of Formula (IV), $R^7$ is $R^8$, $R^9$, $R^{10}$ or $R^{11}$ which are unsubstituted or substituted as defined herein. In another embodiment of Formula (IV), $R^7$ is $R^8$ which is unsubstituted or substituted as defined herein. In another embodiment of Formula (IV), $R^7$ is $R^9$ which is unsubstituted or substituted as defined herein. In another embodiment of Formula (IV), $R^7$ is $R^{10}$ which is unsubstituted or substituted as defined herein. In another embodiment of Formula (IV), $R^7$ is $R^{11}$ which is unsubstituted or substituted as defined herein.

In one embodiment of Formula (IV), $R^8$ is phenyl which is unsubstituted or substituted as defined herein.

In one embodiment of Formula (IV), $R^9$ is heteroaryl which is unsubstituted or substituted as defined herein. In another embodiment of Formula (IV), $R^9$ is furanyl; which is unsubstituted or substituted as defined herein. In another embodiment of Formula (IV), $R^9$ is furanyl; which is unsubstituted.

In one embodiment of Formula (IV), $R^{10}$ is cycloalkyl, cycloalkenyl, heterocycloalkyl or heterocycloalkenyl, heterocycloalkyl which are unsubstituted or substituted as defined herein. In another embodiment of Formula (IV), $R^{10}$ is heterocycloalkyl which is unsubstituted or substituted as defined herein. In another embodiment of Formula (IV), $R^{10}$ is tetrahydrofuranyl, tetrahydropyranyl, morpholinyl, dioxanyl, oxetanyl, piperidinyl, or pyrrolidinyl, which are unsubstituted or substituted as defined herein. In another embodiment of Formula (IV), $R^{10}$ is tetrahydropyranyl; which is unsubstituted or substituted as defined herein. In another embodiment of Formula (IV), $R^{10}$ is morpholinyl; which is unsubstituted or substituted as defined herein. In another embodiment of Formula (IV), $R^{10}$ is cycloalkyl which is unsubstituted or substituted as defined herein. In another embodiment of Formula (IV), $R^{10}$ is cycloalkyl which is unsubstituted or substituted as defined herein. In another embodiment of Formula (IV), $R^{10}$ is cyclohexyl, cyclopropyl, cyclobutyl, or bicyclo[2.2.1]heptanyl, which is unsubstituted or substituted as defined herein. In another embodiment of Formula (IV), $R^{10}$ is heterocycloalkyl which is fused with $R^{10A}$; and $R^{10A}$ is heteroarene. In another embodiment of Formula (IV), $R^{10}$ is 5,6,7,8-tetrahydroimidazo[1,2-a]pyridinyl.

In one embodiment of Formula (IV), $R^{11}$ is alkyl, alkenyl or alkynyl which are unsubstituted or substituted as defined herein. In another embodiment of Formula (IV), $R^{11}$ is alkyl. In another embodiment of Formula (IV), $R^{11}$ is methyl; which is unsubstituted or substituted as defined herein. In another embodiment of Formula (IV), $R^{11}$ is alkyl; which is substituted as defined herein. In another embodiment of Formula (IV), $R^{11}$ is alkyl; which is substituted with $R^{12}$, $OR^{12}$, or $CF_3$. In another embodiment of Formula (IV), $R^{11}$ is alkyl; which is substituted with $OR^{12}$; $R^{12}$ is $R^{16}$; and $R^{16}$ is alkyl. In another embodiment of Formula (IV), $R^{11}$ is alkyl; which is substituted with $CF_3$. In another embodiment of Formula (IV), $R^{11}$ is alkyl; which is substituted with $R^{12}$, $R^{12}$ is $R^{14}$, and $R^{14}$ is heteroaryl.

In one embodiment of Formula (IV),
n, p, r, and s are each 0;
$A^1$ is N or $C(A^2)$;
$A^2$ is H, F, Br, I, or Cl;
$B^1$ is $R^1$, $OR^1$, $NHR^1$, $NHC(O)R^1$, F, Br, I or Cl;
$D^1$ is H, F, Br, I, or Cl;
$E^1$ is H; and
$Y^1$ is H, CN, $NO_2$, F, Cl, Br, I, $CF_3$, $R^{17}$, $OR^{17}$, $SR^{17}$, $SO_2R^{17}$, or $C(O)NH_2$; or
$Y^1$ and $B^1$, together with the atoms to which they are attached, are benzene, heteroarene, or heterocycloalkene; and
$A^2$, $D^1$, and $E^1$ are independently selected H;
$R^1$ is $R^4$ or $R^5$;
$R^4$ is cycloalkyl, or heterocycloalkyl;
$R^5$ is alkyl, or alkynyl, each of which is unsubstituted or substituted with one or two or three of independently selected $R^7$, $OR^7$, $NHR^7$, $N(R^7)_2$, CN, OH, F, Cl, Br or I;
$R^7$ is $R^8$, $R^9$, $R^{10}$, or $R^{11}$;
$R^8$ is phenyl;
$R^9$ is heteroaryl;
$R^{10}$ is cycloalkyl, cycloalkenyl, or heterocycloalkyl; each of which is unfused or fused with $R^{10A}$, $R^{10A}$ is heteroarene;
$R^{11}$ is alkyl each of which is unsubstituted or substituted with one or two or three of independently selected $R^{12}$, $OR^{12}$ or $CF_3$;
$R^{12}$ is $R^{14}$ or $R^{16}$;
$R^{14}$ is heteroaryl;
$R^{16}$ is alkyl;
$R^{17}$ is $R^{21}$;
$R^{21}$ is alkyl, or alkynyl, each of which is unsubstituted or substituted with one or two or three of independently selected $R^{22}$, F, Cl, Br or I;
$R^{22}$ is $R^{25}$;
$R^{25}$ is heterocycloalkyl;
wherein the cyclic moieties represented by $Y^1$ and $B^1$ together, $R^4$, $R^8$, $R^{10}$, and $R^{25}$, are independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br or I;
$R^{57A}$ is spiroalkyl, or spiroheteroalkyl;
$R^{57}$ is $R^{58}$, $R^{60}$ or $R^{61}$;

$R^{58}$ is phenyl;
$R^{60}$ is cycloalkyl, or heterocycloalkyl;
$R^{61}$ is alkyl which is unsubstituted or substituted with one or two or three of independently selected $R^{62}$, $OR^{62}$, $N(R^{62})_2$, C(O)OH, CN, F, Cl, Br or I;
$R^{62}$ is $R^{65}$, or $R^{66}$;
$R^{65}$ is cycloalkyl, or heterocycloalkyl;
$R^{66}$ is alkyl which is unsubstituted or substituted with $OR^{67}$;
$R^{67}$ is alkyl;
wherein the cyclic moieties represented by $R^{57A}$, $R^{58}$, and $R^{60}$ are unsubstituted or substituted with one or two or three or four of independently selected $R^{68}$, F, Cl, Br or I;
$R^{68}$ is $R^{71}$ or $R^{72}$;
$R^{71}$ is heterocycloalkyl; and
$R^{72}$ is alkyl, which is unsubstituted or substituted with one or two F.

Still another embodiment pertains to compounds having Formula (IV), which are 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide; 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide; and therapeutically acceptable salts, and metabolites thereof.

In another aspect, the present invention provides compounds of Formula (V)

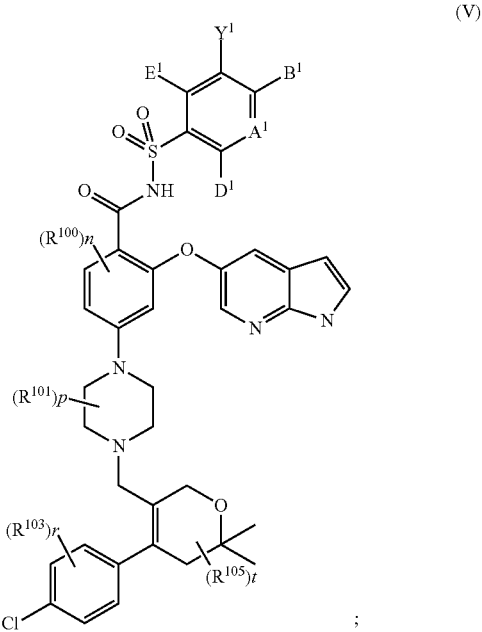

(V)

and therapeutically acceptable salts, and metabolites thereof, wherein $A^1$, $B^1$, $D^1$, $E^1$, and $Y^1$ are as described herein for Formula (I); $R^{100}$ is as described for substituents on $R^{26}$; n is 0, 1, 2, or 3; $R^{101}$ is as described for substituents on $R^{30}$; p is 0, 1, 2, 3, 4, 5, or 6; $R^{105}$ is as described for substituents on $R^{40}$; t is 0, 1, 2, 3, or 4; $R^{103}$ is as described for substituents on $R^{58}$; and r is 0, 1, 2, 3, or 4.

In one embodiment of Formula (V), n, p, r, and t are each 0. In one embodiment of Formula (V), $A^1$ is N. In another embodiment of Formula (V), $A^1$ is $C(A^2)$. In another embodiment of Formula (V), $A^1$ is $C(A^2)$; and $A^2$ is H, F, Cl, Br, or I. In another embodiment of Formula (V), $A^1$ is $C(A^2)$; and $A^2$ is H.

In one embodiment of Formula (V), $B^1$ is $R^1$, $OR^1$, $NHR^1$, $NHC(O)R^1$, F, Cl, Br, or I. In another embodiment of Formula (V), $A^1$ is $C(A^2)$; $A^2$ is H; and $B^1$ is $NHR^1$. In another embodiment of Formula (V), $A^1$ is $C(A^2)$; $A^2$ is H; and $B^1$ is $OR^1$. In another embodiment of Formula (V), $A^1$ is $C(A^2)$; $A^2$ is H; and $B^1$ is Cl. In another embodiment of Formula (V), $A^1$ is $C(A^2)$; $A^2$ is H; and $B^1$ is $R^1$. In another embodiment of Formula (V), $A^1$ is N; and $B^1$ is $NHR^1$. In another embodiment of Formula (V), $A^1$ is N; and $B^1$ is $OR^1$. In another embodiment of Formula (V), $A^1$ is N; and $B^1$ is Cl. In another embodiment of Formula (V), $A^1$ is N; and $B^1$ is $R^1$.

In one embodiment of Formula (V), $D^1$ is H or Cl. In another embodiment of Formula (V), $A^1$ is $C(A^2)$; $A^2$ is H; $B^1$ is $NHR^1$; and $D^1$ is H. In another embodiment of Formula (V), $A^1$ is $C(A^2)$; $A^2$ is H; $B^1$ is $NHR^1$; and $D^1$ is Cl. In another embodiment of Formula (V), $A^1$ is $C(A^2)$; $A^2$ is H; $B^1$ is $OR^1$; and $D^1$ is H. In another embodiment of Formula (V), $A^1$ is $C(A^2)$; $A^2$ is H; $B^1$ is Cl; and $D^1$ is H. In another embodiment of Formula (V), $A^1$ is $C(A^2)$; $A^2$ is H; $B^1$ is $R^1$; and $D^1$ is H. In another embodiment of Formula (V), $A^1$ is N; $B^1$ is $NHR^1$; and $D^1$ is H. In another embodiment of Formula (V), $A^1$ is N; $B^1$ is $NHR^1$; and $D^1$ is Cl. In another embodiment of Formula (V), $A^1$ is N; $B^1$ is $OR^1$; and $D^1$ is H. In another embodiment of Formula (V), $A^1$ is N; $B^1$ is Cl; and $D^1$ is H. In another embodiment of Formula (V), $A^1$ is N; $B^1$ is $R^1$; and $D^1$ is H.

In one embodiment of Formula (V), $E^1$ is H. In another embodiment of Formula (V), $A^1$ is $C(A^2)$; $A^2$ is H; $B^1$ is $NHR^1$; $D^1$ is H; and $E^1$ is H. In another embodiment of Formula (V), $A^1$ is $C(A^2)$; $A^2$ is H; $B^1$ is $NHR^1$; $E^1$ is H; and $D^1$ is Cl. In another embodiment of Formula (V), $A^1$ is $C(A^2)$; $A^2$ is H; $B^1$ is $OR^1$; $D^1$ is H; and $E^1$ is H. In another embodiment of Formula (V), $A^1$ is $C(A^2)$; $A^2$ is H; $B^1$ is Cl; $D^1$ is H; and $E^1$ is H. In another embodiment of Formula (V), $A^1$ is $C(A^2)$; $A^2$ is H; $B^1$ is $R^1$; $D^1$ is H; and $E^1$ is H. In another embodiment of Formula (V), $A^1$ is N; $B^1$ is $NHR^1$; $D^1$ is H; and $E^1$ is H. In another embodiment of Formula (V), $A^1$ is N; $B^1$ is $NHR^1$; $E^1$ is H; and $D^1$ is Cl. In another embodiment of Formula (V), $A^1$ is N; $B^1$ is $OR^1$; $D^1$ is H; and $E^1$ is H. In another embodiment of Formula (V), $A^1$ is N; $B^1$ is Cl; $D^1$ is H; and $E^1$ is H. In another embodiment of Formula (V), $A^1$ is N; $B^1$ is $R^1$; $D^1$ is H; and $E^1$ is H.

In one embodiment of Formula (V), $Y^1$ is H, CN, $NO_2$, F, Cl, Br, I, $CF_3$, $R^{17}$, $OR^{17}$, $SR^{17}$, $SO_2R^{17}$, or $C(O)NH_2$. In another embodiment of Formula (V), $Y^1$ is H. In another embodiment of Formula (V), $Y^1$ is CN. In another embodiment of Formula (V), $Y^1$ is F, Cl, Br, or I. In another embodiment of Formula (V), $Y^1$ is $CF_3$. In another embodiment of Formula (V), $Y^1$ is $SR^{17}$. In another embodiment of Formula (V), $Y^1$ is $OR^{17}$. In another embodiment of Formula (V), $Y^1$ is $NO_2$. In another embodiment of Formula (V), $Y^1$ is $SO_2R^{17}$; wherein $R^{17}$ is as defined herein. In another embodiment of Formula (V), $Y^1$ is $SO_2R^{17}$; wherein $R^{17}$ is alkyl. In another embodiment of Formula (V), $Y^1$ is $R^{17}$; wherein $R^{17}$ is alkynyl. In another embodiment of Formula (V), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (V), $A^1$ is $C(A^2)$; $A^2$ is H; $B^1$ is $NHR^1$; $D^1$ is H; $E^1$ is H; and $Y^1$ is $NO_2$. In another embodiment of Formula (V), $A^1$ is $C(A^2)$; $A^2$ is H; $B^1$ is $NHR^1$; $D^1$ is H; $E^1$ is H; and $Y^1$ is $SO_2R^{17}$; wherein $R^{17}$ is alkyl substituted with three F. In another embodiment of Formula (V), $A^1$ is N; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (V), $A^1$ is N; $B^1$ is $NHR^1$; $D^1$ is H; $E^1$ is H; and $Y^1$ is $NO_2$. In another embodiment of Formula (V), $A^1$ is N; $D^1$ is $NHR^1$; $D^1$ is H; $E^1$ is H; and $Y^1$ is $SO_2R^{17}$; wherein $R^{17}$ is alkyl substituted with three F.

In one embodiment of Formula (V), $Y^1$ and $B^1$, together with the atoms to which they are attached, are benzene. In another embodiment of Formula (V), $Y^1$ and $B^1$, together with the atoms to which they are attached, are heteroarene. In another embodiment of Formula (V), $A^1$ is $C(A^2)$; $A^2$, $G^1$, $E^1$, and $B^1$ are independently selected H; and $Y^1$ and $B^1$, together with the atoms to which they are attached, are benzene. In another embodiment of Formula (V), $A^1$ is $C(A^2)$; $A^2$, $G^1$, $E^1$, and $B^1$ are independently selected H; and $Y^1$ and $B^1$, together with the atoms to which they are attached, are heteroarene.

In one embodiment of Formula (V), $R^1$ is $R^4$ or $R^5$. In one embodiment of Formula (V), $R^1$ is $R^4$. In one embodiment of Formula (V), $R^1$ is $R^5$. In one embodiment of Formula (V), $R^1$ is $R^4$; and $R^4$ is cycloalkyl, cycloalkenyl, heterocycloalkyl or heterocycloalkenyl. In one embodiment of Formula (V), $R^1$ is $R^4$; and $R^4$ is cycloalkyl or heterocycloalkyl. In one embodiment of Formula (V), $R^1$ is $R^4$; and $R^4$ is cycloalkyl. In one embodiment of Formula (V), $R^1$ is $R^4$; and $R^4$ is heterocycloalkyl.

In one embodiment of Formula (V), $R^1$ is $R^4$; and $R^4$ is cycloalkyl; wherein $R^4$ is unsubstituted or substituted as defined herein. In another embodiment of Formula (V), $R^1$ is $R^4$; and $R^4$ is cycloalkyl; wherein the cycloalkyl ring is substituted as defined herein. In another embodiment of Formula (V), $R^1$ is $R^4$; and $R^4$ is cycloalkyl; wherein the cycloalkyl ring is substituted with $R^{57}$ or $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (V), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (V), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl. In another embodiment of Formula (V), $R^1$ is $R^4$; and $R^4$ is cycloalkyl; wherein the cycloalkyl ring is substituted with $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $N(R^{57})_2$; $R^{57}$ is $R^{61}$; and $R^{61}$ is alkyl which is unsubstituted or substituted with $R^{62}$. In another embodiment of Formula (V), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is unsubstituted or substituted with $R^{62}$; $R^{62}$ is $R^{65}$; and $R^{65}$ is cycloalkyl. In another embodiment of Formula (V), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is substituted with $R^{62}$; $R^{62}$ is $R^{65}$; and $R^{65}$ is cyclopropyl In one embodiment of Formula (V), $R^1$ is $R^4$; and $R^4$ is heterocycloalkyl; wherein $R^4$ is unsubstituted or substituted as defined herein. In another embodiment of Formula (V), $R^1$ is $R^4$; and $R^4$ is heterocycloalkyl; wherein the heterocycloalkyl ring is substituted as defined herein. In another embodiment of Formula (V), $R^1$ is $R^4$; and $R^4$ is heterocycloalkyl; wherein the heterocycloalkyl ring is substituted with $R^{57}$. In another embodiment of Formula (V), $R^1$ is $R^4$; and $R^4$ is heterocycloalkyl; wherein the heterocycloalkyl ring is piperidinyl or piperizinyl; and wherein the heterocycloalkyl ring is substituted with $R^{57}$; and $R^{57}$ is $R^{60}$ or $R^{61}$. In another embodiment of Formula (V), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$ or $R^{61}$; $R^{60}$ is heterocycloalkyl; and $R^{61}$ is alkyl. In another embodiment of Formula (V), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$; $R^{60}$ is heterocycloalkyl; wherein the heterocycloalkyl is tetrahydropyranyl. In another embodiment of Formula (V), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{61}$; $R^{61}$ is alkyl; and the alkyl is methyl. In another embodiment of Formula (V), $R^1$ is $R^4$; $R^4$ is heterocycloalkyl; wherein the heterocycloalkyl ring is piperidinyl or piperizinyl; and wherein the piperidinyl or piperizinyl ring is substituted with $C(O)OR^{57}$; $R^{57}$ is $R^{61}$; $R^{61}$ is alkyl; and the alkyl is methyl.

In one embodiment of Formula (V), $R^1$ is $R^5$; and $R^5$ is alkyl which is unsubstituted or substituted. In one embodiment of Formula (V), $R^1$ is $R^5$; and $R^5$ is alkyl which is unsubstituted or substituted with $R^7$, $OR^7$, OH, CN, or F. In another embodiment of Formula (V), $R^1$ is $R^5$; and $R^5$ is alkyl which is substituted with $R^7$, $OR^7$, $NHR^7$, or $N(R^7)_2$.

In one embodiment of Formula (V), $R^7$ is $R^8$, $R^9$, $R^{10}$ or $R^{11}$ which are unsubstituted or substituted as defined herein. In another embodiment of Formula (V), $R^7$ is $R^8$ which is unsubstituted or substituted as defined herein. In another embodiment of Formula (V), $R^7$ is $R^9$ which is unsubstituted or substituted as defined herein. In another embodiment of Formula (V), $R^7$ is $R^{10}$ which is unsubstituted or substituted as defined herein. In another embodiment of Formula (V), $R^7$ is $R^{11}$ which is unsubstituted or substituted as defined herein.

In one embodiment of Formula (V), $R^8$ is phenyl which is unsubstituted or substituted as defined herein.

In one embodiment of Formula (V), $R^9$ is heteroaryl which is unsubstituted or substituted as defined herein. In another embodiment of Formula (V), $R^9$ is furanyl; which is unsubstituted or substituted as defined herein. In another embodiment of Formula (V), $R^9$ is furanyl; which is unsubstituted.

In one embodiment of Formula (V), $R^{10}$ is cycloalkyl, cycloalkenyl, heterocycloalkyl or heterocycloalkenyl, heterocycloalkyl which are unsubstituted or substituted as defined herein. In another embodiment of Formula (V), $R^{10}$ is heterocycloalkyl which is unsubstituted or substituted as defined herein. In another embodiment of Formula (V), $R^{10}$ is tetrahydrofuranyl, tetrahydropyranyl, morpholinyl, dioxanyl, oxetanyl, piperidinyl, or pyrrolidinyl, which are unsubstituted or substituted as defined herein. In another embodiment of Formula (V), $R^{10}$ is tetrahydropyranyl; which is unsubstituted or substituted as defined herein. In another embodiment of Formula (V), $R^{10}$ is morpholinyl; which is unsubstituted or substituted as defined herein. In another embodiment of Formula (V), $R^{10}$ is cycloalkyl which is unsubstituted or substituted as defined herein. In another embodiment of Formula (V), $R^{10}$ is cycloalkyl which is unsubstituted or substituted as defined herein. In another embodiment of Formula (V), $R^{10}$ is cyclohexyl, cyclopropyl, cyclobutyl, or bicyclo[2.2.1]heptanyl; which is unsubstituted or substituted as defined herein. In another embodiment of Formula (V), $R^{10}$ is heterocycloalkyl which is fused with $R^{10A}$; and $R^{10A}$ is heteroarene. In another embodiment of Formula (V), $R^{10}$ is 5,6,7,8-tetrahydroimidazo[1,2-a]pyridinyl.

In one embodiment of Formula (V), $R^{11}$ is alkyl, alkenyl or alkynyl which are unsubstituted or substituted as defined herein. In another embodiment of Formula (V), $R^{11}$ is alkyl. In another embodiment of Formula (V), $R^{11}$ is methyl; which is unsubstituted or substituted as defined herein. In another embodiment of Formula (V), $R^{11}$ is alkyl; which is substituted as defined herein. In another embodiment of Formula (V), $R^{11}$ is alkyl; which is substituted with $R^{12}$, $OR^{12}$, or $CF_3$. In another embodiment of Formula (V), $R^{11}$ is alkyl; which is substituted with $OR^{12}$; $R^{12}$ is $R^{16}$; and $R^{16}$ is alkyl. In another embodiment of Formula (V), $R^{11}$ is alkyl; which is substituted with $CF_3$. In another embodiment of Formula (V), $R^{11}$ is alkyl; which is substituted with $R^{12}$; $R^{12}$ is $R^{14}$; and $R^{14}$ is heteroaryl.

In one embodiment of Formula (V), n, p, r, and t are each 0;

$A^1$ is N or $C(A^2)$;

$A^2$ is H, F, Br, I, or Cl;

$B^1$ is $R^1$, $OR^1$, $NHR^1$, $NHC(O)R^1$, F, Br, I or Cl;

$D^1$ is H, F, Br, I, or Cl;

$E^1$ is H; and $Y^1$ is H, CN, $NO_2$, F, Cl, Br, I, $CF_3$, $R^{17}$, $OR^{17}$, $SR^{17}$, $SO_2R^{17}$, or $C(O)NH_2$; or $Y^1$ and $B^1$, together with the atoms to which they are attached, are benzene, heteroarene, or heterocycloalkene; and $A^2$, $D^1$, and $E^1$ are independently selected H;

$R^1$ is $R^4$ or $R^5$;

$R^4$ is cycloalkyl, or heterocycloalkyl;

$R^5$ is alkyl, or alkynyl, each of which is unsubstituted or substituted with one or two or three of independently selected $R^7$, $OR^7$, $NHR^7$, $N(R^7)_2$, CN, OH, F, Cl, Br or I;

$R^7$ is $R^8$, $R^9$, $R^{10}$, or $R^{11}$;

$R^8$ is phenyl;

$R^9$ is heteroaryl;

$R^{10}$ is cycloalkyl, cycloalkenyl, or heterocycloalkyl; each of which is unfused or fused with $R^{10A}$, $R^{10A}$ is heteroarene;

$R^{11}$ is alkyl each of which is unsubstituted or substituted with one or two or three of independently selected $R^{12}$, $OR^{12}$ or $CF_3$;

$R^{12}$ is $R^{14}$ or $R^{16}$;

$R^{14}$ is heteroaryl;

$R^{16}$ is alkyl;

$R^{17}$ is $R^{21}$;

$R^{21}$ is alkyl, or alkynyl, each of which is unsubstituted or substituted with one or two or three of independently selected $R^{22}$, F, Cl, Br or I;

$R^{22}$ is $R^{25}$;

$R^{25}$ is heterocycloalkyl;

wherein the cyclic moieties represented by $Y^1$ and $B^1$ together, $R^4$, $R^8$, $R^{10}$, and $R^{25}$, are independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br or I;

$R^{57A}$ is spiroalkyl, or spiroheteroalkyl;

$R^{57}$ is $R^{58}$, $R^{60}$ or $R^{61}$;

$R^{58}$ is phenyl;

$R^{60}$ is cycloalkyl, or heterocycloalkyl;

$R^{61}$ is alkyl which is unsubstituted or substituted with one or two or three of independently selected $R^{62}$, $OR^{62}$, $N(R^{62})_2$, C(O)OH, CN, F, Cl, Br or I;

$R^{62}$ is $R^{65}$, or $R^{66}$;

$R^{65}$ is cycloalkyl, or heterocycloalkyl;

$R^{66}$ is alkyl which is unsubstituted or substituted with $OR^{67}$;

$R^{67}$ is alkyl;

wherein the cyclic moieties represented by $R^{57A}$, $R^{58}$, and $R^{60}$ are unsubstituted or substituted with one or two or three or four of independently selected $R^{68}$, F, Cl, Br or I;

$R^{68}$ is $R^{71}$ or $R^{72}$;

$R^{71}$ is heterocycloalkyl; and $R^{72}$ is alkyl, which is unsubstituted or substituted with one or two F.

Still another embodiment pertains to a compound having Formula (V), which is 4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide;

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide;

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide;

4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide;

Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

and therapeutically acceptable salts, and metabolites thereof.

In another aspect, the present invention provides compounds of Formula (VI)

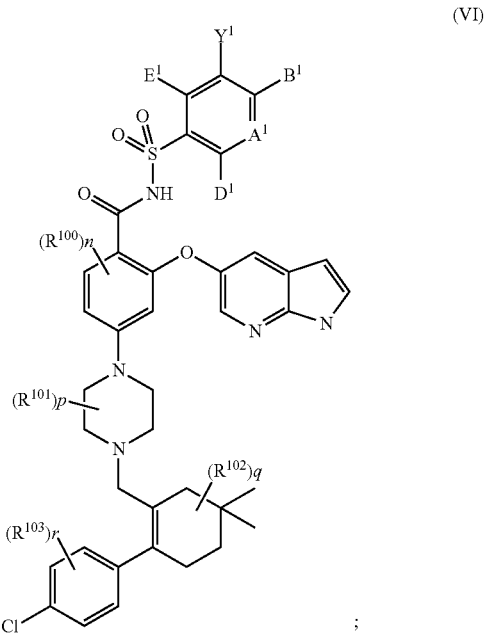

(VI)

and therapeutically acceptable salts, and metabolites thereof, wherein $A^1$, $B^1$, $D^1$, $E^1$, and $Y^1$ are as described herein for Formula (I); $R^{100}$ is as described for substituents on $R^{26}$; n is 0, 1, 2, or 3; $R^{101}$ is as described for substituents on $R^{30}$; p is 0, 1, 2, 3, 4, 5, or 6; $R^{102}$ is as described for substituents on $R^{40}$; q is 0, 1, 2, 3, 4, 5, or 6; $R^{103}$ is as described for substituents on $R^{58}$; and r is 0, 1, 2, 3, or 4.

In one embodiment of Formula (VI), n, p, r, and q are each 0.

In one embodiment of Formula (VI), $A^1$ is N. In another embodiment of Formula (VI), $A^1$ is $C(A^2)$. In another embodiment of Formula (VI), $A^1$ is $C(A^2)$; and $A^2$ is H, F, Cl, Br, or I. In another embodiment of Formula (VI), $A^1$ is $C(A^2)$; and $A^2$ is H.

In one embodiment of Formula (VI), $B^1$ is $R^1$, $OR^1$, $NHR^1$, $NHC(O)R^1$, F, Cl, Br, or I. In another embodiment of Formula (VI), $A^1$ is $C(A^2)$; $A^2$ is H; and $B^1$ is $NHR^1$. In another embodiment of Formula (VI), $A^1$ is $C(A^2)$; $A^2$ is H; and $B^1$ is $OR^1$. In another embodiment of Formula (VI), $A^1$ is $C(A^2)$; $A^2$ is H; and $B^1$ is Cl. In another embodiment of Formula (VI), $A^1$ is $C(A^2)$; $A^2$ is H; and $B^1$ is $R^1$. In another embodiment of Formula (VI), $A^1$ is N; and $B^1$ is $NHR^1$. In another embodiment of Formula (VI), $A^1$ is N; and $B^1$ is $OR^1$. In another embodiment of Formula (VI), $A^1$ is N; and $B^1$ is Cl. In another embodiment of Formula (VI), $A^1$ is N; and $B^1$ is $R^1$.

In one embodiment of Formula (VI), $D^1$ is H or Cl. In another embodiment of Formula (VI), $A^1$ is $C(A^2)$; $A^2$ is H; $B^1$ is $NHR^1$; and $D^1$ is H. In another embodiment of Formula (VI), $A^1$ is $C(A^2)$; $A^2$ is H; $B^1$ is $NHR^1$; and $D^1$ is Cl. In another embodiment of Formula (VI), $A^1$ is $C(A^2)$; $A^2$ is H; $B^1$ is $OR^1$; and $D^1$ is H. In another embodiment of Formula (VI), $A^1$ is $C(A^2)$; $A^2$ is H; $B^1$ is Cl; and $D^1$ is H. In another embodiment of Formula (VI), $A^1$ is $C(A^2)$; $A^2$ is H; $B^1$ is $R^1$; and $D^1$ is H. In another embodiment of Formula (VI), $A^1$ is N; $B^1$ is $NHR^1$; and $D^1$ is H. In another embodiment of Formula (VI), $A^1$ is N; $B^1$ is $NHR^1$; and $D^1$ is Cl. In another embodiment of Formula (VI), $A^1$ is N; $B^1$ is $OR^1$; and $D^1$ is H. In another embodiment of Formula (VI), $A^1$ is N; $B^1$ is Cl; and $D^1$ is H. In another embodiment of Formula (VI), $A^1$ is N; $B^1$ is $R^1$; and $D^1$ is H.

In one embodiment of Formula (VI), $E^1$ is H. In another embodiment of Formula (VI), $A^1$ is $C(A^2)$; $A^2$ is H; $B^1$ is $NHR^1$; $D^1$ is H; and $E^1$ is H. In another embodiment of Formula (VI), $A^1$ is $C(A^2)$; $A^2$ is H; $B^1$ is $NHR^1$; $E^1$ is H; and $D^1$ is Cl. In another embodiment of Formula (VI), $A^1$ is $C(A^2)$; $A^2$ is H; $B^1$ is $OR^1$; $D^1$ is H; and $E^1$ is H. In another embodiment of Formula (VI), $A^1$ is $C(A^2)$; $A^2$ is H; $B^1$ is Cl; $D^1$ is H; and $E^1$ is H. In another embodiment of Formula (VI), $A^1$ is $C(A^2)$; $A^2$ is H; $B^1$ is $R^1$; $D^1$ is H; and $E^1$ is H. In another embodiment of Formula (VI), $A^1$ is N; $B^1$ is $NHR^1$; $D^1$ is H; and $E^1$ is H. In another embodiment of Formula (VI), $A^1$ is N; $B^1$ is $NHR^1$; $E^1$ is H; and $D^1$ is Cl. In another embodiment of Formula (VI), $A^1$ is N; $B^1$ is $OR^1$; $D^1$ is H; and $E^1$ is H. In another embodiment of Formula (VI), $A^1$ is N; $B^1$ is Cl; $D^1$ is H; and $E^1$ is H. In another embodiment of Formula (VI), $A^1$ is N; $B^1$ is $R^1$; $D^1$ is H; and $E^1$ is H.

In one embodiment of Formula (VI), $Y^1$ is H, CN, $NO_2$, F, Cl, Br, I, $CF_3$, $R^{17}$, $OR^{17}$, $SR^{17}$, $SO_2R^{17}$, or $C(O)NH_2$. In another embodiment of Formula (VI), $Y^1$ is H. In another embodiment of Formula (VI), $Y^1$ is CN. In another embodiment of Formula (VI), $Y^1$ is F, Cl, Br, or I. In another embodiment of Formula (VI), $Y^1$ is $CF_3$. In another embodiment of Formula (VI), $Y^1$ is $SR^{17}$. In another embodiment of Formula (VI), $Y^1$ is $OR^{17}$. In another embodiment of Formula (VI), $Y^1$ is $NO_2$. In another embodiment of Formula (VI), $Y^1$ is $SO_2R^{17}$; wherein $R^{17}$ is as defined herein. In another embodiment of Formula (VI), $Y^1$ is $SO_2R^{17}$; wherein $R^{17}$ is alkyl. In another embodiment of Formula (VI), $Y^1$ is $R^{17}$; wherein $R^{17}$ is alkynyl. In another embodiment of Formula (VI), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (VI), $A^1$ is $C(A^2)$; $A^2$ is H; $B^1$ is $NHR^1$; $D^1$ is H; $E^1$ is H; and $Y^1$ is $NO_2$. In another embodiment of Formula (VI), $A^1$ is $C(A^2)$; $A^2$ is H; $B^1$ is $NHR^1$; $D^1$ is H; $E^1$ is H; and $Y^1$ is $SO_2R^{17}$; wherein $R^{17}$ is alkyl substituted with three F. In another embodiment of Formula (VI), $A^1$ is N; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (VI), $A^1$ is N; $B^1$ is $NHR^1$; $D^1$ is H; $E^1$ is H; and $Y^1$ is $NO_2$. In another embodiment of Formula (VI), $A^1$ is N; $D^1$ is $NHR^1$; $D^1$ is H; $E^1$ is H; and $Y^1$ is $SO_2R^{17}$; wherein $R^{17}$ is alkyl substituted with three F.

In one embodiment of Formula (IV), $Y^1$ and $B^1$, together with the atoms to which they are attached, are benzene. In another embodiment of Formula (IV), $Y^1$ and $B^1$, together with the atoms to which they are attached, are heteroarene. In another embodiment of Formula (IV), $A^1$ is $C(A^2)$; $A^2$, $G^1$, $E^1$, and $D^1$ are independently selected H; and $Y^1$ and $B^1$, together with the atoms to which they are attached, are benzene. In another embodiment of Formula (IV), $A^1$ is $C(A^2)$; $A^2$, $G^1$, $E^1$, and $D^1$ are independently selected H; and $Y^1$ and $B^1$, together with the atoms to which they are attached, are heteroarene.

In one embodiment of Formula (VI), $R^1$ is $R^4$ or $R^5$. In one embodiment of Formula (VI), $R^1$ is $R^4$. In one embodiment of Formula (VI), $R^1$ is $R^5$. In one embodiment of Formula (VI), $R^1$ is $R^4$; and $R^4$ is cycloalkyl, cycloalkenyl, heterocycloalkyl or heterocycloalkenyl. In one embodiment of Formula (VI), $R^1$ is $R^4$; and $R^4$ is cycloalkyl or heterocycloalkyl. In one embodiment of Formula (VI), $R^1$ is $R^4$; and $R^4$ is cycloalkyl. In one embodiment of Formula (VI), $R^1$ is $R^4$; and $R^4$ is heterocycloalkyl.

In one embodiment of Formula (VI), $R^1$ is $R^4$; and $R^4$ is cycloalkyl; wherein $R^4$ is unsubstituted or substituted as defined herein. In another embodiment of Formula (VI), $R^1$ is $R^4$; and $R^4$ is cycloalkyl; wherein the cycloalkyl ring is substituted as defined herein. In another embodiment of Formula (VI), $R^1$ is $R^4$; and $R^4$ is cycloalkyl; wherein the cycloalkyl ring is substituted with $R^{57}$ or $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (VI), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (VI), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl. In another embodiment of Formula (VI), $R^1$ is $R^4$; and $R^4$ is cycloalkyl; wherein the cycloalkyl ring is substituted with $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $N(R^{57})_2$; $R^{57}$ is $R^{61}$; and $R^{61}$ is alkyl which is unsubstituted or substituted with $R^{62}$. In another embodiment of Formula (VI), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is unsubstituted or substituted with $R^{62}$; $R^{62}$ is $R^{65}$; and $R^{65}$ is cycloalkyl. In another embodiment of Formula (VI), $R^1$ is $R^4$; and $R^4$ is cycloalkyl; wherein the cycloalkyl ring is cyclohexyl; and wherein the cyclohexyl ring is substituted with $R^{57}$; $R^{57}$ is $R^{61}$; and $R^{61}$ is alkyl which is substituted with $R^{62}$; $R^{62}$ is $R^{65}$; and $R^{65}$ is cyclopropyl.

In one embodiment of Formula (VI), $R^1$ is $R^4$; and $R^4$ is heterocycloalkyl; wherein $R^4$ is unsubstituted or substituted as defined herein. In another embodiment of Formula (VI), $R^1$ is $R^4$; and $R^4$ is heterocycloalkyl; wherein the heterocycloalkyl ring is substituted as defined herein. In another embodiment of Formula (VI), $R^1$ is $R^4$; and $R^4$ is heterocycloalkyl; wherein the heterocycloalkyl ring is substituted with $R^{57}$. In another embodiment of Formula (VI), $R^1$ is $R^4$; and $R^4$ is heterocycloalkyl; wherein the heterocycloalkyl ring is piperidinyl or piperizinyl; and wherein the heterocycloalkyl ring is substituted with $R^{57}$; and $R^{57}$ is $R^{60}$ or $R^{61}$. In another embodiment of Formula (VI), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$ or $R^{61}$; $R^{60}$ is heterocycloalkyl; and $R^{61}$ is alkyl. In another embodiment of Formula (VI), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{60}$; $R^{60}$ is heterocycloalkyl; wherein the heterocycloalkyl is tetrahydropyranyl. In another embodiment of Formula (VI), $R^1$ is $R^4$; $R^4$ is heterocycloalkyl; wherein the heterocycloalkyl ring is piperidinyl or piperizinyl; and wherein the piperidinyl or piperizinyl ring is substituted with $R^{57}$; $R^{57}$ is $R^{61}$; $R^{61}$ is alkyl; and the alkyl is methyl. In another embodiment of Formula (VI), $R^1$ is $R^4$; $R^4$ is heterocycloalkyl; wherein the heterocycloalkyl ring is piperidinyl or piperizinyl; and wherein the piperidinyl or piperizinyl ring is substituted with $C(O)OR^{57}$; $R^{57}$ is $R^{61}$; $R^{61}$ is alkyl; and the alkyl is methyl.

In one embodiment of Formula (VI), $R^1$ is $R^5$; and $R^5$ is alkyl which is unsubstituted or substituted. In one embodiment of Formula (VI), $R^1$ is $R^5$; and $R^5$ is alkyl which is unsubstituted or substituted with $R^7$, $OR^7$, OH, CN, or F. In another embodiment of Formula (VI), $R^1$ is $R^5$; and $R^5$ is alkyl which is substituted with $R^7$, $OR^7$, $NHR^7$, or $N(R^7)_2$.

In one embodiment of Formula (VI), $R^7$ is $R^8$, $R^9$, $R^{10}$ or $R^{11}$ which are unsubstituted or substituted as defined herein. In another embodiment of Formula (VI), $R^7$ is $R^8$ which is unsubstituted or substituted as defined herein. In another embodiment of Formula (VI), $R^7$ is $R^9$ which is unsubstituted or substituted as defined herein. In another embodiment of Formula (VI), $R^7$ is $R^{10}$ which is unsubstituted or substituted as defined herein. In another embodiment of Formula (VI), $R^7$ is $R^{11}$ which is unsubstituted or substituted as defined herein.

In one embodiment of Formula (VI), $R^8$ is phenyl which is unsubstituted or substituted as defined herein.

In one embodiment of Formula (VI), $R^9$ is heteroaryl which is unsubstituted or substituted as defined herein. In another embodiment of Formula (VI), $R^9$ is furanyl; which is unsubstituted or substituted as defined herein. In another embodiment of Formula (VI), $R^9$ is furanyl; which is unsubstituted.

In one embodiment of Formula (VI), $R^{10}$ is cycloalkyl, cycloalkenyl, heterocycloalkyl or heterocycloalkenyl, heterocycloalkyl which are unsubstituted or substituted as defined herein. In another embodiment of Formula (VI), $R^{10}$ is heterocycloalkyl which is unsubstituted or substituted as defined herein. In another embodiment of Formula (VI), $R^{10}$ is tetrahydrofuranyl, tetrahydropyranyl, morpholinyl, dioxanyl, oxetanyl, piperidinyl, or pyrrolidinyl; which are unsubstituted or substituted as defined herein. In another embodiment of Formula (VI), $R^{10}$ is tetrahydropyranyl; which is unsubstituted or substituted as defined herein. In another embodiment of Formula (VI), $R^{10}$ is morpholinyl; which is unsubstituted or substituted as defined herein. In another embodiment of Formula (VI), $R^{10}$ is cycloalkyl which is unsubstituted or substituted as defined herein. In another embodiment of Formula (VI), $R^{10}$ is cycloalkyl which is unsubstituted or substituted as defined herein. In another embodiment of Formula (VI), $R^{10}$ is cyclohexyl, cyclopropyl, cyclobutyl, or bicyclo[2.2.1]heptanyl, which is unsubstituted or substituted as defined herein. In another embodiment of Formula (VI), $R^{10}$ is heterocycloalkyl which is fused with $R^{10A}$; and $R^{10A}$ is heteroarene. In another embodiment of Formula (VI), $R^{10}$ is 5,6,7,8-tetrahydroimidazo[1,2-a]pyridinyl.

In one embodiment of Formula (VI), $R^{11}$ is alkyl, alkenyl or alkynyl which are unsubstituted or substituted as defined herein. In another embodiment of Formula (VI), $R^{11}$ is alkyl. In another embodiment of Formula (VI), $R^{11}$ is methyl; which is unsubstituted or substituted as defined herein. In another embodiment of Formula (VI), $R^{11}$ is alkyl; which is substituted as defined herein. In another embodiment of Formula (VI), $R^{11}$ is alkyl; which is substituted with $R^{12}$, $OR^{12}$, or $CF_3$. In another embodiment of Formula (VI), $R^{11}$ is alkyl, which is substituted with $OR^{12}$; $R^{12}$ is $R^{16}$; and $R^{16}$ is alkyl. In another embodiment of Formula (VI), $R^{11}$ is alkyl; which is substituted with $CF_3$. In another embodiment of Formula (VI), $R^{11}$ is alkyl, which is substituted with $R^{12}$; $R^{12}$ is $R^{14}$; and $R^{14}$ is heteroaryl.

In one embodiment of Formula (VI), n, p, r, and q are each 0;
$A^1$ is N or $C(A^2)$;
$A^2$ is H, F, Br, I, or Cl;
$B^1$ is $R^1$, $OR^1$, $NHR^1$, $NHC(O)R^1$, F, Br, I or Cl;
$D^1$ is H, F, Br, I, or Cl;
$E^1$ is H; and
$Y^1$ is H, CN, $NO_2$, F, Cl, Br, I, $CF_3$, $R^{17}$, $OR^{17}$, $SR^{17}$, $SO_2R^{17}$, or $C(O)NH_2$; or $Y^1$ and $B^1$, together with the atoms to which they are attached, are benzene, heteroarene, or heterocycloalkene; and $A^2$, $D^1$, and $E^1$ are independently selected H;
$R^1$ is $R^4$ or $R^5$;
$R^4$ is cycloalkyl, or heterocycloalkyl;
$R^5$ is alkyl, or alkynyl, each of which is unsubstituted or substituted with one or two or three of independently selected $R^7$, $OR^7$, $NHR^7$, $N(R^7)_2$, CN, OH, F, Cl, Br or I;
$R^7$ is $R^8$, $R^9$, $R^{10}$, or $R^{11}$;
$R^8$ is phenyl;
$R^9$ is heteroaryl;
$R^{10}$ is cycloalkyl, cycloalkenyl, or heterocycloalkyl; each of which is unfused or fused with $R^{10A}$, $R^{10A}$ is heteroarene;
$R^{11}$ is alkyl each of which is unsubstituted or substituted with one or two or three of independently selected $R^{12}$, $OR^{12}$ or $CF_3$;
$R^{12}$ is $R^{14}$ or $R^{16}$;
$R^{14}$ is heteroaryl;
$R^{16}$ is alkyl;
$R^{17}$ is $R^{21}$;
$R^{21}$ is alkyl, or alkynyl, each of which is unsubstituted or substituted with one or two or three of independently selected $R^{22}$, F, Cl, Br or I;
$R^{22}$ is $R^{25}$;
$R^{25}$ is heterocycloalkyl;

wherein the cyclic moieties represented by $Y^1$ and $B^1$ together, $R^4$, $R^8$, $R^{10}$, and $R^{25}$, are independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br or I;
$R^{57A}$ is spiroalkyl, or spiroheteroalkyl;
$R^{57}$ is $R^{58}$, $R^{60}$ or $R^{61}$;
$R^{58}$ is phenyl;
$R^{60}$ is cycloalkyl, or heterocycloalkyl;
$R^{61}$ is alkyl which is unsubstituted or substituted with one or two or three of independently selected $R^{62}$, $OR^{62}$, $N(R^{62})_2$, C(O)OH, CN, F, Cl, Br or I;
$R^{62}$ is $R^{65}$, or $R^{66}$;
$R^{65}$ is cycloalkyl, or heterocycloalkyl;
$R^{66}$ is alkyl which is unsubstituted or substituted with $OR^{67}$;
$R^{67}$ is alkyl;

wherein the cyclic moieties represented by $R^{57A}$, $R^{58}$, and $R^{60}$ are unsubstituted or substituted with one or two or three or four of independently selected $R^{68}$, F, Cl, Br or I;
$R^{68}$ is $R^{71}$ or $R^{72}$;
$R^{71}$ is heterocycloalkyl; and
$R^{72}$ is alkyl, which is unsubstituted or substituted with one or two F.

Still another embodiment pertains to a compound having Formula (VI), which is 4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide;

4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

and therapeutically acceptable salts, and metabolites thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-2 proteins.

Certain precursor compounds which may be metabolized in vitro or in vivo to form compounds having Formula (I) may also have utility for treating diseases associated with expression of anti-apoptotic Bcl-2 proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, buccally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl)benzenesulfonamide) or ABT-737 (i.e., N-(4-(4-((4'-chloro(1,1'-biphenyl)-2-yl) methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, pertuzumab), TAK-165, GW-572016 (Ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptanib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, galarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxane), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbicin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megestrol), MIFEPREX® (mifepristone), NILANDRON™ (nilutamide), NOLVADEX® (tamoxifen citrate), PLENAXIS™ (abarelix), prednisone, PROPECIA® (finasteride), trilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitol (KH1060), fenretinide, PANRETIN® (alitretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), dacarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (raltitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

Data

Determination of the utility of compounds having Formula (I) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 µmol preloaded Wang resin/vessel on an ABI 433A peptide synthesizer using 250 µmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with DCM and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (1×DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 µm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett- Packard 1046A fluorescence detector running HPLC 3D CHEMSTATION software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak

Peptide Probe
Acetyl-GQVGRQLAIIGDK(6-FAM)INR-NH$_2$ (SEQ ID NO:1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak

Acetyl-GQVGRQLAIIGDK(6-FAM)INR-NH$_2$ (SEQ ID NO:1)

The protected peptide was assembled on 0.25 mmol Fmoc-Rink amide MBHA resin (Novabiochem) on an Applied Biosystems 433A automated peptide synthesizer running FAST-MOC™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in DMF and confirmed complete by ninhydrin testing. The peptide was cleaved from the resin and side-chains deprotected by treating with 80:5:5:5:2.5:2.5 TFA/water/phenol/thioanisole/triisopropylsilane:3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)$^+$)).

Time Resolved-Fluorescence Resonance Energy Transfer (TR-FRET) Assay

Representative compounds were serially diluted in dimethyl sulfoxide (DMSO) starting at 50 μM (2× starting concentration; 10% DMSO) and 10 μL were transferred into a 384-well plate. Then 10 μL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the ENVISION plate reader (Perkin Elmer) using a 340/35 nm excitation filter and 520/525 (F-Bak peptide) and 495/510 nm (Tb-labeled anti-Histidine antibody) emission filters. Dissociation constants ($K_i$) are shown in TABLE 2 below and were determined using Wang's equation (Wang Z.-X., An Exact Mathematical Expression For Describing Competitive Binding Of Two Different Ligands To A Protein Molecule. *FEBS Lett.* 1995, 360:111-4).

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak Peptide Probe Acetyl-GQVGRQLAIIGDK(6-FAM)INR-amide (SEQ ID NO: 1) | 1 | 100 | Tb-anti-GST | 1 |

6-FAM = 6-carboxyfluorescein.;
Tb = terbium;
GST = glutathione S-transferase

The samples were then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters.

Inhibition constants ($K_i$) for compounds according to the invention are shown in TABLE 2 below. Where the $K_i$ for a compound is represented as "<" (less than) a certain numerical value, it is intended to mean that the binding affinity value (e.g., for Bcl-2) is lower than the limit of detection of the assay used Inhibition constants were determined using Wang's equation (Wang Zx, An Exact Mathematical Expression For Describing Competitive Binding Of Two Different Ligands To A Protein Molecule. *FEBS Lett.* 1995, 360:111-4).

TABLE 2

| TR-FRET Bcl-2 Binding $K_i$ (μM) | |
|---|---|
| EXAMPLE # | Ki |
| 1 | 0.000225 |
| 2 | <0.000010 |
| 3 | 0.000013 |
| 4 | <0.000010 |
| 5 | <0.000010 |
| 6 | 0.000018 |
| 7 | 0.00492 |
| 8 | 0.000153 |

TABLE 2-continued

TR-FRET Bcl-2 Binding $K_i$ (μM)

| EXAMPLE # | Ki |
|---|---|
| 9 | <0.000010 |
| 10 | <0.000010 |
| 11 | 0.000016 |
| 12 | <0.000010 |
| 13 | <0.000010 |
| 14 | 0.002798 |
| 15 | <0.000010 |
| 16 | 0.000219 |
| 17 | 0.00009 |
| 18 | 0.000017 |
| 19 | 0.000226 |
| 20 | 0.000181 |
| 21 | 0.000912 |
| 22 | 0.000291 |
| 23 | 0.000083 |
| 24 | <0.000010 |
| 25 | <0.000010 |
| 26 | 0.000011 |
| 27 | 0.000134 |
| 28 | <0.000010 |
| 29 | <0.000010 |
| 30 | <0.000010 |
| 31 | <0.000010 |
| 32 | <0.000010 |
| 33 | <0.000010 |
| 34 | 0.00001 |
| 35 | <0.000010 |
| 36 | 0.000017 |
| 37 | <0.000010 |
| 38 | 0.0003 |
| 39 | 0.000012 |
| 40 | <0.000010 |
| 41 | <0.000010 |
| 42 | 0.000439 |
| 43 | 0.000012 |
| 44 | <0.000010 |
| 45 | <0.000010 |
| 46 | 0.000935 |
| 47 | <0.000010 |
| 48 | <0.000010 |
| 49 | 0.000074 |
| 50 | 0.000021 |
| 51 | <0.000010 |
| 52 | 0.000114 |
| 53 | <0.000010 |
| 54 | 0.002071 |
| 55 | <0.000010 |
| 56 | 0.000037 |
| 57 | 0.000063 |
| 58 | <0.000010 |
| 59 | 0.000203 |
| 60 | <0.000010 |
| 61 | 0.000091 |
| 62 | <0.000010 |
| 63 | <0.000010 |
| 64 | <0.000010 |
| 65 | <0.000010 |
| 66 | <0.000010 |
| 67 | <0.000010 |
| 68 | 0.000012 |
| 69 | 0.001157 |
| 70 | 0.003964 |
| 71 | 0.00001 |
| 72 | <0.000010 |
| 73 | <0.000010 |
| 74 | 0.000029 |
| 75 | <0.000010 |
| 76 | 0.000196 |
| 77 | 0.000213 |
| 78 | <0.000010 |
| 79 | <0.000010 |
| 80 | <0.000010 |
| 81 | <0.000010 |
| 82 | 0.000328 |
| 83 | 0.000071 |
| 84 | 0.000123 |
| 85 | 0.000391 |
| 86 | 0.000498 |
| 87 | 0.000618 |
| 88 | 0.000672 |
| 89 | 0.000073 |
| 90 | 0.000013 |
| 91 | 0.000487 |
| 92 | 0.000128 |
| 93 | 0.003461 |
| 94 | 0.000678 |
| 95 | 0.000014 |
| 96 | 0.000014 |
| 97 | 0.000017 |
| 98 | <0.000010 |
| 99 | 0.000233 |
| 100 | <0.000010 |
| 101 | 0.000021 |
| 102 | 0.000094 |
| 103 | <0.000010 |
| 104 | 0.000016 |
| 105 | <0.000010 |
| 106 | 0.000895 |
| 107 | 0.000035 |
| 108 | <0.000010 |
| 109 | 0.000127 |
| 110 | 0.000557 |
| 111 | <0.000010 |
| 112 | <0.000010 |
| 113 | <0.000010 |
| 114 | <0.000010 |
| 115 | <0.000010 |
| 116 | <0.000010 |
| 117 | <0.000010 |
| 118 | <0.000010 |
| 119 | <0.000010 |
| 120 | <0.000010 |
| 121 | <0.000010 |
| 122 | <0.000010 |
| 123 | <0.000010 |
| 124 | <0.000010 |
| 125 | <0.000010 |
| 126 | <0.000010 |
| 127 | <0.000010 |
| 128 | <0.000010 |
| 129 | 0.000002 |
| 130 | <0.000010 |
| 131 | <0.000010 |
| 132 | <0.000010 |
| 133 | <0.000010 |
| 134 | <0.000010 |
| 135 | <0.000010 |
| 136 | <0.000010 |
| 137 | <0.000010 |
| 138 | <0.000010 |
| 139 | <0.000010 |
| 140 | <0.000010 |
| 141 | <0.000010 |
| 142 | 0.00013 |
| 143 | <0.000010 |
| 144 | <0.000010 |
| 145 | <0.000010 |
| 146 | <0.000010 |
| 147 | <0.000010 |
| 148 | <0.000010 |
| 149 | <0.000010 |
| 150 | <0.000010 |
| 151 | 0.000017 |
| 152 | <0.000010 |
| 153 | <0.000010 |
| 154 | <0.000010 |
| 155 | 0.000059 |
| 156 | <0.000010 |
| 157 | <0.000010 |
| 158 | <0.000010 |
| 159 | <0.000010 |
| 160 | <0.000010 |

TABLE 2-continued

TR-FRET Bcl-2 Binding $K_i$ (μM)

| EXAMPLE # | Ki |
|---|---|
| 161 | <0.000010 |
| 162 | <0.000010 |
| 163 | <0.000010 |
| 164 | <0.000010 |
| 165 | <0.000010 |
| 166 | <0.000010 |
| 167 | <0.000010 |
| 168 | <0.000010 |
| 169 | 0.000021 |
| 170 | 0.000022 |
| 171 | <0.000010 |
| 172 | <0.000010 |
| 173 | <0.000010 |
| 174 | <0.000010 |
| 175 | 0.000119 |
| 176 | 0.000023 |
| 177 | 0.000111 |
| 178 | 0.000076 |
| 179 | <0.000010 |
| 180 | <0.000010 |
| 181 | 0.000017 |
| 182 | 0.000068 |
| 183 | <0.000010 |
| 184 | <0.000010 |
| 185 | 0.000022 |
| 186 | 0.000047 |
| 187 | 0.00008 |
| 188 | <0.000010 |
| 189 | 0.000018 |
| 190 | 0.000026 |
| 191 | <0.000010 |
| 192 | <0.000010 |
| 193 | <0.000010 |
| 194 | <0.000010 |
| 195 | <0.000010 |
| 196 | <0.000010 |
| 197 | <0.000010 |
| 198 | <0.000010 |
| 199 | <0.000010 |
| 200 | <0.000010 |
| 201 | 0.000014 |
| 202 | <0.000010 |
| 203 | <0.000010 |
| 204 | <0.000010 |
| 205 | <0.000010 |
| 206 | 0.000036 |
| 207 | 0.00003 |
| 208 | 0.000104 |
| 209 | <0.000010 |
| 210 | 0.000011 |
| 211 | 0.000058 |
| 212 | 0.0001330 |
| 213 | <0.000010 |
| 214 | <0.000010 |
| 215 | <0.000010 |
| 216 | <0.000010 |
| 217 | <0.000010 |
| 218 | 0.000013 |
| 219 | 0.001192 |
| 220 | 0.000988 |
| 221 | 0.000049 |
| 222 | 0.000938 |
| 223 | 0.000053 |
| 224 | <0.000010 |
| 225 | 0.000196 |
| 226 | 0.000139 |
| 227 | <0.000010 |
| 228 | 0.026761 |
| 229 | 0.002109 |
| 230 | 0.000031 |
| 231 | 0.000770 |
| 232 | 0.001631 |
| 233 | 0.001654 |
| 234 | 0.000115 |
| 235 | 0.000023 |
| 236 | 0.000033 |

TABLE 2-continued

TR-FRET Bcl-2 Binding $K_i$ (μM)

| EXAMPLE # | Ki |
|---|---|
| 237 | 0.000024 |
| 238 | <0.000010 |
| 239 | 0.000026 |
| 240 | <0.000010 |
| 241 | <0.000010 |
| 242 | 0.000057 |
| 243 | 0.000546 |
| 244 | 0.000281 |
| 245 | 0.000015 |
| 246 | 0.000144 |
| 247 | 0.000019 |
| 248 | 0.000029 |
| 250 | 0.000412 |
| 251 | 0.000571 |
| 252 | <0.000010 |
| 253 | 0.000052 |
| 254 | <0.000010 |
| 255 | <0.000010 |
| 256 | <0.000010 |
| 257 | 0.000052 |
| 258 | <0.000010 |
| 259 | <0.000010 |
| 260 | 0.000016 |
| 261 | 0.000134 |
| 262 | <0.000010 |
| 263 | 0.000156 |
| 264 | 0.000036 |
| 265 | <0.000010 |
| 266 | <0.000010 |
| 267 | 0.000035 |
| 268 | <0.000010 |
| 269 | 0.000016 |
| 270 | <0.000010 |
| 271 | 0.000039 |
| 272 | 0.000031 |
| 273 | 0.000035 |
| 274 | 0.000040 |
| 275 | <0.000010 |
| 276 | <0.000010 |
| 277 | <0.000010 |
| 278 | 0.000252 |
| 279 | 0.000035 |
| 280 | 0.000071 |
| 281 | 0.000145 |
| 282 | <0.000010 |
| 283 | <0.000010 |
| 284 | 0.000024 |
| 285 | <0.000010 |
| 286 | <0.000010 |
| 287 | 0.000081 |
| 288 | 0.000251 |
| 289 | 0.000090 |
| 290 | <0.000010 |
| 291 | <0.000010 |
| 292 | 0.000190 |
| 293 | 0.000093 |
| 294 | 0.000046 |
| 295 | <0.000010 |
| 296 | 0.000512 |
| 297 | 0.000174 |
| 298 | <0.000010 |
| 299 | 0.000039 |
| 300 | 0.001627 |
| 301 | 0.002065 |
| 302 | 0.000332 |
| 303 | 0.000044 |
| 304 | nd |
| 305 | 0.000033 |
| 306 | 0.002067 |
| 307 | 0.000130 |
| 308 | 0.000141 |
| 309 | 0.000023 |
| 310 | 0.000165 |
| 311 | <0.000010 |
| 312 | <0.000010 |
| 313 | 0.001102 |

TABLE 2-continued

TR-FRET Bcl-2 Binding $K_i$ (μM)

| EXAMPLE # | Ki |
|---|---|
| 314 | 0.000042 |
| 315 | 0.000052 |
| 316 | 0.000601 |
| 317 | <0.000010 |
| 318 | <0.000010 |
| 319 | <0.000010 |
| 320 | <0.000010 |
| 321 | <0.000010 |
| 322 | <0.000010 |
| 323 | 0.000104 |
| 324 | <0.000010 |
| 325 | <0.000010 |
| 326 | <0.000010 |
| 327 | <0.000010 |
| 328 | <0.000010 |
| 329 | 0.000030 |
| 330 | <0.000010 |
| 331 | 0.001086 |
| 332 | 0.000621 |
| 333 | 0.000511 |
| 334 | 0.000572 |
| 335 | 0.000150 |
| 336 | 0.000198 |
| 337 | <0.000010 |
| 338 | 0.000013 |
| 339 | 0.000036 |
| 340 | <0.000010 |
| 341 | <0.000010 |
| 342 | <0.000010 |
| 343 | <0.000010 |
| 344 | <0.000010 |
| 345 | <0.000010 |
| 346 | 0.000042 |
| 347 | 0.000013 |
| 348 | 0.000034 |
| 349 | 0.000023 |
| 350 | <0.000010 |
| 351 | <0.000010 |
| 352 | 0.000014 |
| 353 | <0.000010 |
| 354 | 0.000010 |
| 355 | 0.000014 |
| 356 | 0.000039 |
| 357 | <0.000010 |
| 358 | <0.000010 |
| 359 | <0.000010 |
| 360 | <0.000010 |
| 361 | <0.000010 |
| 362 | 0.000016 |
| 363 | 0.000017 |
| 364 | <0.000010 |
| 365 | <0.000010 |
| 366 | 0.000024 |
| 367 | nd |
| 368 | nd |
| 369 | <0.000010 |
| 370 | 0.000285 |
| 371 | <0.0000010 |
| 372 | nd |
| 373 | <0.0000010 |
| 374 | <0.0000010 |
| 375 | 0.00010999 |
| 376 | <0.0000010 |
| 377 | <0.0000010 |
| 378 | <0.0000010 | nd = not determined

The inhibition constant ($K_i$) is the dissociation constant of an enzyme-inhibitor complex or a protein/small molecule complex, wherein the small molecule is inhibiting binding of one protein to another protein or peptide. So a large $K_i$ value indicates a low binding affinity and a small $K_i$ value indicates a high binding affinity.

TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

RS4;11 Cell Viability Assay

The acute lymphoblastic leukemia (ALL) cell line RS4;11 was used as the primary human cell line to assess the cellular activity of Bcl-2 selective agents in vitro and their efficacy in vivo. Previous studies have shown by BH3 profiling, a mitochondrial assay that classifies blocks in the intrinsic apoptotic pathway, that RS4;11 cells were highly dependent on BCL-2 for survival and sensitive to the Bcl-2 family member inhibitor ABT-737 (Blood, 2008, Vol. 111, 2300-2309). The prevalence of Bcl-2 complexed to the proapoptotic BH3 protein Bim in RS4;11 suggests that these cells are "primed" or more susceptible to cell death by antagonism of the antiapoptotic protein Bcl-2 for which they depend on for survival.

RS4;11 cells were cultured in RPMI-1640 supplemented with 2 mM L-glutamine, 10% FBS, 1 mM sodium pyruvate, 2 mM HEPES, 1% penicillin/streptomycin (Invitrogen), 4.5 g/L glucose and maintained at 37 C containing 5% $CO_2$. To test for the cellular activity of compounds in vitro, cells were treated at 50,000 cells per well in 96-well microtiter plates in the presence of 10% human serum for 48 hours in a humidified chamber with 5% $CO_2$. Cell cytotoxicity $EC_{50}$ values were assessed using CellTiter Glo (Promega) according to the manufacturer's recommendations. The $EC_{50}$ values were determined as a percentage of viable cells following treatment compared to the untreated control cells.

TABLE 3

RS4;11 $EC_{50}$ Values (μM)

| EXAMPLE # | EC50 |
|---|---|
| 1 | 0.712 |
| 2 | 0.783 |
| 3 | 0.0142 |
| 4 | 0.01854 |
| 5 | 0.01241 |
| 6 | 0.03487 |
| 7 | 0.192 |
| 8 | 0.158 |
| 9 | 0.01476 |
| 10 | 0.05202 |
| 11 | 0.01393 |
| 12 | 0.03471 |
| 13 | 0.0232 |
| 14 | 3.8947 |
| 15 | 0.01276 |
| 16 | 1.2098 |
| 17 | 0.475 |
| 18 | 0.086 |
| 19 | 0.465 |
| 20 | 0.191 |
| 21 | 0.062 |
| 22 | 0.085 |
| 23 | 0.045 |
| 24 | 0.00983 |
| 25 | 0.007 |
| 26 | 0.05888 |
| 27 | 0.33237 |
| 28 | 0.0419 |
| 29 | 0.02047 |
| 30 | 0.01529 |
| 31 | 0.01565 |
| 32 | 0.08147 |
| 33 | 0.00711 |
| 34 | 0.00748 |
| 35 | 0.29147 |
| 36 | 0.18137 |
| 37 | 0.00118 |
| 38 | 3.5092 |

TABLE 3-continued

RS4; 11 EC$_{50}$ Values (μM)

| EXAMPLE # | EC50 |
|---|---|
| 39 | 0.01974 |
| 40 | 0.09974 |
| 41 | 0.05801 |
| 42 | 0.53412 |
| 43 | 0.27208 |
| 44 | 0.05309 |
| 45 | 0.00992 |
| 46 | >5 |
| 47 | 0.03265 |
| 48 | 0.00333 |
| 49 | 0.35161 |
| 50 | 0.31264 |
| 51 | 0.02308 |
| 52 | 0.19964 |
| 53 | 0.06674 |
| 54 | 1.9158 |
| 55 | 0.0132 |
| 56 | 0.08654 |
| 57 | 0.42611 |
| 58 | >5 |
| 59 | 0.7215 |
| 60 | 0.05948 |
| 61 | 0.18337 |
| 62 | 0.02506 |
| 63 | 0.00751 |
| 64 | 0.00025 |
| 65 | 0.00025 |
| 66 | 0.01893 |
| 67 | 0.04954 |
| 68 | 0.10846 |
| 69 | 1.7243 |
| 70 | >5 |
| 71 | 0.09165 |
| 72 | 0.00751 |
| 73 | 0.02369 |
| 74 | 0.057 |
| 75 | 0.01509 |
| 76 | 0.51131 |
| 77 | 0.76196 |
| 78 | 0.01252 |
| 79 | 0.0649 |
| 80 | 0.06863 |
| 81 | 0.04814 |
| 82 | 0.68383 |
| 83 | 0.197 |
| 84 | 0.158 |
| 85 | 1.95 |
| 86 | 1.02 |
| 87 | 1.18 |
| 88 | 0.447 |
| 89 | 0.06446 |
| 90 | 0.06299 |
| 91 | 0.18296 |
| 92 | 0.08089 |
| 93 | >5 |
| 94 | 1.6946 |
| 95 | 0.02954 |
| 96 | 0.04356 |
| 97 | 0.05557 |
| 98 | 0.0229 |
| 99 | 1.3923 |
| 100 | 0.13666 |
| 101 | 0.2991 |
| 102 | 0.62178 |
| 103 | 0.03917 |
| 104 | 0.07125 |
| 105 | 0.05357 |
| 106 | 0.82639 |
| 107 | 0.06117 |
| 108 | 0.02407 |
| 109 | 0.18339 |
| 110 | 0.53638 |
| 111 | 0.01451 |
| 112 | 0.02063 |
| 113 | 0.00136 |
| 114 | 0.01078 |

TABLE 3-continued

RS4; 11 EC$_{50}$ Values (μM)

| EXAMPLE # | EC50 |
|---|---|
| 115 | 0.01184 |
| 116 | 0.02853 |
| 117 | 0.0182 |
| 118 | 0.01294 |
| 119 | 0.01138 |
| 120 | 0.00147 |
| 121 | 0.05972 |
| 122 | 0.00185 |
| 123 | 0.00333 |
| 124 | 0.21224 |
| 125 | 0.00838 |
| 126 | 0.05359 |
| 127 | 0.00975 |
| 128 | 0.00589 |
| 129 | 0.01484 |
| 130 | 0.01059 |
| 131 | 0.01266 |
| 132 | 0.02209 |
| 133 | 0.03186 |
| 134 | 0.00251 |
| 135 | 0.00237 |
| 136 | 0.00296 |
| 137 | 0.01272 |
| 138 | 0.00152 |
| 139 | 0.01681 |
| 140 | 0.01275 |
| 141 | 0.02044 |
| 142 | 0.34531 |
| 143 | 0.01914 |
| 144 | 0.0212 |
| 145 | 0.004 |
| 146 | 0.01916 |
| 147 | 0.02618 |
| 148 | 0.00938 |
| 149 | 0.01347 |
| 150 | 0.05103 |
| 151 | 0.03372 |
| 152 | 0.02037 |
| 153 | 0.01723 |
| 154 | 0.02647 |
| 155 | 0.59421 |
| 156 | 0.00805 |
| 157 | 0.01086 |
| 158 | 0.01793 |
| 159 | 0.01179 |
| 160 | 0.08363 |
| 161 | 0.03465 |
| 162 | 0.01297 |
| 163 | 0.00432 |
| 164 | 0.01476 |
| 165 | 0.0051 |
| 166 | 0.01185 |
| 167 | 0.00093 |
| 168 | 0.08867 |
| 169 | 0.07626 |
| 170 | 0.12515 |
| 171 | 0.05272 |
| 172 | 0.02053 |
| 173 | 0.00516 |
| 174 | 0.12621 |
| 175 | >1 |
| 176 | 0.13353 |
| 177 | 0.15936 |
| 178 | 0.20234 |
| 179 | 0.04273 |
| 180 | 0.0118 |
| 181 | 0.10612 |
| 182 | 0.1234 |
| 183 | 0.01753 |
| 184 | 0.02323 |
| 185 | 0.02747 |
| 186 | 0.06443 |
| 187 | 0.21494 |
| 188 | 0.01638 |
| 189 | 0.14397 |
| 190 | 0.55068 |

TABLE 3-continued

RS4; 11 EC$_{50}$ Values (μM)

| EXAMPLE # | EC50 |
|---|---|
| 191 | 0.00691 |
| 192 | 0.00241 |
| 193 | 0.00076 |
| 194 | 0.00819 |
| 195 | 0.00207 |
| 196 | 0.00172 |
| 197 | 0.0125 |
| 198 | 0.03619 |
| 199 | 0.00506 |
| 200 | 0.01099 |
| 201 | 0.59132 |
| 202 | 0.0438 |
| 203 | 0.02208 |
| 204 | 0.16475 |
| 205 | 0.01059 |
| 206 | 0.05291 |
| 207 | 0.00376 |
| 208 | 0.12121 |
| 209 | 0.0045 |
| 210 | 0.06022 |
| 211 | 0.3073 |
| 212 | 0.01283 |
| 213 | 0.0060976 |
| 214 | 0.0043751 |
| 215 | 0.00056038 |
| 216 | 0.68263 |
| 217 | 0.0015528 |
| 218 | 0.0072907 |
| 219 | >1 |
| 220 | >1 |
| 221 | 0.094771 |
| 222 | >1 |
| 223 | 0.18208 |
| 224 | 0.013887 |
| 225 | 0.56001 |
| 226 | 0.1178 |
| 227 | 0.0073566 |
| 228 | >1 |
| 229 | >1 |
| 230 | 0.052821 |
| 231 | 0.52301 |
| 232 | >1 |
| 233 | >1 |
| 234 | 0.13532 |
| 235 | 0.03232 |
| 236 | 0.04292 |
| 237 | 0.05316 |
| 238 | 0.10303 |
| 239 | 0.023699 |
| 240 | 0.017266 |
| 241 | 0.11377 |
| 242 | 0.22275 |
| 243 | 0.80718 |
| 244 | 0.79378 |
| 245 | 0.083614 |
| 246 | 0.40218 |
| 247 | 0.092976 |
| 248 | 0.099588 |
| 250 | >1 |
| 251 | 0.91782 |
| 252 | 0.003475 |
| 253 | 0.049586 |
| 254 | 0.019908 |
| 255 | 0.009004 |
| 256 | 0.017997 |
| 257 | 0.026002 |
| 258 | 0.00055345 |
| 259 | 0.00038795 |
| 260 | 0.0054323 |
| 261 | 0.18366 |
| 262 | 0.016346 |
| 263 | >1 |
| 264 | 0.68866 |
| 265 | 0.0071718 |
| 266 | 0.0072924 |
| 267 | 0.06944 |
| 268 | 0.048792 |
| 269 | 0.0072346 |
| 270 | 0.0025216 |
| 271 | 0.43657 |
| 272 | 0.84006 |
| 273 | 0.20925 |
| 274 | 0.21418 |
| 275 | 0.14303 |
| 276 | 0.0035006 |
| 277 | 0.0081845 |
| 278 | 0.79393 |
| 279 | 0.22492 |
| 280 | 0.45923 |
| 281 | 0.65371 |
| 282 | 0.032187 |
| 283 | 0.013096 |
| 284 | 0.16213 |
| 285 | 0.057413 |
| 286 | 0.034464 |
| 287 | 0.59312 |
| 288 | 0.39042 |
| 289 | 0.6687 |
| 290 | 0.10663 |
| 291 | 0.016079 |
| 292 | 0.88938 |
| 293 | 0.28715 |
| 294 | 0.12525 |
| 295 | 0.014803 |
| 296 | 0.76869 |
| 297 | 0.59157 |
| 298 | 0.070305 |
| 299 | 0.067981 |
| 300 | 0.76334 |
| 301 | >1 |
| 302 | 0.38106 |
| 303 | 0.04776 |
| 304 | 0.29755 |
| 305 | 0.032539 |
| 306 | 0.55348 |
| 307 | 0.12767 |
| 308 | 0.257 |
| 309 | 0.052421 |
| 310 | >1 |
| 311 | 0.035835 |
| 312 | 0.016178 |
| 313 | >1 |
| 314 | 0.66006 |
| 315 | 0.21027 |
| 316 | >1 |
| 317 | 0.013313 |
| 318 | 0.011566 |
| 319 | 0.0044972 |
| 320 | 0.050974 |
| 321 | 0.0188 |
| 322 | 0.012367 |
| 323 | 0.71689 |
| 324 | 0.0045254 |
| 325 | 0.012319 |
| 326 | 0.023133 |
| 327 | 0.0027224 |
| 328 | 0.0098808 |
| 329 | 0.42369 |
| 330 | 0.0097843 |
| 331 | 0.92638 |
| 332 | 0.45738 |
| 333 | 0.46292 |
| 334 | >1 |
| 335 | 0.26951 |
| 336 | 0.35134 |
| 337 | 0.001759 |
| 338 | 0.003399 |
| 339 | 0.45016 |
| 340 | 0.05646 |
| 341 | 0.031652 |
| 342 | 0.050891 |
| 343 | 0.12664 |

TABLE 3-continued

| EXAMPLE # | EC50 |
|---|---|
| 344 | 0.0066616 |
| 345 | 0.0092536 |
| 346 | 0.19003 |
| 347 | 0.018849 |
| 348 | 0.050263 |
| 349 | 0.023086 |
| 350 | 0.0058378 |
| 351 | 0.0020618 |
| 352 | 0.0011961 |
| 353 | 0.0050512 |
| 354 | 0.053231 |
| 355 | 0.018771 |
| 356 | 0.026623 |
| 357 | 0.013235 |
| 358 | 0.0038131 |
| 359 | 0.0059243 |
| 360 | 0.0098968 |
| 361 | 0.00053755 |
| 362 | 0.031726 |
| 363 | 0.02643 |
| 364 | 0.011244 |
| 365 | 0.0030168 |
| 366 | 0.016548 |
| 367 | nd |
| 368 | nd |
| 369 | 0.0079974 |
| 370 | nd |
| 371 | 0.007165 |
| 372 | nd |
| 373 | nd |
| 374 | 0.015475 |
| 375 | 0.56013 |
| 376 | 0.008765 |
| 377 | 0.002377 |
| 378 | 0.006764 |

RS4;11 $EC_{50}$ Values (µM)

nd = not determined

TABLE 3 shows the utility of compounds having Formula I to functionally inhibit anti- apoptotic Bcl-2 protein in a cellular context. The acute lymphoblastic leukemia (ALL) cell line RS4;11 has been shown by BH3 profiling, a mitochondrial assay that classifies blocks in the intrinsic apoptotic pathway, to be highly dependent on Bcl-2 for survival and is sensitive to the Bcl-2 family member inhibitor ABT-737 (*Blood*, 2008, Vol. 111, 2300-2309). The ability of compounds to kill RS4;11 cells is a direct measure of the compounds ability to inhibit anti-apoptotic Bcl-2 protein function. Compounds of Formula I are very effective in killing RS4;11 cells as demonstrated by low $EC_{50}$ values.

Compounds taught in U.S. patent application Ser. No. 12/631,404, entitled "BCL-2-SELECTIVE APOPTOSIS-INDUCING AGENTS FOR THE TREATMENT OF CANCER AND IMMUNE DISEASES," filed on Dec. 4, 2009, have utility for the treatment of various cancers and autoimmune diseases due to their activity against Bcl-2 family proteins, and more specifically Bcl-2. These compounds bind to Bcl-2 with high affinity in a FRET based assay described in Ser. No. 12/631,404. The administration of a one or more of these compounds to cells that are dependent on Bcl-2 or Bcl-2 family proteins for survival, such as the RS4:11 B-cell leukemia human tumor cell line, results in apoptosis, also known as programmed cell death. The amount of apoptosis caused by administration of the compound is represented by the EC50 in the cell viability assay, which is a measure of the number of living cells after administration of compound.

TABLE 4 identifies certain compounds (described below in Examples in 19, 20, 23 and 92 and described more fully in Ser. No. 12/631,404, the disclosure of which is incorporated herein by reference) with the various substituents being defined by R, X and Y as set forth. As can be seen from TABLE 4, these compounds exhibit a trend of increasing binding affinity ($K_i$) for Bcl-2 with increasing levels of apoptosis, or cell death, in the Bcl-2 dependent tumor cell line RS4;11. On this basis, the inventors expect that compounds with even greater affinity towards Bcl-2 than those compounds shown in Table 4 will exhibit a similar trend, potentially eliciting even greater levels of apoptosis, when administered to cells dependent on Bcl-2 for survival.

TABLE 4

Selected compounds in U.S. patent application No. 12/631404

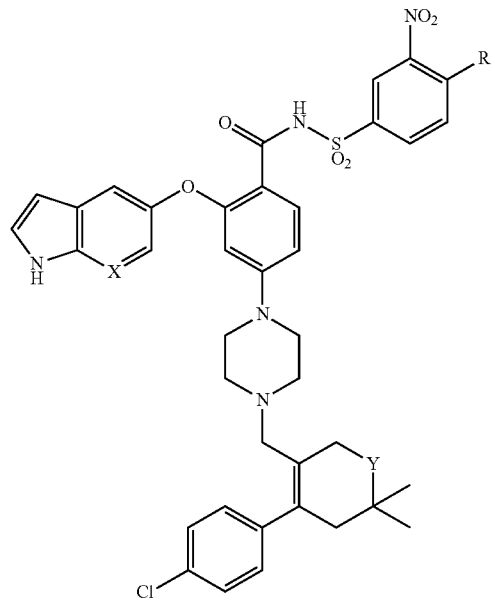

TABLE 4-continued

| EXAMPLE | R | X | Y | Bcl-2 FRET $K_i$ (μM) | RS4;11 EC50 (μM) |
|---|---|---|---|---|---|
| (23) | [structure: NH-CH2-tetrahydropyran] | C | O | 0.000083 | 0.045 |
| (92) | [structure: O-CH2-1,4-dioxane] | C | C | 0.000128 | 0.081 |
| (20) | [structure: NH-CH2CH2-OCH3] | C | C | 0.000181 | 0.191 |
| (19) | [structure: NH-cyclohexyl-morpholine] | C | C | 0.000226 | 0.465 |

To this end, binding affinity and cellular activity for compounds according to the present invention were compared with structurally similar indole compounds. In particular, the compounds of the present invention, in which a nitrogen is contained at a specific position within the heteroarene fused to the heteroaryl ring were compared with the corresponding indole compounds, which latter compounds lack only the specific nitrogen substitution included in the compounds of the present invention.

As can be seen in TABLE 5, compounds of the present invention having the specific nitrogen substitutions shown (i.e., compounds of Examples 1, 2, 3, 4, 5, 6, 9, 10, 11, 12, 13, 15, 16, and 17, where Z=N) in fact achieve relatively greater levels of apoptosis when administered to cells that depend on Bcl-2 for survival and have increased affinity towards Bcl-2 relative to the corresponding structural analogs lacking the specific nitrogen substitution (i.e., compounds of Examples 87, 88, 89, 90, 91, 19, 20, 21, 92, 22, 23, 93, and 94, respectively, where Z=C, taught in 9696USL2, the disclosure of which is incorporated herein by reference).

Specifically, the seventh column of TABLE 5 compares binding affinity of compounds of the present invention (the compound identified by the designated substituents in the uppermost row in each pair of rows set apart by blank rows) to corresponding compounds lacking the described nitrogen substitution. In each comparison, compounds of the present application (upper row of each pair of rows separated by a blank row) bind Bcl-2 with greater affinity to Bcl-2 than the corresponding analogs (lower row of each pair of rows separated by a blank row).

Further, column 8 of TABLE 5 compares the amount of apoptosis in the Bcl-2 dependent RS4;11 cell line achieved using compounds of the present invention (again the compound identified by the designated substituents in the uppermost row in each pair of rows set apart by blank rows) to that achieved using compounds of Examples 87, 88, 89, 90, 91, 19, 20, 21, 92, 22, 23, 93, and 94, where Z=C. In each comparison, compounds of the present invention (upper row of each pair of rows separated by a blank row) achieve greater extent of apoptosis in Bcl-2 dependent RS4;11 cells than the corresponding analogs (lower row of each pair of rows separated by a blank row).

The increase in binding affinity between the compounds of the present invention and corresponding analogs ranges from 2.7× to greater than 100×, and the increased potency in RS4;11 cells ranges from a 1.65× increase to greater than 10× increase.

As detailed below, a specific substitution of a nitrogen atom for a carbon atom leads to unexpected increase in binding affinity to antiapoptotic Bcl-2 and increase in potency in cell viability assays assessing apoptosis in Bcl-2 dependent cell lines.

This invention therefore comprises a series of compounds that demonstrate unexpected properties with respect to their binding to and inhibiting the activity of anti-apoptotic Bcl-2 protein to a significantly greater extent than corresponding analog compounds.

TABLE 5

Direct comparison of compounds of the present invention with corresponding analogs.

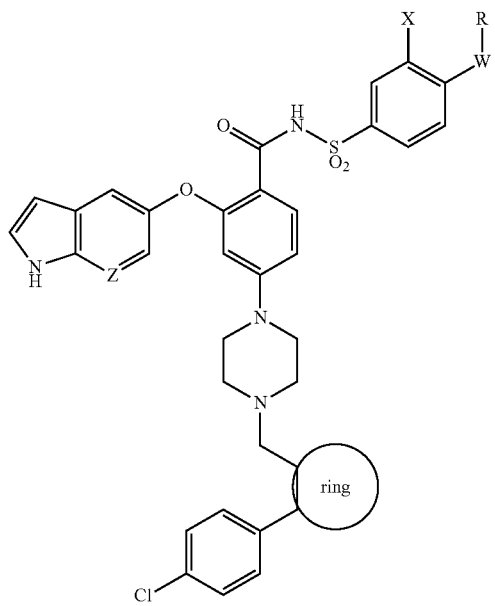

| EXAMPLE | R | W | X | Ring | Z | Bcl-2 FRET $k_i$ (μM) | RS4;11 EC50 (μM) |
|---|---|---|---|---|---|---|---|
| (1) | tetrahydropyranylmethyl | NH | NO$_2$ | benzene | N | 0.000225 | 0.712 |
| (87) | tetrahydropyranylmethyl | NH | NO$_2$ | benzene | C | 0.000618 | 1.180 |
| (2) | morpholinopropyl | NH | NO$_2$ | benzene | N | <0.000010 | 0.783 |
| (88) | morpholinopropyl | NH | NO$_2$ | benzene | C | 0.672 | 0.447 |
| (3) | tetrahydropyranyl-piperidinyl | NH | NO$_2$ | dimethylcyclohexene | N | 0.000013 | 0.0142 |

TABLE 5-continued

| # | R group | X | Y | Ar | Z | IC50 (a) | IC50 (b) |
|---|---|---|---|---|---|---|---|
| (89) | 4-(tetrahydropyran-4-yl)piperidinyl | NH | NO₂ | 4,4-dimethylcyclohexenyl | C | 0.000074 | 0.064 |
| (4) | 1-methylpiperidin-4-yl | NH | NO₂ | 4,4-dimethylcyclohexenyl | N | <0.00001 | 0.019 |
| (90) | 1-methylpiperidin-4-yl | NH | NO₂ | 4,4-dimethylcyclohexenyl | C | 0.000013 | 0.063 |
| (5) | (tetrahydropyran-4-yl)methyl | NH | NO₂ | 4,4-dimethylcyclohexenyl | N | <0.00001 | 0.012 |
| (18) | (tetrahydropyran-4-yl)methyl | NH | NO₂ | 4,4-dimethylcyclohexenyl | C | 0.000017 | 0.086 |
| (6) | 4-methylpiperazin-1-yl methyl | NH | NO₂ | 4,4-dimethylcyclohexenyl | N | 0.000018 | 0.035 |
| (91) | 4-methylpiperazin-1-yl methyl | NH | NO₂ | 4,4-dimethylcyclohexenyl | C | 0.000487 | 0.183 |
| (9) | 4-morpholinocyclohexyl | NH | NO₂ | 4,4-dimethylcyclohexenyl | N | <0.00001 | 0.015 |

TABLE 5-continued

| | | | | | | | |
|---|---|---|---|---|---|---|---|
| (19) | ![morpholine-cyclohexyl] | NH | NO$_2$ | ![cyclohexene-gemdimethyl] | C | 0.000226 | 0.465 |
| (10) | ![methoxypropyl] | NH | NO$_2$ | ![cyclohexene-gemdimethyl] | N | <0.00001 | 0.052 |
| (20) | ![methoxypropyl] | NH | NO$_2$ | ![cyclohexene-gemdimethyl] | C | 0.000181 | 0.191 |
| (11) | ![tetrahydropyran] | NH | NO$_2$ | ![cyclohexene-gemdimethyl] | N | 0.000016 | 0.014 |
| (21) | ![tetrahydropyran] | NH | NO$_2$ | ![cyclohexene-gemdimethyl] | C | 0.000912 | 0.062 |
| (12) | ![dioxane-ethyl] | O | NO$_2$ | ![cyclohexene-gemdimethyl] | N | <0.00001 | 0.035 |
| (92) | ![dioxane-ethyl] | O | NO$_2$ | ![cyclohexene-gemdimethyl] | C | 0.000128 | 0.081 |
| (13) | ![tetrahydropyran-stereo] | NH | NO$_2$ | ![cyclohexene-gemdimethyl] | N | <0.00001 | 0.023 |

TABLE 5-continued
| | | | | | | | |
|---|---|---|---|---|---|---|---|
| (22) | 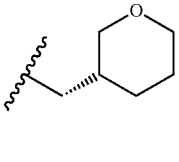 | NH | NO$_2$ | 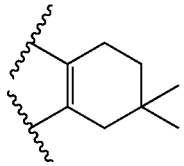 [SMILES: *C1=C(*)CC(C)(C)CC1] | C | 0.000291 | 0.085 |
| (15) | 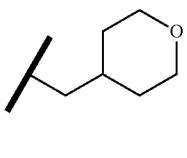 | NH | NO$_2$ | 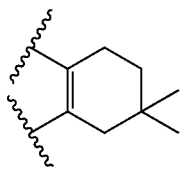 [SMILES: *C1=C(*)CC(C)(C)CC1] | N | <0.00001 | 0.013 |
| (23) | 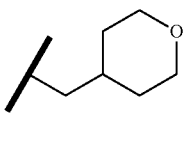 | NH | NO$_2$ | 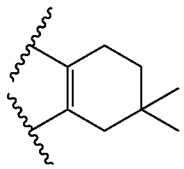 [SMILES: *C1=C(*)CC(C)(C)CC1] | C | 0.000083 | 0.045 |
| (16) | 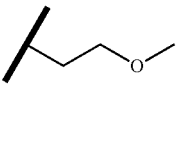 | NH | SO$_2$CF$_3$ | 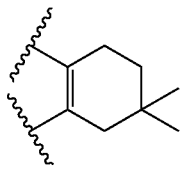 [SMILES: *C1=C(*)CC(C)(C)CC1] | N | 0.000219 | 1.210 |
| (93) | 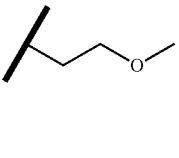 | NH | SO$_2$CF$_3$ | 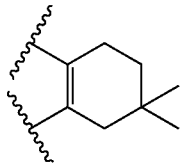 [SMILES: *C1=C(*)CC(C)(C)CC1] | C | 0.035 | >5.000 |
| (17) | 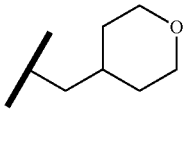 | NH | SO$_2$CF$_3$ | 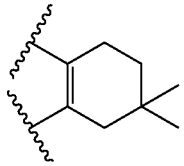 [SMILES: *C1=C(*)CC(C)(C)CC1] | N | 0.000090 | 0.475 |
| (94) | 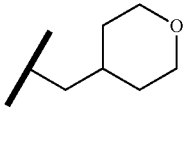 | NH | SO$_2$CF$_3$ | 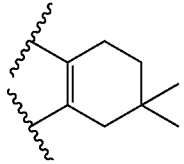 [SMILES: *C1=C(*)CC(C)(C)CC1] | C | 0.000678 | 1.690 |
More specifically, compounds of the present invention contain a substitution pattern shown in the diagram below.
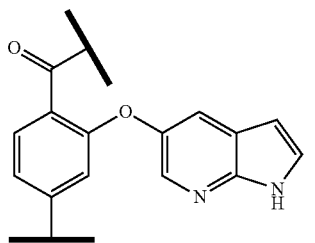

Other compounds that contain isomeric ring systems to that shown above, such as those rings systems containing a nitrogen adjacent to the oxygenated carbon within the ring, as shown below, are compromised by instability.

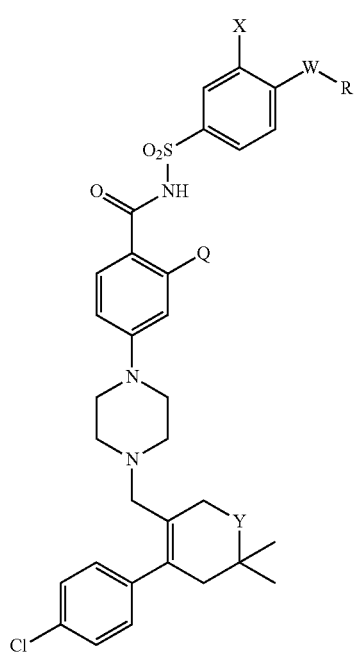

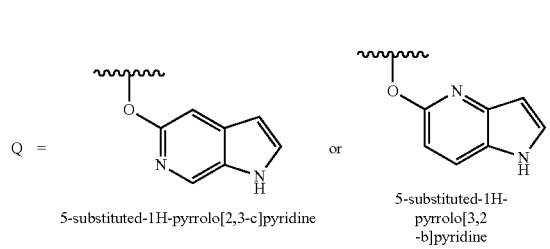

Specifically, this was discovered by the inventors in the following compound preparation. The intermediate structure F, that directly precedes the final product of the unstable compound, was prepared according to the route below. All intermediates A-F were stable and isolable using techniques known to those skilled in the art.

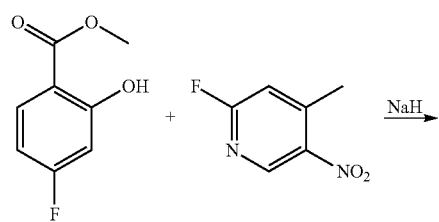

-continued

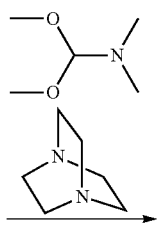

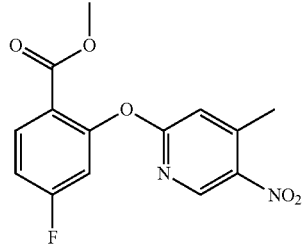

A

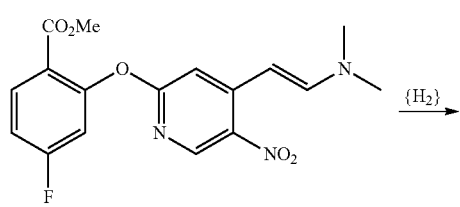

B

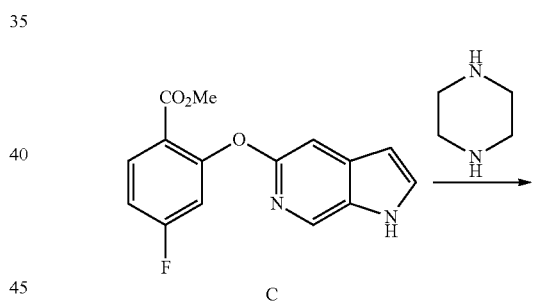

C

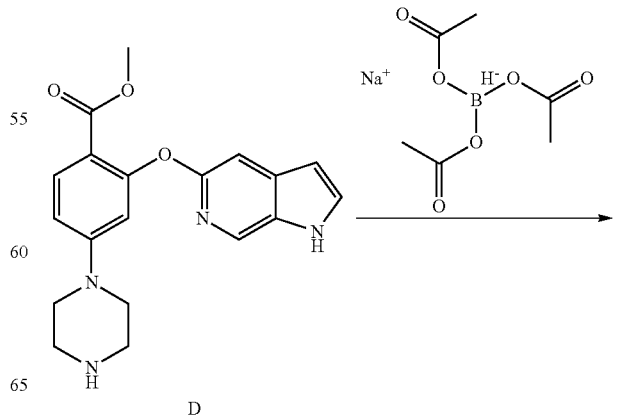

D

-continued

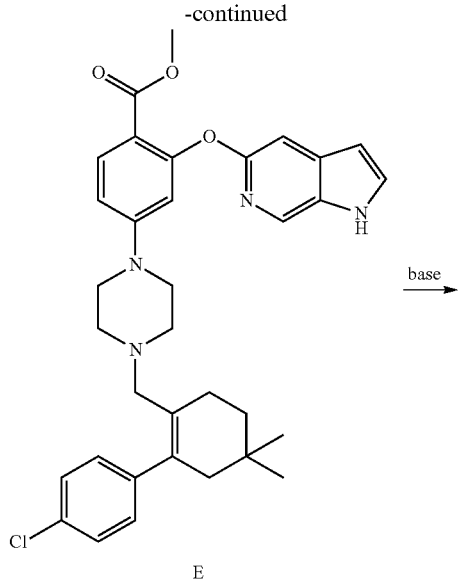

E

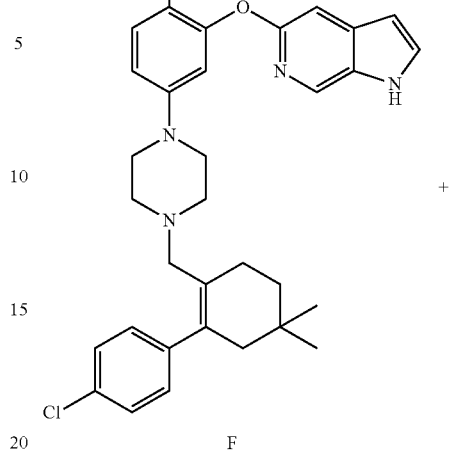

base →

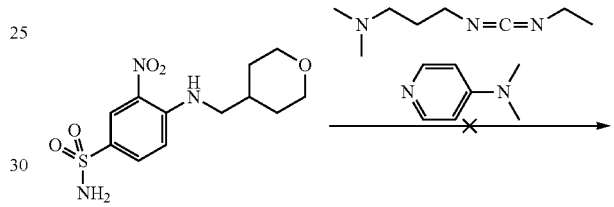

G

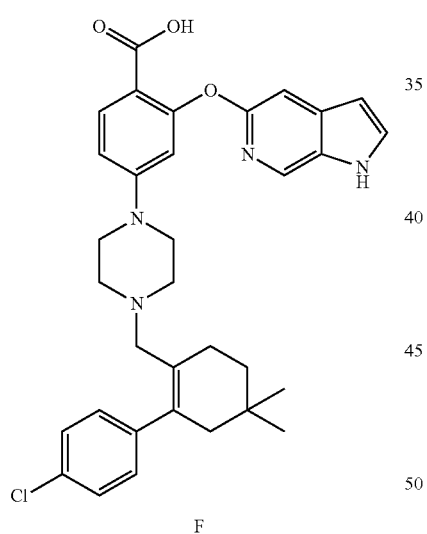

F

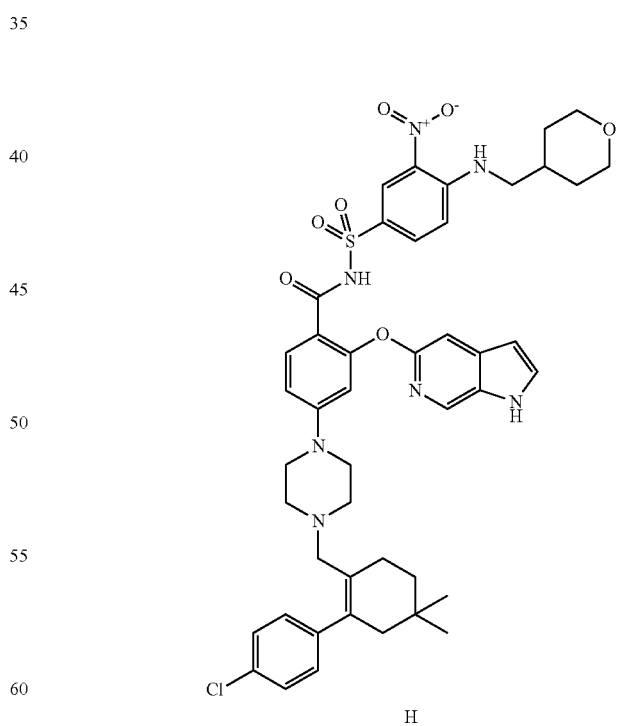

H

Intermediate F, shown in the scheme above, was reacted with intermediate G using standard coupling conditions that are known to those skilled in the art. The reaction mixture was analyzed via HPLC/MS to monitor the formation of a peak corresponding to the compound H. While this peak formed within hours of initiating the reaction below, the peak progressively disappeared during workup and chromatography, until it no longer was present. The lack of stability of the putative compound originates from the position of the nitrogen within the fused ring-system described above. This position, which is adjacent to the oxygen-bearing carbon in the 5-substituted-1H-pyrrolo[2,3-c]pyridine ring system shown below and described above, makes the compound H unstable.

It is expected that a compound containing the fused 5-substituted-1H-pyrrolo[3,2-b]pyridine ring system below would be similarly unstable, since the position of the nitrogen is adjacent to the oxygen-bearing carbon within the ring.

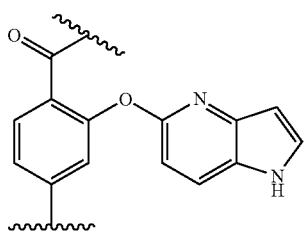 [SMILES: *C(=O)c1ccc(*)cc1Oc1ccc2[nH]ccc2n1]

Therefore, compounds with the 5-substituted-1H-pyrrolo[2,3-b]pyridines are preferred over the isomeric compounds.

It is expected that, because compounds having Formula (I) bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidymitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherloscerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

SCHEMES AND EXPERIMENTALS

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-$BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

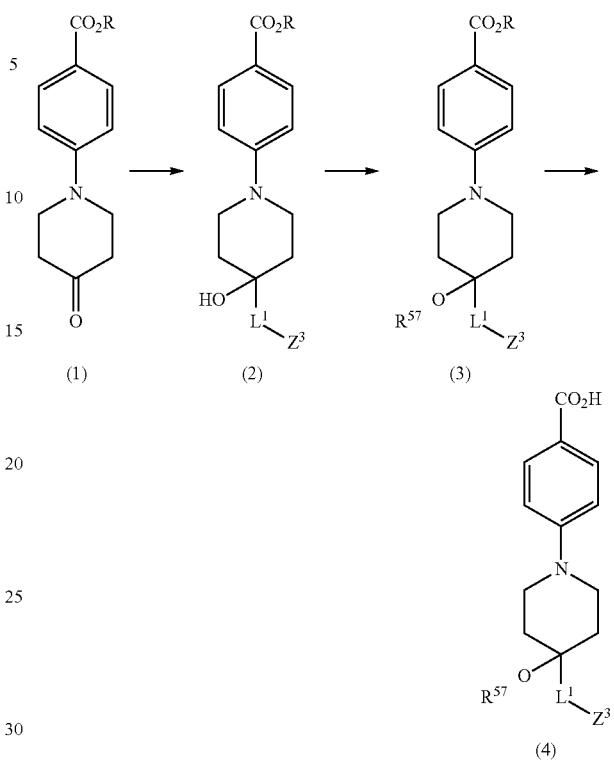

Compounds of Formula (4) can be prepared as shown in SCHEME 1, and can be used as described in SCHEME 8 to prepare compounds of Formula (I), which are representative of the compounds of the present invention. Compounds of Formula (1) wherein R is alkyl, can be converted to compounds of Formula (2) using $Z^3L^1MgX^1$, wherein $X^1$ is a halide, in a solvent such as but not limited to ether or tetrahydrofuran. Compounds of Formula (3) can be prepared from compounds of Formula (2) using a strong base such as NaH and $R^{57}X^2$, wherein $X^2$ is a halide and $R^{57}$ is as described herein. Compounds of Formula (3), when treated with aqueous NaOH or LiOH, will provide compounds of Formula (4).

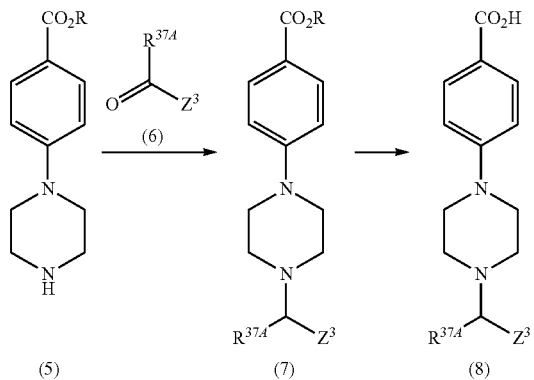

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 8 to prepare compounds of Formula (I).

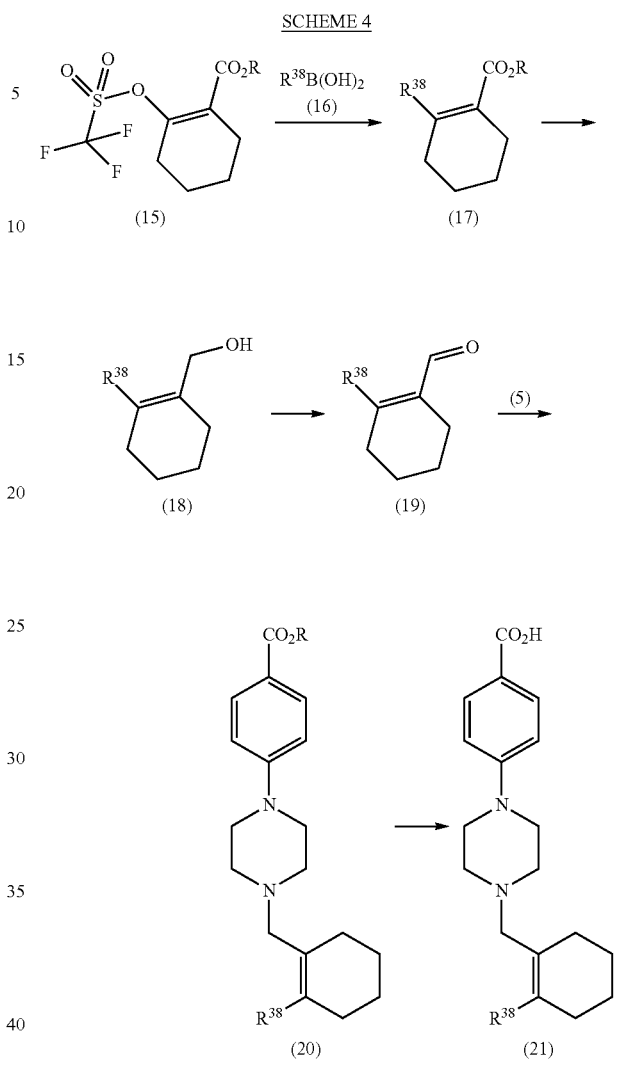

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein Y is as described herein for substituents on $Z^3$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 8 to prepare compounds of Formula (I).

As shown in SCHEME 4, compounds of Formula (17) can be prepared from compounds of Formula (15) and compounds of Formula (16), wherein R is alkyl and $R^{38}$ is as described herein, using Suzuki coupling conditions known to those skilled in the art and readily available in the literature. Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof. Compounds of Formula (21) can be prepared from compounds of Formula (20) as described in SCHEME 1, and can be used as described in SCHEME 8 to prepare compounds of Formula (I).

SCHEME 5

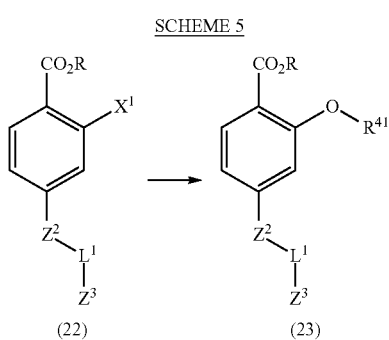

(22)　　(23)

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{41}$—OH and a catalyst, with or without a first base. Examples of catalysts include copper(I)trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof.

Compounds of Formula (22) may also be converted to compounds of Formula (23) by reacting the former, when $X^1$ is Cl, F, or $NO_2$, and compounds of Formula $R^{41}$—OH with a first base. Examples of first bases include triethylamine, N,N-diisopropylethylamine, $Cs_2CO_3$, $Na_2CO_3$, $K_3PO_4$, and mixtures thereof.

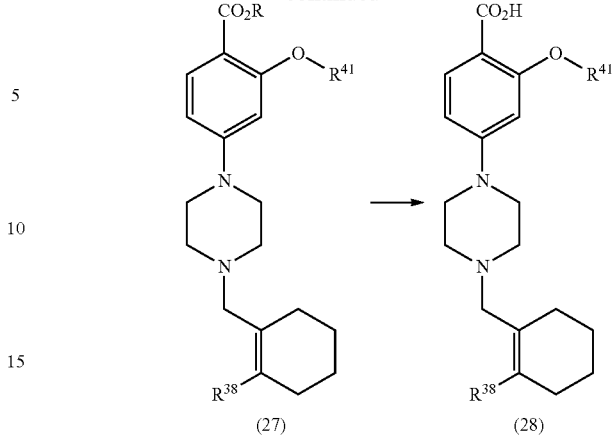

(27)　　(28)

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 8 to prepare compounds of Formula (I).

SCHEME 6

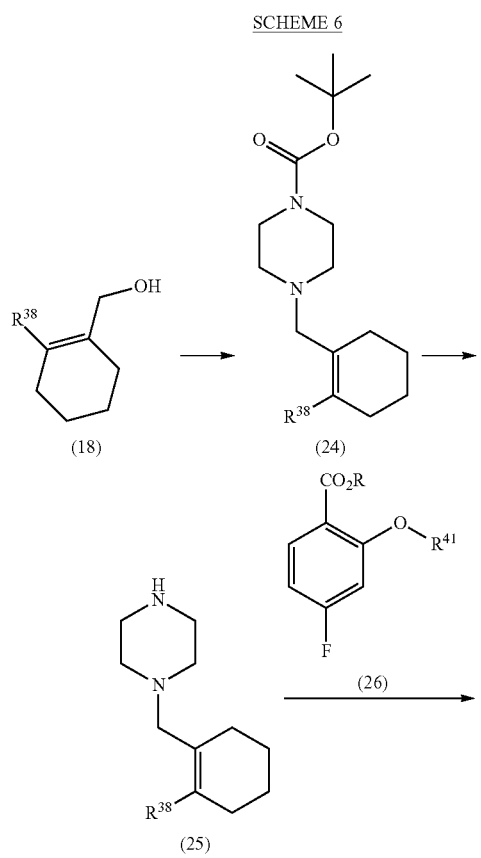

SCHEME 7

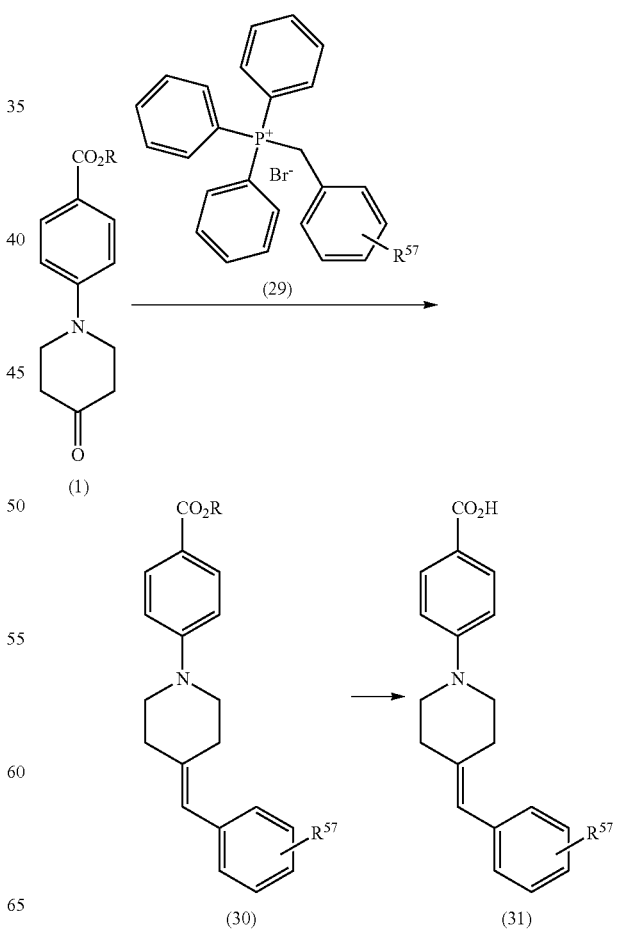

As shown in SCHEME 7, compounds of Formula (1) can be reacted with an appropriate triphenylphosphonium bromide of Formula (29) and a base such as but not limited to sodium hydride or n-butyllithium to provide compounds of Formula (30). The reaction is typically performed in a solvent such as THF or DMSO. Compounds of Formula (31) can be prepared from compounds of Formula (30) as described in SCHEME 1, and can be used as described in SCHEME 8 to prepare compounds of Formula (I).

SCHEME 8

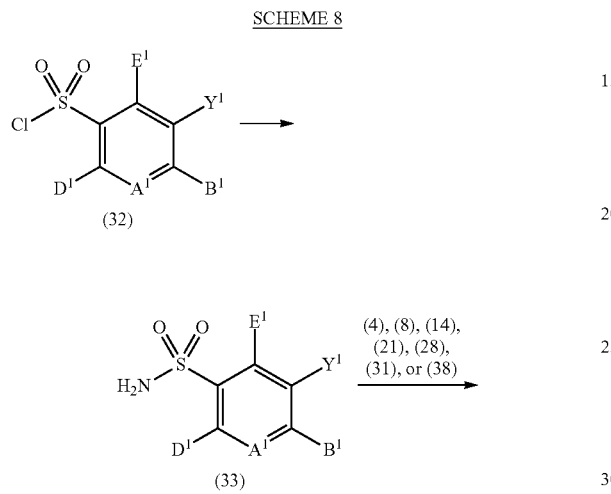

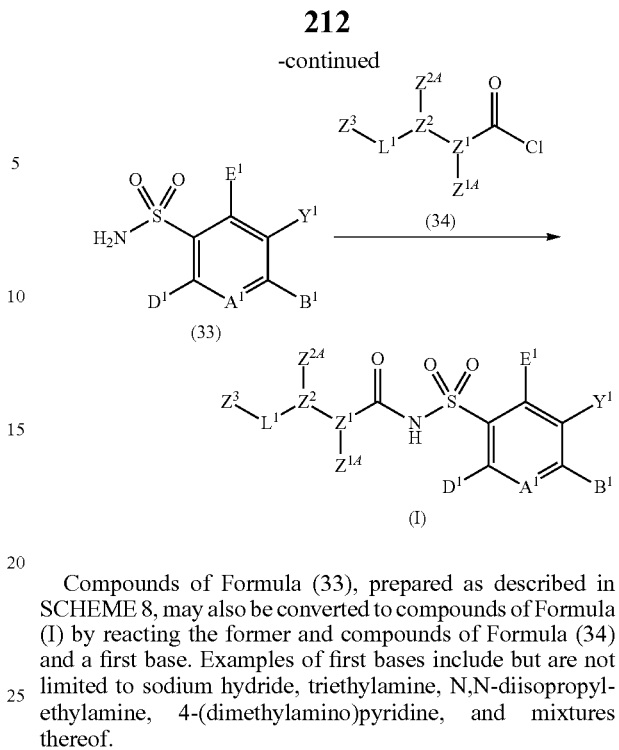

Compounds of Formula (33), prepared as described in SCHEME 8, may also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof.

SCHEME 10

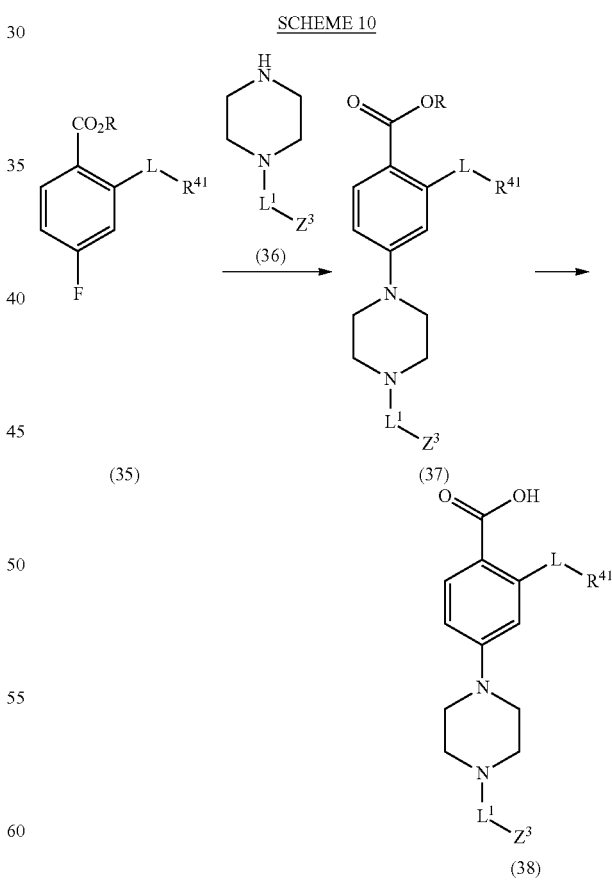

As shown in SCHEME 8, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (28), (31), or (38) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof

SCHEME 9

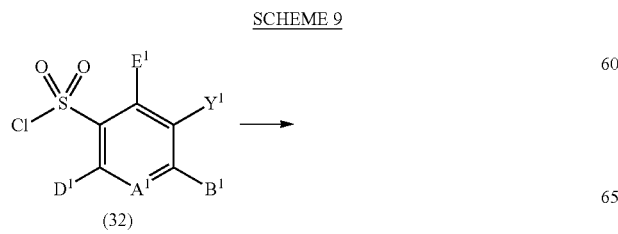

As shown in SCHEME 10, compounds of Formula (35), wherein L is a bond, alkyl, O, S, S(O), S(O)$_2$, NH, etc., can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 8 to prepare compounds of Formula (I).

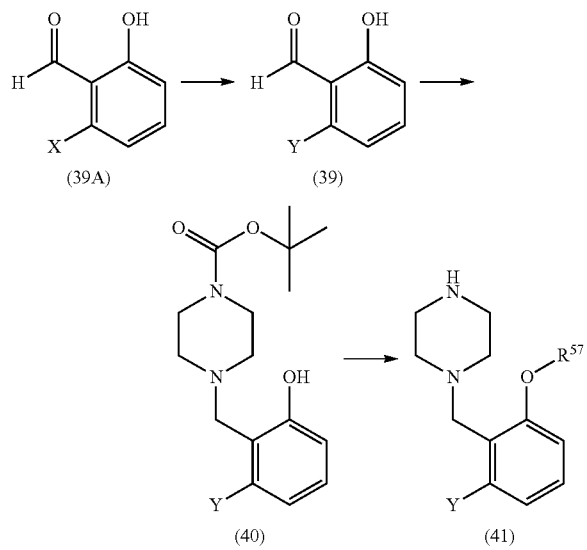

Compounds of Formula (39), wherein Y is as described herein for substituents on $Z^3$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with $R^{57}X$, wherein X is a halide, and NaH in a solvent such as N,N-dimethylformamide, and then the resulting material can be treated with triethylsilane and trifluoroacetic acid in dichloromethane. Compounds of Formula (41) can be used as described in Scheme 10 wherein $L^1$-$Z^3$ is as shown in Formula (41).

SCHEME 12

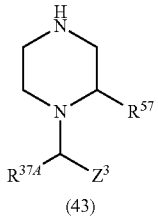

As shown in SCHEME 12, substituted piperazin-2-ones wherein $R^{57}$ is alkyl, can be reacted with compounds of Formula (6) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 10 wherein $L^1$-$Z^3$ is as shown in Formula (43).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 1A tert-butyl 4-((4'-chlorobiphenyl-2-yl)methyl)piperazine-1-carboxylate 4'-Chlorobiphenyl-2-carboxaldehyde (4.1 g), tert-butyl piperazine-1-carboxylate (4.23 g), and sodium triacetoxyborohydride (5.61 g) in CH$_2$Cl$_2$ (60 mL) were stirred for 24 hours. The reaction was quenched with methanol and poured into ether. The solution was washed with water and brine, concentrated, and chromatographed on silica gel with 2-25% ethyl acetate/hexanes.

Example 1B 1-((4'-chlorobiphenyl-2-yl)methyl)piperazine

EXAMPLE 1A (3.0 g) and triethylsilane (1 mL) were stirred in CH$_2$Cl$_2$ (30 mL) and trifluoroacetic acid (30 mL) for 2 hours, and the reaction was concentrated, and then taken up in ether and concentrated again. The material was taken up in dichloromethane (200 mL) and NaHCO$_3$ solution (100 mL), and partitioned. The organic layer was dried over Na$_2$SO$_4$, and condensed to give the title compound.

Example 1C tert-butyl 4-(4-((4'-chlorobiphenyl-2-yl)methyl)piperazin-1-yl)-2-fluorobenzoate Tert-butyl 4-bromo-2-fluorobenzoate (14.0 g), EXAMPLE 1B (16.05 g), Pd$_2$(dba)$_3$ (tris(dibenzylideneacetone)dipalladium(0)) (1.40 g), 2-(di-tert-butylphosphino)biphenyl (1.82 g), and K$_3$PO$_4$ (16.2 g) were stirred in 1,2-dimethoxyethane (300 mL) at 80° C. for 24 hours. The reaction was cooled and concentrated. The crude product was chromatographed on silica gel with 10-20% ethyl acetate/hexanes.

Example 1D tert-butyl 2-(1H-pyrrolo[2,3-b]pyridin-5-yloxy)-4-(4-((4'-chlorobiphenyl-2-yl)methyl)piperazin-1-yl)benzoate 1H-Pyrrolo[2,3-B]pyridine-5-ol (167 mg), EXAMPLE 1C (500 mg), and Cs$_2$CO$_3$ (508 mg) were stirred in dimethylsulfoxide (5 mL) at 130° C. for 24 hours. The mixture was cooled, diluted with ethyl acetate, washed three times with water, and brine, and dried (Na$_2$SO$_4$), filtered and concentrated. The crude product was chromatographed on silica gel with 25% ethyl acetate/hexanes.

Example 1E 2-(1H-pyrrolo[2,3-b]pyridin-5-yloxy)-4-(4-((4'-chlorobiphenyl-2-yl)methyl)piperazin-1-yl)benzoic acid EXAMPLE 1D (200 mg) and triethylsilane (1 mL) were stirred in dichloromethane (15 mL) and trifluoroacetic acid (15 mL) for 1 hour. The mixture was concentrated, taken up in ethyl acetate, washed twice with NaH$_2$PO$_4$, and brine, and dried (Na$_2$SO$_4$), filtered and concentrated.

Example 1F 3-nitro-4-((tetrahydro-2H-pyran-4-yl)methylamino)benzenesulfonamide 4-Fluoro-3-nitrobenzenesulfonamide (2.18 g), 1-(tetrahydropyran-4-yl)methylamine (1.14 g), and triethylamine (1 g) were stirred in tetrahydrofuran (30 mL) for 24 hours. The solution was diluted with ethyl acetate, washed with NaH$_2$PO$_4$ solution and brine, and dried (Na$_2$SO$_4$), filtered and concentrated. The product was triturated from ethyl acetate.

Example 1G

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide EXAMPLE 1E (115 mg), EXAMPLE 1F (67 mg), 1-ethyl-3-[3-(dimethylamino)propyl]-carbodiimide hydrochloride (82 mg), and 4-dimethylaminopyridine (26 mg) were stirred in CH$_2$Cl$_2$ (3 mL) for 24 hours. The reaction was cooled and chromatographed on silica gel with 0-5% methanol/ethyl acetate. $^1$H NMR (300 MHz, dimethylsulfoxide-d$_6$) δ 11.48 (brs, 1H), 8.34 (br s, 1H), 8.31 (m, 1H), 7.90 (d, 1H), 7.68 (m, 1H), 7.58 (m, 2H), 7.46 (m, 4H), 7.35 (m, 2H), 7.21 (dd, 1H), 6.76 (m, 4H), 6.28 (m, 2H), 3.02 (m, 2H), 2.89 (m, 4H), 2.80 (m, 4H), 2.40 (m, 3H), 1.59 (m, 2H), 1.25 (m, 4H), 0.87 (m, 2H).

Example 2

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide

Example 2A 4-(3-morpholinopropylamino)-3-nitrobenzenesulfonamide

This EXAMPLE was prepared by substituting 3-(N-morpholinyl)-propylamine for 1-(tetrahydropyran-4-yl)methylamine in EXAMPLE 1F.

Example 2B

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide This EXAMPLE was prepared by substituting EXAMPLE 2A for EXAMPLE 1F in EXAMPLE 1G. $^1$H NMR (300 MHz, dimethylsulfoxide-d$_6$) δ 11.60 (brs, 1H), 8.60 (m, 1H), 8.43 (d, 1H), 7.94 (d, 1H), 7.64 (m, 2H), 7.54 (d, 1H), 7.45 (m, 4H), 7.33 (m, 2H), 7.23 (dd, 1H), 6.96 (d, 1H), 6.85 (m, 2H), 6.32 (d, 1H), 6.26 (d, 1H), 3.60 (m, 4H), 3.10 (m, 4H), 3.05 (m, 10H), 2.40 (m, 2H), 2.33 (m, 2H), 1.77 (m, 2H).

Example 3

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide

Example 3A methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried (Na$_2$SO$_4$), filtered, and concentrated to give the product.

Example 3B methyl 2-(4-chlorophenyl)-4,4-dimethylcyclohex-1-enecarboxylate

EXAMPLE 3A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concen-

Example 3C (2-(4-chlorophenyl)-4,4-dimethylcyclohex-1-enyl) methanol

To a mixture of LiBH$_4$ (13 g), EXAMPLE 3B (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried (Na$_2$SO$_4$), filtered, and concentrated. The crude product was chromatographed on silica gel with 0-30% ethyl acetate/hexanes.

Example 3D tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 3C (29.3 g) and triethylamine (30 mL) in CH$_2$Cl$_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The crude product was chromatographed on silica gel with 10-20% ethyl acetate/hexanes.

Example 3E 1-((2-(4-chlorophenyl)-4,4-dimethylcyclohex-1-enyl)methyl)piperazine EXAMPLE 3D (1 g) was stirred in dichloromethane (10 mL), trifluoroacetic acid (10 mL), and triethylsilane (1 mL) for 1 hour. The mixture was concentrated, taken up in a mixture of dichloromethane (100 mL) and saturated aqueous Na$_2$CO$_3$ solution (20 mL) and stirred for 10 minutes. The layers were separated, and the organic layer was dried over Na$_2$SO$_4$, filtered, and concentrated to give the product.

Example 3F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried (Na$_2$SO$_4$), filtered, and concentrated. The crude product was chromatographed on silica gel with 10% ethyl acetate/hexanes.

Example 3G 1-(triisopropylsilyl)-1H-pyrrolo[2,3-b]pyridin-5-ol

To a mixture of EXAMPLE 3F (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M NaOH (69 mL) was added, followed by 30% H$_2$O$_2$ (8.43 mL), and the solution was stirred for 1 hour. Na$_2$S$_2$O$_3$ (10 g) was added, and the pH was adjusted to 4-5 with concentrated HCl and solid NaH$_2$PO$_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes.

Example 3H methyl 2-(1H-pyrrolo[2,3-b]pyridin-5-yloxy)-4-fluorobenzoate

A mixture of EXAMPLE 3G (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 3I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 3H (1.55 g), EXAMPLE 3E (2.42 g), and HK$_2$PO$_4$ (1.42 g) in dimethylsulfoxide (20 mL) at 135° C. was stirred for 24 hours. The reaction was cooled, diluted with ether (400 mL), and washed with 3×1M NaOH, and brine, and concentrated. The crude product was chromatographed on silica gel with 10-50% ethyl acetate/hexanes.

Example 3J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 3I (200 mg) in dioxane (10 mL) and 1M NaOH (6 mL) at 50° C. was stirred for 24 hours. The reaction was cooled, added to NaH$_2$PO$_4$ solution, and extracted three times with ethyl acetate. The combined extracts were washed with brine, and concentrated to give the pure product.

Example 3K tert-butyl 1-(tetrahydro-2H-pyran-4-yl)piperidin-4-ylcarbamate

Tert-butyl piperidin-4-ylcarbamate (45.00 g, 225 mmol) and dihydro-2H-pyran-4(3H)-one (24.74 g, 247 mmol) were added to dichloromethane (1000 mL). Sodium triacetoxyborohydride (61.90 g, 292 mmol) was added, and the solution was stirred at room temperature for 16 hours. The solution was extracted with 1M sodium hydroxide and dried over anhydrous sodium sulfate. The solution was filtered and concentrated and purified by flash column chromatography on

Example 3L 1-(tetrahydro-2H-pyran-4-yl)piperidin-4-amine dihydrochloride

A solution of EXAMPLE 3K (52.57 g, 185 mmol) in dichloromethane (900 mL) was treated with 4M aqueous HCl (462 mL), and the solution was mixed vigorously at room temperature for 16 hours. Solvent was removed under vacuum to give crude product as the dihydrochloride salt, which was used without further purification.

Example 3M 3-nitro-4-(1-(tetrahydro-2H-pyran-4-yl)piperidin-4-ylamino)benzenesulfonamide EXAMPLE 3L (22.12 g, 86 mmol) was added to 1,4-dioxane (300 mL) and water (43 mL). Triethylamine (43.6 mL, 31.6 g, 313 mmol) was added, and the mixture was stirred at room temperature until EXAMPLE 3L had completely dissolved. 4-chloro-3-nitrobenzenesulfonamide was added and the mixture was heated at 90° C. for 16 hours. The mixture was cooled, and the solvents were removed under vacuum. 10% methanol (in dichloromethane) was added and the solution was stirred vigorously at room temperature until a fine suspension was obtained. The solid was isolated by vacuum filtration and washed with dichloromethane to give pure product.

Example 3N 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 3M for EXAMPLE 1F in EXAMPLE 1G. $^1$H NMR (300 MHz, dimethylsulfoxide-$d_6$) δ 11.65 (brs, 1H), 8.53 (br s, 1H), 8.18 (m, 1H), 8.00 (br s, 1H), 7.63 (m, 1H), 7.49 (m, 3H), 7.34 (d, 2H), 7.12 (m, 1H), 7.04 (d, 2H), 6.67 (dd, 1H), 6.37 (d, 1H), 6.20 (d, 1H), 3.95 (m, 2H), 3.05 (m, 10H), 2.73 (m, 4H), 2.17 (m, 10H), 1.95 (m, 2H), 1.80 (m, 2H), 1.63 (m, 2H), 1.39 (t, 2H), 0.93 (s, 6H).

Example 4

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide

Example 4A 4-(1-methylpiperidin-4-ylamino)-3-nitrobenzenesulfonamide

This EXAMPLE was prepared by substituting 4-amino-N-methylpiperidine for 1-(tetrahydropyran-4-yl)methylamine in EXAMPLE 1F.

Example 4B 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 4A for EXAMPLE 1F in EXAMPLE 1G. $^1$H NMR (300 MHz, dimethylsulfoxide-$d_6$) δ 11.65 (brs, 1H), 8.55 (br s, 1H), 8.17 (m, 1H), 8.02 (d, 1H), 7.85 (dd, 1H), 7.51 (m, 3H), 7.35 (m, 2H), 7.18 (dd, 1H), 7.05 (d, 2H), 6.68 (dd, 1H), 6.38 (d, 1H), 6.20 (d, 1H), 3.90 (m, 1H), 3.09 (m, 8H), 2.77 (m, 2H), 2.05-2.30 (m, 10H), 1.95 (s, 3H), 1.39 (t, 2H), 1.24 (m, 2H), 0.93 (s, 6H).

Example 5

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 5A 3-nitro-4-((tetrahydro-2H-pyran-4-yl)methylamino)benzenesulfonamide A mixture of 4-fluoro-3-nitrobenzenesulfonamide (2.18 g), 1-(tetrahydropyran-4-yl)methylamine (1.14 g), and triethylamine (1 g) in tetrahydrofuran (30 mL) were stirred overnight, neutralized with concentrated HCl and concentrated. The residue was suspended in ethyl acetate and the precipitates were collected, washed with water and dried to provide the title compound.

Example 5B methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried ($Na_2SO_4$), filtered, and concentrated to give the product.

Example 5C methyl 2-(4-chlorophenyl)-4,4-dimethylcyclohex-1-enecarboxylate

EXAMPLE 5B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product.

Example 5D (2-(4-chlorophenyl)-4,4-dimethylcyclohex-1-enyl) methanol

To a mixture of LiBH$_4$ (13 g), EXAMPLE 5C (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried (Na$_2$SO$_4$), filtered, and concentrated. The crude product was chromatographed on silica gel with 0-30% ethyl acetate/hexanes.

Example 5E tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 5D (29.3 g) and triethylamine (30 mL) in CH$_2$Cl$_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The crude product was chromatographed on silica gel with 10-20% ethyl acetate/hexanes.

Example 5F 1-((2-(4-chlorophenyl)-4,4-dimethylcyclohex-1-enyl)methyl)piperazine EXAMPLE 5E (200 mg) and triethylsilane (1 mL) were stirred in dichloromethane (15 mL) and trifluoroacetic acid (15 mL) for 1 hour. The mixture was concentrated, taken up in ethyl acetate, washed twice with NaH$_2$PO$_4$, and brine, and dried (Na$_2$SO$_4$), filtered and concentrated.

Example 5G 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The mixture was diluted with ether, and the resulting solution was washed twice with water. The extracts were dried (Na$_2$SO$_4$), filtered, and concentrated. The crude product was chromatographed on silica gel with 10% ethyl acetate/hexanes.

Example 5H 1-(triisopropylsilyl)-1H-pyrrolo[2,3-b]pyridin-5-ol

To a mixture of EXAMPLE 5G (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M NaOH (69 mL) was added, followed by 30% H$_2$O$_2$ (8.43 mL), and the solution was stirred for 1 hour. Na$_2$S$_2$O$_3$ (10 g) was added, and the pH was adjusted to 4-5 with concentrated HCl and solid NaH$_2$PO$_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes.

Example 5I methyl 2-(1H-pyrrolo[2,3-b]pyridin-5-yloxy)-4-fluorobenzoate

A mixture of EXAMPLE 5H (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 5J methyl 2-(1H-pyrrolo[2,3-b]pyridin-5-yloxy)-4-((2-(4-chlorophenyl)-4,4-dimethylcyclohex-1-enyl)methyl)piperazin-1-yl)benzoate A mixture of EXAMPLE 5I (1.55 g), EXAMPLE 5F (2.42 g), and HK$_2$PO$_4$ (1.42 g) in dimethylsulfoxide (20 mL) at 135° C. was stirred for 24 hours. The reaction was cooled, diluted with ether (400 mL), and washed with 3×1M NaOH, and brine, and concentrated. The crude product was chromatographed on silica gel with 10-50% ethyl acetate/hexanes.

Example 5K 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 5J (200 mg) in dioxane (10 mL) and 1M NaOH (6 mL) at 50° C. was stirred for 24 hours. The reaction was cooled, added to NaH$_2$PO$_4$ solution, and extracted three times with ethyl acetate. The combined extracts were washed with brine, and concentrated to give the pure product.

Example 5L 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide EXAMPLE 5K (3.39 g), EXAMPLE 5A (1.87 g), 1-ethyl-3-[3-(dimethylamino)propyl]-carbodiimide hydrochloride (2.39 g), and 4-dimethylaminopyridine (1.09 g) were stirred in CH$_2$Cl$_2$ (40 mL) for 24 hours. The reaction was cooled and chromatographed on silica gel with 25-100% ethyl acetate/hexanes, then 10% methanol/ethyl acetate with 1% acetic acid, o give the product (1.62 g, 32%) as a white solid. $^1$H NMR (300 MHz, dimethylsulfoxide-d$_6$) 11.65 (brs, 1H), 8.55 (br s, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 1H), 3.84 (m, 1H), 3.30 (m, 4H), 3.07 (m, 4H), 2.73

(m, 2H), 2.18 (m, 6H), 1.95 (m, 2H), 1.61 (dd, 2H), 1.38 (m, 2H), 1.24 (m, 4H), 0.92 (s, 6H).

Example 6

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide Example 6A 4-(4-methylpiperazin-1-ylamino)-3-nitrobenzenesulfonamide A 50 mL round-bottomed flask was charged with 4-chloro-3-nitrobenzenesulfonamide (1 g, 4.23 mmol), 4-methylpiperazin-1-amine dihydrochloride (1 g, 5.32 mmol), and $N^1,N^1,N^2,N^2$-tetramethylethane-1,2-diamine (3 mL, 20.01 mmol) in dioxane (10 mL). The reaction mixture was refluxed for 12 hours. After this time, the reaction mixture was cooled to room temperature, the salt filtered off via a Buchner funnel, and the solvent removed in vacuo. The crude product was added to a silica gel column (Analogix, SF65-200 g) and purified by eluting with 0-5% methanol in dichloromethane.

Example 6B 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 6A for EXAMPLE 1F in EXAMPLE 1G. $^1$H NMR (300 MHz, dimethylsulfoxide-$d_6$) δ 11.65 (brs, 1H), 9.09 (br s, 1H), 8.47 (d, 1H), 8.24 (dd, 1H), 7.99 (d, 1H), 7.50 (m, 4H), 7.34 (d, 2H), 7.04 (d, 2H), 6.64 (dd, 1H), 6.35 (d, 1H), 6.20 (d, 1H), 3.04 (m, 4H), 2.89 (m, 4H), 2.73 (m, 2H), 2.34 (s, 3H), 2.17 (m, 6H), 1.95 (br s, 2H), 1.38 (t, 2H), 1.05 (m, 4H), 0.93 (s, 6H).

Example 7

2-(9H-carbazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide Example 7A ethyl 2-(9H-carbazol-4-yloxy)-4-fluorobenzoate This EXAMPLE was prepared by substituting ethyl 2,4-difluorobenzoate for methyl 2,4-difluorobenzoate and 4-hydroxycarbazole for EXAMPLE 3G in EXAMPLE 3H.

Example 7B ethyl 2-(9H-carbazol-4-yloxy)-4-(4-((2-(4-chlorophenyl)-4,4-dimethylcyclohex-1-enyl)methyl)piperazin-1-yl)benzoate This EXAMPLE was prepared by substituting EXAMPLE 7A for EXAMPLE 3H in EXAMPLE 3I.

Example 7C 2-(9H-carbazol-4-yloxy)-4-(4-((2-(4-chlorophenyl)-4,4-dimethylcyclohex-1-enyl)methyl)piperazin-1-yl)benzoic acid This EXAMPLE was prepared by substituting EXAMPLE 7B for EXAMPLE 3I in EXAMPLE 3J, except here upon completion of the reaction, water and 2N HCl were added to adjust the pH to 2, and the HCl salt of the product was extracted using CHCl$_3$/CH$_3$OH.

Example 7D 2-(9H-carbazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide This EXAMPLE was prepared by substituting EXAMPLE 7C for EXAMPLE 1E and EXAMPLE 4A for EXAMPLE 1F in EXAMPLE 1G, except here the purification was done by preparative HPLC using a C18 column, 250×50 mm, 10μ, and eluting with a gradient of 20-100% CH$_3$CN vs. 0.1% trifluoroacetic acid in water, giving the product as a bistrifluoroacetate salt. $^1$H NMR (300 MHz, dimethylsulfoxide-$d_6$) δ 11.82 (br s, 1H), 11.40 (s, 1H), 9.70, 9.40 (both v br s, total 2H), 8.40 (d, 1H), 8.10 (br d, 1H), 7.90 (br d, 1H), 7.72 (dd, 1H), 7.60 (d, 1H), 7.48 (d, 1H), 7.38 (m, 3H), 7.22 (m, 2H), 7.07 (m, 4H), 6.78 (dd, 1H), 6.43 (dd, 1H), 6.19 (s, 1H), 3.97 (m, 1H), 3.80 (m, 2H), 3.60, 3.30, 3.10, 2.80 (all br m, total 11H), 2.20, 2.10, 2.00 (all br m, total 8H), 1.78 (m, 2H), 1.42 (m, 2H), 1.25 (m, 2H), 0.92 (s, 6H).

Example 8

2-(9H-carbazol-4-yloxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide Example 8A 3-nitro-4-(3-(pyrrolidin-1-yl)propylamino)benzenesulfonamide This EXAMPLE was prepared by substituting 3-(pyrrolidin-1-yl)propan-1-amine for 1-(tetrahydropyran-4-yl)methylamine in EXAMPLE 1F.

Example 8B 2-(9H-carbazol-4-yloxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide This EXAMPLE was prepared by substituting EXAMPLE 7C for EXAMPLE 1E and EXAMPLE 8A for EXAMPLE 1F in EXAMPLE 1G, except here the purification was done by preparative HPLC using a C18 column, 250×50 mm, 10μ, and eluting with a gradient of 20-100% CH$_3$CN vs. 0.1% trifluoroacetic acid in water, giving the product as a bistrifluoroacetate salt. $^1$H NMR (300 MHz, dimethylsulfoxide-$d_6$) δ 11.80 (br s, 1H), 11.42 (s, 1H), 9.50, 9.25 (both v br s, total 2H), 8.58 (br t, 1H), 8.43 (d, 1H), 7.91 (d, 1H), 7.72 (dd, 1H), 7.60 (d, 1H), 7.50 (d, 1H), 7.38 (m, 3H), 7.23 (m, 2H), 7.07 (m, 3H), 6.93 (d, 1H), 6.78 (dd, 1H), 6.44 (dd, 1H), 6.18 (s, 1H), 3.70, 3.60, 3.20. 3.00 (all br m, total 18H), 2.18 (br m, 2H), 2.00-180 (envelope, 8H), 1.42 (m, 2H), 0.92 (s, 6H).

Example 9

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide

Example 9A

Trans-tert-butyl 4-morpholinocyclohexylcarbamate

A solution of tert-butyl-4-aminocyclohexylcarbamate (20.32 g, 95 mmol), bis(2-bromoethyl)ether (14.30 ml, 114 mmol) and triethylamine (33.0 ml, 237 mmol) in N,N-dimethylformamide (200 ml) was stirred for 16 hours at 70° C. The reaction mixture was cooled down to room temperature, concentrated and the product was extracted with ethyl acetate. The organic layer was washed with sodium carbonate solution (15% aq.), dried and concentrated. The product was used in next step without purification.

Example 9B

Trans-4-morpholinocyclohexanamine dihydrochloride

To a solution of trans-tert-butyl-4-morpholinocyclohexylcarbamate (19.2 g, 67.5 mmol) in dichloromethane (100 ml) was added HCl (100 ml, 400 mmol) (4M in dioxane) and the reaction mixture was stirred for 16 hours at room temperature. The reaction mixture was diluted with ether and solid salt was filtered off, and dried in an oven.

Example 9C

Trans-4-(4-morpholinocyclohexylamino)-3-nitrobenzenesulfonamide

A solution of trans-4-morpholinocyclohexanamine dihydrochloride (5 g, 19.44 mmol), 4-fluoro-3-nitrobenzenesulfonamide (4.32 g, 19.63 mmol) and triethylamine (20 ml, 143 mmol) in tetrahydrofuran (60 ml) was stirred for 16 hours at room temperature. The solid product was filtered off, washed with tetrahydrofuran, ether, dichloromethane (3×) and dried under vacuum.

Example 9D

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 9C for EXAMPLE 1F in EXAMPLE 1G. $^1$H NMR (300 MHz, dimethylsulfoxide-$d_6$) δ 11.61 (brs, 1H), 8.49 (br s, 1H), 8.12 (m, 1H), 7.99 (br s, 1H), 7.71 (m, 1H), 7.50 (m, 3H), 7.35 (d, 2H), 7.04 (d, 2H), 7.01 (m, 1H), 6.65 (dd, 1H), 6.36 (d, 1H), 6.21 (d, 1H), 3.60 (m, 4H), 3.04 (m, 4H), 2.73 (m, 2H), 2.57 (m, 2H), 2.42 (m, 1H), 2.18 (m, 6H), 2.05 (m, 2H), 1.95 (m, 2H), 1.90 (m, 2H), 1.38 (m, 6H), 1.15 (m, 3H), 0.92 (s, 6H).

Example 10

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide

Example 10A 4-(2-methoxyethylamino)-3-nitrobenzenesulfonamide

This EXAMPLE was prepared by substituting 2-methoxyethylamine for 1-(tetrahydropyran-4-yl)methylamine in EXAMPLE 1F.

Example 10B 4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 10A for EXAMPLE 1F in EXAMPLE 1G. $^1$H NMR (300 MHz, dimethylsulfoxide-$d_6$) δ 11.65 (brs, 1H), 8.58-8.49 (m, 1H), 8.55 (d, 1H), 8.03 (d, 1H), 7.79 (m, 1H), 7.49 (m, 3H), 7.34 (m, 2H), 7.06 (m, 1H), 7.04 (d, 2H), 6.68 (dd, 1H), 6.38 (m, 1H), 6.20 (d, 1H), 3.61-3.51 (m, 4H), 3.31 (s, 3H), 3.07 (m, 4H), 2.74 (m, 2H), 2.17 (m, 6H), 1.95 (br s, 2H), 1.38 (t, 2H), 0.92 (s, 6H).

Example 11

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide

Example 11A (S)-3-nitro-4-((tetrahydro-2H-pyran-3-yl)methylamino)benzenesulfonamide and (R)-3-nitro-4-((tetrahydro-2H-pyran-3-yl)methylamino)benzenesulfonamide This EXAMPLE was prepared by substituting (tetrahydro-2H-pyran-3-yl)methanamine for 1-(tetrahydropyran-4-yl)methylamine in EXAMPLE 1F.

Example 11B (S)-3-nitro-4-((tetrahydro-2H-pyran-3-yl)methylamino)benzenesulfonamide The racemic mixture of EXAMPLE 11A was resolved by chiral SFC on an AD column (21 mm i.d.×250 mm in length) using a gradient of 10-30% 0.1% diethylamine methanol in CO₂ over 15 minutes (oven temperature: 40° C.; flow rate: 40 mL/minute) to provide the title compound.

Example 11C (R)-3-nitro-4-((tetrahydro-2H-pyran-3-yl)methylamino)benzenesulfonamide The racemic mixture of EXAMPLE 11A was resolved by chiral SFC on an AD column (21 mm i.d.×250 mm in length) using a gradient of 10-30% 0.1% diethylamine methanol in CO₂ over 15 minutes (oven temperature: 40° C.; flow rate: 40 mL/minute) to provide the title compound.

Example 11D 4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide To a mixture of EXAMPLE 3J (59.8 mg, 0.105 mmol), EXAMPLE 11B (33 mg, 0.105 mmol) and N,N-dimethylpyridin-4-amine (38.4 mg, 0.314 mmol) in dichloromethane (5 ml) was added 1-ethyl-3-[3-(dimethylamino)propyl]-carbodiimide hydrochloride (24.07 mg, 0.13 mmol). The reaction mixture was stirred at room temperature overnight and concentrated. The residue was purified by reverse phase HPLC on a C18 column using a gradient of 40-60% acetonitrile/0.1% trifluoroacetic acid in water to give the title compound as the trifluoroacetate salt. The trifluoroacetic acid salt was dissolved in dichloromethane (6 ml) and washed with 50% aqueous NaHCO₃. The organic layer was dried over anhydrous Na₂SO₄ and concentrated to give the title compound. ¹H NMR (500 MHz, dimethylsulfoxide-d₆) δ 11.68 (s, 1 H), 11.40 (s, br, 1 H), 8.53-8.58 (m, 2 H), 8.04 (d, 1 H), 7.80 (dd, 1 H), 7.47-7.54 (m, 3 H), 7.34 (d, 2 H), 7.02-7.09 (m, 3 H), 6.67 (dd, 1 H), 6.39 (dd, 1 H), 6.19 (d, 1 H), 3.79 (dd, 1 H), 3.69-3.73 (m, 1 H), 3.22-3.37 (m, 3 H), 3.16-3.21 (m, 1 H), 3.07 (s, 4 H), 2.74 (s, 2 H), 2.09-2.24 (m, 6 H), 1.95 (s, 2 H), 1.86-1.93 (m, 1 H), 1.79-1.85 (m, 1 H), 1.58-1.64 (m, 1 H), 1.42-1.51 (m, 1 H), 1.38 (t, 2 H), 1.25-1.34 (m, 1 H), 0.92 (s, 6 H).

Example 12

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide

Example 12A 4-((1,4-dioxan-2-yl)methoxy)-3-nitrobenzenesulfonamide (1,4-Dioxan-2-yl)methanol (380 mg, 3.22 mmol) in tetrahydrofuran (30 ml) was treated with sodium hydride (60%) (245 mg, 6.13 mmol) at room temperature for 30 minutes. The reaction mixture was cooled in an ice bath and 4-fluoro-3-nitrobenzenesulfonamide (675 mg, 3.06 mmol) was added. The resulting mixture was stirred at room temperature for 2 hours and another portion of sodium hydride (60%) (245 mg, 6.13 mmol) was added. The reaction mixture was stirred overnight and quenched with ice water (3 ml). The cloudy mixture was filtered and the filtrate was concentrated. The residue was triturated with methanol to give the title compound.

Example 12B 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide The title compound was prepared as described in EXAMPLE 11D using EXAMPLE 12A in place of EXAMPLE 11B. ¹H NMR (500 MHz, dimethylsulfoxide-d₆) δ 11.67 (s, 1H), 11.42 (s, br, 1 H), 8.34 (s, 1 H), 8.03 (d, 2 H), 7.48-7.55 (m, 3 H), 7.41 (d, 1 H), 7.35 (d, 2 H), 7.04 (d, 2 H), 6.67 (dd, 1 H), 6.39 (dd, 1 H), 6.21 (d, 1 H), 4.20-4.28 (m, 2 H), 3.85-3.91 (m, 1 H), 3.82 (dd, 1 H), 3.74-3.78 (m, 1 H), 3.59-3.69 (m, 2 H), 3.41-3.51 (m, 2 H), 3.05-3.17 (m, 4 H), 2.83 (s, br, 2 H), 2.27 (s, br, 4 H), 2.15 (s, 2 H), 1.96 (s, 2 H), 1.39 (t, 2 H), 0.93 (s, 6 H).

Example 13

4-(4-{[2-(4-chlorophenyl)-4,4-dimethylcyclohex-1-en-1-yl]methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide The title compound was prepared as described in EXAMPLE 11D using EXAMPLE 11C in place of EXAMPLE 11B. The proton NMR spectra of EXAMPLE 13 and EXAMPLE 11D are identical. ¹H NMR (500 MHz, dimethylsulfoxide-d₆) δ 11.68 (s, 1 H), 11.40 (s, br, 1 H), 8.53-8.58 (m, 2 H), 8.04 (d, 1 H), 7.80 (dd, 1H), 7.47-7.54 (m, 3 H), 7.34 (d, 2 H), 7.02-7.09 (m, 3 H), 6.67 (dd, 1 H), 6.39 (dd, 1 H), 6.19 (d, 1 H), 3.79 (dd, 1 H), 3.69-3.73 (m, 1 H), 3.22-3.37 (m, 3 H), 3.16-3.21 (m, 1 H), 3.07 (s, 4 H), 2.74 (s, 2 H), 2.09-2.24 (m, 6 H), 1.95 (s, 2 H), 1.86-1.93 (m, 1 H), 1.79-1.85 (m, 1 H), 1.58-1.64 (m, 1 H), 1.42-1.51 (m, 1 H), 1.38 (t, 2 H), 1.25-1.34 (m, 1 H), 0.92 (s, 6 H).

Example 14

4-(4-{[2-(4-chlorophenyl)-4,4-dimethylcyclohex-1-en-1-yl]methyl}piperazin-1-yl)-N-(2-naphthylsulfonyl)-2-(1H-pyrrolo[2,3-b]pyridin-5-yloxy)benzamide The title compound was prepared as described in EXAMPLE 11D using naphthalene-2-sulfonamide (47 mg, 0.227 mmol) in place of EXAMPLE 11B. ¹H NMR (500 MHz, dimethylsulfoxide-d₆) δ 11.82 (s, 1H), 11.69 (s, 1H), 8.51 (s, 1H), 8.08 (d, 1 H), 8.05 (d, 1 H), 7.97 (dd, 2 H), 7.82 (dd, 1 H), 7.66-7.71 (m, 1 H), 7.63 (t, 1 H), 7.54 (d, 1 H), 7.47-7.52 (m, 2H), 7.34 (d, 2 H), 7.04 (d, 2 H), 6.65 (dd, 1 H), 6.39 (dd, 1 H), 6.18 (s, 1 H), 3.04 (s, 4 H), 2.72 (s, 2 H), 2.10-2.20 (m, 6 H), 1.95 (s, 2 H), 1.38 (t, 2H), 0.92 (s, 6 H).

Example 15

4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 15A methyl 6,6-dimethyl-4-oxotetrahydro-2H-pyran-3-carboxylate

To a suspension of hexane-washed NaH (0.72 g, 60% in mineral oil) in tetrahydrofuran (30 mL) was added a solution of 2,2-dimethyldihydro-2H-pyran-4(3H)-one (2.0 g) in tetrahydrofuran (20 mL). The suspension was stirred at room temperature for 30 minutes. The dimethylcarbonate (6.31 mL) was added dropwise by syringe. The mixture was heated to reflux for 4 h. LC/MS showed the expected product as the major product. The mixture was acidified with 5% HCl and extracted with dichloromethane (100 mL×3) and washed with water, brine and dried over $Na_2SO_4$. After evaporation, the crude product was loaded on a column and eluted with 10% ethyl acetate in hexane to give the product.

Example 15B methyl 6,6-dimethyl-4-(trifluoromethylsulfonyloxy)-5,6-dihydro-2H-pyran-3-carboxylate To a cooled (0° C.) stirring suspension of NaH (0.983 g, 60% in mineral oil) in ether (50 mL) was added EXAMPLE 15A (3.2 g). The mixture was stirred at 0° C. for 30 minutes before the addition of $Tf_2O$ (4.2 mL). The mixture was then stirred at room temperature overnight. The mixture was diluted with ether (200 mL) and washed with 5% HCl, water and brine. After drying over $Na_2SO_4$, evaporation of solvent gave the crude product which was used in the next step without further purification.

Example 15C methyl 4-(4-chlorophenyl)-6,6-dimethyl-5,6-dihydro-2H-pyran-3-carboxylate To a solution of EXAMPLE 15B (2.88 g), 4-chlorophenylboronic acid (1.88 g) and $Pd(Ph_3P)_4$ (0.578 g) in toluene (40 mL) and ethanol (10 mL) was added 2N $Na_2CO_3$ (10 mL). The mixture was stirred at reflux overnight. The mixture was diluted ether (300 mL) and washed with water, brine and dried over $Na_2SO_4$. After evaporation of solvent, the residue was loaded on a column and eluted with 3% ethyl acetate in hexane to give the product.

Example 15D (4-(4-chlorophenyl)-6,6-dimethyl-5,6-dihydro-2H-pyran-3-yl)methanol To a solution of EXAMPLE 15C (1.6 g) in ether (20 mL) was added $LiAlH_4$ (1.2 g). The mixture was stirred for 4 hours. The mixture was acidified carefully with 5% HCl and extracted with ethyl acetate (100 mL×3) and washed with water, brine and dried over $Na_2SO_4$. After concentration, the crude product was loaded on a column and eluted with 10% ethyl acetate in hexane to give the product.

Example 15E 4-(4-chlorophenyl)-6,6-dimethyl-5,6-dihydro-2H-pyran-3-carbaldehyde To a solution of oxalyl chloride (1.1 g) in dichloromethane (30 mL) at −78° C. was added dimethylsulfoxide (6.12 mL). The mixture was stirred at the temperature for 30 minutes, and then a solution of EXAMPLE 15D (1.2 g) in dichloromethane (10 mL) was added. The mixture was stirred at −78° C. for 2 hours before the addition of triethylamine (10 mL). The mixture was stirred overnight and the temperature was allowed to rise to room temperature. The mixture was diluted with ether (300 mL) and washed with water, brine and dried over $Na_2SO_4$. Concentration of the solvent and column purification (5% ethyl acetate in hexane) gave the product.

Example 15F methyl 2-(1H-pyrrolo[2,3-b]pyridin-5-yloxy)-4-(piperazin-1-yl)benzoate A mixture of EXAMPLE 3H (20.5 g) and piperazine (37.0 g) in dimethylsulfoxide (200 mL) was heated to 110° C. for 24 hours, and the mixture was allowed to cool to room temperature. The mixture was poured into water (1 L), extracted three times with dichloromethane, and the combined extracts were washed with 2× water, and brine and filtered and concentrated to give the pure product.

Example 15G methyl 2-(1H-pyrrolo[2,3-b]pyridin-5-yloxy)-4-((4-(4-chlorophenyl)-6,6-dimethyl-5,6-dihydro-2H-pyran-3-yl)methyl)piperazin-1-yl)benzoate To a solution of EXAMPLE 15E (100 mg) and EXAMPLE 15F (177 mg) in dichloromethane (10 mL) was added sodium triacetoxyborohydride (154 mg). The mixture was stirred overnight. The mixture was diluted with ethyl acetate (200 mL) and washed with 2% NaOH, water and brine. After drying over $Na_2SO_4$, the mixture was filtered and the solvent was evaporated under vacuum. The residue was loaded on a column and eluted with 30% ethyl acetate in hexane to give the pure product.

Example 15H 2-(1H-pyrrolo[2,3-b]pyridin-5-yloxy)-4-(4-((4-(4-chlorophenyl)-6,6-dimethyl-5,6-dihydro-2H-pyran-3-yl)methyl)piperazin-1-yl)benzoic acid To a solution of EXAMPLE 15G (254 mg) in tetrahydrofuran (4 mL), methanol (2 mL) and water (2 mL) was added $LiOH\ H_2O$ (126 mg). The mixture was stirred overnight. The mixture was then neutralized with 5% HCl and diluted with ethyl acetate (200 mL). After washing with brine, it was dried over $Na_2SO_4$. Filtration and evaporation of solvent gave the product.

Example 15I 4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in EXAMPLE 1G, substituting EXAMPLE 1E with EXAMPLE 15H. $^1$H NMR (300 MHz, dimethylsulfoxide-$d_6$) δ 11.68 (br s, 1H), 11.42 (s, 1H), 8.60 (m, 1H), 8.57 (d, 1H), 8.05(d, 1H), 7.80 (dd, 1H), 7.48-7.54 (m, 3H), 7.38 (d, 2H), 7.12 (m, 3H), 6.68 (dd, 1H), 6.40 (dd, 1H), 6.20 (s, 1H), 4.11(s, 2H), 3.85(m, 2H), 3.27(m, 6H), 3.07 (m, 2H), 2.84 (m, 2H), 2.14 (m, 5H), 1.92(m, 1H), 1.42 (m, 2H), 1.24(m, 2H), 1.10 (s, 6H).

Example 16

4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide

Example 16A 4-(2-methoxyethylamino)-3-(trifluoromethylsulfonyl)benzenesulfonamide 4-Fluoro-3-(trifluoromethylsulfonyl)benzenesulfonamide (1.536 g, 5 mmol), 2-methoxyethanamine (0.376 g, 5 mmol), and triethylamine (1.939 g, 15 mmol) in anhydrous tetrahydrofuran (30 mL) solution was heated at 55° C. for 3 hours. The solution was diluted with ethyl acetate, washed with water and brine, and dried (Na$_2$SO$_4$), filtered and the filtrate was concentrated. The crude material was used in the next step without further purification.

Example 16B 4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide This EXAMPLE was prepared by substituting EXAMPLE 3J for EXAMPLE 1E and EXAMPLE 16A for EXAMPLE 1F in EXAMPLE 1G. $^1$H NMR (400 MHz, dimethylsulfoxide-$d_6$) δ 11.67 (brs, 1H), 8.14 (m 1H), 8.03 (d, 1H), 7.91 (d, 1H), 7.50 (m, 3H), 7.34 (d, 2H), 7.19 (s, 1H), 7.04 (m, 3H), 6.67 (dd, 1H), 6.39 (m, 1H), 6.19 (d, 1H), 3.51 (m, 4H), 3.28 (s, 3H), 3.06 (m, 4H), 2.75 (m, 2H), 2.17 (m, 6H), 1.95 (m, 2H), 1.39 (t, 2H), 0.93 (s, 6H).

Example 17

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide

Example 17A 4-((tetrahydro-2H-pyran-4-yl)methylamino)-3-(trifluoromethylsulfonyl)benzenesulfonamide This EXAMPLE was prepared by substituting 1-(tetrahydropyran-4-yl)methylamine for 2-methoxyethanamine in EXAMPLE 16A.

Example 17B 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide This EXAMPLE was prepared by substituting EXAMPLE 3J for EXAMPLE 1E and EXAMPLE 17A for EXAMPLE 1F in EXAMPLE 1G. $^1$H NMR (400 MHz, dimethylsulfoxide-$d_6$) δ 11.70 (brs, 1H), 8.15 (m 1H), 8.04 (d, 1H), 7.92 (d, 1H), 7.51 (m, 3H), 7.34 (d, 2H), 7.19 (s, 1H), 7.05 (m, 3H), 6.68 (dd, 1H), 6.40 (m, 1H), 6.18 (d, 1H), 3.85 (m, 2H), 3.25 (m, 4H), 3.07 (m, 4H), 2.77 (m, 2H), 2.17 (m, 6H), 1.95 (m, 2H), 1.84 (m,1 H), 1.54 (m, 2H), 1.39(t, 2H), 1.24 (m, 2H), 0.93 (s, 6H).

Example 18

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 18A methyl 2-(1H-indol-5-yloxy)-4-fluorobenzoate

A mixture of 5-hydroxyindole (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 18B methyl 2-(1H-indol-5-yloxy)-4-(4-((2-(4-chlorophenyl)-4,4-dimethylcyclohex-1-enyl)methyl)piperazin-1-yl)benzoate A mixture of EXAMPLE 18A (1.7 g), EXAMPLE 3E (1.8 g), and HK$_2$PO$_4$ (1.21 g) in dimethylsulfoxide (20 mL) at 135° C. was stirred for 24 hours. The reaction was cooled, diluted with ether (400 mL), and washed with 3×1M NaOH, and brine, and concentrated. The crude product was chromatographed on silica gel with 10-50% ethyl acetate/hexanes.

Example 18C 2-(1H-indol-5-yloxy)-4-(4-((2-(4-chlorophenyl)-4,4-dimethylcyclohex-1-enyl)methyl)piperazin-1-yl)benzoic acid EXAMPLE 18B (200 mg) in dioxane (10 mL) and 1M NaOH (6 mL) at 50° C. was stirred for 24 hours. The reaction was cooled, added to $NaH_2PO_4$ solution, and extracted three times with ethyl acetate. The combined extracts were washed with brine, and concentrated to give the pure product.

Example 18D 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as described in EXAMPLE 11D by replacing EXAMPLE 3J with EXAMPLE 18C, and EXAMPLE 1F for EXAMPLE 11B. $^1$H NMR (300 MHz, dimethylsulfoxide-$d_6$) δ 11.18 (s, 2H), 8.59-8.64 (m, 2H), 7.80 (dd, 1H), 7.52 (d, 1H), 7.39-7.42 (m, 2H), 7.33 (d, 2H), 7.16 (d, 1H), 7.10 (d,1H), 7.03 (d, 2H), 6.8 (dd, 1H), 6.65 (dd, 1H), 6.40)s, 1H), 6.14 (d, 1H), 3.85 (dd, 2H), 3.24-3.32 (m, 4H), 3.03 (s, 3H), 2.73 (s, 2H), 2.12-2.17 (m, 5H), 1.68-1.94 (m, 3H), 1.61 (d, 2H), 1.37 (t, 2H), 1.24-1.27 (m, 2H), 0.92 (s, 6H).

Example 19

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide The title compound was prepared as described in EXAMPLE 11D by replacing EXAMPLE 11B with EXAMPLE 9B and EXAMPLE 3J with EXAMPLE 18C. $^1$H NMR (500 MHz, pyridine-$d_5$) δ 12.29 (s, 1H), 9.29 (d, J=2.1 Hz, 1H), 8.37 (d, J=7.6 Hz, 1H), 8.32 (dd, J=9.3, 2.3 Hz, 1H), 8.18 (d, J=8.8 Hz, 1H), 7.52-7.57 (m, 2H), 7.39-7.47 (m, 3H), 7.10 (dd, J=8.7, 2.3 Hz, 1H), 7.05-7.08 (m, 2H), 6.90 (d, J=9.5 Hz, 1H), 6.74 (dd, J=9.0, 2.3 Hz, 1H), 6.59-6.63 (m, 1H), 6.55 (d, J=2.4 Hz, 1H), 3.72-3.78 (m, 4H), 3.33-3.43 (m, 1H), 2.99-3.09 (m, 4H), 2.76 (s, 2H), 2.46-2.54 (m, 4H), 2.16-2.29 (m, 3H), 2.09-2.14 (m, 4H), 2.05 (d, J=11.9 Hz, 2H), 1.97 (d, J=1.8 Hz, 2H), 1.87 (d, J=11.6 Hz, 2H), 1.19-1.42 (m, 6H), 0.93 (s, 6H).

Example 20

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide The title compound was prepared as described in EXAMPLE 11D by replacing EXAMPLE 11B with EXAMPLE 10A and EXAMPLE 3J with EXAMPLE 18C. $^1$H NMR (400 MHz, dimethylsulfoxide-$d_6$) δ 11.20 (br. s, 1H) 11.15 (s, 1H) 8.59 (m, 2H) 7.81 (dd, 1H) 7.50 (d, 1H) 7.36 (m, 4H) 7.08 (m, 4H) 6.85 (dd, 1H) 6.65 (dd, 1H) 6.38 (m, 1H) 6.14 (m, 1H) 3.58 (m, 4H) 3.30 (s, 3H) 3.03 (m, 4H) 2.73 (s, 2H) 2.15 (m, 6H) 1.96 (s, 2H) 1.38 (t, 2H) 0.92 (s, 6H)

Example 21

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide The title compound was prepared as described in EXAMPLE 11D by replacing EXAMPLE 3J with EXAMPLE 18C. $^1$H NMR (400 MHz, dimethylsulfoxide-$d_6$) δ 11.17 (s, 2 H), 8.53-8.65 (m, 2 H), 7.80 (d, 1 H), 7.51 (d, 1 H), 7.38-7.44 (m, 2 H), 7.33 (d, 2 H), 7.15 (s, 1 H), 7.02-7.09 (m, 3 H), 6.82-6.92 (m, 1 H), 6.65 (d, 1 H), 6.39 (s, 1 H), 6.14 (s, 1 H), 3.68-3.82 (m, 2 H), 3.22-3.32 (m, 2 H), 3.13-3.22 (m, 1 H), 3.03 (s, 4 H), 2.72 (s, 2 H), 2.09-2.23 (m, 6 H), 1.78-1.98 (m, 4 H), 1.56-1.66 (m, 1 H), 1.43-1.51 (m, 1 H), 1.37 (t, 2 H), 1.22-1.33 (m, 1 H), 0.92 (s, 6 H).

Example 22

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide The title compound was prepared as described in EXAMPLE 11D using EXAMPLE 11C in place of EXAMPLE 11B, and EXAMPLE 18C in place of EXAMPLE 3J. $^1$H NMR (400 MHz, dimethylsulfoxide-$d_6$) δ 11.17 (s, 2H), 8.53-8.65 (m, 2 H), 7.80 (d, 1 H), 7.51 (d, 1 H), 7.38-7.44 (m, 2 H), 7.33 (d, 2 H), 7.15 (s, 1 H), 7.02-7.09 (m, 3 H), 6.82-6.92 (m, 1 H), 6.65 (d, 1 H), 6.39 (s, 1 H), 6.14 (s, 1 H), 3.68-3.82 (m, 2 H), 3.22-3.32 (m, 2 H), 3.13-3.22 (m, 1 H), 3.03 (s, 4 H), 2.72 (s, 2 H), 2.09-2.23 (m, 6 H), 1.78-1.98 (m, 4 H), 1.56-1.66 (m, 1 H), 1.43-1.51 (m, 1 H), 1.37 (t, 2 H), 1.22-1.33 (m, 1 H), 0.92 (s, 6 H).

Example 23

4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 23A methyl 2-(1H-indol-5-yloxy)-4-(piperazin-1-yl)benzoate

The title compound was prepared as described in EXAMPLE 15F by replacing EXAMPLE 3H with EXAMPLE 18A.

Example 23B methyl 2-(1H-indol-5-yloxy)-4-(4-((4-(4-chlorophenyl)-6,6-dimethyl-5,6-dihydro-2H-pyran-3-yl)methyl)piperazin-1-yl)benzoate The title compound was prepared as described in EXAMPLE 15G by replacing EXAMPLE 15F with EXAMPLE 23A.

Example 23C 2-(1H-indol-5-yloxy)-4-(4-((4-(4-chlorophenyl)-6,6-dimethyl-5,6-dihydro-2H-pyran-3-yl)methyl)piperazin-1-yl)benzoic acid The title compound was prepared as described in EXAMPLE 15H by replacing EXAMPLE 15G with EXAMPLE 23B.

Example 23D 4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as described in EXAMPLE 11D by replacing EXAMPLE 11B with EXAMPLE 1F, and EXAMPLE 3J with EXAMPLE 23C. $^1$H NMR (400 MHz, dimethylsulfoxide-$d_6$) δ 11.20 (br s, 1H), 11.17 (s, 1H), 8.63 (t, 1 H), 8.59 (d, 1 H), 7.79 (dd, 1 H), 7.51 (d, 1 H), 7.36 (m, 3 H), 7.13 (m, 2 H), 6.86 (dd, 1 H), 6.66 (dd, 1 H), 6.39 (s, 1 H), 6.15 (d, 1 H), 4.10 (s, 2 H), 3.85 (m, 3 H), 3.50 (m, 2 H), 3.42 (m, 2 H), 3.24 (m, 4 H), 3.02 (m, 4 H), 2.82 (m, 2 H), 2.16 (m, 2 H), 1.61 (m, 3 H), 1.25 (m, 4 H), 1.17 (s, 6 H).

Example 24

4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide

Example 24A 3-nitro-4-((tetrahydro-2H-pyran-4-yl)methoxy)benzenesulfonamide (Tetrahydro-2H-pyran-4-yl)methanol (2.0 g) in tetrahydrofuran (20 mL) was treated with 60% NaH (1.377 g). The solution was stirred for 20 minutes at the room temperature. To this solution was added 4-fluoro-3-nitrobenzenesulfonamide (2.84 g) portion-wise. The reaction was stirred for another 2 hours. The mixture was poured into water, neutralized with 10% HCl, and extracted with ethyl acetate three times. The combined organic layers were washed with brine, dried over MgSO$_4$, filtered, and concentrated. The residue was purified with flash column chromatography on silica gel eluting with 20-60% ethyl acetate in hexanes.

Example 24B 4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide The title compound was prepared by substituting EXAMPLE 24A for EXAMPLE 11B in EXAMPLE 11D. $^1$H NMR (500 MHz, dimethylsulfoxide-$d_6$) δ 11.67 (s, 1H), 8.33 (s, 1H), 8.00-8.02 (m, 2H), 7.50-7.53 (m, 3H), 7.34-7.36 (m, 3H), 7.04 (d, 2H), 6.67 (dd, 1H), 6.38 (d, 1H), 6.21 (s, 1H), 4.06 (d, 2H), 3.88 (dd, 2H), 3.08 (s, 4H), 2.80 (s, 2H), 2.25 (s, 4H), 2.15 (s, 2H), 1.96 (s, 2H), 1.63-1.66 (m, 2H), 1.52-1.55 (m, 1H), 1.33-1.40 (m, 4H), 0.92 (s, 6H).

Example 25

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide

Example 25A 4-((1,4-dioxan-2-yl)methylamino)-3-nitrobenzenesulfonamide

The title compound was prepared as described in EXAMPLE 1F using (1,4-dioxan-2-yl)methanamine in place of (tetrahydropyran-4-yl)methanamine.

Example 25B 4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide The title compound was prepared as described in EXAMPLE 11D using EXAMPLE 25A in place of EXAMPLE 11B. $^1$H NMR (500 MHz, dimethylsulfoxide-$d_6$) δ 11.66 (s, 1H), 11.38 (s, 1H), 8.53-8.59 (m, 2H), 8.03 (d, 1H), 7.81 (dd, 1H), 7.46-7.54 (m, 3H), 7.34 (d, 2H), 7.09 (d, 1H), 7.04 (d, 2H), 6.68 (dd, 1H), 6.38 (dd, 1H), 6.19 (d, 1H), 3.75-3.86 (m, 3H), 3.58-3.68 (m, 2H), 3.45-3.52 (m, 2H), 3.35-3.43 (m, 2H), 3.07 (s, 4H), 2.75 (s, 2H), 2.17 (d, 6H), 1.95 (s, 2H), 1.38 (t, 2H), 0.92 (s, 6H)

Example 26

4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide

Example 26A 3-nitro-4-(2,2,2-trifluoroethylamino)benzenesulfonamide

The title compound was prepared by substituting 2,2,2-trifluoroethanamine for (tetrahydropyran-4-yl)methylamine in EXAMPLE 1F.

Example 26B 4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide The title compound was prepared by substituting EXAMPLE 26A for EXAMPLE 11B in EXAMPLE 11D. $^1$H NMR (500 MHz, dimethylsulfoxide-$d_6$) δ 11.48 (s, 1H), 8.40 (m, 2H), 7.90 (d, 1H), 7.71 (dd, 1H), 7.59 (d, 1H), 7.40 (t, 1H), 7.34 (d, 2H), 7.25 (d, 1H), 7.06 (m, 3H), 6.61 (dd, 1H), 6.26 (m, 2H), 4.32 (m, 2H), 3.00 (m, 4H), 2.73 (s, 2H), 2.19 (m, 6H), 1.96 (s, 2H), 1.39 (t, 2H), 0.93 (s, 6H).

Example 27

4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide

Example 27A 3-nitro-4-(3,3,3-trifluoropropylamino)benzenesulfonamide

The title compound was prepared by substituting 3,3,3-trifluoropropan-1-amine for (tetrahydropyran-4-yl)methylamine in EXAMPLE 1F.

Example 27B 4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide The title compound was prepared by substituting EXAMPLE 27A for EXAMPLE 11B in EXAMPLE 11D. $^1$H NMR (500 MHz, dimethylsulfoxide-$d_6$) δ 11.47 (s, 1H), 8.37 (d, 1H), 8.29 (m, 1H), 7.89 (d, 1H), 7.61 (m, 2H), 7.39 (t, 1H), 7.35 (d, 2H), 7.22 (d, 1H), 7.05 (d, 2H), 6.75 (d, 1H), 6.62 (dd, 1H), 6.27 (m, 2H), 3.59 (q, 2H), 3.00 (m, 4H), 2.73 (s, 2H), 2.66 (m, 2H), 2.18 (m, 6H), 1.96 (s, 2H), 1.39 (t, 2H), 0.93 (m, 6H).

Example 28

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide

Example 28A (S)-4-((1,4-dioxan-2-yl)methoxy)-3-nitrobenzenesulfonamide

The racemic mixture of EXAMPLE 12A was resolved on a SFC chiral AD column to provide the title compound.

Example 28B 4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide The title compound was prepared as described in EXAMPLE 11D using EXAMPLE 28A in place of EXAMPLE 11B. $^1$H NMR (500 MHz, dimethylsulfoxide-$d_6$) δ 11.67 (s, 2H), 8.35 (s, 1H), 8.03 (d, 2H), 7.48-7.57 (m, 3H), 7.42 (d, 1H), 7.35 (d, 2H), 7.05 (d, 2H), 6.68 (dd, 1H), 6.39 (dd, 1H), 6.21 (s, 1H), 4.19-4.30 (m, 2H), 3.85-3.92 (m, 1H), 3.73-3.85 (m, 2H), 3.58-3.70 (m, 2H), 3.40-3.52 (m, 2H), 3.10 (s, 4H), 2.85 (s, 2H), 2.18-2.39 (m, 3H), 2.15 (s, 2H), 1.96 (s, 2H), 1.39 (t, 2H), 0.93 (s, 6H).

Example 29

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide

Example 29A

Cis-4-((4-methoxycyclohexyl)methylamino)-3-nitrobenzenesulfonamide

4-Fluoro-3-nitrobenzenesulfonamide (1.098 g) and EXAMPLE 34A (1 g) in tetrahydrofuran (20 mL) was treated with N,N-diisopropylethylamine (0.871 mL) overnight. The reaction mixture was concentrated and the residue was purified by reverse phase chromatography, eluted with 40-55% acetonitrile in 0.1% trifluoroacetic acid in water over 25 min to give the cis isomer EXAMPLE 29A and trans isomer EXAMPLE 34B.

Example 29B

Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 29A in place of EXAMPLE 11B. $^1$H NMR (500 MHz, dimethylsulfoxide-$d_6$) δ 11.69 (s, 1H), 11.36 (s, 1H), 8.53-8.63 (m, 2H), 8.04 (d, 1H), 7.79 (dd, 1H), 7.47-7.56 (m, 3H), 7.34 (d, 2H), 7.00-7.12 (m, 3H), 6.68 (dd, 1H), 6.39 (dd, 1H), 6.19 (d, 1H), 3.37 (s, 1H), 3.26 (t, 2H), 3.20 (s, 3H), 3.07 (s, 4H), 2.75 (s, 2H), 2.17 (d, 6H), 1.95 (s, 2H), 1.81 (dd, 2H), 1.64-1.74 (m, 1H), 1.48 (dd, 2H), 1.23-1.42 (m, 6H), 0.92 (s, 6H).

Example 30

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide

Example 30A (R)-4-((1,4-dioxan-2-yl)methoxy)-3-nitrobenzenesulfonamide

The racemic mixture of EXAMPLE 12A was resolved on a SFC chiral AD column to provide the title compound.

Example 30B 4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide The title compound was prepared as described in EXAMPLE 11D using EXAMPLE 30A in place of EXAMPLE 11B. ¹H NMR (500 MHz, dimethylsulfoxide-$d_6$) δ 11.67 (s, 2H), 8.35 (s, 1H), 8.03 (d, 2H), 7.48-7.57 (m, 3H), 7.42 (d, 1H), 7.35 (d, 2H), 7.05 (d, 2H), 6.68 (dd, 1H), 6.39 (dd, 1H), 6.21 (s, 1H), 4.19-4.30 (m, 2H), 3.85-3.92 (m, 1H), 3.73-3.85 (m, 2H), 3.58-3.70 (m, 2H), 3.40-3.52 (m, 2H), 3.10 (s, 4H), 2.85 (s, 2H), 2.18-2.39 (m, 3H), 2.15 (s, 2H), 1.96 (s, 2H), 1.39 (t, 2H), 0.93 (s, 6H).

Example 31

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide The title compound was prepared as described in EXAMPLE 1G by replacing Example 1E and EXAMPLE 1F with EXAMPLE 15H and EXAMPLE 25A, respectively. ¹H NMR (300 MHz, dimethylsulfoxide-$d_6$) δ 11.66 (s, 1H), 11.46 (m, 1H), 8.54 (m, 2H), 8.45 (m, 1H), 8.03 (d, 1H), 7.83 (m, 2H), 7.50 (m, 3H), 7.34 (m, 3H), 7.12 (m, 2H), 6.68 (dd, 1H), 6.38 (dd, 1H), 6.20 (d, 1H), 4.11 (s, 2H), 3.79 (m, 4H), 3.51 (m, 6H), 3.05 (m, 4H), 2.17 (m, 3H), 1.17 (s, 6H).

Example 32

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide The title compound was prepared as described in EXAMPLE 1G by replacing EXAMPLE 1E and EXAMPLE 1F with EXAMPLE 15H and EXAMPLE 12A, respectively. ¹H NMR (300 MHz, dimethylsulfoxide-$d_6$) δ 11.67 (s, 1H), 8.37 (d, 1H), 8.03 (m, 2H), 7.50 (m, 3H), 7.37 (d, 2H), 7.13 (d, 2H), 6.68 (dd, 1H), 6.40 (dd, 1H), 6.20 (d, 1H), 4.25 (m, 2H), 4.12 (s, 2H), 3.84 (m, 3H), 3.63 (m, 2H), 3.45 (m, 2H), 3.06 (m, 4H), 2.86 (m, 2H), 2.24 (m, 6H), 1.20 (m, 6H).

Example 33

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared as described in EXAMPLE 1G by replacing EXAMPLE 1E and EXAMPLE 1F with EXAMPLE 15H and EXAMPLE 9C, respectively. ¹H NMR (300 MHz, dimethylsulfoxide-$d_6$) δ 11.63 (s, 1H), 8.51 (d, 1H), 8.15 (d, 1H), 8.01 (d, 1H), 7.76 (dd, 1H), 7.48 (m, 3H), 7.38 (d, 2H), 7.13 (d, 2H), 7.06 (d, 1H), 6.66 (dd, 1H), 6.36 (dd, 1H), 6.21 (d, 1H), 4.11 (s, 2H), 3.63 (m, 5H), 3.05 (m, 4H), 2.83 (s, 2H), 2.64 (m, 4H), 2.17 (m, 6H), 2.05 (m, 2H), 1.91 (s, 2H), 1.43 (m, 6H), 1.17 (m, 6H).

Example 34

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide Example 34A (4-methoxycyclohexyl)methanamine (4-Methoxyphenyl)methanamine (1 g, 1.29 mmol) in ethanol (10 ml) was treated with 5% Rh—Al$_2$O$_3$ (99.8 mg, 0.048 mmol) under H$_2$ atmosphere (500 psi) at 50° C. for 16 hours. Additional 5% Rh—Al$_2$O$_3$ (0.4 g) was added. The resulting mixture was stirred under H$_2$ atmosphere (500 psi) at 60° C. for 2 hours. The insoluble material was filtered off and the filtrate was concentrated to provide a mixture of cis and trans product as an oil, which was used in the next step without further purification.

Example 34B

Trans-4-((4-methoxycyclohexyl)methylamino)-3-nitrobenzenesulfonamide

4-Fluoro-3-nitrobenzenesulfonamide (1.098 g) and EXAMPLE 34A (1 g) in tetrahydrofuran (20 mL) was treated with N,N-diisopropylethylamine (0.871 mL) overnight. The reaction mixture was concentrated and the residue was purified by reverse phase chromatography, and was eluted with 40-55% acetonitrile in 0.1% trifluoroacetic acid in water over 25 minutes.

Example 34C

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 34B in place of EXAMPLE 11B. ¹H NMR (500 MHz, dimethylsulfoxide-$d_6$) δ 11.69 (s, 1 H), 11.37 (s, 1 H), 8.52-8.62 (m, 2 H), 8.04 (d, 1 H), 7.79 (dd, 1 H), 7.47-7.55 (m, 3 H), 7.34 (d, 2 H), 7.02-7.09 (m, 3 H), 6.68 (dd, 1 H), 6.39 (dd, 1 H), 6.19 (d, 1 H), 3.21-3.27 (m, 5 H), 3.02-3.12 (m, 5 H), 2.75 (s, 2 H), 2.20 (s, 4 H), 2.14 (s, 2 H), 1.93-2.04 (m, 4 H), 1.79 (d, 2 H), 1.55-1.65 (m, 1 H), 1.38 (t, 2 H), 0.97-1.12 (m, 4 H), 0.92 (s, 6 H).

Example 35

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide The title compound was prepared as described in EXAMPLE 1G by replacing Example 1E and EXAMPLE 1F with EXAMPLE 15H and EXAMPLE 36C, respectively. ¹H NMR (300 MHz, dimethylsulfoxide-$d_6$) δ 11.65 (s, 1H), 8.78 (s, 1H), 8.58 (s, 1H), 8.00 (d, 1H), 7.51 (m, 3H), 7.38 (d, 2H), 7.14 (d, 2H), 6.68 (dd, 1H), 6.37 (dd, 1H), 6.23 (d, 1H), 4.31 (d, 2H), 4.13 (s, 2H), 3.88 (dd, 2H), 3.11 (m, 5H), 2.16 (m, 6H), 1.65 (m, 2H), 1.35 (m, 2H), 1.19 (s, 6H).

Example 36

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide Example 36A 5-Bromo-6-chloropyridine-3-sulfonyl chloride (8.2 g) in methanol (20 mL) was cooled to 0° C. To this solution was added 7N NH₃ in methanol (80 mL). The reaction mixture was stirred overnight. The solvent was removed at low temperature, and the residue was partitioned between ethyl acetate and water. The aqueous layer was extracted with ethyl acetate three times. The combined organic layers were washed with brine, dried (MgSO₄), filtered, and concentrated. The solid was purified by flash column chromatography on silica gel using 20-100% ethyl acetate in hexanes to give the title compound.

Example 36B

The title compound was prepared by substituting EXAMPLE 36A for 4-fluoro-3-nitrobenzenesulfonamide in EXAMPLE 24A.

Example 36C

A mixture of EXAMPLE 36B (0.702 g), dicyanozinc (0.129 g), and tetrakis(triphenylphosphine)palladium(0) (0.231 g) in N,N-dimethylformamide (2 mL) was degassed via vacuum/nitrogen cycle three times. The reaction mixture was heated at 120° C. for 3 hours. After cooling, it was poured into water and extracted with ethyl acetate three times. The combined organic layers were washed with brine, dried over MgSO₄, filtered, and concentrated. The residue was purified with flash column chromatography on silica gel eluting with 20%-60% ethyl acetate in hexanes to give the title compound.

Example 36D 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 36C for EXAMPLE 11B in EXAMPLE 11D. ¹H NMR (500 MHz, dimethylsulfoxide-d₆) δ 11.56 (s, 1H), 8.66 (s, 1H), 8.44 (s, 1H), 7.94 (d, 1H), 7.55 (d, 1H), 7.44 (t, 1H), 7.34-7.35 (m, 3H), 7.04 (d, 2H), 6.65 (dd, 1H), 6.32 (s, 1H), 6.24 (s, 1H), 4.26 (d, 2H), 3.86 (dd, 2H), 3.10 (s, 4H), 2.75 (s, 2H), 2.31-2.35 (m, 2H), 2.01-2.05 (m, 1H), 2.15 (s, 2H), 1.96 (s, 2H), 1.63-1.66 (m, 2H), 1.33-1.40 (m, 4H), 0.92 (s, 6H).

Example 37

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide Example 37A 1,6-dioxaspiro[2.5]octane-2-carbonitrile A mixture of tetrahydropyran-4-one (10 mL) and chloroacetonitrile (6.4 mL) in tert-butanol (10 mL) was stirred for 10 minutes. To this solution was added a solution of potassium tert-butoxide (12.11 g) in 200 mL of tert-butanol at room temperature over 40 minutes. The reaction mixture was stirred for 16 hours, diluted with water and quenched slowly with 1 N HCl. The solvent was partially removed by rotary evaporation. It was then extracted with ether (5×200 mL). The combined extracts was washed with brine, dried over MgSO₄, filtered, and the filtrate was concentrated and purified by flash chromatography on silica with 3:7 to 1:1 ethyl acetate:hexanes to provide the title compound.

Example 37B 2-(4-fluorotetrahydro-2H-pyran-4-yl)-2-hydroxyacetonitrile

EXAMPLE 37A (11.5 g) in dichloromethane (40 mL) in a polypropylene bottle was treated with 70% hydrogen fluoride-pyridine (10.4 mL) dropwise at 0° C. The solution was allowed to warm to room temperature over 3 hours, and stirred for an additional 1.5 hours. The reaction mixture was diluted with ethyl acetate (200 mL) and poured into saturated aqueous NaHCO₃. Additional solid NaHCO₃ was used carefully until bubbling ceased. The organic layer was isolated, and the aqueous layer was extracted with additional ethyl acetate three times (150 mL each). The combined organic layers were washed with 5% HCl (50 mL each, twice), brine, dried over MgSO₄, filtered and concentrated to give the desired product which was used directly in the next step.

Example 37C (4-fluorotetrahydro-2H-pyran-4-yl)methanol

EXAMPLE 37B (11.7 g, 74 mmol) in 2-propanol (150 mL) and water (37.5 mL) was cooled to 0° C. To this solution was added NaBH₄ (4.20 g, 111 mmol). The solution was stirred and allowed to warm to room temperature over 3 hours. It was quenched with acetone, and stirred for another 1 hour. The clear liquid was separated from solid by decanting. Additional ethyl acetate (2×100 mL) was used to wash the solid, and the mixture was decanted. The combined organic solutions were concentrated. The residue was purified by flash chromatography, eluting with 1:1 ethyl acetate:hexanes to provide the title compound.

Example 37D 4-((4-fluorotetrahydro-2H-pyran-4-yl)methoxy)-3-nitrobenzenesulfonamide The title compound was prepared by substituting EXAMPLE 37C for (tetrahydro-2H-pyran-4-yl)methanol in EXAMPLE 24A.

Example 37E 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 37D in place of EXAMPLE 11B. ¹H NMR (dimethylsulfoxide-d₆). 11.64 (s, 2H), 8.33 (s, 1H), 8.00-8.01 (m, 2H), 7.39-7.57 (m, 4H), 7.33 (d, J=8.24 Hz, 2H), 7.03 (d, J=8.54 Hz, 2H), 6.65 (dd, J=9, 1.98 Hz, 1H), 6.37-6.38 (m, 1H), 6.19 (d, J=1.53 Hz, 1H), 4.35 (d, J=20.75 Hz, 2H), 3.74-3.78 (m, 2H), 3.55-3.60 (m, 2H), 3.07 (br, 4H), 2.80 (br, 2H), 2.25 (br, 4H), 2.13 (br, 2H), 1.81-1.94 (m, 6H), 1.38 (t, J=6.26 Hz, 2H), 0.91 (s, 6H).

Example 38

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 38A 3-cyano-4-((tetrahydro-2H-pyran-4-yl)methoxy)benzene sulfonamide The title compound was prepared by substituting 3-cyano-4-fluorobenzenesulfonamide for 4-fluoro-3-nitrobenzenesulfonamide in EXAMPLE 24A.

Example 38B 5-sulfamoyl-2-((tetrahydro-2H-pyran-4-yl)methoxy)benzamide

To a solution of EXAMPLE 38A (0.455 g) in ethanol (3 mL) and tetrahydrofuran (1 mL) was added hydrogen peroxide (30% in water, 2 mL) followed by 1 N aqueous NaOH (1.024 ml) and heated to 35° C. for 3 hours. The reaction was poured into dichloromethane (50 mL) and 1N aqueous HCl (25 mL). The aqueous layer was extracted with dichloromethane (3×50 mL). The precipitate contained in the combined organic layers was collected by filtration to give the title compound.

Example 38C

N-{[3-(amino carbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 38B for EXAMPLE 1F and EXAMPLE 3J for EXAMPLE 1E in EXAMPLE 1G. $^1$H NMR (300 MHz, dimethylsulfoxide-d$_6$) δ 11.79-11.70 (m, 1H), 11.66-11.54 (m, 1H), 9.29-9.08 (m, 1H), 8.27 (d, 1H), 8.08 (d, 1H), 7.97-7.90 (m, 1H), 7.76-7.72 (m, 1H), 7.62 (s, 1H), 7.54 (s, 1H), 7.50 (d, 1H), 7.39 (d, 1H), 7.23 (d, 1H), 7.08 (d, 1H), 6.74-6.67 (m, 1H), 6.44 (s, 1H), 6.22 (s, 1H), 4.03 (d, 6H), 3.74-3.52 (m, 4H), 3.33 (s, 4H), 3.11-2.90 (m, 2H), 2.01 (s, 4H), 1.79-1.58 (m, 2H), 1.24 (s, 5H), 0.94 (s, 6H).

Example 39

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide

Example 39A

Cis-tert-butyl-4-morpholinocyclohexylcarbamate

To a solution of morpholine (4.08 g) and tert-butyl 4-oxocyclohexylcarbamate (10 g) stirred for 24 hours at room temperature in titanium (IV) isopropoxide (27.5 mL), methanol (10 mL) was added followed by careful addition of sodium borohydride (3.55 g). The reaction mixture was quenched with water/NaOH solution, extracted with ether, dried over magnesium sulfate, filtered, and concentrated. The product was separated from the trans isomer and purified by flash chromatography (silica gel, 50%-100% acetone in hexanes) to provide the title compound.

Example 39B cis-4-morpholinocyclohexanamine bis(2,2,2-trifluoroacetate)

To a solution of EXAMPLE 39A (2.43 g) in dichloromethane (15 ml) was added trifluoroacetic acid (5 ml) and the reaction mixture was stirred for 16 hours at room temperature. The reaction mixture was concentrated and the crude product was used without purification.

Example 39C 4-(cis-4-morpholinocyclohexylamino)-3-nitrobenzenesulfonamide

A solution of EXAMPLE 39B (0.40 g), 4-fluoro-3-nitrobenzenesulfonamide (0.478 g) and triethylamine (2 mL) in tetrahydrofuran (10 mL) was stirred for 3 days at room temperature. The reaction mixture was concentrated and purified by flash chromatography (silica gel, 0-30% methanol/dichloromethane) providing the product.

Example 39D

Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared by substituting EXAMPLE 39C for EXAMPLE 11B in EXAMPLE 11D. $^1$H NMR (500 MHz, pyridine-d$_5$) δ 13.07 (s, 1H), 9.30 (d, 1H), 8.64 (d, 1H), 8.43 (d, 1H), 8.38 (dd, 1H), 8.11 (d, 1H), 7.67 (t, 2H), 7.44 (d, 2H), 7.06 (d, 2H), 6.91 (d, 1H), 6.74 (dd, 1H), 6.48-6.55 (m, 2H), 3.65-3.73 (m, 5H), 3.02-3.09 (m, 4H), 2.76 (s, 2H), 2.41-2.48 (m, 4H), 2.25 (t, 2H), 2.09-2.16 (m, 5H), 1.97 (s, 2H), 1.77-1.86 (m, 2H), 1.55-1.63 (m, 6H), 1.39 (t, 2H), 0.93 (s, 6H).

Example 40

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide

Example 40A 5,6-dichloropyridine-3-sulfonamide

The title compound was prepared by substituting 5,6-dichloropyridine-3-sulfonyl chloride for 5-bromo-6-chloropyridine-3-sulfonyl chloride in EXAMPLE 36A.

Example 40B 5-chloro-6-((tetrahydro-2H-pyran-4-yl)methoxy)
pyridine-3-sulfonamide The title compound was prepared by substituting EXAMPLE 40A for 4-fluoro-3-nitrobenzenesulfonamide in EXAMPLE 24A.

Example 40C 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 40B for EXAMPLE 11B in EXAMPLE 11D. $^1$H NMR (500 MHz, dimethylsulfoxide-$d_6$) δ 11.67 (s, 1H), 8.52 (s, 1H), 8.39 (d, 1H), 8.03 (d, 1H), 7.54 (d, 1H), 7.52 (d, 1H), 7.50 (dd, 1H), 7.35 (d, 2H), 7.04 (d, 2H), 6.67 (dd, 1H), 6.39 (m, 1H), 6.21 (d, 1H), 4.25 (d, 2H), 3.87 (dd, 2H), 3.30 (m, 2H), 3.10 (v br s, 4H), 2.90 (v br s, 2H), 2.35 (v br s, 4H), 2.17 (br m, 2H), 2.05 (m, 1H), 1.96 (s, 2H), 1.64 (d, 2H), 1.40 (t, 2H), 1.35 (ddd, 2H), 0.93 (s, 6H).

Example 41

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 15H for EXAMPLE 3J and EXAMPLE 40B for EXAMPLE 11B in EXAMPLE 11D. $^1$H NMR (500 MHz, dimethylsulfoxide-$d_6$) δ 11.68 (s, 1H), 8.55 (d, 1H), 8.41 (d, 1H), 8.04 (d, 1H), 7.54 (m, 2H), 7.50 (dd, 1H), 7.38 (d, 2H), 7.14 (d, 2H), 6.68 (dd, 1H), 6.40 (m, 1H), 6.20 (d, 1H), 4.25 (d, 2H), 4.12 (s, 2H), 3.87 (dd, 2H), 3.30 (m, 2H), 3.10 (v br s, 4H), 2.90 (v br s, 2H), 2.27 (v br s, 4H), 2.17 (br m, 2H), 2.05 (m, 1H), 1.96 (s, 2H), 1.64 (d, 2H), 1.35 (ddd, 2H), 0.97 (s, 6H).

Example 42

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide

Example 42A 4-((tetrahydro-2H-pyran-4-yl)methylamino)-3-(trifluoromethyl)benzenesulfonamide A mixture of 4-fluoro-3-(trifluoromethyl)benzenesulfonamide (1.056 g), (tetrahydro-2H-pyran-4-yl)methanamine (0.5 g) and N,N-diisopropylethylamine (1.68 g) in anhydrous dimethylsulfoxide (15 mL) solution was heated at 90° C. overnight. The reaction mixture was cooled to room temperature and diluted with ethyl acetate. The organic phase was washed with water, brine, dried over anhydrous sodium sulfate, filtered and concentrated to afford the title compound.

Example 42B 4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide The title compound was prepared as described in EXAMPLE 1G by replacing EXAMPLE 1E and EXAMPLE 1F with EXAMPLE 15H and EXAMPLE 42A, respectively. $^1$H NMR (300 MHz, dimethylsulfoxide-$d_6$) δ 11.73 (s, 1H), 11.25 (s, 1H), 8.08 (d, 1H), 7.89 (d, 1H), 7.77 (m, 1H), 7.61 (d, 1H), 7.51 (m, 2H), 7.37 (d, 2H), 7.13 (d, 2H), 6.88 (d, 1H), 6.67 (dd, 1H), 6.53 (m, 1H), 6.43 (m, 1H), 6.15 (d, 1H), 4.11 (s, 2H), 3.82 (dd, 2H), 3.19 (m, 5H), 3.05 (m, 4H), 2.82 (s, 2H), 2.20 (m, 7H), 1.85 (m, 1H), 1.56 (m, 2H), 1.18 (s, 6H).

Example 43

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide The title compound was prepared as described in EXAMPLE 1G by replacing EXAMPLE 1E and EXAMPLE 1F with EXAMPLE 15H and EXAMPLE 17A, respectively. $^1$H NMR (300 MHz, dimethylsulfoxide-$d_6$) δ 11.69 (s, 1H), 11.48 (m, 1H), 8.16 (d, 1H), 8.05 (d, 1H), 7.92 (dd, 1H), 7.52 (m, 3H), 7.37 (d, 2H), 7.27 (m, 1H), 7.11 (m, 3H), 6.68 (dd, 1H), 6.41 (dd, 1H), 6.18 (d, 1H), 4.11 (s, 2H), 3.84 (dd, 2H), 3.25 (m, 4H), 3.07 (m, 4H), 2.84 (m, 2H), 2.23 (m, 5H), 1.84 (m, 1H), 1.55 (m, 2H), 1.25 (m, 3H), 1.18 (s, 6H).

Example 44

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide

Example 44A

Trans-4-(4-morpholinocyclohexylamino)-3-(trifluoromethylsulfonyl)benzenesulfonamide The title compound was prepared as described in EXAMPLE 16A by replacing 2-methoxyethanamine with EXAMPLE 9B.

Example 44B

Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide The title compound was prepared as described in EXAMPLE 1G by replacing EXAMPLE 1E and EXAMPLE 1F with EXAMPLE 15H and EXAMPLE 44A, respectively.

$^1$H NMR (300 MHz, dimethylsulfoxide-$d_6$) δ 11.62 (s, 1H), 8.08 (s, 1H), 8.00 (d, 1H), 7.85 (d, 1H), 7.47 (m, 3H), 7.38 (d, 2H), 7.14 (d, 2H), 6.98 (d, 1H), 6.65 (dd, 1H), 6.55 (m, 1H), 6.37 (m, 1H), 6.21 (d, 1H), 4.12 (s, 2H), 3.54 (m, 6H), 3.04 (m, 4H), 2.83 (s, 2H), 2.57 (m, 3H), 2.24 (m, 6H), 1.91 (m, 5H), 1.34 (m, 4H), 1.20 (s, 6H).

Example 45

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide Example 45A 4-(1-methylpiperidin-4-ylamino)-3-(trifluoromethylsulfonyl)benzenesulfonamide The title compound was prepared as described in EXAMPLE 16A by replacing 2-methoxyethanamine with 1-methyl-4-aminopiperidine.

Example 45B 4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide The title compound was prepared as described in EXAMPLE 1G by replacing EXAMPLE 1E and EXAMPLE 1F with EXAMPLE 15H and EXAMPLE 45A, respectively. $^1$H NMR (300 MHz, dimethylsulfoxide-$d_6$) δ 11.59 (s, 1H), 8.10 (s, 1H), 7.98 (d, 1H), 7.90 (dd, 1H), 7.49 (m, 3H), 7.39 (m, 3H), 7.14 (d, 2H), 7.02 (d, 1H), 6.65 (dd, 2H), 6.36 (dd, 1H), 6.22 (d, 1H), 4.12 (s, 2H), 3.75 (m, 1H), 3.16 (m, 4H), 2.98 (m, 5H), 2.88 (m, 5H), 2.67 (s, 2H), 2.22 (m, 6H), 1.68 (m, 1H), 1.18 (s, 6H).

Example 46

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide 5-sulfamoyl-2-((tetrahydro-2H-pyran-4-yl)methoxy)nicotinamide To EXAMPLE 36C (0.025 g) in ethanol (1 mL) and tetrahydrofuran (1 mL) was added hydrogen peroxide (30% in water, 0.5 mL) followed by 1M aqueous sodium hydroxide (0.056 ml) then another 1 mL of tetrahydrofuran. The reaction was heated to 45° C. for 2 hours, cooled, quenched with 1N aqueous HCl (5 mL), and the product extracted into dichloromethane (10 mL). The organic layer was dried over magnesium sulfate, filtered and concentrated to give the title compound.

Example 46B 5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide The title compound was prepared by substituting EXAMPLE 46A for EXAMPLE 1F and EXAMPLE 3J for EXAMPLE 1E in EXAMPLE 1G. $^1$H NMR (300 MHz, CDCl$_3$) δ 10.31-10.09 (m, 1H), 9.09 (s, 2H), 8.93-8.81 (m, 1H), 8.28-8.18 (m, 1H), 8.03-7.87 (m, 1H), 7.77-7.68 (m, 1H), 7.59-7.51 (m, 1H), 7.48-7.41 (m, 1H), 6.91 (d, 2H), 6.59-6.48 (m, 2H), 5.97 (s, 2H), 4.50 (d, 2H), 4.08-3.98 (m, 2H), 3.45 (s, 4H), 3.13-2.99 (m, 4H), 2.82-2.68 (m, 2H), 2.19 (s, 4H), 1.86 (s, 5H), 1.61-1.35 (m, 4H), 0.94 (s, 6H).

Example 47

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 47A 5-bromo-6-((1-methylpiperidin-4-yl)methoxy)pyridine-3-sulfonamide To (1-methylpiperidin-4-yl)methanol (0.109 g) in tetrahydrofuran (2 mL) was added sodium hydride (0.136 g). After 30 minutes, EXAMPLE 36A (0.230 g) was added as a solution in tetrahydrofuran (1 mL) and the reaction was heated to 50° C. After 4 hours, the reaction was cooled, poured into water (10 mL) and dichloromethane (50 mL), and the pH was adjusted to pH~8. The aqueous layer was extracted with dichloromethane (3×50 mL), and the organic layers were combined, washed with brine (30 mL), dried over magnesium sulfate, filtered, and concentrated to give the title compound.

Example 47B

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 47A for EXAMPLE 1F and EXAMPLE 3J for EXAMPLE 1E in EXAMPLE 1G. $^1$H NMR (300 MHz, dimethylsulfoxide-$d_6$) δ 11.51 (s, 1H), 8.35 (d, 1H), 8.17 (d, 1H), 7.93 (d, 1H), 7.60 (d, 1H), 7.44-7.40 (m, 1H), 7.33 (dd, 3H), 7.05 (d, 2H), 6.61 (d, 1H), 6.31 (dd, 1H), 6.24 (s, 1H), 4.25 (d, 2H), 3.40 (s, 4H), 3.01 (s, 4H), 2.73 (d, J=8.2, 5H), 2.20 (s, 6H), 1.93 (d, 4H), 1.54 (s, 1H), 1.39 (s, 2H), 1.24 (s, 2H), 0.93 (s, 6H).

Example 48

4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide

Example 48A 4-((1-methylpiperidin-4-yl)methoxy)-3-nitrobenzenesulfonamide

The title compound was prepared by substituting (1-methylpiperidin-4-yl)methanol for (tetrahydro-2H-pyran-4-yl)methanol in EXAMPLE 24A.

Example 48B 4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide The title compound was prepared by substituting EXAMPLE 48A for EXAMPLE 1F and EXAMPLE 3J for EXAMPLE 1E in EXAMPLE 1G. $^1$H NMR (300 MHz, dimethylsulfoxide-$d_6$) δ 11.54 (s, 1H), 8.17 (s, 1H), 7.92 (s, 1H), 7.87-7.77 (m, 1H), 7.58 (d, 1H), 7.43 (s, 1H), 7.40-7.00 (m, 7H), 6.70-6.56 (m, 1H), 6.31 (s, 1H), 6.24 (s, 1H), 4.05 (s, 2H), 3.46-3.33 (m, 2H), 3.02 (s, 6H), 2.72 (d, 5H), 2.21 (s, 6H), 1.96 (s, 5H), 1.70-1.48 (m, 2H), 1.39 (s, 2H), 0.93 (s, 6H).

Example 49

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide

Example 49A 6-((1,4-dioxan-2-yl)methoxy)-5-bromopyridine-3-sulfonamide

The title compound was prepared by substituting (1,4-dioxan-2-yl)methanol for (tetrahydro-2H-pyran-4-yl)methanol and EXAMPLE 36A for 4-fluoro-3-nitrobenzenesulfonamide in EXAMPLE 24A.

Example 49B 6-((1,4-dioxan-2-yl)methoxy)-5-cyanopyridine-3-sulfonamide

The title compound was prepared by substituting EXAMPLE 49A for EXAMPLE 36B in EXAMPLE 36C.

Example 49C 4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide The title compound was prepared by substituting EXAMPLE 49B for EXAMPLE 11B in EXAMPLE 11D. $^1$H NMR (400 MHz, dimethylsulfoxide-$d_6$) δ 11.50 (s, 1H), 8.60 (s, 1H), 8.40 (s, 1H), 7.91 (d, 1H), 7.58 (d, 1H), 7.42 (t, 1H), 7.35 (d, 2H), 7.28 (s, 1H), 7.06 (d, 2H), 6.64 (dd, 1H), 6.29 (m, 2H), 4.40 (d, 2H), 3.90 (m, 1H), 3.79 (m, 2H), 3.63 (m, 2H), 3.46 (m, 4H), 3.07 (s, 4H), 2.85 (m, 2H), 2.34 (m, 4H), 2.16 (m, 2H), 1.40 (t, 2H), 0.93 (s, 6H).

Example 50

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 49A for EXAMPLE 11B in EXAMPLE 11D. $^1$H NMR (400 MHz, dimethylsulfoxide-$d_6$) δ 11.60 (s, 1H), 8.46 (s, 1H), 8.27 (s, 1H), 7.99 (d, 1H), 7.56 (d, 1H), 7.46 (m, 2H), 7.35 (d, 2H), 7.05 (d, 2H), 6.65 (dd, 1H), 6.36 (dd, 1H), 6.22 (d, 1H), 4.34 (m, 2H), 3.88 (m, 1H), 3.79 (m, 2H), 3.63 (m, 2H), 3.46 (m, 2H), 3.06 (s, 4H), 2.81 (s, 2H), 2.26 (m, 4H), 2.15 (s, 2H), 1.96 (s, 2H), 1.38 (m, 2H), 0.93 (s, 6H).

Example 51

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide

Example 51A

The title compound was prepared as described in EXAMPLE 12A by replacing (1,4-dioxan-2-yl)methanol with (2,2-dimethyltetrahydro-2H-pyran-4-yl)methanol.

Example 51B 4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 51A in place of EXAMPLE 11B. $^1$H NMR (400 MHz, dimethylsulfoxide-$d_6$) δ 11.69 (s, 2H), 8.35 (s, 2H), 8.03 (d, 4H), 7.47-7.58 (m, 6H), 7.31-7.42 (m, 6H), 7.04 (d, 4H), 6.68 (dd, 2H), 6.40 (s, 2H), 6.20 (d, 2H), 3.96-4.09 (m, 2H), 3.54-3.68 (m, 2H), 3.09 (s, 4H), 2.83 (s, 2H), 2.09-2.37 (m, 7H), 1.96 (s, 2H), 1.55-1.69 (m, 2H), 1.39 (t, 2H), 1.19 (m, 8H), 0.92 (s, 6H).

Example 52

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 52A 3-cyano-4-fluorobenzenesulfonamide

3-Cyano-4-fluorobenzene-1-sulfonyl chloride (1.1 g) in 1,4-dioxane (10 mL) at 0° C. was treated dropwise with a 7 M ammonia solution in methanol (3.57 mL) and stirred for 30 minutes. A small amount of solid was removed by filtration and discarded. The filtrate was concentrated, diluted with ethyl acetate, washed with water and brine, dried (MgSO$_4$), filtered, concentrated and triturated with diethyl ether to give the product.

Example 52B 3-cyano-4-((tetrahydro-2H-pyran-4-yl)methylamino) benzenesulfonamide The title compound was prepared by substituting EXAMPLE 52A for 4-chloro-3-nitrobenzenesulfonamide and (tetrahydro-2H-pyran-4-yl)methanamine for 4-methylpiperazin-1-amine dihydrochloride in EXAMPLE 6A.

Example 52C 3-chloro-5-cyano-4-((tetrahydro-2H-pyran-4-yl)methylamino)benzenesulfonamide EXAMPLE 52B (0.148 g) in acetonitrile (5 mL) was treated with N-chlorosuccinimide (0.080 g), heated at 60° C. for 3 hours and filtered to remove a small amount of solid. The filtrate was concentrated and chromatographed on silica gel with 3-15% ethyl acetate in dichloromethane as eluent. The obtained solid was slurried in water, filtered, rinsed with additional water and dried under vacuum to give the product.

Example 52D

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 52C for EXAMPLE 11B in EXAMPLE 11D. $^1$H NMR (300 MHz, dimethylsulfoxide-d$_6$) δ 11.70 (s, 1H), 11.41 (br s, 1H), 8.07 (d, 1H), 7.89 (s, 2H), 7.61 (m, 1H), 7.53 (m, 2H), 7.35 (d, 2H), 7.18 (m, 1H), 7.05 (d, 2H), 6.69 (m, 1H), 6.42 (dd, 1H), 6.18 (dd, 1H), 3.83 (m, 2H), 3.55 (t, 2H), 3.23 (m, 3H), 3.06 (m, 4H), 2.15 (m, 4H), 1.92 (m, 4H), 1.60 (m, 2H), 1.40 (m, 2H), 1.19 (m, 4H), 0.93 (s, 6H).

Example 53

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 53A

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and 4-chloro-3-nitrobenzenesulfonamide for EXAMPLE 1F in EXAMPLE 1G.

Example 53B

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide A 5 mL round-bottomed flask was charged with EXAMPLE 53A (120 mg), 1-acetylpiperidin-4-amine (28 mg), and triethylamine (0.064 mL) in dioxane (2 ml). The reaction mixture was heated to 90° C. for 24 hours. The reaction mixture was cooled to room temperature, and added to a silica gel column and purified by eluting with 0-5% methanol in dichloromethane. $^1$H NMR (300 MHz, dimethylsulfoxide-d$_6$) δ 11.66 (br s, 1H), 8.65 (d, 1H), 8.24 (d, 1H), 8.03 (d, 1H), 7.83 (dd, 1H), 7.54-7.46 (m, 3H), 7.35 (d, 2H), 7.19 (d, 1H), 7.04 (d, 2H), 6.68 (dd, 1H), 6.39 (m, 1H), 6.20 (d, 1H), 4.28 (d, 1H), 3.97-3.75 (m, 2H), 3.07 (br s, 4H), 2.87-2.70 (m, 4H), 2.29-2.10 (m, 6H), 2.02 (s, 3H), 2.00-1.89 (m, 4H), 1.66-1.54 (m, 2H), 1.39 (t, 2H), 0.92 (s, 6H).

Example 54

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 54A 2-chloro-5-fluoro-4-((tetrahydro-2H-pyran-4-yl)methylamino)benzenesulfonamide The title compound was prepared by substituting 2-chloro-4,5-difluorobenzenesulfonamide for 4-chloro-3-nitrobenzenesulfonamide and (tetrahydro-2H-pyran-4-yl)methanamine for 4-methylpiperazin-1-amine dihydrochloride in EXAMPLE 6A.

Example 54

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 54A for EXAMPLE 11B in EXAMPLE 11D. $^1$H NMR (500 MHz, dimethylsulfoxide-d$_6$) δ 11.76 (s, 1H), 11.31 (s, 1H), 8.08 (d, 1H), 7.69 (d, 1H), 7.60 (d, 1H), 7.55 (m, 2H), 7.34 (d, 2H), 7.04 (d, 2H), 6.90 (s, 1H), 6.84 (d, 1H), 6.69 (dd, 1H), 6.45 (dd, 1H), 6.13 (d, 1H), 3.82 (dd, 2H), 3.24 (t, 2H), 3.05 (m, 6H), 2.73 (s, 2H), 2.14 (m, 6H), 1.95 (s, 2H), 1.81 (m, 1H), 1.61 (m, 2H), 1.38 (t, 2H), 1.17 (m, 2H), 0.92 (s, 6H).

Example 55

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide The title compound was prepared by substituting EXAMPLE 3J for EXAMPLE 1E and EXAMPLE 2A for EXAMPLE 1F in EXAMPLE 1G. $^1$H NMR (300 MHz, dimethylsulfoxide-$d_6$) δ 11.66 (br s, 1H), 8.75 (t, 1H), 8.54 (d, 1H), 8.03 (d, 1H), 7.79 (dd, 1H), 7.54-7.48 (m, 3H), 7.35 (d, 2H), 7.08-7.02 (m, 3H), 6.67 (dd, 1H), 6.38 (m, 1H), 6.20 (d, 1H), 3.61 (t, 4H), 3.43 (q, 2H), 3.29 (m, 2H), 3.06 (br s, 4H), 2.73 (br s, 2H), 2.47 (br s, 4H), 2.18 (m, 6H), 1.95 (br s, 2H), 1.80 (m, 2H), 1.38 (t, 2H), 0.92 (s, 6H).

Example 56

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide Example 56A 5-bromo-6-((4-fluorotetrahydro-2H-pyran-4-yl)methoxy)pyridine-3-sulfonamide The title compound was prepared by substituting EXAMPLE 37C for tetrahydro-2H-pyran-4-yl)methanol and EXAMPLE 36A for 4-fluoro-3-nitrobenzenesulfonamide in EXAMPLE 24A.

Example 56B

The title compound was prepared by substituting EXAMPLE 56A for EXAMPLE 36B in EXAMPLE 36C.

Example 56C 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting EXAMPLE 56B for EXAMPLE 11B in EXAMPLE 11D. $^1$H NMR (500 MHz, dimethylsulfoxide-$d_6$) δ 11.58 (s, 1H), 8.70 (s, 1H), 8.51 (s, 1H), 7.96 (d, 1H), 7.57 (d, 1H), 7.45 (t, 1H), 7.35-7.37 (m, 3H), 7.06 (d, 2H), 6.67 (dd, 1H), 6.33 (d, 1H), 6.26 (s, 1H), 4.56 (d, 2H), 3.76-3.80 (s, 2H), 3.56-3.62 (m, 2H), 3.01-3.10 (m, 4H), 2.14-2.18 (m, 2H), 1.96 (s, 2H), 1.80-1.87 (m, 4H), 1.41 (t, 2H), 0.93 (s, 6H).

Example 57

4-(4-{[2-(4-chlorophenyl)-4,4-dimethylcyclohex-1-en-1-yl]methyl}piperazin-1-yl)-N-{5-cyano-6-(2-morpholin-4-ylethoxy)pyridin-3-yl]sulfonyl}-2-(1H-pyrrolo[2,3-b]pyridin-5-yloxy)benzamide Example 57A 5-bromo-6-(2-morpholinoethoxy)pyridine-3-sulfonamide The title compound was prepared by substituting 2-morpholinoethanol for tetrahydro-2H-pyran-4-yl)methanol and EXAMPLE 36A for 4-fluoro-3-nitrobenzenesulfonamide in EXAMPLE 24A.

Example 57B 5-cyano-6-(2-morpholinoethoxy)pyridine-3-sulfonamide

The title compound was prepared by substituting EXAMPLE 57A for EXAMPLE 36A in EXAMPLE 36B.

Example 57C 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide The title compound was prepared by substituting EXAMPLE 57B for EXAMPLE 11B in EXAMPLE 11D. $^1$H NMR (500 MHz, dimethylsulfoxide-$d_6$) δ 11.56 (s, 1H), 8.64 (s, 1H), 8.41 (s, 1H), 7.92 (d, 1H), 7.58 (d, 1H), 7.44 (t, 1H), 7.36 (d, 2H), 7.31 (s, 1H), 7.06 (d, 2H), 6.65 (dd, 1H), 6.31 (d, 1H), 6.27 (d, 1H), 4.59 (t, 2H), 3.59 (s, 4H), 3.08 (s, 4H), 2.89 (s, 2H), 2.65 (s, 4H), 2.16-2.18 (m, 2H), 1.97 (s, 2H), 1.41 (t, 2H), 0.93 (s, 6H).

Example 58

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 58A 3-chloro-4-(2-(2-methoxyethoxy)ethylthio)benzenesulfonamide In a 25 mL microwave tube was added sodium hydride (0.6 g) in tetrahydrofuran (10 mL) to give a suspension. 2-(2-Methoxyethoxy)ethanethiol (1 g) was added slowly. After stirring for 30 minutes, 3-chloro-4-fluorobenzenesulfonamide (1.54 g) dissolved in 10 mL tetrahydrofuran was added slowly. The mixture was heated at 110° C. for 30 minutes in a Biotage Initiator microwave reactor. Water was added, the product was extracted with ether (20 mL×3), dried over $Na_2SO_4$, filtered, and the solvent was removed under reduced pressure. The crude product was purified by flash chromatography on silica eluting with 0-25% ethyl acetate in hexane.

Example 58B 3-chloro-4-(2-(2-methoxyethoxy)ethylsulfonyl)benzenesulfonamide

EXAMPLE 58A (0.15 g) was suspended in acetic acid (3 mL). Peracetic acid (0.4 mL) was added slowly. The mixture was stirred at room temperature overnight, then poured into $Na_2S_2O_3$ solution, and the product precipitated. After filtration and washing with water, the product was dried under vacuum.

Example 58C

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 58B for EXAMPLE 11B in EXAMPLE 11D. $^1$H NMR (500 MHz, dimethylsulfoxide-$d_6$) δ 11.52 (s, 1H), 7.92 (d, 1H), 7.84 (m, 2H), 7.68 (m, 1H), 7.62 (d, 1H), 7.42 (t, 1H), 7.35 (d, 2H), 7.29 (m, 1H), 7.05 (d, 2H), 6.62 (dd, 1H), 6.32 (m, 1H), 6.26 (d, 1H), 3.74 (t, 2H), 3.68 (t, 2H), 3.24 (m, 2H), 3.06 (m, 5H), 3.01 (m, 4H), 2.74 (s, 2H), 2.19 (m, 6H), 1.96 (s, 2H), 1.39 (t, 2H), 0.93 (s, 6H).

Example 59

4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide Example 59A 4-(2-(2-methoxyethoxy)ethylthio)-3-nitrobenzenesulfonamide The title compound was prepared by substituting 4-fluoro-3-nitrobenzenesulfonamide for 3-chloro-4-fluorobenzenesulfonamide in EXAMPLE 58A.

Example 59B 4-(2-(2-methoxyethoxy)ethylsulfonyl)-3-nitrobenzenesulfonamide

The title compound was prepared by substituting EXAMPLE 59A for EXAMPLE 58A in EXAMPLE 58B.

Example 59C 4-(4-{[2-(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrrolo[2,3-b]pyridin-5-yloxy)benzamide The title compound was prepared by substituting EXAMPLE 59B for EXAMPLE 11B in EXAMPLE 11D. $^1$H NMR (500 MHz, dimethylsulfoxide-$d_6$) δ 11.51 (s, 1H), 8.17 (m, 1H), 7.94 (m, 3H), 7.64 (d, 1H), 7.42 (m, 1H), 7.35 (d, 2H), 7.28 (d, 1H), 7.05 (d, 2H), 6.62 (m, 1H), 6.28 (m, 2H), 3.83 (m, 4H), 3.16 (m, 2H), 3.08 (s, 3H), 3.01 (m, 4H), 2.73 (s, 2H), 2.18 (m, 6H), 1.96 (m, 4H), 1.39 (t, 2H), 0.93 (s, 6H)

Example 60

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide Example 60A Trans-4-(4-aminocyclohexyloxy)-3-nitrobenzenesulfonamide To a solution of tert-butyl 4-hydroxycyclohexylcarbamate (0.250 g) in tetrahydrofuran (5 mL) was added sodium hydride (0.186 g). After stirring for 15 minutes, 4-fluoro-3-nitrobenzenesulfonamide (0.256 g) was added as a solution in tetrahydrofuran (1 mL). The reaction was heated to 60° C. for 1.5 hours, cooled, and poured into a mixture of dichloromethane (100 mL) and water (25 ml). The aqueous layer was adjusted to pH~4 with 1N aqueous HCl and the organic layer was separated, washed with brine (50 ml), dried over magnesium sulfate, filtered, and concentrated. The residue was loaded onto silica gel (GraceResolv 40 g) and eluted using a gradient of 0.5% to 7.5% methanol/dichloromethane over 30 minutes. This solid was treated with HCl (4.0M in dioxane, 5 ml) at room temperature for 1 hour and concentrated to give the title compound.

Example 60B 4-(trans-4-morpholinocyclohexyloxy)-3-nitrobenzenesulfonamide

To EXAMPLE 60A (0.220 g) and 1-bromo-2-(2-bromoethoxy)ethane (0.177 g) in N,N-dimethylformamide (3 mL) was added triethylamine (0.338 ml) and the reaction heated to 70° C. for 5 hours. The reaction was cooled and the resulting precipitate was removed by filtration. The reaction was concentrated and loaded onto silica gel and was eluted using a gradient of 0.5% to 7.5% methanol/dichloromethane to give the title compound.

Example 60C

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide The title compound was prepared by substituting EXAMPLE 60B for EXAMPLE 1F and EXAMPLE 3J for EXAMPLE 1E in EXAMPLE 1G. $^1$H NMR (300 MHz, dimethylsulfoxide-$d_6$) δ 11.62 (s, 1H), 8.23 (s, 1H), 7.99 (s, 1H), 7.96-7.88 (m, 1H), 7.54 (d, 1H), 7.48 (s, 2H), 7.34 (d, 3H), 7.04 (d, 2H), 6.72-6.58 (m, 1H), 6.37 (s, 1H), 6.21 (s, 1H), 4.69-4.47 (m, 1H), 3.66 (s, 4H), 3.05 (s, 4H), 2.76 (s, 6H), 2.22 (s, 9H), 1.96 (s, 4H), 1.39 (s, 6H), 0.92 (s, 6H).

Example 61

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 61A 5-bromo-6-(1-(tetrahydro-2H-pyran-4-yl)piperidin-4-ylamino)pyridine-3-sulfonamide A mixture of EXAMPLE 36A (1.0 g), EXAMPLE 3L (0.95 g) and triethylamine (3.08 mL) in anhydrous dioxane (20 mL) was heated at 110° C. overnight. The organic solvent was removed under vacuum. The residue was purified with flash column chromatography on silica gel eluting with 2%-8% methanol/dichloromethane to give the title compound.

Example 61B

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 61A for EXAMPLE 11B in EXAMPLE 11D. $^1$H NMR (400 MHz, dimethylsulfoxide-d$_6$) δ 11.59 (s, 1H), 8.35 (s, 1H), 8.00 (s, 2H), 7.55 (d, 1H), 7.46 (m, 2H), 7.34 (d, 2H), 7.04 (d, 2H), 6.63 (dd, 1H), 6.49 (m, 1H), 6.36 (s, 1H), 6.20 (s, 1H), 4.05 (m, 1H), 3.94 (d, 2H), 3.28 (m, 6H), 3.01 (s, 4H), 2.72 (s, 2H), 2.16 (m, 6H), 1.93 (m, 4H), 1.80 (m, 4H), 1.57 (m, 2H), 1.38 (t, 2H), 1.17 (t, 2H), 0.90 (s, 6H).

Example 62

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide Example 62A 4-(2-cyanoethylamino)-3-nitrobenzenesulfonamide The title compound was prepared by substituting 3-aminopropanenitrile for EXAMPLE 39B in EXAMPLE 39C.

Example 62B 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide The title compound was prepared by substituting EXAMPLE 62A for EXAMPLE 11B in EXAMPLE 11D. $^1$H NMR (501 MHz, pyridine-d$_5$) δ 13.04 (s, 1H), 9.24 (d, 1H), 9.04 (t, 1H), 8.43 (d, 1H), 8.38 (dd, 1H), 8.13 (d, 1H), 7.64-7.68 (m, 2H), 7.44 (ddd, 2H), 7.07 (ddd, 2H), 7.02 (d, 1H), 6.76 (dd, 1H), 6.55 (d, 1H), 6.48 (dd, 1H), 3.83 (q, 2H), 3.07 (d, 4H), 2.98 (t, 2H), 2.77 (s, 2H), 2.26 (s, 2H), 2.11-2.17 (m, 4H), 1.97 (s, 2H), 1.39 (t, 2H), 0.93 (s, 6H).

Example 63

Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared by substituting EXAMPLE 15H for EXAMPLE 3J and EXAMPLE 39C for EXAMPLE 11B in EXAMPLE 11D. $^1$H NMR (501 MHz, pyridine-d$_5$) δ 13.09 (s, 1H), 9.30 (d, 1H), 8.64 (d, 1H), 8.43 (d, 1H), 8.38 (dd, 1H), 8.10 (d, 1H), 7.68 (dt, 2H), 7.46 (ddd, 2H), 7.12 (ddd, 2H), 6.91 (d, 1H), 6.72 (dd, 1H), 6.51 (dd, 1H), 6.49 (d, 1H), 5.69 (s, 2H), 4.40 (s, 2H), 3.69-3.73 (m, 4H), 3.68 (s, 1H), 2.95-3.02 (m, 4H), 2.84 (s, 2H), 2.40-2.46 (m, 4H), 2.21 (s, 2H), 2.08-2.15 (m, 5H), 1.76-1.84 (m, 2H), 1.55-1.63 (m, 6H), 1.29 (s, 6H).

Example 64

Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 64A tert-butyl (trans)-4-(bis(cyclopropylmethyl)amino)cyclohexylcarbamate The title compound was prepared by substituting cyclopropanecarbaldehyde for 4'-chlorobiphenyl-2-carboxaldehyde and tert-butyl (trans)-4-aminocyclohexylcarbamate for tert-butyl piperazine-1-carboxylate in EXAMPLE 1A.

Example 64B (trans)-N$^1$,N$^1$-bis(cyclopropylmethyl)cyclohexane-1,4-diamine dihydrochloride To a solution of EXAMPLE 64A (1.4 g) in dichloromethane (10 ml) was added hydrogen chloride (10 ml, 4M in dioxane) and the reaction was stirred for 16 hours at room temperature. The reaction mixture was diluted with ether and pure product was filtered off.

Example 64C

Trans-4-(4-(bis(cyclopropylmethyl)amino)cyclohexylamino)-3-nitrobenzenesulfonamide The title compound was prepared by substituting EXAMPLE 64B for EXAMPLE 39B in EXAMPLE 39C.

Example 64D

Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 64C for EXAMPLE 11B in EXAMPLE 11D. $^1$H NMR (500 MHz, pyridine-d$_5$) δ 13.06 (s, 1H), 9.30 (d, 1H), 8.44 (d, 1H), 8.41 (dd, 1H), 8.37 (d, 1H), 8.12 (d, 1H), 7.67 (d, 2H), 7.44 (d, 2H), 7.07 (d, 2H), 7.00 (d, 1H), 6.75 (dd, 1H), 6.53 (d, 1H), 6.49 (dd, 1H), 3.36-3.43 (m, 1H), 3.02-3.09 (m, 4H), 2.87-2.94 (m, 1H), 2.77 (s, 2H), 2.47 (d, 4H), 2.25 (t, 2H), 2.11-2.16 (m, 4H), 2.08 (d, 2H), 1.97 (s, 2H), 1.84 (d, 2H), 1.39 (t, 2H), 1.26-1.35 (m, 4H), 0.90-0.98 (m, 8H), 0.50-0.56 (m, 4H), 0.18-0.23 (m, 4H).

Example 65

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide Example 65A 4-((1-methylpiperidin-4-yl)methylamino)-3-nitrobenzenesulfonamide The title compound was prepared by substituting 4-aminomethyl-1-methyl piperidine for (tetrahydropyran-4-yl)methylamine in EXAMPLE 1F.

Example 65B 4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide The title compound was prepared by substituting EXAMPLE 65A for EXAMPLE 130C in EXAMPLE 130D. $^1$H NMR (500 MHz, dichloromethane-d$_2$) δ 9.57 (bs, 1H), 8.78 (d, 1H), 8.41 (d, 1H), 8.14 (d, 1H), 7.90 (m, 2H), 7.64 (d, 1H), 7.45 (d, 1H), 7.23 (d, 2H), 6.95 (d, 2H), 6.76 (d, 1H), 6.59 (dd, 1H), 6.51 (d, 1H), 6.09 (d, 1H), 3.21 (m, 2H), 3.08 (m, 4H), 3.02 (m, 2H), 2.74 (s, 2H), 2.33 (s, 3H), 2.21-2.17 (m, 6H), 2.16-2.02 (m, 3H), 1.97 (br.s, 2H), 1.78 (m, 4H), 1.41 (t, 2H), 0.94 (s, 6H).

Example 66

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide Example 66A tert-butyl 3-((2-nitro-4-sulfamoylphenylamino)methyl)morpholine-4-carboxylate The title compound was prepared by substituting tert-butyl 3-(aminomethyl)morpholine-4-carboxylate for (tetrahydropyran-4-yl)methylamine in EXAMPLE 1F.

Example 66B tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared by substituting EXAMPLE 66A for EXAMPLE 1F and EXAMPLE 3J for EXAMPLE 1E in EXAMPLE 1F, with the exception that the product was purified on a silica gel column eluted with 4% methanol in dichloromethane.

Example 66C 4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide A solution of EXAMPLE 66B in 50% trifluoroacetic acid and dichloromethane mixture was stirred at ambient temperature for 2 hours. The solvents were evaporated and the residue was purified on a reverse phase HPLC using a gradient of 20-80% acetonitrile in water containing 10 mM ammonium acetate. $^1$H NMR (500 MHz, dimethylsulfoxide-$d_6$) δ 11.61 (s, 1H), 8.52 (bs, 1H), 8.49 (d, 1H), 7.98 (d, 1H), 7.78 (d, 1H), 7.54 (d, 1H), 7.46 (s, 1H), 7.42 (s, 1H), 7.34 (d, 2H), 7.04 (m, 3H), 6.65 (dd, 1H), 6.34 (s, 1H), 6.21 (d, 1H), 3.89 (d, 1H), 3.76 (d, 1H), 3.55-3.46 (m, 2H), 3.40-3.35 (m, 4H), 3.04 (m, 4H), 2.91 (t, 1H), 2.73 (s, 2H), 2.20-2.12 (m, 6H), 1.95 (s, 2H), 1.38 (t, 2H), 0.92 (s, 6H).

Example 67

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide The title compound was prepared as described in EXAMPLE 1G by replacing EXAMPLE 1E and EXAMPLE 1F with EXAMPLE 15H and EXAMPLE 6A, respectively. $^1$H NMR (300 MHz, dimethylsulfoxide-$d_6$) δ 11.58 (s, 1H), 9.04 (s, 1H), 8.44 (d, 1H), 7.97 (d, 1H), 7.76 (dd, 1H), 7.49 (m, 4H), 7.38 (d, 2H), 7.14 (d, 2H), 6.64 (dd, 1H), 6.34 (d, 1H), 6.21 (d, 1H), 4.12 (s, 2H), 3.03 (m, 6H), 2.85 (m, 5H), 2.29 (m, 4H), 2.18 (m, 6H), 1.20 (s, 6H).

Example 68

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide Example 68A 4-morpholinobut-2-yn-1-ol To a solution of morpholine (4.36 g) in toluene (15 mL) was added 4-chlorobut-2-yn-1-ol (2.09 g) in toluene (5 mL). The solution was stirred at 85° C. for 3 hours. After cooling, the solid was filtered off. The filtrate was subjected to vacuum distillation to give the pure title compound.

Example 68B 4-(4-morpholinobut-2-ynyloxy)-3-nitrobenzenesulfonamide

The title compound was prepared by substituting EXAMPLE 68A for (tetrahydro-2H-pyran-4-yl)methanol in EXAMPLE 24A.

Example 68C 4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide The title compound was prepared by substituting EXAMPLE 68B for EXAMPLE 11B in EXAMPLE 11D. $^1$H NMR (500 MHz, dimethylsulfoxide-$d_6$) δ 11.68 (s, 1H), 8.36 (s, 1H), 8.08 (d, 1H), 8.03 (d, 1H), 7.47-7.53 (m, 4H), 7.35 (d, 2H), 7.04 (d, 2H), 6.67 (dd, 1H), 6.40 (dd, 1H), 6.20 (d, 1H), 5.15 (s, 2H), 3.52-3.55 (m, 4H), 3.09 (s, 4H), 2.84 (br s, 2H), 2.23-2.40 (m, 6H), 2.12-2.18 (m, 2H), 1.96 (s, 2H), 1.39 (t, 2H), 0.92 (s, 6H).

Example 69

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide Example 69A 6-((tetrahydro-2H-pyran-4-yl)methoxy)-5-((triisopropylsilyl)ethynyl)pyridine-3-sulfonamide EXAMPLE 36B (0.176 g), bis(triphenylphosphine)palladium(II) chloride (0.176 g), copper(I) iodide (0.010 g), N,N-dimethylacetamide (2.5 mL) and triethylamine (0.105 mL) were combined, flushed with nitrogen and stirred for 2 minutes. (Triisopropylsilyl)acetylene (0.135 mL) was added and the reaction mixture was flushed with nitrogen again, heated at 60° C. overnight, diluted with ethyl acetate, washed with water and brine, dried (MgSO$_4$), filtered, concentrated and chromatographed on silica gel with 10-30% ethyl acetate in hexanes as the eluent to give the product.

Example 69B 5-ethynyl-6-((tetrahydro-2H-pyran-4-yl)methoxy) pyridine-3-sulfonamide EXAMPLE 69A (0.205 g) in tetrahydrofuran (3 mL) at ambient temperature was treated with tetrabutyl ammonium fluoride (1 M in tetrahydrofuran, 0.906 mL) and stirred at ambient temperature for 4 hours. Additional tetrabutyl ammonium fluoride (1 M in tetrahydrofuran, 1.8 mL) was added and the mixture was heated at 40° C. for 45 minutes. Solid tetrabutyl ammonium fluoride (0.253 g) was added and heating was continued for 30 minutes. The reaction mixture was concentrated and then chromatographed on silica gel using 0-2% methanol in dichloromethane as the eluent to give the product.

Example 69

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl] sulfonyl}-2-(1H-pyrrolo[2,3-b]pyridin-5-yloxy) benzamide The title compound was prepared by substituting EXAMPLE 69B for EXAMPLE 11B in EXAMPLE 11D. $^1$H NMR (300 MHz, dimethylsulfoxide-d$_6$) δ 11.69 (s, 1H), 11.41 (s, 1H), 8.58 (d, 1H), 8.19 (d, 1H), 8.05 (d, 1H), 7.53 (m, 3H), 7.35 (d, 2H), 7.04 (d, 2H), 6.67 (dd, 1H), 6.41 (dd, 1H), 6.18 (d, 1H), 4.56 (s, 1H), 4.24 (d, 2H), 3.87 (dd, 2H), 3.38 (m, 3H), 3.07 (m, 4H), 2.86 (m, 2H), 2.29 (m, 5H), 2.04 (m, 3H), 1.64 (dd, 2H), 1.34 (m, 4H), 0.93 (s, 6H).

Example 70

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b] pyridin-5-yloxy)benzamide Example 70A 4-amino-3-cyanobenzenesulfonamide 3-Cyano-4-fluorobenzene-1-sulfonyl chloride (1.1 g) was dissolved in dioxane (4 mL). The solution was cooled to 0° C. and 7 mL of an ammonia (7N in methanol) solution was added. After the addition was complete, the ice bath was removed and the reaction was stirred at room temperature for 24 hours. After concentration of the reaction mixture, the crude material was purified by flash chromatography eluting with a gradient of 30-100% ethyl acetate/hexanes.

Example 70B 2-(1H-pyrrolo[2,3-b]pyridin-5-yloxy)-N-(4-amino-3-cyanophenylsulfonyl)-4-(4-((2-(4-chlorophenyl)-4,4-dimethylcyclohex-1-enyl)methyl)piperazin-1-yl) benzamide The title compound was prepared by substituting EXAMPLE 70A for EXAMPLE 1F and EXAMPLE 3J for EXAMPLE 1E in EXAMPLE 1G.

Example 70C 2-(1H-pyrrolo[2,3-b]pyridin-5-yloxy)-N-(4-amino-3-carbamoylphenylsulfonyl)-4-(4-((2-(4-chlorophenyl)-4,4-dimethylcyclohex-1-enyl)methyl)piperazin-1-yl)benzamide To a solution of EXAMPLE 70B (90 mg) in ethanol (2 mL) was added tetrahydrofuran (2 mL), hydrogen peroxide (30%, 1 mL) and 1M sodium hydroxide solution (0.48 mL), followed by an additional 2 mL of tetrahydrofuran. The reaction was heated to 45° C. for 30 minutes, cooled, and then quenched with 5% HCl solution and extracted twice with dichloromethane. The extracts were combined and concentrated to obtain the product.

Example 70D 4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b] pyridin-5-yloxy)benzamide EXAMPLE 70C (80 mg) was combined with trimethyl orthoformate (2.3 mL) and trifluoroacetic acid (0.03 mL) and the resulting solution was stirred at room temperature for 4 hours. The mixture was purified by flash chromatography, eluting with a gradient of 3-10% methanol/dichloromethane. $^1$H NMR (300 MHz, dimethylsulfoxide-d$_6$) δ 12.61 (s, 1H), 11.71 (s, 1H), 8.65 (d, 1H), 8.24 (s, 1H), 8.17 (dd, 1H), 8.04 (m, 1H), 7.73 (d, 1H), 7.57 (d, 1H), 7.51 (m, 2H), 7.39 (d, 2H), 7.07 (d, 2H), 6.70 (dd, 1H), 6.40 (m, 1H), 6.24 (br s, 1H), 3.61 (m, 6H), 3.03 (m, 2H), 2.75 (m, 2H), 2.17 (m, 2H), 2.01 (m, 2H), 1.44 (m, 2H), 0.94 (s, 6H).

Example 71

Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide Example 71A 8-chlorospiro[4.5]dec-7-ene-7-carbaldehyde To a solution of N,N-dimethylformamide (2.81 mL) in dichloromethane (40 mL) was added dropwise POCl$_3$ (2.78 mL) at 0° C. The reaction mixture was warmed up to room temperature and spiro[4.5]decan-8-one (3.95 g) in dichloromethane (5 mL) was added dropwise. The mixture was stirred overnight. The reaction was quenched with cold aqueous sodium acetate and the resulting mixture was extracted with ether and the organic layer was dried over Na$_2$SO$_4$, filtered, and concentrated to provide the title compound.

Example 71B 8-(4-chlorophenyl)spiro[4.5]dec-7-ene-7-carbaldehyde

To a suspension of EXAMPLE 71A (3 g) in water (50 mL) was added 4-chlorophenylboronic acid (2.83 g), tetrabutylammonium (4.87 g), potassium carbonate (6.26 g) and palladium(II) acetate (0.169 g). The reaction mixture was stirred at 45° C. for 5 hours and extracted with dichloromethane. The organic layer was concentrated and the residue was loaded onto a silica gel column, and eluted with 5-20% ethyl acetate in hexane to give the title compound.

Example 71C methyl 2-(1H-pyrrolo[2,3-b]pyridin-5-yloxy)-4-(4-((8-(4-chlorophenyl)spiro[4.5]dec-7-en-7-yl)methyl)piperazin-1-yl)benzoate To a solution of EXAMPLE 71B (274 mg) in dichloroethane (3.5 mL) was added EXAMPLE 15F (387 mg) and sodium triacetoxyborohydride (317 mg). The reaction mixture was stirred overnight. Sodium cyanoborohydride (37.6 mg) was added and the resulting mixture stirred overnight. The reaction was quenched with water and diluted with dichloromethane. The mixture was washed with water extensively and the organic layer was dried over $Na_2SO_4$, filtered, and concentrated to provide the title compound.

Example 71D 2-(1H-pyrrolo[2,3-b]pyridin-5-yloxy)-4-(4-((8-(4-chlorophenyl)spiro[4.5]dec-7-en-7-yl)methyl)piperazin-1-yl)benzoic acid The title compound was prepared as described in EXAMPLE 3J using EXAMPLE 71C in place of EXAMPLE 3I.

Example 71E

Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared as described in EXAMPLE 11D using EXAMPLE 71D and EXAMPLE 9C in place of EXAMPLE 3J and EXAMPLE 11B, respectively. $^1$H NMR (500 MHz, dimethylsulfoxide-$d_6$) δ 11.64 (s, 1H), 8.51 (s, 1H), 8.15 (d, 1H), 8.01 (d, 1H), 7.76 (d, 1H), 7.44-7.53 (m, 3H), 7.34 (d, 2H), 7.07 (d, 3H), 6.66 (dd, 1H), 6.37 (dd, 1H), 6.20 (d, 1H), 3.50-3.70 (m, 5H), 3.04 (s, 4H), 2.55-2.76 (m, 5H), 2.34-2.39 (m, 1H), 2.20 (d, 6H), 2.03 (s, 4H), 1.91 (s, 2H), 1.61 (q, 4H), 1.51 (t, 2H), 1.36-1.46 (m, 8H).

Example 72

Cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 15H and 29A in place of EXAMPLE 3J and EXAMPLE 11B, respectively. $^1$H NMR (500 MHz, dimethylsulfoxide-$d_6$) δ 11.69 (s, 1H), 11.45 (s, 1H), 8.59 (t, 1H), 8.56 (d, 1H), 8.04 (d, 1H), 7.79 (dd, 1H), 7.54 (d, 1H), 7.47-7.52 (m, 2H), 7.37 (d, 2H), 7.13 (d, 2H), 7.08 (d, 1H), 6.68 (dd, 1H), 6.35-6.42 (m, 1H), 6.19 (d, 1H), 4.11 (s, 2H), 3.37 (s, 1H), 3.26 (t, 2H), 3.20 (s, 3H), 3.07 (s, 4H), 2.83 (s, 2H), 2.17 (d, 6H), 1.81 (dd, 2H), 1.64-1.73 (m, 1H), 1.48 (dd, 2H), 1.23-1.41 (m, 4H), 1.18 (s, 6H).

Example 73

4-(4-{[8-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 71D and EXAMPLE 37D in place of EXAMPLE 3J and EXAMPLE 11B, respectively. $^1$H NMR (500 MHz, dimethylsulfoxide-$d_6$) δ 11.68 (s, 1H), 8.37 (s, 1H), 7.98-8.11 (m, 2H), 4.38 (d, 2H), 3.74-3.82 (m, 2H), 3.54-3.64 (m, 2H), 3.44 (s, 1H), 3.08 (s, 3H), 2.58-2.89 (m, 2H), 2.13-2.35 (m, 4H), 2.04 (s, 2H), 1.78-1.93 (m, 4H), 1.57-1.65 (m, 4H), 1.52 (t, 2H), 1.36-1.47 (m, 4H).

Example 74

Trans-4-(4-{[8-(4-chlorophenyl)spiro[4.5]dec-7-en-7-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 71D and EXAMPLE 34B in place of EXAMPLE 3J and EXAMPLE 11B, respectively. $^1$H NMR (500 MHz, dimethylsulfoxide-$d_6$) δ 11.69 (s, 1H), 11.39 (s, 1H), 8.58 (t, 1H), 8.56 (d, 1H), 8.04 (d, 1H), 7.79 (dd, 1H), 7.47-7.55 (m, 3H), 7.34 (d, 2H), 7.07 (d, 3H), 6.68 (dd, 1H), 6.39 (dd, 1H), 6.19 (d, 1H), 3.25 (t, 2H), 3.22 (s, 3H), 3.06 (s, 5H), 2.71 (s, 2H), 2.21 (s, 6H), 1.94-2.06 (m, 4H), 1.79 (d, 2H), 1.57-1.65 (m, 5H), 1.51 (t, 2H), 1.39 (t, 4H), 0.95-1.11 (m, 4H).

Example 75

4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 75A methyl 5,5-dimethyl-2-(trifluoromethylsulfonyloxy)cyclohex-1-enecarboxylate The title compound was prepared by substituting 4,4-dimethyl-2-methoxycarbonylcyclohexanone for 5,5-dimethyl-2-methoxycarbonylcyclohexanone in EXAMPLE 3A.

Example 75B methyl 2-(4-chlorophenyl)-5,5-dimethylcyclohex-1-enecarboxylate

The title compound was prepared by substituting EXAMPLE 75A for EXAMPLE 3A in EXAMPLE 3B.

Example 75C (2-(4-chlorophenyl)-5,5-dimethylcyclohex-1-enyl)methanol

The title compound was prepared by substituting EXAMPLE 75B for EXAMPLE 3B in EXAMPLE 3C.

Example 75D 2-(4-chlorophenyl)-5,5-dimethylcyclohex-1-enecarbaldehyde

To a solution of EXAMPLE 75C (2.8 g) in dichloromethane (50 mL) was added Dess-Martin Periodinane (5.68 g). The reaction mixture was stirred at room temperature for 3 hours and diluted with ether and washed with 5% NaOH and brine. The organic layer was dried over $Na_2SO_4$, filtered, and concentrated. The residue was purified by flash chromatography using 20% ethyl acetate in hexanes to provide the title compound.

Example 75E methyl 2-(1H-pyrrolo[2,3-b]pyridin-5-yloxy)-4-(4-((2-(4-chlorophenyl)-5,5-dimethylcyclohex-1-enyl)methyl)piperazin-1-yl)benzoate The title compound was prepared by replacing 4'-chlorobiphenyl-2-carboxaldehyde with EXAMPLE 75D and tert-butyl piperazine-1-carboxylate with EXAMPLE 15F in EXAMPLE 1A.

Example 75F 2-(1H-pyrrolo[2,3-b]pyridin-5-yloxy)-4-(4-((2-(4-chlorophenyl)-5,5-dimethylcyclohex-1-enyl)methyl)piperazin-1-yl)benzoic acid The title compound was prepared as described in EXAMPLE 15H by replacing EXAMPLE 15G with EXAMPLE 75E.

Example 75G 4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in EXAMPLE 11D using EXAMPLE 75F and EXAMPLE 1F in place of EXAMPLE 3J and EXAMPLE 11B, respectively. $^1$H NMR (400 MHz, dimethylsulfoxide-$d_6$) δ 11.69 (s, 1H), 11.38 (s, 1H), 8.60 (t, 1H), 8.56 (d, 1H), 8.04 (d, 1H), 7.80 (dd, 1H), 7.47-7.55 (m, 3H), 7.31-7.36 (m, 2H), 7.05-7.13 (m, 3H), 6.68 (dd, 1H), 6.39 (dd, 1H), 6.18 (d, 1H), 3.85 (dd, 2H), 3.22-3.31 (m, 4H), 3.07 (s, 4H), 2.67-2.78 (m, 2H), 2.19 (s, 6H), 1.82-1.98 (m, 3H), 1.56-1.66 (m, 2H), 1.39 (t, 2H), 1.17-1.33 (m, 3H), 0.93 (s, 6H).

Example 76

4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide The title compound was prepared as described in EXAMPLE 11D using EXAMPLE 75F and EXAMPLE 36C in place of EXAMPLE 3J and EXAMPLE 11B, respectively. $^1$H NMR (400 MHz, dimethylsulfoxide-$d_6$) δ 11.62 (s, 1H), 8.73 (s, 1H), 8.52 (s, 1H), 7.98 (d, 1H), 7.56 (d, 1H), 7.45-7.51 (m, 1H), 7.43 (s, 1H), 7.37 (d, 2H), 7.10 (d, 2H), 6.68 (dd, 1H), 6.35 (dd, 1H), 6.25 (s, 1H), 4.29 (d, 2H), 3.88 (dd, 2H), 3.12 (d, 4H), 2.21 (s, 2H), 2.00-2.11 (m, 1H), 1.95 (s, 2H), 1.64 (dd, 2H), 1.27-1.46 (m, 4H), 0.95 (s, 6H)

Example 77 tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate

Example 77A tert-butyl 3-((2-nitro-4-sulfamoylphenoxy)methyl)morpholine-4-carboxylate The title compound was prepared as described in EXAMPLE 12A by replacing (1,4-dioxan-2-yl)methanol with tert-butyl 3-(hydroxymethyl)morpholine-4-carboxylate.

Example 77B tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate The title compound was prepared as described in EXAMPLE 11D using EXAMPLE 77A in place of EXAMPLE 11B. $^1$H NMR (400 MHz, dimethylsulfoxide-$d_6$) δ 11.67 (s, 1H), 8.36 (s, 1H), 8.01-8.11 (m, 2H), 7.47-7.61 (m, 4H), 7.35 (d, 2H), 7.04 (d, 2H), 6.68 (dd, 1H), 6.39 (d, 1H), 6.20 (s, 1H), 4.41-4.52 (m, 2H), 4.15-4.28 (m, 1H), 3.59-3.95 (m, 3H), 3.51 (d, 1H), 3.34-3.43 (m, 1H), 3.10 (s, 5H), 2.84 (s, 2H), 2.28 (s, 4H), 2.15 (s, 2H), 1.96 (s, 2H), 1.20-1.45 (m, 12H), 0.92 (s, 6H).

Example 78

4-(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide EXAMPLE 77B (100 mg) in dichloromethane (10 mL) at 0° C. was treated with trifluoroacetic acid (5 mL) for 20 minutes. The reaction mixture was concentrated. The residue was purified by reverse phase HPLC on a C18 column using a gradient of 35-60% acetonitrile in 0.1% trifluoroacetic acid water to give the title compound as a trifluoroacetate salt. The trifluoroacetic acid salt was dissolved in dichloromethane (10 mL) and washed with 50% aqueous NaHCO$_3$. The organic layer was dried over anhydrous Na$_2$SO$_4$ and concentrated to give the title compound. $^1$H NMR (400 MHz, dimethylsulfoxide-d$_6$) δ 11.56 (s, 1H), 8.23 (d, 1H), 7.94 (d, 1H), 7.90 (dd, 1H), 7.57 (d, 1H), 7.42-7.46 (m, 1H), 7.31-7.37 (m, 3H), 7.25 (d, 1H), 7.01-7.09 (m, 2H), 6.64 (dd, 1H), 6.29-6.37 (m, 1H), 6.24 (d, 1H), 4.17-4.31 (m, 2H), 3.90-4.05 (m, 1H), 3.77-3.85 (m, 1H), 3.45-3.59 (m, 4H), 2.94-3.13 (m, 6H), 2.76 (s, 2H), 2.18 (d, 6H), 1.96 (s, 2H), 1.39 (t, 2H), 0.93 (s, 6H).

Example 79

4-(4-{[8-(4-chlorophenyl)spiro[4.5]dec-7-en-7-yl] methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in EXAMPLE 11D using EXAMPLE 71D and EXAMPLE 1F in place of EXAMPLE 3J and EXAMPLE 11B, respectively. $^1$H NMR (400 MHz, dimethylsulfoxide-d$_6$) δ 11.69 (s, 1H), 11.38 (s, 1H), 8.60 (t, 1H), 8.56 (d, 1H), 8.04 (d, 1H), 7.77-7.84 (m, 1H), 7.45-7.56 (m, 3H), 7.34 (d, 2H), 7.04-7.13 (m, 3H), 6.68 (dd, 1H), 6.39 (d, 1H), 6.19 (d, 1H), 3.85 (dd, 2H), 3.22-3.31 (m, 4H), 3.07 (s, 4H), 2.71 (s, 2H), 2.21 (s, 6H), 2.03 (s, 2H), 1.81-1.94 (m, 1H), 1.56-1.68 (m, 6H), 1.51 (t, 2H), 1.34-1.45 (m, 4H), 1.20-1.33 (m, 2H).

Example 80

4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide The title compound was prepared by substituting 1-(methylsulfonyl)piperidin-4-amine for 1-acetylpiperidin-4-amine in EXAMPLE 53B. $^1$H NMR (300 MHz, dimethylsulfoxide-d$_6$) δ 11.67 (br s, 1H), 8.57 (d, 1H), 8.25 (d, 1H), 8.04 (d, 1H), 7.83 (dd, 1H), 7.54-7.46 (m, 3H), 7.35 (d, 2H), 7.17 (d, 1H), 7.04 (d, 2H), 6.68 (dd, 1H), 6.39 (m, 1H), 6.20 (d, 1H), 3.80 (m, 1H), 3.57 (m, 2H), 3.08 (br s, 4H), 2.95 (td, 2H), 2.92 (s, 3H), 2.85-2.72 (m, 2H), 2.30-2.10 (m, 6H), 2.07-1.93 (m, 4H), 1.70 (m, 2H), 1.39 (t, 2H), 0.93 (s, 6H).

Example 81

4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide Example 81A 1,1-Dioxotetrahydro-2H-thiopyran-4-amine N-Benzyl-1,1-dioxotetrahydro-2H-thiopyran-4-amine (2.00 g) was added to ethanol (40 mL) in a pressure bottle. Palladium hydroxide on carbon (0.587 g,) was added and the solution was stirred under 30 psi of hydrogen at room temperature for 2 hours. The mixture was filtered through a nylon membrane and the solvent was removed under vacuum.

Example 81B 4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide The title compound was prepared by substituting EXAMPLE 81A for 1-acetylpiperidin-4-amine in EXAMPLE 53B. $^1$H NMR (300 MHz, dimethylsulfoxide-d$_6$) δ 11.65 (br s, 1H), 8.55 (d, 1H), 8.25 (d, 1H), 8.03 (d, 1H), 7.86 (dd, 1H), 7.52-7.47 (m, 3H), 7.35 (d, 2H), 7.17 (d, 1H), 7.04 (d, 2H), 6.68 (dd, 1H), 6.39 (m, 1H), 6.21 (d, 1H), 4.05 (m, 1H), 3.22-3.00 (m, 8H), 2.79 (br s, 2H), 2.31-2.11 (m, 10H), 1.96 (br s, 2H), 1.39 (t, 2H), 0.93 (s, 6H).

Example 82

N-[(4-chloro-3-nitrophenyl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting EXAMPLE 3J for EXAMPLE 1E and 4-chloro-3-nitrobenzenesulfonamide for EXAMPLE 1F in EXAMPLE 1G. $^1$H NMR (300 MHz, dimethylsulfoxide-d$_6$) δ 11.60 (br s, 1H), 8.38 (br s, 1H), 7.96 (d, 1H), 7.91 (d, 1H), 7.68 (d, 1H), 7.58 (d, 1H), 7.46 (t, 1H), 7.39-7.35 (m, 3H), 7.07 (d, 2H), 6.67 (dd, 1H), 6.34 (m, 1H), 6.28 (d, 1H), 3.31 (br s, 2H), 3.17 (br s, 8H), 2.18 (m, 2H), 1.98 (br s, 2H), 1.42 (t, 2H), 0.94 (s, 6H).

Example 83

4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy) benzamide Example 83A 3-Nitro-4-[1-(2,2,2-trifluoro-ethyl)-piperidin-4-ylamino]-benzenesulfonamide The title compound was prepared by substituting 1-(2,2,2-trifluoroethyl)piperidin-4-amine hydrochloride for (tetrahydropyran-4-yl)methylamine in EXAMPLE 6A.

Example 83B 4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy) benzamide The title compound was prepared by substituting EXAMPLE 3J for EXAMPLE 1E and EXAMPLE 82A for EXAMPLE 1F in EXAMPLE 1G. $^1$H NMR (300 MHz, dimethylsulfoxide-d$_6$) δ 11.66 (br s, 1H), 8.56 (d, 1H), 8.24 (d, 1H), 8.04 (d, 1H), 7.81 (dd, 1H), 7.52 (dd, 2H), 7.48 (d, 1H), 7.35 (d, 2H), 7.15 (d, 1H), 7.04 (d, 2H), 6.68 (dd, 1H), 6.38 (m, 1H), 6.20 (d, 1H), 3.68 (m, 1H), 3.22 (q, 2H), 3.07 (br s,

Example 84

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy) benzamide

Example 84A 1-(tetrahydro-2H-pyran-4-yl)piperidin-4-ol

Piperidin-4-ol (7.8 g) and dihydro-2H-pyran-4(3H)-one (5.0 g) were dissolved in titanium(IV) isopropoxide (30 mL) and the reaction was stirred at room temperature overnight. Methanol (40 mL) was added and the reaction was cooled to 0° C. Then NaBH$_4$ (3.8 g) was added in portions over one hour. After 2 hours 1N aqueous NaOH was added, followed by ethyl acetate addition. After filtration though celite the layers were separated, the aqueous layer extracted with ethyl acetate, and the combined organic layers were dried over Na$_2$SO$_4$. The crude was purified by column chromatography using dichloromethane having 5-10% 7N NH$_3$ in methanol.

Example 84B 5-bromo-6-(1-(tetrahydro-2H-pyran-4-yl)piperidin-4-yloxy)pyridine-3-sulfonamide The title compound was prepared by substituting EXAMPLE 84A for (tetrahydro-2H-pyran-4-yl)methanol and EXAMPLE 36A for 4-fluoro-3-nitrobenzenesulfonamide in EXAMPLE 24A.

Example 84C 5-cyano-6-(1-(tetrahydro-2H-pyran-4-yl)piperidin-4-yloxy)pyridine-3-sulfonamide The title compound was prepared by substituting EXAMPLE 84B for EXAMPLE 36B in EXAMPLE 36C.

Example 84D 4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy) benzamide The title compound was prepared by substituting EXAMPLE 84C for EXAMPLE 11B in EXAMPLE 11D. $^1$H NMR (500 MHz, dimethylsulfoxide-d$_6$) δ 11.50 (s, 1H), 8.60 (d, 1H), 8.37 (d, 1H), 7.90 (d, 1H), 7.60 (d, 1H), 7.42 (dd, 1H), 7.35 (d, 2H), 7.25 (d, 1H), 7.04 (d, 2H), 6.63 (dd, 1H), 6.28 (m, 1H), 6.24 (d, 1H), 5.30 (br s, 1H), 4.50 (d, 1H), 3.95 (dd, 2H), 3.30 (m, 5H), 3.02 (br s, 4H), 2.95 (br s, 2H), 2.24 (br s, 4H), 2.17 (br m, 4H), 1.96 (s, 2H), 1.90 (br m, 4H), 1.60 (br m, 2H), 1.39 (t, 2H), 0.93 (s, 6H).

4H), 2.90 (m, 2H), 2.75 (br s, 2H), 2.29-2.12 (m, 8H), 1.97-1.86 (m, 4H), 1.63 (m, 2H), 1.38 (t, 2H), 0.92 (s, 6H).

Example 85

4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy) benzamide

Example 85A 5-isopropyl-6-((tetrahydro-2H-pyran-4-yl)methoxy) pyridine-3-sulfonamide EXAMPLE 36B (0.176 g), 2-dicyclohexylphosphino-2',6'-dimethoxybiphenyl (0.041 g), and palladium(II) acetate (0.011 g) were combined in a 10 mL oven-dried flask. Tetrahydrofuran (1 mL) was added and the mixture was flushed with nitrogen and stirred at ambient temperature for 5 minutes. 2-Propylzinc bromide solution (0.5 M in tetrahydrofuran) (1.5 mL) was added and stirring was continued under nitrogen overnight. Additional 2-2-dicyclohexylphosphino-2',6'-dimethoxybiphenyl (0.041 g) and palladium(II) acetate (0.011 g) were added. The mixture was flushed with nitrogen and stirred at ambient temperature for 5 minutes. 2-Propylzinc bromide solution (0.5 M in tetrahydrofuran) (1.5 mL) was added and stirring was continued under nitrogen for 2.5 days. The reaction mixture was diluted with ethyl acetate, washed with water and brine, dried (MgSO$_4$), filtered, concentrated, and chromatographed on silica gel with 0 to 3% methanol in CH$_2$Cl$_2$ as the eluent. The obtained material was chromatographed on silica gel a second time with 10-40% ethyl acetate in CH$_2$Cl$_2$ as the eluent, triturated with diethyl ether and dried under vacuum at 45° C. to give the product.

Example 85B 4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy) benzamide The title compound was prepared by substituting EXAMPLE 85A for EXAMPLE 11B in EXAMPLE 11D. $^1$H NMR (500 MHz, dimethylsulfoxide-d$_6$) δ 11.70 (s, 1H), 8.49 (m, 1H), 8.04 (d, 1H), 7.90 (m, 1H), 7.57 (m, 1H), 7.52 (t, 1H), 7.48 (dd, 1H), 7.34 (d, 2H), 7.04 (d, 2H), 6.67 (dd, 1H), 6.41 (dd, 1H), 6.17 (s, 1H), 4.19 (m, 2H), 3.88 (m, 2H), 3.30 (m, 2H), 3.05 (m, 5H), 2.77 (s, 2H), 2.21 (s, 4H), 2.14 (s, 2H), 2.03 (m, 1H), 1.95 (s, 2H), 1.64 (m, 2H), 1.34 (m, 4H), 1.12 (d, 6H), 0.92 (s, 6H).

Example 86

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide

Example 86A 3-fluoro-4-((tetrahydro-2H-pyran-4-yl)methylamino) benzenesulfonamide The title compound was prepared by substituting 3,4-difluorobenzenesulfonamide for 4-chloro-3-nitrobenzenesulfonamide and (tetrahydro-2H-pyran-4-yl)methanamine for 4-methylpiperazin-1-amine dihydrochloride in EXAMPLE 6A.

Example 86B 3-chloro-5-fluoro-4-((tetrahydro-2H-pyran-4-yl)methylamino)benzenesulfonamide The title compound was prepared by substituting EXAMPLE 86A for EXAMPLE 52B in EXAMPLE 52C.

Example 86C

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 86B for EXAMPLE 11B in EXAMPLE 11D. $^1$H NMR (500 MHz, dimethylsulfoxide-$d_6$) δ 11.72 (s, 1H), 11.20 (s, 1H), 8.08 (d, 1H), 7.61 (m, 2H), 7.50 (m, 3H), 7.34 (d, 2H), 7.04 (d, 2H), 6.68 (dd, 1H), 6.42 (dd, 1H), 6.16 (d, 1H), 6.09 (m, 1H), 3.81 (dd, 2H), 3.25 (m, 4H), 3.07 (m, 4H), 2.76 (s, 2H), 2.18 (m, 6H), 1.95 (s, 2H), 1.72 (m, 1H), 1.53 (d, 2H), 1.38 (t, 2H), 1.16 (m, 2H), 0.92 (s, 6H).

Example 87

4-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide

Example 87A methyl 2-(1H-indol-5-yloxy)-4-fluorobenzoate

The title compound was prepared by substituting 5-hydroxyindole for EXAMPLE 3G in EXAMPLE 3H.

Example 87B methyl 2-(1H-indol-5-yloxy)-4-(4-((2-(4-chlorophenyl)-4,4-dimethylcyclohex-1-enyl)methyl)piperazin-1-yl)benzoate The title compound was prepared by substituting EXAMPLE 87A for EXAMPLE 3H in EXAMPLE 3I.

Example 87C 2-(1H-indol-5-yloxy)-4-(4-((2-(4-chlorophenyl)-4,4-dimethylcyclohex-1-enyl)methyl)piperazin-1-yl)benzoic acid The title compound was prepared by substituting EXAMPLE 87B for EXAMPLE 3I in EXAMPLE 3J.

Example 87D

4-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide The title compound was prepared by substituting EXAMPLE 87C for EXAMPLE 1E in EXAMPLE 1G, except here the crude was purified by preparative HPLC using a 250×50 mm C18 column and eluting with 20-100% CH$_3$CN vs. 0.1% trifluoroacetic acid in water, giving the product as a trifluoroacetate salt. $^1$H NMR (300 MHz, dimethylsulfoxide-$d_6$) δ 11.40 (br s, 1H), 11.17 (s, 1H), 9.50 (v br s, 1H), 8.61 (t, 1H), 8.57 (d, 1H), 7.77 (dd, 1H), 7.70 (br s, 1H), 7.50 (m, 5H), 7.36 (m, 5H), 7.10 (s, 1H), 7.08 (d, 1H), 6.83 (dd, 1H), 6.69 (dd, 1H), 6.37 (m, 1H), 6.21 (d, 1H), 4.30 (br s, 1H), 3.84 (dd, 2H), 3.70 (br s, 1H), 3.30 (m, 6H), 3.20, 2.95, 2.80 (all br s, total 6H), 1.86 (m, 1H), 1.60 (m, 2H), 1.25 (m, 2H).

Example 88

4-{4-[(4'-chloro-1,1'-biphenyl-2-yl)methyl]piperazin-1-yl}-2-(1H-indol-5-yloxy)-N-({4-[(3-morpholin-4-ylpropyl)amino]-3-nitrophenyl}sulfonyl)benzamide The title compound was prepared by substituting EXAMPLE 87C for EXAMPLE 1E and EXAMPLE 2A for EXAMPLE 1F in EXAMPLE 1G, except here the crude was purified by preparative HPLC using a 250×50 mm C18 column and eluting with 20-100% CH$_3$CN vs. 0.1% trifluoroacetic acid in water, giving the product as a trifluoroacetate salt. $^1$H NMR (300 MHz, dimethylsulfoxide-$d_6$) δ 11.40 (br s, 1H), 11.19 (s, 1H), 9.60 (v br s, 1H), 8.69 (t, 1H), 8.60 (d, 1H), 7.83 (dd, 1H), 7.65 (br s, 1H), 7.50 (m, 5H), 7.38 (m, 5H), 7.12 (m, 2H), 6.83 (dd, 1H), 6.69 (dd, 1H), 6.39 (m, 1H), 6.20 (d, 1H), 4.38 (br s, 1H), 4.00 (m, 2H), 3.80 (br s, 1H), 3.40 (m, 4H), 3.30-2.80 (envelope, 10H), 3.20 (m, 4H), 1.96 (m, 2H).

Example 89

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide This EXAMPLE was prepared by substituting EXAMPLE 87C for EXAMPLE 1E and EXAMPLE 3M for EXAMPLE 1F in EXAMPLE 1G. $^1$H NMR (300 MHz, dimethylsulfoxide-$d_6$) δ 11.15 (s, 1H), 8.56 (d, 1H), 8.20 (d, 1H), 7.84 (dd, 1H), 7.52 (d, 1H), 7.39-7.31 (m, 4H), 7.12 (d, 2H), 7.04 (d, 2H), 6.84 (dd, 1H), 6.65 (dd, 1H), 6.38 (t, 1H), 6.14 (d, 1H), 3.94 (m, 2H), 3.84 (m, 1H), 3.02 (m, 8H), 2.79 (m, 3H), 2.72 (s, 2H), 2.20-2.02 (m, 8H), 1.85 (m, 6H), 1.60 (m, 2H), 1.38 (t, 2H), 0.92 (s, 6H).

Example 90

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide The title compound was prepared by substituting EXAMPLE 87C for EXAMPLE 1E and EXAMPLE 4A for EXAMPLE 1F in EXAMPLE 1G. $^1$H NMR (300 MHz, dimethylsulfoxide-$d_6$) δ 11.08 (s, 1H), 8.51 (d, 1H), 8.13 (d, 1H), 7.78 (dd, 1H), 7.52 (d, 1H), 7.37-7.31 (m, 4H), 7.06-7.00 (m, 4H), 6.79 (dd, 1H), 6.59 (dd, 1H), 6.35 (t, 1H), 6.14 (d, 1H), 3.73 (m, 1H), 3.05-2.95 (m, 6H), 2.71 (s, 2H), 2.60 (m, 2H), 2.48 (s, 3H), 2.16 (m, 6H), 2.01 (m, 2H), 1.95 (s, 2H), 1.70 (m, 2H), 1.38 (t, 2H), 0.92 (s, 6H).

Example 91

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide The title compound was prepared by substituting EXAMPLE 6A for EXAMPLE 11B and EXAMPLE 87C for EXAMPLE 3J in EXAMPLE 11D. $^1$H NMR (500 MHz, dimethylsulfoxide-$d_6$) δ 11.14 (s, 1H), 9.18 (s, 1H), 8.53 (d, 1H), 7.84 (dd, 1H), 7.56 (d, 1H), 7.51 (d, 1H), 7.39 (m, 2H), 7.33 (d, 2H), 7.12 (d, 1H), 7.03 (d, 2H), 6.84 (dd, 1H), 6.62 (dd, 1H), 6.38 (m, 1H), 6.13 (d, 1H), 3.00 (m, 4H), 2.90 (m, 4H), 2.71 (s, 2H), 2.33 (s, 3H), 2.15 (m, 6H), 1.94 (s, 2H), 1.37 (t, 2H), 0.92 (s, 6H).

Example 92

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide The title compound was prepared as described in EXAMPLE 11D using EXAMPLE 87C and EXAMPLE 12A in place of EXAMPLE 3J and EXAMPLE 11B, respectively. $^1$H NMR (500 MHz, dimethylsulfoxide-$d_6$) δ 11.16 (s, 2H), 8.39 (d, 1H), 8.06 (dd, 1H), 7.51 (d, 1H), 7.38-7.43 (m, 3H), 7.34 (d, 2H), 7.15 (d, 1H), 7.04 (d, 2H), 6.85 (dd, 1H), 6.64 (dd, 1H), 6.39 (s, 1H), 6.15 (d, 1H), 4.20-4.28 (m, 2H), 3.85-3.91 (m, 1H), 3.82 (dd, 1H), 3.74-3.78 (m, 1H), 3.59-3.69 (m, 2H), 3.40-3.51 (m, 2H), 3.05 (s, 4H), 2.78 (s, 2H), 2.23 (s, 4H), 2.14 (s, 2H), 1.95 (s, 2H), 1.38 (t, 2H), 0.92 (s, 6H).

Example 93

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide The title compound was prepared by substituting EXAMPLE 87C for EXAMPLE 3J and EXAMPLE 16A for EXAMPLE 11B in EXAMPLE 11D. $^1$H NMR (400 MHz, dimethylsulfoxide-$d_6$) δ 11.17 (s, 1H), 8.18 (d, 1H), 7.92 (dd, 1H), 7.49 (d, 1H), 7.40 (m, 2H), 7.33 (d, 2H), 7.26 (m, 1H), 7.17 (d, 1H), 7.04 (m, 3H), 6.86 (dd, 1H), 6.65 (dd, 1H), 6.40 (s, 1H), 6.14 (d, 1H), 3.51 (m, 4H), 3.28 (s, 3H), 3.03 (s, 4H), 2.74 (s, 2H), 2.16 (m, 6H), 1.95 (s, 2H), 1.38 (t, 2H), 0.92 (s, 6H).

Example 94

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide The title compound was prepared by substituting EXAMPLE 87C for EXAMPLE 3J and EXAMPLE 17A for EXAMPLE 11B in EXAMPLE 11D. $^1$H NMR (400 MHz, dimethylsulfoxide-$d_6$) δ 11.20 (s, 1H), 8.19 (d, 1H), 7.90 (dd, 1H), 7.53 (d, 1H), 7.40 (m, 4H), 7.33 (t, 1H), 7.17 (d, 1H), 7.07 (m, 3H), 6.86 (dd, 1H), 6.70 (dd, 1H), 6.41 (s, 1H), 6.21 (d, 1H), 3.84 (dd, 2H), 3.59 (m, 2H), 3.25 (m, 6H), 3.00 (m, 2H), 2.74 (s, 2H), 2.54 (m, 2H), 2.18 (s, 2H), 2.01 (s, 2H), 1.83 (m, 1H), 1.54 (m, 2H), 1.45 (t, 2H), 1.23 (m, 2H), 0.94 (s, 6H).

Example 95

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide

Example 95A 1-(1,3-difluoropropan-2-yl)piperidin-4-amine

Tert-butyl piperidin-4-ylcarbamate (0.212 g), 1,3-difluoropropan-2-one (0.149 g) and sodium triacetoxyborohydride (0.337 g) were stirred together in dichloroethane at room temperature. After stirring overnight the reaction was quenched with water (10 mL) and extracted into dichloromethane (2×20 mL). The organic layer was dried over magnesium sulfate, filtered, and concentrated. The residue was treated with hydrogen chloride (4.0M in dioxane, 1.323 ml) for 1 hour to give the title compound as the HCl salt after concentration.

Example 95B 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide EXAMPLE 95A (0.057 g) and EXAMPLE 53A (0.162 g) were suspended in dioxane (3 mL) and heated to 105° C. overnight. The reaction was concentrated, loaded onto silica gel (GraceResolv 12 g) and eluted with a gradient of 0.5% to 4% methanol/dichloromethane. The product containing fractions were concentrated and loaded onto C18 (SF25-75 g analogix column) and eluted using a gradient of 30% to 60% acetonitrile/water. The product was partitioned between dichloromethane (20 mL) and saturated aqueous NaHCO$_3$ solution (20 mL). The organic layer was dried over magnesium sulfate, filtered, and concentrated to give the title compound. $^1$H NMR (300 MHz, CDCl$_3$) δ 10.10 (s, 1H), 8.88 (d, 2H), 8.45 (d, 1H), 8.20 (s, 1H), 8.18-8.09 (m, 1H), 7.95 (d, 1H), 7.68 (d, 1H), 7.44 (s, 1H), 7.23-7.19 (m, 1H), 6.91 (d, 3H), 6.53 (d, 2H), 5.98 (d, 1H), 4.64 (dd, 4H), 3.68-3.50 (m, 1H), 3.01 (d, 6H), 2.72 (d, 4H), 2.19 (s, 11H), 1.69 (s, 2H), 1.41 (s, 2H), 0.94 (s, 6H).

Example 96

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 96A 5-chloro-6-((4-fluorotetrahydro-2H-pyran-4-yl)methoxy)pyridine-3-sulfonamide The title compound was prepared by substituting EXAMPLE 40A for 4-fluoro-3-nitrobenzenesulfonamide and EXAMPLE 37C for (tetrahydro-2H-pyran-4-yl)methanol in EXAMPLE 24A.

Example 96B

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 96A for EXAMPLE 11B in EXAMPLE 11D. $^1$H NMR (500 MHz, dimethylsulfoxide-$d_6$) δ 11.67 (s, 1H), 8.52 (s, 1H), 8.41 (s, 1H), 8.03 (d, 1H), 7.56 (d, 1H), 7.50 (m, 2H), 7.35 (d, 2H), 7.04 (d, 2H), 6.67 (dd, 1H), 6.39 (m, 1H), 6.22 (s, 1H), 4.50 (d, 2H), 3.78 (m, 2H), 3.60 (m, 2H), 3.12 (v br s, 4H), 2.93 (v br s, 2H), 2.38 (v br s, 4H), 2.17 (br m, 2H), 1.96 (s, 2H), 1.86 (m, 4H), 1.40 (t, 2H), 0.93 (s, 6H).

Example 97

4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide

Example 97A tert-butyl 4-(2-nitro-4-sulfamoylphenylamino)piperidine-1-carboxylate The title compound was prepared by substituting tert-butyl 4-aminopiperidine-1-carboxylate for 4-methylpiperazin-1-amine dihydrochloride in EXAMPLE 6A.

Example 97B 3-nitro-4-(piperidin-4-ylamino)benzenesulfonamide

Tert-butyl 4-(2-nitro-4-sulfamoylphenylamino)piperidine-1-carboxylate was dissolved in dichloromethane (3 mL) and treated with 1N HCl in ether (4 mL). The reaction was stirred overnight then concentrated to give the title compound.

Example 97C 4-(1-(2,2-difluoroethyl)piperidin-4-ylamino)-3-nitrobenzenesulfonamide 3-nitro-4-(piperidin-4-ylamino)benzenesulfonamide hydrochloride (0.100 g), 1,1-difluoro-2-iodoethane (0.063 mL) and diisopropylamine (0.156 mL) were stirred together in N,N-dimethylformamide (3 ml) and heated to 85° C. The reaction was diluted with dichloromethane (50 mL) and washed with water (50 mL), brine (50 mL), dried over magnesium sulfate, filtered, and concentrated. The residue was loaded onto silica gel (GraceResolve 12 g) and eluted using a gradient of 0.5% methanol/dichloromethane to 3% methanol/dichloromethane over 30 minutes to give the title compound.

Example 97D 4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide The title compound was prepared by substituting EXAMPLE 97B for EXAMPLE 1F and EXAMPLE 3J for EXAMPLE 1E in EXAMPLE 1G. $^1$H NMR (300 MHz, dimethylsulfoxide-$d_6$) δ 11.67 (s, 1H), 11.54-11.27 (m, 1H), 8.55 (d, 1H), 8.24 (d, 1H), 8.03 (d, 1H), 7.81 (d, 1H), 7.50 (dd, 3H), 7.34 (d, 2H), 7.13 (d, 1H), 7.04 (d, 2H), 6.68 (d, 1H), 6.38 (dd, 1H), 6.15 (dt, 2H), 3.64 (s, 1H), 3.07 (s, 4H), 2.79 (ddd, 6H), 2.41 (t, 2H), 2.17 (d, 6H), 1.92 (d, 4H), 1.61 (d, 2H), 1.38 (s, 2H), 0.92 (s, 6H).

Example 98

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-pyrrolo[2,3-b]pyridin-5-yloxy)benzamide The title compound was prepared as described in EXAMPLE 53B by replacing 1-acetylpiperidin-4-amine with 4-amino-1-cyclopropylpiperidine. $^1$H NMR (300 MHz, dimethylsulfoxide-$d_6$) δ 11.65 (s, 1H), 8.54 (d, 1H), 8.22 (d, 1H), 8.02 (d, 1H), 7.80 (dd, 1H), 7.49 (m, 3H), 7.34 (d, 2H), 7.11 (d, 1H), 7.04 (d, 2H), 6.67 (dd, 1H), 6.38 (dd, 1H), 6.19 (d, 1H), 3.69 (m, 1H), 3.06 (m, 4H), 2.92 (m, 2H), 2.74 (s, 2H), 2.23 (m, 7H), 1.93 (m, 5H), 1.77 (m, 1H), 1.55 (m, 3H), 1.38 (t, 2H), 0.92 (s, 6H), 0.43 (m, 4H).

Example 99

4-(4-{[2-(4-chlorophenyl)-4,4-dimethylcyclohex-1-en-1-yl]methyl}piperazin-1-yl)-N-[(4-{[(1-morpholin-4-ylcyclohexyl)methyl]amino}-3-nitrophenyl)sulfonyl]-2-(1H-pyrrolo[2,3-b]pyridin-5-yloxy)benzamide The title compound was prepared as described in EXAMPLE 53B by replacing 1-acetylpiperidin-4-amine with 1-(4-morpholino)cyclohexanemethylamine. $^1$H NMR (300 MHz, dimethylsulfoxide-$d_6$) δ 11.70 (s, 1H), 9.06 (s, 1H), 8.59 (d, 1H), 8.06 (d, 1H), 7.83 (dd, 1H), 7.57 (d, 1H), 7.50 (m, 2H), 7.34 (m, 3H), 7.19 (d, 1H), 7.04 (d, 2H), 6.67 (dd, 1H), 6.41 (dd, 1H), 6.17 (d, 1H), 3.56 (m, 6H), 3.44 (m, 2H), 3.07 (m, 5H), 2.57 (m, 5H), 2.24 (m, 6H), 1.95 (s, 3H), 1.45 (m, 6H), 1.23 (m, 3H), 0.92 (s, 6H).

Example 100

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide

Example 100A

Trans-tert-butyl-4-(dicyclopropylamino)cyclohexylcarbamate

A suspension of trans-tert-butyl-4-aminocyclohexylcarbamate (1 g), molecular sieves 3A (1 g), acetic acid (2.67 ml), (1-ethoxycyclopropoxy)trimethysilane (3.74 ml) and sodium cyanoborohydride (0.880 g) in dry methanol (10 ml) was heated at reflux for 3 hours. The insolubles were filtered off, the resulting solution was basified with aqueous NaOH (6 M) to pH 14, and extracted with ether. The combined extracts were washed with brine, dried over $Na_2SO_4$, filtered, and concentrated. The residue was purified by flash chromatography (silica gel 80 g, 30-100% acetone/hexanes) to provide the title compound.

Example 100B (trans)-$N^1,N^1$-dicyclopropylcyclohexane-1,4-diamine bis(2,2,2-trifluoroacetate)

The title compound was prepared by substituting EXAMPLE 100A for EXAMPLE 39A in EXAMPLE 39B.

Example 100C

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide A suspension of EXAMPLE 53A (0.14 g), EXAMPLE 100B (0.112 g) and N,N-diisopropylethylamine (0.310 mL) in dioxane (10 mL) was stirred for 3 days at 100° C. The product was concentrated and purified by RP HPLC(C8, 30%-100% $CH_3CN$/water/0.1% trifluoroacetic acid). $^1H$ NMR (500 MHz, pyridine-$d_5$) δ 13.07 (s, 1H), 9.28 (d, 1H), 8.41-8.45 (m, 2H), 8.37 (d, 1H), 8.12 (d, 1H), 7.67 (d, 2H), 7.44 (d, 2H), 7.07 (d, 2H), 7.01 (d, 1H), 6.75 (dd, 1H), 6.53 (d, 1H), 6.48-6.51 (m, 1H), 3.43 (ddd, 1H), 3.03-3.09 (m, 4H), 2.72-2.79 (m, 3H), 2.22-2.28 (m, 2H), 2.11-2.16 (m, 4H), 2.10 (s, 2H), 2.00-2.05 (m, 2H), 1.97 (s, 2H), 1.89 (s, 1H), 1.86 (s, 3H), 1.62-1.71 (m, 2H), 1.39 (t, 2H), 1.19-1.29 (m, 2H), 0.93 (s, 6H), 0.48 (d, 8H).

Example 101

4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 101A

Ethyl 2-hydroxy-6,6-dimethylcyclohex-1-enecarboxylate

Into a 500 mL flame dried round-bottomed flask was added copper(I) iodide (18 g) in ether (200 mL) to give a suspension. After cooling to −5° C., methyllithium (120 mL, 1.6M in ether) was added dropwise. After stirring at −5° C. for 1 hour, 3-methylcyclohex-2-enone (5.15 mL) in 15 ml ether was added dropwise, and the mixture was stirred at −5° C. for 1 hour. After cooling to −78° C., hexamethylphosphoramide (60 mL) was added dropwise. Ethyl carbonocyanidate (23.74 mL) was added. After stirring at −78° C. for 20 minutes, the mixture was warmed up to room temperature, and stirred for 1 hour. The mixture was poured into cold water, and the layers were separated. The aqueous layer was extracted with ether (3×20 mL). The combined organic layers were washed with saturated aqueous $NH_4Cl$ (3×20 mL), dried over $Na_2SO_4$, filtered, and dried under vacuum. The crude product was added to a silica gel column and purified by eluting with 0-10% ethyl acetate in hexane.

Example 101B

Ethyl 6,6-dimethyl-2-(trifluoromethylsulfonyloxy)cyclohex-1-enecarboxylate

Into a 500 mL round-bottomed flask was added hexane-washed sodium hydride (0.5 g) in dichloromethane (100 mL) to give a suspension. After cooling to −5° C., EXAMPLE 101A (2.0 g) was added. After stirring at −5° C. for 30 minutes, the mixture was cooled to −78° C. Trifluoromethanesulfonic anhydride (2.2 mL) was added. The mixture was warmed to room temperature and stirred overnight. Water was added slowly to the mixture, the aqueous layer was then extracted by dichloromethane (2×20 mL). The combined organic layers were washed with saturated $NH_4Cl$ and brine, dried over $Na_2SO_4$, filtered, and concentrated.

Example 101C ethyl 2-(4-chlorophenyl)-6,6-dimethylcyclohex-1-enecarboxylate

Into a 25 mL microwave tube was added EXAMPLE 101B (2.9 g), 4-chlorophenylboronic acid (2.2 g), and tetrakis(triphenylphosphine)palladium (0.05 g) in 1,2-dimethoxyethane/methanol (2:1, 10 mL) to give a solution. Cesium fluoride (4 g) was then added. The reaction mixture was stirred at 150° C. under (100W) in a Biotage Initiator microwave reactor for 30 minutes. After removing the solvents, water was added, and the mixture was extracted with ethyl acetate (2×). The combined organic layers were dried by $MgSO_4$. After filtering, the crude product was purified by reverse phase chromatography eluting with 50-100% acetonitrile/water with 0.1% trifluoroacetic acid.

Example 101D (2-(4-chlorophenyl)-6,6-dimethylcyclohex-1-enyl)methanol

In a 100 mL round-bottomed flask was placed lithium aluminum hydride (1 g) in ether (20 mL) to give a suspension. EXAMPLE 101C (1 g) dissolved in ether (5 mL) was added slowly by syringe. The mixture was stirred at room temperature overnight. After cooling to 0° C., the reaction was quenched by water. Ether (2×10 mL) was used to extract the product. The crude product was purified by flash chromatography on silica by eluting with 0-15% ethyl acetate in hexane.

Example 101E

Methyl 2-(1H-pyrrolo[2,3-b]pyridin-5-yloxy)-4-(4-((2-(4-chlorophenyl)-6,6-dimethylcyclohex-1-enyl)methyl)piperazin-1-yl)benzoate To a 0° C. solution of EXAMPLE 101D (0.43 g) in dichloromethane (5 mL) was added triethylamine (1 mL). Methanesulfonyl chloride (0.134 mL) was then added slowly. After 5 minutes, EXAMPLE 15F (0.61 g) was added. The mixture was stirred at room temperature overnight. The crude product was purified by flash chromatography on silica with 0 to 25% ethyl acetate in hexanes to provide the title compound.

Example 101F 2-(1H-pyrrolo[2,3-b]pyridin-5-yloxy)-4-(4-((2-(4-chlorophenyl)-6,6-dimethylcyclohex-1-enyl)methyl)piperazin-1-yl)benzoic acid In a 5 mL microwave tube was added lithium hydroxide hydrate (15 mg) and EXAMPLE 101E (45 mg) in dioxane/water (2:1) (2 mL) to give a suspension. The mixture was heated to 130° C. in a Biotage Initiator microwave reactor for 20 minutes. After cooling and neutralization by HCl, the crude product was added to a Prep HPLC column and was eluted with 20-80% acetonitrile/water with 0.1% trifluoroacetic acid.

Example 101G 4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 101F for EXAMPLE 3J and EXAMPLE 1F for EXAMPLE 11B in EXAMPLE 11D. $^1$H NMR (500 MHz, dimethylsulfoxide-$d_6$) δ 11.68 (s, 1H), 11.47 (s, 1H), 8.58 (m, 2H), 8.03 (m, 1H), 7.79 (m, 1H), 7.51 (m, 3H), 7.31 (d, 2H), 7.10 (m, 1H), 7.02 (d, 2H), 6.65 (m, 1H), 6.39 (m, 1H), 6.15 (m, 1H), 3.85 (m, 2H), 3.27 (m, 4H), 2.97 (m, 4H), 2.76 (s, 2H), 2.14 (m, 6H), 1.70 (m, 2H), 1.61 (m, 2H), 1.44 (m, 2H), 1.26 (m, 3H), 1.16 (m, 6H)

Example 102

N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 102A (4-ethylmorpholin-3-yl)methanol

Morpholin-3-ylmethanol (500 mg) and iodoethane (666 mg) in N,N-dimethylformamide was treated with $K_2CO_3$ (1.1 g) overnight. The reaction mixture was diluted with water and extracted with ethyl acetate. The organic layer was dried over $Na_2SO_4$, filtered, and concentrated to provide the title compound.

Example 102B 5-bromo-6-((4-ethylmorpholin-3-yl)methoxy)pyridine-3-sulfonamide The title compound was prepared as described in EXAMPLE 12A by replacing 4-fluoro-3-nitrobenzenesulfonamide and (1,4-dioxan-2-yl)methanol with 5-bromo-6-fluoropyridine-3-sulfonamide and EXAMPLE 102A, respectively.

Example 102C

N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in EXAMPLE 11D using EXAMPLE 102B in place of EXAMPLE 11B. $^1$H NMR (500 MHz, dimethylsulfoxide-$d_6$) δ 11.62 (s, 1H), 8.51 (s, 1H), 8.30 (s, 1H), 8.00 (d, 1H), 7.55 (d, 1H), 7.45-7.50 (m, 2H), 7.35 (d, 2H), 7.05 (d, 2H), 6.66 (dd, 1H), 6.37 (s, 1H), 6.21 (d, 1H), 4.58 (dd, 1H), 4.39-4.50 (m, 1H), 3.78-3.90 (m, 1H), 3.67-3.77 (m, 1H), 3.50-3.65 (m, 2H), 3.08 (s, 4H), 2.59-3.00 (m, 4H), 2.20-2.39 (m, 2H), 2.15 (s, 2H), 1.96 (s, 2H), 1.39 (t, 2H), 0.99-1.11 (m, 3H), 0.93 (s, 6H)

Example 103

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide

Example 103A 4-((4-ethylmorpholin-3-yl)methoxy)-3-nitrobenzenesulfonamide

The title compound was prepared as described in EXAMPLE 12A by replacing (1,4-dioxan-2-yl)methanol with EXAMPLE 102A.

Example 103B 4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 103A in place of EXAMPLE 11B. $^1$H NMR (500 MHz, dimethylsulfoxide-$d_6$) δ 11.66 (s, 1H), 8.33 (s, 1H), 7.99-8.06 (m, 2H), 7.47-7.57 (m, 3H), 7.45 (d, 1H), 7.35 (d, 2H), 7.04 (d, 2H), 6.67 (dd, 1H), 6.38 (dd, 1H), 6.20 (d, 1H), 4.42 (dd, 1H), 4.23 (dd, 1H), 3.81 (d, 1H), 3.69 (d, 1H), 3.49-3.63 (m, 2H), 3.08 (s, 4H), 2.92 (s, 1H), 2.81 (s, 4H), 2.54 (s, 1H), 2.25 (s, 4H), 2.15 (s, 2H), 1.96 (s, 2H), 1.39 (t, 2H), 1.00 (t, 3H), 0.92 (s, 6H)

Example 104

4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide EXAMPLE 78 (20 mg) and dihydro-2H-pyran-4(3H)-one (10 mg) in dichloroethane (2 mL) was treated with $NaCNBH_3$ (9.74 mg) overnight. Additional dihydro-2H-pyran-4(3H)-one (20 mg) and titanium (IV) isoproxide (0.05 mL) were added. The resulting mixture was stirred at room temperature overnight and concentrated. The residue was purified by reverse phase HPLC on a C18 column using a gradient of 35-60% acetonitrile in 0.1% trifluoroacetic acid water to give the title compound as a trifluoroacetate salt. The trifluoroacetic acid salt was dissolved in dichloromethane (6 mL) and washed with 50% aqueous $NaHCO_3$. The organic layer was dried over anhydrous $Na_2SO_4$ and concentrated to give the title compound. $^1H$ NMR (500 MHz, dimethylsulfoxide-$d_6$) δ 11.68 (s, 1H), 8.35 (s, 1H), 8.04 (s, 2H), 7.44-7.58 (m, 4H), 7.35 (d, 2H), 7.04 (d, 2H), 6.67 (dd, 1H), 6.40 (s, 1H), 6.20 (s, 1H), 4.44 (s, 1H), 4.28 (s, 1H), 3.85 (d, 2H), 3.71 (d, 1H), 3.61 (s, 3H), 3.20-3.29 (m, 2H), 3.08 (s, 5H), 2.54-2.96 (m, 5H), 2.06-2.42 (m, 5H), 1.96 (s, 2H), 1.77 (d, 1H), 1.53-1.66 (m, 1H), 1.29-1.51 (m, 4H), 0.92 (s, 6H)

Example 105

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide

Example 105A (S)-tert-butyl 1-(tetrahydro-2H-pyran-4-yl)piperidin-3-ylcarbamate The title compound was prepared by substituting (S)-tert-butyl piperidin-3-ylcarbamate for tert-butyl piperazine-1-carboxylate and dihydro-2H-pyran-4(3H)-one for 4'-chloro-biphenyl-2-carboxaldehyde in EXAMPLE 1A.

Example 105B (S)-1-(tetrahydro-2H-pyran-4-yl)piperidin-3-amine

The title compound was prepared by substituting EXAMPLE 105A for EXAMPLE 1A in EXAMPLE 1B.

Example 105C 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide The title compound was prepared by substituting EXAMPLE 105B for 1-acetylpiperidin-4-amine in EXAMPLE 53B. $^1H$ NMR (300 MHz, dimethylsulfoxide-$d_6$) δ 8.68 (br s, 1H), 8.54 (br s, 1H), 8.02 (d, 1H), 7.77 (m, 1H), 7.50 (m, 3H), 7.34 (d, 2H), 7.03 (m, 3H), 6.67 (dd, 1H), 6.38 (m, 1H), 6.19 (d, 1H), 3.98 (m, 2H), 3.90 (m, 2H), 3.52 (m, 2H), 3.09 (s, 2H), 3.05 (m, 4H), 2.77 (m, 2H), 2.60 (m, 2H), 2.16 (m, 6H), 1.95 (m, 2H), 1.65 (m, 5H), 1.50 (m, 3H), 1.38 (m, 2H), 0.94 (s, 6H).

Example 106

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide

Example 106A

5-Bromo-6-((tetrahydro-2H-pyran-4-yl)methylamino)pyridine-3-sulfonamide

The title compound was prepared by substituting (tetrahydro-2H-pyran-4-yl)methanamine for EXAMPLE 3L in EXAMPLE 61A.

Example 106B 5-cyano-6-((tetrahydro-2H-pyran-4-yl)methylamino)pyridine-3-sulfonamide The title compound was prepared by substituting EXAMPLE 106A for EXAMPLE 36B in EXAMPLE 36C.

Example 106C 4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide The title compound was prepared by substituting EXAMPLE 106B for EXAMPLE 11B in EXAMPLE 11D. $^1H$ NMR (400 MHz, dimethylsulfoxide-$d_6$) δ 11.62 (s, 1H), 8.55 (s, 1H), 8.14 (s, 1H), 8.01 (d, 1H), 7.87 (s, 1H), 7.56 (d, 1H), 7.48 (d, 2H), 7.34 (d, 2H), 7.04 (d, 2H), 6.64 (m, 1H), 6.37 (s, 1H), 6.19 (d, 1H), 3.81 (dd, 2H), 3.25 (m, 4H), 3.04 (s, 4H), 2.74 (s, 2H), 2.17 (m, 6H), 1.95 (s, 2H), 1.87 (m, 1H), 1.53 (m, 2H), 1.37 (t, 2H), 1.18 (m, 2H), 0.91 (s, 6H).

Example 107

Trans-4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide

Example 107A 3-nitro-4-(4-aminothiomorpholine-1,1-dioxide)benzenesulfonamide The title compound was prepared by substituting 4-aminothiomorpholine-1,1-dioxide for (tetrahydropyran-4-yl)methylamine in EXAMPLE 1F.

Example 107B

Trans-4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide The title compound was prepared by substituting EXAMPLE 107A for EXAMPLE 11B in EXAMPLE 11D. $^1$H NMR (400 MHz, dimethylsulfoxide-$d_6$) δ 11.64 (s, 1H), 9.58 (s, 1H), 8.50 (s, 1H), 8.02 (d, 1H), 7.78 (m, 2H), 7.50 (m, 3H), 7.34 (d, 2H), 7.04 (d, 2H), 6.66 (dd, 1H), 6.38 (s, 1H), 6.19 (d, 1H), 3.48 (m, 4H), 3.23 (m, 4H), 3.05 (s, 4H), 2.73 (d, 2H), 2.16 (m, 6H), 1.95 (s, 2H), 1.38 (t, 2H), 0.92 (s, 6H).

Example 108

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 108A 4-((4-aminotetrahydro-2H-pyran-4-yl)methylamino)-3-nitrobenzenesulfonamide The title compound was prepared by substituting 4-(aminomethyl)tetrahydro-2H-pyran-4-amine for (tetrahydro-2H-pyran-4-yl)methanamine in EXAMPLE 1F.

Example 108B

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 108A for EXAMPLE 11B in EXAMPLE 11D. $^1$H NMR (500 MHz, dimethylsulfoxide-$d_6$) δ 11.55 (s, 1H), 8.45 (s, 2H), 7.95 (d, 1H), 7.75-7.77 (m, 1H), 7.57 (d, 2H), 7.44 (s, 1H), 7.34 (d, 2H), 7.09 (d, J=8.85 Hz, 1H), 7.05 (d, 2H), 6.69 (dd, 1H), 6.33 (d, 1H), 6.22 (d, 1H), 3.59-3.71 (m, 6H), 3.01 (s, 4H), 2.73 (s, 2H), 2.15-2.19 (m, 6H), 1.95 (s, 2H), 1.71-1.74 (m, 2H), 1.59-1.61 (m, 1H), 1.38 (t, 2H), 0.93 (s, 6H).

Example 109

Trans-4-(4-{[2-(4-chlorophenyl)-4,4-dimethylcyclohex-1-en-1-yl]methyl}piperazin-1-yl)-N-({5-cyano-6-[(morpholin-4-ylcyclohexyl)amino]pyridin-3-yl}sulfonyl)-2-(1H-pyrrolo[2,3-b]pyridin-5-yloxy)benzamide

Example 109A

Trans-5-bromo-6-(4-morpholinocyclohexyloxy)pyridine-3-sulfonamide

The title compound was prepared by substituting EXAMPLE 9B for EXAMPLE 3L in EXAMPLE 61A.

Example 109B

Trans-5-cyano-6-(4-morpholinocyclohexylamino)pyridine-3-sulfonamide

The title compound was prepared by substituting EXAMPLE 109A for EXAMPLE 36B in EXAMPLE 36C.

Example 109C

Trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy)benzamide The title compound was prepared by substituting EXAMPLE 109B for EXAMPLE 11B in EXAMPLE 11D. $^1$H NMR (400 MHz, dimethylsulfoxide-$d_6$) δ 11.59 (s, 1H), 8.56 (d, 1H), 8.13 (s, 1H), 8.00 (d, 1H), 7.55 (d, 1H), 7.47 (m, 2H), 7.34 (d, 2H), 7.04 (d, 2H), 6.64 (dd, 1H), 6.36 (d, 1H), 6.19 (d, 1H), 4.00 (m, 1H), 3.65 (m, 4H), 3.28 (m, 4H), 3.03 (m, 4H), 2.73 (m, 4H), 2.16 (m, 6H), 1.90 (m, 6H), 1.40 (m, 6H), 0.93 (s, 6H).

Example 110

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 52B for EXAMPLE 11B in EXAMPLE 11D. $^1$H NMR (300 MHz, dimethylsulfoxide-$d_6$) δ 11.71 (s, 1H), 11.23 (s, 1H), 8.08 (d, 1H), 7.91 (d, 1H), 7.74 (dd, 1H), 7.60 (d, 1H), 7.52 (m, 2H), 7.34 (m, 2H), 7.16 (s, 1H), 7.04 (m, 2H), 6.83 (d, 1H), 6.68 (dd, 1H), 6.43 (dd, 1H), 6.16 (d, 1H), 3.83 (dd, 2H), 3.23 (m, 2H), 3.12 (t, 2H), 3.06 (m, 4H), 2.73 (m, 2H), 2.15 (m, 6H), 1.95 (s, 2H), 1.82 (m, 1H), 1.58 (m, 2H), 1.38 (m, 2H), 1.18 (m, 2H), 0.92 (s, 6H).

Example 111

4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy)benzamide

Example 111A benzyl (1S,3R)-3-(tert-butoxycarbonylamino)cyclopentylcarbamate (1S,3R)-3-(tert-butoxycarbonylamino)cyclopentanecarboxylic acid (1.03 g), diphenylphosphoryl azide (DPPA, 1.00 mL), triethylamine (0.929 mL), and benzyl alcohol (0.931 mL) were combined in toluene (10 mL) and stirred at 100° C. for 24 hours. The solution was cooled and chromatographed on silica gel using 10% ethyl acetate/hexanes to give the pure product.

Example 111B benzyl (1S,3R)-3-aminocyclopentylcarbamate

The title compound was prepared by substituting EXAMPLE 111A for EXAMPLE 1A in EXAMPLE 1B.

Example 111C benzyl (1S,3R)-3-morpholinocyclopentylcarbamate

A solution of EXAMPLE 111B (400 mg), 1-bromo-2-(2-bromoethoxy)ethane (0.246 mL), and triethylamine (0.595 mL) in N,N-dimethylformamide (6 mL) was stirred at 70° C. for 24 hours. The solution was cooled and poured into ethyl acetate (200 mL). The solution was extracted with 3× water, washed with brine, concentrated, and chromatographed on silica gel using 10% methanol/ethyl acetate to give the pure product.

Example 111D (1S,3R)-3-morpholinocyclopentanamine

EXAMPLE 111C (300 mg) and ethanol (20 ml) were added to wet 20% Pd(OH)$_2$—C (60.0 mg) in a 50 mL pressure bottle and stirred for 8 hours at 30 psi. The mixture was filtered through a nylon membrane and condensed to give the product.

Example 111E 4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy)benzamide The title compound was prepared by substituting EXAMPLE 3J for EXAMPLE 1E and EXAMPLE 111D for EXAMPLE 1F in EXAMPLE 1G. $^1$H NMR (dimethylsulfoxide-d$_6$) δ 11.65 (s, 1H), 8.45 (d, 1H), 8.28 (dd, 1H), 7.97 (d, 1H), 7.68 (d, 1H), 7.52 (d, 1H), 7.44 (d, 2H), 7.35 (d, 2H), 7.05 (d, 2H), 6.92 (dd, 1H), 6.85 (dd, 1H), 6.33 (s, 1H), 6.22 (s, 1H), 4.08 (m, 1H), 3.60 (br s, 4H), 3.06 (br s, 4H), 2.73 (br s, 3H), 2.48 (m, 4H), 2.28 (m, 1H), 2.18 (m, 6H), 2.07 (m, 1H), 1.95 (s, 2H), 1.79 (m, 2H), 1.63 (m, 2H), 1.38 (t, 2H), 0.93 (s, 6H).

Example 112

4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide

Example 112A tert-butyl (1R,3S)-3-aminocyclopentylcarbamate

The title compound was prepared by substituting EXAMPLE 111A for EXAMPLE 111C in EXAMPLE 111D.

Example 112B tert-butyl (1R,3S)-3-morpholinocyclopentylcarbamate

The title compound was prepared by substituting EXAMPLE 112A for EXAMPLE 111B in EXAMPLE 111C.

Example 112C (1R,3S)-3-morpholinocyclopentanamine

The title compound was prepared by substituting EXAMPLE 112B for EXAMPLE 1A in EXAMPLE 1B.

Example 112D 4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide The title compound was prepared by substituting EXAMPLE 3J for EXAMPLE 1E and EXAMPLE 112C for EXAMPLE 1F in EXAMPLE 1G. $^1$H NMR (dimethylsulfoxide-d$_6$) δ 11.35 (s, 1H), 8.51 (d, 1H), 8.44 (dd, 1H), 8.00 (d, 1H), 7.77 (d, 1H), 7.50 (d, 1H), 7.48 (s, 2H), 7.34 (d, 2H), 7.04 (d, 2H), 7.02 (dd, 1H), 6.67 (dd, 1H), 6.37 (dd, 1H), 6.21 (d, 1H), 4.11 (m, 1H), 3.61 (br s, 4H), 3.06 (br s, 4H), 2.73 (br s, 3H), 2.50 (m, 4H), 2.28 (m, 1H), 2.18 (m, 6H), 2.06 (m, 1H), 1.95 (s, 2H), 1.77 (m, 2H), 1.66 (m, 2H), 1.38 (t, 2H), 0.92 (s, 6H).

Example 113

4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide

Example 113A tert-butyl 2-((2-nitro-4-sulfamoylphenylamino)methyl)morpholine-4-carboxylate The title compound was prepared by substituting tert-butyl 2-(aminomethyl)morpholine-4-carboxylate for (tetrahydropyran-4-yl)methylamine in EXAMPLE 1F.

Example 113B tert-butyl 2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared by substituting EXAMPLE 113A for EXAMPLE 1F and EXAMPLE 3J for EXAMPLE 1E in EXAMPLE 1G, with the exception that the product was purified on a silica gel column eluted with 4% methanol in dichloromethane.

Example 113C 4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide The title compound was prepared by substituting EXAMPLE 113B for EXAMPLE 66B in EXAMPLE 66C. $^1$H NMR (500 MHz, dimethylsulfoxide-$d_6$) δ 11.60 (s, 1H), 8.55 (br, s, 1H), 8.51 (s, 1H), 8.00 (d, 1H), 7.80 (d, 1H), 7.52 (d, 1H), 7.49-7.46 (m, 2H), 7.34 (d, 2H), 7.07 (d, 1H), 7.04 (d, 2H), 6.66 (dd, 1H), 6.36 (s, 1H), 6.20 (d, 1H), 4.00 (dd, 1H), 3.91 (m, 1H), 3.70 (t, 1H), 3.60 (m, 1H), 3.58 (m, 1H), 3.32 (m, 1H), 3.16 (d, 1H), 3.05 (m, 4H), 2.98 (td, 1H), 2.86 (t, 1H), 2.73 (s, 2H), 2.20-2.12 (m, 6H), 1.95 (s, 2H), 1.38 (t, 2H), 0.92 (s, 6H).

Example 114

4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide

Example 114A 3-nitro-4-((tetrahydrofuran-3-yl)methylamino)benzenesulfonamide The title compound was prepared by substituting 3-aminomethyl-tetrahydrofuran for (tetrahydropyran-4-yl)methylamine in EXAMPLE 1F.

Example 114B 4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide The title compound was prepared by substituting EXAMPLE 114A for EXAMPLE 130C in EXAMPLE 130D. $^1$H NMR (500 MHz, dimethylsulfoxide-$d_6$) δ 11.68 (s, 1H), 11.42 (bs, 1H), 8.63 (t, 1H), 8.56 (d, 1H), 8.04 (d, 1H), 7.80 (dd, 1H), 7.53-7.48 (m, 3H), 7.34 (d, 2H), 7.10 (d, 1H), 7.04 (d, 2H), 6.68 (dd, 1H), 6.39 (m, 1H), 6.19 (d, 1H), 3.82-3.79 (m, 1H), 3.71 (t, 1H), 3.62 (dd, 1H), 3.50 (dd, 1H), 3.38 (m, 1H), 3.32 (m, 1H), 3.07 (m, 4H), 2.76 (s, 2H), 2.58 (m, 1H), 2.25-2.00 (m, 6H), 1.98 (m, 1H), 1.95 (s, 2H), 1.65 (m, 1H), 1.38 (t, 2H), 0.92 (s, 6H).

Example 115

4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide

Example 115A

Cis-tert-butyl 1-(3-fluorotetrahydro-2H-pyran-4-yl)piperidin-4-ylcarbamate

The title compound was prepared as a racemate of the cis diastereomer by substituting tert-butyl piperidin-4-ylcarbamate for piperidin-4-ol and 3-fluorodihydro-2H-pyran-4(3H)-one (prepared by the method described in US2005/0101628A1) for dihydro-2H-pyran-4(3H)-one in EXAMPLE 84A.

Example 115B

Cis-1-(3-fluorotetrahydro-2H-pyran-4-yl)piperidin-4-amine

EXAMPLE 115A (0.29 g) was dissolved in $CH_2Cl_2$ (9 mL), then 4N HCl in dioxane (4 mL) was added and the reaction stirred at room temperature for 16 hours. The reaction was diluted with $CH_2Cl_2$ (30 mL), then 4N aqueous NaOH (5 mL) was added. After shaking and separating the layers the aqueous layer was saturated with solid NaCl and extracted with more $CH_2Cl_2$ (10 mL). The combined organic layers were dried over $Na_2SO_4$. After filtration and concentration the amine was used with no further purification.

Example 115C 4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide The title compound was prepared by substituting EXAMPLE 115B for 1-acetylpiperidin-4-amine in EXAMPLE 53B. $^1$H NMR (500 MHz, dimethylsulfoxide-$d_6$) δ 11.64 (s, 1H), 8.54 (d, 1H), 8.43 (br d, 1H), 8.03 (d, 1H), 7.80 (dd, 1H), 7.50 (m, 3H), 7.35 (d, 2H), 7.11 (d, 1H), 7.05 (d, 2H), 6.66 (dd, 1H), 6.38 (m, 1H), 6.20 (d, 1H), 4.92 (d, 1H), 3.95 (m, 2H), 3.70 (v br m, 1H), 3.50, 3.40, 3.30 (all m, total 5H), 3.05, 3.00 (both v br m, total 5H), 2.74 (s, 2H), 2.55 (v br m, 1H), 2.18 (br m, 6H), 1.95 (m, 4H), 1.88 (ddd, 1H), 1.63 (v br m, 3H), 1.38 (t, 2H), 0.92 (s, 6H).

Example 116

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide

Example 116A 1-(tetrahydro-2H-pyran-4-yl)azetidin-3-amine

Tert-butyl azetidin-3-ylcarbamate (0.46 g), dihydro-2H-pyran-4(3H)-one (0.29 g) and sodium triacetoxyborohydride (0.85 g) were stirred together in dichloromethane (5 mL) overnight. The reaction was poured into dichloromethane (50 mL) and saturated aqueous $NaHCO_3$ solution (25 mL). The organic layer was separated, washed with brine (25 mL), dried over $Na_2SO_4$, filtered, and concentrated. Silica gel chromatography (GraceResolv 12 g) eluting with a gradient of 0.75% to 7.5% methanol/dichloromethane over 20 minutes gave the Boc-protected intermediate. Treatment with HCl (4.0M in dioxane, 2 mL) and methanol (1 mL) for 1 hour gave the title compound after concentration as the di-HCl salt.

Example 116B 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide A suspension of 2-(1H-pyrrolo[2,3-b]pyridin-5-yloxy)-N-(4-chloro-3-nitrophenylsulfonyl)-4-(4-((2-(4-chlorophenyl)-4,4-dimethylcyclohex-1-enyl)methyl)piperazin1-yl)benzamide (0.180 g), 1-(tetrahydro-2H-pyran-4-yl)azetidin-3-amine (0.078 g), and triethylamine (0.159 mL) in dioxane (2 mL) was degassed with nitrogen for 30 seconds then sealed. The reaction was heated to 110° C. After stirring for 16 hours, more triethylamine (10 equivalents total) and dimethylsulfoxide (1 mL) were added and the reaction stirred for an additional 18 hours at 110° C. The reaction was cooled, diluted with water (50 mL) and extracted with dichloromethane (2×150 mL). The organic layer was dried over magnesium sulfate, filtered and concentrated. Silica gel chromatography (GraceResolv 12 g) eluting with a gradient of 0.75% to 7.5% methanol/dichloromethane (Flow=36 mL/minutes) gave the title compound. $^1$H NMR (300 MHz, dimethylsulfoxide-$d_6$) δ 11.59 (s, 1H), 8.49 (d, 1H), 8.40 (s, 1H), 7.97 (d, 1H), 7.77 (s, 1H), 7.47 (dd, 3H), 7.34 (d, 2H), 7.04 (d, 2H), 6.90-6.78 (m, 1H), 6.65 (d, 1H), 6.35 (s, 1H), 6.21 (s, 1H), 4.47-4.23 (m, 1H), 3.83 (s, 3H), 3.05 (s, 6H), 2.73 (s, 2H), 2.18 (s, 8H), 1.95 (s, 2H), 1.68 (s, 2H), 1.38 (s, 2H), 1.24 (s, 4H), 0.92 (s, 6H).

Example 117

4-(4-{[2-(4-chlorophenyl)-4,4-dimethylcyclohex-1-en-1-yl]methyl}piperazin-1-yl)-N-({3-nitro-4-[(1-tetrahydro furan-3-ylazetidin-3-yl)amino]phenyl}sulfonyl)-2-(1H-pyrrolo[2,3-b]pyridin-5-yloxy)benzamide

Example 117A 1-(tetrahydrofuran-3-yl)azetidin-3-amine

Tert-butyl azetidin-3-ylcarbamate (0.550 g), dihydrofuran-3(2H)-one (0.412 g) and sodium triacetoxyborohydride (1.015 g) were stirred together in dichloromethane (5 mL). After stirring overnight, the reaction was poured into saturated aqueous NaHCO$_3$ solution (25 mL) and extracted with dichloromethane (50 mL). The organic layer was washed with brine (25 mL), dried over magnesium sulfate, filtered, and concentrated. Silica gel chromatography (GraceResolv 12 g) eluting with a gradient of 0.5% to 7.5% methanol/dichloromethane over 30 minutes gave tert-butyl 1-(tetrahydrofuran-3-yl)azetidin-3-ylcarbamate. The resulting material was treated with HCl/dioxane for 1 hour, and then concentrated to give the title compound.

Example 117B 3-nitro-4-(1-(tetrahydrofuran-3-yl)azetidin-3-ylamino)benzenesulfonamide 4-Fluoro-3-nitrobenzenesulfonamide (0.084 g), 1-(tetrahydrofuran-3-yl)azetidin-3-amine (0.090 g) and triethylamine (0.266 ml) in tetrahydrofuran (3 mL) was heated to 60° C. After stirring for 4 hours, the reaction was cooled, the tetrahydrofuran was removed and the residue was partitioned between dichloromethane (200 mL) and water (20 mL). The organic layer was separated, washed with brine (25 mL), dried over magnesium sulfate, filtered, and concentrated to give the title compound.

Example 117C 4-(4-{[2-(4-chlorophenyl)-4,4-dimethylcyclohex-1-en-1-yl]methyl}piperazin-1-yl)-N-({3-nitro-4-[(1-tetrahydro furan-3-ylazetidin-3-yl)amino]phenyl}sulfonyl)-2-(1H-pyrrolo[2,3-b]pyridin-5-yloxy)benzamide The title compound was prepared by substituting EXAMPLE 117B for EXAMPLE 1F and EXAMPLE 3J for EXAMPLE 1E in EXAMPLE 1G. $^1$H NMR (300 MHz, CDCl$_3$) δ 10.39-9.79 (m, 1H), 9.17 (s, 1H), 8.87 (d, 1H), 8.51 (d, 1H), 8.15 (dd, 2H), 7.94 (d, 1H), 7.68 (d, 1H), 7.48-7.42 (m, 1H), 7.23 (d, 2H), 6.91 (d, 2H), 6.69 (d, 1H), 6.54 (dd, 2H), 5.99 (d, 1H), 4.29 (d, 1H), 4.01-3.73 (m, 4H), 3.66 (d, 2H), 3.08 (s, 6H), 2.76 (s, 2H), 2.21 (s, 6H), 2.03-1.83 (m, 3H), 1.64 (s, 2H), 1.42 (d, 2H), 0.93 (s, 6H).

Example 118

4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide

Example 118A (R)-tert-butyl (1-(tetrahydro-2H-pyran-4-yl)pyrrolidin-3-yl)methylcarbamate The title compound was prepared by substituting (S)-tert-butyl pyrrolidin-3-ylmethylcarbamate for tert-butyl piperazine-1-carboxylate and dihydro-2H-pyran-4(3H)-one for 4'-chlorobiphenyl-2-carboxaldehyde in EXAMPLE 1A.

Example 118B (R)-(1-(tetrahydro-2H-pyran-4-yl)pyrrolidin-3-yl)methanamine

The title compound was prepared by substituting EXAMPLE 118A for EXAMPLE 1A in EXAMPLE 1B.

Example 118C 4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide The title compound was prepared by substituting EXAMPLE 118B for 1-acetylpiperidin-4-amine in EXAMPLE 53B. $^1$H NMR (500 MHz, dimethylsulfoxide-$d_6$) δ 11.57 (s, 1H), 8.59 (br s, 1H), 8.45 (br s, 1H), 8.02 (d, 1H), 7.95 (m, 1H), 7.71 (m, 1H), 7.56 (d, 1H), 7.45 (m, 1H), 7.35 (m, 3H), 7.05 (m, 2H), 6.90 (br s, 1H), 6.64 (d, 1H), 6.33 (m, 1H), 6.22 (m, 1H), 3.90 (m, 2H), 3.44 (m, 2H), 3.27 (m, 4H), 3.02 (m, 5H), 2.73 (m, 3H), 2.59 (m, 2H), 2.19 (m, 6H), 1.95

(m, 2H), 1.85 (m, 2H), 1.64 (m, 1H), 1.50 (m, 2H), 1.39 (m, 2H), 1.23 (m, 1H), 0.94 (s, 6H).

Example 119

4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 75F and EXAMPLE 37D in place of EXAMPLE 3J and EXAMPLE 11B, respectively. $^1$H NMR (500 MHz, dimethylsulfoxide-$d_6$) δ 11.69 (s, 1H), 8.39 (s, 1H), 8.08 (d, 1H), 8.04 (d, 1H), 7.41-7.59 (m, 4H), 7.35 (d, 2H), 7.08 (d, 2H), 6.68 (dd, 1H), 6.37-6.43 (m, 1H), 6.20 (s, 1H), 4.38 (d, 2H), 3.73-3.82 (m, 2H), 3.54-3.63 (m, 2H), 3.09 (s, 4H), 2.81 (s, 2H), 2.16-2.39 (m, 5H), 1.94 (s, 2H), 1.79-1.93 (m, 4H), 1.40 (t, 2H), 0.94 (s, 6H).

Example 120

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide Example 120A Trans-4-(aminomethyl)cyclohexanol Tert-butyl ((1r,4r)-4-hydroxycyclohexyl)methylcarbamate (1 g) in dichloromethane (10 mL) was treated with trifluoroacetic acid (5 mL) at 0° C. for 10 minutes and at room temperature for 30 minutes. The reaction mixture was concentrated and dried in vacuo to provide the title compound as a trifluoroacetic acid salt.

Example 120B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide A mixture of EXAMPLE 53A (211 mg), EXAMPLE 120A (104 mg) and N-ethyl-N-isopropylpropan-2-amine (0.3 mL) in dimethylsulfoxide (2 mL) was heated at 150° C. in a Biotage Initiator microwave synthesizer for 1.5 hours and concentrated. The residue was purified by reverse phase HPLC on a C18 column using a gradient of 40-60% acetonitrile in 0.1% trifluoroacetic acid water to give the title compound as a trifluoroacetate salt. The trifluoroacetic acid salt was dissolved in dichloromethane (30 mL) and washed with 50% aqueous NaHCO$_3$. The organic layer was dried over anhydrous Na$_2$SO$_4$, filtered, and concentrated to give the title compound. $^1$H NMR (500 MHz, dimethylsulfoxide-$d_6$) δ 11.69 (s, 1H), 11.41 (s, 1H), 8.61 (t, 1H), 8.53-8.58 (m, 1H), 8.04 (d, 1H), 7.76-7.83 (m, 1H), 7.47-7.56 (m, 3H), 7.34 (d, 2H), 7.07-7.11 (m, 1H), 7.04 (d, 2H), 6.68 (dd, 1H), 6.39 (dd, 1H), 6.19 (d, 1H), 4.82-4.99 (m, 1H), 4.50 (d, 1H), 3.26-3.31 (m, 2H), 3.23 (t, 1H), 3.07 (s, 4H), 2.76 (s, 2H), 2.10-2.28 (m, 6H), 2.05 (dd, 1H), 1.95 (s, 2H), 1.84 (t, 2H), 1.52-1.76 (m, 2H), 1.41-1.51 (m, 1H), 1.38 (t, 2H), 0.95-1.25 (m, 4H), 0.92 (s, 6H)

Example 121

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide Example 121A (4-methoxycyclohexyl)methanol 4-Methoxycyclohexanecarboxylic acid (7 g) in tetrahydrofuran (20 mL) was treated with 1 M (in tetrahydrofuran) borane-tetrahydrofuran complex (100 mL) overnight. The mixture was concentrated and the residue was dissolved in methanol (100 mL) and concentrated HCl (10 mL). The resulting mixture was stirred for 1 hour and concentrated. The residue was dissolved in dichloromethane and washed with water. The organic layer was dried over Na$_2$SO$_4$, filtered, and concentrated to give the title compound.

Example 121B 4-((4-methoxycyclohexyl)methoxy)-3-nitrobenzenesulfonamide

The title compound was prepared as described in EXAMPLE 12A by replacing (1,4-dioxan-2-yl)methanol with EXAMPLE 121A.

Example 121C 4-((cis-4-methoxycyclohexyl)methoxy)-3-nitrobenzenesulfonamide

Separation of the cis and trans mixture of EXAMPLE 121B on a reverse phase HPLC (gradient: 40-55% acetonitrile in 0.1% TFA in water over 25 minutes) provided the title compound.

Example 121D 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide The title compound was prepared as described in EXAMPLE 11D using EXAMPLE 121C in place of EXAMPLE 11B. $^1$H NMR (500 MHz, dimethylsulfoxide-$d_6$) δ 11.69 (s, 1H), 11.39 (s, 1H), 8.34 (s, 1H), 7.96-8.07 (m, 2H), 7.48-7.56 (m, 3H), 7.31-7.42 (m, 3H), 7.04 (d, 2H), 6.68 (dd, 1H), 6.40 (dd, 1H), 6.20 (d, 1H), 4.02 (d, 2H), 3.39 (s, 1H), 3.20 (s, 3H), 3.09 (s, 4H), 2.82 (s, 2H), 2.09-2.34 (m, 6H), 1.96 (s, 2H), 1.78-1.86 (m, 3H), 1.54 (dd, 2H), 1.28-1.46 (m, 6H), 0.92 (s, 6H)

Example 122

Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide Example 122A Cis-tert-butyl-4-(cyclopropylamino)cyclohexylcarbamate The title compound was prepared by substituting tert-butyl 4-oxocyclohexylcarbamate for 4'-chlorobiphenyl-2-carboxaldehyde and cyclopropylamine for tert-butyl piperazine-1-carboxylate in EXAMPLE 1A.

Example 122B cis-N$^1$-cyclopropylcyclohexane-1,4-diamine bis(2,2,2-trifluoroacetate)

The title compound was prepared by substituting EXAMPLE 122A for EXAMPLE 39A in EXAMPLE 39B.

Example 122C

Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide The title compound was prepared by substituting EXAMPLE 122B for EXAMPLE 100B in EXAMPLE 100C. $^1$H NMR (500 MHz, pyridine-d$_5$) δ 13.06 (s, 1H), 9.28 (d, 1H), 8.59 (d, 1H), 8.44 (d, 1H), 8.37 (dd, 1H), 8.12 (d, 1H), 7.67 (t, 2H), 7.43 (t, 2H), 7.07 (d, 2H), 6.90 (d, 1H), 6.75 (dd, 1H), 6.53 (d, 1H), 6.50 (dd, 1H), 3.56-3.63 (m, 1H), 3.02-3.08 (m, 4H), 2.77 (s, 3H), 2.26 (t, 2H), 2.10-2.16 (m, 4H), 2.06 (ddd, 1H), 1.97 (s, 2H), 1.74-1.82 (m, 2H), 1.61-1.71 (m, 5H), 1.39 (t, 2H), 0.93 (s, 6H), 0.39-0.44 (m, 4H).

Example 123

Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide Example 123A Trans-tert-butyl-4-(tetrahydro-2H-pyran-4-ylamino)cyclohexylcarbamate The title compound was prepared by substituting trans-tert-butyl-4-aminocyclohexylcarbamate for tert-butyl piperazine-1-carboxylate and dihydro-2H-pyran-4(3H)-one for 4'-chlorobiphenyl-2-carboxaldehyde in EXAMPLE 1A.

Example 123B trans-N1-(tetrahydro-2H-pyran-4-yl)cyclohexane-1,4-diamine bis(2,2,2-trifluoroacetate)

The title compound was prepared by substituting EXAMPLE 123A for EXAMPLE 39A in EXAMPLE 39B.

Example 123C

Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide The title compound was prepared by substituting EXAMPLE 123B for EXAMPLE 100B in EXAMPLE 100C. $^1$H NMR (500 MHz, pyridine-d$_5$) δ 13.01 (s, 1H), 9.28 (d, 1H), 8.48 (d, 1H), 8.38 (dd, 1H), 8.32 (d, 1H), 8.24 (d, 1H), 7.67-7.69 (m, 2H), 7.44 (d, 2H), 7.08 (d, 2H), 6.91 (d, 1H), 6.78 (dd, 1H), 6.59 (d, 1H), 6.48 (dd, 1H), 4.01 (d, 2H), 3.44-3.49 (m, 1H), 3.37-3.43 (m, 2H), 3.01-3.09 (m, 5H), 2.85 (t, 1H), 2.78 (s, 2H), 2.27 (t, 2H), 2.13-2.18 (m, 4H), 2.05 (t, 4H), 1.97 (s, 2H), 1.93 (d, 2H), 1.52-1.60 (m, 2H), 1.44-1.50 (m, 2H), 1.39 (t, 2H), 1.25-1.34 (m, 2H), 0.94 (s, 6H).

Example 124

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 124A Trans-4-morpholinocyclohexanol Trans-4-Aminocyclohexanol (0.5 g), 1-bromo-2-(2-bromoethoxy)ethane (1.07 g) and triethylamine (2.42 mL) were dissolved in anhydrous acetonitrile (20 mL). The reaction mixture was heated at 60° C. overnight. The organic solvent was removed under vacuum. The residue was purified with flash column chromatography on silica gel eluting with 7%-10% methanol in dichloromethane to give the title compound.

Example 124B

Trans-5-bromo-6-(4-morpholinocyclohexyloxy)pyridine-3-sulfonamide

The title compound was prepared by substituting EXAMPLE 124A for (tetrahydro-2H-pyran-4-yl)methanol and EXAMPLE 36A for 4-fluoro-3-nitrobenzenesulfonamide in EXAMPLE 24A.

Example 124C

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 124B for EXAMPLE 11B in EXAMPLE 11D. $^1$H NMR (400 MHz, dimethylsulfoxide-d$_6$) δ 11.67 (s, 1H), 8.56 (m, 2H), 8.03 (d, 1H), 7.80 (m, 1H), 7.50 (m, 3H), 7.34 (d, 2H), 7.12 (m, 1H), 7.04 (d, 2H), 6.67 (dd, 1H), 6.39 (dd, 1H), 6.19 (d, 1H), 3.99 (m, 1H), 3.67 (m, 1H), 3.37 (m, 2H), 3.24 (m, 2H), 3.07 (m, 4H), 2.89 (m, 1H), 2.71 (m, 2H), 2.16 (m, 6H), 1.96 (s, 3H), 1.80 (m, 4H), 1.38 (t, 2H), 1.27 (m, 2H), 0.92 (s, 6H).

Example 125

Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide

Example 125A 4-(((trans)-4-methoxycyclohexyl)methoxy)-3-nitrobenzenesulfonamide Separation of the cis and trans mixture of EXAMPLE 121B on a reverse phase HPLC provided the title compound.

Example 125B

Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide The title compound was prepared as described in EXAMPLE 11D using EXAMPLE 125A in place of EXAMPLE 11B. $^1$H NMR (500 MHz, dimethylsulfoxide-$d_6$) δ 11.68 (s, 1H), 8.34 (s, 1H), 7.96-8.09 (m, 2H), 7.51 (dd, 3H), 7.32-7.39 (m, 3H), 7.04 (d, 2H), 6.68 (dd, 1H), 6.39 (dd, 1H), 6.20 (d, 1H), 4.02 (d, 2H), 3.24 (s, 3H), 3.00-3.15 (m, 5H), 2.83 (s, 2H), 2.09-2.36 (m, 6H), 2.03 (d, 2H), 1.96 (s, 2H), 1.77-1.86 (m, 2H), 1.73 (s, 1H), 1.39 (t, 2H), 1.02-1.17 (m, 4H), 0.92 (s, 6H)

Example 126 tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate

Example 126A tert-butyl 4-fluoro-4-(hydroxymethyl)piperidine-1-carboxylate

1-Tert-butyl 4-ethyl 4-fluoropiperidine-1,4-dicarboxylate (1.0 g) in tetrahydrofuran (5 mL) was treated with 1.0 N LiAlH$_4$ in THF (2.54 mL) at 0° C. The reaction mixture was stirred at room temperature for 2 hours. Water (0.6 mL) was added to the reaction mixture drop-wise, followed by 2 N aqueous NaOH (0.2 mL). The reaction was stirred for another 1 hour. The solid was removed by filtration via a pack of Celite and washed with ethyl acetate. The filtrate was washed with brine, dried over MgSO$_4$, filtered, and concentrated to give the product.

Example 126B tert-butyl 4-fluoro-4-((2-nitro-4-sulfamoylphenoxy)methyl)piperidine-1-carboxylate The title compound was prepared by substituting EXAMPLE 126A for (tetrahydro-2H-pyran-4-yl)methanol in EXAMPLE 24A.

Example 126C tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylateyl)oxy]benzamide The title compound was prepared by substituting EXAMPLE 126B for EXAMPLE 11B in EXAMPLE 11D. $^1$H NMR (500 MHz, dimethylsulfoxide-$d_6$) δ 11.67 (s, 1H), 8.36 (s, 2H), 8.02-8.06 (m, 2H), 7.49-7.53 (m, 3H), 7.40 (d, 1H), 7.35 (d, 2H), 7.04 (d, 1H), 6.67 (dd, 1H), 6.39 (dd, 1H), 6.21 (d, 1H), 4.36 (d, 2H), 3.83-3.85 (m, 2H), 3.09 (s, 4H), 2.33 (s, 2H), 2.27-2.32 (m, 4H), 2.13-2.16 (m, 2H), 1.96 (s, 2H), 1.83-1.92 (m, 2H), 1.67-1.75 (m, 2H), 1.38-1.41 (m, 11H), 0.92 (s, 6H).

Example 127

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide The title compound was prepared by substituting EXAMPLE 126C for EXAMPLE 1A in EXAMPLE 1B. $^1$H NMR (500 MHz, dimethylsulfoxide-$d_6$) δ 11.50 (s, 1H), 8.14 (d, 1H), 7.90 (d, 2H), 7.80 (dd, 1H), 7.60 (d, 1H), 7.40 (t, 1H), 7.35 (d, 2H), 7.25 (t, 1H), 7.13 (d, 1H), 7.05 (d, 2H), 6.61 (dd, 1H), 6.30 (dd, 1H), 6.26 (d, 1H), 4.28 (d, 2H), 3.10-3.13 (m, 2H), 2.91-3.00 (m, 6H), 2.73 (s, 2H), 1.96-2.02 (m, 4H), 1.77-1.89 (m, 2H), 1.39 (t, 2H), 0.93 (s, 6H).

Example 128

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide

Example 128A tert-butyl 4-(tetrahydro-2H-pyran-4-yl)piperazine-1-carboxylate The title compound was prepared by substituting tert-butyl piperazine-1-carboxylate for morpholine and dihydro-2H-pyran-4(3H)-one for tert-butyl 4-oxocyclohexylcarbamate in EXAMPLE 39A.

Example 128B 1-(tetrahydro-2H-pyran-4-yl)piperazine dihydrochloride

To a solution of EXAMPLE 128A (3.92 g) in ether was added HCl (25 ml, 2M in ether) and the reaction mixture was stirred for 16 hours at room temperature. The solid product was filtered off, dried and used in next step without further purification.

Example 128C

Trans-tert-butyl-4-(4-(tetrahydro-2H-pyran-4-yl) piperazin-1-yl)cyclohexylcarbamate The title compound was prepared by substituting EXAMPLE 128B for morpholine in EXAMPLE 39A.

Example 128D trans-4-(4-(tetrahydro-2H-pyran-4-yl)piperazin-1-yl) cyclohexanamine tris(2,2,2-trifluoroacetate)

The title compound was prepared by substituting EXAMPLE 128C for EXAMPLE 39A in EXAMPLE 39B.

Example 128E

Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide The title compound was prepared by substituting EXAMPLE 128D for EXAMPLE 100B in EXAMPLE 100C. $^1$H NMR (500 MHz, pyridine-$d_5$) δ 13.07 (s, 1H), 9.28-9.32 (m, 1H), 8.44 (t, 1H), 8.34-8.39 (m, 2H), 8.10-8.14 (m, 1H), 7.66-7.69 (m, 2H), 7.44 (d, 2H), 7.07 (d, 2H), 6.92 (t, 1H), 6.73-6.77 (m, 1H), 6.52-6.55 (m, 1H), 6.49-6.52 (m, 1H), 3.99-4.06 (m, 2H), 3.29-3.36 (m, 2H), 3.03-3.09 (m, 4H), 2.77 (s, 2H), 2.62 (s, 8H), 2.24-2.29 (m, 3H), 2.10-2.16 (m, 5H), 2.05 (s, 2H), 1.97 (s, 2H), 1.92 (s, 2H), 1.70 (d, 2H), 1.57 (td, 2H), 1.34-1.43 (m, 4H), 1.20-1.30 (m, 2H), 0.93 (s, 6H).

Example 129

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide

Example 129A (1-(1,3-difluoropropan-2-yl)piperidin-4-yl)methanol

A suspension of piperidin-4-ylmethanol (0.250 g), sodium triacetoxyborohydride (0.690 g) and 1,3-difluoropropan-2-one (0.245 g) were stirred together in dichloromethane. After stirring overnight the reaction was poured into saturated aqueous NaHCO$_3$ solution (10 mL) and stirred for 15 minutes. The reaction was extracted with dichloromethane (3×25 mL), dried over magnesium sulfate, filtered, and concentrated. Silica gel chromatography (GraceResolv 12 g) eluting with a gradient of 0.75% to 3% methanol/dichloromethane gave the title compound.

Example 129B 4-((1-(1,3-difluoropropan-2-yl)piperidin-4-yl)methoxy)-3-nitrobenzenesulfonamide To a solution of (1-(1,3-difluoropropan-2-yl)piperidin-4-yl)methanol (0.068 g) in tetrahydrofuran (1 mL) was added sodium hydride (0.056 g) and the reaction stirred for 30 minutes at room temperature. 4-Fluoro-3-nitrobenzenesulfonamide (0.077 g) was added in one portion and stirring was continued for 1 hour. The reaction was poured into water (20 mL) and extracted with dichloromethane. The pH of the aqueous layer was adjusted to pH~8 and it was extracted with dichloromethane (50 mL). The organic layer was dried over magnesium sulfate, filtered, and concentrated to give the title compound.

Example 129C 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide The title compound was prepared by substituting EXAMPLE 129B for EXAMPLE 1F and EXAMPLE 3J for EXAMPLE 1E in EXAMPLE 1G. $^1$H NMR (300 MHz, dimethylsulfoxide-$d_6$) δ 11.67 (s, 1H), 11.47-10.98 (m, 1H), 8.33 (d, 1H), 8.03 (d, 2H), 7.50 (dd, 3H), 7.36 (t, 3H), 7.04 (d, 2H), 6.67 (d, 1H), 6.39 (dd, 1H), 6.20 (s, 1H), 4.62 (dd, 4H), 4.06 (d, 2H), 3.18-2.71 (m, 11H), 2.20 (d, 6H), 1.96 (s, 2H), 1.73 (d, 3H), 1.35 (d, 4H), 0.92 (s, 6H).

Example 130

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide

Example 130A (R)-tert-butyl 1-(tetrahydro-2H-pyran-4-yl)pyrrolidin-3-ylcarbamate The title compound was prepared by substituting dihydro-2H-pyran-4(3H)-one for 4'-chlorobiphenyl-2-carboxaldehyde and (R)-tert-butyl pyrrolidin-3-ylcarbamate for tert-butyl piperazine-1-carboxylate in EXAMPLE 1A.

Example 130B (R)-1-(tetrahydro-2H-pyran-4-yl)pyrrolidin-3-amine

A solution of EXAMPLE 130A (550 mg) in dichloromethane (25 ml) was cooled in an ice bath under nitrogen. 2,2,2-Trifluoroacetic acid (8.333 ml) was added and the reaction was stirred for 2 hours. The product was obtained by concentration and high vacuum drying.

Example 130C (R)-3-nitro-4-(1-(tetrahydro-2H-pyran-4-yl)pyrrolidin-3-ylamino)benzenesulfonamide The title compound was prepared by substituting EXAMPLE 130B for (tetrahydropyran-4-yl)methylamine in EXAMPLE 1F.

Example 130D 4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide To a solution of EXAMPLE 3J (90 mg), EXAMPLE 130C (64.2 mg), triethylamine (0.077 ml), N,N-dimethylpyridin-4-amine (38.5 mg) in a mixture of dichloromethane (5 ml) and N,N-dimethylformamide (0.5 ml) was added $N^1$-((ethylimino)methylene)-$N^3$,$N^3$-dimethylpropane-1,3-diamine, hydrochloric acid (60.4 mg) and the mixture was stirred 18 hours. This was concentrated on high vacuum and the crude was purified by reverse phase chromatography with ammonium acetate buffer/acetonitrile. 1H NMR (500 MHz, pyridine-$d_5$) δ 13.03 (s, 1H), 9.27 (d, 1H), 8.59 (d, 1H), 8.43 (d, 1H), 8.37 (dd, 1H), 8.11 (d, 1H), 7.65-7.67 (m, 2H), 7.44 (d, 2H), 7.07 (d, 2H), 6.88 (d, 1H), 6.76 (dd, 1H), 6.54 (d, 1H), 6.48 (m, 1H), 4.06 (m, 1H), 3.98 (d, 2H), 3.35 (t, 2H), 3.07 (m, 4H), 2.73-2.80 (m, 4H), 2.68-2.72 (m, 1H), 2.36 (q, 1H), 2.11-2.30 (m, 9H), 1.97 (m, 2H), 1.62-1.71 (m, 3H), 1.48-1.58 (m, 2H), 1.39 (t, 2H), 0.94 (s, 6H).

Example 131

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide

Example 131A tert-butyl (3R)-1-(2,2-dimethyltetrahydro-2H-pyran-4-yl)pyrrolidin-3-ylcarbamate The title compound was prepared by substituting 2,2-dimethyldihydro-2H-pyran-4(3H)-one for 4'-chlorobiphenyl-2-carboxaldehyde and (R)-tert-butyl pyrrolidin-3-ylcarbamate for tert-butyl piperazine-1-carboxylate in EXAMPLE 1A.

Example 131B (3R)-1-(2,2-dimethyltetrahydro-2H-pyran-4-yl)pyrrolidin-3-amine The title compound was prepared by substituting EXAMPLE 131A for EXAMPLE 130A in EXAMPLE 130B.

Example 131C 4-((3R)-(1-(2,2-dimethyltetrahydro-2H-pyran-4-yl)pyrrolidin-3-ylamino)-3-nitrobenzenesulfonamide The title compound was prepared by substituting EXAMPLE 131B for (tetrahydropyran-4-yl)methylamine in EXAMPLE 1F.

Example 131D 4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 131C for EXAMPLE 130C in EXAMPLE 130D. $^1$H NMR (500 MHz, pyridine-$d_5$) δ 13.03 (d, 1H), 9.28 (m, 1H), 8.61 (m, 1H), 8.44 (d, 1H), 8.38 (dd, 1H), 8.11 (d, 1H), 7.64-7.68 (m, 2H), 7.44 (d, 2H), 7.07 (d, 2H), 6.89 (m, 1H), 6.76 (dd, 1H), 6.54 (m, 1H), 6.49 (m, 1H), 4.08 (m, 1H), 3.78 (m, 1H), 3.61 (m, 1H), 3.07 (m, 4H), 2.71-2.82 (m, 5H), 2.37-2.44 (m, 2H), 2.19-2.29 (m, 3H), 2.14 (m, 5H), 1.97 (s, 2H), 1.76 (m, 1H), 1.66 (m, 2H), 1.32-1.49 (m, 4H), 1.28 (d, 3H), 1.20 (s, 3H), 0.94 (s, 6H).

Example 132

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide

Example 132A (S)-tert-butyl 1-(tetrahydro-2H-pyran-4-yl)pyrrolidin-3-ylcarbamate The title compound was prepared by substituting dihydro-2H-pyran-4(3H)-one for 4'-chlorobiphenyl-2-carboxaldehyde and (S)-tert-butyl pyrrolidin-3-ylcarbamate for tert-butyl piperazine-1-carboxylate in EXAMPLE 1A.

Example 132B (S)-1-(tetrahydro-2H-pyran-4-yl)pyrrolidin-3-amine

The title compound was prepared by substituting EXAMPLE 132A for EXAMPLE 130A in EXAMPLE 130B.

Example 132C (S)-3-nitro-4-(1-(tetrahydro-2H-pyran-4-yl)pyrrolidin-3-ylamino)benzenesulfonamide The title compound was prepared by substituting EXAMPLE 132B for (tetrahydropyran-4-yl)methylamine in EXAMPLE 1F.

Example 132D 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide The title compound was prepared by substituting EXAMPLE 132C for EXAMPLE 130C in EXAMPLE 130D. $^1$H NMR (500 MHz, pyridine-$d_5$) δ 13.04 (m, 1H), 9.27 (d, 1H), 8.58 (d, 1H), 8.43 (d, 1H), 8.37 (dd, 1H), 8.11 (d, 1H), 7.64-7.68 (m, 2H), 7.44 (d, 2H), 7.07 (d, 2H), 6.88 (d, 1H), 6.75 (dd, 1H), 6.54 (m, 1H), 6.49 (m, 1H), 4.06 (m, 1H), 3.98 (d, 2H), 3.36 (t, 2H), 3.07 (m, 4H), 2.68-2.80 (m, 5H), 2.36 (m, 1H), 2.09-2.29 (m, 9H), 1.97 (s, 2H), 1.62-1.72 (m, 3H), 1.48-1.60 (m, 2H), 1.39 (t, 2H), 0.94 (s, 6H).

Example 133

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide

Example 133A tert-butyl (3S)-1-(2,2-dimethyltetrahydro-2H-pyran-4-yl)pyrrolidin-3-ylcarbamate The title compound was prepared by substituting 2,2-dimethyldihydro-2H-pyran-4(3H)-one for 4'-chlorobiphenyl-2-carboxaldehyde and (S)-tert-butyl pyrrolidin-3-ylcarbamate for tert-butyl piperazine-1-carboxylate in EXAMPLE 1A.

Example 133B (3S)-1-(2,2-dimethyltetrahydro-2H-pyran-4-yl)pyrrolidin-3-amine The title compound was prepared by substituting EXAMPLE 133A for EXAMPLE 130A in EXAMPLE 130B.

Example 133C 4-(3S)-(1-(2,2-dimethyltetrahydro-2H-pyran-4-yl)pyrrolidin-3-ylamino)-3-nitro benzenesulfonamide The title compound was prepared by substituting EXAMPLE 133B for (tetrahydropyran-4-yl)methylamine in EXAMPLE 1F.

Example 133D 4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 133C for EXAMPLE 130C in EXAMPLE 130D. $^1$H NMR (500 MHz, pyridine-$d_5$) δ 13.03 (d, 1H), 9.28 (m, 1H), 8.61 (m, 1H), 8.43 (m, 1H), 8.38 (dd, 1H), 8.11 (d, 1H), 7.64-7.68 (m, 2H), 7.44 (d, 2H), 7.07 (d, 2H), 6.89 (m, 1H), 6.76 (dd, 1H), 6.54 (m, 1H), 6.49 (m, 1H), 4.08 (m, 1H), 3.78 (m, 1H), 3.61 (m, 1H), 3.07 (m, 4H), 2.71-2.82 (m, 5H), 2.37-2.44 (m, 2H), 2.19-2.29 (m, 3H), 2.14 (m, 5H), 1.97 (s, 2H), 1.76 (m, 1H), 1.66 (m, 2H), 1.33-1.48 (m, 4H), 1.28 (d, 3H), 1.20 (s, 3H), 0.94 (s, 6H).

Example 134

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide

Example 134A 4-(morpholin-2-ylmethylamino)-3-nitrobenzenesulfonamide

A solution of EXAMPLE 113A (0.8 g) in dichloromethane (10 mL) and trifluoroacetic acid (10 mL) was stirred at room temperature for 2 hours. The solvents were evaporated and the residue triturated with diethyl ether. The resulting solid was dissolved in 5% aqueous sodium carbonate solution (20 mL). The solution was concentrated to dryness and the resulting solid was triturated with a solution of 10% methanol in dichloromethane several times. Evaporation of the organic solvents gave the title compound.

Example 134B 4-((4-methylmorpholin-2-yl)methylamino)-3-nitrobenzenesulfonamide To a solution of EXAMPLE 134A (158 mg) in anhydrous N,N-dimethylformamide (4 mL) was added sodium carbonate (64 mg) and methyl iodide (78 mg). After stirring overnight at room temperature, the mixture was evaporated to dryness. The crude product was then absorbed on silica gel (6 g) and purified on a silica gel column eluting with 10% methanol in dichloromethane to give the title compound.

Example 134C 4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide The title compound was prepared by substituting EXAMPLE 134B for EXAMPLE 130C in EXAMPLE 130D. $^1$H NMR (500 MHz, pyridine-$d_5$) δ 13.00 (s, 1H), 9.27 (d, 1H), 8.87 (t, 1H), 8.43 (d, 1H), 8.32 (dd, 1H), 8.11 (d, 1H), 7.65 (m, 2H), 7.44 (d, 2H), 7.07 (d, 2H), 6.91 (d, 1H), 6.75 (dd, 1H), 6.54 (d, 1H), 6.48 (m, 1H), 3.92 (m, 1H), 3.86 (d, 1H), 3.67 (dt, 1H), 3.49-3.39 (m, 2H), 3.07 (m, 4H), 2.77 (s, 2H), 3.71 (m, 1H), 2.49 (d, 1H), 2.26 (m, 2H), 2.16 (s, 3H), 2.14 (m, 4H), 2.03 (dt, 1H), 1.97 (s, 2H), 1.90 (t, 1H), 1.39 (t, 2H), 0.94 (s, 6H).

Example 135

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide

Example 135A 4-((4-(2-methoxyethyl)morpholin-2-yl)methylamino)-3-nitrobenzenesulfonamide The title compound was prepared by substituting 2-methoxyethyl bromide for methyl iodide in EXAMPLE 134B.

Example 135B 4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 135A for EXAMPLE 130C in EXAMPLE 130D. $^1$H NMR (500 MHz, pyridine-$d_5$) δ 12.98 (s, 1H), 9.26 (d, 1H), 8.88 (t, 1H), 8.43 (d, 1H), 8.32 (dd, 1H), 8.11 (d, 1H), 7.66 (m, 2H), 7.44 (d, 2H), 7.07 (d, 2H), 6.91 (d, 1H), 6.75 (dd, 1H), 6.54 (d, 1H), 6.48 (m, 1H), 3.93 (m, 1H),3.87 (d, 1H), 3.70 (dt, 1H), 3.51 (t, 2H), 3.48-3.38 (m, 2H), 3.27 (s, 3H), 3.07 (m, 4H), 2.95 (d, 1H), 2.77 (s, 2H), 2.70 (m, 1H), 2.57 (t, 2H), 2.27-2.07 (m, 8H), 1.97 (s, 2H), 1.39 (t, 2H), 0.94 (s, 6H).

Example 136

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 136A 4-((4-acetylmorpholin-2-yl)methylamino)-3-nitrobenzenesulfonamide The title compound was prepared by substituting acetic anhydride for methyl iodide in EXAMPLE 134B.

Example 136B

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 136A for EXAMPLE 130C in EXAMPLE 130D. $^1$H NMR (500 MHz, pyridine-$d_5$) δ 13.00 (s, 1H), 9.26 (s, 1H), 8.85 (s, 1H), 8.43 (d, 1H), 8.32 (dd, 1H), 8.10 (d, 1H), 7.65 (m, 2H), 7.44 (d, 2H), 7.07 (d, 2H), 6.91 (dd, 1H), 6.75 (dd, 1H), 6.54 (s, 1H), 6.48 (s, 1H), 4.73 (dd, 1H), 3.93-3.65 (m, 2H), 3.60-3.40 (m, 4H), 3.12 (m, 1H), 3.07 (m, 4H), 2.77 (s, 2H), 2.70 (m, 1H), 2.57 (t, 2H), 2.14 (s, 3H), 2.27-2.07 (m, 4H), 1.97 (s, 2H), 1.39 (t, 2H), 0.93 (s, 6H).

Example 137

4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide

Example 137A ethyl 4-fluorobut-2-enoate

Ethyl 2-fluoroacetate (21.0 g) in $CH_2Cl_2$ (200 mL) at −78° C. was treated dropwise over 45 min with a 1.0 M solution of diisobutylaluminum hydride in $CH_2Cl_2$ (200 mL) maintaining the internal temperature below −70° C. Stirring was continued at −78° C. for 30 minutes and then (carbethoxymethylene)triphenylphosphorane (70.0 g) was added in one portion. The reaction mixture was allowed to slowly reach room temperature while stirring overnight. It was then quenched with methanol, filtered and concentrated to give the product as a mixture of isomers (E/Z=3:1).

Example 137B

Trans-ethyl 1-benzyl-4-(fluoromethyl)pyrrolidine-3-carboxylate

A mixture of N-benzyl-1-methoxy-N-((trimethylsilyl)methyl)methanamine (4.5 g) and EXAMPLE 137A (2.5 g) in dichloromethane (50 mL) was cooled to 0° C., treated dropwise with trifluoroacetic acid (0.15 mL), stirred for 4 hours at 0° C. and neutralized with saturated aqueous $Na_2CO_3$ solution. The mixture was poured into a separatory funnel and the layers separated. The organic layer was washed with water and brine, dried ($MgSO_4$), filtered, concentrated and chromatographed on silica gel with 0-20% ethyl acetate in hexanes as eluent to give both the cis and trans isomers of the product. Only the trans diastereomers were carried on in the following steps.

Example 137C

Trans-ethyl 4-(fluoromethyl)pyrrolidine-3-carboxylate

EXAMPLE 137B (0.83 g) in ethanol (9 mL) was treated with 10% Pd/C (0.208 g) and ammonium formate (1.97 g), refluxed for 1.5 hours, concentrated, dissolved in dichloromethane, filtered through a pad of celite rinsing with dichloromethane, and concentrated to give the product.

Example 137D

Trans-1-benzyl 3-ethyl 4-(fluoromethyl)pyrrolidine-1,3-dicarboxylate

EXAMPLE 137C (0.44 g) in dioxane (4 mL) and water (4 mL) at 0° C. was treated sequentially with $Na_2CO_3$ (0.89 g) and benzyl chloroformate (0.48 mL). The reaction mixture was stirred at 0° C. for 3 hours and was then allowed to slowly warm to room temperature over 1.5 hours. The reaction mixture was diluted with ethyl acetate, washed with water and brine, dried ($MgSO_4$), filtered, concentrated and chromatographed on silica gel with 10-25% ethyl acetate in hexanes as eluent to give the product.

Example 137E

Trans-1-(benzyloxycarbonyl)-4-(fluoromethyl)pyrrolidine-3-carboxylic acid

The title compound was prepared by substituting EXAMPLE 137D for EXAMPLE 15G in EXAMPLE 15H.

Example 137F

Trans-benzyl 3-(fluoromethyl)-4-(hydroxymethyl)pyrrolidine-1-carboxylate

EXAMPLE 137E (0.563 g) in tetrahydrofuran (10 mL) at 0° C. was treated dropwise with a 1 M solution of borane in tetrahydrofuran (4 mL), stirred for 3 hours and then slowly quenched with saturated aqueous $NH_4Cl$ solution. The reaction mixture was diluted with ethyl acetate, washed with water and brine, dried ($MgSO_4$), filtered and concentrated to give the product.

Example 137G

Trans-benzyl 3-(fluoromethyl)-4-((2-nitro-4-sulfamoylphenoxy)methyl)pyrrolidine-1-carboxylate The title compound was prepared by substituting EXAMPLE 137F for (tetrahydro-2H-pyran-4-yl)methanol in EXAMPLE 24A.

Example 137H

Trans-4-((4-(fluoromethyl)pyrrolidin-3-yl)methoxy)-3-nitrobenzenesulfonamide

EXAMPLE 137G (0.232 g) in acetic acid (2.5 ml) was treated with hydrobromic acid (33 wt % in acetic acid) (0.875 mL) at ambient temperature, stirred for 1 hour and concentrated. The product was free-based using a MEGA BE-SCX column with 1:1 $CH_2Cl_2$/methanol as eluent for the hydrobromic acid and acetic acid. The product was released from the column with 10% (7 M ammonia in methanol) in $CH_2Cl_2$ as eluent.

Example 137I

Trans-4-((4-(fluoromethyl)-1-(oxetan-3-yl)pyrrolidin-3-yl)methoxy)-3-nitrobenzenesulfonamide The title compound was prepared by substituting EXAMPLE 137H for tert-butyl piperazine-1-carboxylate and 3-oxetanone for 4'-chlorobiphenyl-2-carboxaldehyde in EXAMPLE 1A.

Example 137J 4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide The title compound was prepared by substituting EXAMPLE 137I for EXAMPLE 11B in EXAMPLE 11D. $^1$H NMR (300 MHz, dimethylsulfoxide-$d_6$) δ 11.67 (s, 1H), 8.35 (d, 1H), 8.03 (m, 2H), 7.51 (m, 3H), 7.37 (m, 3H), 7.04 (m, 2H), 6.67 (dd, 1H), 6.39 (dd, 1H), 6.21 (d, 1H), 4.45 (m, 6H), 4.21 (d, 2H), 3.62 (m, 1H), 3.08 (m, 4H), 2.72 (m, 5H), 2.31 (m, 9H), 1.96 (s, 2H), 1.39 (t, 2H), 0.93 (s, 6H).

Example 138

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide

Example 138A (4-fluorotetrahydro-2H-pyran-4-yl)methyl methanesulfonate

A mixture of EXAMPLE 37C (1.4 g), methanesulfonyl chloride (1.054 mL), triethylamine (2.99 mL), and 4-dimethylaminopyridine (0.051 g) in $CH_2Cl_2$ (20 mL) was stirred at 0° C. for 2 hours, concentrated and chromatographed on silica gel eluting with 30% ethyl acetate in hexanes to give the product.

Example 138B 2-((4-fluorotetrahydro-2H-pyran-4-yl)methyl)isoindoline-1,3-dione A mixture of EXAMPLE 138A (1.8 g) and potassium phthalimide (2.356 g) in N,N-dimethylformamide (30 mL) was heated at 150° C. overnight, diluted with ethyl acetate, washed with water and brine, dried ($MgSO_4$), filtered, concentrated and chromatographed on silica gel eluting with 30% ethyl acetate in hexanes to give the product.

Example 138C (4-fluorotetrahydro-2H-pyran-4-yl)methanamine

A mixture of EXAMPLE 138B (1.4 g) and hydrazine (1.548 mL) in ethanol (40 mL) was heated at 70° C. overnight, cooled to room temperature, slurried with $CH_2Cl_2$ (200 mL) and the solid removed by filtration. The filtrate was concentrated and chromatographed on silica gel eluting with 100:5:1 ethyl acetate/methanol/$NH_4OH$ to give the product.

Example 138D 4-((4-fluorotetrahydro-2H-pyran-4-yl)methylamino)-3-nitrobenzenesulfonamide A mixture of 4-fluoro-3-nitrobenzenesulfonamide (0.44 g), EXAMPLE 138C (0.266 g), and triethylamine (1.11 mL) in tetrahydrofuran (10 mL) was heated at 70° C. overnight, diluted with ethyl acetate, washed with water and brine, dried ($MgSO_4$), filtered, concentrated and chromatographed on silica gel eluting with 50% ethyl acetate in hexanes to give the product.

Example 138E 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 138D for EXAMPLE 11B in EXAMPLE 11D. $^1$H NMR (500 MHz, dimethylsulfoxide-$d_6$) δ 11.68 (s, 1H), 8.62 (t, 1H), 8.56 (d, 1H), 8.04 (d, 1H), 7.82 (dd, 1H), 7.48-7.54 (m, 3H), 7.34 (d, 2H), 7.24 (d, 1H), 7.04 (d, 2H), 6.68 (dd, 1H), 6.39 (dd, 1H), 6.19 (d, 1H), 3.70-3.77 (m, 4H), 3.50-3.55 (m, 2H), 3.07 (s, 4H), 2.76 (s, 2H), 2.14-2.20 (m, 6H), 1.76-1.84 (m, 4H), 1.38 (t, 2H), 0.92 (s, 6H).

Example 139

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide

Example 139A tert-butyl 4-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate The title compound was prepared as described in EXAMPLE 53B by replacing 1-acetylpiperidin-4-amine with 4-amino-piperidine-1-carboxylic acid tert-butyl ester.

Example 139B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide To a cooled (0° C.) solution of EXAMPLE 139A (960 mg) in dichloromethane (10 mL) was added dropwise trifluoroacetic acid (5 mL). The mixture was stirred at the temperature for 3 hours. Then, the mixture was concentrated under vacuum and the residue was dissolved in dichloromethane (200 mL) and washed with aqueous NaHCO$_3$ and brine. After drying over Na$_2$SO$_4$, the mixture was filtered, and evaporation of the solvent from the filtrate gave the title compound.

Example 139C 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide To a solution of EXAMPLE 139B (120 mg) in tetrahydrofuran (3 mL) and acetic acid (1 mL) was added oxetan-3-one (50.8 mg) and MP-cyanoborohydride (2.15 mmol/g, 150 mg). The mixture was stirred at room temperature overnight. The mixture was filtered. The filtrate was concentrated and the residue was loaded on a silica gel cartridge and eluted with 5-10% 7N NH$_3$ in methanol in dichloromethane to give the title compound. $^1$H NMR (300 MHz, dimethylsulfoxide-d$_6$) δ 11.62 (s, 1H), 8.51 (d, 1H), 8.20 (d, 1H), 7.99 (d, 1H), 7.74 (m, 1H), 7.48 (m, 3H), 7.35 (d, 2H), 7.05 (d, 2H), 6.66 (dd, 1H), 6.36 (dd, 1H), 6.20 (d, 1H), 4.54 (t, 2H), 4.43 (t, 2H), 3.66 (m, 1H), 3.44 (m, 3H), 3.04 (m, 5H), 2.73 (s, 2H), 2.61 (m, 2H), 2.12 (m, 11H), 1.61 (m, 2H), 1.38 (t, 2H), 0.93 (m, 6H).

Example 140

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide The title compound was prepared as described in EXAMPLE 139C by replacing oxetan-3-one with cyclobutanone. $^1$H NMR (300 MHz, dimethylsulfoxide-d$_6$) δ 11.58 (s, 1H), 8.47 (d, 1H), 8.12 (d, 1H), 7.97 (d, 1H), 7.74 (d, 1H), 7.53 (d, 1H), 7.45 (m, 1H), 7.36 (m, 3H), 7.02 (m, 3H), 6.64 (dd, 1H), 6.33 (m, 1H), 6.22 (d, 1H), 3.74 (m, 1H), 2.97 (m, 6H), 2.73 (s, 3H), 2.15 (m, 15H), 1.67 (m, 4H), 1.38 (t, 2H), 0.93 (s, 6H).

Example 141

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide The title compound was prepared as described in EXAMPLE 139C by replacing oxetan-3-one with 2,2-dimethyltetrahydropyran-4-one. $^1$H NMR (300 MHz, dimethylsulfoxide-d$_6$) δ 11.60 (s, 1H), 8.50 (d, 1H), 8.15 (m, 1H), 7.99 (d, 1H), 7.78 (m, 1H), 7.62 (m, 1H), 7.47 (m, 3H), 7.34 (m, 3H), 7.05 (m, 3H), 6.65 (m, 2H), 6.35 (dd, 1H), 6.21 (d, 1H), 4.56 (d, 3H), 3.89 (m, 3H), 3.67 (m, 6H), 3.45 (m, 2H), 3.04 (m, 3H), 2.75 (m, 3H), 2.14 (m, 3H), 1.71 (m, 5H), 1.16 (s, 9H).

Example 142

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide

Example 142A (S)-tert-butyl 1-cyclopropylpyrrolidin-3-ylcarbamate (S)-tert-butyl pyrrolidin-3-ylcarbamate (415 mg), (1-ethoxycyclopropoxy)trimethylsilane (1.8 mL) and molecular sieves (500 mg) were combined in methanol (4.5 mL). Acetic acid (1.3 mL) was added, followed by sodium cyanoborohydride (420 mg). The resulting mixture was heated to reflux for 4 hours. Insoluble material was filtered off and reaction was made basic to pH 14 with addition of 6M aqueous NaOH solution. The solution was extracted three times with diethyl ether, and the combined extracts were dried over MgSO$_4$, filtered and concentrated to obtain an oil, which was purified by flash chromatography, eluting first with 100% dichloromethane, followed by 5% methanol/dichloromethane and 10% methanol/dichloromethane.

Example 142B (S)-1-cyclopropylpyrrolidin-3-amine

The title compound was prepared by substituting EXAMPLE 142A for EXAMPLE 1A in EXAMPLE 1B.

Example 142C 4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide The title compound was prepared by substituting EXAMPLE 142B for 1-acetylpiperidin-4-amine in EXAMPLE 53B. $^1$H NMR (500 MHz, dimethylsulfoxide-d$_6$) δ 11.64 (s, 1H), 8.51 (m, 2H), 8.30 (m, 1H), 8.00 (br s, 1H), 7.77 (m, 1H), 7.49 (m, 3H), 7.34 (d, 2H), 7.04 (d, 2H), 6.97 (br s, 1H), 6.67 (dd, 1H), 6.36 (m, 1H), 6.21 (m, 1H), 4.19 (m, 1H), 3.00 (m, 5H), 2.74 (m, 3H), 2.64 (m, 1H), 2.36 (m, 1H), 2.15 (m, 6H), 1.95 (s, 2H), 1.78 (br s, 1H), 1.68 (m, 1H), 1.38 (t, 2H), 1.23 (m, 1H), 0.92 (s, 6H), 0.39 (m, 4H).

Example 143

4-(4-{[2-(4-chlorophenyl)-4,4-dimethylcyclohex-1-en-1-yl]methyl}piperazin-1-yl)-N-({3-nitro-4-[(1-tetrahydro furan-3-ylpiperidin-4-yl)amino]phenyl}sulfonyl)-2-(1H-pyrrolo[2,3-b]pyridin-5-yloxy)benzamide The title compound was prepared as described in EXAMPLE 139C by replacing oxetan-3-one with 3-oxotetrahydrofuran. $^1$H NMR (300 MHz, dimethylsulfoxide-d$_6$) δ 11.65 (s, 1H), 8.53 (d, 1H), 8.21 (m, 1H), 8.02 (m, 1H), 7.80

(dd, 1H), 7.49 (m, 3H), 7.34 (m, 3H), 7.05 (m, 3H), 6.67 (dd, 1H), 6.37 (m, 1H), 6.19 (d, 1H), 4.29 (m, 3H), 3.73 (m, 6H), 3.09 (m, 4H), 2.76 (m, 2H), 2.05 (m, 8H), 1.68 (m, 2H), 1.37 (m, 2H), 0.94 (s, 6H).

Example 144

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide Example 144A (R)-tert-butyl 1-cyclopropylpyrrolidin-3-ylcarbamate The title compound was prepared by substituting (R)-tert-butyl pyrrolidin-3-ylcarbamate for (S)-tert-butyl pyrrolidin-3-ylcarbamate in EXAMPLE 142A.

Example 144B (R)-1-cyclopropylpyrrolidin-3-amine

The title compound was prepared by substituting EXAMPLE 144A for EXAMPLE 1A in EXAMPLE 1B.

Example 144C 4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide The title compound was prepared by substituting EXAMPLE 144B for 1-acetylpiperidin-4-amine in EXAMPLE 53B. $^1$H NMR (500 MHz, dimethylsulfoxide-$d_6$) δ 11.66 (s, 1H), 8.53 (d, 2H), 8.32 (d, 1H), 8.02 (d, 1H), 7.81 (m, 1H), 7.49 (m, 3H), 7.34 (m, 2H), 7.03 (m, 3H), 6.67 (dd, 1H), 6.37 (m, 1H), 6.20 (d, 1H), 4.21 (m, 1H), 3.00 (m, 5H), 2.74 (m, 3H), 2.64 (m, 1H), 2.36 (m, 1H), 2.15 (m, 6H), 1.95 (s, 2H), 1.74 (br s, 1H), 1.66 (m, 1H), 1.38 (t, 2H), 1.23 (m, 1H), 0.92 (s, 6H), 0.39 (m, 4H).

Example 145

4-(4-{[2-(4-chlorophenyl)-4,4-dimethylcyclohex-1-en-1-yl]methyl}piperazin-1-yl)-N-{3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide Example 145A (S)-tert-butyl (1-(tetrahydro-2H-pyran-4-yl)pyrrolidin-3-yl)methylcarbamate The title compound was prepared by substituting (R)-tert-butyl pyrrolidin-3-ylmethylcarbamate for tert-butyl piperazine-1-carboxylate and dihydro-2H-pyran-4(3H)-one for 4'-chlorobiphenyl-2-carboxaldehyde in EXAMPLE 1A.

Example 145B (S)-(1-(tetrahydro-2H-pyran-4-yl)pyrrolidin-3-yl)methanamine

The title compound was prepared by substituting EXAMPLE 145A for EXAMPLE 1A in EXAMPLE 1B.

Example 145C (S)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((1-(tetrahydro-2H-pyran-4-yl)pyrrolidin-3-yl)methylamino)phenylsulfonyl)benzamide The title compound was prepared by substituting EXAMPLE 145B for 1-acetylpiperidin-4-amine in EXAMPLE 53B. $^1$H NMR (500 MHz, dimethylsulfoxide-$d_6$) δ 11.58 (s, 1H), 8.61 (br s, 1H), 8.46 (s, 1H), 7.96 (d, 1H), 7.72 (m, 1H), 7.54 (d, 1H), 7.45 (t, 1H), 7.37 (br s, 2H), 7.34 (d, 2H), 7.04 (m, 2H), 6.94 (m, 1H), 6.64 (dd, 1H), 6.34 (m, 1H), 6.22 (d, 1H), 3.89 (m, 2H), 3.38 (m, 4H), 3.27 (m, 4H), 3.02 (m, 5H), 2.73 (s, 2H), 2.61 (m, 1H), 2.18 (m, 6H), 2.05 (m, 1H), 1.95 (m, 2H), 1.85 (m, 2H), 1.64 (m, 1H), 1.50 (m, 2H), 1.38 (m, 2H), 0.94 (s, 6H).

Example 146

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide The title compound was prepared as described in EXAMPLE 120B using 3-amino-2,2-dimethylpropan-1-ol in place of EXAMPLE 120A. $^1$H NMR (500 MHz, dimethylsulfoxide-$d_6$) δ 11.68 (s, 1H), 11.35 (s, 1H), 8.96 (t, 1H), 8.56 (d, 1H), 8.05 (d, 1H), 7.79 (dd, 1H), 7.46-7.56 (m, 3H), 7.34 (d, 2H), 7.10 (d, 1H), 7.04 (d, 2H), 6.68 (dd, 1H), 6.39 (dd, 1H), 6.19 (d, 1H), 5.10 (t, 1H), 3.29 (d, 1H), 3.24 (d, 1H), 3.07 (s, 4H), 2.75 (s, 2H), 2.17 (d, 6H), 1.95 (s, 2H), 1.38 (t, 2H), 0.93 (d, 12H).

Example 147

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide Example 147A tert-butyl (1-(methylsulfonyl)piperidin-3-yl)methylcarbamate tert-Butyl piperidin-3-ylmethylcarbamate (500 mg) was dissolved in anhydrous dichloromethane (10 mL) and methanesulfonyl chloride (0.181 mL) was added followed by the addition of triethylamine (1.3 mL). The reaction mixture was stirred at room temperature overnight. The organic solvent was removed under vacuum. The residue was purified with flash column chromatography on silica gel eluting with 0-70% ethyl acetate in hexane to give the title compound.

Example 147B (1-(methylsulfonyl)piperidin-3-yl)methanamine

EXAMPLE 147A (400 mg) was suspended in 4N HCl in dioxane (10 mL) followed by the addition of anhydrous methanol (1 mL). The clear solution was stirred at room temperature for 2 hours. The organic solvent was removed under vacuum. The solid residue was used in the next step without further purification.

Example 147C 4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide EXAMPLE 53A (50 mg), EXAMPLE 147B (26 mg) and triethylamine (0.088 mL) were dissolved in anhydrous dioxane (1 mL) and N,N-dimethylformamide (0.2 mL). The reaction vial was heated in a Biotage Initiator microwave reactor at 130° C. for 25 minutes. The solvent was removed under vacuum. The residue was purified by reverse phase HPLC on a C18 column using a gradient of 20-80% acetonitrile/0.1% trifluoroacetic acid in water to give the title compound as the trifluoroacetate salt. The trifluoroacetic acid salt was dissolved in dichloromethane (6 mL) and washed with 50% aqueous NaHCO$_3$. The organic layer was dried over anhydrous Na$_2$SO$_4$ and concentrated to give the title compound. $^1$H NMR (400 MHz, dimethylsulfoxide-d$_6$) δ 11.65 (s, 1H), 8.56 (m, 2H), 8.03 (d, 1H), 7.80 (m, 1H), 7.50 (m, 3H), 7.35 (d, 2H), 7.12 (m, 1H), 7.04 (d, 2H), 6.67 (dd, 1H), 6.38 (dd, 1H), 6.19 (d, 1H), 3.52 (m, 1H), 3.40 (m, 2H), 3.06 (m, 4H), 2.84 (s, 3H), 2.75 (m, 2H), 2.75 (m, 4H), 2.58 (m, 1H), 2.16 (m, 6H), 1.95 (s, 3H), 1.76 (m, 2H), 1.52 (m, 1H), 1.37 (m, 2H), 0.92 (s, 6H).

Example 148

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 148A tert-butyl (1-acetylpiperidin-3-yl)methylcarbamate

The title compound was prepared by substituting acetyl chloride for methanesulfonyl chloride in EXAMPLE 147A.

Example 148B 1-(3-(aminomethyl)piperidin-1-yl)ethanone

The title compound was prepared by substituting EXAMPLE 148A for EXAMPLE 147A in EXAMPLE 147B.

Example 148C

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 148B for EXAMPLE 147B in EXAMPLE 147C. $^1$H NMR (400 MHz, dimethylsulfoxide-d$_6$) δ 11.67 (s, 1H), 8.56 (m, 2H), 8.03 (d, 1H), 7.80 (m, 1H), 7.50 (m, 3H), 7.34 (d, 2H), 7.12 (m, 1H), 7.04 (d, 2H), 6.67 (dd, 1H), 6.39 (dd, 1H), 6.19 (d, 1H), 3.99 (m, 1H), 3.67 (m, 1H), 3.37 (m, 2H), 3.24 (m, 2H), 3.07 (m, 4H), 2.89 (m, 1H), 2.71 (m, 2H), 2.16 (m, 6H), 1.96 (s, 3H), 1.80 (m, 4H), 1.38 (t, 2H), 1.27 (m, 2H), 0.92 (s, 6H).

Example 149

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide

Example 149A (R)-tert-butyl 1-(methylsulfonyl)pyrrolidin-3-ylcarbamate

The title compound was prepared by substituting (R)-tert-butyl pyrrolidin-3-ylcarbamate for tert-butyl piperidin-3-ylmethylcarbamate in EXAMPLE 147A.

Example 149B (R)-1-(methylsulfonyl)pyrrolidin-3-amine

The title compound was prepared by substituting EXAMPLE 149A for EXAMPLE 147A in EXAMPLE 147B.

Example 149C 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 149B for EXAMPLE 147B in EXAMPLE 147C. $^1$H NMR (400 MHz, dimethylsulfoxide-d$_6$) δ 11.65 (s, 1H), 8.55 (d, 1H), 8.29 (d, 1H), 8.02 (d, 1H), 7.86 (dd, 1H), 7.49 (m, 3H), 7.33 (d, 2H), 7.17 (d, 1H), 7.04 (d, 2H), 6.68 (dd, 1H), 6.38 (dd, 1H), 6.20 (d, 1H), 4.41 (m, 1H), 3.69 (m, 1H), 3.39 (m, 3H), 3.06 (m, 4H), 2.97 (s, 3H), 2.76 (m, 2H), 2.27 (m, 8H), 1.93 (m, 2H), 1.54 (m, 1H), 1.38 (t, 2H), 0.92 (s, 6H).

Example 150

4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 150A

Ethyl 2-hydroxy-3,3-dimethylcyclohex-1-enecarboxylate

Into a 500 mL round-bottomed flask was added diisopropylamine (3.5 mL) in ether (200 mL). After cooling to −30° C., butyllithium (16 mL) (1.6M in hexane) was added slowly. After stirring 30 minutes, the temperature was cooled to −5° C. 2,2-Dimethylcyclohexanone (3 g) was added slowly. The mixture was warmed up to 0° C. and stirred for 1 hour. After cooling to −5° C., hexamethylphosphoramide (8 mL) and ethyl carbonocyanidate (2.5 mL) were added. After stirring at −5° C. for 20 minutes, and warming to room temperature, the reaction was stirred for 1 hour. The mixture was poured into cold water, and the layers were separated. The aqueous layer was extracted with ether (3×20 mL). The combined the organic layers were washed with saturated aqueous NH$_4$Cl (3×20 mL). After drying over Na$_2$SO$_4$, the mixture was filtered and the filtrate was concentrated. The crude product was purified by flash chromatography on silica with 0-10% ethyl acetate in hexanes to provide the title compound.

Example 150B

Ethyl 3,3-dimethyl-2-(trifluoromethylsulfonyloxy)cyclohex-1-enecarboxylate

The title compound was prepared by substituting EXAMPLE 150A for EXAMPLE 101A in EXAMPLE 101B.

Example 150C

Ethyl 2-(4-chlorophenyl)-3,3-dimethylcyclohex-1-enecarboxylate

The title compound was prepared by substituting EXAMPLE 150B for EXAMPLE 101B in EXAMPLE 101C.

Example 150D (2-(4-chlorophenyl)-3,3-dimethylcyclohex-1-enyl)methanol

In a 200 mL round-bottomed flask was added EXAMPLE 150C (0.97 g) and lithium borohydride (0.47 g) in ether (20 mL) to give a suspension. Methanol (2.2 mL) was added slowly. The mixture was refluxed overnight. The reaction was then cooled, and methanol was added to quench the reaction. 1N aqueous HCl was then added until the pH<7, and ether (3×30 mL) was used to extract the product. The combined organic layers were dried over Na$_2$SO$_4$, filtered, and concentrated. The crude material was purified by flash chromatography on silica with 0-25% ethyl acetate in hexanes to provide the title compound.

Example 150E 2-(4-chlorophenyl)-3,3-dimethylcyclohex-1-enecarbaldehyde

Into a 100 mL round-bottomed flask was added EXAMPLE 150D (0.3 g) and Dess-Martin Periodinane (0.6 g) in dichloromethane (10 mL) to give a suspension. The mixture was stirred at room temperature overnight. After filtration, the mixture was washed with saturated aqueous NaHCO$_3$ (2×20 mL), dried over Na$_2$SO$_4$, filtered, and concentrated. The crude product was purified by flash chromatography on silica with 0-25% ethyl acetate in hexanes to provide the title compound.

Example 150F

Methyl 2-(1H-pyrrolo[2,3-b]pyridin-5-yloxy)-4-(4-((2-(4-chlorophenyl)-3,3-dimethylcyclohex-1-enyl)methyl)piperazin-1-yl)benzoate The title compound was prepared by substituting EXAMPLE 150E for 4'-chlorobiphenyl-2-carboxaldehyde and EXAMPLE 15F for tert-butyl piperazine-1-carboxylate in EXAMPLE 1A.

Example 150G 2-(1H-pyrrolo[2,3-b]pyridin-5-yloxy)-4-(4-((2-(4-chlorophenyl)-3,3-dimethylcyclohex-1-enyl)methyl)piperazin-1-yl)benzoic acid The title compound was prepared by substituting EXAMPLE 150F for EXAMPLE 101E in EXAMPLE 101F.

Example 150H 4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 150G for EXAMPLE 3J and EXAMPLE 1F for EXAMPLE 11B in EXAMPLE 11D. $^1$H NMR (500 MHz, dimethyl sulfoxide-d$_6$) δ 11.50 (s, 1H), 8.36 (m, 1H), 8.32 (m, 1H), 7.91 (d, 1H), 7.59 (m, 2H), 7.40 (t, 1H), 7.35 (d, 2H), 7.25 (m, 1H), 6.94 (d, 2H), 6.79 (d, 1H), 6.60 (m, 1H), 6.29 (m, 1H), 6.24 (d, 1H), 3.83 (m, 2H), 3.25 (m, 4H), 2.98 (m, 4H), 2.42 (s, 2H), 2.14 (m, 6H), 1.60 (m, 6H), 1.25 (m, 3H), 0.86 (s, 6H).

Example 151

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide

Example 151A 1-(1,3-difluoropropan-2-yl)azetidin-3-amine

To a solution of tert-butyl azetidin-3-ylcarbamate (0.256 g) and 1,3-difluoropropan-2-one (0.154 g) in dichloromethane (2 mL) was added sodium triacetoxyborohydride (0.473 g) and the reaction was allowed to stirred at room temperature. After 16 hours, the reaction was quenched with saturated NaHCO₃ solution (10 mL) and extracted into dichloromethane (25 mL). The organic layer was dried and concentrated. Silica gel chromatography (GraceResolv 12 g) eluting with a gradient of 0.5% to 3.5% methanol/dichloromethane followed by treatment with HCl (4.0M in dioxane, 3 mL) and methanol (0.5 mL) for 2 hours gave the title compound after concentration.

Example 151B 4-(1-(1,3-difluoropropan-2-yl)azetidin-3-ylamino)-3-nitrobenzenesulfonamide To a suspension of 4-chloro-3-nitrobenzenesulfonamide (0.225 g) and 1-(1,3-difluoropropan-2-yl)azetidin-3-amine (0.193 g) in dioxane (5 mL) was added diisopropylamine (0.832 mL). The reaction was sonicated and then heated to 100° C. After stirring overnight, the reaction was concentrated and loaded onto silica gel (GraceResolv 12 g) and eluted with a gradient of 0.5% to 3.5% methanol/dichloromethane to give the title compound.

Example 151C 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide The title compound was prepared by substituting EXAMPLE 151B for EXAMPLE 1F and EXAMPLE 3J for EXAMPLE 1E in EXAMPLE 1G. ¹H NMR (300 MHz, dimethylsulfoxide-d₆) δ 11.66 (s, 1H), 11.54-11.28 (m, 1H), 8.54 (d, 1H), 8.45 (s, 1H), 8.01 (d, 1H), 7.82 (d, 1H), 7.48 (d, 3H), 7.34 (d, 2H), 7.04 (d, 2H), 6.90 (d, 1H), 6.67 (d, 1H), 6.37 (s, 1H), 6.20 (s, 1H), 4.64-4.23 (m, 6H), 3.81 (s, 2H), 3.08 (s, 4H), 2.75 (s, 3H), 2.15 (s, 7H), 1.95 (s, 2H), 1.38 (s, 2H), 0.92 (s, 6H).

Example 152

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide Example 152A tert-butyl (1-(methylsulfonyl)pyrrolidin-3-yl)methylcarbamate The title compound was prepared by substituting tert-butyl pyrrolidin-3-ylmethylcarbamate for tert-butyl piperidin-3-ylmethylcarbamate in EXAMPLE 147A.

Example 152B (1-(methylsulfonyl)pyrrolidin-3-yl)methanamine

The title compound was prepared by substituting EXAMPLE 152A for EXAMPLE 147A in EXAMPLE 147B.

Example 152C 4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide The title compound was prepared by substituting EXAMPLE 152B for EXAMPLE 147B in EXAMPLE 147C. ¹H NMR (400 MHz, dimethylsulfoxide-d₆) δ11.60 (s, 1H), 8.49 (m, 2H), 7.99 (s, 1H), 7.73 (m, 1H), 7.53 (d, 1H), 7.47 (s, 1H), 7.42 (m, 1H), 7.34 (d, 2H), 7.04 (m, 3H), 6.65 (m, 1H), 6.35 (s, 1H), 6.22 (s, 1H), 3.41 (m, 4H), 3.22 (m, 2H), 3.03 (m, 4H), 2.89 (s, 3H), 2.73 (m, 2H), 2.59 (m, 1H), 2.17 (m, 6H), 2.00 (m, 4H), 1.68 (m, 1H), 1.38 (t, 2H), 0.92 (s, 6H).

Example 153

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 153A tert-butyl (1-acetylpyrrolidin-3-yl)methylcarbamate The title compound was prepared by substituting tert-butyl pyrrolidin-3-ylmethylcarbamate for tert-butyl piperidin-3-ylmethylcarbamate and acetyl chloride for methanesulfonyl chloride in EXAMPLE 147A.

Example 153B 1-(3-(aminomethyl)pyrrolidin-1-yl)ethanone

The title compound was prepared by substituting EXAMPLE 153A for EXAMPLE 147A in EXAMPLE 147B.

Example 153C

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 153B for EXAMPLE 147B in EXAMPLE 147C. ¹H NMR (400 MHz, dimethylsulfoxide-d₆) δ 11.66 (s, 1H), 8.62 (m, 1H), 8.54 (s, 1H), 8.03 (m, 1H), 7.78 (d, 1H), 7.50 (m, 3H), 7.35 (t, 2H), 7.09 (s, 1H), 7.04 (d, 2H), 6.67 (dd, 1H), 6.37 (d, 1H), 6.20 (s, 1H), 3.56 (m, 1H), 3.42 (m, 4H), 3.43 (m, 4H), 3.23 (m, 1H), 3.07 (m, 4H), 2.74 (m, 2H), 2.16 (m, 6H), 1.93 (m, 5H), 1.38 (t, 2H), 0.93 (s, 6H).

Example 154

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 154A (R)-tert-butyl 1-acetylpyrrolidin-3-ylcarbamate The title compound was prepared by substituting (R)-tert-butyl pyrrolidin-3-ylcarbamate for tert-butyl piperidin-3-ylmethylcarbamate and acetyl chloride for methanesulfonyl chloride in EXAMPLE 147A.

Example 154B (R)-1-(3-aminopyrrolidin-1-yl)ethanone

The title compound was prepared by substituting EXAMPLE 154A for EXAMPLE 147A in EXAMPLE 147B.

Example 154C

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 154B for EXAMPLE 147B in EXAMPLE 147. $^1$H NMR (400 MHz, dimethylsulfoxide-$d_6$) δ 11.61 (s, 1H), 8.50 (s, 1H), 8.17 (d, 1H), 7.98 (s, 1H), 7.78 (s, 1H), 7.49 (m, 3H), 7.34 (d, 2H), 7.10 (m, 1H), 7.04 (d, 2H), 6.66 (dd, 1H), 6.35 (s, 1H), 6.22 (s, 1H), 4.34 (m, 1H), 3.81 (m, 1H), 3.58 (m, 1H), 3.43 (m, 1H), 3.05 (m, 4H), 2.74 (s, 2H), 2.19 (m, 9H), 1.96 (m, 5H), 1.38 (t, 2H), 0.94 (s, 6H).

Example 155

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide The title compound was prepared as described in EXAMPLE 120B using 3-methoxy-2,2-dimethylpropan-1-amine in place of EXAMPLE 120A. $^1$H NMR (500 MHz, dimethylsulfoxide-$d_6$) δ 11.69 (s, 1H), 11.32 (s, 1H), 8.92 (t, 1H), 8.57 (d, 1H), 8.04 (d, 1H), 7.80 (dd, 1H), 7.46-7.55 (m, 3H), 7.34 (d, 2H), 7.08 (d, 1H), 7.04 (d, 2H), 6.68 (dd, 1H), 6.36-6.42 (m, 1H), 6.19 (d, 1H), 3.25-3.30 (m, 5H), 3.19 (s, 2H), 3.07 (s, 4H), 2.76 (s, 2H), 2.17 (d, 6H), 1.95 (s, 2H), 1.38 (t, 2H), 0.96 (s, 6H), 0.92 (s, 6H).

Example 156

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide

Example 156A 4-(((1R,3R)-3-hydroxycyclopentyl)methylamino)-3-nitrobenzenesulfonamide The title compound was prepared by substituting (1R,3R)-3-hydroxycyclopentyl)methylamine for (tetrahydropyran-4-yl)methylamine in EXAMPLE 1F.

Example 156B 4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide The title compound was prepared by substituting EXAMPLE 156A for EXAMPLE 130C in EXAMPLE 130D. $^1$H NMR (500 MHz, pyridine-$d_5$) δ 13.05 (s, 1H), 9.29 (s, 1H), 8.62 (t, 1H), 8.43 (d, 1H), 8.32 (dd, 1H), 8.10 (d, 1H), 7.66 (m, 2H), 7.44 (d, 2H), 7.07 (d, 2H), 6.85 (d, 1H), 6.74 (dd, 1H), 6.54 (s, 1H), 6.49 (m, 1H), 4.60 (m, 1H), 3.19 (dd, 2H), 3.06 (m, 4H), 2.77 (s, 2H), 2.70 (m, 1H), 2.26 (t, 2H), 2.20-2.07 (m, 6H), 2.00 (m, 1H), 1.97 (s, 2H), 1.90 (m, 1H), 1.56 (m, 1H), 1.39 (t, 2H), 1.34 (m, 1H), 0.93 (s, 6H).

Example 157

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide

Example 157A 4-(((1S,3S)-3-hydroxycyclopentyl)methylamino)-3-nitrobenzenesulfonamide The title compound was prepared by substituting (1S,3S)-3-hydroxycyclopentyl)methylamine for (tetrahydropyran-4-yl)methylamine in EXAMPLE 1F.

Example 157B 4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide The title compound was prepared by substituting EXAMPLE 157A for EXAMPLE 130C in EXAMPLE 130D. $^1$H NMR (500 MHz, pyridine-$d_5$) δ 13.03 (s, 1H), 9.29 (s, 1H), 8.60 (t, 1H), 8.44 (d, 1H), 8.32 (dd, 1H), 8.14 (d, 1H), 7.66 (m, 2H), 7.44 (d, 2H), 7.07 (d, 2H), 6.83 (d, 1H), 6.75 (dd, 1H), 6.55 (s, 1H), 6.49 (m, 1H), 4.60 (m, 1H), 3.19 (dd, 2H), 3.06 (m, 4H), 2.77 (s, 2H), 2.70 (m, 1H), 2.26 (t, 2H), 2.20-2.07 (m, 6H), 2.00 (m, 1H), 1.97 (s, 2H), 1.90 (m, 1H), 1.56 (m, 1H), 1.39 (t, 2H), 1.34 (m, 1H), 0.93 (s, 6H).

Example 158

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide

Example 158A 4-(((1S,3R)-3-hydroxycyclopentyl)methylamino)-3-nitrobenzenesulfonamide The title compound was prepared by substituting (1S,3R)-3-hydroxycyclopentyl)methylamine for (tetrahydropyran-4-yl)methylamine in EXAMPLE 1F.

Example 158B 4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide The title compound was prepared by substituting EXAMPLE 158A for EXAMPLE 130C in EXAMPLE 130D. $^1$H NMR (500 MHz, pyridine-d$_5$) δ 12.94 (s, 1H), 9.25 (d, 1H), 8.59 (t, 1H), 8.48 (d, 1H), 8.27 (m, 2H), 7.66 (m, 2H), 7.45 (d, 2H), 7.08 (d, 2H), 6.77 (dd, 1H), 6.72 (d, 1H), 6.60 (d, 1H), 6.47 (m, 1H), 4.53 (m, 1H), 3.30 (m, 2H), 3.06 (m, 4H), 2.78 (s, 2H), 2.27 (m, 3H), 2.19-2.10 (m, 5H), 1.98 (m, 3H), 1.85-1.66 (m, 4H), 1.39 (t, 2H), 0.94 (s, 6H).

Example 159

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide Example 159A 4-(((1R,3S)-3-hydroxycyclopentyl)methylamino)-3-nitrobenzenesulfonamide The title compound was prepared by substituting (1R,3S)-3-hydroxycyclopentyl)methylamine for (tetrahydropyran-4-yl)methylamine in EXAMPLE 1F.

Example 159B 4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide The title compound was prepared by substituting EXAMPLE 158A for EXAMPLE 130C in EXAMPLE 130D. $^1$H NMR (500 MHz, pyridine-d$_5$) δ 13.02 (s, 1H), 9.28 (d, 1H), 8.59 (t, 1H), 8.44 (d, 1H), 8.29 (d, 1H), 8.13 (d, 1H), 7.66 (m, 2H), 7.44 (d, 2H), 7.08 (d, 2H), 6.82 (dd, 1H), 6.74 (d, 1H), 6.55 (d, 1H), 6.48 (m, 1H), 4.53 (m, 1H), 3.34 (m, 2H), 3.06 (m, 4H), 2.77 (s, 2H), 2.27 (m, 3H), 2.19-2.10 (m, 5H), 1.97 (m, 3H), 1.85-1.66 (m, 4H), 1.39 (t, 2H), 0.93 (s, 6H).

Example 160

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide The title compound was prepared by substituting (S)-3-aminopiperidin-2-one for 1-acetylpiperidin-4-amine in EXAMPLE 53B. $^1$H NMR (300 MHz, dimethylsulfoxide-d$_6$) δ 11.68 (br s, 1H), 8.88 (d, 1H), 8.57 (d, 1H), 8.04 (d, 1H), 7.95 (br s, 1H), 7.83 (dd, 1H), 7.55-7.46 (m, 3H), 7.35 (d, 2H), 7.16 (d, 1H), 7.05 (d, 2H), 6.68 (dd, 1H), 6.38 (m, 1H), 6.21 (d, 1H), 4.41 (m, 1H), 3.22 (m, 2H), 3.09 (br s, 4H), 2.78 (br s, 2H), 2.35-2.09 (m, 8H), 1.96 (br s, 2H), 1.86 (m, 2H), 1.39 (t, 2H), 0.93 (s, 6H).

Example 161

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide Example 161A tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)azetidine-1-carboxylate EXAMPLE 82 (305 mg). tert-butyl 3-(aminomethyl)azetidine-1-carboxylate (86 mg) and diisopropyl amine (0.202 mL) in dioxane (3 mL) were heated to 110° C. After stirring overnight, the reaction was concentrated. Silica gel chromatography (Reveleris, 12 g) eluting with a gradient of 0.5% to 3% methanol/dichloromethane (Flow=36 ml/minute) gave the title compound.

Example 161B 2-(1H-pyrrolo[2,3-b]pyridin-5-yloxy)-N-(4-(azetidin-3-ylmethylamino)-3-nitrophenylsulfonyl)-4-(4-((2-(4-chlorophenyl)-4,4-dimethylcyclohex-1-enyl)methyl)piperazin-1-yl)benzamide To a solution of EXAMPLE 161A (0.257 g) in dichloromethane (5 mL) was added trifluoroacetic acid (0.211 mL). After 30 minutes an additional 0.2 ml of trifluoroacetic acid was added. After 3 hours, the reaction was concentrated to give the title compound.

Example 161C 4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide A solution of EXAMPLE 161B (0.118 g), sodium triacetoxyborohydride (0.035 g) and 1,3-difluoropropan-2-one (0.012 g) were stirred together in dichloromethane (1 mL) overnight. The reaction was quenched with saturated aqueous NaHCO$_3$ solution (10 mL) and extracted into dichloromethane (30 mL). The organic layer was dried and concentrated. Silica gel chromatography (Reveleris 12 g) eluting with a gradient of 0.5% to 3.5% methanol/dichloromethane over 30 minutes (Flow=36 ml/min) gave the title compound. $^1$H NMR (300 MHz, dimethylsulfoxide-d$_6$) δ 11.67 (s, 1H), 11.47-11.21 (m, 1H), 8.85 (s, 1H), 8.55 (d, 1H), 8.03 (d, 1H), 7.80 (dd, 1H), 7.54-7.45 (m, 3H), 7.33 (s, 2H), 7.04 (d, 3H), 6.67 (d, 1H), 6.38 (dd, 1H), 6.20 (d, 1H), 4.43 (dt, 4H), 3.56 (t, 2H), 3.46 (s, 2H), 3.12 (m, 6H), 2.74 (m, 3H), 2.17 (m, 7H), 1.95 (s, 2H), 1.39 (d, 2H), 0.92 (s, 6H).

Example 162

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide The title compound was prepared by substituting oxetan-3-one for 1,3-difluoropropan-2-one in EXAMPLE 161C. $^1$H NMR (300 MHz, dimethylsulfoxide-d$_6$) δ 11.66 (s, 1H), 11.51-11.03 (m, 1H), 8.81 (s, 1H), 8.54 (d, 1H), 8.02 (d, 1H), 7.79 (dd, 1H), 7.50 (dd, 3H), 7.34 (d, 2H), 7.04 (d, 3H), 6.67 (d, 1H), 6.38 (dd, 1H), 6.20 (d, 1H), 4.57 (s, 2H), 4.43-4.35 (m, 2H), 3.82 (s, 1H), 3.59 (t, 2H), 3.44 (t, 2H), 3.20 (s, 2H), 3.06 (s, 4H), 2.73 (s, 3H), 2.18 (s, 6H), 1.95 (s, 2H), 1.39 (d, 2H), 0.92 (s, 6H).

Example 163

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide Example 163A tert-butyl 4-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)piperidine-1-carboxylate The title compound was prepared by substituting tert-butyl 4-(aminomethyl)piperidine-1-carboxylate for 1-acetylpiperidin-4-amine in EXAMPLE 53B.

Example 163B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylmethylamino)phenylsulfonyl)benzamide The title compound was prepared by substituting EXAMPLE 163A for EXAMPLE 1A in EXAMPLE 1B.

Example 163C 4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide The title compound was prepared by substituting EXAMPLE 163B for EXAMPLE 161B and oxetan-3-one for 1,3-difluoropropan-2-one in EXAMPLE 161C. $^1$H NMR (500 MHz, dimethylsulfoxide-d$_6$) δ 11.68 (s, 1H), 8.60 (t, 1H), 8.54 (d, 1H), 8.03 (d, 1H), 7.79 (dd, 1H), 7.50 (m, 3H), 7.34 (d, 2H), 7.09 (d, 1H), 7.04 (d, 2H), 6.67 (dd, 1H), 6.39 (m, 1H), 6.19 (d, 1H), 4.55 (t, 2H), 4.46 (t, 2H), 3.52 (br s, 1H), 3.28 (m, 2H), 3.17 (d, 1H), 3.06 (m, 4H), 2.82 (m, 2H), 2.74 (m, 2H), 2.17 (m, 6H), 1.95 (m, 3H), 1.72 (m, 3H), 1.38 (t, 2H), 1.28 (m, 2H), 0.92 (s, 6H).

Example 164

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide The title compound was prepared by substituting EXAMPLE 163B for (S)-tert-butyl pyrrolidin-3-ylcarbamate in EXAMPLE 142A. $^1$H NMR (500 MHz, dimethylsulfoxide-d$_6$) δ 11.96 (br s, 1H), 11.62 (br s, 1H), 8.50 (m, 2H), 7.98 (d, 1H), 7.72 (m, 1H), 7.52 (d, 1H), 7.45 (m, 2H), 7.34 (d, 2H), 7.04 (m, 2H), 6.94 (m, 1H), 6.64 (dd, 1H), 6.34 (m, 1H), 6.22 (d, 1H), 3.28 (m, 3H), 3.04 (m, 5H), 2.72 (s, 2H), 2.64 (m, 1H), 2.64 (m, 1H), 2.36 (m, 1H), 2.16 (m, 7H), 1.95 (s, 2H), 1.68 (m, 3H), 1.38 (t, 2H), 1.18 (m, 3H), 0.94 (s, 6H), 0.35 (m, 3H).

Example 165

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide Example 165A 4-((4-(2-fluoroethyl)morpholin-2-yl)methylamino)-3-nitrobenzenesulfonamide The title compound was prepared by substituting 2-fluoroethyl bromide for methyl iodide in EXAMPLE 134B.

Example 165B 4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 165A for EXAMPLE 130C in EXAMPLE 130D. $^1$H NMR (500 MHz, pyridine-d$_5$) δ 13.00 (s, 1H), 9.26 (d, 1H), 8.87 (t, 1H), 8.43 (d, 1H), 8.32 (dd, 1H), 8.11 (d, 1H), 7.66 (m, 2H), 7.44 (d, 2H), 7.07 (d, 2H), 6.92 (d, 1H), 6.75 (dd, 1H), 6.54 (d, 1H), 6.48 (dd, 1H), 3.93 (m, 1H), 4.63, 4.51 (dt, 2H), 3.95-3.85 (m, 2H), 3.68 (dt, 1H), 3.43-3.37 (m, 2H), 3.07 (m, 4H), 2.92 (d, 1H), 2.77 (s, 2H), 2.65 (m, 2H), 2.59 (m, 1H), 2.26 (m, 2H), 2.17-2.08 (m, 5H), 1.97 (s, 2H), 1.39 (t, 2H), 0.93 (s, 6H).

Example 166

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide Example 166A 4-((4-(2,2-difluoroethyl)morpholin-2-yl)methylamino)-3-nitrobenzenesulfonamide The title compound was prepared by substituting 2,2-difluoro-ethyl bromide for methyl iodide in EXAMPLE 134B.

Example 166B 4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 166A for EXAMPLE 130C in EXAMPLE 130D. ¹H NMR (500 MHz, pyridine-d₅) δ 13.01 (s, 1H), 9.26 (d, 1H), 8.86 (t, 1H), 8.43 (d, 1H), 8.34 (dd, 1H), 8.11 (d, 1H), 7.66 (m, 2H), 7.44 (d, 2H), 7.07 (d, 2H), 6.93 (d, 1H), 6.75 (dd, 1H), 6.54 (d, 1H), 6.48 (m, 1H), 6.31, 6.20, 6.09 (tt, 1H), 3.90 (m, 1H), 3.85 (d, 1H), 3.67 (dt, 1H), 3.49-3.30 (m, 2H), 3.07 (m, 4H), 2.84 (d, 1H), 2.82-2.75 (m, 4H), 2.69 (d, 1H), 2.33 (dt, 1H), 2.27-2.20 (m, 3H), 2.14 (m, 4H), 1.97 (s, 2H), 1.39 (t, 2H), 0.93 (s, 6H).

Example 167

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide Example 167A 4-((4-fluoro-1-(oxetan-3-yl)piperidin-4-yl)methoxy)-3-nitrobenzenesulfonamide The title compound was prepared by substituting EXAMPLE 173A for tert-butyl piperazine-1-carboxylate and 3-oxetanone for 4'-chlorobiphenyl-2-carboxaldehyde in EXAMPLE 1A.

Example 167B 4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide The title compound was prepared by substituting EXAMPLE 167A for EXAMPLE 11B in EXAMPLE 11D. ¹H NMR (300 MHz, dimethylsulfoxide-d₆) δ 11.69 (s, 1H), 8.39 (s, 1H), 8.09 (d, 1H), 8.04 (d, 1H), 7.52 (m, 4H), 7.35 (d, 2H), 7.05 (m, 2H), 6.68 (dd, 1H), 6.40 (dd, 1H), 6.20 (s, 1H), 4.57 (t, 2H), 4.48 (m, 2H), 4.38 (d, 2H), 4.02 (m, 1H), 3.63 (m, 2H), 3.08 (m, 4H), 2.74 (m, 4H), 2.17 (m, 6H), 1.88 (m, 6H), 1.40 (t, 2H), 0.93 (s, 6H).

Example 168

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide Example 168A (S)-methyl 4,4-difluoropyrrolidine-2-carboxylate (S)-1-tert-butyl 2-methyl 4,4-difluoropyrrolidine-1,2-dicarboxylate (0.472 g) in CH₂Cl₂ (1 mL) was treated with trifluoroacetic acid (1.4 mL), stirred at ambient temperature for 4 hours, and concentrated. The product was free-based using a MEGA BE-SCX column with 1:1 CH₂Cl₂/methanol as eluent for the trifluoroacetic acid. The product was released from the column with 5% (7 M ammonia in methanol) in CH₂Cl₂ as eluent.

Example 168B (S)-methyl 4,4-difluoro-1-(oxetan-3-yl)pyrrolidine-2-carboxylate

The title compound was prepared by substituting EXAMPLE 168A for tert-butyl piperazine-1-carboxylate and 3-oxetanone for 4'-chlorobiphenyl-2-carboxaldehyde in EXAMPLE 1A.

Example 168C (S)-(4,4-difluoro-1-(oxetan-3-yl)pyrrolidin-2-yl)methanol

EXAMPLE 168B (0.180 g) in tetrahydrofuran (3 mL) was treated sequentially with a solution of calcium chloride (0.245 g) in ethanol (3 mL) and NaBH₄ (0.167 g) and then stirred at ambient temperature for 7 hours. The reaction was quenched with saturated aqueous NH₄Cl solution and extracted with ethyl acetate. The combined extracts were washed with brine, dried (MgSO₄), filtered, concentrated and chromatographed on silica gel with 50% ethyl acetate in hexanes as eluent to give the product.

Example 168D (S)-4-((4,4-difluoro-1-(oxetan-3-yl)pyrrolidin-2-yl)methoxy)-3-nitrobenzenesulfonamide The title compound was prepared by substituting EXAMPLE 168C for (tetrahydro-2H-pyran-4-yl)methanol in EXAMPLE 24A.

Example 168E 4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide The title compound was prepared by substituting EXAMPLE 168D for EXAMPLE 11B in EXAMPLE 11D. ¹H NMR (300 MHz, dimethylsulfoxide-d₆) δ 11.69 (s, 1H), 8.38 (s, 1H), 8.06 (m, 2H), 7.49 (m, 4H), 7.35 (d, 2H), 7.05 (d, 2H), 6.68 (dd, 1H), 6.40 (m, 1H), 6.21 (s, 1H), 4.54 (m, 3H), 4.43 (t, 1H), 4.23 (m, 1H), 4.12 (m, 2H), 3.44 (m, 2H), 3.12 (m, 7H), 2.58 (m, 1H), 2.29 (m, 7H), 1.97 (s, 2H), 1.40 (t, 2H), 0.93 (s, 6H).

Example 169

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide

Example 169A tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared as described in EXAMPLE 53B by replacing 1-acetylpiperidin-4-amine with tert-butyl 3-(aminomethyl)morpholine-4-carboxylate.

Example 169B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-(morpholin-3-ylmethylamino)-3-nitrophenylsulfonyl)benzamide The title compound was prepared as described in EXAMPLE 139B by replacing EXAMPLE 139A with EXAMPLE 169A.

Example 169C 4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide The title compound was prepared as described in EXAMPLE 139C by replacing EXAMPLE 139B and oxetan-3-one with EXAMPLE 169B and tetrahydropyran-4-one, respectively. $^1$H NMR (300 MHz, dimethylsulfoxide-$d_6$) δ 11.69 (s, 1H), 8.77 (m, 1H), 8.57 (d, 1H), 8.05 (d, 1H), 7.84 (dd, 1H), 7.52 (m, 3H), 7.34 (m, 2H), 7.03 (m, 3H), 6.68 (dd, 1H), 6.40 (dd, 1H), 6.18 (d, 1H), 3.86 (m, 2H), 3.72 (m, 2H), 3.11 (m, 6H), 2.74 (m, 4H), 2.20 (m, 6H), 1.95 (m, 3H), 1.51 (m, 7H), 0.92 (s, 6H).

Example 170

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide The title compound was prepared as described in EXAMPLE 139C by replacing EXAMPLE 139B and oxetan-3-one with EXAMPLE 169B and cyclobutanone. $^1$H NMR (300 MHz, dimethylsulfoxide-$d_6$) δ 11.68 (s, 1H), 8.72 (s, 1H), 8.57 (d, 1H), 8.04 (d, 1H), 7.84 (dd, 1H), 7.52 (m, 3H), 7.34 (m, 3H), 7.03 (m, 4H), 6.67 (dd, 1H), 6.39 (dd, 1H), 6.18 (d, 1H), 3.47 (m, 3H), 3.10 (m, 6H), 2.72 (m, 6H), 2.25 (m, 8H), 1.95 (m, 4H), 1.56 (m, 3H), 1.38 (m, 2H), 0.92 (s, 6H).

Example 171

4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide The title compound was prepared as described in EXAMPLE 139C by replacing EXAMPLE 139B and oxetan-3-one with EXAMPLE 169B and 3-oxotetrahydrofuran, respectively. $^1$H NMR (300 MHz, dimethylsulfoxide-$d_6$) δ 11.64 (s, 1H), 8.66 (s, 1H), 8.53 (d, 1H), 8.01 (d, 1H), 7.80 (d, 1H), 7.50 (m, 3H), 7.35 (d, 2H), 7.05 (d, 2H), 6.98 (d, 1H), 6.66 (dd, 1H), 6.37 (d, 1H), 6.19 (d, 1H), 3.68 (m, 8H), 3.05 (m, 6H), 2.85 (m, 3H), 2.73 (s, 2H), 2.25 (m, 6H), 1.91 (m, 3H), 1.37 (m, 3H), 0.95 (m, 6H).

Example 172

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide The title compound was prepared by substituting EXAMPLE 163B for tert-butyl piperazine-1-carboxylate and 1,3-difluoropropan-2-one for 4'-chlorobiphenyl-2-carboxaldehyde in EXAMPLE 1A. $^1$H NMR (500 MHz, dimethylsulfoxide-$d_6$) δ 11.67 (s, 1H), 11.40 (br s, 1H), 8.57 (m, 2H), 8.03 (d, 1H), 7.78 (d, 1H), 7.50 (m, 3H), 7.34 (d, 2H), 7.07 (d, 1H), 7.04 (d, 2H), 6.67 (dd, 1H), 6.38 (m 1H), 6.19 (d, 1H), 4.63 (d, 2H), 4.53 (d, 2H), 3.28 (m, 2H), 3.07 (m, 4H), 2.89 (m, 2H), 2.74 (m, 2H), 2.40 (m, 2H), 2.16 (m, 6H), 1.95 (s, 2H), 1.67 (m, 3H), 1.38 (t, 2H), 1.23 (m, 3H), 0.94 (s, 6H).

Example 173

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide

Example 173A 4-((4-fluoropiperidin-4-yl)methoxy)-3-nitrobenzenesulfonamide

The title compound was prepared by substituting EXAMPLE 126B for EXAMPLE 1A in EXAMPLE 1B.

Example 173B 4-((1-cyclopropyl-4-fluoropiperidin-4-yl)methoxy)-3-nitrobenzenesulfonamide To EXAMPLE 173A (0.24 g) in methanol (3 mL) was added 3 Å molecular sieves (0.1 g), followed sequentially by acetic acid (0.31 mL), (1-ethoxycyclopropoxy)trimethylsilane (0.64 mL), and sodium cyanoborohydride (0.148 g). The reaction was heated under reflux overnight. After cooling, the reaction mixture was loaded onto a silica gel column. After drying, the column was eluted with 100:2:0.2 ethyl acetate/methanol/NH$_4$OH to give the title compound.

Example 173C 4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide The title compound was prepared by substituting EXAMPLE 173B for EXAMPLE 11B in EXAMPLE 11D. $^1$H NMR (500 MHz, dimethylsulfoxide-$d_6$) δ 11.65 (s, 1H), 8.33 (s, 1H), 8.01 (m, 2H), 7.53 (d, 1H), 7.48-7.49 (m, 2H), 7.34-7.38 (m, 3H), 7.04 (d, 2H), 6.66 (dd, 1H), 6.38 (dd, 1H), 6.21 (d, 1H), 4.32 (d, 2H), 3.70-3.77 (m, 2H), 3.07 (s, 4H), 2.92 (s, 2H), 2.80 (s, 2H), 2.58 (s, 2H), 2.25 (s, 4H), 2.13-2.16 (m 2H), 1.38 (t, 2H), 0.92 (s, 6H), 0.40-0.49 (m, 4H).

Example 174

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide A suspension of EXAMPLE 53A (120 mg), (4-methoxyphenyl)methanamine (31 mg) and Hunig's Base (0.159 mL) in dimethylsulfoxide (2 mL) was heated for 2 hours at 150° C. in a Biotage Initiator microwave reactor. The reaction mixture was diluted with methanol (2 mL) and purified by reverse phase HPLC (C8, 30%-100% $CH_3CN$/water/0.1% trifluoroacetic acid). $^1$H NMR (500 MHz, pyridine-$d_5$) δ 13.07 (s, 1H), 9.32 (d, 1H), 9.17 (t, 1H), 8.43 (d, 1H), 8.28 (dd, 1H), 8.08 (d, 1H), 7.64-7.68 (m, 2H), 7.44 (d, 2H), 7.38 (d, 2H), 7.07 (d, 2H), 6.97-7.02 (m, 2H), 6.90 (d, 1H), 6.74 (dd, 1H), 6.52 (d, 1H), 6.49 (dd, 1H), 4.55 (d, 2H), 3.68 (s, 3H), 3.03-3.09 (m, 4H), 2.77 (s, 2H), 2.26 (t, 2H), 2.10-2.17 (m, 4H), 1.97 (s, 2H), 1.39 (t, 2H), 0.93 (s, 6H).

Example 175

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide The title compound was prepared by substituting (3-trifluoromethoxyphenyl)methanamine for (4-methoxyphenyl)methanamine in EXAMPLE 174. $^1$H NMR (500 MHz, pyridine-$d_5$) δ 13.06 (s, 1H), 9.38 (t, 1H), 9.31 (d, 1H), 8.42 (d, 1H), 8.28 (dd, 1H), 8.08 (d, 1H), 7.65 (ddd, 2H), 7.41-7.46 (m, 3H), 7.36-7.40 (m, 2H), 7.07 (d, 2H), 6.88 (d, 1H), 6.74 (dd, 1H), 6.52 (d, 1H), 6.49 (d, 1H), 4.73 (d, 2H), 3.02-3.08 (m, 4H), 2.77 (s, 2H), 2.22-2.28 (m, 2H), 2.09-2.16 (m, 4H), 1.97 (s, 2H), 1.39 (t, 2H), 0.93 (s, 6H).

Example 176

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide The title compound was prepared by substituting (3-methoxyphenyl)methanamine for (4-methoxyphenyl)methanamine in EXAMPLE 174. $^1$H NMR (500 MHz, pyridine-$d_5$) δ 13.06 (s, 1H), 9.27-9.32 (m, 2H), 8.42 (d, 1H), 8.26 (dd, 1H), 8.08 (d, 1H), 7.64-7.67 (m, 2H), 7.44 (d, 2H), 7.32 (t, 1H), 7.14 (s, 1H), 7.04-7.09 (m, 3H), 6.88-6.94 (m, 2H), 6.74 (dd, 1H), 6.52 (d, 1H), 6.48-6.50 (m, 1H), 4.64 (d, 2H), 3.68 (s, 3H), 3.03-3.09 (m, 4H), 2.77 (s, 2H), 2.26 (t, 2H), 2.10-2.18 (m, 4H), 1.97 (s, 2H), 1.39 (t, 2H), 0.93 (s, 6H).

Example 177

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide The title compound was prepared by substituting (4-difluoromethoxyphenyl)methanamine for (4-methoxyphenyl)methanamine in EXAMPLE 174. $^1$H NMR (500 MHz, pyridine-$d_5$) δ 13.06 (s, 1H), 9.32 (d, 1H), 9.28 (t, 1H), 8.42 (d, 1H), 8.28 (dd, 1H), 8.07 (d, 1H), 7.66 (t, 1H), 7.64 (d, 1H), 7.58 (s, 1H), 7.44 (s, 2H), 7.26 (s, 1H), 7.25 (d, 1H), 7.07 (d, 2H), 6.87 (d, 1H), 6.74 (dd, 1H), 6.52 (d, 1H), 6.49 (dd, 1H), 4.64 (d, 2H), 3.03-3.10 (m, 4H), 2.77 (s, 2H), 2.26 (t, 2H), 2.11-2.17 (m, 4H), 1.97 (s, 2H), 1.39 (t, 2H), 0.93 (s, 6H).

Example 178

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide The title compound was prepared by substituting 1,4-dioxa-spiro[4.5]dec-8-ylamine for 1-acetylpiperidin-4-amine in EXAMPLE 53B. $^1$H NMR (300 MHz, dimethylsulfoxide-$d_6$) δ 11.67 (br s, 1H), 8.55 (d, 1H), 8.26 (d, 1H), 8.04 (d, 1H), 7.81 (dd, 1H), 7.54-7.46 (m, 3H), 7.35 (d, 2H), 7.15 (d, 1H), 7.04 (d, 2H), 6.68 (dd, 1H), 6.38 (m, 1H), 6.19 (d, 1H), 3.89 (s, 4H), 3.78 (m, 1H), 3.07 (br s, 4H), 2.78 (br s, 2H), 2.28-2.11 (m, 6H), 2.00-1.88 (m, 4H), 1.75-1.57 (m, 4H), 1.54-1.35 (m, 4H), 0.92 (s, 6H).

Example 179

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 179A tert-butyl trans-4-acetamidocyclohexylcarbamate

Tert-butyl (trans)-4-aminocyclohexylcarbamate (1.500 g) and triethylamine (2.93 mL, 2.125 g) were added to dichloromethane and stirred until the tert-butyl (trans)-4-aminocyclohexylcarbamate had dissolved completely. Acetyl chloride (0.577 g) was added slowly, and the solution was stirred at room temperature for 16 hours. The solvent was removed, and the residue taken up in ethyl acetate, washed with pH 4 buffer, washed with brine, dried with anhydrous sodium sulfate, and filtered. The filtrate was concentrated under vacuum.

Example 179B

N-(trans-4-aminocyclohexyl)acetamide

The title compound was prepared by substituting EXAMPLE 179A for EXAMPLE 1A in EXAMPLE 1B.

Example 179C

Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 179B for 1-acetylpiperidin-4-amine in EXAMPLE 53B. $^1$H NMR (300 MHz, dimethylsulfoxide-$d_6$) δ 11.67 (br s, 1H), 8.55 (d, 1H), 8.20 (d, 1H), 8.04 (d, 1H), 7.82-7.76 (m, 2H), 7.53-7.46 (m, 3H), 7.35 (d, 2H), 7.16 (d, 1H), 7.04 (d, 2H), 6.68 (dd, 1H), 6.39 (m, 1H), 6.19 (d, 1H), 3.57 (m, 2H), 3.07 (br s, 4H), 2.75 (br s, 2H), 2.28-2.10 (m, 6H), 2.03-1.94 (m, 4H), 1.83 (d, 2H), 1.80 (s, 3H), 1.55-1.24 (m, 6H), 0.92 (s, 6H).

Example 180

4-(4-{[2-(4-chlorophenyl)-4,4-dimethylcyclohex-1-en-1-yl]methyl}piperazin-1-yl)-N-[(4-{[(3R)-1-(2,2-difluoro ethyl)pyrrolidin-3-yl]amino}-3-nitrophenyl)sulfonyl]-2-(1H-pyrrolo[2,3-b]pyridin-5-yloxy)benzamide

Example 180A (R)-tert-butyl 1-(2,2-difluoroethyl)pyrrolidin-3-ylcarbamate

To a solution of (R)-tert-butyl pyrrolidin-3-ylcarbamate (500 mg) and 1,1-difluoro-2-iodoethane (618 mg) in N,N-dimethylformamide (6 mL) was added N-ethyl-N-isopropylpropan-2-amine (1.403 ml) and the mixture was stirred at 70° C. for 72 hours. The reaction mixture was concentrated and the crude product was purified on silica gel with methanol/dichloromethane.

Example 180B (R)-1-(2,2-difluoro ethyl)pyrrolidin-3-amine

To a solution of EXAMPLE 180A (525 mg) in a mixture of dichloromethane (3 mL) and methanol (4.0 mL) was added hydrogen chloride, 4M in dioxane (5.24 mL) and the reaction was stirred for 1.5 hours. The reaction was concentrated and the crude material was taken up in dichloromethane and the solvent evaporated, then taken up in ether and the solvent evaporated, and then dried on high vacuum.

Example 180C (R)-4-(1-(2,2-difluoroethyl)pyrrolidin-3-ylamino)-3-nitrobenzenesulfonamide The title compound was prepared by substituting EXAMPLE 180B for (tetrahydropyran-4-yl)methylamine in EXAMPLE 1F.

Example 180D 4-(4-{[2-(4-chlorophenyl)-4,4-dimethylcyclohex-1-en-1-yl]methyl}piperazin-1-yl)-N-[(4-{[(3R)-1-(2,2-difluoro ethyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 180C for EXAMPLE 130C in EXAMPLE 130D. $^1$H NMR (500 MHz, pyridine-$d_5$) δ 13.02 (m, 1H), 9.27 (d, 1H), 8.55 (d, 1H), 8.43 (d, 1H), 8.35 (dd, 1H), 8.10 (d, 1H), 7.64-7.68 (m, 2H), 7.44 (d, 2H), 7.07 (d, 2H), 6.83 (d, 1H), 6.75 (dd, 1H), 6.54 (m, 1H), 6.48 (m, 1H), 6.04-6.29 (m, 1H), 4.06 (m, 1H), 3.07 (m, 4H), 2.83-2.95 (m, 4H), 2.74-2.82 (m, 3H), 2.47 (m, 1H), 2.09-2.30 (m, 8H), 1.97 (s, 2H), 1.67 (m, 1H), 1.39 (t, 2H), 0.93 (s, 6H).

Example 181

4-(4-{[2-(4-chlorophenyl)-4,4-dimethylcyclohex-1-en-1-yl]methyl}piperazin-1-yl)-N-[(4-{[(3S)-1-(2-fluoro ethyl)pyrrolidin-3-yl]amino}-3-nitrophenyl)sulfonyl]-2-(1H-pyrrolo[2,3-b]pyridin-5-yloxy)benzamide

Example 181A (S)-tert-butyl 1-(2-fluoroethyl)pyrrolidin-3-ylcarbamate

The title compound was prepared by substituting 1-fluoro-2-iodoethane for 1,1-difluoro-2-iodoethane and (S)-tert-butyl pyrrolidin-3-ylcarbamate for (R)-tert-butyl pyrrolidin-3-ylcarbamate in EXAMPLE 180A.

Example 181B (S)-1-(2-fluoroethyl)pyrrolidin-3-amine

The title compound was prepared by substituting EXAMPLE 181A for EXAMPLE 180A in EXAMPLE 180B.

Example 181C (S)-4-(1-(2-fluoroethyl)pyrrolidin-3-ylamino)-3-nitrobenzenesulfonamide The title compound was prepared by substituting EXAMPLE 181B for (tetrahydropyran-4-yl)methylamine in EXAMPLE 1F.

Example 181D 4-(4-{[2-(4-chlorophenyl)-4,4-dimethylcyclohex-1-en-1-yl]methyl}piperazin-1-yl)-N-[(4-{[(3S)-1-(2-fluoro ethyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 181C for EXAMPLE 130C in EXAMPLE 130D. $^1$H NMR (500 MHz, pyridine-$d_5$) δ 13.00 (m, 1H), 9.26 (d, 1H), 8.56 (d, 1H), 8.43 (d, 1H), 8.34 (dd, 1H), 8.10 (d, 1H), 7.63-7.66 (m, 2H), 7.44 (d, 2H), 7.07 (d, 2H), 6.82 (d, 1H), 6.75 (dd, 1H), 6.54 (d, 1H), 6.48 (m, 1H), 4.60 (t, 1H), 4.51 (t, 1H), 4.05 (m, 1H), 3.07 (m, 4H), 2.84 (m, 1H), 2.66-2.79 (m, 6H), 2.39 (q, 1H), 2.20-2.29 (m, 3H), 2.15 (m, 5H), 1.97 (s, 2H), 1.66 (m, 1H), 1.39 (t, 2H), 0.94 (s, 6H).

Example 182

4-(4-{[2-(4-chlorophenyl)-4,4-dimethylcyclohex-1-en-1-yl]methyl}piperazin-1-yl)-N-[(4-{[(3S)-1-(2,2-difluoro ethyl)pyrrolidin-3-yl]amino}-3-nitrophenyl)sulfonyl]-2-(1H-pyrrolo[2,3-b]pyridin-5-yloxy)benzamide

Example 182A (S)-tert-butyl 1-(2,2-difluoroethyl)pyrrolidin-3-ylcarbamate

The title compound was prepared by substituting (S)-tert-butyl pyrrolidin-3-ylcarbamate for (R)-tert-butyl pyrrolidin-3-ylcarbamate in EXAMPLE 180A.

Example 182B (S)-1-(2,2-difluoroethyl)pyrrolidin-3-amine

The title compound was prepared by substituting EXAMPLE 182A for EXAMPLE 180A in EXAMPLE 180B.

Example 182C (S)-4-(1-(2,2-difluoroethyl)pyrrolidin-3-ylamino)-3-nitrobenzenesulfonamide The title compound was prepared by substituting EXAMPLE 182B for (tetrahydropyran-4-yl)methylamine in EXAMPLE 1F.

Example 182D 4-(4-{[2-(4-chlorophenyl)-4,4-dimethylcyclohex-1-en-1-yl]methyl}piperazin-1-yl)-N-[(4-{[(3S)-1-(2,2-difluoro ethyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 182C for EXAMPLE 130C in EXAMPLE 130D. $^1$H NMR (500 MHz, pyridine-$d_5$) δ 13.02 (m, 1H), 9.27 (d, 1H), 8.54 (d, 1H), 8.43 (d, 1H), 8.35 (dd, 1H), 8.11 (d, 1H), 7.64-7.68 (m, 2H), 7.44 (d, 2H), 7.07 (d, 2H), 6.82 (d, 1H), 6.75 (dd, 1H), 6.54 (d, 1H), 6.48 (m, 1H), 6.04-6.29 (m, 1H), 4.06 (m, 1H), 3.07 (m, 4H), 2.83-2.95 (m, 4H), 2.74-2.82 (m, 3H), 2.47 (m, 1H), 2.09-2.30 (m, 8H), 1.97 (s, 2H), 1.67 (m, 1H), 1.39 (t, 2H), 0.93 (s, 6H).

Example 183

4-(4-{[2-(4-chlorophenyl)-4,4-dimethylcyclohex-1-en-1-yl]methyl}piperazin-1-yl)-N-[(4-{[(3R)-1-(2-fluoro ethyl)pyrrolidin-3-yl]amino}-3-nitrophenyl)sulfonyl]-2-(1H-pyrrolo[2,b]pyridin-5-yloxy)benzamide

Example 183A (R)-tert-butyl 1-(2-fluoroethyl)pyrrolidin-3-ylcarbamate

The title compound was prepared by substituting 1-fluoro-2-iodoethane for 1,1-difluoro-2-iodoethane in EXAMPLE 180A.

Example 183B (R)-1-(2-fluoroethyl)pyrrolidin-3-amine

The title compound was prepared by substituting EXAMPLE 183A for EXAMPLE 180A in EXAMPLE 180B.

Example 183C (R)-4-(1-(2-fluoroethyl)pyrrolidin-3-ylamino)-3-nitrobenzenesulfonamide The title compound was prepared by substituting EXAMPLE 183B for (tetrahydropyran-4-yl)methylamine in EXAMPLE 1F.

Example 183D 4-(4-{[2-(4-chlorophenyl)-4,4-dimethylcyclohex-1-en-1-yl]methyl}piperazin-1-yl)-N-[(4-{[(3R)-1-(2-fluoro ethyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 183C for EXAMPLE 130C in EXAMPLE 130D. $^1$H NMR (500 MHz, pyridine-$d_5$) δ 13.00 (m, 1H), 9.26 (d, 1H), 8.56 (d, 1H), 8.43 (d, 1H), 8.34 (dd, 1H), 8.10 (d, 1H), 7.63-7.66 (m, 2H), 7.44 (d, 2H), 7.07 (d, 2H), 6.83 (d, 1H), 6.75 (dd, 1H), 6.54 (d, 1H), 6.48 (m, 1H), 4.60 (t, 1H), 4.50 (t, 1H), 4.04 (m, 1H), 3.07 (m, 4H), 2.84 (m, 1H), 2.66-2.79 (m, 6H), 2.39 (q, 1H), 2.19-2.28 (m, 3H), 2.14 (m, 5H), 1.97 (s, 2H), 1.66 (m, 1H), 1.39 (t, 2H), 0.94 (s, 6H).

Example 184

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide

Example 184A (S)-tert-butyl 3-((2-nitro-4-sulfamoylphenoxy)methyl)pyrrolidine-1-carboxylate To a solution of (S)-tert-butyl 3-(hydroxymethyl)pyrrolidine-1-carboxylate (0.300 g) in tetrahydrofuran (5 mL) was added sodium hydride (0.238 g). After stirring for 15 minutes, 4-fluoro-3-nitrobenzenesulfonamide (0.295 g) was added and reaction stirred at room temperature. After 1 hour, the reaction was partitioned between water (25 mL) and dichloromethane (50 mL) and the reaction quenched with 1N aqueous HCl (5.96 mL). The organic layer was separated, dried over magnesium sulfate, filtered, and concentrated. Silica gel chromatography (Reveleris 12 g) eluting with a gradient of 0.2% to 2% methanol/dichloromethane over 30 minutes (flow=36 m/minute) gave the title compound.

Example 184B (S)-3-nitro-4-((1-(oxetan-3-yl)pyrrolidin-3-yl)methoxy)benzenesulfonamide To (S)-tert-butyl 3-((2-nitro-4-sulfamoylphenoxy)methyl)pyrrolidine-1-carboxylate (0.433 g) was added hydrogen chloride (4.0M in dioxane, 1.0 mL). After stirring for 1 hour, the reaction was concentrated and partitioned between dichloromethane (50 mL) and saturated aqueous NaHCO$_3$ solution (50 mL). The aqueous layer was separated and concentrated. The residue was triturated with methanol (100 mL), filtered and concentrated and treated with sodium cyanoborohyde (0.068 g) and cyclobutanone (0.078 g) and stirred overnight. The reaction was partitioned between dichloromethane (50 mL) and water (25 mL) and saturated aqueous NaHCO$_3$ (10 mL). The organic layer was dried over magnesium sulfate, filtered, and concentrated to give the title compound.

Example 184C 4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide The title compound was prepared by substituting EXAMPLE 184B for EXAMPLE 1F and EXAMPLE 3J for EXAMPLE 1E in EXAMPLE 1G $^1$H NMR (300 MHz, dimethylsulfoxide-d$_6$) δ 11.64 (s, 1H), 11.45-11.01 (m, 1H), 8.30 (d, 1H), 7.98 (dd, 2H), 7.60-7.43 (m, 3H), 7.33 (t, 3H), 7.04 (d, 2H), 6.74-6.59 (m, 1H), 6.37 (dd, 1H), 6.21 (d, 1H), 4.49 (td, 2H), 4.33 (s, 1H), 4.13 (dd, 2H), 3.79 (s, 2H), 3.44 (dd, 2H), 3.07 (s, 4H), 2.74 (d, 6H), 2.19 (d, 6H), 1.98 (d, 2H), 1.74-1.52 (m, 1H), 1.39 (t, 2H), 0.92 (s, 6H).

Example 185

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide The title compound was prepared by substituting (4-hydroxyphenyl)methanamine for (4-methoxyphenyl)methanamine in EXAMPLE 174. $^1$H NMR (500 MHz, pyridine-d$_5$) δ 13.06 (s, 1H), 11.67 (bs, 1H), 9.32 (d, 1H), 9.14 (s, 1H), 8.44 (d, 1H), 8.28 (dd, 1H), 8.09 (d, 1H), 7.65-7.68 (m, 2H), 7.44 (d, 2H), 7.37-7.41 (m, 2H), 7.19 (s, 2H), 7.07 (d, 2H), 6.93 (d, 1H), 6.75 (dd, 1H), 6.53 (d, 1H), 6.49 (dd, 1H), 4.54 (d, 2H), 3.02-3.09 (m, 4H), 2.77 (s, 2H), 2.22-2.29 (m, 2H), 2.10-2.17 (m, 4H), 1.97 (d, 2H), 1.39 (t, 2H), 0.94 (s, 6H).

Example 186

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide The title compound was prepared by substituting (3-hydroxyphenyl)methanamine for (4-methoxyphenyl)methanamine in EXAMPLE 174. $^1$H NMR (500 MHz, pyridine-d$_5$) δ 13.06 (s, 1H), 11.67 (bs, 1H), 9.27-9.32 (m, 2H), 8.43 (d, 1H), 8.20 (dd, 1H), 8.08 (d, 1H), 7.66 (t, 2H), 7.44 (d, 2H), 7.33 (t, 1H), 7.25 (s, 1H), 7.13 (dd, 1H), 7.07 (d, 2H), 6.98 (d, 1H), 6.88 (d, 1H), 6.74 (dd, 1H), 6.52 (d, 1H), 6.49 (dd, 1H), 4.64 (d, 2H), 3.02-3.09 (m, 4H), 2.77 (s, 2H), 2.22-2.28 (m, 2H), 2.09-2.16 (m, 4H), 1.97 (s, 2H), 1.39 (t, 2H), 0.93 (s, 6H).

Example 187

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide The title compound was prepared by substituting (3-difluoromethoxyphenyl)methanamine for (4-methoxyphenyl)methanamine in EXAMPLE 174. $^1$H NMR (500 MHz, pyridine-d$_5$) δ 13.06 (s, 1H), 9.34 (t, 1H), 9.30 (d, 1H), 8.42 (d, 1H), 8.26 (dd, 1H), 8.08 (d, 1H), 7.66 (ddd, 2H), 7.40-7.45 (m, 3H), 7.36 (t, 1H), 7.27-7.30 (m, 2H), 7.19 (d, 1H), 7.07 (d, 2H), 6.87 (d, 1H), 6.74 (dd, 1H), 6.52 (d, 1H), 6.49 (dd, 1H), 4.69 (d, 2H), 3.02-3.08 (m, 4H), 2.77 (s, 2H), 2.26 (t, 2H), 2.09-2.16 (m, 4H), 1.97 (s, 2H), 1.39 (t, 2H), 0.93 (s, 6H).

Example 188

4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide Example 188A Cis-methyl 3-morpholinocyclopentanecarboxylate The title compound was prepared by substituting methyl 3-oxocyclopentanecarboxylate for 4'-chlorobiphenyl-2-carboxaldehyde and morpholine for tert-butyl piperazine-1-carboxylate in EXAMPLE 1A.

Example 188B

Cis-3-morpholinocyclopentyl)methanol

The title compound was prepared by substituting EXAMPLE 188A for EXAMPLE 101C in EXAMPLE 101D.

Example 188C 4-((Cis-3-morpholinocyclopentyl)methoxy)-3-nitrobenzenesulfonamide

The title compound was prepared by substituting EXAMPLE 188B for (1,4-dioxan-2-yl)methanol in EXAMPLE 12A.

Example 188D 4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide The title compound was prepared by substituting EXAMPLE 188C for EXAMPLE 11B in EXAMPLE 11D. $^1$H NMR (500 MHz, dimethylsulfoxide-$d_6$) δ 11.57 (s, 1H), 8.17 (m, 1H), 7.94 (m, 1H), 7.82 (m, 1H), 7.56 (d, 1H), 7.44 (t, 1H), 7.34 (m, 3H), 7.16 (m, 1H), 7.05 (d, 2H), 6.64 (dd, 1H), 6.33 (m, 1H), 6.24 (d, 1H), 4.06 (m, 2H), 3.62 (m, 4H), 3.03 (m, 4H), 2.75 (s, 2H), 2.35 (m, 2H), 2.19 (m, 6H), 2.03 (m, 2H), 1.96 (s, 2H), 1.78 (m, 2H), 1.51 (m, 4H), 1.39 (t, 2H), 0.93 (s, 6H)

Example 189

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide

Example 189A

Trans-(4-Methanesulfonylamino-cyclohexyl)-carbamic acid tert-butyl ester

The title compound was prepared by substituting methanesulfonyl chloride for acetyl chloride in EXAMPLE 179A.

Example 189B

Trans-N-(4-Aminocyclohexyl)-methanesulfonamide

The title compound was prepared by substituting EXAMPLE 189A for EXAMPLE 1A in EXAMPLE 1B.

Example 189C

Trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide The title compound was prepared by substituting EXAMPLE 189B for 1-acetylpiperidin-4-amine in EXAMPLE 53B. $^1$H NMR (300 MHz, dimethylsulfoxide-$d_6$) δ 11.68 (br s, 1H), 8.55 (d, 1H), 8.18 (d, 1H), 8.04 (d, 1H), 7.84 (d, 1H), 7.79 (dd, 1H), 7.56-7.47 (m, 3H), 7.34 (d, 2H), 7.16 (d, 1H), 7.04 (d, 2H), 6.68 (dd, 1H), 6.39 (m, 1H), 6.19 (d, 1H), 3.56 (m, 1H), 3.17 (m, 1H), 3.07 (br s, 4H), 2.93 (s, 3H), 2.75 (br s, 2H), 2.28-2.10 (m, 6H), 2.05-1.90 (m, 6H), 1.55-1.32 (m, 6H), 0.92 (s, 6H).

Example 190

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide

Example 190A 4-(1-cyclopropylpiperidin-4-ylamino)-3-(trifluoromethylsulfonyl)benzene sulfonamide The title compound was prepared as described in EXAMPLE 17A by replacing (tetrahydropyran-4-yl)methylamine with 4-amino-1-cyclopropylpiperidine.

Example 190B 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide The title compound was prepared as described in EXAMPLE 1G by replacing Example 1E and EXAMPLE 1F with EXAMPLE 3J and EXAMPLE 190A, respectively. $^1$H NMR (300 MHz, dimethylsulfoxide-$d_6$) δ 11.66 (s, 1H), 8.13 (d, 1H), 8.02 (d, 1H), 7.91 (m, 1H), 7.48 (m, 3H), 7.34 (d, 2H), 7.04 (d, 2H), 6.67 (m, 2H), 6.38 (dd, 1H), 6.19 (d, 1H), 3.64 (m, 1H), 3.13 (m, 5H), 2.73 (m, 5H), 2.22 (m, 6H), 1.92 (m, 5H), 1.70 (m, 1H), 1.41 (m, 5H), 0.94 (s, 6H), 0.41 (m, 4H).

Example 191

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide

Example 191A 3-nitro-4-(piperidin-4-ylmethoxy)benzenesulfonamide

To a solution of tert-butyl 4-(hydroxymethyl)piperidine-1-carboxylate (0.300 g) in tetrahydrofuran (5 mL) was added sodium hydride (0.223 g). After stirring for 15 minutes, 4-fluoro-3-nitrobenzenesulfonamide (0.276 g) was added and reaction stirred at room temperature. After 1 hour the reaction was partitioned between water (25 mL) and dichloromethane (50 mL) and the reaction quenched with 1N aqueous HCl (5.57 mL). The organic layer was separated, dried over magnesium sulfate, filtered, and concentrated. Treatment with HCl (4.0M in dioxane, 2 mL) and methanol (2 mL) for 1 hour, followed by concentration, trituration with dichloromethane and filtration gave the title compound.

Example 191B 3-nitro-4-((1-(oxetan-3-yl)piperidin-4-yl)methoxy)benzenesulfonamide To a suspension of 3-nitro-4-(piperidin-4-ylmethoxy)benzenesulfonamide (0.100 g) and cyclobutanone (0.030 g) in methanol (1 mL) was added sodium cyanoborohydride (0.027 g). After stirring overnight, the reaction was quenched with saturated NaHCO₃ (5 mL) and extracted into dichloromethane (2×10 mL). The organic layer was dried over magnesium sulfate, filtered, and concentrated to give the title compound.

Example 191C 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide The title compound was prepared by substituting EXAMPLE 191B for EXAMPLE 1F and EXAMPLE 3J for EXAMPLE 1E in EXAMPLE 1G $^1$H NMR (300 MHz, dimethylsulfoxide-$d_6$) δ 11.64 (s, 1H), 11.46-10.46 (m, 1H), 8.29 (s, 1H), 8.00 (d, 2H), 7.61-7.41 (m, 3H), 7.35 (d, 3H), 7.04 (d, 2H), 6.66 (d, 1H), 6.37 (s, 1H), 6.21 (s, 1H), 4.67-4.40 (m, 4H), 4.08 (d, 2H), 3.06 (s, 4H), 2.78 (s, 4H), 2.19 (m, 6H), 1.96 (s, 4H), 1.79 (m, 4H), 1.39 (s, 4H), 0.93 (s, 6H).

Example 192

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide Example 192A 4-((4-fluoro-1-(tetrahydro-2H-pyran-4-yl)piperidin-4-yl)methoxy)-3-nitrobenzenesulfonamide A mixture of EXAMPLE 173A (0.4 g), dihydro-2H-pyran-4(3H)-one (0.179 g), sodium cyanoborohydride (0.112 g), and acetic acid (0.5 mL) in tetrahydrofuran (3 mL) was stirred overnight. The solvents were removed under reduced pressure. The residue was purified with flash column chromatography on silica gel eluting with 100:5:0.5 ethyl acetate/methanol/NH₄OH to give the desired product.

Example 192B 4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide The title compound was prepared by substituting EXAMPLE 192A for EXAMPLE 11B in EXAMPLE 11D. $^1$H NMR (500 MHz, dimethylsulfoxide-$d_6$) δ 11.58 (s, 1H), 8.25 (s, 1H), 7.96 (d, 1H), 7.93 (d, 1H), 7.57 (d, 1H), 7.45 (t, 1H), 7.34-7.37 (m, 3H), 7.26 (d, 1H), 7.05 (d, 2H), 6.64 (dd, 1H), 6.34 (dd, 1H), 6.23 (d, 1H), 4.34 (d, 2H), 3.93 (dd, 2H), 3.03 (s, 6H), 2.76 (s, 4H), 2.09-2.22 (m, 6H), 1.96 (s, 2H), 1.52-1.27 (m, 2H), 1.39 (t, 2H), 0.93 (s, 6H).

Example 193

4-(4-{[2-(4-chlorophenyl)-4,4-dimethylcyclohex-1-en-1-yl]methyl}piperazin-1-yl)-N-({4-[(4-fluoro-1-tetrahydro furan-3-ylpiperidin-4-yl)methoxy]-3-nitrophenyl}sulfonyl)-2-(1H-pyrrolo[2,3-b]pyridin-5-yloxy)benzamide Example 193A 4-((4-fluoro-1-(tetrahydrofuran-3-yl)piperidin-4-yl)methoxy)-3-nitrobenzenesulfonamide The title compound was prepared by substituting dihydrofuran-3(2H)-one for dihydro-2H-pyran-4(3H)-one in EXAMPLE 192A.

Example 193B 4-(4-{[2-(4-chlorophenyl)-4,4-dimethylcyclohex-1-en-1-yl]methyl}piperazin-1-yl)-N-({4-[(4-fluoro-1-tetrahydro furan-3-ylpiperidin-4-yl)methoxy]-3-nitrophenyl}sulfonyl)-2-(1H-pyrrolo[2,3-b]pyridin-5-yloxy)benzamide The title compound was prepared by substituting EXAMPLE 193A for EXAMPLE 11B in EXAMPLE 11D. $^1$H NMR (500 MHz, dimethylsulfoxide-$d_6$) δ 11.63 (s, 1H), 8.31 (s, 1H), 7.99-8.00 (m, 2H), 7.54 (d, 1H), 7.46-7.48 (m, 2H), 7.34-7.35 (m, 3H), 7.05 (d2H), 6.66 (dd, 1H), 6.37 (dd, 1H), 6.21 (d, 1H), 4.34 (d, 2H), 3.76-3.83 (m, 3H), 3.62-3.65 (m, 2H), 3.03 (s, 4H), 2.79 (s, 4H), 2.24 (s, 2H), 2.15 (s, 2H), 1.84-1.99 (m, 8H), 1.52-1.27 (m, 2H), 1.39 (t, 2H), 0.93 (s, 6H).

Example 194

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide Example 194A 4-((4-fluoro-1-(methylsulfonyl)piperidin-4-yl)methoxy)-3-nitrobenzenesulfonamide A mixture of EXAMPLE 173A (0.4 g), methanesulfonyl chloride (0.113 g), and triethylamine (0.64 mL) in dichloromethane (5 mL) was stirred overnight. The reaction mixture was loaded onto a silica gel column and eluted with 100:1 ethyl acetate:methanol to give the clean product.

Example 194B 4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide The title compound was prepared by substituting EXAMPLE 194A for EXAMPLE 11B in EXAMPLE 11D.

¹H NMR (500 MHz, dimethylsulfoxide-$d_6$) δ 11.66 (s, 1H), 8.37 (s, 1H), 8.06 (d, 1H), 8.02 (d, 1H), 7.49-7.53 (m, 3H), 7.42 (d, 1H), 7.35 (d, 2H), 7.05 (d, 2H), 6.67 (dd, 1H), 6.38-6.39 (m, 1H), 6.21 (d, 1H), 4.40 (d, 2H), 3.51-3.54 (m, 2H), 3.09 (s, 4H), 2.96-3.01 (m, 4H), 2.92 (s, 3H), 2.82 (s, 2H), 2.25-2.34 (m, 4H), 2.13-2.16 (m, 6H), 2.01-2.07 (m, 2H0, 1.99 (s, 2H), 1.39 (t, 2H), 0.93 (s, 6H).

Example 195

4-(4-{[2-(4-chlorophenyl)-4,4-dimethylcyclohex-1-en-1-yl]methyl}piperazin-1-yl)-N-{[3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide

Example 195A (R)-tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)pyrrolidine-1-carboxylate The title compound was prepared by substituting (R)-tert-butyl 3-(aminomethyl)pyrrolidine-1-carboxylate for 1-acetylpiperidin-4-amine in EXAMPLE 53B.

Example 195B (S)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(pyrrolidin-3-ylmethylamino)phenylsulfonyl)benzamide The title compound was prepared by substituting EXAMPLE 195A for EXAMPLE 1A in EXAMPLE 1B.

Example 195C (R)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((1-(oxetan-3-yl)pyrrolidin-3-yl)methylamino)phenylsulfonyl)benzamide The title compound was prepared by substituting EXAMPLE 195B for tert-butyl piperazine-1-carboxylate and oxetan-3-one for 4'-chlorobiphenyl-2-carboxaldehyde in EXAMPLE 1A. ¹H NMR (500 MHz, dimethylsulfoxide-$d_6$) 11.67 (s, 1H), 8.81 (t, 1H), 8.55 (d, 1H), 8.02 (d, 1H), 7.79 (dd, 1H), 7.50 (m, 3H), 7.35 (m, 2H), 7.04 (m, 3H), 6.67 (dd, 1H), 6.39 (m, 1H), 6.19 (d, 1H), 4.57 (m, 2H), 4.48 (m, 2H), 3.68 (m, 2H), 3.30 (m, 2H), 3.06 (m, 4H), 2.74 (m, 3H), 2.56 (m, 3H), 2.44 (m, 1H), 2.18 (m, 5H), 1.95 (m, 3H), 1.58 (m, 1H), 1.36 (m, 2H), 0.94 (s, 6H).

Example 196

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide

Example 196A

Trans-4-(4-(tert-butyldimethylsilyloxy)cyclohexyl)methoxy)-3-nitrobenzenesulfonamide The title compound was prepared as described in EXAMPLE 12A by replacing (1,4-dioxan-2-yl)methanol with trans-(4-(tert-butyldimethylsilyloxy)cyclohexyl)methanol (made according to the procedures in WO 2008/124878).

Example 196B

Trans-2-(1H-pyrrolo[2,3-b]pyridin-5-yloxy)-N-(4-(((1r,4r)-4-(tert-butyldimethylsilyloxy)cyclohexyl)methoxy)-3-nitrophenylsulfonyl)-4-(4-((2-(4-chlorophenyl)-4,4-dimethylcyclohex-1-enyl)methyl)piperazin-1-yl)benzamide The title compound was prepared as described in EXAMPLE 1G using EXAMPLE 196A in place of EXAMPLE 1F and EXAMPLE 3J in place of EXAMPLE 1E.

Example 196C

Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide EXAMPLE 196B (150 mg) in dichloromethane (5 mL) and methanol (2 mL) was treated with 10% aqueous HCl (3 mL) for 1 hour and concentrated. The residue was purified by reverse phase HPLC on a C18 column using a gradient of 40-60% acetonitrile in 0.1% trifluoroacetic acid water to give the title compound as a trifluoroacetate salt. The trifluoroacetic acid salt was dissolved in dichloromethane (30 mL) and washed with 50% aqueous NaHCO₃. The organic layer was dried over anhydrous $Na_2SO_4$, filtered, and concentrated to give the title compound. ¹H NMR (400 MHz, dimethylsulfoxide-$d_6$) δ 11.69 (s, 1H), 11.27 (s, 1H), 8.34 (d, 1H), 7.95-8.08 (m, 2H), 7.47-7.55 (m, 3H), 7.32-7.40 (m, 3H), 7.01-7.07 (m, 2H), 6.68 (dd, 1H), 6.39 (dd, 1H), 6.20 (d, 1H), 4.54 (d, 1H), 3.96-4.06 (m, 2H), 3.10 (s, 4H), 2.84 (s, 2H), 2.05-2.39 (m, 6H), 1.96 (s, 2H), 1.46-1.93 (m, 5H), 1.39 (t, 2H), 0.98-1.29 (m, 4H), 0.92 (s, 6H)

Example 197

4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide

Example 197A 3-(4-(aminomethyl)phenoxy)-N,N-dimethylpropan-1-amine 4-(3-(Dimethylamino)propoxy)benzonitrile (300 mg) in methanol (20 mL) was treated with Raney nickel (wet, 1.5 g) under H₂ (30 psi) for 4 hour. The insoluble material was filtered off and the filtrate was concentrated to provide the title compound.

Example 197B 4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide The title compound was prepared as described in EXAMPLE 120B using EXAMPLE 197A in place of EXAMPLE 120A. ¹H NMR (400 MHz, dimethylsulfoxide-$d_6$) δ 11.56 (s, 1H), 8.80 (t, 1H), 8.42 (d, 1H), 7.93 (d, 1H), 7.52-7.61 (m, 2H), 7.41-7.47 (m, 1H), 7.26-7.36 (m, 5H), 7.03-7.08 (m, 2H), 6.89 (d, 2H), 6.73 (d, 1H), 6.61 (dd, 1H), 6.31 (dd, 1H), 6.22 (d, 1H), 4.52 (d, 2H), 3.99 (t, 2H), 2.90-3.05 (m, 7H), 2.72 (s, 2H), 2.61 (s, 6H), 2.09-2.24 (m, 6H), 1.89-2.04 (m, 5H), 1.38 (t, 2H), 0.92 (s, 6H)

Example 198

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide Example 198A (4-(2-morpholinoethoxy)phenyl)methanamine The title compound was prepared as described in EXAMPLE 197A using 4-(2-morpholinoethoxy)benzonitrile in place of 4-(3-(dimethylamino)propoxy)benzonitrile.

Example 198B 4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide The title compound was prepared as described in EXAMPLE 120B using EXAMPLE 198A in place of EXAMPLE 120A. ¹H NMR (400 MHz, dimethylsulfoxide-$d_6$) δ 11.69 (s, 1H), 9.00 (t, 1H), 8.56 (d, 1H), 8.02 (d, 1H), 7.72 (dd, 1H), 7.46-7.54 (m, 3H), 7.27-7.36 (m, 4H), 7.01-7.07 (m, 2H), 6.89-6.95 (m, 3H), 6.66 (dd, 1H), 6.38 (dd, 1H), 6.18 (d, 1H), 4.56 (d, 2H), 4.07 (t, 2H), 3.54-3.61 (m, 4H), 3.06 (s, 4H), 2.71-2.78 (m, 4H), 2.07-2.24 (m, 6H), 1.95 (s, 2H), 1.38 (t, 2H), 0.92 (s, 6H).

Example 199

4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide Example 199A 4-[((E)-4-Hydroxy-adamantan-1-ylmethyl)-amino]-3-nitro-benzenesulfonamide 4-Fluoro-3-nitrobenzenesulfonamide (0.5 g) and 5-(aminomethyl)adamantan-2-ol (0.6 g) in tetrahydrofuran (10 mL) were treated with triethylamine (1 mL) overnight. The reaction mixture was concentrated and the residue was purified by reverse phase HPLC, eluting 40-60% acetonitrile in 0.1 trifluoroacetic acid water to give two isomers, which were temporarily assigned as EXAMPLE 199A and EXAMPLE 199B, respectively.

Example 199B

4-[((Z)-4-Hydroxy-adamantan-1-ylmethyl)-amino]-3-nitro-benzenesulfonamide

4-Fluoro-3-nitrobenzenesulfonamide (0.5 g) and 5-(aminomethyl)adamantan-2-ol (0.6 g) in tetrahydrofuran (10 mL) were treated with triethylamine (1 mL) overnight. The reaction mixture was concentrated and the residue was purified by reverse phase HPLC, eluting 40-60% acetonitrile in 0.1 trifluoroacetic acid water to give two isomers, which were temporarily assigned as EXAMPLE 199A and EXAMPLE 199B, respectively.

Example 199C 4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide The title compound was prepared as described in EXAMPLE 11D using EXAMPLE 199A in place of EXAMPLE 11B. ¹H NMR (400 MHz, dimethylsulfoxide-$d_6$) δ 11.68 (s, 1H), 11.40 (s, 1H), 8.55 (d, 1H), 8.50 (t, 1H), 8.03 (d, 1H), 7.77 (dd, 1H), 7.46-7.54 (m, 3H), 7.31-7.38 (m, 2H), 7.14 (d, 1H), 7.01-7.06 (m, 2H), 6.68 (dd, 1H), 6.38 (dd, 1H), 6.19 (d, 1H), 4.61 (d, 1H), 3.63 (d, 1H), 3.02-3.16 (m, 6H), 2.75 (s, 2H), 2.17 (d, 6H), 2.04 (d, 2H), 1.95 (s, 2H), 1.76-1.88 (m, 3H), 1.49-1.61 (m, 6H), 1.38 (t, 2H), 1.29 (d, 2H), 0.92 (s, 6H).

Example 200

4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide The title compound was prepared as described in EXAMPLE 11D using EXAMPLE 199B in place of EXAMPLE 11B. ¹H NMR (400 MHz, dimethylsulfoxide-$d_6$) δ 11.68 (s, 1H), 11.39 (s, 1H), 8.55 (d, 1H), 8.51 (t, 1H), 8.04 (d, 1H), 7.77 (dd, 1H), 7.46-7.55 (m, 3H), 7.31-7.37 (m, 2H), 7.14 (d, 1H), 7.01-7.06 (m, 2H), 6.68 (dd, 1H), 6.39 (dd, 1H), 6.19 (d, 1H), 4.61 (d, 1H), 3.61 (d, 1H), 3.08 (d, 6H), 2.75 (s, 2H), 2.17 (d, 6H), 1.79-1.99 (m, 7H), 1.55-1.69 (m, 4H), 1.49 (s, 2H), 1.38 (t, 2H), 1.22 (d, 2H), 0.92 (s, 6H).

Example 201

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 201A 4-((1S,4S)-bicyclo[2.2.1]hept-5-en-2-ylmethoxy)-3-nitrobenzenesulfonamide The title compound was prepared as described in EXAMPLE 12A by replacing (1,4-dioxan-2-yl)methanol with (1S,4S)-bicyclo[2.2.1]hept-5-en-2-ylmethanol.

Example 201B

N-({4-[(1S,4S)-bicyclo[2.2.1]hept-5-en-2-yl-methoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in EXAMPLE 11D using EXAMPLE 201A in place of EXAMPLE 11B. $^1$H NMR (500 MHz, dimethylsulfoxide-$d_6$) δ 11.69 (s, 1H), 8.35 (d, 1H), 7.95-8.10 (m, 2H), 7.47-7.58 (m, 3H), 7.30-7.45 (m, 3H), 7.04 (d, 2H), 6.68 (dd, 1H), 6.40 (d, 1H), 5.92-6.23 (m, 3H), 3.65-4.39 (m, 3H), 3.00-3.22 (m, 4H), 2.76-2.98 (m, 4H), 2.28 (s, 4H), 2.15 (s, 2H), 1.96 (s, 2H), 1.71-1.91 (m, 1H), 1.33-1.47 (m, 3H), 1.20-1.32 (m, 2H), 0.92 (s, 6H), 0.50-0.66 (m, 1H).

Example 202

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide EXAMPLE 82 (140 mg) was dissolved in dioxane (3.0 mL), and 4-amino-1-methylpyrrolidin-2-one hydrochloride (30 mg) and triethylamine (0.100 mL) were added. The reaction mixture was heated at 110° C. for 40 hours. The reaction was concentrated and the crude material was purified by preparative HPLC using a C18 column, 250×50 mm, 10µ, and eluting with a gradient of 20-100% CH$_3$CN vs. 0.1% trifluoroacetic acid in water, giving the product as a trifluoroacetate salt. The salt was dissolved in dichloromethane (6 mL) and washed with 50% aqueous NaHCO$_3$. The organic layer was dried over anhydrous Na$_2$SO$_4$ and concentrated to give the title compound. $^1$H NMR (400 MHz, dimethylsulfoxide-$d_6$) δ 11.65 (s, 1H), 8.74 (d, 1H), 8.37 (br d, 1H), 8.02 (d, 1H), 7.83 (dd, 1H), 7.49 (m, 3H), 7.34 (d, 2H), 7.07 (d, 1H), 7.04 (d, 2H), 6.68 (dd, 1H), 6.38 (m, 1H), 6.21 (d, 1H), 4.46 (m, 1H), 3.81 (dd, 1H), 3.38 (dd, 1H), 3.08 (br m, 4H), 2.82 (dd, 1H), 2.75 (s, 5H), 2.43 (dd, 1H), 2.21 (br m, 4H), 2.16 (br t, 2H), 1.95 (s, 2H), 1.39 (t, 2H), 0.94 (s, 6H).

Example 203

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide

Example 203A 4-(((1R,4R,5R,6S)-5,6-dihydroxybicyclo[2.2.1]heptan-2-yl)methoxy)-3-nitrobenzenesulfonamide To a solution of EXAMPLE 201A (340 mg) in tetrahydrofuran (10 mL) and water (1 mL) was added N-methylmorpholine N-oxide (184 mg) and OsO$_4$ (2.5% in 2-methyl-2-propanol) (1.05 mL). The reaction mixture was stirred overnight and purified by reverse phase HPLC to provide two isomers, which were temporarily assigned as EXAMPLE 203A and EXAMPLE 203B, respectively.

Example 203B 4-(((1R,4R,5S,6R)-5,6-dihydroxybicyclo[2.2.1]heptan-2-yl)methoxy)-3-nitrobenzenesulfonamide To a solution of EXAMPLE 201A (340 mg) in tetrahydrofuran (10 mL) and water (1 mL) was added N-methylmorpholine N-oxide (184 mg) and OsO$_4$ (2.5% in 2-methyl-2-propanol) (1.05 mL). The reaction mixture was stirred overnight and purified by reverse phase HPLC to provide two isomers, which were temporarily assigned as EXAMPLE 203A and EXAMPLE 203B, respectively.

Example 203C 4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide The title compound was prepared as described in EXAMPLE 11D using EXAMPLE 203A in place of EXAMPLE 11B. $^1$H NMR (400 MHz, dimethylsulfoxide-$d_6$) δ 11.68 (s, 1H), 8.33 (s, 1H), 7.97-8.07 (m, 2H), 7.48-7.55 (m, 3H), 7.41 (d, 1H), 7.32-7.37 (m, 2H), 7.02-7.07 (m, 2H), 6.67 (dd, 1H), 6.40 (dd, 1H), 6.20 (d, 1H), 4.58 (dd, 2H), 4.07-4.19 (m, 2H), 3.82 (t, 1H), 3.51 (t, 1H), 3.09 (s, 4H), 2.81 (s, 2H), 2.09-2.34 (m, 8H), 2.04-2.09 (m, 2H), 1.93-2.01 (m, 3H), 1.62-1.77 (m, 2H), 1.39 (t, 2H), 1.11 (d, 1H), 0.92 (s, 6H), 0.67-0.76 (m, 1H).

Example 204

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide The title compound was prepared as described in EXAMPLE 11D using EXAMPLE 203B in place of EXAMPLE 11B. $^1$H NMR (400 MHz, dimethylsulfoxide-$d_6$) δ 11.68 (s, 1H), 8.33 (s, 1H), 7.98-8.07 (m, 2H), 7.49-7.54 (m, 3H), 7.41 (d, 1H), 7.32-7.36 (m, 2H), 7.02-7.07 (m, 2H), 6.67 (dd, 1H), 6.40 (dd, 1H), 6.20 (d, 1H), 4.58 (dd, 2H), 4.13 (dd, 2H), 3.82 (t, 1H), 3.51 (t, 1H), 3.09 (s, 4H), 2.81 (s, 2H), 2.09-2.35 (m, 8H), 2.07 (s, 2H), 1.93-2.02 (m, 3H), 1.61-1.80 (m, 2H), 1.39 (t, 2H), 1.11 (d, 1H), 0.92 (s, 6H), 0.66-0.78 (m, 1H).

Example 205

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide

Example 205A

Methyl 1,4-dioxaspiro[4.5]decane-7-carboxylate

To a solution of trimethylsilyltrifluoromethanesulfonate (0.034 mL) in dry dichloromethane (5 mL) was added 1,2-bis(trimethylsiloxy)ethane (4.55 mL) followed by methyl 3-oxocyclohexanecarboxylate (2.9 g). The reaction mixture was stirred for 3 hours at −78° C. The reaction mixture was quenched with dry pyridine (0.5 mL), poured into saturated aqueous NaHCO$_3$, and extracted with ether. The ether layer was dried over Na$_2$CO$_3$/Na$_2$SO$_4$. The reaction mixture was concentrated and purified by flash chromatography on silica with 5 to 30% ethyl acetate in hexanes to provide the title compound.

Example 205B 1,4-dioxaspiro[4.5]decan-7-ylmethanol

The title compound was prepared by substituting EXAMPLE 205A for EXAMPLE 101C in EXAMPLE 101D.

Example 205C 3-nitro-4-((3-oxocyclohexyl)methoxy)benzenesulfonamide

Into a 250 mL round-bottomed flask was added sodium hydride (0.5 g) in tetrahydrofuran (10 mL) and then 1,4-dioxaspiro[4.5]decan-7-ylmethanol (0.5 g) was added. After the mixture stirred at room temperature for 20 minutes, 4-fluoro-3-nitrobenzenesulfonamide (0.65 g) was added. The mixture was stirred at room temperature for overnight. Water (20 mL) was added slowly. The aqueous layer was extracted by dichloromethane (3×20 mL). The combined organic layers were dried over Na$_2$SO$_4$. After filtration, and concentration of the filtrate, the residue was purified by reverse phase chromatography, eluting with 30-60% acetonitrile in water with 0.1% trifluoroacetic acid.

Example 205D 4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide The title compound was prepared by substituting EXAMPLE 205C for EXAMPLE 11B in EXAMPLE 11D. $^1$H NMR (400 MHz, dimethylsulfoxide-d$_6$) δ 11.59 (s, 1H), 8.22 (s, 1H), 7.96 (d, 1H), 7.87 (m, 1H), 7.55 (d, 1H), 7.45 (t, 1H), 7.35 (m, 3H), 7.20 (m, 1H), 7.04 (d, 2H), 6.64 (dd, 1H), 6.34 (m, 1H), 6.23 (d, 1H), 4.07 (d, 2H), 3.04 (m, 4H), 2.76 (s, 2H), 2.35 (m, 2H), 2.20 (m, 8H), 1.96 (m, 4H), 1.58 (m, 2H), 1.39 (t, 2H), 0.93 (s, 6H).

Example 206

4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 206A 2-chloro-5,5-dimethylcyclohexa-1,3-dienecarbaldehyde In a 250 ml, round-bottomed flask was added N,N-dimethylformamide (3.5 mL) in dichloromethane (30 mL), and the mixture was cooled to −10° C. Phosphoryl trichloride (4 mL) was added dropwise, and the solution was warmed up to room temperature. 4,4-Dimethylcyclohex-2-enone (5.5 mL) was then added slowly, and the mixture was heated to reflux overnight. The reaction mixture was cooled and quenched with a 0° C. solution of sodium acetate (25 g in 50 mL water). The aqueous layer was extracted with diethyl ether (200 mL×3). The combined organic layers were dried over Na$_2$SO$_4$, filtered, and concentrated to give the product.

Example 206B 2-(4-chlorophenyl)-5,5-dimethylcyclohexa-1,3-dienecarbaldehyde

Into a 1 L round-bottomed flask was added EXAMPLE 206A (6.8 g), 4-chlorophenylboronic acid (6.5 g), and palladium (II) acetate (0.2 g) in water (100 mL) to give a suspension. Potassium carbonate (15 g) and tetrabutylammonium bromide (10 g) were added. After degassing, the mixture was stirred at 45° C. for 4 hours. After cooling and filtering though silica gel in a funnel, diethyl ether (4×200 mL) was used to extract the product. The combined organic layers were dried over Na$_2$SO$_4$, and filtered. The filtrate was concentrated and purified by flash chromatography on silica with 0-10% ethyl acetate in hexanes to provide the title compound.

Example 206C

Methyl 2-(1H-pyrrolo[2,3-b]pyridin-5-yloxy)-4-(4-((2-(4-chlorophenyl)-5,5-dimethylcyclohexa-1,3-dienyl)methyl)piperazin-1-yl)benzoate The title compound was prepared by substituting EXAMPLE 206B for 4'-chlorobiphenyl-2-carboxaldehyde and EXAMPLE 15F for tert-butyl piperazine-1-carboxylate in EXAMPLE 1A.

Example 206D 2-(1H-pyrrolo[2,3-b]pyridin-5-yloxy)-4-(4-((2-(4-chlorophenyl)-5,5-dimethylcyclohexa-1,3-dienyl)methyl)piperazin-1-yl)benzoic acid The title compound was prepared by substituting EXAMPLE 206C for EXAMPLE 101E in EXAMPLE 101F.

Example 206E 4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 206D for EXAMPLE 3J and EXAMPLE 1F for EXAMPLE 11B in EXAMPLE 11D. $^1$H NMR (400 MHz, dimethylsulfoxide-d$_6$) δ 11.61 (s, 1H), 8.49 (m, 2H), 7.99 (m, 1H), 7.72 (m, 1H), 7.53 (d, 1H), 7.41 (m, 4H), 7.12 (d, 2H), 6.99 (m, 1H), 6.66 (dd, 1H), 6.35 (m, 1H), 6.23 (d, 1H), 5.74 (d, 1H), 5.58 (d, 1H), 3.84 (m, 2H), 3.26 (m, 4H), 3.06 (m, 4H), 2.88 (s, 2H), 2.24 (m, 6H), 1.61 (m, 2H), 1.26 (m, 3H), 1.00 (s, 6H).

Example 207

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide

Example 207A (R)-1-(1,3-difluoropropan-2-yl)pyrrolidin-3-amine

The title compound was prepared by substituting (R)-tert-butyl pyrrolidin-3-ylcarbamate for tert-butyl azetidin-3-ylcarbamate in EXAMPLE 151A.

Example 207B (R)-4-(1-(1,3-difluoropropan-2-yl)pyrrolidin-3-ylamino)-3-nitrobenzenesulfonamide The title compound was prepared by substituting EXAMPLE 207A for EXAMPLE 151A in EXAMPLE 151B.

Example 207C 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide The title compound was prepared by substituting EXAMPLE 207B for EXAMPLE 1F and EXAMPLE 3J for EXAMPLE 1E in EXAMPLE 1G. $^1$H NMR (300 MHz, dimethylsulfoxide-$d_6$) δ 11.67 (s, 1H), 11.52-11.24 (m, 1H), 8.55 (d, 1H), 8.37 (d, 1H), 8.03 (d, 1H), 7.83 (dd, 1H), 7.57-7.45 (m, 3H), 7.34 (d, 2H), 7.06 (t, 3H), 6.67 (d, 1H), 6.38 (dd, 1H), 6.20 (d, 1H), 4.70 (d, 2H), 4.54 (d, 2H), 4.23 (s, 1H), 3.11-2.87 (m, 7H), 2.74 (dd, 4H), 2.35-2.13 (m, 7H), 1.95 (s, 2H), 1.70 (s, 1H), 1.39 (d, 2H), 0.92 (s, 6H).

Example 208

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide

Example 208A 2-((4-fluorotetrahydro-2H-pyran-4-yl)methoxy)-5-iodo-3-(trifluoromethyl)pyridine A mixture of EXAMPLE 37C (0.537 g), 5-iodo-3-(trifluoromethyl)pyridine-2-ol (1.156 g), and triphenylphosphine (1.574 g) in tetrahydrofuran (20 mL) was cooled to 0° C. To this solution was added (E)-di-tert-butyl diazene-1,2-dicarboxylate (0.921 g). The reaction mixture was stirred overnight. The solvent was removed, and the residue was purified with column flash chromatography on silica gel eluting with 4:1 hexanes/ethyl acetate to give the desired product.

Example 208B 6-((4-fluorotetrahydro-2H-pyran-4-yl)methoxy)-5-(trifluoromethyl)pyridine-3-sulfonamide EXAMPLE 207A (1.3 g) in tetrahydrofuran (10 mL) was cooled to −42° C. with a cold bath of CH$_3$CN/dry ice. To this solution was added 2.0 M isopropylmagnesium chloride (1.6 mL) dropwise over 5 minutes. The reaction mixture was stirred for 30 minutes at −42° C., then allowed to warm to 0° C. over 10 minutes. The reaction mixture was cooled again to −42° C., and SO$_2$ was bubbled though it for 10 minutes. The reaction mixture was stirred for another 30 minutes. To this solution was sulfuryl dichloride (0.433 g). On warming to room temperature, concentrated NH$_4$OH (10 mL) was added and the reaction mixture was stirred for another 2 hours. The reaction mixture was partitioned between water and ethyl acetate. The aqueous layer was extracted with additional ethyl acetate three times. The combined organic layers were washed with brine, dried over MgSO$_4$, filtered, and concentrated. The residue was purified by flash column chromatography on silica gel eluting with 3:1 hexanes/ethyl acetate to give the title compound.

Example 208C 4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide The title compound was prepared by substituting EXAMPLE 208B for EXAMPLE 11B in EXAMPLE 11D. $^1$H NMR (500 MHz, dimethylsulfoxide-$d_6$) δ 11.61 (s, 1H), 8.72 (s, 1H), 8.36 (s, 1H), 7.98 (d, 1H), 7.55 (d, 1H), 7.42-7.47 (m, 2H), 7.36 (d, 2H), 7.05 (d, 2H), 6.66 (dd, 1H), 6.35 (s, 1H), 6.23 (s, 1H), 4.56 (d, 2H), 3.75-3.79 (m, 2H), 3.56-3.61 (m, 2H), 3.09 (s, 4H), 2.32-2.37 (m, 2H), 2.16 (s, 2H), 1.97-1.99 (m, 2H), 1.79-1.86 (m, 4H), 1.40 (t, 2H), 0.93 (s, 6H).

Example 209

4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide

Example 209A (S)-tert-butyl (1-(oxetan-3-yl)pyrrolidin-3-yl)methylcarbamate

The title compound was prepared by substituting (R)-tert-butyl pyrrolidin-3-ylmethylcarbamate for tert-butyl piperazine-1-carboxylate and 3-oxetanone for 4'-chlorobiphenyl-2-carboxaldehyde in EXAMPLE 1A.

Example 209B (S)-(1-(oxetan-3-yl)pyrrolidin-3-yl)methanamine

The title compound was prepared by substituting EXAMPLE 209A for (S)-1-tert-butyl 2-methyl 4,4-difluoropyrrolidine-1,2-dicarboxylate in EXAMPLE 168A.

Example 209C (S)-3-nitro-4-((1-(oxetan-3-yl)pyrrolidin-3-yl)methylamino)benzenesulfonamide The title compound was prepared by substituting 4-fluoro-3-nitrobenzenesulfonamide for 4-chloro-3-nitrobenzenesulfonamide and EXAMPLE 209B for 4-methylpiperazin-1-amine dihydrochloride in EXAMPLE 6A.

Example 209D 4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide The title compound was prepared by substituting EXAMPLE 209C for EXAMPLE 11B in EXAMPLE 11D. $^1$H NMR (500 MHz, pyridine-d$_5$) δ 13.05 (s, 1H), 9.30 (d, 1H), 9.02 (t, 1H), 8.42 (d, 1H), 8.34 (dd, 1H), 8.10 (d, 1H), 7.67 (dd, 2H), 7.44 (d, 2H), 7.07 (d, 2H), 6.82 (d, 1H), 6.75 (m, 1H), 6.52 (m, 2H), 4.82 (t, 1H), 4.75 (t, 1H), 4.67 (t, 2H), 3.57 (m, 1H), 3.24 (t, 2H), 3.07 (m, 4H), 2.75 (m, 3H), 2.57 (dd, 1H), 2.45 (s, 1H), 2.36 (t, 1H), 2.26 (s, 2H), 2.18 (m, 5H), 1.93 (m, 3H), 1.56 (m, 1H), 1.39 (t, 2H), 0.93 (s, 6H).

Example 210

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 210A (4-methoxycyclohexyl)methanol

The title compound was prepared by substituting 4-methoxycyclohexanecarboxylic acid for 1-tert-butyl 4-ethyl 4-fluoropiperidine-1,4-dicarboxylate in EXAMPLE 126A.

Example 210B

Trans-5-chloro-6-((4-methoxycyclohexyl)methoxy)pyridine-3-sulfonamide

The title compound was prepared by substituting EXAMPLE 210A for tetrahydro-2H-pyran-4-yl)methanol and EXAMPLE 40A for 4-fluoro-3-nitrobenzenesulfonamide in EXAMPLE 24A.

Example 210C

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 210C for EXAMPLE 11B in EXAMPLE 11D. $^1$H NMR (500 MHz, dimethylsulfoxide-d$_6$) δ 11.67 (s, 1H), 8.50 (s, 1H), 8.17 (s, 1H), 8.02 (d, 1H), 7.49-7.54 (m, 3H), 7.35 (d, 2H), 7.05 (d, 2H), 6.67 (dd, J 1H), 6.39 (s, 1H), 6.21 (s, 1H), 4.20 (d, 2H), 3.23 (s, 3H), 3.06-3.09 (m, 4H), 2.15-2.37 (m, 4H), 1.96-2.03 (m, 4H), 1.74-1.84 (m, 2H), 1.40 (t, 2H), 1.04-1.13 (m, 4H), 0.93 (s, 6H).

Example 211

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 211A

Cis-5-chloro-6-((4-methoxycyclohexyl)methoxy)pyridine-3-sulfonamide

The title compound was isolated as a by-product in the synthesis of EXAMPLE 210B.

Example 211B

Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 211A for EXAMPLE 11B in EXAMPLE 11D. $^1$H NMR (500 MHz, dimethylsulfoxide-d$_6$) δ 11.67 (s, 1H), 8.51 (s, 1H), 8.17 (s, 1H), 8.03 (d, 1H), 7.49-7.54 (m, 3H), 7.35 (d, 2H), 7.05 (d, 2H), 6.68 (dd, 1H), 6.39 (s, 1H), 6.21 (s, 1H), 4.21 (d, 2H), 3.20 (s, 3H), 3.06 (s, 4H), 2.15-2.37 (m, 4H), 1.96 (s, 2H), 1.80-1.84 (m, 2H), 1.50-1.54 (m, 2H), 1.34-1.44 (m, 6H), 0.93 (s, 6H).

Example 212

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide

Example 212A (S)-tert-butyl 1-(oxetan-3-yl)pyrrolidin-3-ylcarbamate

The title compound was prepared by substituting (S)-tert-butyl pyrrolidin-3-ylcarbamate for tert-butyl piperazine-1-carboxylate and 3-oxetanone for 4'-chlorobiphenyl-2-carboxaldehyde in EXAMPLE 1A.

Example 212B (S)-1-(oxetan-3-yl)pyrrolidin-3-amine

The title compound was prepared by substituting EXAMPLE 212A for (S)-1-tert-butyl 2-methyl 4,4-difluoropyrrolidine-1,2-dicarboxylate in EXAMPLE 168A.

Example 212C (S)-3-nitro-4-(1-(oxetan-3-yl)pyrrolidin-3-ylamino)benzenesulfonamide The title compound was prepared by substituting 4-fluoro-3-nitrobenzenesulfonamide for 4-chloro-3-nitrobenzenesulfonamide and EXAMPLE 212B for 4-methylpiperazin-1-amine dihydrochloride in EXAMPLE 6A.

Example 212D 4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide The title compound was prepared by substituting EXAMPLE 212C for EXAMPLE 11B in EXAMPLE 11D. $^1$H NMR (500 MHz, pyridine-$d_5$) δ 13.03 (s, 1H), 9.27 (d, 1H), 8.58 (d, 1H), 8.42 (d, 1H), 8.37 (dd, 1H), 8.09 (d, 1H), 7.67 (t, 1H), 7.64 (d, 1H), 7.44 (d, 2H), 7.07 (d, 2H), 6.86 (d, 1H), 6.75 (dd, 1H), 6.54 (d, 1H), 6.48 (dd, 1H), 4.67 (m, 4H), 4.09 (m, 1H), 3.59 (m, 1H), 3.07 (m, 4H), 2.77 (s, 2H), 2.69 (m, 2H), 2.62 (dd, 1H), 2.28 (m, 4H), 2.14 (m, 4H), 1.97 (s, 2H), 1.68 (m, 1H), 1.39 (t, 2H), 0.93 (s, 6H).

Example 213

4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide

Example 213A 4-((4-(2-(2-methoxyethoxy)ethyl)morpholin-2-yl)methylamino)-3-nitrobenzenesulfonamide The title compound was prepared by substituting 2-(2'-methoxyethoxy)ethyl bromide for methyl iodide in EXAMPLE 134B.

Example 213B 4-(4-{[2-(4-chlorophenyl)-4,4-dimethylcyclohex-1-en-1-yl]methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide The title compound was prepared by substituting EXAMPLE 213A for EXAMPLE 130C in EXAMPLE 130D. $^1$H NMR (500 MHz, pyridine-$d_5$) δ 12.98 (s, 1H), 9.26 (d, 1H), 8.87 (t, 1H), 8.43 (d, 1H), 8.32 (dd, 1H), 8.11 (d, 1H), 7.66 (m, 2H), 7.44 (d, 2H), 7.07 (d, 2H), 6.91 (d, 1H), 6.75 (dd, 1H), 6.54 (d, 1H), 6.48 (m, 1H), 3.96-3.86 (m, 2H), 3.72 (dd, 1H), 3.67-3.61 (m, 4H), 3.51 (t, 2H), 3.48-3.38 (m, 2H), 3.28 (s, 3H), 3.07 (m, 4H), 2.95 (d, 1H), 2.77 (s, 2H), 2.70 (m, 1H), 2.60 (t, 2H), 2.30-2.05 (m, 8H), 1.97 (s, 2H), 1.39 (t, 2H), 0.94 (s, 6H).

Example 214

4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide

Example 214A 4-((4-(cyanomethyl)morpholin-2-yl)methylamino)-3-nitrobenzenesulfonamide The title compound was prepared by substituting 2-bromoacetonitrile for methyl iodide in EXAMPLE 134B.

Example 214B 4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 214A for EXAMPLE 130C in EXAMPLE 130D. $^1$H NMR (500 MHz, pyridine-$d_5$) δ 13.01 (s, 1H), 9.26 (d, 1H), 8.86 (t, 1H), 8.43 (d, 1H), 8.35 (dd, 1H), 8.11 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.93 (m, 1H), 3.87 (d, 1H), 3.77 (s, 2H), 3.65 (dt, 1H), 3.51-3.40 (m, 2H), 3.07 (m, 4H), 2.87 (d, 1H), 2.77 (s, 2H), 2.60 (d, 1H), 2.50 (m, 1H), 2.38 (t, 1H), 2.26 (m, 2H), 2.14 (m, 4H), 1.97 (s, 2H), 1.39 (t, 2H), 0.94 (s, 6H).

Example 215

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide

Example 215A 4-((4-(2-(dimethylamino)acetyl)morpholin-2-yl)methylamino)-3-nitrobenzenesulfonamide The title compound was prepared by substituting 2-dimethylaminoacetyl chloride hydrochloride for methyl iodide in EXAMPLE 134B.

Example 215B 4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 215A for EXAMPLE 130C in EXAMPLE 130D. $^1$H NMR (500 MHz, pyridine-$d_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 1H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Example 216

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid

Example 216A tert-butyl 2-(2-((2-nitro-4-sulfamoylphenylamino)methyl)morpholino)acetate The title compound was prepared by substituting tert-butyl 2-bromoacetate for methyl iodide in EXAMPLE 134B.

Example 216B tert-butyl 2-(2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholino)acetate The title compound was prepared by substituting EXAMPLE 216A for EXAMPLE 130C in EXAMPLE 130D.

Example 216C (2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid The title compound was prepared by treating EXAMPLE 216B with 50% trifluoroacetic acid in dichloromethane. $^1$H NMR (500 MHz, pyridine-$d_5$) δ 12.97 (s, 1H), 9.26 (d, 1H), 8.87 (t, 1H), 8.43 (d, 1H), 8.30 (dd, 1H), 8.12 (d, 1H), 7.69 (t, 1H), 7.64 (d, 1H), 7.43 (d, 2H), 7.08 (d, 2H), 6.88 (d, 1H), 6.76 (dd, 1H), 6.55 (d, 1H), 6.47 (m, 1H), 4.05-4.00 (m, 1H), 3.91 (d, 1H), 3.79 (dt, 1H), 3.50 (s, 2H), 3.45 (m, 2H), 3.13 (d, 1H), 3.07 (m, 4H), 2.88 (d, 1H), 2.78 (s, 2H), 2.57 (dt, 1H), 2.43 (t, 1H), 2.26 (m, 2H), 2.14 (m, 4H), 1.97 (s, 2H), 1.39 (t, 2H), 0.94 (s, 6H).

Example 217

4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide

Example 217A

The title compound was prepared by substituting EXAMPLE 134A for tert-butyl piperazine-1-carboxylate and 3-oxetanone for 4'-chlorobiphenyl-2-carboxaldehyde in EXAMPLE 1A.

Example 217B 4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide The title compound was prepared by substituting EXAMPLE 217A for EXAMPLE 130C in EXAMPLE 130D. $^1$H NMR (500 MHz, pyridine-$d_5$) δ 13.00 (s, 1H), 9.26 (d, 1H), 8.87 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 4.64 (m, 4H), 3.93 (m, 1H), 3.89 (d, 1H), 3.68 (dt, 1H), 3.53-3.35 (m, 3H), 3.07 (m, 4H), 2.77 (s, 2H), 2.72 (d, 1H), 2.44 (d, 1H), 2.26 (m, 2H), 2.14 (m, 4H), 1.97 (s, 2H), 1.85 (t, 1H), 1.39 (t, 2H), 0.94 (s, 6H).

Example 218

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide

Example 218A 4-((4-cyclopropylmorpholin-2-yl)methylamino)-3-nitrobenzenesulfonamide The title compound was prepared by substituting EXAMPLE 134A for EXAMPLE 173A in EXAMPLE 173B.

Example 218B 4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide The title compound was prepared by substituting EXAMPLE 218A for EXAMPLE 130C in EXAMPLE 130D. $^1$H NMR (500 MHz, pyridine-$d_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Example 219

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide

Example 219A 5-(methylthio)-6-((tetrahydro-2H-pyran-4-yl)methoxy)pyridine-3-sulfonamide A mixture of EXAMPLE 36B (0.1 g) and sodium methanethiolate (0.04 g) in N,N-dimethylformamide (2 mL) was heated at 80° C. overnight. After cooling, the reaction mixture was partitioned between water and ethyl acetate. The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Example 219B 5-(methylsulfonyl)-6-((tetrahydro-2H-pyran-4-yl) methoxy)pyridine-3-sulfonamide A mixture of EXAMPLE 219A (0.15 g) and 75% metachloroperoxybenzoic acid (0.217 g) in chloroform (4 mL) was stirred at room temperature. The reaction mixture was stirred overnight. The reaction mixture was then partitioned between ethyl acetate and water. The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Example 219C 4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 219B for EXAMPLE 11B in EXAMPLE 11D. $^1$H NMR (500 MHz, dimethylsulfoxide-d$_6$) δ 11.65 (s, 1H), 8.81 (s, 1H), 8.55 (d, 1H), 8.01 (d, 1H), 7.55 (d, 1H), 7.49-7.50 (m, 2H), 7.37 (d, 2H), 7.05 (d, 2H), 6.67 (dd, 1H), 6.38 (dd, 1H), 6.21 (d, 1H), 4.36 (d, 2H), 3.88 (dd, 2H), 3.13 (s, 4H), 2.95 (s, 2H), 2.36-2.38 (m, 2H), 2.03-2.16 (m, 4H), 1.97 (s, 3H), 1.66-1.69 (m, 2H), 1.38-1.402 (m, 4H), 0.93 (s, 6H).

Example 220

4-(4-{[2-(4-chlorophenyl)-4,4-dimethylcyclohex-1-en-1-yl]methyl 1 piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide Example 220A 4-((4-fluorotetrahydro-2H-pyran-4-yl)methoxy)-3-(trifluoromethylsulfonyl)benzenesulfonamide To a solution of EXAMPLE 37C (0.500 g) in tetrahydrofuran (5 mL) was added sodium hydride (0.596 g). Additional tetrahydrofuran (25 mL) was added and the mixture stirred for 30 minutes, then 4-fluoro-3-(trifluoromethylsulfonyl) benzenesulfonamide (1.145 g) was added as a solution in tetrahydrofuran (5 mL). After stirring for 2 hours, the reaction mixture was partioned between 1N aqueous HCl (50 mL) and dichloromethane (200 mL). The organic layer was dried over magnesium sulfate, filtered, and concentrated. The resulting solid was chromatographed over silica gel (Reveleris 80 g) eluting with a gradient of 0.5% to 7.5% methanol/dichloromethane over 30 minutes (flow=40 mL/min) to provide the title compound.

Example 220B 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 220A for EXAMPLE 1F in EXAMPLE 1G. $^1$H NMR (300 MHz, dimethylsulfoxide-d$_6$) δ 11.66 (s, 1H), 8.42 (s, 1H), 8.35-8.22 (m, 1H), 8.01 (s, 1H), 7.49 (d, 4H), 7.35 (d, 2H), 7.05 (d, 2H), 6.68 (s, 1H), 6.38 (s, 1H), 6.21 (s, 1H), 4.42 (d, 2H), 3.76 (s, 2H), 3.59 (s, 2H), 3.10 (s, 6H), 2.15 (s, 6H), 2.02-1.74 (m, 6H), 1.40 (s, 2H), 0.93 (s, 6H).

Example 221

4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide Example 221A 4-((4-methyltetrahydro-2H-pyran-4-yl)methoxy)-3-nitrobenzenesulfonamide The title compound was prepared by substituting (4-methyltetrahydro-2H-pyran-4-yl)methanol for (tetrahydro-2H-pyran-4-yl)methanol in EXAMPLE 24A.

Example 221B 4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide The title compound was prepared by substituting EXAMPLE 221A for EXAMPLE 11B in EXAMPLE 11D. $^1$H NMR (500 MHz, dimethylsulfoxide-d$_6$) δ 11.69 (s, 1H), 8.36 (s, 1H), 8.04-8.06 (m, 2H), 7.50-7.53 (m, 3H), 7.41 (d, 1H), 7.35 (d, 2H), 7.04 (d, 2H), 6.67 (dd, 1H), 6.40 (dd, 1H), 6.20 (d, 1H), 4.00 (s, 2H), 3.63-3.67 (m, 2H), 3.53-3.58 (m, 2H), 3.09 (s, 4H), 2.82 (s, 2H), 2.27 (s, 2H), 2.15 (s, 2H), 1.58-1.63 (m, 2H), 1.39 (t, 2H), 1.30-1.34 (m, 2H), 1.09 (s, 3H), 0.92 (s, 6H).

Example 222 ethyl 4-(4-{[4-(4-{[2-(4-chlorophenyl)-4,4-dimethyl-cyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate

Example 222A ethyl 4-(2-nitro-4-sulfamoylphenyl)piperazine-1-carboxylate

The title compound was prepared by substituting ethyl piperazine-1-carboxylate for 1-(tetrahydropyran-4-yl)methylamine in EXAMPLE 1F.

Example 222B ethyl 4-(4-{[4-(4-{[2-(4-chlorophenyl)-4,4-dimethyl-cyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate The title compound was prepared by substituting EXAMPLE 3J for EXAMPLE 1E and EXAMPLE 222A for EXAMPLE 1F in EXAMPLE 1G. $^1$H NMR (500 MHz, dimethylsulfoxide-$d_6$) δ 11.52 (br. s, 1H), 8.08 (d, 1H), 7.89 (d, 1H), 7.59 (m, 2H), 7.43 (t, 1H), 7.35 (d, 2H), 7.23 (d, 1H), 7.05 (d, 2H), 6.94 (d, 1H), 6.63 (dd, 1H), 6.29 (m, 2H), 4.07 (q, 2H), 3.47 (m, 4H), 3.17 (d, 2H), 3.00 (m, 8H), 2.73 (s, 2H), 2.18 (m, 6H), 1.96 (s, 2H), 1.39 (t, 2H), 1.20 (t, 3H), 0.93 (s, 6H).

Example 223

4-(4-{[2-(4-chlorophenyl)-4,4-dimethylcyclohex-1-en-1-yl]methyl}piperazin-1-yl)-N-({4-[4-(morpholin-4-yl)piperidin-1-yl]-3-nitrophenyl}sulfonyl)-2-(1H-pyrrolo[2,3-b]pyridin-5-yloxy)benzamide

Example 223A

The title compound was prepared by substituting 4-(piperidin-4-yl)morpholine for 1-(tetrahydropyran-4-yl)methylamine in EXAMPLE 1F.

Example 223B 4-(4-{[2-(4-chlorophenyl)-4,4-dimethylcyclohex-1-en-1-yl]methyl}piperazin-1-yl)-N-({4-[4-(morpholin-4-yl)piperidin-1-yl]-3-nitrophenyl}sulfonyl)-2-(1H-pyrrolo[2,3-b]pyridin-5-yloxy)benzamide The title compound was prepared by substituting EXAMPLE 3J for EXAMPLE 1E and EXAMPLE 223A for EXAMPLE 1F in EXAMPLE 1G. $^1$H NMR (500 MHz, dimethylsulfoxide-$d_6$) δ 11.53 (br. s, 1H), 8.05 (d, 1H), 7.91 (d, 1H), 7.58 (m, 2H), 7.43 (t, 1H), 7.35 (d, 2H), 7.26 (d, 1H), 7.05 (d, 2H), 6.91 (d, 1H), 6.62 (dd, 1H), 6.29 (m, 2H), 5.76 (s, 1H), 3.57 (m, 4H), 3.20 (m, 2H), 3.01 (m, 4H), 2.80 (t, 2H), 2.73 (s, 2H), 2.47 (m, 4H), 2.32 (m, 1H), 2.18 (m, 6H), 1.96 (m, 3H), 1.82 (m, 2H), 1.44 (m, 4H), 0.93 (s, 6H).

Example 224

4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide

Example 224A (R)-tert-butyl 1-(oxetan-3-yl)pyrrolidin-3-ylcarbamate

The title compound was prepared by substituting (R)-tert-butyl pyrrolidin-3-ylcarbamate for tert-butyl piperazine-1-carboxylate and 3-oxetanone for 4'-chlorobiphenyl-2-carboxaldehyde in EXAMPLE 1A.

Example 224B (R)-1-(oxetan-3-yl)pyrrolidin-3-amine

The title compound was prepared by substituting EXAMPLE 224A for (S)-1-tert-butyl 2-methyl 4,4-difluoropyrrolidine-1,2-dicarboxylate in EXAMPLE 168A.

Example 224C (R)-3-nitro-4-(1-(oxetan-3-yl)pyrrolidin-3-ylamino)benzenesulfonamide The title compound was prepared by substituting 4-fluoro-3-nitrobenzenesulfonamide for 4-chloro-3-nitrobenzenesulfonamide and EXAMPLE 224B for 4-methylpiperazin-1-amine dihydrochloride in EXAMPLE 6A.

Example 224D 4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide The title compound was prepared by substituting EXAMPLE 224C for EXAMPLE 11B in EXAMPLE 11D. $^1$H NMR (400 MHz, pyridine-$d_5$) δ 13.03 (s, 1H), 9.26 (d, 1H), 8.57 (d, 1H), 8.42 (d, 1H), 8.36 (dd, 1H), 8.09 (d, 1H), 7.66 (m, 1H), 7.64 (d, 1H), 7.44 (m, 2H), 7.07 (m, 2H), 6.86 (d, 1H), 6.75 (dd, 1H), 6.54 (d, 1H), 6.48 (dd, 1H), 4.67 (m, 4H), 3.58 (m, 1H), 3.07 (m, 4H), 2.77 (m, 2H), 2.68 (m, 2H), 2.61 (m, 1H), 2.28 (m, 4H), 2.14 (m, 4H), 1.97 (m, 2H), 1.67 (m, 1H), 1.39 (t, 2H), 0.93 (s, 6H).

Example 225

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide

Example 225A (R)-4-(1-(1,3-difluoropropan-2-yl)pyrrolidin-3-ylamino)-3-(trifluoromethylsulfonyl)benzenesulfonamide To EXAMPLE 207A (0.217 g) and 4-fluoro-3-(trifluoromethylsulfonyl)benzenesulfonamide (0.281 g) in tetrahydrofuran (5 mL) was added diisopropylethylamine (0.559 mL) and the reaction was allowed to stir at room temperature for 1 hour and was then heated to 50° C. for 1 hour. The reaction was concentrated, the residue was loaded onto silica gel (Reveleris 40 g) and eluted with a gradient of 0.75% methanol/dichloromethane to 7.5% methanol/dichloromethane to provide the title compound.

Example 225B 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide The title compound was prepared by substituting EXAMPLE 3J for EXAMPLE 1E and EXAMPLE 225A for EXAMPLE 1F in EXAMPLE 1G. $^1$H NMR (300 MHz, dimethylsulfoxide-$d_6$) δ 11.69 (s, 1H), 11.52-11.23 (m, 1H), 8.17 (d, 1H), 8.04 (d, 1H), 7.95 (d, 1H), 7.54 (d, 1H), 7.53-7.50 (m, 1H), 7.48 (d, 1H), 7.34 (d, 2H), 7.10-6.97 (m, 4H), 6.67 (d, 1H), 6.40 (dd, 1H), 6.18 (d, 1H), 4.60 (dd, 4H), 4.20 (s, 1H), 3.11-2.63 (m, 12H), 2.19 (d, 6H), 1.95 (s, 2H), 1.58 (s, 1H), 1.40 (d, 2H), 0.92 (s, 6H).

Example 226

4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide Example 226A tert-butyl 4-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate To a solution of EXAMPLE 82 (800 mg) and tert-butyl 4-aminopiperidine-1-carboxylate (203 mg) in dioxane (10 mL) was added Hunig's Base (1 mL). The mixture was stirred at 120° C. overnight. The mixture was diluted with ethyl acetate (200 mL) and washed with water, brine and dried over $Na_2SO_4$. After filtration and evaporation of solvent, the residue was loaded on a silica gel cartridge and eluted with 3% methanol in dichloromethane to give the title compound.

Example 226B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide To a solution of EXAMPLE 226A (902 mg) in dichloromethane (10 mL) was added trifluoroacetic acid (5 mL). The mixture was stirred at room temperature for 3 hours. The mixture was concentrated under vacuum and co-concentrated with dichloromethane twice to afford the crude product which was used in the next step without further purification.

Example 226C 4-(4-{[2-(4-chlorophenyl)-4,4-dimethylcyclohex-1-en-1-yl]methyl 1 piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide To a solution of EXAMPLE 226B (79 mg) in tetrahydrofuran (3 mL) and acetic acid (1 mL) was added acetone (54 mg) and MP-cyanoborohydride (150 mg, 2.25 mmol/g). The mixture was stirred overnight. The mixture was filtered. The filtrate was concentrated and the residue was loaded on a silica gel cartridge and eluted with 5 to 10% 7N $NH_3$ in methanol in dichloromethane to provide the title compound. $^1$H NMR (300 MHz, dimethylsulfoxide-$d_6$) δ 12.09 (s, 1H), 8.34 (m, 1H), 7.93 (m, 2H), 7.66 (m, 4H), 7.35 (d, 2H), 7.06 (d, 2H), 6.89 (m, 1H), 6.74 (dd, 1H), 6.59 (dd, 1H), 6.50 (d, 1H), 3.11 (m, 6H), 2.73 (m, 4H), 2.26 (m, 9H), 1.97 (s, 3H), 1.40 (t, 2H), 1.23 (s, 8H), 0.94 (s, 6H).

Example 227

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 227A 1-tert-butylpiperidin-4-amine To a solution of 1-tert-butylpiperidin-4-one (5.0 g) in methanol (100 mL) and water (10 mL) was added ammonium formate (20.3 g) and 0.5 g of Pd/C (10%). The mixture was stirred overnight. The mixture was filtered and the filtrate was concentrated under vacuum and the residue was diluted with ethyl acetate (500 mL) and washed with water and brine. After drying over $Na_2SO_4$ and filtration, the solvent was evaporated under vacuum to provide the title compound.

Example 227B 4-(1-tert-butylpiperidin-4-ylamino)-3-nitrobenzenesulfonamide

To a mixture of 4-fluoro-3-nitrobenzenesulfonamide (2.2 g) and EXAMPLE 227A (1.56 g) in tetrahydrofuran (20 mL) was added Hunig's Base (6 mL). The mixture was stirred for 3 days. The mixture was diluted with ethyl acetate (300 mL) and water (100 mL) and stirred until the solid disappeared into the solution. The layers were separated and the organic phase was washed with water and brine, dried over $Na_2SO_4$, and filtered. The combined aqueous layers were extracted again with ethyl acetate and the combined organic phases were dried over $Na_2SO_4$. After filtration, the solvent was evaporated to provide the title compound.

Example 227C

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 227B for EXAMPLE 1F in EXAMPLE 1G. $^1$H NMR (300 MHz, dimethylsulfoxide-$d_6$) δ 11.51 (s, 1H), 8.43 (d, 1H), 8.04 (m, 1H), 7.93 (d, 1H), 7.72 (m, 1H), 7.56 (dd, 1H), 7.42 (m, 1H), 7.34 (m, 3H), 7.05 (d, 2H), 6.93 (dd, 1H), 6.62 (dd, 1H), 6.28 (m, 1H), 3.04 (m, 6H), 2.73 (s, 3H), 2.25 (m, 9H), 1.95 (s, 2H), 1.68 (m, 2H), 1.32 (m, 9H), 0.93 (s, 6H).

Example 228

4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide

Example 228A tert-butyl 3-((2-nitro-4-sulfamoylphenylamino)methyl)piperidine-1-carboxylate The title compound was prepared by substituting tert-butyl 3-(aminomethyl)piperidine-1-carboxylate for (tetrahydropyran-4-yl)methylamine in EXAMPLE 1F.

Example 228B 3-nitro-4-(piperidin-3-ylmethylamino)benzenesulfonamide

The title compound was prepared by substituting EXAMPLE 228A for EXAMPLE 113A in EXAMPLE 134A.

Example 228C 4-((1-(2-methoxyethyl)piperidin-3-yl)methylamino)-3-nitrobenzenesulfonamide The title compound was prepared by substituting EXAMPLE 228B for EXAMPLE 134A and 2-methoxyethyl bromide for methyl iodide in EXAMPLE 134B.

Example 228D 4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide The title compound was prepared by substituting EXAMPLE 228C for EXAMPLE 130C in EXAMPLE 130D. $^1$H NMR (500 MHz, pyridine-$d_5$, 90° C.) δ 12.40 (s, 1H), 8.52 (s, 1H), 8.43 (s, 1H), 8.20 (m, 2H), 7.95 (bs, 1H), 7.80 (s, 1H), 7.46 (d, 1H), 7.36 (d, 2H), 7.07 (d, 2H), 7.05 (s, 1H), 6.75 (d, 1H), 6.59 (s, 1H), 6.47 (s, 1H), 3.65-3.50 (m, 5H), 3.20 (s, 3H), 3.04 (m, 5H), 2.81 (s, 3H), 2.74 (m, 3H), 2.24 (m, 7H), 2.06 (s, 2H), 2.00 (s, 2H), 1.75 (m, 1H), 1.57 (m, 2H), 1.42 (t, 2H), 1.15 (m, 1H), 0.95 (s, 6H).

Example 229

4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide

Example 229A 4-((1-(cyanomethyl)piperidin-3-yl)methylamino)-3-nitrobenzenesulfonamide The title compound was prepared by substituting EXAMPLE 228B for EXAMPLE 134A and 2-bromoacetonitrile for methyl iodide in EXAMPLE 134B.

Example 229B 4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide The title compound was prepared by substituting EXAMPLE 229A for EXAMPLE 130C in EXAMPLE 130D. $^1$H NMR (500 MHz, pyridine-$d_5$) δ 13.06 (s, 1H), 9.03 (s, 1H), 8.42 (s, 1H), 8.30 (d, 1H), 8.10 (d, 1H), 7.68 (m, 2H), 7.44 (d, 2H), 7.08 (m, 3H), 6.99 (d, 1H), 6.75 (d, 1H), 6.51 (m, 2H), 3.78 (m, 2H), 3.43 (d, 1H), 3.13 (m, 1H), 3.04 (m, 4H), 2.76 (s, 2H), 2.71-2.65 (m, 3H), 2.52 (m, 1H), 2.25 (m, 2H), 2.14 (m, 4H), 1.97 (s, 2H), 1.84 (m, 1H), 1.68 (m, 1H), 1.50 (m, 2H), 1.39 (t, 2H), 1.07-0.99 (m, 1H), 0.93 (s, 6H).

Example 230

4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide

Example 230A 4-((4-fluoro-1-methylpiperidin-4-yl)methoxy)-3-(trifluoromethylsulfonyl)benzenesulfonamide To a solution of (4-fluoro-1-methylpiperidin-4-yl)methanol (0.315 g) in tetrahydrofuran (5 mL) was added sodium hydride (0.342 g). After stirring for 15 minutes, 4-fluoro-3-(trifluoromethylsulfonyl)benzenesulfonamide (0.658 g) was added as a solution in tetrahydrofuran (2 mL) followed by additional tetrahydrofuran (5 mL). After stirring for 1 hour, the reaction was poured in dichloromethane (50 mL) and water (25 mL) and the pH of the water layer was adjusted to 8. The organic layer was dried over magnesium sulfate, filtered, and concentrated. The resulting oil was chromatographed over silica gel (Reveleris 40 g) eluting with a gradient of 1.0% to 10% 7N $NH_3$ in methanol/dichloromethane over 20 minutes then maintaining 10% 7N $NH_3$ in methanol/dichloromethane for 5 minutes (flow=30 mL/min) to provide the title compound.

Example 230B 4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 230A for EXAMPLE 1F in EXAMPLE 1G. $^1$H NMR (300 MHz, dimethylsulfoxide-$d_6$) δ 11.63-11.57 (m, 1H), 8.40-8.36 (m, 1H), 8.28-8.17 (m, 1H), 7.97 (s, 1H), 7.53 (d, 1H), 7.50-7.32 (m, 5H), 7.05 (d, 1H), 7.05 (d, 1H), 6.68-6.61 (m, 1H), 6.35 (s, 1H), 6.22 (s, 1H), 4.55-4.40 (m, 2H), 3.06 (s, 8H), 2.79 (s, 4H), 2.06 (d, 13H), 1.39 (s, 2H), 0.93 (s, 6H).

Example 231

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 231A (R)-5-chloro-6-(1-(1,3-difluoropropan-2-yl)pyrrolidin-3-ylamino)pyridine-3-sulfonamide To EXAMPLE 207A (0.051 g) and EXAMPLE 40A (0.049 g) in dioxane (5 mL) was added diisopropylethylamine (0.131 mL) and the reaction was heated to 75° C. for 1 hour then 85° C. for 2 days. The reaction was concentrated, loaded onto silica gel (Reveleris 12 g) and eluted with a gradient of 0.75% methanol/dichloromethane to 7.5% methanol/dichloromethane to provide the title compound.

Example 231B

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 231A for EXAMPLE 1F in EXAMPLE 1G. $^1$H NMR (300 MHz, dimethylsulfoxide-$d_6$) δ 11.71 (s, 1H), 11.44-11.11 (m, 1H), 8.44 (d, 1H), 8.07 (d, 1H), 7.90 (d, 1H), 7.61 (d, 1H), 7.52 (dd, 2H), 7.34 (d, 2H), 7.19 (s, 1H), 7.04 (d, 2H), 6.67 (d, 1H), 6.42 (dd, 1H), 6.16 (s, 1H), 4.77-4.39 (m, 5H), 3.19-2.63 (m, 11H), 2.19 (s, 7H), 1.91 (d, 3H), 1.38 (s, 2H), 0.92 (s, 6H).

Example 232 tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate

Example 232A tert-butyl 4-nitrosopiperazine-1-carboxylate

In a 500 mL round-bottomed flask, 6N aqueous HCl (30 mL) was cooled to −10° C., and tert-butyl piperazine-1-carboxylate (10 g) was added. Sodium nitrite (4.5 g) dissolved in 35 ml water was added slowly. NaOH (10 g in 20 mL water) was used to neutralize the solution. Dichloromethane (3×50 mL) was used to extract the product. After drying over Na$_2$SO$_4$ and filtration, the solution was concentrated. The crude product was added to a silica gel column (Analogix, SF65-400 g,) and purified by eluting with 0-30% ethyl acetate in hexane.

Example 232B tert-butyl 4-aminopiperazine-1-carboxylate

In a 100 mL round-bottomed flask was added EXAMPLE 232A (0.15 g) and zinc (1 g) in water/methanol (1:1, 10 mL) to give a suspension. The mixture was cooled to 0° C. 12N Aqueous HCl (2 ml) was added slowly, and the mixture was stirred at 0° C. for 30 minutes. 2N Aqueous NaOH solution was used to adjust the mixture to basic pH. The mixture was filtered, and extracted with ether (3×30 mL). After drying over Na$_2$SO$_4$, filtration, and concentration, the crude product was added to a silica gel column (Analogix, SF15-12 g,) and purified by eluting with 0-25% ethyl acetate in hexane.

Example 232C tert-butyl 4-(2-nitro-4-sulfamoylphenylamino)piperazine-1-carboxylate The title compound was prepared by substituting EXAMPLE 232B for 1-(tetrahydropyran-4-yl)methylamine in EXAMPLE 1F.

Example 232D tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate The title compound was prepared by substituting EXAMPLE 3J for EXAMPLE 1E and EXAMPLE 232C for EXAMPLE 1F in EXAMPLE 1G. $^1$H NMR (300 MHz, dimethylsulfoxide-$d_6$) δ 11.47 (br. s, 1H), 8.86 (s, 1H), 8.34 (d, 1H), 7.90 (d, 1H), 7.59 (m, 2H), 7.36 (m, 4H), 7.23 (m, 1H), 7.05 (d, 2H), 6.61 (dd, 1H), 6.27 (m, 2H), 2.99 (m, 5H), 2.76 (m, 6H), 2.19 (m, 6H), 1.96 (s, 2H), 1.41 (m, 11H), 1.24 (m, 4H), 0.93 (s, 6H).

Example 233

4-(4-{[2-(4-chlorophenyl)-4,4-dimethylcyclohex-1-en-1-yl]methyl}piperazin-1-yl)-N-({3-(pentafluoro-lambda-6-sulfanyl)-4-[(tetrahydro-2H-pyran-4-ylmethyl)amino]phenyl}sulfonyl)-2-(1H-pyrrolo[2,3-b]pyridin-5-yloxy)benzamide

Example 233A 2-(5-bromo-2-nitrophenyl)sulfur pentafluoride

To a solution of 3-bromophenylsulfur pentafluoride (2.18 g) in concentrated H$_2$SO$_4$ (5 mL) was added KNO$_3$ (780 mg). The mixture was stirred overnight. The mixture was diluted with diethyl ether (100 mL) and washed with water and brine.

After drying over Na$_2$SO$_4$ and filtration, the solvent was evaporated under vacuum to provide the title compound.

Example 233B 2-(5-bromo-2-aminophenyl)sulfur pentafluoride

EXAMPLE 233A (6.4 g) and tetrahydrofuran (300 mL) were added to Ra—Ni, (12.80 g) in a 50 ml, pressure bottle and the mixture stirred for 2 hours at 30 psi and room temperature. The mixture was filtered though a nylon membrane and the filtrate was concentrated under vacuum to provide the title compound.

Example 233C 4-bromo-2-pentafluorosulfanyl-N-(tetrahydro-2H-pyran-4-ylmethyl)aniline To a solution of EXAMPLE 233B (4.4 g) in methanol (50 mL) was added tetrahydro-2H-pyran-4-carbaldehyde (1.68 g) and decaborane (1.1 g). The mixture was stirred and monitored by thin layer chromatography. More tetrahydro-2H-pyran-4-carbaldehyde (500 mg) was added to the stirring mixture to drive the reaction to completion. The reaction mixture was concentrated under vacuum and ethyl acetate (500 mL) and brine (200 mL) were added. The organic phase was dried over Na$_2$SO$_4$. Filtration and evaporation of the solvent and flash chromatography (20% ethyl acetate in hexane) gave the title compound.

Example 233D 4-thioacetoxy-2-pentafluorosulfanyl-N-(tetrahydro-2H-pyran-4-ylmethyl)aniline To a solution of EXAMPLE 233C (456 mg) and potassium ethanethioate (197 mg) in dioxane (4 mL) was added tris(dibenzylideneacetone)dipalladium(0) (27 mg) and xantphos (33 mg) followed by N,N-diisopropylethylamine (0.5 mL). The mixture was purged with argon, sealed and stirred under microwave irradiation for 60 minutes at 120° C. The mixture was dissolved in ethyl acetate (300 mL) and water (100 mL). The organic phase was washed with brine and dried over Na$_2$SO$_4$. Filtration and evaporation of the solvent followed by flash chromatography (20% ethyl acetate in hexane) provided the title compound.

Example 233E 3-pentafluorosulfanyl-4-[(tetrahydro-2H-pyran-4-ylmethyl)amino]phenylsulfonamide N-chlorosuccinimide (527 mg) was added to a mixture of 2N aqueous HCl (1.5 mL) and acetonitrile (12 mL) and then cooled to 0° C. A solution of EXAMPLE 233D (386 mg) in acetonitrile (3 mL) was added to the mixture which was then stirred at 0° C. for 2 hours, and then diluted with ethyl acetate (300 mL) and washed with brine and dried over Na$_2$SO$_4$. After filtration and evaporation of solvent, the residue was dissolved in isopropyl alcohol (20 mL) and cooled to 0° C. with stirring. Then, ammonium hydroxide (conc. 10 mL) was added to mixture. After stirring for 2 hours, the mixture was concentrated under vacuum and the residue was added to ethyl acetate (400 mL) and water (150 mL). The organic layer was washed with brine and dried over Na$_2$SO$_4$. After filtration and evaporation of solvent, the residue was purified by flash column (20% ethyl acetate in dichloromethane) to provide the title compound.

Example 233F 4-(4-{[2-(4-chlorophenyl)-4,4-dimethylcyclohex-1-en-1-yl]methyl}piperazin-1-yl)-N-({3-(pentafluoro-lambda-6-sulfanyl)-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 233E for EXAMPLE 1F in EXAMPLE 1G. $^1$H NMR (300 MHz, dimethylsulfoxide-d$_6$) δ 11.71 (s, 1H), 11.33 (m, 1H), 8.12 (m, 2H), 7.72 (d, 1H), 7.54 (m, 3H), 7.33 (m, 2H), 7.02 (m, 3H), 6.67 (m, 2H), 6.42 (m, 1H), 6.16 (d, 1H), 3.82 (m, 2H), 3.21 (m, 4H), 3.05 (m, 4H), 2.73 (s, 2H), 2.21 (m, 8H), 1.97 (m, 3H), 1.29 (m, 4H), 0.92 (s, 6H).

Example 234

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide Example 234A 4-vinyltetrahydro-2H-pyran-4-ol Dihydro-2H-pyran-4(3H)-one (8.01 g) in anhydrous ethyl ether (50 mL) was treated with 1.0 M vinylmagnesium bromide (104 mL) over 20 minutes at 0° C. The reaction mixture was stirred at room temperature overnight. The reaction was quenched with saturated NH$_4$Cl, and the organic layer was separated. The aqueous layer was extracted with additional ethyl ether three times. The combined organic layers were washed with brine, dried, filtered, and concentrated. The residue was purified by flash column chromatography on silica gel using 20% ethyl acetate in hexanes to provide the title compound.

Example 234B 4-methoxy-4-vinyltetrahydro-2H-pyran

To a solution of EXAMPLE 234A (9.4 g) in tetrahydrofuran (150 mL) was added 60% sodium hydride (5.28 g) at 0° C. portionwise. After the addition was complete, the solution was heated under reflux for three hours. After cooling, to this suspension was added dimethyl sulfate (8.41 mL) slowly. The solution was heated under reflux overnight, cooled to room temperature, and hydrolyzed with cool saturated aqueous NH$_4$Cl. After extraction with diethyl ether several times, the combined organic layers were washed with brine, dried over MgSO$_4$, filtered, and concentrated. The residue was purified by flash column chromatograph on silica gel using 1-10% ethyl acetate in hexanes to provide the title compound.

Example 234C 4-methoxytetrahydro-2H-pyran-4-carbaldehyde

EXAMPLE 234B (4.3 g) in tetrahydrofuran (200 mL) and water (67 mL) was treated with 4% osmium tetroxide in water (9.24 mL). To this solution was added potassium periodate (13.91 g) portionwise over 2 hours. The solution was stirred overnight at room temperature. Water was added to the mixture followed by repeat extractions with diethyl ether. The combined organic layers were dried over MgSO$_4$, filtered, and concentrated. The residue was purified by flash column chromatography on silica gel using 5-20% ethyl acetate in hexanes to provide the title compound.

Example 234D (4-methoxytetrahydro-2H-pyran-4-yl)methanol

EXAMPLE 234C (1.8 g) in 2-propanol (28 mL) and water (7 mL) was cooled to 0° C. To this solution was added sodium borohydride (0.709 g). The solution was stirred and allowed to warm to room temperature over 3 hours. The reaction was quenched with acetone, and stirred for another 1 hour. The clear liquid was separated from solid by decanting. Additional ethyl acetate was used to wash the solid, and was the mixture was decanted. The combined organic solutions were concentrated. The residue was purified by flash chromatography on silica gel eluting 1:1 ethyl acetate:hexane to provide the title compound.

Example 234E 4-((4-methoxytetrahydro-2H-pyran-4-yl)methoxy)-3-nitrobenzenesulfonamide The title compound was prepared by substituting EXAMPLE 234D for (tetrahydro-2H-pyran-4-yl)methanol in EXAMPLE 24A.

Example 234F 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide The title compound was prepared by substituting EXAMPLE 234E for EXAMPLE 11B in EXAMPLE 11D. $^1$H NMR (500 MHz, dimethylsulfoxide-d$_6$) δ 11.68 (s, 1H), 8.36 (s, 1H), 8.04-8.07 (m, 2H), 7.50-7.53 (m, 3H), 7.45 (d, 1H), 7.35 (d, 2H), 7.05 (d, 2H), 6.68 (dd, 1H), 6.40 (dd, 1H), 6.20 (d, 1H), 4.21 (s, 2H), 3.65-3.67 (m, 2H), 3.53-3.56 (m, 2H), 3.19 (s, 3H), 3.10 (s, 4H), 2.86 (s, 2H), 2.30 (s, 4H), 2.15 (s, 2H), 1.96 (s, 2H), 1.61-1.74 (m, 4H), 1.39 (t, 2H), 0.93 (s, 6H).

Example 235

4-(4-{[2-(4-chlorophenyl)-4,4-dimethylcyclohex-1-en-1-yl]methyl 1 piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide Example 235A (R)-tert-butyl 3-(2-nitro-4-sulfamoylphenoxy)pyrrolidine-1-carboxylate The title compound was prepared by substituting (R)-tert-butyl 3-hydroxypyrrolidine-1-carboxylate for (tetrahydro-2H-pyran-4-yl)methanol in EXAMPLE 24A.

Example 235B (R)-tert-butyl 3-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenoxy)pyrrolidine-1-carboxylate The title compound was prepared by substituting EXAMPLE 3J for EXAMPLE 1E and EXAMPLE 235A for EXAMPLE 1F in EXAMPLE 1G.

Example 235C 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide To a solution of EXAMPLE 235B (0.230 g) in dichloromethane (3 mL) was added trifluoroacetic acid (0.377 mL). After stirring for 4 hours, the reaction was concentrated then dissolved in dichloromethane (3 mL) and treated with 1,3-difluoropropan-2-one (0.028 g) followed by sodium triacetoxyborohydride (0.078 g). After stirring for 4 hours, the reaction was quenched by the addition of saturated aqueous NaHCO$_3$ and dichloromethane (5 mL). The reaction was diluted with dichloromethane (250 mL) and saturated aqueous NaHCO$_3$ (100 mL) was added. The organic layer was separated, washed with brine (100 mL), dried over magnesium sulfate, filtered and concentrated. Trituration with acetonitrile gave the title compound. $^1$H NMR (300 MHz, dimethylsulfoxide-d$_6$) δ 11.67 (s, 1H), 8.34 (s, 1H), 8.03 (s, 2H), 7.52 (d, 3H), 7.35 (d, 3H), 7.04 (d, 2H), 6.75-6.60 (m, 1H), 6.40 (s, 1H), 6.20 (s, 1H), 5.17-5.06 (m, 1H), 4.60 (d, 4H), 2.98 (d, 12H), 2.37-2.02 (m, 6H), 1.96 (s, 3H), 1.39 (s, 2H), 0.93 (s, 6H).

Example 236

4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide Example 236A 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperazin-1-ylamino)phenylsulfonyl)benzamide The title compound was prepared by substituting EXAMPLE 232D for EXAMPLE 1A in EXAMPLE 1B.

Example 236B 4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide The title compound was prepared by substituting EXAMPLE 236A for tert-butyl piperazine-1-carboxylate and oxetan-3-one for 4'-chlorobiphenyl-2-carboxaldehyde in EXAMPLE 1A. $^1$H NMR (400 MHz, dimethylsulfoxide-d$_6$) δ 11.67 (br. s, 1H), 9.20 (s, 1H), 8.53 (d, 1H), 8.04 (d, 1H), 7.83 (dd, 1H), 7.53 (m, 4H), 7.34 (d, 2H), 7.04 (d, 2H), 6.67 (dd, 1H), 6.39 (m, 1H), 6.18 (d, 1H), 4.55 (t, 2H), 4.44 (t, 2H), 3.47 (m, 1H), 3.06 (m, 4H), 2.88 (m, 4H), 2.74 (m, 4H), 2.09 (m, 11H), 1.38 (t, 2H), 0.91 (s, 6H).

Example 237

4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide The title compound was prepared by substituting EXAMPLE 236A for tert-butyl piperazine-1-carboxylate and dihydro-2H-pyran-4(3H)-one for 4'-chlorobiphenyl-2-carboxaldehyde in EXAMPLE 1A. $^1$H NMR (400 MHz, pyridine-d$_5$) δ 13.05 (br. s, 1H), 9.27 (d, 1H), 9.23 (s, 1H), 8.44 (m, 2H), 8.12 (d, 1H), 7.68 (m, 3H), 7.44 (m, 2H), 7.06 (m, 2H), 6.75 (dd, 1H), 6.51 (m, 2H), 4.02 (m, 2H), 3.31 (m, 2H), 3.06 (m, 4H), 2.91 (m, 5H), 2.76 (s, 2H), 2.38 (m, 2H), 2.26 (m, 2H), 2.14 (m, 4H), 1.97 (s, 2H), 1.65 (m, 2H), 1.39 (m, 7H), 0.93 (s, 6H).

Example 238

4-(4-{[2-(4-chlorophenyl)-4,4-dimethylcyclohex-1-en-1-yl]methyl}piperazin-1-yl)-N-({3-nitro-4-[(3R)-tetrahydro furan-3-ylamino]phenyl}sulfonyl)-2-(1H-pyrrolo[2,3-b]pyridin-5-yloxy)benzamide

Example 238A (R)-3-nitro-4-(tetrahydrofuran-3-ylamino)benzenesulfonamide

The title compound was prepared by substituting (R)-tetrahydrofuran-3-amine for 4-methylpiperazin-1-amine dihydrochloride in EXAMPLE 6A.

Example 238B 4-(4-{[2-(4-chlorophenyl)-4,4-dimethylcyclohex-1-en-1-yl]methyl}piperazin-1-yl)-N-({3-nitro-4-[(3R)-tetrahydro furan-3-ylamino]phenyl}sulfonyl)-2-(1H-pyrrolo[2,3-b]pyridin-5-yloxy)benzamide The title compound was prepared by substituting EXAMPLE 238A for EXAMPLE 1F and EXAMPLE 3J for EXAMPLE 1E in EXAMPLE 1G. $^1$H NMR (400 MHz, dimethylsulfoxide-d$_6$) δ 11.59 (s, 1H), 8.47 (d, 1H), 8.19 (m, 2H), 7.97 (d, 1H), 7.74 (m, 1H), 7.52 (d, 1H), 7.46 (t, 1H), 7.34 (m, 2H), 7.05 (m, 2H), 6.96 (d, 1H), 6.89 (d, 1H), 6.65 (dd, 1H), 6.33 (m, 1H), 6.22 (d, 1H), 4.31 (m, 1H), 3.92 (m, 1H), 3.87 (m, 1H), 3.76 (m, 1H), 3.69 (m, 1H), 3.04 (m, 4H), 2.73 (m, 2H), 2.33 (m, 1H), 2.18 (m, 6H), 1.95 (m, 2H), 1.88 (m, 1H), 1.39 (t, 2H), 0.92 (s, 6H).

Example 239

4-(4-{[2-(4-chlorophenyl)-4,4-dimethylcyclohex-1-en-1-yl]methyl}piperazin-1-yl)-N-[(4-{[(4,4-difluoro cyclohexyl)methyl]amino}-3-nitrophenyl)sulfonyl]-2-(1H-pyrrolo[2,3-b]pyridin-5-yloxy)benzamide

Example 239A tert-butyl (4,4-difluorocyclohexyl)methylcarbamate

Tert-butyl (4-oxocyclohexyl)methylcarbamate (5 g) and diethylaminosulfur trifluoride (7.45 g) were stirred in dichloromethane (100 mL) for 24 hours. The mixture was quenched with pH 7 buffer (100 mL), and poured into ether (400 mL). The resulting solution was separated, and the organic layer was washed twice with water, and once with brine, and then concentrated to give the crude product and fluoroolefin by-product in a 3:2 ratio. The crude material was taken up in tetrahydrofuran (70 mL) and water (30 mL), and N-methylmorpholine-N-oxide (1.75 g), and OsO$_4$ (2.5 wt % solution in t-butanol) were added, and the mixture was stirred for 24 hours. Na$_2$S$_2$O$_3$ (10 g) was then added, and the mixture was stirred for 30 minutes. The mixture was then diluted with ether (300 mL), and the resulting solution was separated, and rinsed twice with water, and once with brine, and concentrated. The crude product was chromatographed on silica gel using 5-10% ethyl acetate in hexanes to provide the title compound.

Example 239B (4,4-difluorocyclohexyl)methanamine

A solution of EXAMPLE 239A (3 g) in dichloromethane (35 mL), trifluoroacetic acid (15 mL), and triethylsilane (1 mL) was stirred for 2 hours. The solution was concentrated, then concentrated from toluene, and left on high vacuum for 24 hours. The semi-solid was taken up in ether/hexane and filtered to provide the title compound as its trifluoroacetic acid salt.

Example 239C 4-((4,4-difluorocyclohexyl)methylamino)-3-nitrobenzenesulfonamide The title compound was prepared by substituting EXAMPLE 239B for (tetrahydropyran-4-yl)methylamine in EXAMPLE 1F.

Example 239D 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide The title compound was prepared by substituting EXAMPLE 3J for EXAMPLE 1E and EXAMPLE 239C for EXAMPLE 1F in EXAMPLE 1G. $^1$H NMR (300 MHz, dimethylsulfoxide-d$_6$) δ 12.40 (s, 1H), 11.61 (br s, 1H), 8.53 (m, 1H), 8.50 (d, 1H), 7.99 (d, 1H), 7.73 (d, 1H), 7.49 (m, 2H), 7.32 (d, 2H), 7.04 (d, 2H), 7.00 (d, 1H), 6.65 (d, 1H), 6.32 (s, 1H), 6.21 (s, 1H), 3.37 (m, 4H), 3.06 (m, 4H), 2.73 (m, 2H), 2.18 (m, 4H), 1.97 (m, 4H), 1.81 (m, 4H), 1.38 (m, 2H), 1.20 (m, 4H), 0.92 (s, 6H).

Example 240

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 240A 4-(1-tert-butylpiperidin-4-ylamino)-3-(trifluoromethylsulfonyl)benzenesulfonamide To a mixture of 4-fluoro-3-(trifluoromethylsulfonyl)benzenesulfonamide (307 mg) and EXAMPLE 227A (156 mg)

in tetrahydrofuran (4 mL) was added Hunig's Base (1 mL). The mixture was stirred for 3 days. The mixture was diluted with ethyl acetate (300 mL) and water (100 mL) and stirred until the solid disappeared into the solution. The layers were separated and the organic phase was washed with water, brine and dried over $Na_2SO_4$. After filtration, the combined aqueous layers were extracted again with ethyl acetate and the combined organic phase was dried over $Na_2SO_4$. After filtration, the solvent was evaporated to provide the title compound.

Example 240B

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 240A for EXAMPLE 1F in EXAMPLE 1G. $^1$H NMR (300 MHz, dimethylsulfoxide-$d_6$) δ 11.53 (s, 1H), 8.04 (s, 1H), 7.94 (d, 1H), 7.86 (m, 1H), 7.55 (d, 2H), 7.44 (d, 1H), 7.33 (m, 3H), 7.05 (d, 2H), 6.92 (m, 1H), 6.62 (dd, 1H), 6.43 (m, 1H), 6.29 (d, 2H), 3.79 (m, 1H), 3.05 (m, 6H), 2.73 (s, 3H), 2.19 (m, 8H), 1.96 (s, 3H), 1.27 (m, 12H), 0.92 (s, 6H).

Example 241

4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide Example 241A tert-butyl 2-((4-sulfamoyl-2-(trifluoromethylsulfonyl)phenylamino)methyl)morpholine-4-carboxylate The title compound was prepared by substituting tert-butyl 2-(aminomethyl)morpholine-4-carboxylate for (tetrahydropyran-4-yl)methylamine and 4-fluoro-3-(trifluoromethylsulfonyl)benzenesulfonamide for 4-fluoro-3-nitrobenzenesulfonamide in EXAMPLE 1F.

Example 241B tert-butyl 2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-(trifluoromethylsulfonyl)phenylamino)methyl)morpholine-4-carboxylate The title compound was prepared by substituting EXAMPLE 241A for EXAMPLE 1F and EXAMPLE 3J for EXAMPLE 1E in EXAMPLE 1G.

Example 241C 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-(morpholin-2-ylmethylamino)-3-(trifluoromethylsulfonyl)phenylsulfonyl)benzamide The title compound was prepared by substituting EXAMPLE 241B for EXAMPLE 1A in EXAMPLE 1B.

Example 241D 4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide The title compound was prepared by substituting EXAMPLE 241C for tert-butyl piperazine-1-carboxylate and oxetan-3-one for 4'-chlorobiphenyl-2-carboxaldehyde in EXAMPLE 1A. $^1$H NMR (300 MHz, dimethylsulfoxide-$d_6$) δ 11.69 (s, 1H), 8.15 (d, 1H), 8.04 (d, 1H), 7.92 (dd, 1H), 7.54 (d, 1H), 7.51 (t, 1H), 7.48 (d, 1H), 7.34 (d, 2H), 7.25 (m, 1H), 7.04 (m, 3H), 6.68 (dd, 1H), 6.41 (m, 1H), 6.19 (d, 1H), 4.54 (t, 2H), 4.43 (m, 2H), 3.85 (m, 1H), 3.69 (m, 1H), 3.52 (m, 1H), 3.48 (m, 1H), 3.39 (m, 2H), 3.07 (m, 4H), 2.77 (br s, 2H), 2.69 (d, 1H), 2.56 (d, 1H), 2.21 (br s, 4H), 2.15 (t, 2H), 1.94 (m, 3H), 1.76 (t, 1H), 1.38 (t, 2H), 0.92 (s, 6H).

Example 242

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 242A 5-chloro-6-((4-fluorotetrahydro-2H-pyran-4-yl)methylamino)pyridine-3-sulfonamide The title compound was prepared by substituting EXAMPLE 40A for 4-fluoro-3-nitrobenzenesulfonamide in EXAMPLE 138D.

Example 242B

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 242A for EXAMPLE 11B in EXAMPLE 11D. $^1$H NMR (500 MHz, dimethylsulfoxide-$d_6$) δ 11.71 (s, 1H), 8.41 (d, 1H), 8.07 (d, 1H), 7.93 (d, 1H), 7.60 (d, 1H), 7.51-7.53 (m, 2H), 7.40 (s, 1H), 7.33-7.35 (m, 2H), 7.03-7.05 (m, 2H), 6.68 (dd, 1H), 6.42 (dd, 1H), 6.16 (d, 1H), 3.77 (d, 1H), 3.69-3.71 (m, 3H), 3.48-3.53 (m, 2H), 3.07 (s, 4H), 2.76 (s, 2H), 2.14-2.20 (m, 6H), 1.96 (s, 2H), 1.65-1.76 (m, 4H), 1.38 (t, 2H), 0.93 (s, 6H).

Example 243

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 243A 5-chloro-6-(1-cyclopropylpiperidin-4-ylamino)pyridine-3-sulfonamide The title compound was prepared by substituting EXAMPLE 40A for 4-chloro-3-nitrobenzenesulfonamide, 1-cyclopropylpiperidin-4-amine for 4-methylpiperazin-1-amine dihydrochloride and Hunig's base for $N^1,N^1,N^2,N^2$-tetramethylethane-1,2-diamine in EXAMPLE 6A.

Example 243B

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 243A for EXAMPLE 11B in EXAMPLE 11D. $^1$H NMR (400 MHz, dimethylsulfoxide-d$_6$) δ 11.67 (s, 1H), 8.40 (d, 1H), 8.05 (d, 1H), 7.88 (d, 1H), 7.56 (d, 1H), 7.50 (m, 2H), 7.34 (d, 2H), 7.03 (d, 2H), 6.97 (br d, 1H), 6.66 (dd, 1H), 6.40 (m, 1H), 6.16 (d, 1H), 4.04 (m, 1H), 3.03 (br m, 6H), 2.73 (s, 2H), 2.42 (br m, 2H), 2.18 (br m, 6H), 1.95 (s, 2H), 1.80 (m, 3H), 1.62 (m, 2H), 1.38 (t, 2H), 0.91 (s, 6H), 0.47 (m, 2H), 0.40 (br m, 2H).

Example 244

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 244A (S)-tert-butyl 2-((3-chloro-5-sulfamoylpyridin-2-yloxy)methyl)morpholine-4-carboxylate The title compound was prepared by substituting (S)-tert-butyl 2-(hydroxymethyl)-morpholine-4-carboxylate for tetrahydro-2H-pyran-4-yl-methanol and EXAMPLE 40A for 4-fluoro-3-nitrobenzenesulfonamide in EXAMPLE 24A.

Example 244B (S)-5-chloro-6-(morpholin-2-ylmethoxy)pyridine-3-sulfonamide

The title compound was prepared by substituting EXAMPLE 244A for EXAMPLE 113A in EXAMPLE 134A.

Example 244C (S)-5-chloro-6-((4-(cyanomethyl)morpholin-2-yl)methoxy)pyridine-3-sulfonamide The title compound was prepared by substituting EXAMPLE 244B for EXAMPLE 134A and 2-bromoacetonitrile for methyl iodide in EXAMPLE 134B.

Example 244D

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 244C for EXAMPLE 130C in EXAMPLE 130D.

$^1$H NMR (500 MHz, pyridine-d$_5$) δ 12.99 (s, 1H), 9.09 (d, 1H), 8.70 (d, 1H), 8.42 (d, 1H), 8.12 (d, 1H), 7.66 (m, 2H), 7.44 (d, 2H), 7.07 (d, 2H), 6.75 (dd, 1H), 6.53 (d, 1H), 6.48 (m, 1H), 4.55 (dd, 1H), 4.43 (dd, 1H), 4.05 (m, 1H), 3.85 (d, 1H), 3.76 (s, 2H), 3.63 (dt, 1H), 3.06 (m, 4H), 2.91 (d, 1H), 2.77 (s, 2H), 2.58 (d, 1H), 2.51-2.44 (m, 2H), 2.26 (m, 2H), 2.14 (m, 4H), 1.97 (s, 2H), 1.39 (t, 2H), 0.94 (s, 6H).

Example 245

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 245A (S)-5-chloro-6-((4-(2-(dimethylamino)acetyl)morpholin-2-yl)methoxy)pyridine-3-sulfonamide The title compound was prepared by substituting EXAMPLE 244B for EXAMPLE 134A and 2-(dimethylamino)acetyl chloride hydrochloride for methyl iodide in EXAMPLE 134B.

Example 245B

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 245A for EXAMPLE 130C in EXAMPLE 130D. $^1$H NMR (500 MHz, pyridine-d$_5$) δ 13.00 (s, 1H), 9.09 (d, 1H), 8.69 (s, 1H), 8.42 (s, 1H), 8.11 (t, 1H), 7.66 (m, 2H), 7.44 (d, 2H), 7.07 (d, 2H), 6.76 (s, 1H), 6.54 (s, 1H), 6.49 (s, 1H), 4.85-4.46 (m, 3H), 4.45-3.87 (m, 3H), 3.50 (m, 1H), 3.37 (dd, 1H), 3.21 (m, 2H), 3.07 (m, 4H), 2.86 (t, 1H), 2.77 (s, 2H), 2.27 (m, 8H), 2.14 (m, 4H), 1.97 (s, 2H), 1.39 (t, 2H), 0.94 (s, 6H).

Example 246

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 246A (R)-tert-butyl 2-((3-chloro-5-sulfamoylpyridin-2-yloxy)methyl)morpholine-4-carboxylate The title compound was prepared by substituting (R)-tert-butyl 2-(hydroxymethyl)-morpholine-4-carboxylate for tetrahydro-2H-pyran-4-yl-methanol and EXAMPLE 40A for 4-fluoro-3-nitrobenzenesulfonamide in EXAMPLE 24A.

Example 246B (R)-5-chloro-6-(morpholin-2-ylmethoxy)pyridine-3-sulfonamide

The title compound was prepared by substituting EXAMPLE 246A for EXAMPLE 113A in EXAMPLE 134A.

Example 246C (R)-5-chloro-6-((4-(cyanomethyl)morpholin-2-yl)methoxy)pyridine-3-sulfonamide The title compound was prepared by substituting EXAMPLE 246B for EXAMPLE 134A and 2-bromoacetonitrile for methyl iodide in EXAMPLE 134B.

Example 246D

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 246C for EXAMPLE 130C in EXAMPLE 130D. $^1$H NMR (500 MHz, pyridine-$d_5$) δ 12.99 (s, 1H), 9.09 (d, 1H), 8.70 (d, 1H), 8.42 (d, 1H), 8.12 (d, 1H), 7.66 (m, 2H), 7.44 (d, 2H), 7.07 (d, 2H), 6.75 (dd, 1H), 6.53 (d, 1H), 6.48 (m, 1H), 4.55 (dd, 1H), 4.43 (dd, 1H), 4.05 (m, 1H), 3.85 (d, 1H), 3.76 (s, 2H), 3.63 (dt, 1H), 3.06 (m, 4H), 2.91 (d, 1H), 2.77 (s, 2H), 2.58 (d, 1H), 2.51-2.44 (m, 2H), 2.26 (m, 2H), 2.14 (m, 4H), 1.97 (s, 2H), 1.39 (t, 2H), 0.94 (s, 6H).

Example 247

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 247A (R)-5-chloro-6-((4-(2-(dimethylamino)acetyl)morpholin-2-yl)methoxy)pyridine-3-sulfonamide The title compound was prepared by substituting EXAMPLE 246B for EXAMPLE 134A and 2-(dimethylamino)acetyl chloride hydrochloride for methyl iodide in EXAMPLE 134B.

Example 247B

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 247A for EXAMPLE 130C in EXAMPLE 130D. $^1$H NMR (500 MHz, pyridine-$d_5$) δ 13.00 (s, 1H), 9.09 (d, 1H), 8.69 (s, 1H), 8.42 (s, 1H), 8.11 (t, 1H), 7.66 (m, 2H), 7.44 (d, 2H), 7.07 (d, 2H), 6.76 (s, 1H), 6.54 (s, 1H), 6.49 (s, 1H), 4.85-4.46 (m, 3H), 4.45-3.87 (m, 3H), 3.50 (m, 1H), 3.37 (dd, 1H), 3.21 (m, 2H), 3.07 (m, 4H), 2.86 (t, 1H), 2.77 (s, 2H), 2.27 (m, 8H), 2.14 (m, 4H), 1.97 (s, 2H), 1.39 (t, 2H), 0.94 (s, 6H).

Example 248

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide

Example 248A 5-bromo-3-fluoro-2-((4-fluorotetrahydro-2H-pyran-4-yl)methoxy)pyridine The title compound was prepared by substituting 5-bromo-2,3-difluoropyridine for 4-fluoro-3-nitrobenzenesulfonamide and EXAMPLE 37C for (tetrahydro-2H-pyran-4-yl)methanol in EXAMPLE 24A.

Example 248B tert-butyl 5-fluoro-6-((4-fluorotetrahydro-2H-pyran-4-yl)methoxy)pyridin-3-ylcarbamate EXAMPLE 248A (0.308 g), tert-butyl carbamate (0.141 g), palladium(II) acetate (0.011 g), Xantphos (0.043 g) and cesium carbonate (0.489 g) were combined with dioxane (5.0 mL) in a 20-mL vial equipped with a magnetic stir bar. The vial was flushed with nitrogen, capped and stirred at 100° C. overnight. Additional palladium(II) acetate (0.011 g), Xantphos (0.043 g) and tert-butyl carbamate (0.141 g) were added and heating was continued at 100° C. for 8 hours. The cooled reaction mixture was diluted with ethyl acetate, washed with water and brine, dried (MgSO$_4$), filtered and concentrated. The concentrate was chromatographed on silica gel with 7-25% ethyl acetate in hexanes as the eluent.

Example 248C 5-fluoro-6-((4-fluorotetrahydro-2H-pyran-4-yl)methoxy)pyridine-3-sulfonyl chloride Under ice-cooling, thionyl chloride (1.563 mL) was added dropwise over 20 minutes to water (9 mL). The mixture was stirred for 12 hours to give a SO$_2$-containing solution. Separately, EXAMPLE 248B (0.295 g) was added to a mixture of 1,4-dioxane (3.2 mL) and concentrated HCl (8 mL) at 0° C. After stirring for 15 minutes, a solution of sodium nitrite (0.065 g) in water (2 mL) was added dropwise and stirring was continued at 0° C. for 3 hours. Copper(I)chloride (0.042 g) and then the freshly prepared solution of diazotized material were added sequentially to the previously prepared SO$_2$-containing solution. The resulting solution was stirred for 30 minutes and then extracted with ethyl acetate (2×125 mL). The combined extracts were dried (MgSO$_4$), filtered and concentrated. The concentrate was chromatographed on silica gel with 5% ethyl acetate in hexanes as the eluent.

Example 248D 5-fluoro-6-((4-fluorotetrahydro-2H-pyran-4-yl)methoxy)pyridine-3-sulfonamide EXAMPLE 248C (0.08 g) in isopropanol (2 mL) at 0° C. was treated with ammonium hydroxide (1.697 mL), stirred overnight and then concentrated to dryness. The obtained solid was slurried in water, filtered, rinsed with water and dried under high vacuum to provide the title compound.

Example 248E 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting EXAMPLE 248D for EXAMPLE 11B in EXAMPLE 11D. $^1$H NMR (500 MHz, pyridine-$d_5$) δ 13.05 (s, 1H), 9.03 (d, 1H), 8.44 (dd, 1H), 8.41 (d, 1H), 8.10 (d, 1H), 7.67 (m, 1H), 7.65 (d, 1H), 7.44 (m, 2H), 7.07 (m, 2H), 6.77 (dd, 1H), 6.53 (d, 1H), 6.49 (dd, 1H), 4.55 (d, 2H), 3.80 (m, 4H), 3.08 (m, 4H), 2.77 (s, 2H), 2.26 (t, 2H), 2.14 (m, 4H), 1.97 (s, 2H), 1.88 (m, 4H), 1.39 (t, 2H), 0.94 (s, 6H).

Example 250

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 250A 5-chloro-6-((3-methyloxetan-3-yl)methoxy)pyridine-3-sulfonamide The title compound was prepared by substituting (3-methyloxetan-3-yl)methanol for (tetrahydro-2H-pyran-4-yl)methanol and EXAMPLE 40A for 4-fluoro-3-nitrobenzenesulfonamide in EXAMPLE 24A.

Example 250B

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 250A for EXAMPLE 11B in EXAMPLE 11D. $^1$H NMR (500 MHz, pyridine-$d_5$) δ 13.05 (s, 1H), 9.22 (d, 1H), 8.51 (d, 1H), 8.42 (d, 1H), 8.09 (d, 1H), 7.66 (t, 2H), 7.43-7.46 (m, 2H), 7.04-7.09 (m, 2H), 6.75 (dd, 1H), 6.45-6.54 (m, 2H), 4.47 (s, 2H), 3.81-3.84 (m, 2H), 3.74 (d, 2H), 3.03-3.11 (m, 4H), 2.77 (s, 2H), 2.26 (t, 2H), 2.10-2.17 (m, 4H), 1.97 (s, 2H), 1.39 (t, 2H), 1.16 (s, 3H), 0.94 (s, 6H).

Example 251

4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide Example 251A 5-bromo-6-((4-fluorotetrahydro-2H-pyran-4-yl)methoxy)pyridine-3-sulfonamide The title compound was prepared by substituting (4-fluorotetrahydro-2H-pyran-4-yl)methanol for (tetrahydro-2H-pyran-4-yl)methanol and 5-bromo-6-chloropyridine-3-sulfonamide for 4-fluoro-3-nitrobenzenesulfonamide in EXAMPLE 24A.

Example 251B 6-((4-fluorotetrahydro-2H-pyran-4-yl)methoxy)pyridine-3-sulfonamide To a suspension of 5-bromo-6-((4-fluorotetrahydro-2H-pyran-4-yl)methoxy)pyridine-3-sulfonamide (200 mg) and cyclohexene (0.549 mL) in ethyl acetate (10 mL) was added 10% palladium on carbon (57.6 mg). The suspension was stirred for 60 minutes at 120° C. The reaction mixture was filtered and concentrated. The product was purified by reverse-phase flash chromatography (C18, 150 g, 10%-100% acetonitrile/$H_2O$/trifluoroacetic acid 0.1%).

Example 251C 4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting EXAMPLE 251B for EXAMPLE 11B in EXAMPLE 11D. $^1$H NMR (500 MHz, pyridine-$d_5$) δ 13.06 (s, 1H), 9.29 (d, 1H), 8.50 (dd, 1H), 8.41 (d, 1H), 8.07 (d, 1H), 7.66-7.70 (m, 1H), 7.64 (d, 1H), 7.44 (d, 2H), 7.07 (d, 2H), 6.84 (d, 1H), 6.75 (dd, 1H), 6.52 (d, 1H), 6.49 (dd, 1H), 4.50 (d, 2H), 3.81-3.89 (m, 2H), 3.70-3.81 (m, 2H), 3.02-3.12 (m, 4H), 2.77 (s, 2H), 2.26 (t, 2H), 2.10-2.18 (m, 4H), 1.97 (s, 2H), 1.77-1.94 (m, 4H), 1.39 (t, 2H), 0.94 (s, 6H).

Example 252

4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide Example 252A tert-butyl (4-(1,3-difluoropropan-2-yl)morpholin-2-yl)methylcarbamate The title compound was prepared by substituting 1,3-difluoropropan-2-one for 4'-chlorobiphenyl-2-carboxaldehyde and tert-butyl morpholin-2-ylmethylcarbamate for tert-butyl piperazine-1-carboxylate in EXAMPLE 1A.

Example 252B (4-(1,3-difluoropropan-2-yl)morpholin-2-yl)methanamine

A solution of EXAMPLE 252A (538 mg) in dioxane (4 mL) was treated with 4.0M HCl in dioxane solution (1.8 mL).

The reaction was stirred at room temperature overnight. The reaction mixture was concentrated under vacuum and used without further purification.

Example 252C 4-((4-(1,3-difluoropropan-2-yl)morpholin-2-yl)methylamino)-3-nitrobenzenesulfonamide The title compound was prepared by substituting EXAMPLE 252B for (tetrahydropyran-4-yl)methylamine in EXAMPLE 1F.

Example 252D 4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 252C for EXAMPLE 1F and EXAMPLE 3J for EXAMPLE 1E in EXAMPLE 1G. $^1$H NMR (300 MHz, dimethylsulfoxide-$d_6$) δ 11.64 (s, 1H), 8.59 (t, 1H), 8.57 (d, 1H), 8.04 (d, 1H), 7.83 (dd, 1H), 7.51 (m, 3H), 7.33 (d, 2H), 7.07 (d, 1H), 7.03 (d, 2H), 6.66 (dd, 1H), 6.39 (m, 1H), 6.19 (d, 1H), 4.69 (t, 2H), 4.57 (t, 2H), 3.85 (m, 1H), 3.70 (m, 1H), 3.52 (m, 2H), 3.41 (m, 2H), 3.07 (br s, 4H), 2.91 (d, 1H), 2.74 (m, 3H), 2.59 (m, 1H), 2.43 (m, 1H), 2.20 (m, 4H), 2.15 (m, 2H), 1.95 (br s, 2H), 1.39 (t, 2H), 0.92 (s, 6H).

Example 253

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl 1 piperazin-1-yl)-2-(1H-pyrrolo[2,3-b]pyridin-5-yloxy)benzamide Example 253A tert-butyl 4-((3-chloro-5-sulfamoylpyridin-2-yloxy)methyl)piperidine-1-carboxylate The title compound was prepared by substituting tert-butyl 4-(hydroxymethyl)piperidine-1-carboxylate for tetrahydro-2H-pyran-4-yl)methanol and EXAMPLE 40A for 4-fluoro-3-nitrobenzenesulfonamide in EXAMPLE 24A.

Example 253B 5-chloro-6-(piperidin-4-ylmethoxy)pyridine-3-sulfonamide ditrifluoroacetic acid The title compound was prepared by substituting EXAMPLE 253A for EXAMPLE 39A in EXAMPLE 39B.

Example 253C 5-chloro-6-((1-(cyanomethyl)piperidin-4-yl)methoxy)pyridine-3-sulfonamide EXAMPLE 253B (0.061 g), 2-chloroacetonitrile (0.017 g), sodium carbonate (0.025 g) and N,N-dimethylformamide (1 mL) were combined in a 4-mL vial and heated at 60° C. overnight. The cooled reaction mixture was diluted with ethyl acetate, washed with water and brine, dried (MgSO$_4$), filtered and concentrated. The concentrate was chromatographed on silica gel with 2-10% methanol in CH$_2$Cl$_2$ as the eluent.

Example 253D

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 253C for EXAMPLE 1F in EXAMPLE 1G. $^1$H NMR (400 MHz, pyridine-$d_5$) δ 13.04 (s, 1H), 9.14 (d, 1H), 8.41 (d, 1H), 8.10 (d, 1H), 7.66 (t, 2H), 7.44 (m, 2H), 7.07 (m, 2H), 6.74 (dd, 1H), 6.50 (m, 2H), 4.18 (d, 2H), 3.64 (s, 2H), 3.05 (s, 4H), 2.77 (m, 4H), 2.24 (m, 4H), 2.13 (m, 4H), 1.97 (s, 2H), 1.69 (m, 3H), 1.41 (m, 4H), 0.93 (s, 6H).

Example 254

4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide Example 254A (R)-tert-butyl 3-(2-nitro-4-sulfamoylphenylamino)pyrrolidine-1-carboxylate The title compound was prepared by substituting (R)-tert-butyl 3-aminopyrrolidine-1-carboxylate for 1-(tetrahydropyran-4-yl)methylamine in EXAMPLE 1F.

Example 254B (R)-3-nitro-4-(pyrrolidin-3-ylamino)benzenesulfonamide

The title compound was prepared by substituting EXAMPLE 254A for EXAMPLE 113A in EXAMPLE 134A.

Example 254C (R)-4-(1-(2-(2-methoxyethoxy)ethyl)pyrrolidin-3-ylamino)-3-nitrobenzenesulfonamide To a solution of (R)-3-nitro-4-(pyrrolidin-3-ylamino)benzenesulfonamide (440 mg) in N,N-dimethylformamide (10 mL) was added sodium carbonate (132 mg) and 1-bromo-2-(2-methoxyethoxy)ethane (0.155 mL). The reaction mixture was heated at 60° C. for 18 hours and after an aqueous workup, the crude product was purified on silica gel with a 2.5-10% methanol in methylene chloride gradient to provide the title compound.

Example 254D 4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yl-oxy)benzamide The title compound was prepared by substituting EXAMPLE 254C for EXAMPLE 130C in EXAMPLE 130D.

¹H NMR (500 MHz, pyridine-d₅) δ 12.96 (m, 1H), 9.25 (m, 1H), 8.57 (d, 1H), 8.43 (d, 1H), 8.34 (dd, 1H), 8.11 (d, 1H), 7.66 (t, 1H) 7.64 (d, 1H), 7.44 (d, 2H), 7.07 (d, 2H), 6.82 (d, 1H), 6.76 (dd, 1H), 6.55 (m, 1H), 6.47 (m, 1H), 5.26 (br s, 1H), 4.02 (m, 1H), 3.63 (m, 4H), 3.53 (m, 2H), 3.28 (s, 3H), 3.07 (m, 4H), 2.89-2.81 (m, 2H), 2.78 (s, 2H), 2.75-2.66 (m, 3H), 2.37 (m, 1H), 2.26 (m, 2H), 2.24-2.18 (m, 1H), 2.15 (m, 4H), 1.97 (s, 2H), 1.65 (m, 1H), 1.39 (t, 2H), 0.94 (s, 6H).

Example 255

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide

Example 255A (R)-4-(1-(2-(dimethylamino)acetyl)pyrrolidin-3-ylamino)-3-nitrobenzenesulfonamide The title compound was prepared by substituting 2-(dimethylamino)acetyl chloride, hydrochloric acid for 1-bromo-2-(2-methoxyethoxy)ethane in EXAMPLE 254C except the reaction was stirred at ambient temperature for 18 hours.

Example 255B 4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 255A for EXAMPLE 130C in EXAMPLE 130D. ¹H NMR (500 MHz, pyridine-d₅) δ 13.01 (d, 1H), 9.26 (m, 1H), 8.46-8.33 (m, 3H), 8.14 (d, 1H), 7.66 (m, 2H), 7.44 (d, 2H), 7.07 (d, 2H), 7.01-6.89 (m, 1H), 6.76 (dd, 1H), 6.55 (m, 1H), 6.48 (m, 1H), 5.32 (br s, 1H), 4.27-4.14 (m, 1H), 4.05-3.95 (m, 1H), 3.82-3.62 (m, 3H), 3.27-3.15 (m, 2H), 3.07 (m, 4H), 2.77 (s, 2H), 2.34 (2, 3H), 2.32 (s, 3H), 2.30-2.20 (m, 3H), 2.15 (m, 4H), 1.97 (s, 2H), 1.87-1.81 (m, 1H), 1.39 (t, 2H), 0.94 (s, 6H).

Example 256

4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide

Example 256A tert-butyl 3-(2-nitro-4-sulfamoylphenylamino)azetidine-1-carboxylate The title compound was prepared by substituting tert-butyl 3-aminoazetidine-1-carboxylate for 4-methylpiperazin-1-amine dihydrochloride in EXAMPLE 6A.

Example 256B 4-(azetidin-3-ylamino)-3-nitrobenzenesulfonamide

The title compound was prepared by substituting EXAMPLE 256A for (S)-1-tert-butyl 2-methyl 4,4-difluoropyrrolidine-1,2-dicarboxylate in EXAMPLE 168A.

Example 256C 3-nitro-4-(1-(oxetan-3-yl)azetidin-3-ylamino)benzenesulfonamide The title compound was prepared by substituting EXAMPLE 256B for tert-butyl piperazine-1-carboxylate and 3-oxetanone for 4'-chlorobiphenyl-2-carboxaldehyde in EXAMPLE 1A.

Example 256D 4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide The title compound was prepared by substituting EXAMPLE 256C for EXAMPLE 11B in EXAMPLE 11D. ¹H NMR (500 MHz, pyridine-d₅) δ 13.04 (s, 1H), 9.27 (d, 1H), 8.62 (d, 1H), 8.42 (d, 1H), 8.35 (dd, 1H), 8.09 (d, 1H), 7.67 (m, 1H), 7.63 (d, 1H), 7.44 (m, 2H), 7.07 (m, 2H), 6.76 (dd, 1H), 6.67 (d, 1H), 6.55 (d, 1H), 6.48 (dd, 1H), 4.66 (t, 2H), 4.58 (m, 2H), 4.23 (m, 1H), 3.71 (m, 3H), 3.12 (dd, 2H), 3.07 (m, 4H), 2.77 (s, 2H), 2.26 (t, 2H), 2.14 (t, 4H), 1.97 (s, 2H), 1.39 (t, 2H), 0.94 (s, 6H).

Example 257

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 257A tert-butyl 4-((3-chloro-5-sulfamoylpyridin-2-yloxy)methyl)-4-fluoropiperidine-1-carboxylate The title compound was prepared by substituting EXAMPLE 126A for (tetrahydro-2H-pyran-4-yl)methanol and EXAMPLE 40A for 4-fluoro-3-nitrobenzenesulfonamide in EXAMPLE 24A.

Example 257B 5-chloro-6-((4-fluoropiperidin-4-yl)methoxy)pyridine-3-sulfonamide ditrifluoroacetic acid The title compound was prepared by substituting EXAMPLE 257A for EXAMPLE 39A in EXAMPLE 39B.

Example 257C 5-chloro-6-((1-(cyanomethyl)-4-fluoropiperidin-4-yl)methoxy)pyridine-3-sulfonamide EXAMPLE 257B (0.166 g) in acetonitrile (3 mL) was treated with 2-chloroacetonitrile (0.027 g) and sodium carbonate (0.064 g), heated at 60° C. overnight, cooled to room temperature and chromatographed on silica gel with 0 to 3% methanol in CH$_2$Cl$_2$ as the eluent. The obtained solid was slurried in water, filtered, rinsed with water and diethyl ether, and dried in a vacuum oven at 80° C.

Example 257D

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 257C for EXAMPLE 1F in EXAMPLE 1G. $^1$H NMR (400 MHz, pyridine-d$_5$) δ 13.05 (s, 1H), 9.12 (d, 1H), 8.72 (d, 1H), 8.41 (d, 1H), 8.10 (d, 1H), 7.66 (m, 2H), 7.44 (m, 2H), 7.07 (m, 2H), 6.75 (dd, 1H), 6.50 (m, 2H), 4.49 (d, 2H), 3.72 (s, 2H), 3.06 (m, 4H), 2.77 (s, 2H), 2.73 (m, 4H), 2.26 (t, 2H), 2.13 (m, 4H), 2.07 (m, 2H), 1.90 (m, 4H), 1.39 (t, 2H), 0.93 (s, 6H).

Example 258

4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide

Example 258A (S)-tert-butyl 2-(tosyloxymethyl)morpholine-4-carboxylate

To a solution of (S)-tert-butyl 2-(hydroxymethyl)morpholine-4-carboxylate (1 g) in dichloromethane (50 mL) was added triethylamine (1.604 mL) and 4-methylbenzene-1-sulfonyl chloride (1.097 g). The mixture was stirred at ambient temperature under nitrogen for 72 hours. The reaction was diluted with methylene chloride (50 mL) and brine (100 mL). The brine layer was extracted with methylene chloride (75 mL). The combined organics were dried over sodium sulfate, filtered and concentrated. The crude material was purified on a silica gel column eluting with a 15-65% ethyl acetate in hexane gradient to provide the title compound.

Example 258B (S)-tert-butyl 2-(azidomethyl)morpholine-4-carboxylate

A solution of EXAMPLE 258A (1.66 g) and sodium azide (0.581 g) in anhydrous N,N-dimethylformamide (10 mL) was stirred at 90° C. for 4 hours. The mixture was cooled and concentrated to dryness. The residue was taken up in 5% aqueous sodium carbonate solution and extracted with methylene chloride. The organic solution was dried (MgSO$_4$), filtered and concentrated to give a solid.

Example 258C (R)-tert-butyl 2-(aminomethyl)morpholine-4-carboxylate

This compound was obtained by hydrogenation of EXAMPLE 258B under 60 psi of hydrogen over 10% palladium on carbon in methanol for 24 hours, followed by filtration and evaporation of the solvent.

Example 258D (R)-tert-butyl 2-((2-nitro-4-sulfamoylphenylamino)methyl)morpholine-4-carboxylate The title compound was prepared by substituting EXAMPLE 258C for (tetrahydropyran-4-yl)methylamine in EXAMPLE 1F.

Example 258E (S)-4-(morpholin-2-ylmethylamino)-3-nitrobenzenesulfonamide

The title compound was prepared by substituting EXAMPLE 258D for EXAMPLE 113A in EXAMPLE 134A.

Example 258F (R)-4-((4-(2-(dimethylamino)acetyl)morpholin-2-yl)methylamino)-3-nitrobenzenesulfonamide The title compound was prepared by substituting EXAMPLE 258E for EXAMPLE 134A and 2-(dimethylamino)acetyl chloride hydrochloride for methyl iodide in EXAMPLE 134B.

Example 258G 4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 258F for EXAMPLE 130C in EXAMPLE 130D. $^1$H NMR (500 MHz, pyridine-d$_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 2H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Example 259

4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide

Example 259A (R)-tert-butyl 2-(tosyloxymethyl)morpholine-4-carboxylate

The title compound was prepared by substituting (R)-tert-butyl 2-(hydroxymethyl)morpholine-4-carboxylate for (S)-tert-butyl 2-(hydroxymethyl)morpholine-4-carboxylate in EXAMPLE 258A.

Example 259B (R)-tert-butyl 2-(azidomethyl)morpholine-4-carboxylate

The title compound was prepared by substituting EXAMPLE 259A for EXAMPLE 258A in EXAMPLE 258B.

Example 259C (S)-tert-butyl 2-(aminomethyl)morpholine-4-carboxylate

The title compound was prepared by substituting EXAMPLE 259B for EXAMPLE 258B in EXAMPLE 258C.

Example 259D (S)-tert-butyl 2-((2-nitro-4-sulfamoylphenylamino)methyl)morpholine-4-carboxylate The title compound was prepared by substituting EXAMPLE 259C for (tetrahydropyran-4-yl)methylamine in EXAMPLE 1F.

Example 259E (R)-4-(morpholin-2-ylmethylamino)-3-nitrobenzenesulfonamide

The title compound was prepared by substituting EXAMPLE 259D for EXAMPLE 113A in EXAMPLE 134A.

Example 259F (S)-4-((4-(2-(dimethylamino)acetyl)morpholin-2-yl)methylamino)-3-nitrobenzenesulfonamide The title compound was prepared by substituting EXAMPLE 259E for EXAMPLE 134A and 2-(dimethylamino)acetyl chloride hydrochloride for methyl iodide in EXAMPLE 134B.

Example 259G 4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 259F for EXAMPLE 130C in EXAMPLE 130D. $^1$H NMR (500 MHz, pyridine-$d_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 2H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Example 260

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 260A 5-chloro-6-((1-(2-(dimethylamino)acetyl)piperidin-4-yl)methoxy)pyridine-3-sulfonamide EXAMPLE 253B (0.061 g), 2-(dimethylamino)acetyl chloride, hydrochloric acid (0.061 g), and sodium carbonate (0.032 g) were combined in a 4-mL vial with N,N-dimethylformamide (2 mL). The mixture was stirred at ambient temperature for 3 days. Additional 2-(dimethylamino)acetyl chloride, hydrochloric acid (0.037 g), sodium carbonate (0.032 g) and N,N-dimethylformamide (1 mL) were added and stirring was continued for 24 hours. The reaction mixture was diluted with ethyl acetate, washed with water and brine, dried (MgSO$_4$), filtered, concentrated and chromatographed on silica gel with 0 to 20% methanol in CH$_2$Cl$_2$ as the eluent.

Example 260B

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 260A for EXAMPLE 11B in EXAMPLE 11D. $^1$H NMR (400 MHz, pyridine-$d_5$) δ 12.91 (s, 1H), 9.16 (d, 1H), 8.75 (d, 1H), 8.51 (d, 1H), 8.33 (d, 1H), 7.70 (d, 1H), 7.62 (d, 1H), 7.45 (m, 2H), 7.09 (m, 2H), 6.77 (dd, 1H), 6.60 (d, 1H), 6.45 (d, 1H), 4.81 (d, 1H), 4.15 (m, 3H), 3.24 (m, 2H), 3.04 (m, 4H), 2.89 (m, 1H), 2.79 (s, 2H), 2.53 (m, 1H), 2.29 (m, 6H), 2.26 (m, 2H), 2.18 (m, 4H), 1.98 (m, 2H), 1.91 (m, 1H), 1.71 (m, 2H), 1.39 (t, 2H), 1.25 (m, 2H), 0.94 (s, 6H).

Example 261

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 261A (R)-tert-Butyl 3-(3-chloro-5-sulfamoylpyridin-2-yloxy)pyrrolidine-1-carboxylate The title compound was prepared by substituting EXAMPLE 40A for 4-fluoro-3-nitrobenzenesulfonamide

Example 261B (R)-5-Chloro-6-(pyrrolidin-3-yloxy)pyridine-3-sulfonamide

The title compound was prepared by substituting EXAMPLE 261A for tert-butyl (4-(1,3-difluoropropan-2-yl)morpholin-2-yl)methylcarbamate in EXAMPLE 252B.

Example 261C (R)-5-chloro-6-(1-(2,2-difluoroethyl)pyrrolidin-3-yloxy)pyridine-3-sulfonamide A mixture of EXAMPLE 261B (353 mg), 1,1-difluoro-2-iodoethane (268 mg), sodium carbonate (283 mg) in N,N-dimethylformamide (10 mL) was heated at 80° C. overnight. The reaction mixture was cooled to room temperature and diluted with ethyl acetate. The organic phase was washed with water, brine, dried over magnesium sulfate, filtered, and concentrated. The residue was loaded onto silica gel column and eluted using a gradient of 0.5 to 3% methanol in dichloromethane to provide the title compound.

Example 261D

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 261C for EXAMPLE 11B in EXAMPLE 11D. $^1$H NMR (400 MHz, dimethylsulfoxide-$d_6$) δ 11.55 (s, 1 H), 8.04 (s, 1 H), 7.95 (d, 1 H), 7.58 (d, 1 H), 7.44 (t, 1 H), 7.35 (m, 3 H), 7.05 (d, 2 H), 6.64 (dd, 1 H), 6.33 (m, 1 H), 6.24 (d, 1 H), 6.25-5.97 (m, 1 H), 5.39 (m, 1 H), 2.98 (m, 6 H), 2.86 (m, 6 H), 2.55 (m, 2 H), 2.24 (m, 7 H), 1.96 (s, 2 H), 1.83 (m, 1 H), 1.39 (t, 2 H), 0.93 (s, 6 H)

Example 262

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide

Example 262A (R)-4-(1-(cyanomethyl)pyrrolidin-3-ylamino)-3-nitrobenzenesulfonamide The title compound was prepared by substituting 2-bromoacetonitrile for 1-bromo-2-(2-methoxyethoxy)ethane in EXAMPLE 254C.

Example 262B 4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide The title compound was prepared by substituting EXAMPLE 262A for EXAMPLE 130C in EXAMPLE 130D. $^1$H NMR (400 MHz, pyridine-$d_5$) δ 13.03 (s, 1H), 9.27 (d, 1H), 8.53 (d, 1H), 8.43 (d, 1H), 8.35 (dd, 1H), 8.10 (d, 1H), 7.67-7.64 (m, 2H), 7.44 (d, 2H), 7.07 (d, 2H), 6.81 (d, 1H), 6.76 (dd, 1H), 6.54 (m, 1H), 6.48 (m, 1H), 5.15 (br s, 1H), 4.10 (m, 1H), 3.89 (s, 2H), 3.07 (m, 4H), 2.93-2.86 (m, 2H), 2.80-2.77 (m, 3H), 2.61-2.53 (m, 1H), 2.31-2.21 (m, 3H), 2.14 (m, 4H), 1.97 (s, 2H), 1.75-1.68 (m, 1H), 1.39 (t, 2H), 0.94 (m, 6H).

Example 263

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide

Example 263A tert-butyl 1-oxa-6-azaspiro[2.5]octane-6-carboxylate

Sodium hydride (6.63 g, 60% in mineral oil) was added to trimethylsulfoxonium iodide (36.5 g) in dimethyl sulfoxide (150 mL) and tetrahydrofuran (150 mL), was and stirred for 30 minutes. tert-Butyl 4-oxopiperidine-1-carboxylate (25.4 g) was added and the reaction was stirred for 3 hours. The reaction was poured into water (800 mL) and extracted three times with ether. The combined extracts were washed three times with water, and brine, dried over $Na_2SO_4$, filtered, and concentrated to yield the crude product which was used without further purification.

Example 263B tert-butyl 4-(2-(benzyloxy)benzyl)-4-hydroxypiperidine-1-carboxylate (2-(Benzyloxy)phenyl)magnesium bromide (33.8 mL, 1M) was added to a solution of EXAMPLE 263A (6.0 g) and CuI (1.07 g) in tetrahydrofuran (220 mL) at 0° C. over 10 minutes. The reaction was quenched with pH 7 buffer (20 mL), extracted twice with ether, and the combined extracts were washed with brine, dried over $Na_2SO_4$, filtered, and concentrated. The crude product was chromatographed on silica gel using 2-20% ethyl acetate in hexanes to provide the title compound.

Example 263C tert-butyl 4-hydroxy-4-(2-hydroxybenzyl)piperidine-1-carboxylate EXAMPLE 263B (11.5 g) and methanol (120 mL) were added to Raney Nickel (1.150 g) in a 250 mL SS pressure bottle and stirred for 1 hour at 30 psi under hydrogen. The mixture was filtered through a nylon membrane and the solution was concentrated to yield the title compound.

Example 263D tert-butyl 4-hydroxy-4-(2-(trifluoromethylsulfonyloxy)benzyl)piperidine-1-carboxylate A mixture of EXAMPLE 263C (4.6 g), N-phenylbis(trifluoromethanesulfonimide) (5.88 g), and Hunig's base (2.88 mL) in dichloromethane (100 mL) was stirred for 24 hours.

Example 263E tert-butyl 4-((4'-chlorobiphenyl-2-yl)methyl)-4-hydroxypiperidine-1-carboxylate A mixture of EXAMPLE 263D (4.3 g), 4-chlorophenylboronic acid (1.84 g), $K_3PO_4$ (2.91 g), and [1,1'-bis(diphenylphosphino)ferrocene]dichloropalladium(II) (0.36 g) in 2-methyltetrahydrofuran (50 mL) was stirred at 70° C. for 24 hours. The reaction was cooled and quenched with water (50 mL), extracted twice with ether, and the combined extracts were washed with brine, dried over $Na_2SO_4$, filtered, and concentrated. The crude product was chromatographed on silica gel using 5-30% ethyl acetate in hexanes to provide the title compound.

Example 263F tert-butyl 4-((4'-chlorobiphenyl-2-yl)methyl)-4-methoxypiperidine-1-carboxylate Sodium hydride (0.36 g, 60% in mineral oil) was added to EXAMPLE 263E (4.3 g), in tetrahydrofuran (40 mL) and the reaction was stirred for 10 minutes. Hexamethylphosphoramide (5 mL) and $CH_3I$ (2.34 mL) were added and the reaction was stirred at 50° C. for 18 hours. The reaction was cooled and quenched with water (50 mL), extracted twice with ether, and the combined extracts were washed with brine, dried over $Na_2SO_4$, filtered, and concentrated. The crude product was chromatographed on silica gel using 5-25% ethyl acetate in hexanes to provide the title compound.

Example 263G 4-((4'-chlorobiphenyl-2-yl)methyl)-4-methoxypiperidine

The title compound was prepared by substituting EXAMPLE 263F for EXAMPLE 1A in EXAMPLE 1B.

Example 263H methyl 2-(1H-pyrrolo[2,3-b]pyridin-5-yloxy)-4-(4-((4'-chlorobiphenyl-2-yl)methyl)-4-methoxypiperidin-1-yl)benzoate A solution of EXAMPLE 263G (1.4 g), EXAMPLE 3H (1.06 g) and Hunig's base (0.75 mL) in dimethylsulfoxide (20 mL) was stirred at 120° C. for 18 hours. The reaction was cooled and quenched with water (200 mL), extracted three times with ether, and the combined extracts were washed three times with water, and brine, dried over $Na_2SO_4$, filtered, and concentrated. The crude product was chromatographed on silica gel using 5-50% ethyl acetate in hexanes to provide the title compound.

Example 263I 2-(1H-pyrrolo[2,3-b]pyridin-5-yloxy)-4-(4-((4'-chlorobiphenyl-2-yl)methyl)-4-methoxypiperidin-1-yl) benzoic acid The title compound was prepared by substituting EXAMPLE 263H for EXAMPLE 3I in EXAMPLE 3J.

Example 263J

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting EXAMPLE 263I for EXAMPLE 1E and EXAMPLE 96A for EXAMPLE 1F in EXAMPLE 1G. $^1$H NMR (300 MHz, dimethylsulfoxide-$d_6$) δ 11.71 (s, 1H), 11.58 (br s, 1H), 8.58 (d, 1H), 8.28 (d, 1H), 8.05 (d, 1H), 7.56 (d, 1H), 7.52 (m, 1H), 7.46 (d, 1H), 7.44 (d, 2H), 7.28 (m, 5H), 7.11 (dd, 1H), 6.62 (dd, 1H), 6.41 (dd, 1H), 6.11 (d, 1H), 4.54 (d, 2H), 3.75 (m, 2H), 3.59 (m, 2H), 3.20 (m, 2H), 2.97 (s, 3H), 2.81 (m, 2H), 2.74 (m, 2H), 1.89 (m, 2H), 1.83 (m, 2H), 1.36 (m, 2H), 1.09 (m, 2H).

Example 264

4-{4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 263I for EXAMPLE 1E in EXAMPLE 1G. $^1$H NMR (300 MHz, dimethylsulfoxide-$d_6$) δ 11.71 (s, 1H), 11.40 (br s, 1H), 8.62 (t, 1H), 8.58 (d, 1H), 8.03 (d, 1H), 7.81 (dd, 1H), 7.54 (m, 2H), 7.44 (m, 3H), 7.28 (m, 5H), 7.13 (dd, 1H), 6.62 (dd, 1H), 6.41 (dd, 1H), 6.11 (d, 1H), 3.85 (dd, 2H), 3.31 (m, 4H), 3.20 (m, 2H), 2.97 (s, 3H), 2.81 (m, 2H), 2.73 (m, 2H), 1.89 (m, 1H), 1.62 (m, 2H), 1.38 (m, 2H), 1.25 (m, 2H), 1.09 (m, 2H).

Example 265

4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 265A benzyl 4-(piperidin-1-ylmethylene)piperidine-1-carboxylate

To a solution of benzyl 4-formylpiperidine-1-carboxylate (12.5 g) in toluene (120 mL) was added piperidine (6.46 g). The mixture was stirred at reflux under a Dean-Stark trap overnight. The mixture was then concentrated under vacuum and the residue was used directly in the next step.

Example 265B benzyl 9-oxo-3-azaspiro[5.5]undec-7-ene-3-carboxylate

To a solution of EXAMPLE 265A (15.88 g) in ethanol (300 mL) was added but-3-enone (3.89 g). The mixture was stirred at reflux overnight. Then acetic acid (30 mL) was added to the mixture which was stirred at reflux again overnight. The mixture was then concentrated under vacuum and the residue was diluted with ethyl acetate (400 mL) and washed with water and brine and dried over Na$_2$SO$_4$. After filtration and evaporation of the solvent, column purification gave the title compound.

Example 265C benzyl 9-hydroxy-3-azaspiro[5.5]undecane-3-carboxylate

EXAMPLE 265B (21 g) and tetrahydrofuran (160 mL) were added to 5% Pt—C wet (3.15 g) in a 250 mL pressure bottle and stirred for 1 hour at 30 psi and room temperature. The mixture was filtered though a nylon membrane and the filtrate was concentrated under vacuum to provide the title compound.

Example 265D benzyl 9-oxo-3-azaspiro[5.5]undecane-3-carboxylate

To a solution of EXAMPLE 265C (8.0 g) in dichloromethane (200 mL) was added Dess-Martin Periodinane (11.2 g). The mixture was stirred overnight. The mixture was diluted with ethyl acetate (400 mL) and washed with 2N aqueous NaOH, water, and brine. After drying over Na$_2$SO$_4$ and filtration, concentration of the solvent gave the crude product which was used directly in the next reaction without further purification.

Example 265E benzyl 9-chloro-8-formyl-3-azaspiro[5.5]undec-8-ene-3-carboxylate Phosphorus oxychloride (2.33 mL) was added dropwise to a cooled (0° C.) solution of EXAMPLE 265D (7.5 g) in N,N-dimethylformamide (10 mL) and dichloromethane (30 mL). The mixture was then stirred overnight before it was diluted with ethyl acetate (300 mL) and washed with aqueous sodium acetate, water (3×), and brine and dried over Na$_2$SO$_4$. After filtration and concentration, the crude product was used directly in the next reaction without further purification.

Example 265F benzyl 9-(4-chlorophenyl)-8-formyl-3-azaspiro[5.5] undec-8-ene-3-carboxylate To a mixture of 4-chlorophenylboronic acid (5.94 g), EXAMPLE 265E (11.01 g), palladium(II) acetate (142 mg), K$_2$CO$_3$ (13.2 g) and tetrabutylammonium bromide (10.2 g) was added water (120 mL). The mixture was stirred at 50° C. overnight. The mixture was diluted with ethyl acetate (400 mL) and washed with water (3×) and brine and dried over Na$_2$SO$_4$. After filtration and concentration, the residue was loaded on a column and eluted with 5 to 20% ethyl acetate in hexane to provide the title compound.

Example 265G benzyl 8-((4-(3-(1H-pyrrolo[2,3-b]pyridin-5-yloxy)-4-(methoxycarbonyl)phenyl)piperazin-1-yl)methyl)-9-(4-chlorophenyl)-3-azaspiro[5.5]undec-8-ene-3-carboxylate To a solution of EXAMPLE 15F (1.37 g) and EXAMPLE 265F (1.65 g) in dichloromethane (20 mL) was added sodium triacetoxyborohydride (1.24 g). The mixture was stirred overnight. The mixture was diluted with ethyl acetate (200 mL) and washed with 2N aqueous NaOH, water and brine. After drying over Na$_2$SO$_4$, the mixture was filtered and the solvent was evaporated under vacuum to provide the title compound.

Example 265H methyl 2-(1H-pyrrolo[2,3-b]pyridin-5-yloxy)-4-(4-((9-(4-chlorophenyl)-3-azaspiro[5.5]undec-8-en-8-yl)methyl)piperazin-1-yl)benzoate EXAMPLE 265G (2 g) and tetrahydrofuran (10 mL) were added to 20% Pd(OH)$_2$—C, wet (0.400 g) in a 50 mL pressure bottle and stirred for 16 hours at 30 psi and room temperature. The mixture was filtered though a nylon membrane and evaporation of the solvent gave the title compound.

Example 265I methyl 2-(1H-pyrrolo[2,3-b]pyridin-5-yloxy)-4-(4-((9-(4-chlorophenyl)-3-(1,3-difluoropropan-2-yl)-3-azaspiro[5.5]undec-8-en-8-yl)methyl)piperazin-1-yl) benzoate To a solution of EXAMPLE 265H (320 mg) in dichloromethane (5 mL) was added 1,3-difluoroacetone (139 mg) and sodium triacetoxyborohydride (157 mg). The mixture was stirred overnight. The mixture was diluted with ethyl acetate (200 mL) and washed with 2N aqueous NaOH, water and brine. After drying over Na$_2$SO$_4$, the mixture was filtered and the solvent was evaporated under vacuum to provide the title compound.

Example 265J 2-(1H-pyrrolo[2,3-b]pyridin-5-yloxy)-4-(4-((9-(4-chlorophenyl)-3-(1,3-difluoropropan-2-yl)-3-azaspiro[5.5]undec-8-en-8-yl)methyl)piperazin-1-yl) benzoic acid To a solution of EXAMPLE 265I (320 mg) in tetrahydrofuran (4 mL) and methanol (2 mL) was added LiOH H$_2$O (120 mg) and the solution was stirred overnight. The reaction was cooled, carefully neutralized with 1N aqueous HCl and extracted with dichloromethane (3×50 mL). The combined organic layers were washed with brine (25 mL), dried over sodium sulfate, filtered and concentrated under vacuum to provide the title compound.

Example 265K 4-(4-{[9-(4-chlorophenyl)-3-(1,3-difluoropropan-2-yl)-3-azaspiro[5.5]undec-8-en-8-yl] methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 265J for EXAMPLE 1E in EXAMPLE 1G. $^1$H NMR (300 MHz, dimethylsulfoxide-d$_6$) δ 11.61 (s, 1 H), 8.49 (d, 2 H), 7.72 (m, 1 H), 7.49 (m, 2 H), 7.32 (d, 2 H), 7.07 (m, 3 H), 6.65 (dd, 1 H), 6.35 (d, 1 H), 6.20 (m, 1 H), 4.66 (m, 2 H), 4.50 (m, 2 H), 3.84 (m, 2 H), 3.04 (m, 5 H), 2.70 (m, 6 H), 2.23 (m, 6 H), 2.00 (m, 4 H), 1.35 (m, 12 H).

Example 266

4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 266A methyl 2-(1H-pyrrolo[2,3-b]pyridin-5-yloxy)-4-(4-((9-(4-chlorophenyl)-3-isopropyl-3-azaspiro[5.5]undec-8-en-8-yl)methyl)piperazin-1-yl)benzoate To a solution of EXAMPLE 265H (320 mg) in dichloromethane (5 mL) was added acetone (143 mg) and sodium triacetoxyborohydride (157 mg). The mixture was stirred overnight. The mixture was diluted with ethyl acetate (200 mL) and washed with 2N aqueous NaOH, water and brine. After drying over $Na_2SO_4$, the mixture was filtered and the solvent was evaporated under vacuum to provide the title compound.

Example 266B 2-(1H-pyrrolo[2,3-b]pyridin-5-yloxy)-4-(4-((9-(4-chlorophenyl)-3-isopropyl-3-azaspiro[5.5]undec-8-en-8-yl)methyl)piperazin-1-yl)benzoic acid The title compound was prepared by substituting EXAMPLE 266A for EXAMPLE 265I in EXAMPLE 265J.

Example 266C 4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 266B for EXAMPLE 1E in EXAMPLE 1G. $^1$H NMR (300 MHz, dimethylsulfoxide-$d_6$) δ 11.54 (s, 1 H), 8.38 (m, 2 H), 7.93 (d, 1 H), 7.60 (m, 3 H), 7.39 (m, 4 H), 7.09 (d, 2 H), 6.85 (d, 1 H), 6.63 (dd, 1 H), 6.27 (dd, 2 H), 3.84 (m, 3 H), 3.08 (m, 8 H), 2.71 (s, 3 H), 2.15 (m, 8 H), 1.71 (m, 9 H), 1.24 (m, 11 H)

Example 267

4-(4-{[9-(4-chlorophenyl)-3-(1,3-difluoropropan-2-yl)-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 265J for EXAMPLE 1E and EXAMPLE 40B for EXAMPLE 1F in EXAMPLE 1G. $^1$H NMR (300 MHz, dimethylsulfoxide-$d_6$) δ 11.56 (s, 1 H), 8.38 (s, 1 H), 8.06 (m, 1 H), 7.57 (d, 1 H), 7.38 (m, 5 H), 7.07 (m, 3 H), 6.64 (dd, 1 H), 6.33 (d, 1 H), 6.23 (m, 1 H), 4.68 (d, 2 H), 4.52 (d, 2 H), 4.21 (d, 2 H), 3.86 (dd, 2 H), 3.08 (m, 8 H), 2.71 (m, 6 H), 2.10 (m, 12 H), 1.42 (m, 7 H).

Example 268

4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 266B for EXAMPLE 1E and EXAMPLE 40B for EXAMPLE 1F in EXAMPLE 1G. $^1$H NMR (300 MHz, dimethylsulfoxide-$d_6$) δ 11.49 (s, 1 H), 8.28 (d, 1 H), 7.94 (dd, 2 H), 7.60 (d, 1 H), 7.35 (m, 4 H), 7.08 (m, 2 H), 6.61 (dd, 1 H), 6.28 (dd, 2 H), 4.18 (d, 2 H), 3.85 (m, 2 H), 3.05 (m, 7 H), 2.71 (s, 3 H), 2.25 (m, 6 H), 2.02 (m, 2 H), 1.63 (m, 8 H), 1.30 (m, 9 H).

Example 269

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 269A 5-chloro-6-((4-fluoro-1-methylpiperidin-4-yl)methoxy)pyridine-3-sulfonamide EXAMPLE 257B (0.131 g) in N,N-dimethylformamide (3.0 mL) was treated with iodomethane (0.043 g) and sodium carbonate (0.079 g) and stirred at ambient temperature for 3 days. The N,N-dimethylformamide was removed on high vacuum and the concentrate was chromatographed on amine functionalized silica gel with 0 to 2% methanol in $CH_2Cl_2$ as the eluent.

Example 269B

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 269A for EXAMPLE 11B in EXAMPLE 11D. $^1$H NMR (400 MHz, pyridine-$d_5$) δ 13.01 (s, 1H), 9.11 (d, 1H), 8.71 (d, 1H), 8.44 (d, 1H), 8.16 (d, 1H), 7.66 (m, 2H), 7.44 (m, 2H), 7.07 (m, 2H), 6.76 (dd, 1H), 6.54 (d, 1H), 6.49 (dd, 1H), 4.49 (d, 2H), 3.06 (m, 4H), 2.77 (s, 2H), 2.68 (m, 2H), 2.38 (m, 2H), 2.26 (m, 5H), 2.14 (t, 4H), 1.97 (m, 6H), 1.39 (t, 2H), 0.94 (s, 6H).

Example 270

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 270A 5-chloro-6-((1-(2-(dimethylamino)acetyl)-4-fluoropiperidin-4-yl)methoxy)pyridine-3-sulfonamide EXAMPLE 257B (0.131 g), 2-(dimethylamino)acetyl chloride, hydrochloric acid (0.139 g), and sodium carbonate (0.048 g) were combined in a 5-mL vial with N,N-dimethylformamide (3.0 mL) and stirred overnight at ambient temperature. Additional sodium carbonate (0.048 g) was added followed by 2-(dimethylamino)acetyl chloride, hydrochloric acid (0.139 g) and stirring was continued over a second night. The reaction mixture was concentrated under high vacuum, slurried in $CH_2Cl_2$, filtered, concentrated and chromatographed on amine functionalized silica gel with 0 to 4% methanol in $CH_2Cl_2$ as the eluent.

Example 270B

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 270A for EXAMPLE 11B in EXAMPLE 11D. $^1$H NMR (500 MHz, pyridine-$d_5$) δ 13.04 (s, 1H), 9.12 (d, 1H), 8.73 (d, 1H), 8.42 (d, 1H), 8.11 (d, 1H), 7.66 (m, 2H), 7.44 (m, 2H), 7.07 (m, 2H), 6.76 (dd, 1H), 6.52 (d, 1H), 6.49 (dd, 1H), 4.66 (d, 1H), 4.52 (dd, 2H), 4.07 (d, 1H), 3.46 (m, 1H), 3.40 (m, 1H), 3.30 (m, 1H), 3.11 (m, 1H), 3.06 (m, 4H), 2.77 (s, 2H), 2.35 (s, 6H), 2.26 (t, 2H), 2.14 (m, 4H), 2.05 (m, 2H), 1.97 (s, 2H), 1.81 (m, 2H), 1.39 (t, 2H), 0.93 (s, 6H).

Example 271

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 271A tert-butyl 4-((4'-chlorobiphenyl-2-yl)methyl)-4-fluoropiperidine-1-carboxylate A solution of EXAMPLE 263E (2.0 g) and diethylaminosulfur trifluoride (1.39 mL) in dichloromethane (40 mL) was stirred for 24 hours. The reaction was quenched with water (30 mL), extracted twice with ether, and the combined extracts were washed with water, and brine, dried over $Na_2SO_4$, filtered, and concentrated. The crude product was chromatographed on silica gel using 5% ethyl acetate in hexanes to provide the title compound.

Example 271B 4-((4'-chlorobiphenyl-2-yl)methyl)-4-fluoropiperidine

The title compound was prepared by substituting EXAMPLE 271A for EXAMPLE 1A in EXAMPLE 1B.

Example 271C methyl 2-(1H-pyrrolo[2,3-b]pyridin-5-yloxy)-4-(4-((4'-chlorobiphenyl-2-yl)methyl)-4-fluoropiperidin-1-yl)benzoate The title compound was prepared by substituting EXAMPLE 271B for EXAMPLE 263G in EXAMPLE 263H.

Example 271D 2-(1H-pyrrolo[2,3-b]pyridin-5-yloxy)-4-(4-((4'-chlorobiphenyl-2-yl)methyl)-4-fluoropiperidin-1-yl)benzoic acid The title compound was prepared by substituting EXAMPLE 271C for EXAMPLE 3I in EXAMPLE 3J.

Example 271E

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 271D for EXAMPLE 1E EXAMPLE 1G. $^1$H NMR (300 MHz, dimethylsulfoxide-$d_6$) δ 11.66 (s, 1H), 11.46 (br s, 1H), 8.62 (t, 1H), 8.56 (d, 1H), 8.03 (d, 1H), 7.81 (dd, 1H), 7.52 (m, 3H), 7.44 (d, 2H), 7.28 (m, 5H), 7.14 (m, 1H), 6.68 (dd, 1H), 6.40 (dd, 1H), 6.19 (d, 1H), 3.84 (dd, 2H), 3.31 (m, 9H), 2.95 (d, 2H), 2.81 (m, 2H), 1.91 (m, 1H), 1.62 (m, 2H), 1.45 (m, 2H), 1.29 (m, 2H).

Example 272

4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting EXAMPLE 271D for EXAMPLE 1E and EXAMPLE 96A for EXAMPLE 1F in EXAMPLE 1G. $^1$H NMR (300 MHz, dimethylsulfoxide-$d_6$) δ 11.68 (s, 1H), 11.64 (br s, 1H), 8.58 (m, 1H), 8.25 (m, 1H), 8.03 (d, 1H), 7.70 (m, 4H), 7.43 (m, 3H), 7.28 (m, 4H), 7.15 (m, 1H), 6.68 (dd, 1H), 6.40 (dd, 1H), 6.19 (d, 1H), 4.54 (d, 2H), 4.04 (m, 1H), 3.75

(m, 2H), 3.58 (m, 2H), 2.95 (d, 2H), 2.80 (m, 2H), 1.88 (m, 2H), 1.82 (m, 2H), 1.48 (m, 2H), 1.28 (m, 2H), 0.85 (m, 2H).

Example 273

4-(4-{[9-(4-chlorophenyl)-3-isopropyl-3-azaspiro [5.5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl) phenyl}sulfonyl)benzamide The title compound was prepared by substituting EXAMPLE 266B for EXAMPLE 1E and EXAMPLE 42A for EXAMPLE 1F in EXAMPLE 1G. $^1$H NMR (300 MHz, dimethylsulfoxide-$d_6$) δ 11.57 (s, 1 H), 7.97 (d, 1 H), 7.77 (s, 1 H), 7.55 (m, 2 H), 7.45 (m, 1 H), 7.36 (m, 3 H), 7.08 (d, 2 H), 6.62 (dd, 2 H), 6.35 (dd, 1 H), 6.21 (d, 1 H), 3.82 (m, 3 H), 3.06 (m, 9 H), 2.72 (m, 3 H), 2.25 (m, 8 H), 2.09 (m, 2 H), 1.56 (m, 9 H), 1.20 (m, 10 H).

Example 274

N-[(5-chloro-6-{[(3R)-1-(1,3-difluoropropan-2-yl) pyrrolidin-3-yl]oxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide Example 274A (R)-5-chloro-6-(1-(3-fluoro-2-(fluoromethyl)propyl) pyrrolidin-3-yloxy)pyridine-3-sulfonamide The title compound was prepared by substituting 1,3-difluoropropan-2-one for 4'-chlorobiphenyl-2-carboxaldehyde and EXAMPLE 261B for tert-butyl piperazine-1-carboxylate in EXAMPLE 1A.

Example 274B

N-[(5-chloro-6-{[(3R)-1-(1,3-difluoropropan-2-yl) pyrrolidin-3-yl]oxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting EXAMPLE 274A for EXAMPLE 11B in EXAMPLE 11D. $^1$H NMR (400 MHz, dimethylsulfoxide-$d_6$) δ 11.52 (s, 1 H), 8.32 (d, 1 H), 8.01 (d, 1 H), 7.93 (d, 1 H), 7.59 (d, 1 H), 7.42 (m, 1 H), 7.33 (m, 3 H), 7.05 (d, 2 H), 6.63 (dd, 1 H), 6.31 (dd, 1 H), 6.25 (d, 1 H), 5.38 (m, 1 H), 4.65 (t, 2 H), 4.53 (t, 2 H), 3.02 (s, 4 H), 2.94 (m, 5 H), 2.75 (s, 2 H), 2.66 (m, 1 H), 2.23 (m, 7 H), 1.96 (s, 2 H), 1.82 (m, 1H), 1.39 (t, 2 H), 0.93 (s, 6 H).

Example 275

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide Example 275A 3-(2-(benzyloxy)ethoxy)tetrahydrofuran Tetrahydrofuran-3-ol (0.881 g) in tetrahydrofuran (15 mL) was treated with 60% sodium hydride (0.8 g). After 10 minutes, ((2-bromoethoxy)methyl)benzene (3.23 g) was added. The solution was stirred for 16 hours. The reaction mixture was partitioned between water and ethyl acetate. The aqueous layer was separated, and was extracted with additional ethyl acetate twice. The combined organic layers were washed with brine, dried over MgSO$_4$, filtered, and concentrated. The residue was purified by flash chromatography on silica gel eluting with 1:1 ethyl acetate:hexane to provide the title compound.

Example 275B 2-(tetrahydrofuran-3-yloxy)ethanol

EXAMPLE 275A (0.85 g) and 5% palladium on carbon (0.1 g) in ethanol (10 mL) was treated with a balloon of hydrogen. The reaction was stirred overnight. The solid was filtered off, and the filtrate was concentrated to give the title compound.

Example 275C 3-nitro-4-(2-(tetrahydrofuran-3-yloxy)ethoxy)benzenesulfonamide

The title compound was prepared by substituting EXAMPLE 275B for (tetrahydro-2H-pyran-4-yl)methanol in EXAMPLE 24A.

Example 275D 4-(4-{[2-(4-chlorophenyl)-4,4-dimethylcyclohex-1-en-1-yl]methyl}piperazin-1-yl)-N-({3-nitro-4-[2-(tetrahydro furan-3-yloxy)ethoxy]phenyl}sulfonyl)-2-(1H-pyrrolo[2,3-b]pyridin-5-yloxy)benzamide The title compound was prepared by substituting EXAMPLE 275C for EXAMPLE 11B in EXAMPLE 11D. $^1$H NMR (500 MHz, dimethylsulfoxide-$d_6$) δ 11.65 (s, 1H), 8.32 (s, 1H), 8.00-8.02 (m, 2H), 7.49-7.52 (m, 2H), 7.39-7.41 (m, 1H), 7.38 (d, 2H), 7.04 (d, 2H), 6.68 (dd, 1H), 6.39 (dd, 1H), 6.21 (d, 1H), 4.33-4.35 (m, 2H), 4.18-4.21 (m, 1H), 3.62-3.67 (m, 4H), 3.09 (s, 4H), 2.83 (s, 2H), 2.26 (s, 2H), 2.15 (s, 2H), 1.96 (s, 2H), 1.85-1.94 (m, 2H), 1.39 (t, 2H), 0.92 (s, 6H).

Example 276

4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy) benzamide Example 276A trans-4-(aminomethyl)cyclohexanecarbonitrile To a solution of tert-butyl (trans-4-(cyanomethyl)cyclohexyl)methylcarbamate (500 mg) in dichloromethane (10 mL) was slowly added trifluoroacetic acid (2 mL) at 0° C. The reaction mixture was warmed to room temperature, stirred for 1 hour and concentrated to provide the title compound.

Example 276B 4-((trans-4-cyanocyclohexyl)methylamino)-3-nitrobenzenesulfonamide

A mixture of 4-fluoro-3-nitrobenzenesulfonamide (347 mg) and EXAMPLE 276A (300 mg) in tetrahydrofuran (20 mL) was treated with triethylamine (1.4 mL) overnight and concentrated. The residue was triturated with ethyl acetate to provide the title compound.

Example 276C 4-(4-{[2-(4-chlorophenyl)-4,4-dimethylcyclohex-1-en-1-yl]methyl}piperazin-1-yl)-N-[(4-{[(trans-4-cyano cyclohexyl)methyl]amino}-3-nitrophenyl) sulfonyl]-2-(1H-pyrrolo[2,3-b]pyridin-5-yloxy)benzamide The title compound was prepared as described in EXAMPLE 11D using EXAMPLE 276B in place of EXAMPLE 11B. $^1$H NMR (400 MHz, dimethylsulfoxide-$d_6$) δ 11.69 (s, 1 H), 11.36 (s, 1 H), 8.60 (t, 1 H), 8.56 (d, 1 H), 8.04 (d, 1 H), 7.79 (dd, 1 H), 7.47-7.54 (m, 3 H), 7.34 (d, 2 H), 7.01-7.09 (m, 3 H), 6.68 (dd, 1 H), 6.39 (dd, 1 H), 6.19 (d, 1 H), 3.25 (t, 2 H), 3.07 (s, 4 H), 2.76 (s, 2 H), 2.57-2.68 (m, 1 H), 2.17 (d, 6 H), 1.92-2.06 (m, 4 H), 1.78 (d, 2 H), 1.66 (s, 1 H), 1.35-1.53 (m, 4 H), 0.96-1.10 (m, 2 H), 0.92 (s, 6 H).

Example 277

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 277A methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried ($Na_2SO_4$), filtered, and concentrated to give the product.

Example 277B methyl 2-(4-chlorophenyl)-4,4-dimethylcyclohex-1-enecarboxylate EXAMPLE 277A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product.

Example 277C (2-(4-chlorophenyl)-4,4-dimethylcyclohex-1-enyl)methanol

To a mixture of $LiBH_4$ (13 g), EXAMPLE 277B (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried ($Na_2SO_4$), filtered, and concentrated. The crude product was chromatographed on silica gel with 0-30% ethyl acetate/hexanes.

Example 277D tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 277C (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Example 277E 1-((2-(4-chlorophenyl)-4,4-dimethylcyclohex-1-enyl)methyl)piperazine EXAMPLE 277D (1 g) was stirred in dichloromethane (10 mL), trifluoroacetic acid (10 mL), and triethylsilane (1 mL) for 1 hour. The mixture was concentrated, taken up in a mixture of dichloromethane (100 mL) and saturated aqueous $Na_2CO_3$ solution (20 mL) and stirred for 10 minutes. The layers were separated, and the organic layer was dried over $Na_2SO_4$, filtered, and concentrated to give the product.

Example 277F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Example 277G 1-(triisopropylsilyl)-1H-pyrrolo[2,3-b]pyridin-5-ol

To a mixture of EXAMPLE 277F (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M NaOH (69 mL) was added, followed by 30% $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Example 277H methyl 2-(1H-pyrrolo[2,3-b]pyridin-5-yloxy)-4-fluorobenzoate

A mixture of EXAMPLE 277G (8.5 g), methyl 2,4-difluorobenzoate (7.05 g), and $K_3PO_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 277I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 277H (1.55 g), EXAMPLE 277E (2.42 g), and $HK_2PO_4$ (1.42 g) in dimethylsulfoxide (20 mL) at 135° C. was stirred for 24 hours. The reaction was cooled, diluted with ether (400 mL), and washed three times with 1M NaOH, and brine, and concentrated. The crude product was chromatographed on silica gel with 10-50% ethyl acetate/hexanes.

Example 277J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 277I (200 mg) in dioxane (10 mL) and 1M NaOH (6 mL) at 50° C. was stirred for 24 hours. The reaction was cooled, added to $NaH_2PO_4$ solution, and extracted three times with ethyl acetate. The combined extracts were washed with brine, and concentrated to give the pure product.

Example 277K 5,6-dichloropyridine-3-sulfonamide

To a solution of 5,6-dichloropyridine-3-sulfonyl chloride (32.16 g) in isopropyl alcohol (300 mL) at 0° C. was added a 30% aqueous solution of $NH_4OH$ (50.8 mL). After stirring overnight, the solvent was reduced to ⅓ of the original volume. It was then partitioned between water and ethyl acetate. The aqueous layer was extracted with additional ethyl acetate. The combined organic layers were washed with brine, dried over $MgSO_4$, filtered, and concentrated. The residue was chromatographed on silica gel. The material was then slurried in 1:9 ethyl acetate/hexanes, filtered and dried under vacuum to give the title compound.

Example 277L tert-butyl 4-fluoro-4-(hydroxymethyl)piperidine-1-carboxylate

1-Tert-butyl 4-ethyl 4-fluoropiperidine-1,4-dicarboxylate (1.0 g) in tetrahydrofuran (5 mL) was treated with 1.0 N $LiAlH_4$ in tetrahydrofuran (2.54 mL) at 0° C. The reaction mixture was stirred at room temperature for 2 hours. Water (0.6 mL) was added to the reaction mixture drop-wise, followed by 2 N aqueous NaOH (0.2 mL). The reaction was stirred for another 1 hour. The solid was removed by filtration via a pack of diatomaceous earth and washed with ethyl acetate. The filtrate was washed with brine, dried over $MgSO_4$, filtered, and concentrated to give the product.

Example 277M tert-butyl 4-((3-chloro-5-sulfamoylpyridin-2-yloxy)methyl)-4-fluoropiperidine-1-carboxylate To a solution of EXAMPLE 277L (1 g) in tetrahydrofurab (15 mL) was added NaH (60% dispersion in mineral oil, 685 mg), and the solution was stirred for 10 minutes. EXAMPLE 227K (1 g) was added and the reaction stirred for 24 hours. The mixture was poured into water, neutralized with 10% HCl, and extracted with ethyl acetate three times. The combined organic layers were washed with brine, dried over $MgSO_4$, filtered, and concentrated. The residue was purified with flash column chromatography on silica gel eluting with 30% ethyl acetate in hexanes.

Example 277N 5-chloro-6-((4-fluoropiperidin-4-yl)methoxy)pyridine-3-sulfonamide ditrifluoroacetic acid EXAMPLE 277M (13 mL) was treated with trifluoroacetic acid (2.363 mL), stirred at ambient temperature for 2 hours, concentrated and dried to give the title compound.

Example 277O 5-chloro-6-((4-fluoro-1-(oxetan-3-yl)piperidin-4-yl)methoxy)pyridine-3-sulfonamide EXAMPLE 277N (0.088 g) and oxetan-3-one (0.014 g) were combined in dichloromethane (2.0 mL) and dimethylformamide (1.0 mL) and stirred at ambient temperature for 45 minutes. Sodium triacetoxyborohydride (0.064 g) was added in portions. Stirring was continued overnight at ambient temperature. Additional oxetan-3-one (0.014 g) was added and stirring was continued for 30 minutes at ambient temperature before more sodium triacetoxyborohydride (0.064 g) was added. The reaction mixture was stirred for 72 hours at ambient temperature, concentrated, chromatographed on silica gel with 0 to 5% methanol in dichloromethane as the eluent, and dried in a vacuum oven at 80° C. to give the title compound.

Example 277P

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide EXAMPLE 277J (0.063 g), EXAMPLE 277O (0.042 g), 1-ethyl-3-[3-(dimethylamino)propyl]-carbodiimide hydrochloride (0.032 g), and 4-dimethylaminopyridine (0.027 g) were combined in a 4-mL vial with dichloromethane (1.0 mL) and stirred overnight at ambient temperature. The reaction mixture was chromatographed directly without aqueous workup on silica gel with 0-4% methanol in dichloromethane as the eluent. Fractions containing the desired product were concentrated, slurried in acetonitrile, concentrated and dried overnight in a vacuum oven at 80° C. to give the title compound. $^1$H NMR (500 MHz, pyridine-$d_5$) δ 13.05 (s, 1H), 9.13 (d, 1H), 8.72 (d, 1H), 8.41 (d, 1H), 8.10 (d, 1H), 7.67 (m, 1H), 7.66 (d, 1H), 7.44 (m, 2H), 7.07 (m, 2H), 6.76 (dd, 1H), 6.51

(m, 2H), 4.63 (m, 4H), 4.53 (d, 2H), 3.39 (m, 1H), 3.07 (m, 4H), 2.77 (s, 2H), 2.51 (m, 2H), 2.25 (m, 2H), 2.18 (m, 2H), 2.13 (m, 4H), 2.06 (t, 2H), 1.97 (s, 2H), 1.89 (m, 2H), 1.39 (t, 2H), 0.93 (s, 6H).

Example 278

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide Example 278A 5-bromo-6-(2-(tetrahydro-2H-pyran-4-yl)ethoxy)pyridine-3-sulfonamide The title compound was prepared by substituting 2-(tetrahydro-2H-pyran-4-yl)ethanol for (tetrahydro-2H-pyran-4-yl)methanol in EXAMPLE 36B.

Example 278B 5-cyano-6-(2-(tetrahydro-2H-pyran-4-yl)ethoxy)pyridine-3-sulfonamide The title compound was prepared by substituting EXAMPLE 278A for EXAMPLE 36B in EXAMPLE 36C.

Example 278C 4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide The title compound was prepared by substituting EXAMPLE 278B for EXAMPLE 11B in EXAMPLE 11D. $^1$H NMR (500 MHz, dimethylsulfoxide-$d_6$) δ 11.60 (s, 1H), 8.70 (s, 1H), 8.48 (s, 1H), 7.96 (d, 1H), 7.56 (d, 1H), 7.45-7.47 (m, 1H), 7.40 (s, 1H), 7.36 (d, 2H), 7.06 (d, 2H), 6.67 (dd, 1H), 6.34 (dd, 1H), 6.25 (d, 1H), 4.47 (d, 2H), 3.80-3.84 (m, 2H), 3.24-3.28 (m, 2H), 3.12 (s, 2H), 2.16 (s, 2H), 1.97 (s, 2H), 1.61-1.71 (m, 4H), 1.40 (t, 2H), 1.21-1.25 (m, 2H), 0.93 (s, 6H).

Example 279

4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide Example 279A 4-(furan-3-ylmethoxy)-3-nitrobenzenesulfonamide The title compound was prepared by substituting furan-3-ylmethanol for (tetrahydro-2H-pyran-4-yl)methanol in EXAMPLE 24A.

Example 279B 4-(4-{[2-(4-chlorophenyl)-4,4-dimethylcyclohex-1-en-1-yl]methyl}piperazin-1-yl)-N-{[4-(3-furylmethoxy)-3-nitrophenyl]sulfonyl}-2-(1H-pyrrolo[2,3-b]pyridin-5-yloxy)benzamide The title compound was prepared by substituting EXAMPLE 279A for EXAMPLE 11B in EXAMPLE 11D. $^1$H NMR (500 MHz, dimethylsulfoxide-$d_6$) δ 11.69 (s, 1H), 8.34 (s, 1H), 8.03-8.06 (m, 2H), 7.83 (s, 1H), 7.69 (t, 1H), 7.51-7.53 (m, 4H), 7.34-7.36 (m, 2H), 7.04-7.06 (m, 2H), 6.68 (dd, 1H), 6.57 (s, 1H), 6.40 (dd, 1H), 6.20 (d, 1H), 5.23 (s, 2H), 3.10 (s, 4H), 2.83 (s, 2H), 2.15-2.32 (m, 6H), 1.39 (t, 2H), 0.92 (s, 6H).

Example 280

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 280A (R)-tert-butyl 3-((3-chloro-5-sulfamoylpyridin-2-yloxy)methyl)pyrrolidine-1-carboxylate The title compound was prepared by substituting EXAMPLE 40A for 4-fluoro-3-nitrobenzenesulfonamide and (R)-tert-butyl 3-(hydroxymethyl)pyrrolidine-1-carboxylate for (tetrahydro-2H-pyran-4-yl)methanol in EXAMPLE 24A.

Example 280B (R)-5-chloro-6-(pyrrolidin-3-ylmethoxy)pyridine-3-sulfonamide

The title compound was prepared by substituting EXAMPLE 280A for tert-butyl (4-(1,3-difluoropropan-2-yl)morpholin-2-yl)methylcarbamate in EXAMPLE 252B.

Example 280C (R)-5-chloro-6-((1-(1,3-difluoropropan-2-yl)pyrrolidin-3-yl)methoxy)pyridine-3-sulfonamide The title compound was prepared by substituting 1,3-difluoropropan-2-one for 4'-chlorobiphenyl-2-carboxaldehyde and EXAMPLE 280B for tert-butyl piperazine-1-carboxylate in EXAMPLE 1A.

Example 280D

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 280C for EXAMPLE 11B in EXAMPLE 11D. $^1$H NMR (400 MHz, dimethylsulfoxide-$d_6$) δ 11.57 (s, 1 H), 8.38 (d, 1 H), 8.07 (d, 1 H), 7.96 (d, 1 H), 7.57 (d, 1 H), 7.44 (m, 1 H), 7.35 (m, 3 H), 7.05 (d, 2 H), 6.64 (dd, 1 H), 6.33 (dd, 1 H), 6.23 (d, 1 H), 4.65 (d, 2 H), 4.53 (dd, 2 H), 2.92 (m, 8 H), 2.75 (m, 4 H), 2.58 (m, 2 H), 2.20 (m, 6 H), 1.96 (m, 4 H), 1.53 (m, 1 H), 1.39 (t, 2 H), 0.89 (s, 6 H).

Example 281

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 281A (R)-5-chloro-6-((1-(2,2-difluoroethyl)pyrrolidin-3-yl)methoxy)pyridine-3-sulfonamide The title compound was prepared by substituting EXAMPLE 280B for EXAMPLE 261B in EXAMPLE 261C.

Example 281B

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 281A for EXAMPLE 11B in EXAMPLE 11D. $^1$H NMR (400 MHz, dimethylsulfoxide-$d_6$) δ 11.59 (s, 1 H), 8.41 (d, 1 H), 8.10 (d, 1 H), 7.98 (d, 1 H), 7.56 (d, 1 H), 7.46 (m, 1 H), 7.41 (d, 1 H), 7.34 (d, 2 H), 7.04 (d, 2 H), 6.65 (dd, 1 H), 6.35 (dd, 1 H), 6.23 (m, 1 H), 6.03 (m, 1 H), 3.06 (s, 4 H), 2.84 (m, 6 H), 2.63 (m, 4 H), 2.20 (m, 6 H), 1.94 (m, 3 H), 1.53 (m, 1 H), 1.39 (t, 2 H), 0.91 (s, 6 H).

Example 282

N-[(5-chloro-6-{1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 282A 5-chloro-6-((1-(1,3-difluoropropan-2-yl)-4-fluoropiperidin-4-yl)methoxy)pyridine-3-sulfonamide EXAMPLE 257B (0.088 g) and 1,3-difluoropropan-2-one (0.028 g) were combined in dichloromethane (2 mL) and N,N-dimethylformamide (0.500 mL) and stirred at ambient temperature for 45 minutes. Sodium triacetoxyborohydride (0.064 g) was added in portions and then the reaction mixture was stirred overnight at ambient temperature. Additional 1,3-difluoropropan-2-one (0.028 g) was added, followed 30 minutes later by the addition of more sodium triacetoxyborohydride (0.064 g). The reaction mixture was stirred at ambient temperature for 72 hours. Additional 1,3-difluoropropan-2-one (0.028 g) was again added, followed 30 minutes later by the addition of more sodium triacetoxyborohydride (0.064 g). The reaction mixture was stirred overnight at ambient temperature. Additional 1,3-difluoropropan-2-one (0.028 g) was again added, followed 30 minutes later by the addition of more sodium triacetoxyborohydride (0.064 g). The reaction mixture was stirred overnight at ambient temperature. The reaction mixture was concentrated under high vacuum to remove N,N-dimethylformamide and then chromatographed on silica gel with 0 to 4% methanol in $CH_2Cl_2$ as the eluent.

Example 282B

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 282A for EXAMPLE 11B in EXAMPLE 11D. $^1$H NMR (400 MHz, pyridine-$d_5$) δ 13.05 (s, 1H), 9.12 (t, 1H), 8.72 (d, 1H), 8.41 (d, 1H), 8.10 (d, 1H), 7.66 (m, 2H), 7.44 (m, 2H), 7.07 (m, 2H), 6.75 (dd, 1H), 6.50 (m, 2H), 4.77 (dd, 1H), 4.65 (dd, 1H), 4.52 (dd, 2H), 3.06 (m, 4H), 2.93 (t, 1H), 2.80 (m, 5H), 2.52 (m, 1H), 2.26 (t, 2H), 2.13 (m, 4H), 2.04 (m, 2H), 1.97 (s, 2H), 1.85 (m, 2H), 1.39 (t, 2H), 1.28 (m, 2H), 0.93 (s, 6H).

Example 283

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 283A 3-chloro-4-((4-fluoro-1-methylpiperidin-4-yl)methoxy)benzenesulfonamide To a solution of (4-fluoro-1-methylpiperidin-4-yl)methanol (0.265 g) in tetrahydrofuran (2 mL) was added sodium hydride (0.288 g). After 15 minutes, 3-chloro-4-fluorobenzenesulfonamide (0.377 g) was added as a solution in tetrahydrofuran (1 mL). The reaction was stirred for 2 hours, quenched with water (5 mL), adjusted to pH~7 with 1N aqueous HCl, and extracted with dichloromethane (2×25 mL). The organic layer was washed with brine (25 mL), dried over magnesium sulfate, filtered and concentrated. Silica gel chromatography (Reveleris 40 g) eluting with a gradient of 0.1% to 10% methanol containing 2N $NH_3$/dichloromethane over 30 minutes gave the title compound.

Example 283B

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 283A for EXAMPLE 1F in EXAMPLE 1G. $^1$H NMR (300 MHz, dimethylsulfoxide-$d_6$) δ 11.60 (s, 1H), 10.68-9.84 (m, 1H), 7.99 (d, 1H), 7.79 (d, 1H), 7.63 (t, 1H), 7.54 (d, 1H), 7.50-7.38 (m, 2H), 7.34 (d, 2H), 7.04 (d, 3H), 6.64 (dd, 1H), 6.36 (dd, 1H), 6.22 (s, 1H), 4.23 (d, 2H), 3.03 (s, 6H), 2.71 (m, 4H), 2.07 (m, 12H), 1.38 (s, 3H), 1.24 (s, 2H), 0.92 (s, 6H).

Example 284

4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide

Example 284A 3-cyano-4-((tetrahydro-2H-pyran-4-yl)methoxy)benzenesulfonamide To a solution of (tetrahydro-2H-pyran-4-yl)methanol (0.258 g) in tetrahydrofuran (5 mL) was added sodium hydride (0.355 g) and the reaction stirred at room temperature for 15 minutes. EXAMPLE 52A (0.400 g) was added and the reaction stirred for an additional 1 hour. The reaction was poured into ethyl acetate (50 mL) and 1N aqueous HCl (35 mL). The organic layer was washed with brine (35 mL) dried over magnesium sulfate, filtered, and concentrated. Silica gel chromatography (Reveleris 40 g) eluting with a gradient of 10% to 100% ethyl acetate/hexanes over 30 minutes gave the title compound.

Example 284B 4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide The title compound was prepared by substituting EXAMPLE 3J for EXAMPLE 1E and EXAMPLE 284A for EXAMPLE 1F in EXAMPLE 1G. $^1$H NMR (300 MHz, dimethylsulfoxide-$d_6$) δ 11.69 (s, 1H), 11.60-11.16 (m, 1H), 8.15 (s, 1H), 8.08-8.01 (m, 2H), 7.58-7.46 (m, 3H), 7.35 (d, J=8.4, 2H), 7.29 (d, 1H), 7.04 (d, 2H), 6.68 (d, 1H), 6.40 (dd, 1H), 6.20 (s, 1H), 4.05 (d, 2H), 3.89 (d, 2H), 3.37 (d, 4H), 3.09 (s, 4H), 2.81 (s, 2H), 2.21 (d, 7H), 1.96 (s, 2H), 1.67 (d, 2H), 1.39 (s, 2H), 0.92 (s, 6H).

Example 285

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 285A 5-chloro-6-((1-(2,2-difluoroethyl)-4-fluoropiperidin-4-yl)methoxy)pyridine-3-sulfonamide EXAMPLE 257B (0.263 g), 1,1-difluoro-2-iodoethane (0.23 g), and sodium carbonate (0.254 g) were combined in a 20-mL vial with N,N-dimethylformamide (6 ml) and stirred at 70° C. overnight. The reaction mixture was concentrated under high vacuum and then chromatographed on silica gel with 0 to 5% methanol in CH$_2$Cl$_2$ as the eluent.

Example 285B

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 285A for EXAMPLE 11B in EXAMPLE 11D. $^1$H NMR (400 MHz, pyridine-$d_5$) δ 13.05 (s, 1H), 9.12 (d, 1H), 8.72 (d, 1H), 8.41 (d, 1H), 8.10 (d, 1H), 7.66 (m, 2H), 7.43 (m, 2H), 7.06 (m, 2H), 6.75 (dd, 1H), 6.50 (m, 2H), 6.18 (tt, 2H), 4.51 (d, 2H), 3.07 (m, 4H), 2.80 (m, 6H), 2.60 (td, 2H), 2.25 (t, 2H), 2.13 (m, 4H), 2.03 (t, 2H), 1.97 (s, 2H), 1.93 (m, 1H), 1.85 (m, 1H), 1.39 (t, 2H), 0.93 (s, 6H).

Example 286

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 286A 3-chloro-4-((4-fluorotetrahydro-2H-pyran-4-yl)methoxy)benzenesulfonamide The title compound was prepared by substituting EXAMPLE 37C for (4-fluoro-1-methylpiperidin-4-yl)methanol in EXAMPLE 283A.

Example 286B

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 286A for EXAMPLE 1F in EXAMPLE 1G. $^1$H NMR (300 MHz, dimethylsulfoxide-$d_6$) δ 11.71 (s, 1H), 11.56-11.16 (m, 1H), 8.06 (d, 1H), 7.90 (d, 1H), 7.81 (d, 1H), 7.64-7.45 (m, 3H), 7.34 (d, 2H), 7.26 (d, 1H), 7.04 (d, 2H), 6.68 (d, 1H), 6.42 (dd, 1H), 6.18 (s, 1H), 4.28 (d, 2H), 3.78 (d, 2H), 3.61 (dd, 2H), 3.07 (s, 4H), 2.76 (s, 2H), 2.17 (d, 6H), 1.87 (dd, 6H), 1.38 (t, 2H), 0.92 (s, 6H).

Example 287

N-({5-chloro-6-[(4,4-difluoro cyclo hexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 287A (4,4-difluorocyclohexyl)methanol

Ethyl 4,4-difluorocyclohexanecarboxylate (1.0 g, 5.20 mmol) in diethyl ether (2 mL) was added dropwise to lithium aluminium hydride (0.24 g) in diethyl ether (15 mL), and heated under reflux for 4 hours. The reaction was then cooled to 0° C., and water was added (0.24 mL), followed by 5N aqueous NaOH (0.24 mL) and water (0.72 mL). Then $Na_2SO_4$ and more diethyl ether (40 mL) were added, and the mixture was stirred for 30 minutes, then filtered through celite. After concentration, the residue was diluted with $CH_2Cl_2$ and $Na_2SO_4$ was added, and the mixture was filtered and concentrated to provide the title compound.

Example 287B 5-chloro-6-((4,4-difluorocyclohexyl)methoxy)pyridine-3-sulfonamide

The title compound was prepared by substituting EXAMPLE 40A for 4-fluoro-3-nitrobenzenesulfonamide and EXAMPLE 287A for (tetrahydro-2H-pyran-4-yl)methanol in EXAMPLE 24A.

Example 287C

N-({5-chloro-6-[(4,4-difluoro cyclo hexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 287B for EXAMPLE 11B in EXAMPLE 11D. $^1$H NMR (400 MHz, dimethylsulfoxide-$d_6$) δ 11.63 (s, 1H), 8.46 (d, 1H), 8.14 (d, 1H), 8.00 (d, 1H), 7.56 (d, 1H), 7.47 (m, 2H), 7.35 (d, 2H), 7.03 (d, 2H), 6.66 (dd, 1H), 6.37 (m, 1H), 6.21 (d, 1H), 4.25 (d, 2H), 3.07 (br m, 4H), 2.82 (br s, 2H), 2.30 (br m, 4H), 2.16 (br m, 2H), 2.00, 1.95, 1.85 (all m, total 9H), 1.40 (t, 2H), 1.37 (m, 2H), 0.92 (s, 6H).

Example 288

4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide Example 288A 5-Nitro-3-(trifluoromethyl)pyridin-2-ol 3-(Trifluoromethyl)pyridin-2-ol (2.3 g) was added to concentrated sulfuric acid (15 mL) at 0° C. The mixture was stirred at 0° C. for 5 minutes. To this solution was added fuming nitric acid (6 mL) dropwise over 5 minutes. The reaction mixture was stirred at room temperature for 2 hours, and then heated at 50° C. for 3 hours. After cooling, the reaction mixture was poured onto ice (200 g), and the mixture was extracted with ethyl acetate three times. The combined organic layers were washed with brine, dried over $MgSO_4$, filtered, and concentrated under reduced pressure to provide the title compound.

Example 288B

2-Chloro-5-nitro-3-(trifluoromethyl)pyridine

A mixture of EXAMPLE 288A (1.69 g), phosphorus pentachloride (2.03 g), and phosphoryl trichloride (0.97 mL) was heated at 90° C. for 3 hours. After cooling, the reaction mixture was poured into ice, and extracted with ethyl acetate three times. The extract was washed with brine, dried over $MgSO_4$, filtered, and concentrated under reduced pressure. The residue was purified by flash column chromatography on silica gel eluting with 10% ethyl acetate in hexanes to provide the title compound.

Example 288C

6-Chloro-5-(trifluoromethyl)pyridin-3-amine

A mixture of iron (1.5 g) and ammonium chloride (2.38 g) in water (40 mL) was stirred at room temperature for 5 minutes. To this suspension was added EXAMPLE 288B in methanol (40 mL). The reaction mixture was stirred at room temperature for 1 hour. More iron (1.8 g) was added to the reaction mixture, and it was stirred for another 3 hours. The solid from the reaction mixture was filtered off, and the filtrate was partitioned between water and ethyl acetate. The combined organic layers were washed with brine, dried over $MgSO_4$, filtered, and concentrated under reduced pressure. The residue was purified by flash column chromatography on silica gel eluting with 20% ethyl acetate in hexanes to provide the title compound.

Example 288D 6-chloro-5-(trifluoromethyl)pyridine-3-sulfonyl chloride

Under ice-cooling, thionyl chloride (4 mL) was added dropwise over 20 minutes to water (27 mL). The mixture was stirred overnight for 12 hours to give a $SO_2$ containing solution. Separately, EXAMPLE 288C (1.14 g) in dioxane (5 mL) was added to concentrated HCl (20 mL) at 0° C. The solution was stirred for 5 minutes. To this suspension/solution was added sodium nitrite (0.44 g) in water (6 mL) dropwise at 0° C. The solution was stirred at 0° C. for 3 hours. During this time, any solid formed was crushed with a glass rod to make sure that EXAMPLE 288C was completely reacted. To the $SO_2$ containing solution was added copper(I)chloride (0.115 g). Then, to this solution was added the diazotized EXAMPLE 288C at 0° C. The solution was stirred for 30 minutes. The reaction mixture was extracted with ethyl acetate. The combined organic layers were washed with brine, dried over $MgSO_4$, filtered, and concentrated under reduced pressure. The residue was purified by flash column chromatography on silica gel eluting with 5% ethyl acetate in hexanes to provide the title compound.

Example 288E 6-chloro-5-(trifluoromethyl)pyridine-3-sulfonamide

EXAMPLE 288D (2.03 g) in dioxane (20 mL) solution was cooled to 0° C. Ammonium hydroxide solution was added dropwise. The reaction mixture was stirred at 0° C. for 2 hours followed by room temperature over night. The solvent was partially removed, and the residue was partitioned between water and ethyl acetate. The organic phase was washed with brine, dried over $MgSO_4$, filtered, and concentrated under reduced pressure. The residue was purified by flash column chromatography on silica gel eluting with 0-3% methanol in dichloromethane to afford the title compound.

Example 288F tert-butyl 4-fluoro-4-((5-sulfamoyl-3-(trifluoromethyl)pyridin-2-yloxy)methyl)piperidine-1-carboxylate The title compound was prepared by substituting EXAMPLE 288E for 4-fluoro-3-nitrobenzenesulfonamide and EXAMPLE 322A for (tetrahydro-2H-pyran-4-yl)methanol in EXAMPLE 24A.

Example 288G 6-((4-fluoropiperidin-4-yl)methoxy)-5-(trifluoromethyl)pyridine-3-sulfonamide The title compound was prepared by substituting EXAMPLE 288F for tert-butyl (4-(1,3-difluoropropan-2-yl)morpholin-2-yl)methylcarbamate in EXAMPLE 252B.

Example 288H 6-((1-(1,3-difluoropropan-2-yl)-4-fluoropiperidin-4-yl)methoxy)-5-(trifluoromethyl)pyridine-3-sulfonamide The title compound was prepared by substituting 1,3-difluoropropan-2-one for 4'-chlorobiphenyl-2-carboxaldehyde and EXAMPLE 288G for tert-butyl piperazine-1-carboxylate in EXAMPLE 1A.

Example 288I 4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide The title compound was prepared by substituting EXAMPLE 288H for EXAMPLE 11B in EXAMPLE 11D. $^1$H NMR (400 MHz, dimethylsulfoxide-$d_6$) δ 11.50 (s, 1 H), 8.57 (s, 1 H), 8.27 (d, 1 H), 7.91 (d, 1 H), 7.58 (d, 1 H), 7.40 (m, 1 H), 7.35 (d, 2 H), 7.28 (d, 1 H), 7.05 (d, 2 H), 6.61 (dd, 1 H), 6.29 (dd, 1 H), 6.24 (d, 1 H), 4.67 (d, 2 H), 4.55 (d, 2 H), 4.50 (s, 1 H), 4.44 (s, 1 H), 3.06 (m, 5 H), 2.73 (m, 6 H), 2.19 (d, 6 H), 1.90 (m, 7 H), 1.39 (t, 2 H), 0.93 (s, 6 H).

Example 289

4-(4-{[2-(4-chlorophenyl)-4,4-dimethylcyclohex-1-en-1-yl]methyl}piperazin-1-yl)-N-({5-chloro-6-[2-(tetrahydro furan-2-yl)ethoxy]pyridin-3-yl}sulfonyl)-2-(1H-pyrrolo[2,3-b]pyridin-5-yloxy)benzamide

Example 289A 5-chloro-6-(2-(tetrahydrofuran-2-yl)ethoxy)pyridine-3-sulfonamide The title compound was prepared by substituting 2-(tetrahydro-2H-pyran-4-yl)ethanol for (tetrahydro-2H-pyran-4-yl)methanol and EXAMPLE 40A for EXAMPLE 36A in EXAMPLE 36B.

Example 289B 4-(4-{[2-(4-chlorophenyl)-4,4-dimethylcyclohex-1-en-1-yl]methyl}piperazin-1-yl)-N-({5-chloro-6-[2-(tetrahydro furan-2-yl)ethoxy]pyridin-3-yl}sulfonyl)-2-(1H-pyrrolo[2,3-b]pyridin-5-yloxy)benzamide The title compound was prepared by substituting EXAMPLE 289A for EXAMPLE 11B in EXAMPLE 11D. $^1$H NMR (500 MHz, dimethylsulfoxide-$d_6$) δ 11.66 (s, 1H), 8.52 (d, 1H), 8.18 (s, 1H), 8.02 (s, 1H), 7.50-7.55 (m, 3H), 7.35 (d, 2H), 7.05 (d, 2H), 6.68 (dd, 1H), 6.38 (dd, 1H), 6.21 (d, 1H), 4.39-4.51 (m, 4H), 3.87-3.94 (m, 1H), 3.73-3.78 (m, 1H), 3.57-3.62 (m, 1H), 3.11 (s, 4H), 2.89 (s, 2H), 2.33 (s, 4H), 2.15 (s, 2H), 1.77-2.01 (m, 7H), 1.45-1.54 (m, 1H), 1.40 (t, 2H), 0.93 (s, 6H).

Example 290

4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 290A 2-chloro-4,4-dimethylcyclohex-1-enecarbaldehyde

Into a 250 ml round-bottomed flask was added N,N-dimethylformamide (3.5 mL) in dichloromethane (30 mL). The mixture was cooled to −10° C., and phosphoryl trichloride (4 mL) was added dropwise. The solution was warmed up to room temperature and 3,3-dimethylcyclohexanone (5.5 mL) was added slowly. The mixture was heated to reflux overnight. The reaction mixture was quenched by 0° C. solution of sodium acetate (25 g in 50 mL water). The aqueous layer was extracted with ether (3×200 mL). The organic layers were combined, dried over $Na_2SO_4$, filtered, and dried under vacuum.

Example 290B 2-(4-chlorophenyl)-4,4-dimethylcyclohex-1-enecarbaldehyde

Into a 1 L round-bottomed flask was added EXAMPLE 290A (6.8 g), 4-chlorophenylboronic acid (6.5 g) and palladium(II) acetate (0.2 g) in water (100 mL) to give a suspension. Potassium carbonate (15 g) and tetrabutylammonium bromide (10 g) were added. After degassing after subjecting to vacuum and nitrogen, the mixture was stirred at 45° C. for 4 hours. After filtering through silica gel, diethyl ether (4×200 mL) was used to extract the product. The combined organic layers were dried over $Na_2SO_4$ and filtered. The filtrate was concentrated and purified by flash chromatography on silica with 0-10% ethyl acetate in hexanes to provide the title compound.

Example 290C tert-butyl 4-((2-(4-chlorophenyl)-4,4-dimethylcyclohex-1-enyl)methyl)-3-methylpiperazine-1-carboxylate To a solution of tert-butyl 3-methylpiperazine-1-carboxylate (0.256 g) and EXAMPLE 290B (0.350 g) in dichloromethane (2 mL) was added sodium triacetoxyborohydride (0.406 g) and the reaction was stirred at room temperature overnight. The reaction was quenched with NaHCO$_3$ solution (50 mL) and extracted with dichloromethane (50 mL). The organic layer was dried over magnesium sulfate, filtered and concentrated. Silica gel chromatography (Reveleris 40 g) eluting with a gradient of 0.5% to 2.5% methanol/dichloromethane gave the title compound.

Example 290D 1-((2-(4-chlorophenyl)-4,4-dimethylcyclohex-1-enyl)methyl)-2-methylpiperazine A solution of EXAMPLE 290C (0.298 g) and HCl (4.0M in dioxane, 2 mL) were stirred for 1 hour. The reaction was concentrated and partioned between dichloromethane (100 mL) and NaHCO$_3$ (100 mL). The organic layer was washed with brine (50 mL), dried over magnesium sulfate, filtered and concentrated to provide the title compound.

Example 290E methyl 2-(1H-pyrrolo[2,3-b]pyridin-5-yloxy)-4-(4-((2-(4-chlorophenyl)-4,4-dimethylcyclohex-1-enyl)methyl)-3-methylpiperazin-1-yl)benzoate The title compound was prepared by substituting EXAMPLE 290D for EXAMPLE 3E in EXAMPLE 3I.

Example 290F 2-(1H-pyrrolo[2,3-b]pyridin-5-yloxy)-4-(4-((2-(4-chlorophenyl)-4,4-dimethylcyclohex-1-enyl)methyl)-3-methylpiperazin-1-yl)benzoic acid The title compound was prepared by substituting EXAMPLE 290E for EXAMPLE 15G in EXAMPLE 15H.

Example 290G 4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 290F for EXAMPLE 1E in EXAMPLE 1G. $^1$H NMR (300 MHz, dimethylsulfoxide-d$_6$) δ 11.66 (s, 1H), 11.54-11.30 (m, 1H), 8.62-8.53 (m, 2H), 8.03 (d, 1H), 7.78 (d, 1H), 7.48 (d, 3H), 7.34 (d, 2H), 7.06 (t, 3H), 6.68 (d, 1H), 6.38 (dd, 1H), 6.21 (s, 1H), 3.84 (d, 2H), 3.23 (s, 4H), 2.75 (s, 4H), 1.64 (s, 8H), 1.62 (d, 2H), 1.42-1.17 (m, 6H), 0.92 (s, 6H), 0.87 (s, 3H).

Example 291

4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide Example 291A tert-butyl 2-cyanoethyl(cyclopropyl)carbamate To a solution of 3-(cyclopropylamino)propanenitrile (5.0 g) in tetrahydrofuran (30 mL) was added di-tert-butyl dicarbonate (9.91 g) and a catalytic amount of 4-dimethylaminopyridine. The mixture was stirred overnight. The mixture was diluted with ethyl acetate (400 mL) and washed with 5% aqueous HCl, water and brine. After drying over Na$_2$SO$_4$, the mixture was filtered, and the solvent was evaporated under vacuum to provide the title compound.

Example 291B tert-butyl 3-aminopropyl(cyclopropyl)carbamate

Example 291A (9.75 and 7M H3-methanol (25 mL) were added to a Ra—Ni 2800, water slurry 09:50 g, 332 mmol) in a 250 mL pressure bottle and stirred for 2 hours at 30 psi and room temperature. The mixture was filtered through a nylon membrane and evaporation of the solvent gave the title compound.

Example 291C tert-butyl cyclopropyl(3-(2-nitro-4-sulfamoylphenylamino)propyl)carbamate To a solution of 4-chloro-3-nitrobenzenesulfonamide (2.5 g), and EXAMPLE 291B (2.26 g) in dioxane (20 mL) was added N,N-diisopropylethylamine (5 mL). The mixture was stirred at reflux overnight. The mixture was diluted with ethyl acetate (400 mL) and washed with water and brine. After drying over Na$_2$SO$_4$, the mixture was filtered, and the solvent was evaporated under vacuum to provide the title compound.

Example 291D tert-butyl 3-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)propyl(cyclopropyl)carbamate The title compound was prepared by substituting EXAMPLE 3J for EXAMPLE 1E and EXAMPLE 291C for EXAMPLE 1F in EXAMPLE 1G.

Example 291E 4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide To a solution of EXAMPLE 291D (2.56 g) in dichloromethane (10 mL) was added trifluoroacetic acid (10 mL). The mixture was stirred for 2 hours. The mixture was concentrated under vacuum and the residue was dissolved in dichloromethane (300 mL) and washed with aqueous NaHCO$_3$, water, and brine and dried over Na$_2$SO$_4$. Filtration and evaporation of the solvent gave the crude product. The title compound was obtained by dissolving 200 mg of the crude material in dimethylsulfoxide/methanol (1:1, 10 mL) and loaded on Gilson, C18 (100A) 250×121.2 mm (10 micron), eluting with 30% acetonitrile to 65% acetonitrile over 40 minutes. $^1$H NMR (300 MHz, dimethylsulfoxide-d$_6$) δ 11.54 (s, 1 H), 8.43 (m, 2 H), 7.94 (d, 1 H), 7.71 (dd, 1 H), 7.57 (d, 1 H), 7.43 (m, 1 H), 7.34 (m, 3 H), 7.05 (d, 2 H), 6.90 (d, 1 H), 6.63 (dd, 1 H), 6.29 (d, 2 H), 3.43 (m, 2 H), 2.96 (m, 6 H), 2.73 (m, 2 H), 2.22 (m, 7 H), 1.87 (m, 4 H), 1.38 (m, 3 H), 0.94 (m, 6 H), 0.62 (m, 4 H).

Example 292

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 292A 5-chloro-6-(2-methoxyethoxy)pyridine-3-sulfonamide

The title compound was prepared by substituting EXAMPLE 40A for 4-fluoro-3-nitrobenzenesulfonamide and 2-methoxyethanol for (tetrahydro-2H-pyran-4-yl)methanol in EXAMPLE 24A.

Example 292B

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 292A for EXAMPLE 11B in EXAMPLE 11D. $^1$H NMR (400 MHz, dimethylsulfoxide-$d_6$) δ 11.63 (s, 1H), 8.48 (d, 1H), 8.17 (d, 1H), 8.01 (d, 1H), 7.56 (d, 1H), 7.49 (m, 2H), 7.35 (d, 2H), 7.04 (d, 2H), 6.66 (dd, 1H), 6.37 (m, 1H), 6.21 (d, 1H), 4.52 (m, 2H), 3.70 (m, 2H), 3.28 (s, 3H), 3.13 (br m, 4H), 2.88 (br s, 2H), 2.34 (br m, 4H), 2.16 (br m, 2H), 1.97 (s, 2H), 1.40 (t, 2H), 0.92 (s, 6H).

Example 293

4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide

Example 293A

The title compound was prepared by substituting 5-bromo-2,3-difluoropyridine for 4-fluoro-3-nitrobenzenesulfonamide in EXAMPLE 24A.

Example 293B tert-butyl 5-fluoro-6-((tetrahydro-2H-pyran-4-yl)methoxy)pyridin-3-ylcarbamate The title compound was prepared by substituting EXAMPLE 293A for EXAMPLE 248A in EXAMPLE 248B.

Example 293C 5-fluoro-6-((tetrahydro-2H-pyran-4-yl)methoxy)pyridine-3-sulfonyl chloride The title compound was prepared by substituting EXAMPLE 293B for EXAMPLE 248B in EXAMPLE 248C.

Example 293D 5-fluoro-6-((tetrahydro-2H-pyran-4-yl)methoxy)pyridine-3-sulfonamide The title compound was prepared by substituting EXAMPLE 293C for EXAMPLE 248C in EXAMPLE 248D.

Example 293E 4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting EXAMPLE 293D for EXAMPLE 11B in EXAMPLE 11D. $^1$H NMR (400 MHz, pyridine-$d_5$) δ 13.07 (s, 1H), 9.05 (d, 1H), 8.44 (dd, 1H), 8.41 (d, 1H), 8.09 (d, 1H), 7.67 (t, 1H), 7.65 (d, 1H), 7.44 (m, 2H), 7.07 (m, 2H), 6.76 (dd, 1H), 6.53 (d, 1H), 6.49 (dd, 1H), 4.21 (d, 2H), 3.96 (dd, 2H), 3.31 (td, 2H), 3.07 (m, 4H), 2.77 (s, 2H), 2.26 (t, 2H), 2.14 (m, 4H), 1.97 (m, 3H), 1.58 (dd, 2H), 1.38 (m, 4H), 0.94 (s, 6H).

Example 294

N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 294A tert-butyl 4-((2-chloro-4-sulfamoylphenoxy)methyl)piperidine-1-carboxylate The title compound was prepared by substituting tert-butyl-4-(hydroxymethyl)piperidine-1-carboxylate for (4-fluoro-1-methylpiperidin-4-yl)methanol in EXAMPLE 283A.

Example 294B tert-butyl 4-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-chlorophenoxy)methyl)piperidine-1-carboxylate The title compound was prepared by substituting EXAMPLE 3J for EXAMPLE 1E and EXAMPLE 294A for EXAMPLE 1F in EXAMPLE 1G.

Example 294C 2-(1H-pyrrolo[2,3-b]pyridin-5-yloxy)-N-(3-chloro-4-(piperidin-4-ylmethoxy)phenylsulfonyl)-4-(4-((2-(4-chlorophenyl)-4,4-dimethylcyclohex-1-enyl)methyl)piperazin-1-yl)benzamide To EXAMPLE 294B (0.286 g) in dichloromethane (3 mL) was added trifluoroacetic acid (1 mL) and the reaction stirred at room temperature. After 3 hours the reaction was concentrated to provide the title compound.

Example 294D

N-[(3-chloro-4-{[1-(methoxyacetyl)piperidin-4-yl]
methoxy}phenyl)sulfonyl]-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide To EXAMPLE 294C (0.75 g) as a solution in dichloromethane (1 mL) was added N,N-diisopropylethylamine (0.055 mL) followed by 2-methoxyacetyl chloride (6 µl). After stirring for 10 minutes the reaction was loaded onto silica gel (Reveleris 40 g) and eluted using a gradient of 0.5% to 3.5% methanol/dichloromethane over 30 minutes (flow=40 mL/minutes) to provide the title compound. $^1$H NMR (300 MHz, dimethylsulfoxide-$d_6$) δ 11.71 (s, 1H), 11.55-11.24 (m, 1H), 8.06 (d, 1H), 7.88 (d, 1H), 7.78 (d, 1H), 7.57 (s, 1H), 7.51 (s, 1H), 7.48 (d, 1H), 7.34 (d, 2H), 7.21 (d, 1H), 7.04 (d, 2H), 6.67 (d, 1H), 6.42 (dd, 1H), 6.18 (s, 1H), 4.42-4.32 (m, 1H), 4.03 (dd, 4H), 3.86-3.74 (m, 1H), 3.28 (s, 3H), 3.07 (s, 5H), 2.77 (s, 3H), 2.30-1.92 (m, 9H), 1.77 (s, 2H), 1.31 (d, 4H), 0.92 (s, 6H).

Example 295

N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide The title compound was prepared by substituting 2-(dimethylamino)acetyl chloride for 2-methoxyacetyl chloride in EXAMPLE 294D. $^1$H NMR (300 MHz, dimethylsulfoxide-$d_6$) δ 11.58 (s, 1H), 10.35-9.94 (m, 1H), 7.96 (d, 1H), 7.74 (d, 1H), 7.55 (d, 2H), 7.45 (s, 1H), 7.41-7.29 (m, 3H), 7.05 (d, 3H), 6.63 (d, 1H), 6.37-6.32 (m, 1H), 6.22 (d, 1H), 4.39 (d, 1H), 3.94 (s, 6H), 3.01 (s, 6H), 2.73 (m, 4H), 2.55 (m, 5H), 2.19 (s, 6H), 1.95 (m, 2H), 1.82 (m, 2H), 1.38 (s, 4H), 0.93 (s, 6H).

Example 296

4-(4-{[2-(4-chlorophenyl)-4,4-dimethylcyclohexyl]
methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 296A tert-butyl 4-((4,4-dimethyl-2-oxocyclohexyl)methyl)piperidine-1-carboxylate 3,3-Dimethylcyclohexanone (5.60 mL) was added to sodium bis(trimethylsilyl)amide (45.3 mL, 1M in tetrahydrofuran), and the reaction was stirred for 1 hour. tert-Butyl 4-(bromomethyl)piperidine-1-carboxylate (11.1 g) in dimethylsulfoxide (30 mL) was added, and the reaction was stirred at 50° C. for 24 hours. The reaction was cooled, poured into water (300 mL), extracted three times with ether, and the combined extracts were washed three times with water, and brine, dried over Na$_2$SO$_4$, filtered, and concentrated. The crude product was chromatographed on silica gel using 5-20% ethyl acetate in hexanes to provide the title compound.

Example 296B tert-butyl 4-((2-(4-chlorophenyl)-2-hydroxy-4,4-dimethylcyclohexyl)methyl)piperidine-1-carboxylate (4-Chlorophenyl)magnesium bromide (14.1 mL, 1M in ether) was added to EXAMPLE 296A (3.25 g) in tetrahydrofuran (40 mL) at −78° C., and the reaction was stirred for 20 minutes, and then allowed to warm to room temperature overnight. The reaction was quenched with pH 7 buffer (20 mL), extracted with 2× ether, and the combined extracts were washed with brine, dried over Na$_2$SO$_4$, filtered, and concentrated. The crude product was chromatographed on silica gel using 1-20% ethyl acetate in hexanes to provide the title compound.

Example 296C trans-4-((2-(4-chlorophenyl)-4,4-dimethylcyclohexyl)methyl)piperidine The title compound was prepared by substituting EXAMPLE 296B for EXAMPLE 1A in EXAMPLE 1B.

Example 296D

Trans-methyl 2-(1H-pyrrolo[2,3-b]pyridin-5-yloxy)-4-(4-((2-(4-chlorophenyl)-4,4-dimethylcyclohexyl)methyl)piperidin-1-yl)benzoate The title compound was prepared by substituting EXAMPLE 296C for EXAMPLE 263G in EXAMPLE 263H.

Example 296E

Trans-2-(1H-pyrrolo[2,3-b]pyridin-5-yloxy)-4-(4-((2-(4-chlorophenyl)-4,4-dimethylcyclohexyl)methyl)piperidin-1-yl)benzoic acid The title compound was prepared by substituting EXAMPLE 296D for EXAMPLE 3I in EXAMPLE 3J.

Example 296F

Trans-4-(4-{[2-(4-chlorophenyl)-4,4-dimethylcyclohexyl]methyl}piperidin-1-yl)-N-({3-nitro-4-[(tetrahydro-2H-pyran-4-ylmethyl)amino]
phenyl}sulfonyl)-2-(1H-pyrrolo[2,3-b]pyridin-5-yloxy)benzamide The title compound was prepared by substituting EXAMPLE 296E for EXAMPLE 1E in EXAMPLE 1G. $^1$H NMR (300 MHz, dimethylsulfoxide-$d_6$) δ 11.69 (s, 1H), 11.36 (br s, 1H), 8.60 (t, 1H), 8.55 (d, 1H), 8.03 (d, 1H), 7.78 (dd, 1H), 7.52 (m, 3H), 7.27 (d, 2H), 7.16 (d, 2H), 7.09 (m, 1H), 6.63 (dd, 1H), 6.38 (dd, 1H), 6.11 (d, 1H), 3.83 (dd, 2H), 3.52 (m, 2H), 3.26 (m, 4H), 2.61 (m, 2H), 2.35 (m, 1H), 1.89 (m, 2H), 1.76 (m, 1H), 1.62 (m, 2H), 1.38 (m, 4H), 1.25 (m, 6H), 1.12 (m, 2H), 0.95 (m, 2H), 0.94 (s, 3H), 0.88 (s, 3H).

Example 297

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide

Example 297A 6-((tetrahydro-2H-pyran-4-yl)methoxy)-5-(trifluoromethyl)pyridine-3-sulfonamide The title compound was prepared by substituting EXAMPLE 288E for 4-fluoro-3-nitrobenzenesulfonamide in EXAMPLE 24A.

Example 297B 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide The title compound was prepared by substituting EXAMPLE 297A for EXAMPLE 11B in EXAMPLE 11D. $^1$H NMR (400 MHz, dimethylsulfoxide-$d_6$) δ 11.49 (s, 1 H), 8.56 (d, 1 H), 8.23 (d, 1 H), 7.90 (d, 1 H), 7.58 (d, 1 H), 7.40 (m, 1 H), 7.34 (m, 2 H), 7.26 (d, 1 H), 7.05 (d, 2 H), 6.61 (dd, 1 H), 6.28 (dd, 1 H), 6.24 (d, 1 H), 4.24 (d, 2 H), 3.86 (dd, 2 H), 3.30 (m, 4 H), 3.00 (s, 4 H), 2.73 (s, 2 H), 2.16 (m, 6 H), 1.97 (m, 2 H), 1.61 (dd, 2 H), 1.33 (m, 4 H), 0.93 (s, 6 H).

Example 298

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 298A 6-((trans-4-(tert-butyldimethylsilyloxy)cyclohexyl)methoxy)-5-chloropyridine-3-sulfonamide The title compound was prepared by substituting (trans-4-(tert-butyldimethylsilyloxy)cyclohexyl)methanol for (tetrahydro-2H-pyran-4-yl)methanol and EXAMPLE 40A for EXAMPLE 36A in EXAMPLE 36B.

Example 298B

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 298A for EXAMPLE 11B in EXAMPLE 11D. After the reaction was over, the solvent was removed, and the residue was treated with 1:1 trifluoroacetic acid/dichloromethane for two hours. The solvents were removed, and the residue was purified by reverse phase Gilson Prep HPLC system with a Phenomenex prep column (Luna, 5μ, C18(2), 250×21.20 mm, 5 Å) eluting with 20-80% acetonitrile in water with 0.1% trifluoroacetic acid to provide the title compound. $^1$H NMR (500 MHz, dimethylsulfoxide-$d_6$) δ 11.65 (s, 1H), 8.47 (s, 1H), 8.15 (s, 1H), 8.01 (d, 1H), 7.54 (d, 1H), 7.48-7.49 (m, 1H), 7.35 (d, 2H), 7.05 (d, 2H), 6.67 (dd, 1H), 6.37 (d, 1H), 6.21 (s, 1H), 4.53 (t, 1H), 4.18 (d, 2H), 3.08 (s, 4H), 2.84 (s, 2H), 2.29 (s, 4H), 2.15 (s, 2H), 1.96 (s, 2H), 1.79-1.83 (m, 5H), 1.39 (t, 2H), 1.08-1.13 (m, 5H), 0.93 (s, 6H).

Example 299

4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide

Example 299A 3-cyano-4-((4-fluorotetrahydro-2H-pyran-4-yl)methoxy)benzenesulfonamide The title compound was prepared by substituting EXAMPLE 37C for (tetrahydro-2H-pyran-4-yl)methanol in EXAMPLE 284A.

Example 299B 4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 299A for EXAMPLE 1F in EXAMPLE 1G. $^1$H NMR (300 MHz, dimethylsulfoxide-$d_6$) δ 11.72 (s, 1H), 10.24-9.27 (m, 1H), 8.21 (d, 1H), 8.12 (dd, 1H), 8.05 (d, 1H), 7.63-7.46 (m, 3H), 7.45-7.31 (m, 3H), 7.07 (d, 2H), 6.70 (dd, 1H), 6.42 (s, 1H), 6.23 (s, 1H), 4.38 (d, 2H), 3.91-3.73 (m, 2H), 3.68-3.51 (m, 2H), 3.22-2.96 (m, 10H), 2.31-2.12 (m, 2H), 1.99 (s, 6H), 1.43 (t, 2H), 0.93 (s, 6H).

Example 300

4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide

Example 300A 6-((trans-4-methoxycyclohexyl)methoxy)-5-(trifluoromethyl)pyridine-3-sulfonamide The title compound was prepared by substituting EXAMPLE 288E for 4-fluoro-3-nitrobenzenesulfonamide and EXAMPLE 121A for (tetrahydro-2H-pyran-4-yl)methanol in EXAMPLE 24A.

Example 300B 4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide The title compound was prepared by substituting EXAMPLE 300A for EXAMPLE 11B in EXAMPLE 11D. $^1$H NMR (400 MHz, dimethylsulfoxide-$d_6$) δ 11.50 (s, 1 H), 8.56 (d, 1 H), 8.23 (d, 1 H), 7.90 (d, 1 H), 7.58 (d, 1 H), 7.40 (m, 1 H), 7.35 (d, 2 H), 7.27 (d, 1 H), 7.05 (d, 2 H), 6.61 (dd, 1 H), 6.28 (dd, 1 H), 6.24 (d, 1 H), 4.20 (d, 2 H), 3.23 (s, 3 H), 3.03 (m, 5 H), 2.73 (s, 2 H), 2.18 (m, 6 H), 1.98 (m, 5 H), 1.80 (m, 3 H), 1.39 (t, 2 H), 1.09 (m, 4 H), 0.93 (s, 6 H).

Example 301

4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide

Example 301A 6-((cis-4-methoxycyclohexyl)methoxy)-5-(trifluoromethyl)pyridine-3-sulfonamide The title compound was prepared by substituting EXAMPLE 288E for 4-fluoro-3-nitrobenzenesulfonamide and EXAMPLE 121A for (tetrahydro-2H-pyran-4-yl)methanol in EXAMPLE 24A.

Example 301B 4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3b]pyridin-5-yloxy)benzamide The title compound was prepared by substituting EXAMPLE 301A for EXAMPLE 11B in EXAMPLE 11D. $^1$H NMR (400 MHz, dimethylsulfoxide-$d_6$) δ 11.49 (m, 1 H), 8.54 (m, 1 H), 8.23 (d, 1 H), 7.91 (d, 1 H), 7.59 (d, 1 H), 7.40 (m, 1 H), 7.34 (m, 2 H), 7.27 (d, 1 H), 7.04 (d, 2 H), 6.61 (dd, 1 H), 6.29 (dd, 1 H), 6.24 (d, 1 H), 4.20 (d, 2 H), 3.37 (m, 2 H), 3.19 (s, 3 H), 3.00 (s, 4 H), 2.73 (s, 2 H), 2.18 (m, 6 H), 1.96 (s, 2 H), 1.80 (m, 3 H), 1.50 (dd, 2 H), 1.37 (m, 6 H), 0.93 (s, 6 H).

Example 302

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide

Example 302A 4-((2-(4-chlorophenyl)-4,4-dimethylcyclohex-1-enyl)methyl)piperidine EXAMPLE 296B (1.0 g) was stirred in dichloromethane (15 mL) and trifluoroacetic acid (15 mL) at 35° C. for 48 hours. The mixture was concentrated, taken up in dichloromethane (100 mL), and stirred, and saturated $Na_2CO_3$ solution (20 mL) was added slowly. The solution was separated and the organic layer was dried over $Na_2SO_4$, filtered, and concentrated to provide the title compound.

Example 302B methyl 2-(1H-pyrrolo[2,3-b]pyridin-5-yloxy)-4-(4-((2-(4-chlorophenyl)-4,4-dimethylcyclohex-1-enyl)methyl)piperidin-1-yl)benzoate The title compound was prepared by substituting EXAMPLE 302A for EXAMPLE 263G in EXAMPLE 263H.

Example 302C 2-(1H-pyrrolo[2,3-b]pyridin-5-yloxy)-4-(4-((2-(4-chlorophenyl)-4,4-dimethylcyclohex-1-enyl)methyl)piperidin-1-yl)benzoic acid The title compound was prepared by substituting EXAMPLE 302B for EXAMPLE 31 in EXAMPLE 3J.

Example 302D 1,1-difluoro-4-methylenecyclohexane

Butyllithium (12.32 mL, 2.5 M solution in hexanes) was added to a solution of methyltriphenylphosphonium chloride (9.63 g) in tetrahydrofuran (50 mL) at 0° C., and the reaction was stirred for 5 minutes. 4,4-Difluorocycleohexanone (3.76 g) in dioxane (150 mL) was then added, and the reaction was stirred for 30 minutes. Water (3 mL) was added, and then hexane (150 mL) was slowly added, the reaction was filtered, and the solution carried on.

Example 302E 4,4-difluoro-1-(hydroxymethyl)cyclohexanol

To the solution from EXAMPLE 302D was added water (75 mL), then N-methylmorpholine-N-oxide (6.4 mL, 50% solution in water) and $OsO_4$ (14.2 g, 2.5 wt % solution in tert-butanol) were added, and the reaction was stirred for 96 hours at 50° C. The solution was cooled to room temperature, treated with saturated aqueous $Na_2S_2O_3$ solution (100 mL) for 30 minutes, and then acidified with concentrated aqueous HCl. The solution was then extracted three times with ethyl acetate, and the organic layers were combined, washed with 1M HCl, and brine, and concentrated. The crude mixture was chromatographed on silica gel using 10-100% ethyl acetate in hexanes, and then 5% methanol in ethyl acetate to give the product.

Example 302F 5-chloro-6-((4,4-difluoro-1-hydroxycyclohexyl)methoxy)pyridine-3-sulfonamide This example was prepared by substituting EXAMPLE 302E for tetrahydro-2H-pyran-4-yl)methanol and EXAMPLE 40A for 4-fluoro-3-nitrobenzenesulfonamide in EXAMPLE 24A.

Example 302G

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide The title compound was prepared by substituting EXAMPLE 302C for EXAMPLE 1E and EXAMPLE 302F for EXAMPLE 1F in EXAMPLE 1G. $^1$H NMR (300 MHz, dimethylsulfoxide-$d_6$) δ 11.65 (br s, 2H), 8.51 (s, 1H), 8.18 (s, 1H), 8.02 (d, 1H), 7.53 (m, 3H), 7.35 (d, 2H), 7.04 (d, 2H), 6.69 (dd, 1H), 6.39 (dd, 1H), 6.21 (d, 1H), 4.88 (s, 1H), 4.27 (s, 2H), 3.10 (m, 4H), 2.88 (m, 1H), 2.33 (m, 2H), 2.15 (m, 4H), 1.97 (s, 2H), 1.91 (m, 2H), 1.73 (m, 4H), 1.52 (m, 1H), 1.40 (m, 2H), 1.31 (m, 1H), 0.93 (s, 3H), 0.91 (m, 2H).

Example 303

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 303A trans-4-morpholinocyclohexyl)methanol

To tert-butyl trans-4-(hydroxymethyl)cyclohexylcarbamate (0.500 g) was added hydrogen chloride (4.0M in dioxane, 2.2 mL) and the reaction was stirred for 1 hour and concentrated. The resulting solid was dissolved in acetonitrile (4 mL) and treated with N,N-diisopropylethylamine (1.523 mL) followed by 1-bromo-2-(2-bromoethoxy)ethane (0.556 g) and heated to 60° C. After stirring overnight the reaction was concentrated, loaded onto silica gel (Reveleris 40 g) and eluted using a gradient of 1% to 10% methanol/dichloromethane over 30 minutes (flow=40 mL/min) to provide the title compound.

Example 303B 3-chloro-4-(((1r,4r)-4-morpholinocyclohexyl)methoxy)benzenesulfonamide The title compound was prepared by substituting EXAMPLE 303A for (4-fluoro-1-methylpiperidin-4-yl)methanol in EXAMPLE 283A.

Example 303C

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 303B for EXAMPLE 1F in EXAMPLE 1G. $^1$H NMR (300 MHz, dimethylsulfoxide-$d_6$) δ 11.65 (s, 1H), 10.96-10.59 (m, 1H), 8.02 (d, 1H), 7.82 (d, 1H), 7.69 (s, 1H), 7.50 (dd, 3H), 7.38-7.30 (m, 2H), 7.15-6.99 (m, 3H), 6.65 (dd, 1H), 6.39 (dd, 1H), 6.20 (d, 1H), 3.91 (d, 2H), 3.64 (s, 4H), 3.04 (s, 4H), 2.73 (s, 7H), 2.18 (s, 6H), 1.93 (m, 6H), 1.80-1.65 (m, 1H), 1.32 (m, 6H), 0.92 (s, 6H).

Example 304

4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide To a solution of EXAMPLE 291E (95 mg) in dichloromethane (2 mL) and acetic acid (0.5 mL) was added thiazole-5-carbaldehyde (13 mg) followed by sodium triacetoxyborohydride (35 mg). The mixture was stirred overnight. The mixture was diluted with dichloromethane (300 mL) and washed with aqueous NaHCO$_3$, water, and brine and dried over Na$_2$SO$_4$. Filtration and evaporation of the solvent gave crude product which was dissolved in dimethylsulfoxide/methanol (6 mL, 1:1) and loaded on Gilson, C18 (100A) 250×121.2 mm (10 micron), with 30% acetonitrile to 65% acetonitrile over 40 minutes. $^1$H NMR (300 MHz, dimethylsulfoxide-$d_6$) δ 11.67 (s, 1 H), 8.95 (s, 1 H), 8.57 (m, 2 H), 8.03 (d, 1 H), 7.78 (m, 2 H), 7.49 (m, 3 H), 7.35 (m, 2 H), 7.02 (m, 3 H), 6.67 (dd, 1 H), 6.38 (dd, 1 H), 6.19 (d, 1 H), 4.00 (s, 2 H), 3.05 (d, 4 H), 2.73 (m, 2 H), 2.60 (m, 2 H), 2.18 (m, 7 H), 1.95 (s, 2 H), 1.79 (m, 3 H), 1.37 (m, 3 H), 0.92 (s, 6 H), 0.45 (m, 4 H).

Example 305

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 305A 3-chloro-4-((trans-4-hydroxycyclohexyl)methoxy)benzenesulfonamide (Trans-4-(tert-butyldimethylsilyloxy)cyclohexyl)methanol (275 mg, prepared according to a procedures in WO 2008/124878) and 3-chloro-4-fluorobenzenesulfonamide (259 mg) in tetrahydrofuran (15 mL) were treated with sodium hydride (180 mg, 60%) overnight. The reaction was quenched with water (1 mL) and trifluoroacetic acid (4 mL) was added. The resulting mixture was stirred for 1 hour and concentrated. The residue was triturated with water and methanol to provide the title compound.

Example 305B

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in EXAMPLE 11D using EXAMPLE 305A in place of EXAMPLE 11B. $^1$H NMR (500 MHz, dimethylsulfoxide-$d_6$) δ 11.71 (s, 1 H), 11.38 (s, 1 H), 8.06 (d, 1 H), 7.87 (d, 1 H), 7.76 (dd, 1 H), 7.57 (d, 1 H), 7.51-7.55 (m, 1 H), 7.49 (d, 1 H), 7.34 (d, 2 H), 7.18 (d, 1 H), 7.04 (d, 2 H), 6.67 (dd, 1 H), 6.42 (dd, 1 H), 6.18 (d, 1 H), 4.54 (d, 1 H), 3.91 (d, 2 H), 3.07 (s, 4 H), 2.75 (s, 2 H), 2.17 (d, 6 H), 1.95 (s, 2 H), 1.78-1.90 (m, 4 H), 1.63-1.75 (m, 1 H), 1.38 (t, 2 H), 1.00-1.25 (m, 4 H), 0.92 (s, 6 H).

Example 306

4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide

Example 306A 3-chloro-4-((tetrahydro-2H-pyran-4-yl)methylamino)benzenesulfonamide The title compound was prepared by substituting 4-fluoro-3-chlorobenzenesulfonamide for 4-chloro-3-nitrobenzenesulfonamide, (tetrahydro-2H-pyran-4-yl)methanamine for 4-methylpiperazin-1-amine dihydrochloride and Hunig's base for $N^1,N^1,N^2,N^2$-tetramethylethane-1,2-diamine in EXAMPLE 6A.

Example 306B 4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 306A for EXAMPLE 11B in EXAMPLE 11D. $^1$H NMR (400 MHz, dimethylsulfoxide-$d_6$) δ 11.80 (s, 1H), 11.17 (br s, 1H), 8.09 (d, 1H), 7.71 (d, 1H), 7.63 (d, 1H), 7.58 (dd, 1H), 7.53 (dd, 1H), 7.50 (d, 1H), 7.34 (d, 2H), 7.03 (d, 2H), 6.74 (d, 1H), 6.66 (dd, 1H), 6.42 (m, 1H), 6.40 (t, 1H), 6.16 (d, 1H), 3.83 (m, 2H), 3.24 (m, 2H), 3.10 (m, 2H), 3.06 (br m, 4H), 2.72 (s, 2H), 2.17 (br m, 6H), 1.95 (s, 2H), 1.83 (m, 1H), 1.59 (br m, 2H), 1.38 (t, 2H), 1.20 (ddd, 2H), 0.92 (s, 6H).

Example 307

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide

Example 307A 4-((4-fluorotetrahydro-2H-pyran-4-yl)methoxy)-3-(trifluoromethyl)benzenesulfonamide The title compound was prepared by substituting 4-fluoro-3-(trifluoromethyl)benzenesulfonamide for 4-fluoro-3-nitrobenzenesulfonamide and EXAMPLE 37C for (tetrahydro-2H-pyran-4-yl)methanol in EXAMPLE 24A.

Example 307B 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 307A for EXAMPLE 1F in EXAMPLE 1G. $^1$H NMR (400 MHz, pyridine-$d_5$) δ 13.07 (s, 1H), 8.78 (d, 1H), 8.58 (dd, 1H), 8.42 (d, 1H), 8.09 (d, 1H), 7.67 (t, 1H), 7.65 (d, 1H), 7.43 (m, 2H), 7.16 (d, 1H), 7.06 (m, 2H), 6.74 (dd, 1H), 6.51 (m, 2H), 4.21 (d, 2H), 3.87 (m, 2H), 3.78 (td, 2H), 3.06 (m, 4H), 2.76 (s, 2H), 2.25 (t, 2H), 2.13 (m, 4H), 1.95 (m, 6H), 1.39 (t, 2H), 0.93 (s, 6H).

Example 308

4-(4-{[2-(4-chlorophenyl)-4,4-dimethylcyclohex-1-en-1-yl]methyl}piperazin-1-yl)-N-{[4-({3-[cyclopropyl(2,2,2-trifluoro ethyl)amino]propyl}amino)-3-nitrophenyl]sulfonyl}-2-(1H-pyrrolo[2,3-b]pyridin-5-yloxy)benzamide

Example 308A 4-(3-(cyclopropylamino)propylamino)-3-nitrobenzenesulfonamide

To a solution of EXAMPLE 291C (4.14 g) in dichloromethane (10 mL) was added trifluoroacetic acid (10 mL). The mixture was stirred for 2 hours. The mixture was concentrated under vacuum and the residue was dissolved in dichloromethane (300 mL) and washed with aqueous NaHCO$_3$, water, and brine and dried over Na$_2$SO$_4$. Filtration and evaporation of solvent gave the title compound.

Example 308B 4-(3-(cyclopropyl(2,2,2-trifluoroethyl)amino)propylamino)-3-nitrobenzenesulfonamide To a solution of EXAMPLE 308A (314 mg) in dichloromethane (6 mL) was added 2,2,2-trifluoroethyl trifluoromethanesulfonate (255 mg) and N,N-diisopropylethylamine (258 mg). The mixture was stirred overnight. The mixture was diluted with dichloromethane (300 mL) and washed with aqueous NaHCO$_3$, water, brine and dried over Na$_2$SO$_4$. Filtration and evaporation of solvent gave the title compound.

Example 308C 4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide The title compound was prepared by substituting EXAMPLE 3J for EXAMPLE 1E and EXAMPLE 308B for EXAMPLE 1F in EXAMPLE 1G. $^1$H NMR (300 MHz, dimethylsulfoxide-d$_6$) δ 11.67 (s, 1 H), 11.38 (m, 1 H), 8.55 (d, 2 H), 8.03 (d, 1 H), 7.81 (dd, 1 H), 7.50 (m, 3 H), 7.34 (d, 2 H), 7.05 (m, 3 H), 6.67 (dd, 1 H), 6.38 (dd, 1 H), 6.19 (d, 1 H), 3.07 (m, 4 H), 2.82 (m, 4 H), 2.18 (m, 7 H), 1.38 (m, 2 H), 0.92 (s, 6 H), 0.44 (m, 4 H).

Example 309

N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide To a solution of EXAMPLE 294B (0.150 g) in dichloromethane (2 mL) was added trifluoroacetic acid (1 mL). After stirring for 1 hour the reaction was concentrated and dried under high vacuum. The residue was dissolved in dichloromethane (2 mL) and treated with sodium triacetoxyborohydride (0.050 g) and oxetan-3-one (0.017 g) and stirred overnight at room temperature. The reaction was quenched with saturated aqueous NaHCO$_3$ (20 mL) and extracted into dichloromethane (50 mL). The organic layer was separated, washed with brine (25 mL), dried over Na$_2$SO$_4$, filtered, and concentrated. Silica gel chromatography (Reveleris 40 g) eluting with a gradient of 0.5% to 5% methanol/dichloromethane over 30 minutes (flow=40 mL/min) provided the title compound. $^1$H NMR (300 MHz, dimethylsulfoxide-d$_6$) δ 11.70 (s, 1H), 11.21 (s, 1H), 8.05 (d, 1H), 7.87 (dl H), 7.75 (dd, 1H), 7.61-7.42 (m, 3H), 7.42-7.26 (m, 2H), 7.18 (d, 1H), 7.14-6.97 (m, 2H), 6.67 (dd, 1H), 6.41 (dd, 1H), 6.18 (d, 1H), 4.51 (dt, 4H), 3.99 (d, 2H), 3.56-3.32 (m, 1H), 3.06 (s, 4H), 2.89-2.68 (m, 4H), 2.16 (d, 6H), 2.01-1.69 (m, 7H), 1.50-1.07 (m, 4H), 0.92 (s, 6H).

Example 310

4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide

Example 310A 3,5-difluoro-4-((4-fluorotetrahydro-2H-pyran-4-yl)methoxy)benzenesulfonamide EXAMPLE 37C (0.423 g) in tetrahydrofuran (30 mL) was treated with NaH (60% oil dispersion) (0.480 g), stirred 20 minutes at ambient temperature, treated with 3,4,5-trifluorobenzenesulfonamide (0.633 g) and stirred 30 minutes. N,N-Dimethylacetamide (15 mL) was added to increase solubility of the reactants and stirring was continued overnight at ambient temperature. Additional NaH (60% oil dispersion) (0.480 g) and N,N-dimethylacetamide (15 mL) were added and the mixture was heated overnight at 50° C. The reaction was quenched with saturated aqueous NH$_4$Cl solution and then partitioned between saturated aqueous NH$_4$Cl solution and ethyl acetate. The organic layer was washed with water and brine, dried (MgSO$_4$), filtered and concentrated. The concentrate was chromatographed on amine functionalized silica gel with 0 to 2% methanol in CH$_2$Cl$_2$ as the eluent. The residue was further purified by reverse phase HPLC on a C18 column using a gradient of 10-70% acetonitrile/0.1% trifluoroacetic acid in water to provide the title compound.

Example 310B 4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 310A for EXAMPLE 1F in EXAMPLE 1G. $^1$H NMR (500 MHz, pyridine-d$_5$) δ 13.06 (s, 1H), 8.41 (d, 1H), 8.11 (m, 2H), 8.08 (d, 1H), 7.66 (m, 2H), 7.44 (m, 2H), 7.07 (m, 2H), 6.75 (dd, 1H), 6.52 (d, 1H), 6.50 (dd, 1H), 4.26 (d, 2H), 3.85 (dd, 1H), 3.83 (dd, 1H), 3.74 (m, 2H), 3.07 (m, 4H), 2.77 (s, 2H), 2.26 (t, 2H), 2.14 (m, 4H), 1.97 (s, 2H), 1.87 (m, 4H), 1.39 (t, 2H), 0.94 (s, 6H).

Example 311

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide

Example 311A 4-(3-(cyclopropyl(oxetan-3-yl)amino)propylamino)-3-nitrobenzenesulfonamide To a solution of EXAMPLE 308A (314 mg) in dichloromethane (5 mL) was added oxetan-3-one (72 mg) followed by sodium triacetoxyborohydride (318 mg). The mixture was stirred overnight. The mixture was diluted with dichloromethane (300 mL) and washed with aqueous NaHCO$_3$, water and brine and dried over Na$_2$SO$_4$. After filtration, evaporation of the solvent gave the crude title compound.

Example 311B 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide The title compound was prepared by substituting EXAMPLE 3J for EXAMPLE 1E and EXAMPLE 311A for EXAMPLE 1F in EXAMPLE 1G. $^1$H NMR (300 MHz, dimethylsulfoxide-d$_6$) δ 11.65 (s, 1 H), 11.37 (s, 1 H), 8.68 (s, 1 H), 8.54 (d, 1 H), 8.02 (d, 1 H), 7.79 (d, 1 H), 7.49 (m, 3 H), 7.34 (d, 2 H), 7.03 (m, 3 H), 6.67 (dd, 1 H), 6.38 (dd, 1 H), 6.19 (d, 1 H), 4.62 (m, 2 H), 4.48 (t, 2 H), 3.98 (m, 1 H), 3.37 (m, 2 H), 3.06 (m, 4 H), 2.73 (d, 2 H), 2.59 (m, 2 H), 2.23 (m, 6 H), 1.95 (s, 2 H), 1.74 (m, 3 H), 1.38 (t, 2 H), 0.92 (s, 6 H), 0.41 (m, 4 H).

Example 312

N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide To EXAMPLE 294B (0.065 g) was added hydrogen chloride (4.0M in dioxane, 0.339 mL) and a few drops of methanol. After 30 minutes, the reaction was concentrated, and (S)-1-methylpyrrolidine-2-carboxylic acid (0.013 g), $N^1$-((ethylimino)methylene)-$N^3$,$N^3$-dimethylpropane-1,3-diamine hydrochloride (0.026 g), suspended in dichloromethane (0.5 mL) were added followed by diisopropylethylamine (0.036 mL). The mixture stirred at room temperature. After stirring overnight, the reaction mixture was loaded onto silica gel (Reveleris 40 g) and eluted using a gradient of 1% to 10% methanol (containing 1N NH$_3$)/dichloromethane over 30 minutes (flow=40 mL/minutes) to provide the title compound. $^1$H NMR (300 MHz, dimethylsulfoxide-d$_6$) δ 11.51 (s, 1H), 10.00-9.22 (m, 1H), 7.92 (d, 1H), 7.68 (d, 1H), 7.57 (d, 1H), 7.47 (dd, 1H), 7.44-7.38 (m, 1H), 7.38-7.31 (m, 2H), 7.29 (d, 1H), 7.12-7.01 (m, 2H), 6.90 (d, 1H), 6.61 (dd, 1H), 6.31 (dd, 1H), 6.25 (d, 1H), 5.85 (d, 1H), 4.40 (s, 1H), 3.92 (s, 4H), 3.17-2.89 (m, 8H), 2.73 (s, 4H), 2.38 (s, 3H), 2.18 (m, 6H), 1.96 (s, 2H), 1.80 (m, 2H), 1.57 (s, 2H), 1.39 (s, 2H), 1.22 (m, 2H), 0.96 (m, 6H).

Example 313

4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide

Example 313A 3,4-difluoro-5-((4-fluorotetrahydro-2H-pyran-4-yl)methoxy)benzenesulfonamide The title compound was obtained as a side product in EXAMPLE 310A.

Example 313B 4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting EXAMPLE 3J for EXAMPLE 1E and EXAMPLE 313A for EXAMPLE 1F in EXAMPLE 1G. $^1$H NMR (400 MHz, pyridine-d$_5$) δ 13.05 (s, 1H), 8.41 (d, 1H), 8.10 (d, 1H), 7.98 (m, 2H), 7.66 (m, 1H), 7.63 (d, 1H), 7.44 (m, 2H), 7.07 (m, 2H), 6.77 (dd, 1H), 6.54 (d, 1H), 6.48 (dd, 1H), 4.12 (d, 2H), 3.83 (m, 2H), 3.75 (m, 2H), 3.08 (m, 4H), 2.77 (s, 2H), 2.26 (t, 2H), 2.15 (m, 4H), 1.97 (s, 2H), 1.82 (m, 4H), 1.39 (t, 2H), 0.94 (s, 6H).

Example 314

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 314A (S)-5-chloro-6-((4-cyclopropylmorpholin-2-yl)methoxy)pyridine-3-sulfonamide A solution of EXAMPLE 244B (250 mg), anhydrous methanol (6 mL), (1-ethoxycyclopropoxy)trimethylsilane (0.474 mL), and acetic acid (0.509 mL) was heated at 70° C. for 30 minutes. After cooling to ambient temperature, sodium cyanoborohydride (112 mg) was added and the mixture was stirred for 18 hours. Additional sodium cyanoborohydride (75 mg) was added and stirring was continued 18 hours. The reaction was concentrated and the residue was partitioned between methylene chloride and saturated sodium bicarbonate solution. The crude product was isolated from the dried methylene chloride layer and was purified on silica gel and was eluted with a 1, 2.5, 5, 10% methanol in methylene chloride step gradient to provide the title compound.

Example 314B

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 314A for EXAMPLE 130C in EXAMPLE 130D. $^1$H NMR (400 MHz, pyridine-d$_5$) δ 12.98 (s, 1H), 9.09 (d, 1H), 8.69 (d, 1H), 8.41 (d, 1H), 8.11 (d, 1H), 7.66-7.64 (m, 2H), 7.44 (d, 2H), 7.07 (d, 2H), 6.75 (dd, 1H), 6.53 (m, 1H), 6.48 (m, 1H), 5.72 (br s, 1H), 4.62-4.57 (m, 1H), 4.51-4.47 (m, 1H), 3.99 (m, 1H), 3.85 (m, 1H), 3.57 (m, 1H), 3.08-3.01 (m, 5H), 2.77 (s, 2H), 2.69 (m, 1H), 2.39-2.24 (m, 4H), 2.14 (m, 4H), 1.97 (s, 2H), 1.57 (m, 1H), 1.39 (t, 2H), 0.94 (m, 6H), 0.48-0.3 (m, 4H).

Example 315

4-(4-{[2-(4-chlorophenyl)-4,4-dimethylcyclohex-1-en-1-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 302C for EXAMPLE 1E and EXAMPLE 3J for EXAMPLE 1E in EXAMPLE 1G. $^1$H NMR (300 MHz, dimethylsulfoxide-d$_6$) δ 11.70 (s, 1H), 11.35 (br s, 1H), 8.61 (m, 1H), 8.57 (d, 1H), 8.04 (d, 1H), 7.82 (dd, 1H), 7.45-7.57 (m, 3H), 7.33 (d, 2H), 7.15 (d, 1H), 7.01 (d, 2H), 6.65 (dd, 1H), 6.40 (dd, 1H), 6.11 (d, 1H), 3.85 (dd, 2H), 3.53 (m, 2H), 3.27 (m, 4H), 2.63 (m, 2H), 2.04 (m, 2H), 1.91 (s, 2H), 1.77 (m, 2H), 1.62 (m, 4H), 1.45 (m, 2H), 1.38 (m, 2H), 1.27 (m, 1H), 1.23 (m, 4H), 0.92 (s, 6H).

Example 316

4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide

Example 316A 3-chloro-4-((tetrahydro-2H-pyran-4-yl)methoxy)benzenesulfonamide The title compound was prepared by substituting (tetrahydro-2H-pyran-4-yl)methanol for (4-fluoro-1-methylpiperidin-4-yl)methanol in EXAMPLE 283A.

Example 316B 4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide The title compound was prepared by substituting EXAMPLE 302C for EXAMPLE 1E and EXAMPLE 316A for EXAMPLE 1F in EXAMPLE 1G. $^1$H NMR (300 MHz, dimethylsulfoxide-$d_6$) δ 11.77 (s, 1H), 11.35 (br s, 1H), 8.06 (m, 1H), 7.88 (d, 1H), 7.79 (dd, 1H), 7.58 (s, 1H), 7.53 (t, 1H), 7.46 (d, 1H), 7.34 (d, 2H), 7.22 (d, 1H), 7.01 (d, 2H), 6.66 (dd, 1H), 6.42 (dd, 1H), 6.11 (d, 1H), 3.99 (d, 2H), 3.88 (dd, 2H), 3.52 (m, 2H), 3.34 (m, 4H), 2.62 (m, 2H), 2.04 (m, 4H), 1.76 (m, 2H), 1.68 (m, 2H), 1.46 (m, 2H), 1.38 (m, 4H), 0.92 (s, 6H), 0.75 (m, 2H).

Example 317 methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate

Example 317A methyl 2-((2-nitro-4-sulfamoylphenylamino)methyl)morpholine-4-carboxylate The title compound was prepared by substituting methyl chloroformate for methyl iodide in EXAMPLE 134B.

Example 317B methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate The title compound was prepared by substituting EXAMPLE 317A for EXAMPLE 130C in EXAMPLE 130D. $^1$H NMR (500 MHz, pyridine-$d_5$) δ 13.00 (s, 1H), 9.26 (d, 1H), 8.84 (t, 1H), 8.43 (d, 1H), 8.35 (d, 1H), 8.12 (d, 1H), 7.66 (m, 2H), 7.44 (d, 2H), 7.07 (d, 2H), 6.91 (bs, 1H), 6.75 (dd, 1H), 6.54 (d, 1H), 6.48 (m, 1H), 4.29-4.03 (m, 1H), 3.89-3.70 (m, 3H), 3.71 (s, 3H), 3.55-3.38 (m, 3H), 3.07 (m, 4H), 2.96 (dt, 1H), 2.86 (dd, 1H), 2.77 (s, 2H), 2.26 (m, 2H), 2.14 (m, 4H), 1.97 (s, 2H), 1.39 (t, 2H), 0.94 (s, 6H).

Example 318

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide

Example 318A

N-ethyl-N-methyl-2-((2-nitro-4-sulfamoylphenylamino)methyl)morpholine-4-carboxamide The title compound was prepared by substituting N-methyl-N-ethyl carbamyl chloride for methyl iodide in EXAMPLE 134B.

Example 318B

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide The title compound was prepared by substituting EXAMPLE 318A for EXAMPLE 130C in EXAMPLE 130D. $^1$H NMR (500 MHz, pyridine-$d_5$) δ 13.00 (s, 1H), 9.26 (d, 1H), 8.86 (t, 1H), 8.44 (d, 1H), 8.33 (dd, 1H), 8.12 (d, 1H), 7.67 (t, 1H), 7.64 (d, 1H), 7.44 (d, 2H), 7.07 (d, 2H), 6.91 (d, 1H), 6.75 (dd, 1H), 6.54 (d, 1H), 6.48 (m, 1H), 3.92-3.85 (m, 2H), 3.75 (d, 1H), 3.62 (dt, 1H), 3.55-3.48 (m, 1H), 3.45-3.39 (m, 2H), 3.21 (q, 2H), 3.07 (m, 4H), 2.99 (dt, 1H), 2.90 (dd, 1H), 2.77 (s, 2H), 2.76 (s, 3H), 2.26 (m, 2H), 2.14 (m, 4H), 1.97 (s, 2H), 1.39 (t, 2H), 1.06 (t, 3H), 0.93 (s, 6H).

Example 319

4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide

Example 319A 4-((4-(methylsulfonyl)morpholin-2-yl)methylamino)-3-nitrobenzenesulfonamide The title compound was prepared by substituting methanesulfonyl chloride for methyl iodide in EXAMPLE 134B.

Example 319B 4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 319A for EXAMPLE 130C in EXAMPLE 130D. $^1$H NMR (500 MHz, pyridine-$d_5$) δ 13.00 (s, 1H), 9.25 (d, 1H), 8.84 (t, 1H), 8.43 (d, 1H), 8.32 (dd, 1H), 8.13 (d, 1H), 7.67 (t, 1H), 7.65 (d, 1H), 7.44 (d, 2H), 7.07 (d, 2H), 6.92 (d, 1H), 6.75 (dd, 1H), 6.54 (d, 1H), 6.48 (m, 1H), 3.99 (m, 1H), 3.92-3.88 (m, 2H), 3.64 (m, 2H), 3.56 (m, 1H), 3.50 (m, 1H), 3.07 (m, 4H), 3.04 (s, 3H), 2.95-2.88 (m, 2H), 2.77 (s, 2H), 2.26 (m, 2H), 2.14 (m, 4H), 1.97 (s, 2H), 1.39 (t, 2H), 0.94 (s, 6H).

Example 320

4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide

Example 320A 4-(3-(cyclobutyl(cyclopropyl)amino)propylamino)-3-nitrobenzenesulfonamide To a solution of EXAMPLE 308A (314 mg) in dichloromethane (5 mL) was added cyclobutanone (70 mg) fol-

Example 320B 4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide The title compound was prepared by substituting EXAMPLE 3J for EXAMPLE 1E and EXAMPLE 320A for EXAMPLE 1F in EXAMPLE 1G. $^1$H NMR (300 MHz, dimethylsulfoxide-$d_6$) δ 11.65 (s, 1 H), 8.70 (m, 1 H), 8.54 (d, 1 H), 8.02 (d, 1 H), 7.79 (dd, 1 H), 7.49 (m, 3 H), 7.34 (d, 2 H), 7.03 (m, 3 H), 6.66 (dd, 1 H), 6.38 (dd, 1 H), 6.19 (d, 1 H), 3.37 (q, 2 H), 3.06 (m, 4 H), 2.73 (s, 2 H), 2.63 (m, 2 H), 2.21 (m, 8 H), 1.82 (m, 3 H), 1.53 (m, 2 H), 1.38 (t, 2 H), 0.94 (m, 6 H), 0.41 (m, 4 H).

Example 321

4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 321A ethyl 5,5-difluoro-2-oxocyclohexanecarboxylate

To a solution of diethyl 4,4-difluoroheptanedioate (4.3 g) in toluene (50 mL) was added potassium 2-methylpropan-2-olate (2.87 g) and the reaction stirred overnight at room temperature. The reaction was quenched with 1N aqueous HCl (100 mL) and extracted with diethyl ether (150 mL). The ether layer was washed with brine (50 mL), dried over magnesium sulfate, filtered, and concentrated. Silica gel chromatography (Reveleris 40 g) eluting with a gradient of 1% to 5% ethyl acetate/hexanes gave the title compound.

Example 321B ethyl 5,5-difluoro-2-(trifluoromethylsulfonyloxy)cyclohex-1-enecarboxylate To a solution of EXAMPLE 321A (2.37 g) in dichloromethane (40 mL) at 0° C. was added N,N-diisopropylethylamine (5.02 mL) followed by trifluoromethanesulfonic anhydride (2.33 mL) and the reaction was allowed to slowly warm to room temperature. After stirring overnight the reaction was quenched with 10 ml of water then 1N aqueous HCl (100 mL). The reaction was extracted with dichloromethane (3×75 mL), and the combined organics were washed with brine (50 mL) and concentrated. Silica gel chromatography (Reveleris 40 g) eluting with a gradient of 1% to 25% ethyl acetate/hexanes gave the title compound.

Example 321C ethyl 2-(4-chlorophenyl)-5,5-difluorocyclohex-1-enecarboxylate

A solution of EXAMPLE 321B (3.47 g), 4-chlorophenylboronic acid (1.925 g) and cesium fluoride (3.43 g) in 30 ml of 1,2-dimethoxyethane and 15 ml of ethanol was degassed with nitrogen for 5 minutes. Tetrakis(triphenylphosphine)palladium(0) (0.237 g) was added and the reaction was heated to 70° C. The reaction was diluted with ether (200 mL) and washed with 1N aqueous HCl (100 mL) and brine (100 mL), dried over magnesium sulfate, filtered, and concentrated. Silica gel chromatography (Reveleris 40 g) eluting with a gradient of 1% to 8% ethyl acetate/hexanes over 40 minutes gave the title compound.

Example 321D (2-(4-chlorophenyl)-5,5-difluorocyclohex-1-enyl)methanol

To a solution of EXAMPLE 321C (1.84 g) in diethyl ether (25 mL) at 0° C. was added lithium aluminum hydride (1.0M, 4.28 mL). The reaction was quenched with the dropwise addition of water, then 1N aqueous HCl (50 mL) was added and the reaction diluted with diethyl ether (100 mL). The organic layer was separated, washed with brine (50 mL) dried over magnesium sulfate, filtered and concentrated to provide the title compound.

Example 321E 2-(4-chlorophenyl)-5,5-difluorocyclohex-1-enecarbaldehyde

To a solution of EXAMPLE 321D (1.38 g) in dichloromethane (25 mL) was added Dess-Martin periodinane (2.489 g) and the reaction stirred for 1 hour at room temperature. The reaction was quenched with 1N aqueous NaOH solution (75 mL) and the product was extracted into dichloromethane (2×100 mL). The combined organics were washed with brine (75 mL), dried over magnesium sulfate, filtered, and concentrated. Silica gel chromatography (Reveris 80 g) eluting with a gradient of 1% to 10% ethyl acetate/hexanes over 40 minutes gave the title compound.

Example 321F methyl 2-(1H-pyrrolo[2,3-b]pyridin-5-yloxy)-4-(4-((2-(4-chlorophenyl)-5,5-difluorocyclohex-1-enyl)methyl)piperazin-1-yl)benzoate The title compound was prepared by substituting EXAMPLE 321E for EXAMPLE 15E in EXAMPLE 15G.

Example 321G 2-(1H-pyrrolo[2,3-b]pyridin-5-yloxy)-4-(4-((2-(4-chlorophenyl)-5,5-difluorocyclohex-1-enyl)methyl)piperazin-1-yl)benzoic acid The title compound was prepared by substituting EXAMPLE 321F for EXAMPLE 15G in EXAMPLE 15H.

Example 321H 4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 321G for EXAMPLE 1E and EXAMPLE 3J for EXAMPLE 1E in EXAMPLE 1G. $^1$H NMR (300 MHz, dimethylsulfoxide-d$_6$) δ 11.74-11.63 (m, 1H), 11.53-11.29 (m, 1H), 8.57 (d, 2H), 8.05 (d, 1H), 7.85-7.77 (m, 1H), 7.49 (d, 3H), 7.38 (d, 2H), 7.16-7.06 (m, 3H), 6.73-6.64 (m, 1H), 6.43-6.36 (m, 1H), 6.21-6.14 (m, 1H), 3.93-3.77 (m, 2H), 3.29 (d, 4H), 3.07 (s, 4H), 2.79-2.57 (m, 4H), 2.45 (dd, 2H), 2.19 (s, 6H), 1.99-1.80 (m, 1H), 1.70-1.54 (m, 2H), 1.38-1.13 (m, 2H).

Example 322

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 322A tert-butyl 4-fluoro-4-(hydroxymethyl)piperidine-1-carboxylate 1-Tert-butyl 4-ethyl 4-fluoropiperidine-1,4-dicarboxylate (2 g) was taken up in tetrahydrofuran (20 ml) and cooled in an ice bath. Lithium aluminum hydride (1.0M in dioxane, 5.09 mL) was added dropwise. The reaction was stirred at room temperature for 2 hours. The reaction was quenched with water and with 1M aqueous NaOH solution and then stirred another 1 hour at room temperature. The mixture was extracted with ethyl acetate, and the extracts were combined and washed with water and with brine, dried over MgSO$_4$, filtered and concentrated under vacuum. The crude product was used without further purification.

Example 322B tert-butyl 4-((2-chloro-4-sulfamoylphenoxy)methyl)-4-fluoropiperidine-1-carboxylate The title compound was prepared by substituting EXAMPLE 322A for (tetrahydro-2H-pyran-4-yl)methanol and 3-chloro-4-fluorobenzenesulfonamide for 4-fluoro-3-nitrobenzenesulfonamide in EXAMPLE 24A.

Example 322C 3-chloro-4-((4-fluoropiperidin-4-yl)methoxy)benzenesulfonamide

The title compound was prepared by substituting EXAMPLE 322B for EXAMPLE 1A in EXAMPLE 1B.

Example 322D 3-chloro-4-((4-fluoro-1-(oxetan-3-yl)piperidin-4-yl)methoxy)benzenesulfonamide To a solution of EXAMPLE 322C (830 mg) in tetrahydrofuran (15 mL) and acetic acid (5 mL) was added oxetan-3-one (163 mg) and MP-cyanoborohydride (2.38 mmol/g, 1.9 g). The mixture was stirred at room temperature overnight. The reaction was then filtered and the filtrate was concentrated under vacuum. The residue was slurried in ether and the solid product was collected by filtration.

Example 322E

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 322D for EXAMPLE 1F and EXAMPLE 3J for EXAMPLE 1E in EXAMPLE 1G. $^1$H NMR (400 MHz, dimethylsulfoxide-d$_6$) δ 11.71 (s, 1H), 8.06 (d, 1H), 7.89 (d, 1H), 7.79 (m, 1H), 7.58 (d, 1H), 7.52 (t, 1H), 7.49 (d, 1H), 7.34 (d, 2H), 7.25 (d, 1H), 7.04 (d, 2H), 6.67 (dd, 1H), 6.42 (m, 1H), 6.18 (d, 1H), 4.55 (t, 2H), 4.44 (t, 2H), 4.24 (d, 2H), 3.44 (m, 2H), 3.07 (br s, 4H), 2.74 (m, 2H), 2.59 (m, 2H), 2.14 (m, 7H), 1.95 (m, 4H), 1.78 (m, 2H), 1.38 (t, 2H), 0.92 (s, 6H).

Example 323

4-(4-{[2-(4-chlorophenyl)-4,4-dimethylcyclohex-1-en-1-yl]methyl}piperazin-1-yl)-N-{[3-chloro-4-(tetrahydro furan-3-ylmethoxy)phenyl]sulfonyl}-2-(1H-pyrrolo[2,3-b]pyridin-5-yloxy)benzamide Example 323A 3-chloro-4-((tetrahydrofuran-3-yl)methoxy)benzenesulfonamide The title compound was prepared by substituting 4-fluoro-3-chlorobenzenesulfonamide for 4-fluoro-3-nitrobenzenesulfonamide and (tetrahydrofuran-3-yl)methanol for (tetrahydro-2H-pyran-4-yl)methanol in EXAMPLE 24A, except here, dimethylformamide was used in place of tetrahydrofuran and the reaction was heated at 70° C. for two days.

Example 323B 4-(4-{[2-(4-chlorophenyl)-4,4-dimethylcyclohex-1-en-1-yl]methyl}piperazin-1-yl)-N-{[3-chloro-4-(tetrahydro furan-3-ylmethoxy)phenyl]sulfonyl}-2-(1H-pyrrolo[2,3-b]pyridin-5-yloxy)benzamide The title compound was prepared by substituting EXAMPLE 323A for EXAMPLE 11B in EXAMPLE 11D. $^1$H NMR (500 MHz, dimethylsulfoxide-d$_6$) δ 11.73 (s, 1H), 8.07 (d, 1H), 7.89 (d, 1H), 7.80 (dd, 1H), 7.59 (d, 1H), 7.51 (dd, 1H), 7.49 (d, 1H), 7.34 (d, 2H), 7.23 (d, 1H), 7.03 (d, 2H), 6.66 (dd, 1H), 6.42 (m, 1H), 6.19 (d, 1H), 4.07 (m, 2H), 3.80 (m, 2H), 3.68 (m, 1H) 3.56 (m, 1H), 3.10 (br m, 4H), 2.85 (br s, 2H), 2.69 (m, 1H), 2.32 (br m, 4H), 2.17 (br m, 2H), 2.02 (m, 1H), 1.96 (s, 2H), 1.69 (m, 1H), 1.40 (t, 2H), 0.92 (s, 6H).

Example 324

4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide

Example 324A 4-((trans-4-hydroxycyclohexyl)methylamino)-3-nitrobenzenesulfonamide The title compound was prepared by substituting EXAMPLE 120A for EXAMPLE 39B in EXAMPLE 39C.

Example 324B 4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide The title compound was prepared by substituting EXAMPLE 321G for EXAMPLE 1E and EXAMPLE 324A for EXAMPLE 1F in EXAMPLE 1G. $^1$H NMR (300 MHz, dimethylsulfoxide-$d_6$) δ 11.69 (s, 1H), 11.41 (s, 1H), 8.65-8.50 (m, 2H), 8.05 (d, 1H), 7.80 (dd, 1H), 7.60-7.44 (m, 3H), 7.41-7.34 (m, 2H), 7.14-7.02 (m, 3H), 6.68 (dd, 1H), 6.39 (dd, 1H), 6.17 (d, 1H), 4.50 (d, 1H), 3.23 (t, 2H), 3.06 (s, 4H), 2.70 (d4H), 2.44 (s, 2H), 2.33-1.94 (m, 6H), 1.78 (dd, 4H), 1.51 (d, 2H), 1.23 (s, 2H), 1.16-0.92 (m, 2H).

Example 325

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide

Example 325A methyl 2-(1H-pyrrolo[2,3-b]pyridin-5-yloxy)-4-(4-((9-(4-chlorophenyl)-3-(oxetan-3-yl)-3-azaspiro[5.5]undec-8-en-8-yl)methyl)piperazin-1-yl)benzoate The title compound was prepared by substituting oxetan-3-one for 1,3-difluoropropan-2-one in EXAMPLE 265G.

Example 325B 2-(1H-pyrrolo[2,3-b]pyridin-5-yloxy)-4-(4-((9-(4-chlorophenyl)-3-(oxetan-3-yl)-3-azaspiro[5.5]undec-8-en-8-yl)methyl)piperazin-1-yl)benzoic acid The title compound was prepared by substituting EXAMPLE 325A for EXAMPLE 15G in EXAMPLE 15H.

Example 325C

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide The title compound was prepared by substituting EXAMPLE 325B for EXAMPLE 1E and EXAMPLE 286A for EXAMPLE 1F in EXAMPLE 1G. $^1$H NMR (300 MHz, dimethylsulfoxide-$d_6$) δ 11.67 (s, 1H), 11.13 (s, 1H), 8.05 (d, 1H), 7.87 (d, 1H), 7.80-7.70 (m, 1H), 7.59-7.46 (m, 3H), 7.34 (d, 2H), 7.21 (d, 1H), 7.11-7.03 (m, 2H), 6.66 (d, 1H), 6.41 (dd, 1H), 6.18 (d, 1H), 4.50 (dd, 4H), 4.26 (d, 2H), 3.85-3.69 (m, 2H), 3.61 (d, 3H), 3.05 (s, 4H), 2.69 (s, 2H), 2.37 (s, 4H), 2.17 (s, 6H), 2.04 (s, 2H), 1.87 (d, 4H), 1.49 (d, 6H).

Example 326

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide

Example 326A (R)-4-((4-cyclopropylmorpholin-2-yl)methylamino)-3-nitrobenzenesulfonamide The title compound was prepared by substituting EXAMPLE 258E for EXAMPLE 173A in EXAMPLE 173B.

Example 326B 4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 326A for EXAMPLE 130C in EXAMPLE 130D. $^1$H NMR (500 MHz, pyridine-$d_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Example 327

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide

Example 327A (S)-4-((4-cyclopropylmorpholin-2-yl)methylamino)-3-nitrobenzenesulfonamide The title compound was prepared by substituting EXAMPLE 259E for EXAMPLE 173A in EXAMPLE 173B.

Example 327B 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide The title compound was prepared by substituting EXAMPLE 327A for EXAMPLE 130C in EXAMPLE 130D. $^1$H NMR (500 MHz, pyridine-d$_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Example 328

4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 328A spiro[2.5]octan-5-one To a solution of 3-ethoxycyclohex-2-enone (48.1 mL) in ether (1000 mL) was added titanium(IV) isopropoxide (110 mL) followed by addition of ethylmagnesium bromide (357 mL) at ambient temperature. The reaction mixture was stirred for 2 hours at ambient temperature and was then quenched with water (500 mL). The organic layer was separated (decanted) and the water layer was extracted with ether (3×300 mL). The combined extracts were partially concentrated to approximately 300 mL. p-Toluenesulfonic acid monohydrate (3.0 g) was added and the reaction mixture was stirred overnight at ambient temperature. The reaction mixture was then washed with saturated aqueous NaHCO$_3$ solution, dried (MgSO$_4$), filtered and concentrated. The concentrate was purified by fractional distillation (1st fraction b.p. 27° C. at 23 torr (not product), 2nd fraction (product) b.p. 75° C. at 8 torr).

Example 328B 5-chlorospiro[2.5]oct-5-ene-6-carbaldehyde

N,N-dimethylformamide (2.1 mL) in dichloromethane (3.2 ml) at −5° C. was treated slowly with POCl$_3$ (2.33 ml) keeping the bath temperature less than 0° C. The cooling bath was removed and the mixture was stirred at ambient temperature for 30 minutes. The reaction mixture was returned to the cooling bath and EXAMPLE 328A (2.484 g) in dichloromethane (4 mL) was added slowly to the reaction mixture. The reaction mixture was heated at 45° C. for 15 hours, cooled to room temperature and then poured into a mixture of ice and saturated aqueous sodium acetate solution. After the ice melted, the mixture was extracted with diethyl ether. The combined extracts were washed with saturated aqueous NaHCO$_3$ solution and brine, dried (MgSO$_4$), filtered and concentrated. The concentrate was chromatographed with 0 to 10% CH$_2$Cl$_2$ in hexanes, then 25% CH$_2$Cl$_2$ in hexanes and then 100% CH$_2$Cl$_2$ as the eluents.

Example 328C 5-(4-chlorophenyl)spiro[2.5]oct-5-ene-6-carbaldehyde

EXAMPLE 328B (2.9 g), 4-chlorophenylboronic acid (2.87 g), palladium(II) acetate (0.103 g), K$_2$CO$_3$ (5.28 g) and tetrabutylammonium bromide (4.93 g) were combined in a 100-mL round bottomed flask with water (17.0 mL). The flask was flushed with nitrogen and stirred at 45° C. for 14 hours. The reaction mixture was partitioned between brine and diethyl ether. The organic layer was washed with brine, dried (MgSO$_4$), filtered through a plug of celite, concentrated and chromatographed on silica gel with 0 to 2% ethyl acetate in hexanes as the eluent.

Example 328D methyl 2-(1H-pyrrolo[2,3-b]pyridin-5-yloxy)-4-(4-((5-(4-chlorophenyl)spiro[2.5]oct-5-en-6-yl)methyl)piperazin-1-yl)benzoate The title compound was prepared by substituting EXAMPLE 15F for tert-butyl piperazine carboxylate and EXAMPLE 328C for 4-chlorobiphenyl-2-carboxaldehyde in EXAMPLE 1A.

Example 328E 2-(1H-pyrrolo[2,3-b]pyridin-5-yloxy)-4-(4-((5-(4-chlorophenyl)spiro[2.5]oct-5-en-6-yl)methyl)piperazin-1-yl)benzoic acid hydrochloride EXAMPLE 328D (0.85 g) in a mixture of tetrahydrofuran (4.8 mL), methanol (2.4 mL) and water (2.4 mL) was treated with LiOH.H$_2$O (0.184 g) and heated overnight at 50° C. The reaction mixture was cooled to room temperature, concentrated to remove tetrahydrofuran and methanol and acidified with 1 N aqueous HCl causing precipitation of the product. The solid was collected by filtration, rinsed with water and dried overnight in a vacuum oven at 80° C. to provide the title compound.

Example 328F 4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting EXAMPLE 328E for EXAMPLE 1E in EXAMPLE 1G. $^1$H NMR (500 MHz, pyridine-d$_5$) δ 13.07 (s, 1H), 9.32 (d, 1H), 8.68 (t, 1H), 8.44 (d, 1H), 8.38 (dd, 1H), 8.10 (d, 1H), 7.68 (m, 1H), 7.66 (d, 1H), 7.43 (m, 2H), 7.10 (m, 2H), 6.91 (d, 1H), 6.75 (dd, 1H), 6.51 (m, 2H), 3.97 (dd, 2H), 3.30 (td, 2H), 3.16 (t, 2H), 3.06 (m, 4H), 2.81 (s, 2H), 2.37 (t, 2H), 2.16 (m, 4H), 2.11 (s, 2H), 1.81 (m, 1H), 1.58 (dd, 2H), 1.45 (t, 2H), 1.32 (qd, 2H), 0.38 (s, 4H).

Example 329

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 329A ethyl 4-(cyclopropylamino)cyclohexanecarboxylate To a solution of ethyl 4-oxocyclohexanecarboxylate (3.4 g) in dichloromethane (30 mL) was added cyclopropanamine (1.14 g) followed by sodium triacetoxyborohydride (4.24 g). The mixture was stirred overnight. The mixture was diluted with dichloromethane (300 mL) and washed with 2N NaOH, water, brine and dried over Na$_2$SO$_4$. Filtration and evaporation of the solvent gave the title compound.

Example 329B ethyl 4-(cyclopropyl(oxetan-3-yl)amino)cyclohexanecarboxylate

To a solution of EXAMPLE 329A (1.05 g) in dichloromethane (10 mL) was added oxetan-3-one (0.358 g) followed by sodium triacetoxyborohydride (1.05 g). The mixture was stirred overnight. The mixture was diluted with dichloromethane (300 mL) and washed with 2N aqueous NaOH, water, brine and dried over Na$_2$SO$_4$. Filtration and evaporation of the solvent gave the title compound.

Example 329C (4-(cyclopropyl(oxetan-3-yl)amino)cyclohexyl)methanol

To a solution of EXAMPLE 329B (1.2 g) in tetrahydrofuran (20 mL) was added lithium aluminum hydride (0.681 g). The mixture was stirred overnight. 2N aqueous NaOH solution was added dropwise to the reaction mixture. The mixture was then diluted with ethyl acetate (300 mL) and washed with water, brine and dried over Na$_2$SO$_4$. Filtration and evaporation of the solvent gave the title compound.

Example 329D 5-chloro-6-((4-(cyclopropyl(oxetan-3-yl)amino)cyclohexyl)methoxy)pyridine-3-sulfonamide To a solution of EXAMPLE 329C (706 mg) in N,N-dimethylformamide (6 mL) was added NaH (60% in mineral oil, 300 mg). The mixture was stirred for 30 minutes, and then 5,6-dichloropyridine-3-sulfonamide (706 mg) was added. The mixture was stirred overnight. The mixture was poured over aqueous NH$_4$Cl and extracted with ethyl acetate (3×200 mL). The combined organic layers were washed with water, brine and dried over Na$_2$SO$_4$. After filtration and evaporation of the solvent the residue was loaded on a silica gel cartridge and eluted with 5 to 10% 7N NH$_3$ in methanol in dichloromethane to provide the title compound.

Example 329E

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 329D for EXAMPLE 1F in EXAMPLE 1G. $^1$H NMR (300 MHz, dimethylsulfoxide-d$_6$) δ 11.64 (s, 1 H), 8.50 (m, 1 H), 8.16 (s, 1 H), 8.02 (d, 1 H), 7.51 (m, 3 H), 7.35 (d, 2 H), 7.04 (d, 2 H), 6.67 (dd, 1 H), 6.38 (m, 1 H), 6.21 (s, 1 H), 4.70 (m, 2 H), 4.43 (t, 3 H), 4.19 (m, 2 H), 3.12 (m, 4 H), 2.84 (m, 2 H), 2.19 (m, 6 H), 1.96 (s, 3 H), 1.77 (m, 3 H), 1.38 (m, 7 H), 0.93 (s, 6 H), 0.44 (m, 4 H).

Example 330

4-(4-{[5-(4-chlorophenyl)spiro[2.5]oct-5-en-6-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide The title compound was prepared by substituting EXAMPLE 328E for EXAMPLE 3J and EXAMPLE 218A for EXAMPLE 11B in EXAMPLE 11D. $^1$H NMR (400 MHz, pyridine-d$_5$) δ 13.01 (s, 1H), 9.26 (d, 1H), 8.88 (t, 1H), 8.43 (d, 1H), 8.34 (dd, 1H), 8.11 (d, 1H), 7.66 (m, 2H), 7.42 (m, 2H), 7.09 (m, 2H), 6.95 (d, 1H), 6.75 (dd, 1H), 6.53 (d, 1H), 6.49 (dd, 1H), 3.84 (m, 2H), 3.58 (td, 1H), 3.45 (m, 2H), 3.06 (m, 4H), 2.93 (d, 1H), 2.81 (s, 2H), 2.69 (d, 1H), 2.35 (m, 3H), 2.19 (m, 5H), 2.11 (s, 2H), 1.58 (m, 1H), 1.45 (t, 2H), 0.42 (m, 8H).

Example 331

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 331A tert-butyl 2-((2-chloro-4-sulfamoylphenoxy)methyl)morpholine-4-carboxylate To a solution of tert-butyl 2-(hydroxymethyl)morpholine-4-carboxylate (0.478 g) in anhydrous N,N-dimethylformamide (5 mL) was added sodium hydride (0.280 g). The mixture was stirred at room temperature for 30 minutes, followed by addition of 3-chloro-4-fluorobenzenesulfonamide (0.419 g). The mixture was stirred at 40° C. overnight. The reaction was quenched with water (10 mL), and the mixture was adjusted to pH 7 and extracted with ethyl acetate. The crude product was purified on a silica gel column eluting with 60% ethyl acetate in hexane to provide the title compound.

Example 331B 3-chloro-4-(morpholin-2-ylmethoxy)benzenesulfonamide

The title compound was prepared by substituting EXAMPLE 331A for EXAMPLE 113A in EXAMPLE 134A.

Example 331C 3-chloro-4-((4-cyclopropylmorpholin-2-yl)methoxy)benzenesulfonamide The title compound was prepared by substituting EXAMPLE 331B for EXAMPLE 173A in EXAMPLE 173B.

Example 331D

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 331C for EXAMPLE 130C in EXAMPLE 130D.

¹H NMR (500 MHz, pyridine-d₅) δ 13.04 (s, 1H), 8.54 (d, 1H), 8.43 (d, 1H), 8.27 (dd, 1H), 8.09 (d, 1H), 7.66 (m, 2H), 7.44 (d, 2H), 7.07 (d, 2H), 7.05 (d, 1H), 6.75 (dd, 1H), 6.52 (d, 1H), 6.50 (m, 1H), 4.20 (dd, 1H), 4.10 (dd, 1H), 3.94 (m, 1H), 3.86 (d, 1H), 3.58 (dt, 1H), 3.06 (m, 5H), 2.77 (s, 2H), 2.69 (d, 1H), 2.40-2.20 (m, 4H), 2.14 (m, 4H), 1.97 (s, 2H), 1.60 (m, 1H), 1.39 (t, 2H), 0.94 (s, 6H), 0.41 (m, 4H).

Example 332

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 332A tert-butyl 2-((2-chloro-4-sulfamoylphenylamino)methyl)morpholine-4-carboxylate A solution of 3-chloro-4-fluorobenzenesulfonamide (1.0 g), tert-butyl 2-(aminomethyl)morpholine-4-carboxylate (1.135 g) and N-ethyl-N-isopropylpropan-2-amine (1.246 mL) in dimethylsulfoxide (15 mL) was stirred at 115° C. for 72 hours. The mixture was concentrated, and the residue was purified on a silica gel column eluting with 60% ethyl acetate to provide the title compound.

Example 332B 3-chloro-4-(morpholin-2-ylmethylamino)benzenesulfonamide

The title compound was prepared by substituting EXAMPLE 332A for EXAMPLE 113A in EXAMPLE 134A.

Example 332C

The title compound was prepared by substituting EXAMPLE 332B for EXAMPLE 173A in EXAMPLE 173B.

Example 332D

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 332C for EXAMPLE 130C in EXAMPLE 130D. ¹H NMR (500 MHz, pyridine-d₅) δ 13.05 (s, 1H), 8.45 (m, 2H), 8.21 (dd, 1H), 8.12 (d, 1H), 7.69 (d, 1H), 7.67 (t, 1H), 7.44 (d, 2H), 7.07 (d, 2H), 6.78 (d, 1H), 6.74 (dd, 1H), 6.52 (d, 1H), 6.50 (m, 1H), 6.37 (m, 1H), 3.84 (d, 1H), 3.77 (m, 1H), 3.54 (dt, 1H), 3.35 (m, 2H), 3.05 (m, 4H), 2.94 (d, 1H), 2.77 (s, 2H), 2.68 (d, 1H), 2.32 (dt, 1H), 2.26 (m, 2H), 2.18-2.12 (m, 5H), 1.97 (s, 2H), 1.55 (m, 1H), 1.39 (t, 2H), 0.94 (s, 6H), 0.41 (m, 4H).

Example 333

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide

Example 333A 2-((2-chloro-4-sulfamoylphenylamino)methyl)-N-ethyl-N-methylmorpholine-4-carboxamide The title compound was prepared by substituting EXAMPLE 332B for EXAMPLE 134A and N-methyl-N-ethyl carbamyl chloride for methyl iodide in EXAMPLE 134B.

Example 333B

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide The title compound was prepared by substituting EXAMPLE 333A for EXAMPLE 130C in EXAMPLE 130D. ¹H NMR (500 MHz, pyridine-d₅) δ 13.05 (s, 1H), 8.46 (s, 1H), 8.45 (s, 1H), 8.20 (dd, 1H), 8.10 (d, 1H), 7.69 (d, 1H), 7.67 (t, 1H), 7.44 (d, 2H), 7.07 (d, 2H), 6.79 (d, 1H), 6.73 (dd, 1H), 6.52 (dd, 1H), 6.49 (d, 1H), 6.43 (m, 1H), 3.83 (d, 2H), 3.73 (d, 1H), 3.59 (dt, 1H), 3.41-3.35 (m, 3H), 3.20 (q, 2H), 3.05 (m, 4H), 2.95 (t, 1H), 2.84 (dd, 1H), 2.76 (s, 2H), 2.73 (s, 3H), 2.25 (m, 2H), 2.14 (m, 4H), 1.97 (s, 2H), 1.39 (t, 2H), 1.04 (t, 3H), 0.94 (s, 6H).

Example 334

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide

Example 334A (S)-2-((3-chloro-5-sulfamoylpyridin-2-yloxy)methyl)-N-ethyl-N-methylmorpholine-4-carboxamide The title compound was prepared by substituting EXAMPLE 244B for EXAMPLE 134A and N-methyl-N-ethyl carbamyl chloride for methyl iodide in EXAMPLE 134B.

Example 334B (2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide The title compound was prepared by substituting EXAMPLE 334A for EXAMPLE 130C in EXAMPLE 130D. ¹H NMR (500 MHz, pyridine-d₅) δ 12.98 (s, 1H), 9.08 (d, 1H), 8.70 (d, 1H), 8.42 (d, 1H), 8.11 (d, 1H), 7.67 (t, 1H), 7.64 (d, 1H), 7.44 (d, 2H), 7.07 (d, 2H), 6.75 (dd, 1H), 6.53 (d, 1H), 6.48 (m, 1H), 4.58 (dd, 1H), 4.47 (dd, 1H), 4.03 (m, 1H), 3.84 (m, 2H), 3.63 (dt, 1H), 3.45 (d, 1H), 3.22 (q, 2H), 3.07 (m, 4H), 3.05-2.95 (m, 2H), 2.78 (s, 3H), 2.77 (s, 2H), 2.26 (m, 2H), 2.14 (m, 4H), 1.97 (s, 2H), 1.39 (t, 2H), 1.07 (t, 3H), 0.94 (s, 6H).

Example 335

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 335A tert-butyl 2-((3-chloro-5-sulfamoylpyridin-2-ylamino)methyl)morpholine-4-carboxylate The title compound was prepared by substituting EXAMPLE 40A for 4-fluoro-3-nitrobenzenesulfonamide and tert-butyl 2-(aminomethyl)morpholine-4-carboxylate for (tetrahydropyran-4-yl)methylamine in EXAMPLE 1F.

Example 335B 5-chloro-6-(morpholin-2-ylmethylamino)pyridine-3-sulfonamide

The title compound was prepared by substituting EXAMPLE 335A for EXAMPLE 113A in EXAMPLE 134A.

Example 335C 5-chloro-6-((4-cyclopropylmorpholin-2-yl)methylamino)pyridine-3-sulfonamide The title compound was prepared by substituting EXAMPLE 335B for EXAMPLE 173A in EXAMPLE 173B.

Example 335D

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 335C for EXAMPLE 130C in EXAMPLE 130D. $^1$H NMR (500 MHz, pyridine-$d_5$) δ 13.02 (s, 1H), 9.15 (d, 1H), 8.49 (d, 1H), 8.43 (d, 1H), 8.11 (d, 1H), 7.80 (t, 1H), 7.69 (d, 1H), 7.65 (t, 1H), 7.44 (d, 2H), 7.07 (d, 2H), 6.73 (dd, 1H), 6.52 (m, 1H), 6.49 (d, 1H), 3.92 (m, 1H), 3.84 (m, 2H), 3.70 (m, 1H), 3.54 (dt, 1H), 3.05 (m, 4H), 2.99 (d, 1H), 2.76 (s, 2H), 2.68 (d, 1H), 2.32 (dt, 1H), 2.25 (m, 2H), 2.12 (m, 5H), 1.97 (s, 2H), 1.53 (m, 1H), 1.39 (t, 2H), 0.93 (s, 6H), 0.40 (m, 4H).

Example 336

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide

Example 336A 2-((3-chloro-5-sulfamoylpyridin-2-ylamino)methyl)-N-ethyl-N-methylmorpholine-4-carboxamide The title compound was prepared by substituting EXAMPLE 335B for EXAMPLE 134A and N-methyl-N-ethyl carbamyl chloride for methyl iodide in EXAMPLE 134B.

Example 336B

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide The title compound was prepared by substituting EXAMPLE 336A for EXAMPLE 130C in EXAMPLE 130D. $^1$H NMR (500 MHz, pyridine-$d_5$) δ 13.03 (s, 1H), 9.14 (d, 1H), 8.51 (d, 1H), 8.43 (d, 1H), 8.11 (d, 1H), 7.89 (m, 1H), 7.69 (d, 1H), 7.66 (t, 1H), 7.44 (d, 2H), 7.07 (d, 2H), 6.74 (dd, 1H), 6.51 (m, 1H), 6.48 (d, 1H), 3.96 (m, 1H), 3.90-3.70 (m, 4H), 3.59 (dt, 1H), 3.43 (d, 1H), 3.17 (q, 2H), 3.05 (m, 4H), 2.95 (dt, 1H), 2.81 (dd, 1H), 2.76 (s, 2H), 2.72 (s, 3H), 2.25 (m, 2H), 2.13 (m, 4H), 1.97 (s, 2H), 1.39 (t, 2H), 1.03 (t, 3H), 0.93 (s, 6H).

Example 337

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide

Example 337A methyl 4,4-dimethyl-2-(trifluoromethyl sulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried (Na$_2$SO$_4$), filtered, and concentrated to give the product.

Example 337B methyl 2-(4-chlorophenyl)-4,4-dimethylcyclohex-1-enecarboxylate EXAMPLE 337A (62.15 g), 4-chlorophenylboronic acid (32.24 g), CsF (64 g) and tetrakis(triphenylphosphine)palladium(0) (2 g) in 2:1 dimethoxyethane/methanol (600 mL)

Example 337C (2-(4-chlorophenyl)-4,4-dimethylcyclohex-1-enyl)methanol

To a mixture of LiBH$_4$ (13 g), EXAMPLE 337B (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried (Na$_2$SO$_4$), filtered, and concentrated. The crude product was chromatographed on silica gel with 0-30% ethyl acetate/hexanes.

Example 337D tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 337C (29.3 g) and triethylamine (30 mL) in CH$_2$Cl$_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The crude product was chromatographed on silica gel with 10-20% ethyl acetate/hexanes.

Example 337E 1-((2-(4-chlorophenyl)-4,4-dimethylcyclohex-1-enyl)methyl)piperazine EXAMPLE 337D (1 g) was stirred in dichloromethane (10 mL), trifluoroacetic acid (10 mL), and triethylsilane (1 mL) for 1 hour. The mixture was concentrated, taken up in a mixture of dichloromethane (100 mL) and saturated aqueous Na$_2$CO$_3$ solution (20 mL) and stirred for 10 minutes. The layers were separated, and the organic layer was dried over Na$_2$SO$_4$, and concentrated to give the product.

Example 337F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried (Na$_2$SO$_4$), filtered, and concentrated. The crude product was chromatographed on silica gel with 10% ethyl acetate/hexanes.

Example 337G 1-(triisopropylsilyl)-1H-pyrrolo[2,3-b]pyridin-5-ol

To a mixture of EXAMPLE 337F (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M aqueous NaOH (69 mL) was added, followed by 30% aqueous H$_2$O$_2$ (8.43 mL), and the solution was stirred for 1 hour. Na$_2$S$_2$O$_3$ (10 g) was added, and the pH was adjusted to 4-5 with concentrated HCl and solid NaH$_2$PO$_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes.

Example 337H methyl 2-(1H-pyrrolo[2,3-b]pyridin-5-yloxy)-4-fluorobenzoate

A mixture of EXAMPLE 337G (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 337I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 337H (1.55 g), EXAMPLE 337E (2.42 g), and HK$_2$PO$_4$ (1.42 g) in dimethylsulfoxide (20 mL) at 135° C. was stirred for 24 hours. The reaction was cooled, diluted with ether (400 mL), and washed three times with 1M aqueous NaOH, and brine, and concentrated. The crude product was chromatographed on silica gel with 10-50% ethyl acetate/hexanes.

Example 337J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 337I (200 mg) in dioxane (10 mL) and 1M aqueous NaOH (6 mL) at 50° C. was stirred for 24 hours. The reaction was cooled, added to NaH$_2$PO$_4$ solution, and extracted three times with ethyl acetate. The combined extracts were washed with brine, and concentrated to give the pure product.

Example 337K tert-butyl (4-hydroxy-4-methylcyclohexyl)methylcarbamate

To a vigorous stirring solution of tert-butyl (4-oxocyclohexyl)methylcarbamate (1.7 g) in tetrahydrofuran (40 mL) at −78° C. was dropwise added 1.6 M methyllithium (14.02 mL) in ether. After completion of the addition, the mixture was stirred at −78° C. for 1.2 hours and poured into a cold NH$_4$Cl aqueous solution. The resulting mixture was extracted with dichloromethane (100 ml, three times) and the organic layer was dried over Na$_2$SO$_4$, filtered, and concentrated. The resiwere heated to 70° C. for 24 hours. The mixture was concentrated. Ether (4×200 mL) was added and the mixture was filtered. The combined ether solution was concentrated to give the product.

Example 337L 4-(aminomethyl)-1-methylcyclohexanol

EXAMPLE 337K (1.3 g) in dichloromethane (5 mL) at 0° C. was treated with trifluoroacetic acid (2.1 mL) and a few drops of water for 1 hour. The reaction mixture was concentrated and the residue was directly used for next step.

Example 337M 4-((trans-4-hydroxy-4-methylcyclohexyl)methylamino)-3-nitrobenzenesulfonamide EXAMPLE 337L (732 mg) and 4-fluoro-3-nitrobenzenesulfonamide (1.1 g) in tetrahydrofuran (15 mL) was treated with triethylamine overnight. The reaction mixture, was concentrated and the residue was purified by a reverse phase chromatography, eluting with 30%-50% acetonitrile in 0.1% trifluoroacetic acid water solution to isolate the title compound.

Example 337N 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide A mixture of EXAMPLE 337J (3.0 g), EXAMPLE 337M (1.98 g), N,N-dimethylpyridin-4-amine (1.93 g) and $N^1$-((ethylimino)methylene)-$N^3$,$N^3$-dimethylpropane-1,3-diamine hydrochloride (1.31 g) in dichloromethane (50 ml) was stirred overnight and concentrated. The residue was purified by reverse chromatography, eluted with 40%-70% acetonitrile in 0.1% TFA water. The desired fractions were concentrated to remove acetonitrile, neutralized with $NaHCO_3$ and extracted with dichloromethane. The organic layer was dried over $Na_2SO_4$, concentrated and dried to provide the title compound. $^1H$ NMR (400 MHz, dimethylsulfoxide-$d_6$) δ 11.68 (s, 1 H), 8.52-8.58 (m, 2 H), 8.04 (d, 1 H), 7.79 (dd, 1 H), 7.53 (d, 1 H), 7.47-7.52 (m, 2 H), 7.30-7.37 (m, 2 H), 7.07 (d, 1 H), 7.01-7.06 (m, 2 H), 6.68 (dd, 1 H), 6.39 (dd, 1 H), 6.19 (d, 1 H), 4.25 (s, 1 H), 3.25-3.32 (m, 4 H), 3.07 (s, 4 H), 2.75 (s, 2 H), 2.09-2.24 (m, 6 H), 1.95 (s, 2 H), 1.50-1.73 (m, 5 H), 1.28-1.43 (m, 4 H), 1.06-1.18 (m, 5 H), 0.92 (s, 6 H).

Example 338

4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide

Example 338A methyl 4,4-dimethyl-2-(trifluoromethylsulfonyloxy)cyclohex-1-enecarboxylate To a suspension of hexane washed NaH (17 g) in dichloromethane (700 ml,) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried ($Na_2SO_4$), filtered, and concentrated to give the product.

Example 338B methyl 2-(4-chlorophenyl)-4,4-dimethylcyclohex-1-enecarboxylate EXAMPLE 338A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product.

Example 338C (2-(4-chlorophenyl)-4,4-dimethylcyclohex-1-enyl)methanol

To a mixture of $LiBH_4$ (13 g), EXAMPLE 338B (53.8 g) and ether (400 mL), was added methanol (25 mL) slowly by syringe. The mixture was stirred at room temperature for 24 hours. The reaction was quenched with 1N aqueous HCl with ice-cooling. The mixture was diluted with water and extracted with ether (3×100 mL). The extracts were dried ($Na_2SO_4$), filtered, and concentrated. The crude product was chromatographed on silica gel with 0-30% ethyl acetate/hexanes.

Example 338D tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 338C (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Example 338E 1-((2-(4-chlorophenyl)-4,4-dimethylcyclohex-1-enyl)methyl)piperazine EXAMPLE 338D (1 g) was stirred in dichloromethane (10 mL), trifluoroacetic acid (10 mL), and triethylsilane (1 mL) for 1 hour. The mixture was concentrated, taken up in a mixture of dichloromethane (100 mL) and saturated aqueous $Na_2CO_3$ solution (20 mL) and stirred for 10 minutes. The layers were separated, and the organic layer was dried over $Na_2SO_4$, filtered, and concentrated to give the product.

Example 338F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Example 338G 1-(triisopropylsilyl)-1H-pyrrolo[2,3-b]pyridin-5-ol

To a mixture of EXAMPLE 338F (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M aqueous NaOH (69 mL) was added, followed by 30% aqueous $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Example 338H methyl 2-(1H-pyrrolo[2,3-b]pyridin-5-yloxy)-4-fluorobenzoate

A mixture of EXAMPLE 338G (8.5 g), methyl 2,4-difluorobenzoate (7.05 g), and $K_3PO_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 338I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of EXAMPLE 338H (1.55 g), EXAMPLE 338E (2.42 g), and $HK_2PO_4$ (1.42 g) in dimethylsulfoxide (20 mL) at 135° C. was stirred for 24 hours. The reaction was cooled, diluted with ether (400 mL), and washed three times with 1M aqueous NaOH, and brine, and concentrated. The crude product was chromatographed on silica gel with 10-50% ethyl acetate/hexanes.

Example 338J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid EXAMPLE 338I (200 mg) in dioxane (10 mL) and 1M NaOH (6 mL) at 50° C. was stirred for 24 hours. The reaction was cooled, added to $NaH_2PO_4$ solution, and extracted three times with ethyl acetate. The combined extracts were washed with brine, and concentrated to give the pure product.

Example 338K tert-butyl (4-hydroxy-4-methylcyclohexyl)methylcarbamate

To a vigorous stirring solution of tert-butyl (4-oxocyclohexyl)methylcarbamate (1.7 g) in tetrahydrofuran (40 mL) at −78° C. was dropwise added 1.6 M methyllithium (14.02 mL) in ether. After completion of the addition, the mixture was stirred at −78° C. for 1.2 hours and poured into a cold $NH_4Cl$ aqueous solution. The resulting mixture was extracted with dichloromethane (100 ml, three times) and the organic layer was dried over $Na_2SO_4$, filtered, and concentrated. The residue was dissolved in dichloromethane and loaded onto an Analogix purification system, and it was eluted with 0-50% ethyl acetate in dichloromethane to provide the title compound.

Example 338L 4-(aminomethyl)-1-methylcyclohexanol

EXAMPLE 338K (1.3 g) in dichloromethane (5 mL) at 0° C. was treated with trifluoroacetic acid (2.1 mL) and a few drops of water for 1 hour. The reaction mixture was concentrated and the residue was directly used for next step.

Example 338M 4-((cis-4-hydroxy-4-methylcyclohexyl)methylamino)-3-nitrobenzenesulfonamide EXAMPLE 338L (732 mg) and 4-fluoro-3-nitrobenzenesulfonamide (1.1 g) in tetrahydrofuran (15 mL) was treated with triethylamine overnight. The reaction mixture, was concentrated and the residue was purified by a reverse phase chromatography, eluting with 30%-50% acetonitrile in 0.1% trifluoroacetic acid water solution to isolate the title compound.

Example 338N 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide A mixture of EXAMPLE 338J (144 mg), EXAMPLE 338M (95 mg), N,N-dimethylpyridin-4-amine (123 mg) and $N^1$-((ethylimino)methylene)-$N^3$,$N^3$-dimethylpropane-1,3-diamine hydrochloride (62.7 mg) in dichloromethane (7 ml) was stirred overnight and concentrated. The residue was purified by reverse chromatography, eluted with 40%-70% acetonitrile in 0.1% TFA water. The desired fractions were concentrated, neutralized with $NaHCO_3$ and extracted with dichloromethane. The organic layer was dried over $Na_2SO_4$, filtered, concentrated and dried to provide the title compound. $^1$H NMR (400 MHz, dimethylsulfoxide-$d_6$) δ 11.69 (s, 1 H), 11.38 (s, 1 H), 8.59 (t, 1 H), 8.55 (d, 1 H), 8.04 (d, 1 H), 7.79 (dd, 1 H), 7.54 (d, 1 H), 7.46-7.52 (m, 2 H), 7.30-7.38 (m, 2 H), 7.00-7.10 (m, 3 H), 6.68 (dd, 1 H), 6.39 (dd, 1 H), 6.19 (d, 1 H), 3.95 (s, 1 H), 3.25 (t, 4 H), 3.07 (s, 4 H), 2.75 (s, 2 H), 2.10-2.26 (m, 6 H), 1.95 (s, 2 H), 1.29-1.62 (m, 8 H), 1.16-1.30 (m, 2 H), 1.08 (s, 3 H), 0.92 (s, 6 H).

Example 339

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 339A (1R,4S)-methyl spiro[bicyclo[2.2.1]heptane-2,2'-[1,3]dioxolane]-5-carboxylate A reaction mixture of 1,4-dioxaspiro[4.4]non-6-ene (5 g), methyl acrylate (10.24 g), and hydroquinone (0.13 g) was heated at 100° C. in acetonitrile (12 mL) for three days. After cooling, the solvent was removed, and residue was purified by flash chromatography on silica gel eluting with 4:1 hexane/ethyl acetate to provide the title compound as a mixture of two isomers.

Example 339B (1R,4S)-spiro[bicyclo[2.2.1]heptane-2,2'-[1,3]dioxolane]-5-ylmethanol EXAMPLE 339A (1.0 g) in tetrahydrofuran was cooled to 0° C. To this solution was added 1.0 N lithium aluminum hydride (2.8 mL) dropwise. The reaction mixture was stirred for 2 hours. Water (0.4 mL) was added followed by 2 N aqueous NaOH (0.2 mL). The solid was filtered off, and the filtrate was concentrated. Toluene was added, and it was then distilled to remove any trace amount of water. The title compound was used for the next reaction without further purification.

Example 339C 5-chloro-6-(((1S,2R,4R)-5-oxobicyclo[2.2.1]heptan-2-yl)methoxy)pyridine-3-sulfonamide The title compound was prepared by substituting EXAMPLE 339B for (tetrahydro-2H-pyran-4-yl)methanol and EXAMPLE 40A for EXAMPLE 36A in EXAMPLE 36B. The two stereoisomers at the 5 position were isolated by reverse phase Gilson Prep HPLC system with a Phenomenex prep column (Luna, 5µ, C18(2), 250×21.20 mm, 5 Å) eluting with 20-80% acetonitrile in water with 0.1% trifluoroacetic acid. The desired fractions were collected, and the solvents were removed under reduced vacuum at 60° C. During this process, a lot of solid formed. It was then partitioned between water and ethyl acetate. The organic layer was separated, and the aqueous layer was extracted with additional ethyl acetate. The combined organic layers were washed with brine, dried over MgSO$_4$, filtered and concentrated to give the title compound.

Example 339D 5-chloro-6-(((1S,2R,4R,5R)-5-hydroxy-5-methylbicyclo[2.2.1]heptan-2-yl)methoxy)pyridine-3-sulfonamide EXAMPLE 339C (0.44 g) in tetrahydrofuran (15 mL) was treated with 3.0 M methylmagnesium bromide (5.3 mL) at 0° C. The solution was stirred for 16 hours. The reaction mixture was then partitioned between ethyl acetate and 0.05 N aqueous HCl (20 mL). The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Example 339E

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 339D for EXAMPLE 11B in EXAMPLE 11D. $^1$H NMR (500 MHz, dimethylsulfoxide-d$_6$) δ 11.66 (s, 1H), 8.50 (s, 1H), 8.16 (s, 1H), 8.02 (d, 1H), 7.49-7.55 (m, 3H), 7.35 (d, 2H), 7.05 (d, 2H), 6.67 (dd, 1H), 6.38 (dd, 1H), 6.20 (s, 1H), 4.40-4.48 (m, 2H), 4.31 (s, 1H), 3.09 (s, 4H), 2.83 (s, 2H), 2.15-2.33 (m, 7H), 1.96 (s, 2H), 1.87 (d, 1H), 1.65-1.69 (m, 1H), 1.54-1.56 (m, 2H), 1.36-1.47 (m, 6H), 1.26-1.30 (m, 1H), 1.19 (s, 3H), 0.93 (s, 6H).

Example 340

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide Example 340A 4-(1,4-dioxaspiro[4.5]decan-8-ylamino)-3-nitrobenzenesulfonamide To a solution of 4-fluoro-3-nitrobenzenesulfonamide (1.4 g) in tetrahydrofuran (30 mL) was added 1,4-dioxaspiro[4.5]decan-8-amine (1.0 g) and diisopropylethylamine (5 mL). The mixture was stirred overnight. The mixture was diluted with ethyl acetate (300 mL) and washed with water, brine and dried over Na$_2$SO$_4$. Filtration and evaporation of the solvent gave the title compound.

Example 340B

N-(4-(1,4-dioxaspiro[4.5]decan-8-ylamino)-3-nitrophenylsulfonyl)-2-(1H-pyrrolo[2,3-b]pyridin-5-yloxy)-4-(4-((2-(4-chlorophenyl)-4,4-dimethylcyclohex-1-enyl)methyl)piperazin-1-yl)benzamide To a solution of EXAMPLE 3J (617 mg) and EXAMPLE 340A (386 mg) in dichloromethane (10 mL) was added 1-ethyl-3-[3-(dimethylamino)propyl]-carbodiimide hydrochloride (288 mg) and 4-(dimethylamino)pyridine (183 mg). The mixture was stirred overnight. The mixture was diluted with dichloromethane (300 mL) and washed with aqueous

Example 340C 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(4-oxocyclohexylamino)phenylsulfonyl)benzamide To a solution of EXAMPLE 340B (386 mg) in acetone (10 mL) and water (5 mL) was added para-toluenesulfonic acid monohydrate (50 mg). The mixture was stirred at 120° C. in a Biotage Initiator microwave reactor for 30 minutes. The mixture was diluted with dichloromethane (300 mL) and washed with aqueous $NaHCO_3$, water, brine and dried over $Na_2SO_4$. Filtration and evaporation of the solvent gave the title compound.

Example 340D 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide To a solution of EXAMPLE 340C (240 mg) and 3-(cyclopropylamino)propanenitrile (62 mg) in tetrahydrofuran (10 mL) was added acetic acid (2 mL) and MP-cyanoborohydride (300 mg, 2.15 mmol/g). The mixture was stirred overnight. The mixture was filtered and concentrated under vacuum and the residue was dissolved in dimethylsulfoxide/methanol (1:1, 10 mL) and loaded on Gilson, C18 (100A) 250×121.2 mm (10 micron), with 30% acetonitrile to 65% acetonitrile over 40 minutes. $^1$H NMR (300 MHz, dimethylsulfoxide-$d_6$) δ 11.66 (s, 1 H), 8.55 (dd, 1 H), 8.17 (d, 1 H), 8.03 (d, 1 H), 7.79 (d, 1 H), 7.49 (m, 3 H), 7.34 (d, 2 H), 7.11 (m, 1 H), 7.04 (d, 2 H), 6.67 (dd, 1 H), 6.38 (d, 1 H), 6.19 (d, 1 H), 4.01 (m, 1 H), 3.56 (m, 1 H), 3.06 (m, 4 H), 2.88 (t, 2 H), 2.65 (m, 6 H), 2.19 (m, 6 H), 2.00 (m, 7 H), 1.51 (m, 6 H), 0.92 (s, 6 H), 0.42 (m, 4 H).

Example 341

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide

Example 341A ethyl 1,4-dioxaspiro[4.5]decane-8-carboxylate

To a solution of ethyl 4-oxocyclohexanecarboxylate (31.8 g) in toluene (100 mL) was added ethylene glycol (36.5 mL) and p-toluenesulfonic acid monohydrate (0.426 g). The two phase mixture was stirred rapidly at ambient temperature for 72 hours. The reaction was diluted with water (900 mL) and extracted with ether (900 mL). The organic layer was washed with saturated sodium bicarbonate solution and brine, and then dried over anhydrous sodium sulfate. After filtration, the title compound was obtained by concentration under high vacuum.

Example 341B 1,4-dioxaspiro[4.5]decan-8-ylmethanol

To a suspension of lithium aluminum hydride (8.19 g) in tetrahydrofuran (400 mL) was added dropwise a solution of EXAMPLE 341A (37.8 g) in tetrahydrofuran (75 mL). The mixture was then heated at reflux for 2 hours. The reaction mixture was cooled in an ice bath and quenched very slowly with water (8 mL). Then added sequentially were 4N sodium hydroxide (8 mL), ether (200 mL), water (24 mL), ether (500 mL) and anhydrous sodium sulfate (250 g). The resulting mixture was stirred rapidly for 2 hours and was filtered. The title compound was isolated by concentration of the filtrate.

Example 341C 8-(benzyloxymethyl)-1,4-dioxaspiro[4.5]decane

To a suspension of sodium hydride (60% oil dispersion, 8.86 g) in tetrahydrofuran (170 mL) was added a solution of EXAMPLE 341B (30.52 g) in tetrahydrofuran (100 mL). This mixture was stirred for 30 minutes and benzyl bromide (24 mL) was added. After stirring for 72 hours, the reaction was quenched with saturated ammonium chloride solution (400 mL) and diluted with ether (500 mL). The layers were separated and the aqueous layer was extracted with ether (2×150 mL). The combined organics were dried over sodium sulfate, filtered and concentrated. The crude product was purified on silica gel eluting with a 0, 10, 15, 75% ethyl acetate in hexanes step gradient to provide the title compound.

Example 341D 4-(benzyloxymethyl)cyclohexanone

To a solution of EXAMPLE 341C (43.02 g) in dioxane (500 mL) was added water (125 mL) and 2M hydrochloric acid (90 mL). The mixture was heated at 85° C. for 18 hours. Upon cooling, the reaction mixture was diluted with brine (1500 ml), saturated sodium bicarbonate solution (300 mL) and ether (1000 mL). The organic layer was dried over sodium sulfate, filtered and concentrated. The crude product was purified on silica gel eluting with a 5-50% ethyl acetate in hexanes step gradient to provide the title compound.

Example 341E trans-4-(benzyloxymethyl)-1-methylcyclohexanol

To 2,6-di-t-butyl-4-methylphenol (83.4 g) in toluene (1100 mL) was added 2.0M (in hexanes) trimethylaluminum (95 mL) somewhat carefully to control methane evolution and a small exotherm. The reaction mixture was stirred at ambient temperature under $N_2$ for 75 minutes and was then cooled to −77° C. A solution of EXAMPLE 341D (14 g) in toluene (15 mL) was added dropwise, keeping the temperature below −74° C. Methyllithium (1.6M in diethyl ether, 120 mL) was then added dropwise, keeping the temperature below −65° C. The resulting mixture was stirred at −77° C. under $N_2$ for 2 hours. The reaction mixture was then poured into 1N aqueous HCl (1600 mL), rinsing the flask with toluene. The organic layer was washed with brine and the combined aqueous layers were extracted with diethyl ether. The combined organic layers were dried ($Na_2SO_4$), filtered and concentrated. The concentrate was chromatographed on 650 g of spherical silica gel using 2.5 L of 80/20 hexanes/ethyl acetate, then 3.0 L of 75/25 hexanes/ethyl acetate, and finally 4.0 L of 70/30 hexanes/ethyl acetate as the eluents to provide the title compound.

Example 341F

Trans-4-(hydroxymethyl)-1-methylcyclohexanol

EXAMPLE 341E (12.6 g) and ethanol (120 ml) were added to 20% Pd(OH)$_2$/C, wet (1.260 g) in a 500 mL SS pressure bottle. The reaction mixture was stirred at ambient temperature under 30 psi hydrogen gas. Hydrogen uptake ceased at 5 minutes. The mixture was filtered through a nylon membrane rinsing with ethanol. The filtrate was concentrated and then azeotroped with toluene (100 mL) to remove any remaining ethanol. The concentrate was dried under high vacuum for 40 minutes to provide the title compound.

Example 341G 5-chloro-6-((trans-4-hydroxy-4-methylcyclohexyl)methoxy)pyridine-3-sulfonamide The title compound was prepared by substituting EXAMPLE 40A for 4-fluoro-3-nitrobenzenesulfonamide and EXAMPLE 341F for (tetrahydro-2H-pyran-4-yl)methanol in EXAMPLE 24A.

Example 341H

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide The title compound was prepared by substituting EXAMPLE 328E for EXAMPLE 3J and EXAMPLE 341G for EXAMPLE 11B in EXAMPLE 11D. $^1$H NMR (500 MHz, pyridine-d$_5$) δ 13.09 (s, 1H), 9.18 (d, 1H), 8.74 (d, 1H), 8.41 (d, 1H), 8.09 (d, 1H), 7.67 (m, 2H), 7.42 (m, 2H), 7.09 (m, 2H), 6.74 (dd, 1H), 6.52 (dd, 1H), 6.49 (d, 1H), 4.29 (d, 2H), 3.05 (m, 4H), 2.80 (s, 2H), 2.37 (t, 2H), 2.15 (m, 4H), 2.11 (s, 2H), 1.89 (m, 6H), 1.75 (m, 2H), 1.45 (t, 2H), 1.41 (s, 3H), 1.32 (m, 2H), 0.37 (m, 4H).

Example 342

4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide

Example 342A methyl 5,6,7,8-tetrahydroimidazo[1,2-a]pyridine-6-carboxylate

To a 50 ml pressure bottle were placed methyl imidazo[1,2-a]pyridine-6-carboxylate (0.26 g), acetic acid (10 ml), and wet 5% palladium on carbon (0.052 g). The reaction mixture was stirred for 16 hours at 30 psi and 50° C. The solid was filtered off, and the filtrate was concentrated. The residue was taken up in ethyl acetate. It was then washed with saturated sodium bicarbonate, brine, dried over MgSO$_4$, filtered, and concentrated. The residue was purified by flash column chromatography on silica gel using 10-100% ethyl acetate in hexanes to provide the title compound.

Example 342B (5,6,7,8-tetrahydroimidazo[1,2-a]pyridin-6-yl)methanol

The title compound was prepared by substituting EXAMPLE 342A for EXAMPLE 339A in EXAMPLE 339B.

Example 342C 5-chloro-6-((5,6,7,8-tetrahydroimidazo[1,2-a]pyridin-6-yl)methoxy)pyridine-3-sulfonamide The title compound was prepared by substituting EXAMPLE 342B for (tetrahydro-2H-pyran-4-yl)methanol and EXAMPLE 40A for EXAMPLE 36A in EXAMPLE 36B.

Example 342D 4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide The title compound was prepared by substituting EXAMPLE 342C for EXAMPLE 11B in EXAMPLE 11D. $^1$H NMR (500 MHz, dimethylsulfoxide-d$_6$) δ 11.54 (s, 1H), 8.36 (s, 1H), 8.06 (s, 1H), 7.93 (s, 1H), 7.58 (d, 1H), 7.41-7.44 (m, 2H), 7.2-7.36 (m, 4H), 7.05 (d, 2H), 6.63 (dd, 1H), 6.32 (dd, 1H), 6.24 (d, 1H), 4.42-4.51 (m, 1H), 4.37-4.40 (m, 1H), 4.29 (dd, 1H), 3.91 (dd, 1H), 3.03 (s, 4H), 2.90-2.95 (m, 2H), 2.77 (s, 2H), 2.51-2.52 (m, 1H), 2.07-2.23 (m, 7H), 1.96 (s, 2H), 1.76-1.82 (m, 1H), 1.65-1.69 (m, 2H), 1.54-1.56 (m, 2H), 1.39 (t, 2H), 0.93 (s, 6H).

Example 343

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 343A 5-chloro-6-(((1S,2S,4R)-5-oxobicyclo[2.2.1]heptan-2-yl)methoxy)pyridine-3-sulfonamide The title compound was isolated as another isomer in EXAMPLE 339C.

Example 343B 5-chloro-6-(((1S,2S,4R,5R)-5-hydroxy-5-methylbicyclo[2.2.1]heptan-2-yl)methoxy)pyridine-3-sulfonamide The title compound was prepared by substituting EXAMPLE 343A for EXAMPLE 339B in EXAMPLE 339C.

Example 343C

N-[(5-chloro-6-{[(1R,2S,4R,5R)-5-hydroxy-5-methylbicyclo[2.2.1]hept-2-yl]methoxy}pyridin-3-yl) sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 343B for EXAMPLE 11B in EXAMPLE 11D. $^1$H NMR (500 MHz, dimethylsulfoxide-$d_6$) δ 11.67 (s, 1H), 8.51 (s, 1H), 8.17 (s, 1H), 8.03 (s, 1H), 7.49-7.55 (m, 3H), 7.35 (d, 2H), 7.05 (d, 2H), 6.67 (dd, 1H), 6.39 (dd, 1H), 6.20 (d, 1H), 4.27 (s, 1H), 4.11-4.19 (m, 2H), 3.11 (s, 4H), 2.87 (s, 2H), 1.96-2.23 (m, 10H), 1.88 (d, 1H), 1.50 (dd, 1H), 1.33-1.44 (m, 2H), 1.13-1.19 (m, 4H), 0.88-0.93 (m, 8H).

Example 344

4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide

Example 344A 4-((cis-4-hydroxy-4-methylcyclohexyl)methoxy)-3-nitrobenzenesulfonamide EXAMPLE 347A (732 mg) and 4-fluoro-3-nitrobenzenesulfonamide (1.2 g) in tetrahydrofuran (40 mL) were treated with 60% sodium hydride (1.6 g) for 3 days. The reaction was quenched with water. The resulting mixture was neutralized with diluted aqueous HCl, and extracted with ethyl acetate. The organic layer was dried over $Na_2SO_4$, filtered, and concentrated. The residue was purified by a reverse phase chromatography, eluting with 30-50% $CH_3CN$ in 0.1% trifluoroacetic acid water to provide the title compound as a single enantiomer.

Example 344B 4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide The title compound was prepared by substituting EXAMPLE 344A for EXAMPLE 1F and EXAMPLE 3J for EXAMPLE 1E in EXAMPLE 1G. $^1$H NMR (400 MHz, dimethylsulfoxide-$d_6$) δ 11.69 (s, 1H), 8.34 (d, 1H), 8.04 (m, 2H), 7.52 (m, 3H), 7.40 (d, 1H), 7.35 (d, 2H), 7.04 (d, 2H), 6.68 (dd, 1H), 6.40 (m, 1H), 6.20 (d, 1H), 4.02 (d, 2H), 3.96 (s, 1H), 3.10 (br s, 4H), 2.85 (m, 2H), 2.29 (m, 3H), 2.15 (t, 2H), 1.96 (br s, 2H), 1.68 (m, 1H), 1.55 (m, 4H), 1.42 (m, 4H), 1.27 (m, 2H), 1.10 (s, 3H), 0.92 (s, 6H).

Example 345

N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide The title compound was prepared by substituting EXAMPLE 328E for EXAMPLE 3J and EXAMPLE 277O for EXAMPLE 11B in EXAMPLE 11D. $^1$H NMR (500 MHz, pyridine-$d_5$) δ 13.07 (s, 1H), 9.13 (d, 1H), 8.41 (d, 1H), 8.09 (d, 1H), 7.68 (t, 1H), 7.66 (d, 1H), 7.42 (m, 2H), 7.09 (m, 2H), 6.75 (dd, 1H), 6.51 (m, 2H), 4.64 (d, 4H), 4.53 (d, 2H), 3.39 (m, 1H), 3.06 (m, 4H), 2.81 (s, 2H), 2.51 (m, 2H), 2.37 (m, 2H), 2.12 (m, 10H), 1.90 (m, 2H), 1.45 (t, 2H), 0.38 (s, 4H).

Example 346

4-(4-{[2-(4-chlorophenyl)-4,4-dimethylcyclohex-1-en-1-yl]methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide The title compound was prepared by substituting 3,3-difluoropyrrolidine hydrochloride for 3-(cyclopropylamino)propanenitrile in EXAMPLE 340D. $^1$H NMR (300 MHz, dimethylsulfoxide-$d_6$) δ 11.68 (s, 1 H), 11.38 (m, 1 H), 8.55 (m, 1 H), 8.36 (d, 1 H), 8.03 (d, 1 H), 7.80 (m, 1 H), 7.50 (m, 3 H), 7.34 (d, 2 H), 7.13 (d, 1 H), 7.04 (d, 2 H), 6.83 (m, 1 H), 6.68 (m, 1 H), 6.38 (d, 1 H), 6.19 (s, 1 H), 4.02 (s, 1 H), 3.83 (m, 1 H), 3.06 (m, 4 H), 2.96 (m, 2 H), 2.73 (m, 4 H), 2.26 (m, 8 H), 1.97 (m, 4 H), 1.68 (m, 4 H), 1.37 (m, 2 H), 0.92 (s, 6 H).

Example 347

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide

Example 347A 4-(hydroxymethyl)-1-methylcyclohexanol 4-(Hydroxymethyl)cyclohexanone (800 mg) in tetrahydrofuran (15 mL) was treated with 3 M methylmagnesium chloride in tetrahydrofuran (6.24 mL) at 0° C. The reaction was warmed to room temperature over 2 hours and quenched with methanol and water. The resulting mixture was concentrated and the residue was suspended in ethyl acetate. The precipitates were filtered off and the filtrate was concentrated. The residue was purified by chromatography, eluting with 0-100% ethyl acetate in hexane to provide the title compound.

Example 347B 5-chloro-6-((trans-4-hydroxy-4-methylcyclohexyl)methoxy)pyridine-3-sulfonamide EXAMPLE 347A (970 mg) and EXAMPLE 40A (1.6 g) in N,N-dimethylformamide (8 mL) were treated with sodium hydride (1.8 g, 60%) at room temperature for 2 days. The reaction was quenched with water. The resulting mixture was neutralized with diluted aqueous HCl, and extracted with ethyl acetate. The organic layer was dried over $Na_2SO_4$, filtered, and concentrated. The residue was purified by a reverse phase chromatography, eluting with 30-45% acetonitrile in 0.1% trifluoroacetic acid water to isolate the title compound.

Example 347C 5-chloro-6-((cis-4-hydroxy-4-methylcyclohexyl) methoxy)pyridine-3-sulfonamide The title compound was prepared and isolated as described in Example 347B.

Example 347D

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in EXAMPLE 11D using EXAMPLE 347B in place of EXAMPLE 11B. $^1$H NMR (400 MHz, dimethylsulfoxide-$d_6$) δ 11.67 (s, 1 H), 8.51 (d, 1 H), 8.18 (d, 1 H), 8.03 (d, 1 H), 7.48-7.56 (m, 3 H), 7.35 (d, 2 H), 7.05 (d, 2 H), 6.68 (dd, 1 H), 6.39 (dd, 1 H), 6.21 (d, 1 H), 4.17-4.34 (m, 3 H), 3.11 (s, 4 H), 2.89 (s, 2 H), 2.24-2.42 (m, 4 H), 2.15 (s, 2 H), 1.96 (s, 2 H), 1.66-1.82 (m, 3 H), 1.55 (d, 2 H), 1.31-1.44 (m, 4 H), 1.12-1.27 (m, 2 H), 1.10 (s, 3 H), 0.93 (s, 6 H).

Example 348

N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in EXAMPLE 11D using EXAMPLE 347C in place of EXAMPLE 11B. $^1$H NMR (400 MHz, dimethylsulfoxide-$d_6$) δ 11.67 (s, 1 H), 8.51 (d, 1 H), 8.18 (d, 1 H), 8.03 (d, 1 H), 7.47-7.58 (m, 3 H), 7.35 (d, 2 H), 7.05 (d, 2 H), 6.68 (dd, 1 H), 6.39 (dd, 1 H), 6.21 (d, 1 H), 4.21 (d, 2 H), 3.95 (s, 1 H), 3.11 (s, 4 H), 2.89 (s, 2 H), 2.33 (d, 4 H), 2.15 (s, 2 H), 1.96 (s, 2 H), 1.63-1.77 (m, 1 H), 1.48-1.60 (m, 4 H), 1.35-1.48 (m, 4 H), 1.20-1.33 (m, 2 H), 1.09 (s, 3 H), 0.93 (s, 6 H).

Example 349

4-(4-{[2-(4-chlorophenyl)-4,4-dimethylcyclohex-1-en-1-yl]methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide The title compound was prepared by substituting 2,2-difluorocyclopropanamine hydrochloride for 3-(cyclopropylamino)propanenitrile in EXAMPLE 340D. $^1$H NMR (300 MHz, dimethylsulfoxide-$d_6$) δ 11.60 (s, 1 H), 8.47 (m, 2 H), 8.12 (m, 1 H), 7.98 (m, 1 H), 7.72 (m, 2 H), 7.47 (m, 3 H), 7.34 (m, 3 H), 7.05 (m, 3 H), 6.65 (dd, 1 H), 6.35 (m, 1 H), 6.22 (d, 1 H), 3.54 (m, 2 H), 3.08 (m, 4 H), 2.74 (m, 4 H), 2.25 (m, 4 H), 2.01 (m, 4 H), 1.38 (m, 4 H), 0.92 (s, 6 H).

Example 350

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 350A ethyl spiro[benzo[d][1,3]dioxole-2,1'-cyclohexane]-4'-carboxylate To a solution of ethyl 4-oxocyclohexanecarboxylate (22.75 g) and pyrocatechol (14.75 g) in toluene (200 mL) was added catalytic amount of para-toluenesulfonic acid monohydrate and the mixture was stirred under reflux and a Dean-Stark trap overnight. The mixture was diluted with diethyl ether (600 mL) and washed with aqueous NaHCO$_3$, water and brine. After drying over Na$_2$SO$_4$, the mixture was filtered and the solvent was evaporated under vacuum to provide the title compound.

Example 350B ethyl 4'-fluorospiro[benzo[d][1,3]dioxole-2,1'-cyclohexane]-4'-carboxylate A solution of EXAMPLE 350A (5.25 g) in tetrahydrofuran (40 mL) was added dropwise to a solution of lithium diisopropylamide (12 mL, 2.0M in tetrahydrofuran/heptane/ethylbenzene) at 0° C. The solution was stirred at 0° C. for 30 minutes, and then was transferred by cannula to a pre-cooled (0° C.) stirring solution of N-fluorobenzenesulfonimide (7.89 g) in dry tetrahydrofuran (20 mL). The reaction mixture was stirred at 0° C. for 30 minutes, and then at 20° C. for 18 hours. The reaction mixture was poured over aqueous NH$_4$Cl and extracted with diethyl ether (3×200 mL). The combined organic layers were washed with water, brine and dried over Na$_2$SO$_4$. Filtration and evaporation of the solvent gave the crude product.

Example 350C (4'-fluorospiro[benzo[d][1,3]dioxole-2,1'-cyclohexane]-4'-yl)methanol To a solution of EXAMPLE 350B (23 g) in tetrahydrofuran (150 mL) was added lithium aluminum hydride (3.11 g). The mixture was stirred overnight. Aqueous 2N NaOH solution was added dropwise to the reaction mixture. The mixture was then diluted with ethyl acetate (600 mL) and washed with water, brine and dried over Na$_2$SO$_4$. Filtration and evaporation of the solvent gave the crude product which was loaded on a 600 g analogics column and eluted with 10% to 20% ethyl acetate in hexane to provide the title compound.

Example 350D 5-chloro-6-((4'-fluorospiro[benzo[d][1,3]dioxole-2,1'-cyclohexane]-4'-yl)methoxy)pyridine-3-sulfonamide To a solution of EXAMPLE 350C (89 mg) in N,N-dimethylformamide (3 mL) was added NaH (65% in mineral oil, 36 mg). The mixture was stirred for 30 minutes, and then 5,6-dichloropyridine-3-sulfonamide (85 mg) was added. The mixture was stirred overnight. The mixture was poured over aqueous NH$_4$Cl and extracted with ethyl acetate (100 mL). The combined organic layers were washed with water, brine and dried over Na$_2$SO$_4$. After filtration and evaporation of the solvent, the residue was loaded on a silica gel cartridge and eluted with 30% ethyl acetate in hexane to provide the title compound.

Example 350E 5-chloro-6-((1-fluoro-4-oxocyclohexyl)methoxy)pyridine-3-sulfonamide To a solution of EXAMPLE 350D (1.6 g) and pyridinium p-toluenesulfonate (1.2 g) in acetone (10 mL) was added water (2 mL) and the mixture was stirred under microwave irradiation at 100° C. for 10 minutes. The mixture was diluted with dichloromethane (300 mL) and washed with aqueous NaHCO$_3$, water, brine and dried over Na$_2$SO$_4$. Filtration and evaporation of the solvent gave the title compound.

Example 350F 5-chloro-6-((cis-1-fluoro-4-hydroxycyclohexyl) methoxy)pyridine-3-sulfonamide To a solution of EXAMPLE 350E (336 mg) in tetrahydrofuran (10 mL) was added NaBH$_4$ (75 mg). The mixture was stirred for 45 minutes. The mixture was diluted with ethyl acetate (300 mL) and washed with 2N aqueous NaOH, water, and brine. After drying over Na$_2$SO$_4$, the mixture was filtered and the solvent was evaporated to give the crude product.

Example 350G

N-({5-chloro-6-[(cis-1-fluoro-4-hydroxycyclohexyl) methoxy]pyridin-3-yl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 350F for EXAMPLE 1F in EXAMPLE 1G. $^1$H NMR (300 MHz, dimethylsulfoxide-d$_6$) δ 11.63 (s, 1 H), 8.48 (s, 1 H), 8.18 (s, 1 H), 8.01 (d, 1 H), 7.50 (m, 3 H), 7.35 (d, 2 H), 7.05 (d, 2 H), 6.67 (dd, 1 H), 6.37 (dd, 1 H), 6.21 (d, 1 H), 4.62 (d, 1 H), 4.47 (s, 1 H), 4.40 (s, 1 H), 3.46 (m, 1 H), 3.06 (m, 4 H), 2.88 (m, 1 H), 2.25 (m, 6 H), 1.99 (m, 4 H), 1.58 (m, 8 H), 0.93 (s, 6 H).

Example 351

4-(4-{[2-(4-chlorophenyl)-4,4-dimethylcyclohex-1-en-1-yl]methyl}piperazin-1-yl)-N-{[3-nitro-4-(2-oxaspiro[3.5]non-7-ylmethoxy)phenyl]sulfonyl}-2-(1H-pyrrolo[2,3-b]pyridin-5-yloxy)benzamide Example 351A diethyl 1,4-dioxaspiro[4.5]decane-8,8-dicarboxylate A 500 mL round-bottomed flask was charged with diisopropylamine (16 mL) and tetrahydrofuran (311 mL). The solution was cooled to −78° C. under N$_2$ and n-BuLi (2.5 M in hexanes, 44.8 mL)) was added. The reaction was stirred for 30 minutes at −78° C. and ethyl 1,4-dioxaspiro[4.5]decane-8-carboxylate (20 g) was added as a tetrahydrofuran solution (ca. 10 mL). The solution was stirred at −78° C. for 1 hour and ethyl chloroformate (9 mL) was added neat. After stirring at −78° C. for 10 minutes, the reaction was warmed to room temperature over 2 hours. The reaction was quenched with saturated aqueous NH$_4$Cl and was diluted with diethyl ether. The layers were separated, the aqueous layer was extracted with diethyl ether and the combined organics were dried (Na$_2$SO$_4$), filtered and concentrated by rotary evaporation. The residue was purified by regular phase flash column chromatography (Analogix, 0-65% hexanes/ethyl acetate).

Example 351B 1,4-dioxaspiro[4.5]decane-8,8-diyldimethanol

To a 1 L round-bottomed flask was added EXAMPLE 351A (26.6 g) and tetrahydrofuran (310 mL) to give a colorless solution. The solution was cooled to 0° C. and lithium aluminum hydride (2M in tetrahydrofuran, 62 mL) was added via syringe. The reaction was allowed to warm to room temperature and stirred overnight. The mixture was cooled back down to 0° C. and quenched slowly with 4.7 mL water, 4.7 mL 10% aqueous NaOH and 14 mL water. The mixture was allowed to stir until salts were formed and was then filtered through a Supelco 90 mm silica gel Buchner funnel. The filtrate was concentrated by rotary evaporation and the residue was purified by regular phase flash column chromatography (Analogix, 0-80% hexanes/ethyl acetate).

Example 351C 2,8,11-trioxa-dispiro[3.2.4]tridecane

1. To a 1 L round-bottomed flask was added EXAMPLE 351B (13 g) in tetrahydrofuran (321 mL). The solution was cooled to −78° C. under N$_2$ and n-BuLi (25.7 mL) was added dropwise via syringe. After addition was complete, the mixture stirred for 30 minutes and a tetrahydrofuran solution of 4-toluenesulfonyl chloride (12.25 g) was added via addition funnel. The reaction was allowed to stir overnight, and gradually warm to room temperature. The reaction mixture was cooled to −78° C. and n-BuLi (25.7 mL) was added. The mixture was warmed to room temperature and stirred for 3 hours. The reaction was quenched with sat aqueous NH$_4$Cl and diluted with diethyl ether. The layers were separated, the aqueous layers extracted with diethyl ether and the combined organics were dried (Na$_2$SO$_4$), filtered and concentrated by rotary evaporation. The residue was purified by regular phase flash column chromatography (Analogix, 0-20% acetone/hexanes).

Example 351D 2-oxaspiro[3.5]nonan-7-one

To a 500 mL round-bottomed flask was added EXAMPLE 351C (11 g) in 80% aqueous acetic acid (200 mL). The reaction was heated to 65° C. and stirred for about 4 hours. Most of the acetic acid and water were removed by rotary evaporation and the residue was purified by regular phase flash column chromatography (Analogix, 0-65% hexanes/ethyl acetate).

Example 351E 7-methylene-2-oxaspiro[3.5]nonane

To a 250 mL round-bottomed flask was added methyltriphenylphosphonium iodide (4.33 g) in tetrahydrofuran (35.7 mL) to give a suspension. The suspension was cooled to −15° C. n-BuLi (2.5 M in hexanes, 4.28 mL) was added dropwise and the mixture was stirred at −15° C. for 40 minutes and EXAMPLE 351D (1 g) was added as a tetrahydrofuran (ca. 5 mL) solution. The mixture was stirred at −15° C. for about 15 minutes and warmed to room temperature. After 1.5 hours, the reaction was complete and was quenched with saturated aqueous NH$_4$Cl and diluted with diethyl ether. The layers were separated and the aqueous layer was extracted (2×) with diethyl ether. The combined organics were washed with brine, dried (Na$_2$SO$_4$), filtered and concentrated by rotary evaporation. The residue was purified by regular phase chromatography (Analogix, 80 g Grace silica gel column, 0-50% hexanes/ethyl acetate).

Example 351F 2-oxaspiro[3.5]nonan-7-ylmethanol

To a 25 mL round-bottomed flask was added EXAMPLE 351E (568 mg) and EXAMPLE 351F tetrahydrofuran (4.11 mL) to give a colorless solution. 9-Borabicyclo[3.3.1]nonane (0.5 M in tetrahydrofuran, 24.7 mL) was added and the reaction was allowed to stir for 2 hours at room temperature. Ethanol (11 mL) was added followed by aqueous NaOH (5M, 4.11 mL) and then hydrogen peroxide (2.1 mL) was added. The reaction was heated at 50° C. for 2 hours. The mixture was concentrated by rotary evaporation, and diluted with water and ethyl acetate. The aqueous layer was extracted with ethyl acetate (3×) and the combined organics were dried ($Na_2SO_4$), filtered and concentrated by rotary evaporation. The residue was purified by regular phase flash column chromatography (Analogix, 80 g Grace, 0-70% hexanes/ethyl acetate).

Example 351G 4-(2-oxaspiro[3.5]nonan-7-ylmethoxy)-3-nitrobenzenesulfonamide

EXAMPLE 351G was prepared substituting EXAMPLE 351F for (tetrahydro-2H-pyran-4-yl)methanol in EXAMPLE 24A.

Example 351H 2-(1H-pyrrolo[2,3-b]pyridin-5-yloxy)-N-(4-(2-oxaspiro[3.5]nonan-7-ylmethoxy)-3-nitrophenylsulfonyl)-4-(4-((2-(4-chlorophenyl)-4,4-dimethylcyclohex-1-enyl)methyl)piperazin-1-yl)benzamide The title compound was prepared by substituting EXAMPLE 3J for EXAMPLE 1E and EXAMPLE 351G for EXAMPLE 1F in EXAMPLE 1G. $^1$H NMR (300 MHz, dimethylsulfoxide-$d_6$) δ 11.67 (s, 1 H) 8.34 (s, 1 H) 8.03 (d, 2 H) 7.45-7.57 (m, 3 H) 7.30-7.40 (m, 3 H) 7.04 (d, 2 H) 6.67 (dd, 1 H) 6.39 (dd, 1 H) 6.17-6.23 (m, 1 H) 4.29 (s, 2 H) 4.20 (s, 2 H) 4.00 (d, 2 H) 3.08 (s, 4 H) 2.73-2.90 (m, 2 H) 2.72 (s, 1 H) 2.01-2.32 (m, 6 H) 1.96 (s, 2 H) 1.64-1.78 (m, 4 H) 1.33-1.50 (m, 6 H) 0.96-1.15 (m, 2 H) 0.92 (s, 6 H).

Example 352

4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide

Example 352A 4-((trans-4-hydroxy-4-methylcyclohexyl)methoxy)-3-nitrobenzenesulfonamide The title compound was prepared by substituting EXAMPLE 341F for (tetrahydro-2H-pyran-4-yl)methanol in EXAMPLE 24A.

Example 352B 4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide The title compound was prepared by substituting EXAMPLE 352A for EXAMPLE 1F and EXAMPLE 3J for EXAMPLE 1E in EXAMPLE 1G. $^1$H NMR (400 MHz, dimethylsulfoxide-$d_6$) δ 11.66 (s, 1H), 8.31 (br s, 1H), 8.01 (m, 2H), 7.49 (m, 3H), 7.33 (m, 3H), 7.03 (m, 2H), 6.66 (dd, 1H), 6.37 (m, 1H), 6.19 (d, 1H), 4.27 (s, 1H), 4.05 (d, 2H), 3.40 (m, 2H), 3.17 (s, 1H), 3.07 (m, 3H), 2.79 (m, 1H), 2.24 (m, 3H), 2.14 (m, 2H), 1.94 (m, 2H), 1.71 (m, 3H), 1.52 (m, 2H), 1.38 (m, 4H), 1.22 (m, 2H), 1.09 (s, 3H), 0.91 (s, 6H).

Example 353

4-(4-{[2-(4-chlorophenyl)-5,5-bis(fluoromethyl)cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 353A 1,4-dioxaspiro[4.5]decane-8,8-diylbis(methylene)bis(4-methylbenzenesulfonate)

To a 500 mL round-bottomed flask was added EXAMPLE 351B (10 g) and dichloromethane (165 mL) to give a colorless solution. Triethylamine (24.1 mL) and toluene-2-sulfonyl chloride (19.8 g) were added followed by 4-dimethylaminopyridine (0.604 g). The reaction was refluxed overnight. Saturated aqueous $NH_4Cl$ was added followed by dilution with water and additional dichloromethane. The aqueous layer was extracted with dichloromethane (2×) and the combined organics were dried ($MgSO_4$), filtered and concentrated by rotary evaporation. The residue was purified by regular phase flash column chromatography (Analogix, 0-55% hexanes/ethyl acetate).

Example 353B 8,8-bis(fluoromethyl)-1,4-dioxaspiro[4.5]decane

To a 500 mL round-bottomed flask was added EXAMPLE 353A (20 g). tetra-n-Butylammonium fluoride (1M in tetrahydrofuran, 200 mL) was added and the resulting solution was refluxed for 6 days. The reaction was cooled, diluted with diethyl ether and washed with water (3×). The organics were dried ($Na_2SO_4$), filtered and concentrated by rotary evaporation. The residue was purified by regular phase flash column chromatography (Analogix, 0-30% hexanes/ethyl acetate).

Example 353C 4,4-bis(fluoromethyl)cyclohexanone

To a 250 mL round bottom flask was added EXAMPLE 353B (1.1 g) and 80% aqueous acetic acid (50 mL). The reaction was heated at 65° C. for 3 hours, cooled and concentrated by rotary evaporation to remove most of the acetic acid

Example 353D 2-chloro-5,5-bis(fluoromethyl)cyclohex-1-enecarbaldehyde

To a 100 mL pear flask was added N,N-dimethylformamide (498 µl) and dichloromethane (8.9 mL) to give a colorless solution. The solution was cooled to 0° C. and POCl$_3$ (550 µl) was added dropwise and then the mixture was warmed to room temperature for 30 minutes. In the meantime, to a 100 mL pear shaped flask was added EXAMPLE 353C (870 mg, 5.36 mmol) in dichloromethane (8941 µl) to give a colorless solution. The Vilsmeier reagent was then taken up in a syringe and added dropwise to the 4,4-bis(fluoromethyl)cyclohexanone (870 mg) solution at room temperature. The resulting solution was stirred overnight. The reaction was poured into saturated aqueous NaHCO$_3$ and ice, warmed to room temperature and extracted with dichloromethane (3×30 mL). The organics were combined, dried over MgSO$_4$, filtered and concentrated by rotary evaporation. The residue was purified by regular phase flash column chromatography (Analogix (0-60% hexanes/ethyl acetate).

Example 353E 2-(4-chlorophenyl)-5,5-bis(fluoromethyl)cyclohex-1-enecarbaldehyde To a 20 mL vial was added EXAMPLE 353D (460 mg), 4-chlorophenylboronic acid (414 mg), potassium carbonate (762 mg), tetrabutylammonium bromide (711 mg), palladium (II) acetate (14.85 mg) and water (2450 µl) to give a suspension which was degassed with N$_2$ for 2 minutes. The reaction was stirred at 45° C. overnight, cooled, and poured over a Supelco silica gel Buchner funnel, washing with ethyl acetate several times. The filtrate was concentrated by rotary evaporation and the residue was purified by regular phase flash column chromatography (Analogix, 0-60% hexanes/ethyl acetate).

Example 353F methyl 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)benzoate To a 20 mL vial was added EXAMPLE 353E (240 mg), EXAMPLE 15F (297 mg) and dichloromethane (4.2 mL). Sodium triacetoxyborohydride (268 mg) was added and the reaction was stirred overnight at room temperature. The reaction was loaded directly onto silica gel and purified by regular phase flash column chromatography (Analogix, 0-80% hexanes/ethyl acetate).

Example 353G 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)benzoic acid The title compound was prepared by substituting EXAMPLE 353F for EXAMPLE 15G in EXAMPLE 15H.

Example 353H 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)-N-(3-nitro-4-((tetrahydro-2H-pyran-4-yl)methylamino)phenylsulfonyl)benzamide EXAMPLE 353H was prepared by replacing EXAMPLE 3J with EXAMPLE 353G and EXAMPLE 11B with EXAMPLE 1F in EXAMPLE 11D. $^1$H NMR (300 MHz, dimethylsulfoxide-d$_6$) δ11.69 (s, 1 H) 11.44 (s, 1 H) 8.48-8.70 (m, 1 H) 8.05 (d, 2 H) 7.81 (dd, 1 H) 7.46-7.59 (m, 3 H) 7.35 (d, 2 H) 7.12 (d, 2 H) 6.68 (dd, 1 H) 6.40 (dd, 1 H) 6.16 (d, 1 H) 4.39-4.49 (m, 2 H) 4.23-4.35 (m, 2 H) 3.85 (dd, J=11.87, 2.71 Hz, 2 H) 3.20-3.30 (m, 4 H) 2.98-3.10 (m, 4 H) 2.66-2.77 (m, 2 H) 2.11-2.30 (m, 6 H) 2.02-2.12 (m, 3 H) 1.99 (s, 1 H) 1.82-1.97 (m, 1 H) 1.54-1.67 (m, 4 H) 1.20-1.34 (m, 2 H).

Example 354

4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide

Example 354A tert-butyl 2-((2-nitro-4-sulfamoylphenoxy)methyl)morpholine-4-carboxylate The title compound was prepared by substituting tert-butyl 2-(hydroxymethyl)-morpholine-4-carboxylate for tetrahydro-2H-pyran-4-yl-methanol EXAMPLE 24A.

Example 354B 4-(morpholin-2-ylmethoxy)-3-nitrobenzenesulfonamide

The title compound was prepared by substituting EXAMPLE 354A for EXAMPLE 113A in EXAMPLE 134A.

Example 354C 4-((4-cyclopropylmorpholin-2-yl)methoxy)-3-nitrobenzenesulfonamide The title compound was prepared by substituting EXAMPLE 354B for EXAMPLE 173A in EXAMPLE 173B.

Example 354D 4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide The title compound was prepared by substituting EXAMPLE 354C for EXAMPLE 130C in EXAMPLE 130D. $^1$H NMR (500 MHz, pyridine-d$_5$) δ 12.98 (s, 1H), 9.06 (d, 1H), 8.50 (dd, 1H), 8.41 (d, 1H), 8.09 (d, 1H), 7.66 (t, 1H), 7.62 (d, 1H), 7.44 (d, 2H), 7.26 (d, 1H), 7.07 (d, 2H), 6.75 (dd, 1H), 6.54 (d, 1H), 6.48 (m, 1H), 4.31 (dd, 1H), 4.22 (dd, 1H), 3.92 (m, 1H), 3.83 (d, 1H), 3.56 (dt, 1H), 3.07 (m, 5H), 2.77 (s, 2H), 2.68 (d, 1H), 2.35 (m, 2H), 2.26 (m, 2H), 2.14 (m, 4H), 1.97 (s, 2H), 1.59 (m, 1H), 1.39 (t, 2H), 0.94 (s, 6H), 0.40 (m, 4H).

Example 355

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 355A 5-chloro-6-((trans-1-fluoro-4-hydroxy-4-methylcyclohexyl)methoxy)pyridine-3-sulfonamide To a cooled (0° C.) solution of EXAMPLE 350E (1.2 g) in tetrahydrofuran (30 mL) was added dropwise a solution of methylmagnesium bromide (5 mL, 3.0M in ether). Upon addition, the reaction mixture solidified. More tetrahydrofuran (10 mL) was added to the mixture and stirring was continued for 1 hour. The mixture was poured over aqueous NH$_4$Cl and extracted with ethyl acetate (3×150 mL). The combined organic layers were washed with water, brine and dried over Na$_2$SO$_4$. The mixture was filtered and concentrated. The residue was dissolved in dimethylsulfoxide/methanol (20 mL, 1:1) and loaded on loaded on Gilson, C18 (100A) 250×121.2 mm (10 micron), with 30% acetonitrile to 65% acetonitrile over 40 minutes to separate the two isomers and isolate the title compound.

Example 355B

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 355A for EXAMPLE 1F in EXAMPLE 1G. $^1$H NMR (300 MHz, dimethylsulfoxide-d$_6$) δ 11.63 (s, 1 H), 8.47 (s, 1 H), 8.17 (s, 1 H), 7.54 (d, 1 H), 7.48 (m, 2 H), 7.35 (d, 2 H), 7.05 (d, 2 H), 6.67 (dd, 1 H), 6.37 (d, 1H), 6.22 (d, 1 H), 4.49 (s, 1 H), 4.42 (s, 1 H), 4.15 (s, 1 H), 3.06 (m, 4 H), 2.84 (m, 1 H), 2.25 (m, 6 H), 1.96 (s, 3 H), 1.83 (m, 4 H), 1.44 (m, 6 H), 1.14 (s, 3 H), 0.93 (s, 6 H).

Example 356

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 356A 5-chloro-6-((cis-1-fluoro-4-hydroxy-4-methylcyclohexyl)methoxy)pyridine-3-sulfonamide The title compound was prepared as described in EXAMPLE 355A.

Example 356B

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 3J for EXAMPLE 1E and EXAMPLE 356A for EXAMPLE 1F in EXAMPLE 1G. $^1$H NMR (300 MHz, dimethylsulfoxide-d$_6$) δ 11.65 (s, 1 H), 8.52 (s, 1 H), 8.20 (s, 1 H), 8.03 (d, 1 H), 7.51 (m, 3 H), 7.35 (d, 2 H), 7.05 (d, 2 H), 6.67 (dd, 1 H), 6.39 (dd, 1 H), 6.21 (d, 1 H), 4.55 (s, 1 H), 4.48 (s, 1 H), 4.34 (s, 1 H), 3.08 (m, 4 H), 2.89 (d, 2 H), 2.27 (d, 5 H), 1.93 (m, 4 H), 1.66 (m, 4 H), 1.43 (m, 4 H), 1.11 (s, 3 H), 0.93 (s, 6 H).

Example 357

4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide

Example 357A ethyl 4-fluoro-1-(oxetan-3-yl)piperidine-4-carboxylate

To 1-tert-butyl 4-ethyl 4-fluoropiperidine-1,4-dicarboxylate (1.000 g) was added HCl (4.0M in dioxane, 4.54 mL). After 1 hour the reaction was concentrated and dried under high vacuum. The resulting solid was dissolved in dichloromethane (5 mL) and treated with sodium triacetoxyborohydride (1.155 g) and oxetan-3-one (0.262 g) and stirred overnight. The reaction was quenched with saturated NaHCO$_3$ solution (20 mL) and extracted into dichloromethane (2×25 mL). The organic layer was dried over magnesium sulfate, filtered, and concentrated. Silica gel chromatography (Reveleris 80 g) eluting with a gradient of 0.5% to 3.75% methanol/dichloromethane over 40 minutes (flow=30 mL/min) gave the title compound.

Example 357B (4-fluoro-1-(oxetan-3-yl)piperidin-4-yl)methanol

To a solution of EXAMPLE 357A (0.59 g) in tetrahydrofuran (5 mL) was added lithium aluminum hydride (1.80 mL) at 0° C. The reaction was removed from the ice bath and allowed to warm to room temperature. The reaction was quenched by the dropwise addition of 0.6 ml of water followed by 0.2 ml of 2N aqueous NaOH. The reaction was filtered through celite and rinsed with ethyl acetate (50 mL). The mixture and the residue was loaded onto silica gel (Reveleris 40 g) and eluted using a gradient of 0.75% to 7.5% methanol/dichloromethane over 30 minutes (flow=40 mL/minutes) to provide the title compound.

Example 357C 3-cyano-4-((4-fluoro-1-(oxetan-3-yl)piperidin-4-yl)methoxy)benzenesulfonamide The title compound was prepared by substituting EXAMPLE 357B for (tetrahydro-2H-pyran-4-yl)methanol in EXAMPLE 284A.

Example 357D 4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide The title compound was prepared by substituting EXAMPLE 3J for EXAMPLE 1E and EXAMPLE 357C for EXAMPLE 1F in EXAMPLE 1G. $^1$H NMR (300 MHz, dimethylsulfoxide-$d_6$) δ 11.67 (s, 1H), 11.49-11.14 (m, 1H), 8.17 (d, 1H), 8.03 (d, 2H), 7.51 (dd, 3H), 7.43-7.26 (m, 3H), 7.12-6.96 (m, 2H), 6.67 (dd, 1H), 6.40 (dd, 1H), 6.20 (d, 1H), 4.55 (t, 2H), 4.45 (t, 2H), 4.34 (d, 2H), 3.49 (s, 1H), 3.09 (s, 8H), 2.39-1.66 (m, 14H), 1.39 (s, 2H), 0.92 (s, 6H).

Example 358

4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide

Example 358A benzyl (4-ethyl-4-hydroxycyclohexyl)methylcarbamate

To a vigorous stirring solution of benzyl (4-oxocyclohexyl)methylcarbamate (1 g) in tetrahydrofuran (20 mL) at −78° C. was slowly added 1 Methylmagnesium bromide (11.48 ml, 11.48 mmol) in ether. After completion of the addition, the mixture was stirred at −78° C. for 2 hours and was warmed to 0° C., and stirred in an ice bath for 30 minutes. The reaction was quenched with a cold NH$_4$Cl aqueous solution. The precipitates were filtered off and washed with ethyl acetate. The filtrate was concentrated. The residue was dissolved in dichloromethane and loaded onto Analogix purification system, and was eluted with 0-50% ethyl acetate in dichloromethane to provide the title compound.

Example 358B 4-(aminomethyl)-1-ethylcyclohexanol

A mixture of EXAMPLE 358A (500 mg) and 10% Pd/C (100 mg) in tetrahydrofuran (15 mL) was stirred under H$_2$ for 3 hours. The insoluble material was removed by filtration, and the filtrate was concentrated to provide the title compound.

Example 358C 4-((trans-4-ethyl-4-hydroxycyclohexyl)methylamino)-3-nitrobenzenesulfonamide EXAMPLE 358B (270 mg) and 4-fluoro-3-nitrobenzenesulfonamide (417 mg) in tetrahydrofuran were treated with triethylamine (0.8 mL) overnight. The reaction was quenched with water. The resulting mixture was neutralized with diluted aqueous HCl, and extracted with ethyl acetate. The organic layer was dried over Na$_2$SO$_4$, filtered and concentrated. The residue was purified by a reverse phase chromatography, eluting with 40-55% acetonitrile in 0.1% trifluoroacetic acid water to isolate the title compound.

Example 358D 4-((cis-4-ethyl-4-hydroxycyclohexyl)methylamino)-3-nitrobenzenesulfonamide The title compound was prepared and isolated as described in Example 358C.

Example 358E 4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 358C in place of EXAMPLE 11B. $^1$H NMR (400 MHz, dimethylsulfoxide-$d_6$) δ 11.69 (s, 1 H), 11.35 (s, 1 H), 8.56 (d, 2 H), 8.05 (d, 1 H), 7.80 (dd, 1 H), 7.45-7.57 (m, 3 H), 7.34 (d, 2 H), 7.00-7.10 (m, 3 H), 6.68 (dd, 1 H), 6.39 (dd, 1 H), 6.19 (d, 1 H), 3.98 (s, 1 H), 3.24-3.31 (m, 4 H), 3.07 (s, 4 H), 2.75 (s, 2 H), 2.17 (d, 6 H), 1.95 (s, 2 H), 1.54-1.73 (m, 5 H), 1.35-1.47 (m, 4 H), 1.20-1.32 (m, 2 H), 1.03-1.18 (m, 2 H), 0.92 (s, 6 H), 0.81 (t, 3 H).

Example 359

4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide The title compound was prepared as described in EXAMPLE 11D using EXAMPLE 358D in place of EXAMPLE 11B. $^1$H NMR (400 MHz, dimethylsulfoxide-$d_6$) δ 11.69 (s, 1H), 11.34 (s, 1 H), 8.60 (t, 1 H), 8.56 (d, 1 H), 8.05 (d, 1 H), 7.80 (dd, 1 H), 7.54 (d, 1 H), 7.47-7.52 (d, 2 H), 7.34 (d, 2 H), 7.01-7.10 (m, 3 H), 6.68 (dd, 1 H), 6.39 (dd, 1 H), 6.19 (d, 1 H), 3.77 (s, 1 H), 3.26 (t, 2H), 3.07 (s, 4 H), 2.76 (s, 2 H), 2.10-2.26 (m, 6 H), 1.95 (s, 2 H), 1.46-1.61 (dd, 5 H), 1.28-1.46 (m, 6 H), 1.12-1.24 (dd, 2 H), 0.92 (s, 6 H), 0.82 (t, 3H).

Example 360

4-(4-{[2-(4-chlorophenyl)-5-(methoxymethyl)-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 360A ethyl 8-methyl-1,4-dioxaspiro[4.5]decane-8-carboxylate

Into a 500 mL round-bottomed flask was added diisopropylamine (7.98 mL) in tetrahydrofuran (233 mL) to give a colorless solution. The mixture was cooled to −78° C. under N₂ and n-BuLi (2.5 M in hexanes, 22.40 mL) was added. The reaction was stirred for 30 minutes and ethyl 1,4-dioxaspiro [4.5]decane-8-carboxylate (10 g) was added. The reaction was allowed to stir for 1.5 hours upon which time CH₃I (4.38 mL) was added. The reaction was allowed to warm to room temperature overnight with stirring. Water was added and the aqueous layer was extracted with ethyl acetate. The combined organics were dried (Na₂SO₄), filtered and concentrated by rotary evaporation. The residue was purified by normal phase flash column chromatography (Analogix, 0-50% hexanes/ ethyl acetate).

Example 360B (8-methyl-1,4-dioxaspiro[4.5]decan-8-yl)methanol

In a 500 ml, round-bottomed flask was lithium aluminum hydride (1.772 g) in tetrahydrofuran (234 mL) to give a suspension. This suspension was cooled to 0° C. and ethyl 8-methyl-1,4-dioxaspiro[4.5]decane-8-carboxylate (10.66 g) was added via addition funnel. The reaction was stirred overnight at room temperature and then cooled back down to 0° C. The excess lithium aluminum hydride was slowly quenched with 1.8 mL water, 1.8 mL aqueous NaOH (5N) and 5.6 mL water. The suspension was stirred until the salts turned white and was then filtered through a plug of silica gel. The filtrate was concentrated by rotary evaporation and the residue was purified by regular phase flash column chromatography (Analogix, 0-75% hexanes/ethyl acetate).

Example 360C 8-(methoxymethyl)-8-methyl-1,4-dioxaspiro[4.5] decane

To a 250 mL round-bottomed flask was added NaH (0.902 g) and tetrahydrofuran (37.6 mL) to give a suspension. EXAMPLE 360B was added as a tetrahydrofuran solution at room temperature. The suspension was stirred for 30 minutes and then CH₃I (0.611 mL) was added. The reaction was stirred under N₂ overnight, carefully quenched with brine and diluted with water and ether. The aqueous layer was extracted with ether (2×) and the combined organics were dried (Na₂SO₄), filtered and concentrated by rotary evaporation. The residue was purified by flash column chromatography (Analogix, 0-60% hexanes/ethyl acetate).

Example 360D 4-(methoxymethyl)-4-methylcyclohexanone

The title compound was prepared by substituting EXAMPLE 360C for EXAMPLE 353B in EXAMPLE 353C.

Example 360E 2-chloro-5-(methoxymethyl)-5-methylcyclohex-1-enecarbaldehyde

The title compound was prepared by substituting EXAMPLE 360D for EXAMPLE 353C in EXAMPLE 353D.

Example 360F 2-(4-chlorophenyl)-5-(methoxymethyl)-5-methylcyclohex-1-enecarbaldehyde The title compound was prepared by substituting EXAMPLE 360E for EXAMPLE 353D in EXAMPLE 353E.

Example 360G methyl 2-(1H-pyrrolo[2,3-b]pyridin-5-yloxy)-4-(4-((2-(4-chlorophenyl)-5-(methoxymethyl)-5-methyl-cyclohex-1-enyl)methyl)piperazin-1-yl)benzoate The title compound was prepared by substituting EXAMPLE 360F for EXAMPLE 353E in EXAMPLE 353F.

Example 360H 2-(1H-pyrrolo[2,3-b]pyridin-5-yloxy)-4-(4-((2-(4-chlorophenyl)-5-(methoxymethyl)-5-methylcyclohex-1-enyl)methyl)piperazin-1-yl)benzoic acid The title compound was prepared by substituting EXAMPLE 360G for EXAMPLE 15G in EXAMPLE 15H.

Example 360I 2-(1H-pyrrolo[2,3-b]pyridin-5-yloxy)-4-(4-((2-(4-chlorophenyl)-5-(methoxymethyl)-5-methylcyclohex-1-yl)methyl)piperazin-1-yl)-N-(3-nitro-4-((tetrahydro-2H-pyran-4-yl)methylamino) phenylsulfonyl)benzamide The title compound was prepared by replacing EXAMPLE 3J with EXAMPLE 360H and EXAMPLE 11B with EXAMPLE 1F in EXAMPLE 11D. ¹H NMR (300 MHz, dimethylsulfoxide-d₆) δ 11.68 (s, 1 H) 11.43 (s, 1 H) 8.45-8.72 (m, 2 H) 8.04 (d, 1 H) 7.80 (dd, 1 H) 7.44-7.61 (m, 3 H) 7.34 (d, 2 H) 6.99-7.20 (m, 3 H) 6.68 (dd, 1 H) 6.39 (dd, 1 H) 6.18 (d, 1 H) 3.85 (dd, 2 H) 3.25-3.30 (dd, 4 H) 3.24 (s, 3 H) 3.02-3.17 (m, 6 H) 2.72 (dd, 2 H) 2.18 (s, 5H) 2.03-2.13 (m, 2 H) 1.81-1.93 (m, 2 H) 1.57-1.67 (m, 2 H) 1.47-1.56 (m, 1H) 1.17-1.41 (m, 3 H) 0.91 (s, 3 H).

Example 361

4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl] methyl}amino)phenyl]sulfonyl}-2-(1H-pyrrolo[2,3-b]pyridin-5-yloxy)benzamide

Example 361A (S)-3-nitro-4-((4-(oxetan-3-yl)morpholin-2-yl)methylamino)benzenesulfonamide The title compound was prepared by substituting EXAMPLE 259E for tert-butyl piperazine-1-carboxylate and 3-oxetanone for 4'-chlorobiphenyl-2-carboxaldehyde in EXAMPLE 1A.

Example 361B 4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide The title compound was prepared by substituting EXAMPLE 361A for EXAMPLE 130C in EXAMPLE 130D. $^1$H NMR (500 MHz, pyridine-$d_5$) δ 13.00 (s, 1H), 9.26 (d, 1H), 8.87 (t, 1H), 8.43 (d, 1H), 8.35 (dd, 1H), 8.11 (d, 1H), 7.66 (m, 2H), 7.44 (d, 2H), 7.07 (d, 2H), 6.96 (d, 1H), 6.75 (dd, 1H), 6.54 (d, 1H), 6.48 (m, 1H), 4.64 (m, 4H), 3.93 (m, 1H), 3.89 (d, 1H), 3.68 (dt, 1H), 3.53-3.35 (m, 3H), 3.07 (m, 4H), 2.77 (s, 2H), 2.72 (d, 1H), 2.44 (d, 1H), 2.26 (m, 2H), 2.14 (m, 4H), 1.97 (s, 2H), 1.85 (t, 1H), 1.39 (t, 2H), 0.94 (s, 6H).

Example 362

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Example 362A 3-chloro-4-(((1r, 4r)-4-hydroxy-4-methylcyclohexyl)methoxy)benzenesulfonamide To a solution of EXAMPLE 341F (300 mg) in N,N-dimethylformamide (10 mL) was added sodium hydride (416 mg) portionwise. The resulting suspension was stirred for 15 minutes. 3-Chloro-4-fluorobenzenesulfonamide (425 mg) was added and stirring was continued for 72 hours. The reaction was quenched with water and the pH was adjusted to ca. 7. The mixture was diluted with brine (75 mL) and extracted with methylene chloride. The crude product was isolated from the dried methylene chloride layer by concentration and was purified on silica gel eluted with a 10, 25, 50% ethyl acetate in methylene chloride step gradient to provide the title compound.

Example 362B

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 362A for EXAMPLE 130C in EXAMPLE 130D. $^1$H NMR (400 MHz, pyridine-$d_5$) δ 13.07 (m, 1H), 8.58 (d, 1H), 8.45 (d, 1H), 8.31 (dd, 1H), 8.11 (d, 1H), 7.69-7.67 (m, 2H), 7.44 (d, 2H), 7.07 (d, 2H), 6.97 (d, 1H), 6.74 (dd, 1H), 6.52 (m, 2H), 5.34 (br s, 2H), 3.82 (d, 2H), 3.06 (m, 4H), 2.77 (s, 2H), 2.25 (m, 2H), 2.13 (m, 4H), 1.97-1.85 (m, 7H), 1.82-1.73 (m, 2H), 1.44-1.32 (m, 7H), 0.94 (m, 6H).

Example 363

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide

Example 363A 4-((4'-fluorospiro[benzo[d][1,3]dioxole-2,1'-cyclohexane]-4'-yl)methoxy)-3-nitrobenzenesulfonamide To a solution of EXAMPLE 350C (495 mg) in N,N-dimethylformamide (6 mL) was added NaH (65% in mineral oil, 320 mg). The mixture was stirred for 30 minutes, and then 4-fluoro-3-nitrobenzenesulfonamide (457 mg) was added. The mixture was stirred overnight. The mixture was poured over aqueous NH$_4$Cl and extracted with ethyl acetate (300 mL). The combined organic layers were washed with water, brine and dried over Na$_2$SO$_4$. After filtration and evaporation of the solvent, the residue was loaded on a silica gel cartridge and was eluted with 30% ethyl acetate in hexane to provide the title compound.

Example 363B 4-((1-fluoro-4-oxocyclohexyl)methoxy)-3-nitrobenzenesulfonamide To a solution of EXAMPLE 363A (860 mg) in ethanol (30 mL) was added concentrated HCl (10 mL) and the mixture was stirred at 100° C. for 3 hours. The mixture was neutralized with solid Na$_2$CO$_3$ and extracted with dichloromethane (300 mL) and washed with aqueous NaHCO$_3$, water, brine and dried over Na$_2$SO$_4$. Filtration and evaporation of the solvent gave the title compound.

Example 363C 4-((4-((2-cyanoethyl)(cyclopropyl)amino)-1-fluorocyclohexyl)methoxy)-3-nitrobenzenesulfonamide To a solution of EXAMPLE 363B (200 mg) in dichloromethane (6 mL) was added 3-(cyclopropylamino)propanenitrile (64 mg) followed by sodium triacetoxyborohydride (184 mg). The mixture was stirred overnight. The reaction mixture was diluted with dichloromethane (400 mL) and washed with 2N aqueous NaOH, water, and brine. After drying over Na$_2$SO$_4$, the mixture was filtered and evaporation of the solvent gave the title compound.

Example 363D 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide The title compound was prepared by substituting EXAMPLE 3J for EXAMPLE 1E and EXAMPLE 363C for EXAMPLE 1F in EXAMPLE 1G. $^1$H NMR (300 MHz, dimethylsulfoxide-$d_6$) δ 11.66 (s, 1H), 8.35 (s, 1 H), 8.02 (d, 2 H), 7.51 (m, 3H), 7.40 (m, 1 H), 7.35 (d, 2 H), 7.04 (d, 2 H), 6.67 (dd, 1 H), 6.39 (d, 1 H), 6.20 (s, 1 H), 4.27 (d, 2 H), 3.13 (m, 4 H), 2.88 (m, 3H), 2.67 (m, 4 H), 2.09 (m, 10H), 1.49 (m, 9 H), 0.93 (s, 6 H), 0.45 (m, 4 H).

Example 364

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide Example 364A 6-amino-5-nitropyridine-3-sulfonic acid 6-Aminopyridine-3-sulfonic acid (20 g) in concentrated $H_2SO_4$ (80 mL) was heated at 50° C. until it was completely dissolved. To this solution was added fuming $HNO_3$ slowly over 20 minutes, so the internal temperature did not exceed 55° C. After the addition was complete, the reaction mixture was heated at 50° C. for 1 hour. After it was cooled to room temperature, it was poured into 150 g of ice. The mixture was stirred for another hour. The flask was cooled to 0° C., and was kept at 0° C. for another 2 hours. The solid was collected by filtration, and washed with cold 1:1 water/ethanol (20 mL), followed by diethyl ether (10 mL). The solid was dried in a vacuum oven overnight to provide the title compound.

Example 364B 6-hydroxy-5-nitropyridine-3-sulfonic acid

EXAMPLE 364A (4.0 g) in aqueous HCl (37%, 12 mL) and water (50 mL) was treated with sodium nitrite (1.19 g) in water (8 mL) dropwise at 0° C. After the addition was complete, the reaction mixture was stirred at 0° C. for 1 hour. The mixture was heated at reflux for 2 hours. Water was distilled off to give a dry residue. After the residue was cooled to room temperature, a solution of 1:1 (20 mL) was added. The resulting suspension was cooled to 0° C., and kept at 0° C. for 1 hour. The solid was collected by filtration to provide the title compound.

Example 364C 6-chloro-5-nitropyridine-3-sulfonyl chloride

A mixture of EXAMPLE 364B (2.6 g), $PCl_5$ (5.91 g), and $POCl_3$ (10 mL) was heated at 120° C. for 4 hours. The initial suspension became a clear solution. The excess of $POCl_3$ was distilled off. After it was cooled to room temperature, the residue was poured into 50 g of crushed ice. The solid was extracted into ethyl acetate. The aqueous layer was extracted with additional ethyl acetate. The combined organic layers were washed with brine, dried over $MgSO_4$, filtered, and concentrated to give crude product that was used in the next step without further purification.

Example 364D 6-chloro-5-nitropyridine-3-sulfonamide

EXAMPLE 364C in tetrahydrofuran (10 mL) was cooled to −10° C. To this solution was added concentrated ammonium hydroxide (0.82 mL) dropwise. The solution was stirred at −10° C. for 10 minutes. The solvent was removed under pressure at room temperature. The residue was partitioned between water and ethyl acetate. The aqueous layer was extracted with additional ethyl acetate. The combined organic layers were washed with brine, dried over $MgSO_4$, filtered, and concentrated. The residue was purified by flash column chromatography on silica gel using 5-50% ethyl acetate in hexanes to provide the title compound.

Example 364E 5-nitro-6-((tetrahydro-2H-pyran-4-yl)methylamino)pyridine-3-sulfonamide The title compound was prepared by substituting EXAMPLE 364D for 4-fluoro-3-nitrobenzenesulfonamide and (tetrahydro-2H-pyran-4-yl)methanamine for (4-fluorotetrahydro-2H-pyran-4-yl)methanamine in EXAMPLE 138D.

Example 364F 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide The title compound was prepared by substituting EXAMPLE 364E for EXAMPLE 11B in EXAMPLE 11D. $^1$H NMR (500 MHz, dimethylsulfoxide-$d_6$) δ 11.63 (s, 1H), 8.93 (s, 1H), 8.73 (d, 1H), 8.69 (d, 1H), 8.00 (d, 1H), 7.54 (d, 1H), 7.47-7.48 (m, 2H), 7.35 (d, 2H), 7.05 (d, 2H), 6.68 (dd, 1H), 6.35 (dd, 1H), 6.22 (d, 1H), 3.83 (dd, 2H), 3.51 (t, 2H), 3.21-3.27 (m, 2H), 3.10 (s, 4H), 2.83 (s, 2H), 1.90-2.27 (m, 12H), 1.58 (dd, 2H), 1.39 (t, 2H), 1.18-1.28 (m, 2H), 0.88-0.93 (m, 8H).

Example 365

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide Example 365A 7-(azidomethyl)-2-oxaspiro[3.5]nonane To a 250 mL round-bottomed flask was EXAMPLE 351F (350 mg) in tetrahydrofuran (75.0 mL) to give a colorless solution. The solution was cooled to 0° C., triphenylphosphine (2.94 g), diisopropyl azodicarboxylate (2.18 mL) and diphenyl phosphorazidate (2.32 mL) were added and the reaction was stirred for 30 minutes at room temperature. The mixture was concentrated and purified the residue by regular phase flash column chromatography (Analogix, 0-20% hexanes/ethyl acetate).

Example 365B 2-oxaspiro[3.5]nonan-7-ylmethanamine

To a 50 mL round-bottomed flask was added 10% palladium on carbon (58.7 mg). The flask was flushed with $N_2$ and EXAMPLE 365A (400 mg) was added as a methanol solution (10.5 mL). The flask was then flushed several times with $H_2$ (via balloon) and heated to 45° C. for 2 hours. The reaction was cooled to room temperature, filtered through celite and the filtrate was concentrated by rotary evaporation. The residue was used in the next step without further purification.

Example 365C 4-(2-oxaspiro[3.5]nonan-7-ylmethylamino)-3-nitrobenzenesulfonamide The title compound was prepared by substituting EXAMPLE 365B for 1-(tetrahydropyran-4-yl)methylamine in EXAMPLE 1F.

Example 365D 2-(1H-pyrrolo[2,3-b]pyridin-5-yloxy)-N-(4-(2-oxaspiro[3.5]nonan-7-ylmethylamino)-3-nitrophenylsulfonyl)-4-(4-((2-(4-chlorophenyl)-4,4-dimethylcyclohex-1-enyl)methyl)piperazin-1-yl)benzamide The title compound was prepared by substituting EXAMPLE 3J for EXAMPLE 1E and EXAMPLE 365C for EXAMPLE 1F in EXAMPLE 1G. $^1$H NMR (300 MHz, dimethylsulfoxide-$d_6$) δ 11.67 (s, 1 H) 11.25-11.49 (m, 1 H) 8.48-8.66 (m, 2 H) 8.03 (d, 1 H) 7.79 (dd, 1 H) 7.41-7.61 (m, 3 H) 7.27-7.40 (m, 2 H) 7.05 (t, 3 H) 6.67 (dd, 1 H) 6.39 (dd, 1 H) 6.18 (d, 1 H) 4.29 (s, 2 H) 4.19 (s, 2 H) 3.17-3.27 (m, 2 H) 2.99-3.14 (m, 4 H) 2.69-2.79 (m, 2 H) 2.09-2.28 (m, 6 H) 2.04 (d, 2 H) 1.95 (s, 2 H) 1.66 (d, 2 H) 1.49-1.61 (m, 1 H) 1.29-1.45 (m, 4 H) 0.93-1.05 (m, 2 H) 0.92 (s, 6 H).

Example 366

4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide

Example 366A tert-butyl (4-cyano-4-methylcyclohexyl)methylcarbamate

To a cooled (−78° C.) solution of tert-butyl (4-cyanocyclohexyl)methylcarbamate (500 mg) in tetrahydrofuran (10 mL) was added lithium diisopropylamide (2.0 mL, 2M in heptane). The mixture was stirred at −78° C. for 30 minutes before the addition of CH$_3$I (1 mL). The mixture was then stirred and the temperature was allowed to warm to room temperature. The reaction was quenched with aqueous NH$_4$Cl and the mixture was extracted with ethyl acetate (300 mL) and washed with water, brine and dried over Na$_2$SO$_4$. Filtration and evaporation of the solvent and silica gel chromatography (40% ethyl acetate in hexane) of the crude material gave the title compound.

Example 366B 4-(aminomethyl)-1-methylcyclohexanecarbonitrile

To a solution of EXAMPLE 366A (480 mg) in dichloromethane (10 mL) was added trifluoroacetic acid (10 mL). The mixture was stirred for 3 hours. The mixture was then concentrated under vacuum and was used directly in the next reaction without further purification.

Example 366C 4-((4-cyano-4-methylcyclohexyl)methylamino)-3-nitrobenzenesulfonamide To a solution of 4-fluoro-3-nitrobenzenesulfonamide (362 mg) in tetrahydrofuran (10 mL) was added EXAMPLE 366B (250 mg) and N,N-diisopropylethylamine (2 mL). The mixture was stirred overnight. The mixture was diluted with ethyl acetate (300 mL) and washed with water, brine and dried over Na$_2$SO$_4$. Filtration and evaporation of the solvent gave the title compound.

Example 366D 4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide The title compound was prepared by substituting EXAMPLE 3J for EXAMPLE 1E and EXAMPLE 366C for EXAMPLE 1F in EXAMPLE 1G. $^1$H NMR (300 MHz, dimethylsulfoxide-$d_6$) δ 11.67 (s, 1 H), 11.37 (m, 1 H), 8.59 (m, 2 H), 8.04 (d, 1 H), 7.80 (d, 1 H), 7.51 (m, 3 H), 7.34 (d, 2 H), 7.10 (d, 1 H), 7.04 (d, 2 H), 6.68 (dd, 1 H), 6.39 (m, 1 H), 6.19 (s, 1 H), 3.07 (m, 4 H), 2.75 (m, 2 H), 2.17 (m, 7 H), 1.76 (m, 9 H), 1.32 (m, 9 H), 0.92 (s, 6 H).

Example 367

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl pivalate This example was prepared by substituting chloromethyl pivalate for chloromethyl butyrate in EXAMPLE 368. $^1$H NMR (400 MHz, dimethylsulfoxide-$d_6$) δ 11.72 (s, 1H), 8.43 (d, 1H), 8.22 (dd, 1H), 8.01 (d, 1H), 7.55 (m, 3H), 7.36 (m, 3H), 7.03 (d, 2H), 6.68 (dd, 1H), 6.41 (m, 1H), 6.17 (d, 1H), 5.83 (s, 2H), 4.40 (d, 2H), 3.78 (m, 2H), 3.59 (m, 2H), 3.08 (br m, 4H), 2.73 (br s, 2H), 2.18 (br m, 6H), 1.96 (s, 2H), 1.84 (m, 4H), 1.39 (m, 2H), 1.00 (s, 9H), 0.92 (s, 6H).

Example 368

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl butyrate EXAMPLE 37E (500 mg) was dissolved in acetonitrile (3.7 mL) and chloromethyl butyrate (77 mg) and Hunig's base (73 mg) were added. The reaction was heated under reflux for one day. After cooling and dilution with dimethylsulfoxide (4 mL) the reaction was purified by preparative HPLC using a 250×50 mm C18 column and eluting with 20-100% CH$_3$CN vs. 0.1% trifluoroacetic acid in water, giving the product as a trifluoroacetate salt. The trifluoroacetic acid salt was dissolved in dichloromethane (6 ml) and washed with 50% aqueous NaHCO$_3$. The organic layer was dried over anhydrous Na$_2$SO$_4$, filtered, and concentrated to provide the title compound. $^1$H NMR (400 MHz, dimethylsulfoxide-d$_6$) δ 11.72 (s, 1H), 8.43 (d, 1H), 8.22 (dd, 1H), 8.01 (d, 1H), 7.55 (m, 3H), 7.36 (m, 3H), 7.03 (d, 2H), 6.68 (dd, 1H), 6.41 (m, 1H), 6.17 (d, 1H), 5.83 (s, 2H), 4.40 (d, 2H), 3.78 (m, 2H), 3.59 (m, 2H), 3.08 (br m, 4H), 2.73 (br s, 2H), 2.18 (m, 8H), 1.96 (s, 2H), 1.84 (m, 4H), 1.39 (m, 4H), 0.92 (s, 6H), 0.75 (t, 3H).

Example 369

4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 369A methyl 4-[(2,2,3,3,5,5,6,6-$^2$H$_8$)piperazin-1-yl]-2-(1H-pyrrolo[2,3-b]pyridin-5-yloxy)benzoate Into a 40 mL vial were added EXAMPLE 3H (1.55 g) and piperazine-d$_8$ (2.040 g) in dimethylsulfoxide (13 mL). The solution was heated to 85° C. for 2.5 hours, and was then allowed to cool to room temperature overnight. The mixture was transferred to a 120 mL flask and was cooled to 5-10° C. Dichloromethane (30 mL) was added, then water (10 mL) was added via syringe over 5 minutes maintaining temp at no more than 15° C. The layers were separated and the organic layer was washed with water (4×10-15 mL) until pH of aqueous layer was 8-9. The organic layer was filtered through Na$_2$SO$_4$ and rinsed with dichloromethane (5 mL), and concentrated to provide the title compound.

Example 369B methyl 4-[4-{[2-(4-chlorophenyl)-4,4-dimethylcyclohex-1-en-1-yl]methyl}($^2$H$_8$)piperazin-1-yl]-2-(1H-pyrrolo[2,3-b]pyridin-5-yloxy)benzoate In a 100 mL round-bottomed flask, EXAMPLE 369A (3.4 g), EXAMPLE 290B (1.321 g) and dichloromethane (3 mL) were added to a 100 mL round bottom flask at room temperature. To a separate 50 mL 3 neck round bottom flask, sodium triacetoxyborohydride (1.330 g) and dichloromethane (12 mL) were added to give a slurry. After cooling the 50 mL round bottom flask to 18-20° C., the piperazine adduct/aldehyde solution was added via syringe over 5 minutes. The triacetoxyborohydride gradually dissolved to give a clear solution after ~5 minutes. After an additional 10 minutes, the solution became hazy. After 16 hours, the reaction was cooled to 5-10° C. Saturated aqueous NaHCO$_3$ (12 mL) was added over 5 minutes maintaining the temperature at no more than 10° C. The layers were separated and the organic layer was washed with saturated aqueous NaHCO$_3$, and 10% NaCl (12 mL), and then filtered through Na$_2$SO$_4$ and rinsed with dichloromethane (4 mL). The solution was concentrated on a rotovap, and chase concentrated with methanol (40 mL). The resulting solution was cooled to 5-10° C., and the product precipitated. The solution was mixed at room temperature for 30 minutes, then filtered and rinsed with methanol (5 mL), and the product was air dried.

Example 369C

4-[4-{[2-(4-chlorophenyl)-4,4-dimethylcyclohex-1-en-1-yl]methyl}($^2$H$_8$)piperazin-1-yl]-2-(1H-pyrrolo[2,3-b]pyridin-5-yloxy)benzoic acid The title compound was prepared by substituting EXAMPLE 369B for EXAMPLE 15G in EXAMPLE 15H.

Example 369D

4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide To a mixture of EXAMPLE 369C (2.0 g), EXAMPLE 1F (1.1 g) and N,N-dimethylpyridin-4-amine (0.7 g) in dichloromethane (20 mL) was added 1-ethyl-3-[3-(dimethylamino)propyl]-carbodiimide hydrochloride (0.8 g). The reaction mixture was stirred at room temperature overnight. The reaction was quenched with N,N-dimethylethane-1,2-diamine (0.6 g) and stirred at room temperature for 3 hours. The mixture was extracted with 20% aqueous acetic acid and washed with 5% aqueous NaCl. Methanol (2 mL) and ethyl acetate (18 mL) were added and the precipitate was collected by filtration to provide the title compound. $^1$H NMR (400 MHz, dimethylsulfoxide-d$_6$) δ 11.71 (s, 1H), 11.37 (s, br, 1H), 8.60 (t, 1H), 8.55 (d, 1H), 8.04 (d, 1H), 7.80 (dd, 1H), 7.47-7.54 (m, 3H), 7.31-7.34 (m, 2H), 7.09 (d, 1H), 7.01-7.03 (m, 2H), 6.67 (dd, 1H), 6.39 (dd, 1H), 6.19 (d, 1H), 3.83 (dd, 2H), 3.21-3.30 (m, 4H), 3.00-3.10 (s, 4H), 2.75 (s, 2H), 2.05-2.24 (m, 6H), 1.95 (s, 2H), 1.80-1.93 (m, 1H), 1.55-1.64 (m, 2H), 1.37 (t, 2H), 1.18-1.31 (m, 2H), 0.90 (s, 6H).

Example 370

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide

Example 370A 5-amino-6-((tetrahydro-2H-pyran-4-yl)methylamino)pyridine-3-sulfonamide A mixture of EXAMPLE 364E (0.16 g) and 5% palladium on carbon (0.025 g) in ethanol (5 mL) was treated with a balloon of hydrogen. The reaction mixture was stirred overnight. The solid was filtered off. The filtrate was concentrated. The residue was purified by flash chromatography on silica gel to give the title compound.

Example 370B 3-((tetrahydro-2H-pyran-4-yl)methyl)-3H-[1,2,3]triazolo[4,5-b]pyridine-6-sulfonamide EXAMPLE 370A (0.085 g) in water (10 mL) was treated with concentrated H$_2$SO$_4$ (0.5 mL). The solution was cooled to 0° C. To this solution was added NaNO$_2$ (0.023 g) in water (1 mL) dropwise. The solution was stirred for 1 hour at 0° C. The reaction mixture was poured into saturated NaHCO$_3$ solution, and extracted with ethyl acetate three times. The

Example 370C 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-((tetrahydro-2H-pyran-4-yl)methyl)-3H-[1,2,3]triazolo[4,5-b]pyridin-6-ylsulfonyl)benzamide This example was prepared by substituting EXAMPLE 370B for EXAMPLE 11B in EXAMPLE 11D. $^1$H NMR (500 MHz, dimethylsulfoxide-$d_6$) δ 11.60 (s, 1H), 9.11 (s, 1H), 8.92 (d, 1H), 7.96 (d, 1H), 7.55 (d, 1H), 7.45-7.46 (m, 1H), 7.42 (s, 1H), 7.36 (d, 2H), 7.05 (d, 2H), 6.66 (dd, 1H), 6.32 (s, 1H), 6.22 (s, 1H), 4.63 (d, 2H), 3.80 (dd, 2H), 3.21-3.30 (m, 2H), 3.16 (s, 4H), 2.83 (s, 2H), 2.19-2.29 (m, 6H), 1.97 (s, 2H), 1.33-1.41 (m, 6H), 0.93 (s, 2H).

Example 371

4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide

Example 371A 6-((trans-4-hydroxy-4-methylcyclohexyl)methylamino)-5-nitropyridine-3-sulfonamide This example was prepared by substituting EXAMPLE 364D for 4-fluoro-3-nitrobenzenesulfonamide and EXAMPLE 376B for EXAMPLE 138C in EXAMPLE 138D. The title compound was isolated by reverse phase Gilson Prep HPLC system with a Phenomenex prep column (Luna, 5μ, C18(2), 250×21.20 mm, 5 Å) eluting with 20-80% acetonitrile in water with 0.1% TFA.

Example 371B 4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide The title compound was prepared by substituting EXAMPLE 371A for EXAMPLE 11B in EXAMPLE 11D. $^1$H NMR (300 MHz, dimethylsulfoxide-$d_6$) δ 11.63 (s, 1H), 11.53-10.99 (m, 1H), 8.91 (s, 1H), 8.71 (dd, 2H), 8.01 (d, 1H), 7.61-7.44 (m, 3H), 7.44-7.28 (m, 2H), 7.12-6.97 (m, 2H), 6.76-6.61 (m, 1H), 6.36 (dd, 1H), 6.21 (d, 1H), 3.92 (s, 1H), 3.48 (t, 2H), 3.10 (s, 4H), 2.83 (s, 2H), 2.24 (dd, 6H), 1.96 (s, 2H), 1.37 (ddd, 11H), 1.07 (s, 3H), 0.93 (s, 6H).

Example 372

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide

Example 372A ethyl 4-fluoro-1-(oxetan-3-yl)piperidine-4-carboxylate

To 1-tert-butyl 4-ethyl 4-fluoropiperidine-1,4-dicarboxylate (1.00 g) was added HCl (4.0M in dioxane, 4.54 mL). After 1 hour the reaction was concentrated and dried under high vacuum. The resulting solid was dissolved in dichloromethane (5 ml) and treated with sodium triacetoxyborohydride (1.155 g) and oxetan-3-one (0.262 g) and stirred overnight. The reaction was quenched with saturated NaHCO3 solution (20 mL) and extracted into dichloromethane (2×25 mL). The organic layer was dried over magnesium sulfate, filtered, and concentrated. Silica gel chromatography (Reveleris 80 g) eluting with a gradient of 0.5% to 3.75% methanol/dichloromethane over 40 minutes (flow=30 mL/minute) gave the title compound.

Example 372B (4-fluoro-1-(oxetan-3-yl)piperidin-4-yl)methanol

To a solution of EXAMPLE 372A (0.59 g) in tetrahydrofuran (5 mL) was added lithium aluminum hydride (1.80 mL) at 0° C. The reaction was removed from the ice bath and allowed to warm to room temperature. The reaction was quenched by the dropwise addition of 0.6 mL of water followed by 0.2 ml of 2N aqueous NaOH. The reaction was filtered through diatomaceous earth and rinsed with ethyl acetate (50 mL). The organics were concentrated and loaded onto silica gel (Reveleris 40 g) and eluted using a gradient of 0.75% to 7.5% methanol/dichloromethane over 30 minute (flow=40 mL/minutes) to give the title compound.

Example 372C 5-bromo-6-((4-fluoro-1-(oxetan-3-yl)piperidin-4-yl)methoxy)pyridine-3-sulfonamide This example was prepared by substituting EXAMPLE 372B for (tetrahydro-2H-pyran-4-yl)methanol and EXAMPLE 36A for 4-fluoro-3-nitrobenzenesulfonamide in EXAMPLE 24A.

Example 372D 5-cyano-6-((4-fluoro-1-(oxetan-3-yl)piperidin-4-yl)methoxy)pyridine-3-sulfonamide This example was prepared by substituting EXAMPLE 372C for EXAMPLE 36B in EXAMPLE 36C.

Example 372E 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(5-cyano-6-((4-fluoro-1-(oxetan-3-yl)piperidin-4-yl)methoxy)pyridin-3-ylsulfonyl)benzamide The title compound was prepared by substituting EXAMPLE 372D for EXAMPLE 11B in EXAMPLE 11D.

$^1$H NMR (300 MHz, dimethylsulfoxide-d$_6$) δ 11.58 (s, 1H), 8.71 (s, 1H), 8.52 (s, 1H), 7.96 (d, 1H), 7.57 (d, 1H), 7.48-7.30 (m, 4H), 7.06 (d, 2H), 6.68 (d, 1H), 6.37-6.22 (m, 2H), 4.65-4.40 (m, 6H), 3.58 (s, 1H), 3.12 (s, 6H), 2.84-2.59 (m, 4H), 2.17 (s, 6H), 1.96 (d, 6H), 1.41 (s, 2H), 0.93 (s, 6H).

Example 373

N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide Example 373A morpholine-4-carboxamide A solution of morpholine-4-carbonyl chloride (2.0 g) in methanol (10 mL) and 7 N NH$_3$ in methanol (5 mL) was stirred at 45° C. overnight. The mixture was concentrated to give a solid, which was dried under vacuum.

Example 373B

N-(2-nitro-4-sulfamoylphenyl)morpholine-4-carboxamide

This example was prepared by substituting EXAMPLE 373A for (tetrahydro-2H-pyran-4-yl)methanol in EXAMPLE 24A.

Example 373C

N-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenyl)morpholine-4-carboxamide This example was prepared by substituting EXAMPLE 373B for EXAMPLE 130C in EXAMPLE 130D. $^1$H NMR (500 MHz, pyridine-d$_5$) δ 13.02 (s, 1H), 10.41 (s, 1H), 9.27 (d, 1H), 8.81 (d, 1H), 8.50 (dd, 1H), 8.40 (d, 1H), 8.09 (d, 1H), 7.65 (m, 2H), 7.44 (d, 2H), 7.07 (d, 2H), 6.76 (dd, 1H), 6.54 (d, 1H), 6.48 (m, 1H), 3.67 (m, 4H), 3.58 (m, 4H), 3.07 (m, 4H), 2.77 (s, 2H), 2.26 (t, 2H), 2.14 (m, 4H), 1.97 (s, 2H), 1.39 (t, 2H), 0.94 (s, 6H).

Example 374

4-(4-{[2-(4-chlorophenyl)-4,4-dimethylcyclohex-1-en-1-yl]methyl}piperazin-1-yl)-N-{[4-({[4-(methoxymethyl)cyclohexyl]methyl}amino)-3-nitrophenyl]sulfonyl}-2-(1H-pyrrolo[2,3-b]pyridin-5-yloxy)benzamide Example 374A (4,4-diethoxycyclohexyl)methanol Ethyl 4,4-diethoxycyclohexanecarboxylate (6.67 g) synthesized according to a literature procedure (*European Journal of Organic Chemistry*, 2008, 5, 895) in tetrahydrofuran (60 mL) was treated with 2 M lithium aluminum hydride in tetrahydrofuran (14.5 mL) at 0° C. for 1 hour. Water (3 mL) was slowly added to quench the reaction. The precipitates were filtered off and washed with ethyl acetate. The filtrate was dried over Na$_2$SO$_4$, filtered, and concentrated to provide the title compound.

Example 374B 1,1-diethoxy-4-(methoxymethyl)cyclohexane

EXAMPLE 374A (665 mg) in tetrahydrofuran (20 mL) was treated with NaH (394 mg) for 30 minutes and then CH$_3$I (0.267 mL) was slowly added. The resulting mixture was stirred overnight and the reaction was quenched with a few drops of water. The mixture was concentrated and the residue was suspended in water and extracted with dichloromethane. The organic layer was dried over Na$_2$SO$_4$, filtered and concentrated. The residue was purified by flash chromatography, and was eluted with 0-15% ethyl acetate in dichloromethane to provide the title compound.

Example 374C 4-(methoxymethyl)cyclohexanone

EXAMPLE 374B (2.2 g) in a mixture of water (3 mL) and acetic acid (12 mL) was heated at 65° C. for 2 hours. The reaction mixture was concentrated. The residue was mixed with water and saturated aqueous NaHCO$_3$ and extracted with dichloromethane. The dichloromethane layer was dried over Na$_2$SO$_4$, filtered, and concentrated to provide the title compound.

Example 374D 4-(methoxymethyl)cyclohexanecarbonitrile

To a cold (−10° C.) solution of EXAMPLE 374C (1.18 g) and toluenesulfonylmethyl isocyanide (2.268 g) in dimethoxyethane (3 mL) and absolute ethanol (0.1 mL) was added (in small portions) potassium tert-butoxide (2.235 g). The reaction mixture was continued to stir at <5° C. for 30 minutes, warmed to room temperature, heated at 35° C. for 30 minutes and then at room temperature for 2 hours. The reaction mixture was concentrated and the residue was dissolved in water-brine, and extracted with dichloromethane. The dichloromethane layer was purified by flash chromatography, and was eluted with 5% ethyl acetate in dichloromethane to provide the title compound.

Example 374E (4-(methoxymethyl)cyclohexyl)methanamine

To a solution of EXAMPLE 374D (460 mg) in tetrahydrofuran (15 mL) was added 2M lithium aluminum hydride in tetrahydrofuran (2.252 mL) slowly. The reaction mixture was stirred at room temperature for 1 hour, refluxed for 1 hour and cooled. 2 ml of 2M aqueous NaOH and water (5 mL) was added. The solid was filtered off and washed with ether. The filtrate was concentrated. The residue was mixed with dichloromethane (50 mL) and the resulting mixture was dried over Na$_2$SO$_4$ and concentrated to provide the title compound.

Example 374F 4-((4-(methoxymethyl)cyclohexyl)methylamino)-3-nitrobenzenesulfonamide EXAMPLE 374E (450 mg) and 4-fluoro-3-nitrobenzenesulfonamide (693 mg) in tetrahydrofuran (10 mL) were stirred overnight. The reaction mixture was concentrated and the residue was suspended in a mixture of CH$_3$CN, methanol and water. The precipitates were collected, washed with water and dried to give the title compound.

Example 374G 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((4-(methoxymethyl)cyclohexyl)methylamino)-3-nitrophenylsulfonyl)benzamide The title compound was prepared as described in EXAMPLE 11D using EXAMPLE 374F in place of EXAMPLE 11B. $^1$H NMR (400 MHz, dimethylsulfoxide-d$_6$) δ 11.69 (s, 1H), 11.40 (s, 1H), 8.53-8.61 (m, 2H), 8.04 (d, 1H), 7.77-7.82 (m, 1H), 7.47-7.55 (m, 3H), 7.34 (d, 2H), 7.02-7.09 (m, 3H), 6.68 (dd, 1H), 6.39 (dd, 1H), 6.19 (d, 1H), 3.18-3.27 (m, 5H), 3.04-3.14 (m, 5H), 2.75 (s, 2H), 2.11-2.24 (m, 6H), 1.95 (s, 2H), 1.69-1.84 (m, 3H), 1.33-1.63 (m, 7H), 0.84-1.05 (m, 9H).

Example 375

4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide

Example 375A methyl 1-(thiazol-2-yl)piperidine-4-carboxylate

A mixture of methyl piperidine-4-carboxylate (2.045 g), 2-bromothiazole (1.64 g), and Cs$_2$CO$_3$ (5.86 g) in dimethylformamide (15 mL) was heated at 100° C. overnight. After it cooled to room temperature, the reaction mixture was partitioned between water and ethyl acetate. The organic layer was separated, and the aqueous layer was extracted with additional ethyl acetate three times. The combined organic layers were washed with brine, dried over MgSO$_4$, filtered, and concentrated. The residue was purified by flash chromatography on silica gel to give the title compound.

Example 375B (1-(thiazol-2-yl)piperidin-4-yl)methanol

This example was prepared by substituting EXAMPLE 375A for EXAMPLE 339A in EXAMPLE 339B.

Example 375C 5-chloro-6-((1-(thiazol-2-yl)piperidin-4-yl)methoxy)pyridine-3-sulfonamide This example was prepared by substituting EXAMPLE 375B for (tetrahydro-2H-pyran-4-yl)methanol and EXAMPLE 40A for EXAMPLE 36A in EXAMPLE 36B.

Example 375D 2-(1H-pyrrolo[2,3-b]pyridin-5-yloxy)-N-(5-chloro-6-((1-(thiazol-2-yl)piperidin-4-yl)methoxy)pyridin-3-ylsulfonyl)-4-(4-((2-(4-chlorophenyl)-4,4-dimethylcyclohex-1-enyl)methyl)piperazin-1-yl)benzamide This example was prepared by substituting EXAMPLE 375C for EXAMPLE 11B in EXAMPLE 11D. $^1$H NMR (500 MHz, dimethylsulfoxide-d$_6$) δ 11.65 (s, 1H), 8.49 (s, 1H), 8.17 (s, 1H), 8.01 (d, 1H), 7.54 (d, 1H), 7.48-7.49 (m, 2H), 7.35 (d, 2H), 7.14 (d, 1H), 7.05 (d, 2H), 6.80 (d, 1H), 6.67 (dd, 1H), 6.38 (dd, 1H), 6.21 (d, 1H), 4.28 (d, 2H), 3.92 (d, 2H), 2.98-3.10 (m, 6H), 2.86 (s, 2H), 2.30 (m, 4H), 2.03-2.15 (m, 3H), 1.96 (s, 2H), 1.96 (s, 2H), 1.82-1.86 (m, 2H), 1.33-1.44 (m, 4H), 0.93 (s, 6H).

Example 376

4-(4-{[2-(4-chlorophenyl)-4,4-dimethylcyclohex-1-en-1-yl]methyl 1 piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide

Example 376A tert-butyl (4-hydroxy-4-methylcyclohexyl)methylcarbamate

A solution of tert-butyl (4-oxocyclohexyl)methylcarbamate (1.00 g) was dissolved in tetrahydrofuran (20 mL) and cooled to −78° C. Methylmagnesium bromide (4.40 mL) was added dropwise. The reaction was stirred for 2 hours at −78° C. then allowed to warm to 0° C. and stirred for 30 minutes. The resulting suspension was quenched with water (10 mL), diluted with ether (50 mL), washed with ammonium chloride (25 mL), washed with brine (25 mL), dried over magnesium sulfate, filtered, and concentrated. Silica gel chromatography (Reveleris 80 g) eluting using a gradient of 5% to 50% ethyl acetate/dichloromethane over 30 minutes (flow=60 mL/min) gave the title compound as a 2:1 mixture of cis and trans isomers.

Example 376B 4-(aminomethyl)-1-methylcyclohexanol

To a solution of EXAMPLE 376A (0.75 g) in dichloromethane (3 mL) was added a few drops of water followed by trifluoroacetic acid (1.19 mL) and the reaction stirred at room temperature. After stirring for 2 h added additional trifluoroacetic acid (0.5 mL). After an additional 4 h the reaction was concentrated and dried under high vacuum. The resulting oily solid was triturated with diethyl ether with sonication. Filtration and washing with diethyl ether gave the title compound as a trifluoroacetic acid salt and a mixture of cis and trans isomers.

Example 376C 6-((cis-4-hydroxy-4-methylcyclohexyl)methylamino)-5-nitropyridine-3-sulfonamide This example was prepared by substituting EXAMPLE 364D for 4-fluoro-3-nitrobenzenesulfonamide and EXAMPLE 376B for (4-fluorotetrahydro-2H-pyran-4-yl)

Example 376D 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide This example was prepared by substituting EXAMPLE 376C for EXAMPLE 11B in EXAMPLE 11D. $^1$H NMR (500 MHz, dimethylsulfoxide-d$_6$) δ 11.64 (s, 1H), 8.91 (s, 1H), 8.72 (d, 1H), 8.70 (d, 1H), 8.01 (d, 1H), 7.47-7.54 (m, 3H), 7.35 (d, 2H), 7.04 (d, 2H), 6.68 (dd, 1H), 6.36 (dd, 1H), 6.21 (d, 1H), 3.93 (s, 1H), 3.48 (t, 2H), 3.10 (s, 4H), 2.83 (s, 2H), 2.15-2.33 (m, 6H), 1.96 (s, 1H), 1.34-1.59 (m, 9H), 1.17-1.24 (m, 2H), 1.07 (s, 2H), 0.92 (s, 6H).

Example 377

4-(4-{[2-(4-chlorophenyl)-5-methoxy-5-methylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide The title compound was prepared by substituting EXAMPLE 378D for EXAMPLE 1E and EXAMPLE 337M for EXAMPLE 1F in EXAMPLE 1G. $^1$H NMR (500 MHz, pyridine-d$_5$) δ 13.07 (s, 1H), 9.31 (d, 1H), 8.68 (t, 1H), 8.44 (d, 1H), 8.37 (dd, 1H), 8.10 (d, 1H), 7.68 (m, 1H), 7.66 (d, 1H), 7.41 (m, 2H), 7.09 (m, 2H), 6.92 (d, 1H), 6.74 (dd, 1H), 6.52 (d, 1H), 6.50 (dd, 1H), 3.20 (m, 5H), 3.06 (t, 4H), 2.77 (m, 2H), 2.57 (d, 1H), 2.49 (m, 1H), 2.17 (m, 6H), 1.86 (m, 5H), 1.69 (m, 4H), 1.40 (s, 3H), 1.23 (m, 5H).

Example 378

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Example 378A 2-chloro-5-methoxy-5-methylcyclohex-1-enecarbaldehyde

Dimethylformamide (1.298 mL) in dichloromethane (2.0 mL) at −10° C. was treated dropwise with POCl$_3$ (1.426 mL) to give a colorless solution. The mixture was stirred 5 minutes and then warmed to room temperature and stirred 30 minutes. The solution was cooled to −10° C., treated dropwise with a solution of 4-methoxy-4-methylcyclohexanone (1.74 g) in dichloromethane (2.5 mL), and stirred for 4 hours at ambient temperature. The reaction mixture was poured over a mixture of ice and 25% aqueous sodium acetate solution. After the ice melted, the reaction mixture was poured into a separatory funnel and extracted with diethyl ether (4×125 mL). The diethyl ether extracts were washed with NaHCO$_3$ solution and brine, dried (MgSO$_4$), filtered and concentrated. The concentrate was chromatographed on silica gel with 0 to 5% ethyl acetate in hexanes as the eluent.

Example 378B 2-(4-chlorophenyl)-5-methoxy-5-methylcyclohex-1-enecarbaldehyde EXAMPLE 378A (1.55 g), 4-chlorophenylboronic acid (1.542 g), PdOAc$_2$ (0.055 g), K$_2$CO$_3$ (2.84 g) and tetrabuylammonium bromide (2.65 g) were combined in a 50-mL round-bottomed flask equipped with a magnetic stir bar. Water (9.13 mL) was added. The vial was flushed with nitrogen, capped and stirred at 45° C. for 14 hours. The reaction mixture was cooled to room temperature and partitioned between brine and diethyl ether. The organic layer was washed with brine, dried (MgSO$_4$), filtered through a plug of celite, concentrated and chromatographed on silica gel with 5 to 20% ethyl acetate in hexanes as the eluent.

Example 378C methyl 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)benzoate The title compound was prepared by substituting EXAMPLE 378B for 4'-chlorobiphenyl-2-carboxaldehyde and EXAMPLE 15F for tert-butyl piperazine-1-carboxylate in EXAMPLE 1A except that a small amount of DMSO was added to the reaction mixture.

Example 378D 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)benzoic acid The title compound was prepared by substituting EXAMPLE 378C for EXAMPLE 15G in EXAMPLE 15H.

Example 378E 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 378D for EXAMPLE 1E in EXAMPLE 1G. $^1$H NMR (500 MHz, pyridine-d$_5$) δ 13.07 (s, 1H), 9.31 (d, 1H), 8.68 (t, 1H), 8.43 (d, 1H), 8.37 (dd, 1H), 8.09 (d, 1H), 7.68 (m, 1H), 7.66 (d, 1H), 7.41 (m, 2H), 7.09 (m, 2H), 6.90 (d, 1H), 6.74 (dd, 1H), 6.52 (d, 1H), 6.50 (dd, 1H), 3.97 (dd, 2H), 3.30 (td, 2H), 3.21 (s, 3H), 3.15 (m, 2H), 3.06 (t, 4H), 2.77 (m, 2H), 2.57 (d, 1H), 2.50 (m, 1H), 2.16 (m, 6H), 1.81 (m, 2H), 1.63 (m, 1H), 1.57 (dd, 2H), 1.32 (m, 2H), 1.21 (s, 3H).

What is claimed is:

1. 4-(4-{[2-(4-Chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

2. A pharmaceutical composition comprising an excipient and a therapeutically effective amount of 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

* * * * *